(12) United States Patent
Kamata et al.

(10) Patent No.: US 8,501,804 B2
(45) Date of Patent: Aug. 6, 2013

(54) BICYCLIC COMPOUND

(75) Inventors: Makoto Kamata, Osaka (JP); Tohru Yamashita, Osaka (JP); Asato Kina, Osaka (JP); Michiko Amano, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 198 days.

(21) Appl. No.: 13/126,103

(22) PCT Filed: Oct. 26, 2009

(86) PCT No.: PCT/JP2009/068356
§ 371 (c)(1),
(2), (4) Date: Apr. 26, 2011

(87) PCT Pub. No.: WO2010/050445
PCT Pub. Date: May 6, 2010

(65) Prior Publication Data
US 2012/0010247 A1    Jan. 12, 2012

(30) Foreign Application Priority Data

Oct. 27, 2008  (JP) .................. 2008-276171
Feb. 20, 2009  (JP) .................. 2009-037468
Jun. 15, 2009  (JP) .................. 2009-142769

(51) Int. Cl.
*A61K 31/343* (2006.01)
*C07D 307/83* (2006.01)

(52) U.S. Cl.
USPC .......................... 514/469; 549/467

(58) Field of Classification Search
USPC .......................... 514/469; 549/467
See application file for complete search history.

(56) References Cited

U.S. PATENT DOCUMENTS

| | | | |
|---|---|---|---|
| 4,873,259 A | 10/1989 | Summers, Jr. et al. |
| 4,992,464 A | 2/1991 | Brooks et al. |
| 5,250,565 A | 10/1993 | Brooks et al. |
| 5,290,798 A | 3/1994 | Gillard et al. |
| 5,510,376 A | 4/1996 | Epstein et al. |
| 5,750,524 A | 5/1998 | Mera et al. |
| 6,518,292 B1 | 2/2003 | Robl et al. |
| 6,525,203 B1 | 2/2003 | Tino |
| 6,660,760 B1 | 12/2003 | Robl et al. |
| 2003/0158177 A1 | 8/2003 | Ishihara et al. |
| 2004/0002525 A1 | 1/2004 | Robl et al. |
| 2004/0019016 A1 | 1/2004 | Potter et al. |
| 2004/0029935 A1 | 2/2004 | Robl et al. |
| 2004/0063709 A1 | 4/2004 | Taveras et al. |
| 2004/0072881 A1 | 4/2004 | Robl et al. |
| 2004/0077628 A1 | 4/2004 | Ishihara et al. |
| 2004/0147568 A1 | 7/2004 | Yu et al. |
| 2006/0063798 A1 | 3/2006 | Yu et al. |
| 2006/0079549 A1 | 4/2006 | Yu et al. |
| 2006/0142360 A1 | 6/2006 | Potter et al. |
| 2006/0217380 A1 | 9/2006 | Chaffee et al. |
| 2006/0252778 A1 | 11/2006 | Guo et al. |
| 2006/0258728 A1 | 11/2006 | Tani et al. |
| 2007/0149521 A1 | 6/2007 | Crew et al. |
| 2008/0009530 A1 | 1/2008 | Abe et al. |
| 2008/0119456 A1 | 5/2008 | Ulven et al. |
| 2008/0261970 A1 | 10/2008 | Saunders et al. |
| 2008/0269220 A1 | 10/2008 | Yasuma et al. |
| 2009/0012093 A1 | 1/2009 | Fukatsu et al. |
| 2009/0111862 A1 | 4/2009 | Potter et al. |
| 2009/0247746 A1 | 10/2009 | Yasuma et al. |
| 2009/0270631 A1 | 10/2009 | Abe et al. |
| 2009/0318703 A1 | 12/2009 | Tani et al. |
| 2009/0324625 A1 | 12/2009 | Yu et al. |
| 2010/0016233 A1 | 1/2010 | Yu et al. |
| 2010/0041892 A1 | 2/2010 | Abe et al. |
| 2010/0145048 A1 | 6/2010 | Guo et al. |
| 2010/0160283 A1 | 6/2010 | Chaffee et al. |
| 2010/0305114 A1 | 12/2010 | Yu et al. |
| 2011/0052562 A1 | 3/2011 | Feng et al. |
| 2011/0065681 A1 | 3/2011 | Wei et al. |
| 2012/0053173 A1 | 3/2012 | Banno et al. |

FOREIGN PATENT DOCUMENTS

| | | |
|---|---|---|
| EP | 0 535 926 | 4/1993 |
| EP | 0 773 019 | 5/1997 |
| EP | 0 608 568 | 3/1998 |

(Continued)

OTHER PUBLICATIONS

English translation of the International Preliminary Report on Patentability and Written Opinion dated Jun. 7, 2011.
Supplementary European Search Report dated Apr. 12, 2012 in EP Application No. 09823555.9.
International Search Report issued Dec. 8, 2009 in International (PCT) Application No. PCT/JP2009/068356.
C. V. C. Prasad et al., "Enantioselective Synthesis of Aminobenzazepinones", Tetrahedron Letters, vol. 48, No. 15, pp. 2661-2665, 2007.

*Primary Examiner* — Taofiq A Solola
(74) *Attorney, Agent, or Firm* — Wenderoth, Lind & Ponack, L.L.P.

(57) ABSTRACT

The present invention provides a compound having an ACC inhibitory action, which is useful as an agent for the prophylaxis or treatment of obesity, diabetes, hypertension, hyperlipidemia, cardiac failure, diabetic complications, metabolic syndrome, sarcopenia, cancer and the like, and has superior efficacy.
The present invention relates to a compound represented by the formula (I):

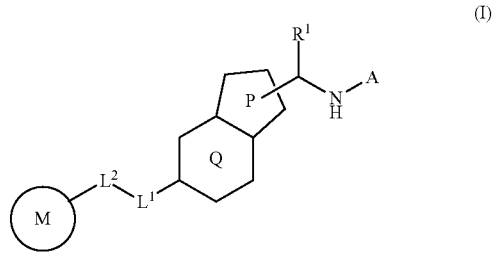

wherein each symbol is as defined in the specification, or a salt thereof.

9 Claims, No Drawings

FOREIGN PATENT DOCUMENTS

| | | |
|---|---|---|
| EP | 1 283 199 | 2/2003 |
| EP | 1 285 651 | 2/2003 |
| EP | 1 431 267 | 6/2004 |
| EP | 1 559 422 | 8/2005 |
| EP | 1 726 580 | 11/2006 |
| EP | 1 873 144 | 1/2008 |
| EP | 2 251 326 | 11/2010 |
| JP | 63-264456 | 11/1988 |
| JP | 7-224063 | 8/1995 |
| JP | 9-235278 | 9/1997 |
| JP | 2005-194191 | 7/2005 |
| JP | 2006-502162 | 1/2006 |
| WO | 95/09159 | 4/1995 |
| WO | 99/65942 | 12/1999 |
| WO | 00/01704 | 1/2000 |
| WO | 00/54729 | 9/2000 |
| WO | 02/069965 | 9/2002 |
| WO | 03/045925 | 6/2003 |
| WO | 03/057676 | 7/2003 |
| WO | 03/075921 | 9/2003 |
| WO | 2004/021984 | 3/2004 |
| WO | 2004/033440 | 4/2004 |
| WO | 2004/071448 | 8/2004 |
| WO | 2004/072047 | 8/2004 |
| WO | 2005/066137 | 7/2005 |
| WO | 2005/066147 | 7/2005 |
| WO | 2005/068460 | 7/2005 |
| WO | 2005/103029 | 11/2005 |
| WO | 2005/116001 | 12/2005 |
| WO | 2005/121130 | 12/2005 |
| WO | 2006/036932 | 4/2006 |
| WO | 2006/044823 | 4/2006 |
| WO | 2006/094209 | 9/2006 |
| WO | 2006/124874 | 11/2006 |
| WO | 2007/002764 | 1/2007 |
| WO | 2007/018314 | 2/2007 |
| WO | 2007/022241 | 2/2007 |
| WO | 2007/064993 | 6/2007 |
| WO | 2007/095602 | 8/2007 |
| WO | 2009/026701 | 3/2009 |
| WO | 2009/079011 | 6/2009 |
| WO | 2009/110520 | 9/2009 |
| WO | 2009/110985 | 9/2009 |

BICYCLIC COMPOUND

This application is a U.S. national stage of International Application No. PCT/JP2009/068356 filed Oct. 26, 2009.

TECHNICAL FIELD

The present invention relates to a bicyclic compound having an acetyl-CoA carboxylase (in the present specification, sometimes to be abbreviated as ACC) inhibitory action, which is useful for the prophylaxis or treatment of obesity, diabetes, hypertension, hyperlipidemia, cardiac failure, diabetic complications, metabolic syndrome, sarcopenia, cancer and the like.

BACKGROUND OF THE INVENTION

ACC is an enzyme that converts acetyl-CoA to malonyl-CoA, and catalyzes a rate determining reaction in fatty acid metabolism. Malonyl-CoA, which is produced by an ACC catalyst reaction, inhibits fatty acid oxidation in mitochondria based on the feedback inhibition of carnitine palmitoyl transferase-1 (CPT-1). Accordingly, ACC plays a key role in controlling the balance between use of carbohydrate and fatty acid in the liver and skeletal muscle, and further, controlling insulin sensitivity in the liver, skeletal muscle and adipose tissue.

A reduced level of malonyl-CoA by ACC inhibition can promote an increase in fatty acid oxidation, decreased secretion of triglyceride (TG)-rich lipoprotein (VLDL) in the liver, regulation of insulin secretion in the pancreas, and further, improvement in the insulin sensitivity in the liver, skeletal muscle and adipose tissue.

In addition, long-term administration of a compound having an ACC inhibitory action can strikingly decrease the TG content of the liver and adipose tissues and selectively decrease body fat in obese test subjects taking low fat diet, by promoting fatty acid oxidation and suppressing de novo synthesis of fatty acid.

Accordingly, a compound having an ACC inhibitory action is extremely useful for the prophylaxis or treatment of metabolic syndrome, obesity, hypertension, diabetes, cardiovascular diseases associated with atherosclerosis and the like.

On the other hand, the following compounds have been reported.

(1) A compound represented by the formula:

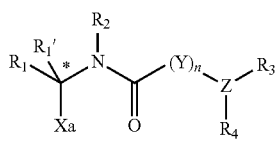

wherein
$R_1$ is alkyl, aryl or the like,
$R_1'$ is a hydrogen atom, alkyl or the like,
$R_2$, $R_3$ and $R_4$ are each independently a hydrogen atom, alkyl or the like,
Xa is optionally substituted cycloalkyl, optionally substituted heteroaryl (the heteroaryl may be optionally a fused ring or a spiro ring) and or like,
Y is linker such as alkylene, alkenylene or the like,
Z is N, and
n is an integer of 1 to 6,
(see Patent Document 1).

(2) A compound represented by the formula:

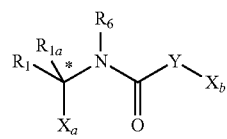

wherein
$R_1$ is alkyl, aryl or the like,
$R_{1a}$ is a hydrogen atom, alkyl or the like,
Xa is

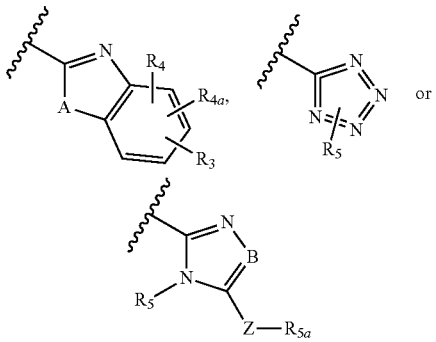

or the like,
$R_3$ is a hydrogen atom, optionally substituted alkyl or the like,
$R_4$ and $R_{4a}$ are each independently a hydrogen atom, alkyl or the like,
$R_6$ is a hydrogen atom, alkyl or the like,
A is O, S, NH or the like,
Y is

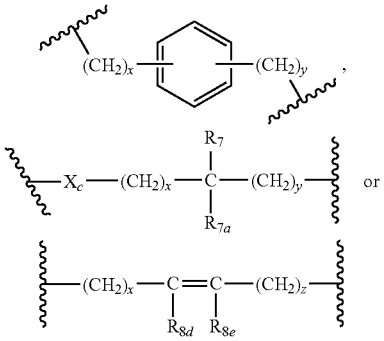

wherein
x and y are each independently an integer of 0 to 3, and z is an integer of 0 to 3, and
Xb is

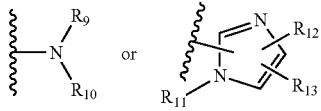

(see Patent Document 2).

(3) A compound represented by the formula:

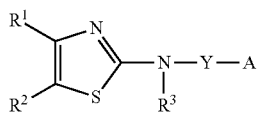

wherein
$R^1$, $R^2$ and $R^3$ are each independently a hydrogen atom, optionally substituted alkyl or the like,
A is optionally substituted aryl, heterocyclic group or cycloalkyl,
Y is

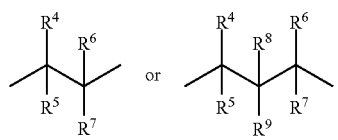

$R^4$ and $R^5$ are each independently a hydrogen atom, optionally substituted alkyl, carboxyl group or the like,
$R^6$ and $R^7$ are each independently a hydrogen atom, halogen, —OH, —CN or the like,
$R^8$ and $R^9$ are each independently a hydrogen atom, optionally substituted alkyl or the like, and
$R^3$-$R^9$ optionally form an optionally substituted carbocycle or an optionally substituted heterocycle,
(see Patent Document 3).

(4) A compound represented by the formula:

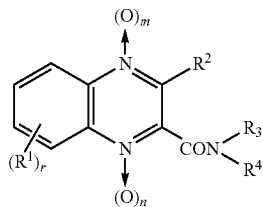

wherein
$R^1$ is a hydrogen atom, lower alkyl or the like,
$R^2$ is a hydrogen atom, optionally substituted alkyl or the like,
$R_3$ and $R^4$ are each independently a hydrogen atom, lower alkyl,

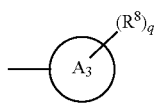

or the like,
$A_3$ is lower alkyl substituted by 5- to 14-membered heterocycle(s) (the heterocycle is optionally condensed),
$R^8$ is a hydrogen atom, oxo, —CONR$^9$R$^{10}$ or the like, $R^9$ and $R^{10}$ are each independently a hydrogen atom, phenyl or the like,
n is 0,
m is 0 or 1, and
r is 1 or 2,
(see Patent Document 4).

(5) A compound represented by the formula:

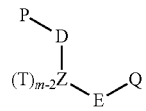

wherein
T is a hydrogen atom, hydrocarbon, —F—R, or a bond to the one of D, E, P and Q, or form, together with the one of P and Q, a ring,
Z is an atom having valence m,
M is a valence of Z,
D, E and F are each independently a linker (when Z is N, E is neither $CH_2$ nor CO), and
P, Q and R are each independently a ring (Q contains sulfamate group),
(see Patent Document 5).

(6) A compound represented by the formula:

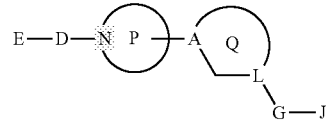

wherein
E is an optionally substituted cyclic group (provided that the cyclic group is not a spiro ring group, and when the cyclic group is a monocyclic group, the cyclic group has at least two optionally substituted cyclic groups as substituents);
D and G are independently carbonyl group or sulfonyl group;
ring P is an optionally substituted nitrogen-containing 5- or 6-membered non-aromatic heterocycle,
ring Q is an optionally substituted aromatic ring or an optionally substituted non-aromatic heterocycle (provided that the non-aromatic heterocycle contains two or more hetero atoms);
A and L are independently C, CH or N; and
J is an optionally substituted hydrocarbon group, an optionally substituted hydroxy group, an optionally substituted heterocyclic group or an optionally substituted amino group,
(see Patent Document 6).

(7) A compound represented by the formula:

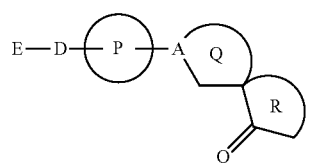

wherein
E is an optionally substituted cyclic group;
D is a carbonyl group or a sulfonyl group;
A is CH or N;
ring P is an optionally further substituted 5- to 7-membered ring;
ring Q is an optionally further substituted 5- to 7-membered non-aromatic ring; and
ring R is an optionally fused 5- to 7-membered non-aromatic ring which is optionally further substituted,
(see Patent Document 7).

(8) A compound represented by the formula:

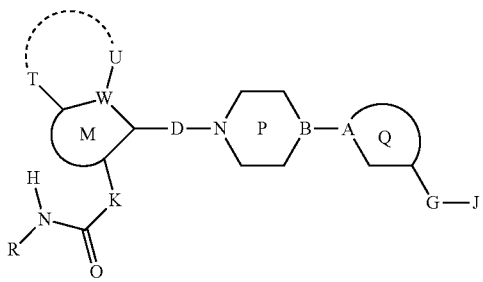

wherein ring M is a 5- or 6-membered aromatic ring;

W is C or N;

K is an optionally substituted methylene group or an optionally substituted imino group;

R is a hydrogen atom, an optionally substituted hydrocarbon group, an optionally substituted hydroxy group or an optionally substituted heterocyclic group;

T and U are independently a hydrogen atom or a substituent, or T and U form, together with ring M, an optionally substituted bicyclic ring;

D and G are independently a carbonyl group or a sulfonyl group;

ring P is optionally substituted piperidine or an optionally substituted piperazine;

B is CH or N;

ring Q is an optionally substituted monocyclic ring;

A is C, CH or N; and

J is an optionally substituted hydrocarbon group, an optionally substituted heterocyclic group or an optionally substituted amino group, provided that when the W moiety of ring M is =N— or —N=, U is absent, (see Patent Document 8).

(9) A compound represented by the formula:

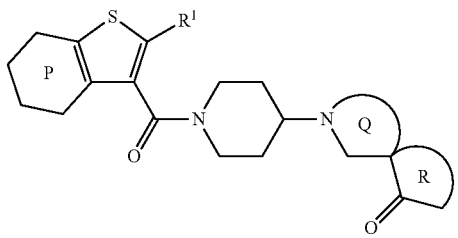

wherein $R^1$ is a hydrogen atom or a substituent; ring P is an optionally substituted 6-membered nitrogen-containing aromatic heterocycle;

ring Q is an optionally further substituted 5- to 7-membered nitrogen-containing non-aromatic heterocycle;

ring R is an optionally fused 5- to 7-membered non-aromatic ring which is optionally further substituted, (see Patent Document 9).

(10) A compound represented by the formula:

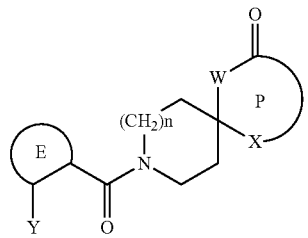

wherein ring E is an optionally further substituted 6-membered aromatic ring, or an optionally fused 5-membered aromatic heterocycle which is optionally further substituted;

ring P is an optionally fused non-aromatic ring which is optionally further substituted;

W is O, S, a $C_{1-4}$ alkylene or $NR^{3a}$ wherein $R^{3a}$ is a hydrogen atom or a substituent;

X is O, S, SO, $SO_2$, CO, $CR^1R^2$ or $NR^{3b}$ wherein $R^1$, $R^2$ and $R^{3b}$ are the same or different and each is a hydrogen atom or a substituent;

Y is an optionally substituted amino group; and n is 0, 1, 2 or 3, (see Patent Document 10).

(11) A compound represented by

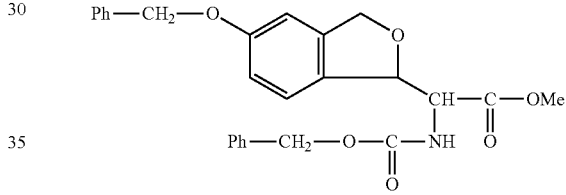

(see non-Patent Document 1).

However, none of the above-mentioned documents reports on the bicyclic compound of the present invention.

DOCUMENT LIST

Patent Documents

Patent Document 1: WO 2004/021984
Patent Document 2: WO 00/54729
Patent Document 3: JP-A-9-235278
Patent Document 4: WO 95/09159
Patent Document 5: WO 03/045925
Patent Document 6: JP-A-2006-131559
Patent Document 7: WO 2007/013691
Patent Document 8: WO 2007/119833
Patent Document 9: WO 2008/090944
Patent Document 10: WO 2008/102749

Non-Patent Document

Non-Patent Document 1: Tetrahedron Letters, 48(15), 2661-2665 (2007)

SUMMARY OF THE INVENTION

Problems to be Solved by the Invention

There is a demand for the development of a compound having an ACC inhibitory action, which is useful as an agent for the prophylaxis or treatment of obesity, diabetes, hypertension, hyperlipidemia, cardiac failure, diabetic complications, metabolic syndrome, sarcopenia, cancer and the like, and has superior efficacy.

Means of Solving the Problems

The present inventors have found for the first time that a compound represented by the formula (I):

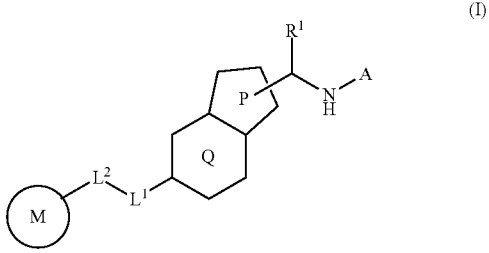

wherein

A is an acyl group or an optionally substituted 5- or 6-membered aromatic ring group;

ring M is an optionally fused 5- to 7-membered ring which is optionally further substituted; as to ring P and ring Q, (1) ring P is optionally further substituted 5-membered heterocycle, ring Q is optionally further substituted 6-membered ring, and ring P and ring Q are condensed to form an optionally further substituted bicyclic aromatic heterocycle, or (2) ring P is an optionally further substituted 5-membered non-aromatic ring, ring Q is an optionally substituted 6-membered aromatic ring, and ring P and ring Q are condensed to form an optionally substituted bicyclic non-aromatic ring;

$R^1$ is an optionally substituted $C_{1-6}$ alkyl group or an optionally substituted $C_{3-6}$ cycloalkyl group; and as to $L^1$ and $L^2$, (1) $L^1$ and $L^2$ are independently optionally substituted methylene, O, S, SO or $SO_2$, or (2) $L^1$ and $L^2$ in combination form optionally substituted vinylene, or ethynylene, provided that the following compounds are excluded:

(a) a compound wherein A is an α-aminoisobutyloyl group; and (b) a compound wherein A is a 5- or 6-membered aromatic ring group substituted by a group represented by the formula: —CO—$(CH_2)_3$—$COOR^{41}$ wherein $R^{41}$ is a hydrogen atom or a $C_{1-6}$ alkyl group, or a group represented by the formula: —CO—$NR^{42}$—$CR^{43}R^{44}$—$CR^{45}R^{46}$—$COOR^{47}$ wherein $R^{42}$, $R^{43}$, $R^{44}$, $R^{45}$ and $R^{47}$ are independently a hydrogen atom or a $C_{1-6}$ alkyl group; and $R^{46}$ is a hydrogen atom, a $C_{1-6}$ alkyl group or a hydroxy group, or a salt thereof [hereinafter sometimes to be referred to as compound (I)] has a superior ACC inhibitory action, which is useful for the prophylaxis or treatment of obesity, diabetes, hypertension, hyperlipidemia, cardiac failure, diabetic complications, metabolic syndrome, sarcopenia, cancer and the like, and has superior efficacy. Based on this finding, the present inventors have conducted intensive studies and completed the present invention.

Accordingly, the present invention relates to
(1) compound (I);
(2) a compound represented by the formula (I):

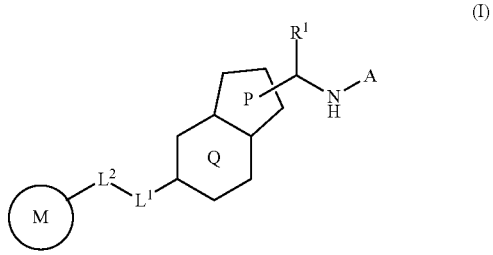

wherein

A is an acyl group or an optionally substituted 5- or 6-membered aromatic ring group;

ring M is an optionally fused 5- to 7-membered ring which is optionally further substituted;

ring P is optionally further substituted 5-membered heterocycle, ring Q is optionally further substituted 6-membered ring, and ring P and ring Q are condensed to form an optionally further substituted bicyclic aromatic heterocycle;

$R^1$ is an optionally substituted $C_{1-6}$ alkyl group or an optionally substituted $C_{3-6}$ cycloalkyl group;

$L^1$ and $L^2$ are independently optionally substituted methylene, O, S, SO or $SO_2$, provided that the following compounds are excluded:

(a) a compound wherein A is an α-aminoisobutyloyl group; and (b) a compound wherein A is a 5- or 6-membered aromatic ring group substituted by a group represented by the formula: —CO—$(CH_2)_3$—$COOR^{41}$ wherein $R^{41}$ is a hydrogen atom or a $C_{1-6}$ alkyl group, or a group represented by the formula: —CO—$NR^{42}$—$CR^{43}R^{44}$—$CR^{45}R^{46}$—$COOR^{47}$ wherein $R^{42}$, $R^{43}$, $R^{44}$, $R^{45}$ and $R^{47}$ are independently a hydrogen atom or a $C_{1-6}$ alkyl group; and $R^{46}$ is a hydrogen atom, a $C_{1-6}$ alkyl group or a hydroxy group, or a salt thereof;

(3) the compound of the above-mentioned (1), wherein $R^1$ is a $C_{1-6}$ alkyl group or a $C_{3-6}$ cycloalkyl group;

(4) the compound of the above-mentioned (1), wherein $R^1$ is a $C_{1-6}$ alkyl group;

(5) the compound of the above-mentioned (1), wherein A is
(1) a $C_{1-6}$ alkyl-carbonyl group, or
(2) a 5-membered aromatic heterocyclic group optionally substituted by 1 to 3 substituents selected from (i) a halogen atom and (ii) a $C_{1-6}$ alkyl group;

(6) the compound of the above-mentioned (1), wherein ring M is a benzene ring or pyridine ring, each of which is optionally substituted by 1 to 3 substituents selected from
(1) a halogen atom,
(2) a $C_{1-6}$ alkyl group,
(3) a $C_{1-6}$ alkoxy group optionally substituted by 1 to 3 substituents selected from (i) a halogen atom, (ii) a $C_{1-6}$ alkoxy group, (iii) a $C_{3-10}$ cycloalkyl group, (iv) a heterocyclic group and (v) a $C_{6-14}$ aryl group,
(4) a $C_{3-10}$ cycloalkoxy group optionally substituted by 1 to 3 substituents selected from (i) a halogen atom and (ii) a $C_{1-6}$ alkoxy group, and
(5) a hydroxy group;

(7) the compound of the above-mentioned (1), wherein ring P and ring Q are condensed to form

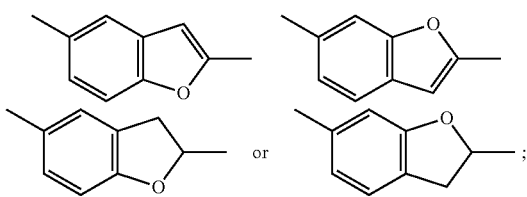

(8) the compound of the above-mentioned (1), wherein
(1) $L^1$ and $L^2$ are independently methylene or O, or
(2) $L^1$ and $L^2$ in combination form ethynylene or vinylene;
(9) the compound of the above-mentioned (1), wherein
A is
(1) a $C_{1-6}$ alkyl-carbonyl group, or
(2) a 5-membered aromatic heterocyclic group optionally substituted by 1 to 3 substituents selected from (i) a halogen atom and (ii) a $C_{1-6}$ alkyl group;
$R^1$ is a $C_{1-6}$ alkyl group; ring M is
a benzene ring or pyridine ring, each of which is optionally substituted by 1 to 3 substituents selected from
(1) a halogen atom,
(2) a $C_{1-6}$ alkyl group,
(3) a $C_{1-6}$ alkoxy group optionally substituted by 1 to 3 substituents selected from (i) a halogen atom, (ii) a $C_{1-6}$ alkoxy group, (iii) a $C_{3-10}$ cycloalkyl group, (iv) a heterocyclic group and (v) a $C_{6-14}$ aryl group,
(4) a $C_{3-10}$ cycloalkoxy group optionally substituted by 1 to 3 substituents selected from (i) a halogen atom and (ii) a $C_{1-6}$ alkoxy group, and
(5) a hydroxy group;
ring P and ring Q are condensed to form

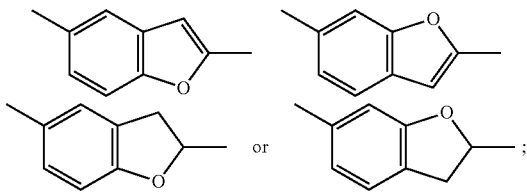

and
as to $L^1$ and $L^2$,
(1) $L^1$ and $L^2$ are independently methylene or O, or
(2) $L^1$ and $L^2$ in combination form ethynylene or vinylene;
(10) N-{(1S)-1-[(2S)-6-{[4-(cyclopropylmethoxy)-2-fluorobenzyl]oxy}-2,3-dihydro-1-benzofuran-2-yl]ethyl}acetamide or a salt thereof;
(11) N-[1-(5-{[6-(cyclopropylmethoxy)-4-fluoropyridin-3-yl]methoxy}-1-benzofuran-2-yl)ethyl]acetamide or a salt thereof;
(12) N-(1-{6-[2-(4-ethoxyphenyl)ethyl]-1-benzofuran-2-yl}ethyl)acetamide or a salt thereof;
(13) N-[1-(5-{[4-(cyclopropylmethoxy)benzyl]oxy}-1-benzofuran-2-yl)ethyl]acetamide or a salt thereof;
(14) a prodrug of the compound of the above-mentioned (1);
(15) a medicament comprising the compound of the above-mentioned (1) or a prodrug thereof;
(16) the medicament of the above-mentioned (15), which is an acetyl-CoA carboxylase inhibitor;
(17) the medicament of the above-mentioned (15), which is an agent for the prophylaxis or treatment of obesity, diabetes, hypertension, hyperlipidemia, cardiac failure, diabetic complications, metabolic syndrome, sarcopenia or cancer;
(18) a method for the prophylaxis or treatment of obesity, diabetes, hypertension, hyperlipidemia, cardiac failure, diabetic complications, metabolic syndrome, sarcopenia or cancer in a mammal, which comprises administering an effective amount of the above-mentioned compound (I) or a prodrug thereof to the mammal;
(19) use of the compound of the above-mentioned (1) or a prodrug thereof, for the production of an agent for the prophylaxis or treatment of obesity, diabetes, hypertension, hyperlipidemia, cardiac failure, diabetic complications, metabolic syndrome, sarcopenia or cancer; and the like.

Effect of the Invention

Compound (I) has an ACC inhibitory action, which is useful for the prophylaxis or treatment of obesity, diabetes, hypertension, hyperlipidemia, cardiac failure, diabetic complications, metabolic syndrome, sarcopenia, cancer and the like, and has superior efficacy.

DETAILED DESCRIPTION OF THE INVENTION

The definition of each symbol in the formula (I) is described in detail in the following.

The "halogen atom" in the present specification means, unless otherwise specified, a fluorine atom, a chlorine atom, a bromine atom or an iodine atom.

The "$C_{1-3}$ alkylenedioxy group" in the present specification means, unless otherwise specified, methylenedioxy, ethylenedioxy or the like.

The "$C_{1-4}$ alkyl group" in the present specification means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

The "$C_{1-6}$ alkoxy group" in the present specification means, unless otherwise specified, methoxy, ethoxy, propoxy, isopropoxy, butoxy, isobutoxy, sec-butoxy, tert-butoxy or the like.

The "$C_{1-6}$ alkoxy-carbonyl group" in the present specification means, unless otherwise specified, methoxycarbonyl, ethoxycarbonyl, propoxycarbonyl, tert-butoxycarbonyl or the like.

The "$C_{1-6}$ alkyl-carbonyl group" in the present specification means, unless otherwise specified, acetyl, propanoyl, butanoyl, isobutanoyl, pentanoyl, isopentanoyl, hexanoyl or the like.

A is an acyl group or an optionally substituted 5- or 6-membered aromatic ring group.

Examples of the "acyl group" for A include a group represented by the formula: —$COR^A$, —CO—$OR^A$, —$SO_3R^A$, —$SO_2R^A$, —$SOR^A$, —CO—$NR^{A'}R^{B'}$, —CS—$NR^{A'}R^{B'}$ or —$SO_2NR^{A'}R^{B'}$ wherein $R^A$ is a hydrogen atom, an optionally substituted hydrocarbon group or an optionally substituted heterocyclic group. $R^{A'}$ and $R^{B'}$ are the same or different and each is a hydrogen atom, a sulfamoyl group mono- or di-optionally substituted by $C_{1-6}$ alkyl group(s), sulfonyl group optionally substituted by a $C_{1-6}$ alkyl group, an optionally substituted hydrocarbon group or an optionally substituted heterocyclic group, or $R^{A'}$ and $R^{B'}$ form, together with the adjacent nitrogen atom, an optionally substituted nitrogen-containing heterocycle, and the like.

Examples of the "hydrocarbon group" of the above-mentioned "optionally substituted hydrocarbon group" for $R^A$, $R^{A'}$ or $R^{B'}$ include a $C_{1-10}$ alkyl group, a $C_{2-10}$ alkenyl group, a C$_{2-10}$ alkynyl group, a C$_{3-10}$ cycloalkyl group, a C$_{3-10}$ cycloalkenyl group, a C$_{4-20}$ cycloalkadienyl group, a C$_{6-14}$ aryl group, a C$_{7-13}$ aralkyl group, a C$_{8-13}$ arylalkenyl group and the like.

Examples of the C$_{1-10}$ alkyl group include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like.

Examples of the C$_{2-10}$ alkenyl group include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

Examples of the C$_{2-10}$ alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like.

Examples of the C$_{3-10}$ cycloalkyl group include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Examples of the C$_{3-10}$ cycloalkenyl group include 2-cyclopenten-1-yl, 3-cyclopenten-1-yl, 2-cyclohexen-1-yl, 3-cyclohexen-1-yl and the like.

Examples of the C$_{4-10}$ cycloalkadienyl group include 2,4-cyclopentadien-1-yl, 2,4-cyclohexadien-1-yl, 2,5-cyclohexadien-1-yl and the like.

The above-mentioned C$_{3-10}$ cycloalkyl group, C$_{3-10}$ cycloalkenyl group and C$_{4-10}$ cycloalkadienyl group are each optionally condensed with a benzene ring to form a fused ring group. Examples of the fused ring group include indanyl, dihydronaphthyl, tetrahydronaphthyl, fluorenyl and the like.

Examples of the C$_{6-14}$ aryl group include phenyl, naphthyl, anthryl, phenanthryl, acenaphthyl, biphenylyl and the like.

Examples of the C$_{7-13}$ aralkyl group include benzyl, phenethyl, naphthylmethyl, biphenylylmethyl and the like.

Examples of the C$_{8-13}$ arylalkenyl group include styryl and the like.

The C$_{1-10}$ alkyl group, C$_{2-10}$ alkenyl group and C$_{2-10}$ alkynyl group which are exemplified as the above-mentioned "hydrocarbon group" optionally have 1 to 3 substituents at substitutable positions.

Examples of the substituent include
(1) a C$_{3-10}$ cycloalkyl group (e.g., cyclopropyl, cyclohexyl);
(2) a C$_{6-14}$ aryl group (e.g., phenyl, naphthyl) optionally substituted by 1 to 3 substituents selected from
   (a) a C$_{1-6}$ alkyl group optionally substituted by 1 to 3 halogen atoms,
   (b) a hydroxy group,
   (c) a C$_{1-6}$ alkoxy group optionally substituted by 1 to 3 halogen atoms, and
   (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
   (a) a C$_{1-6}$ alkyl group optionally substituted by 1 to 3 halogen atoms,
   (b) a hydroxy group,
   (c) a C$_{1-6}$ alkoxy group optionally substituted by 1 to 3 halogen atoms, and
   (d) a halogen atom;
(4) a non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
   (a) a C$_{1-6}$ alkyl group optionally substituted by 1 to 3 halogen atoms,
   (b) a hydroxy group,
   (c) a C$_{1-6}$ alkoxy group optionally substituted by 1 to 3 halogen atoms,
   (d) a halogen atom, and
   (e) an oxo group;
(5) an amino group optionally mono- or di-substituted by substituent(s) selected from
   (a) a C$_{1-6}$ alkyl group optionally substituted by 1 to 3 halogen atoms,
   (b) a C$_{1-6}$ alkyl-carbonyl group optionally substituted by 1 to 3 halogen atoms,
   (c) a C$_{1-6}$ alkoxy-carbonyl group optionally substituted by 1 to 3 halogen atoms,
   (d) a alkylsulfonyl group (e.g., methylsulfonyl) optionally substituted by 1 to 3 halogen atoms,
   (e) a carbamoyl group optionally mono- or di-substituted by C$_{1-6}$ alkyl group(s) optionally substituted by 1 to 3 halogen atoms, and
   (f) an aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a C$_{1-6}$ alkyl-carbonyl group optionally substituted by 1 to 3 halogen atoms;
(7) a C$_{1-6}$ alkoxy-carbonyl group optionally substituted by 1 to 3 substituents selected from
   (a) a halogen atom,
   (b) a C$_{1-6}$ alkoxy group,
   (c) a C$_{6-14}$ aryl group (e.g., phenyl), and
   (d) a heterocyclic group (e.g., tetrahydrofuryl);
(8) a C$_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by C$_{1-6}$ alkyl group(s) optionally substituted by 1 to 3 halogen atoms;
(10) a thiocarbamoyl group optionally mono- or di-substituted by C$_{1-6}$ alkyl group(s) optionally substituted by 1 to 3 halogen atoms;
(11) a sulfamoyl group optionally mono- or di-substituted by C$_{1-6}$ alkyl group(s) optionally substituted by 1 to 3 halogen atoms;
(12) a carboxy group;
(13) a hydroxy group;
(14) a C$_{1-6}$ alkoxy group optionally substituted by 1 to 3 substituents selected from
   (a) a halogen atom,
   (b) a carboxy group,
   (c) a C$_{1-6}$ alkoxy group,
   (d) a C$_{1-6}$ alkoxy-carbonyl group optionally substituted by 1 to 3 C$_{6-14}$ aryl groups (e.g., phenyl),
   (e) an amino group optionally mono- or di-substituted by substituent(s) selected from a C$_{1-6}$ alkyl group and a C$_{1-6}$ alkoxy-carbonyl group,
   (f) a heterocyclic group (e.g., tetrahydrofuryl), and
   (g) a C$_{3-10}$ cycloalkyl group;
(15) a C$_{2-6}$ alkenyloxy group (e.g., ethenyloxy) optionally substituted by 1 to 3 halogen atoms;
(16) a C$_{7-13}$ aralkyloxy group (e.g., benzyloxy);
(17) a C$_{6-14}$ aryloxy group (e.g., phenyloxy, naphthyloxy);
(18) a C$_{1-6}$ alkyl-carbonyloxy group (e.g., acetyloxy, tert-butylcarbonyloxy);

(19) a $C_{6-14}$ aryl-carbonyl group (e.g., benzoyl) optionally substituted by 1 to 3 substituents selected from
   (a) a halogen atom, and
   (b) a $C_{1-6}$ alkyl group optionally substituted by 1 to 3 halogen atoms;
(20) a non-aromatic heterocyclylcarbonyl group (e.g., pyrrolidinylcarbonyl, morpholinylcarbonyl) optionally substituted by 1 to 3 $C_{1-6}$ alkyl groups optionally substituted by 1 to 3 halogen atoms;
(21) a mercapto group;
(22) a $C_{1-6}$ alkylthio group (e.g., methylthio, ethylthio) optionally substituted by 1 to 3 substituents selected from
   (a) a halogen atom, and
   (b) a $C_{1-6}$ alkoxy-carbonyl group;
(23) a $C_{7-13}$ aralkylthio group (e.g., benzylthio);
(24) a $C_{6-14}$ arylthio group (e.g., phenylthio, naphthylthio);
(25) a cyano group;
(26) a nitro group;
(27) a halogen atom;
(28) a $C_{1-3}$ alkylenedioxy group;
(29) a $C_{1-3}$ alkyleneoxy group (e.g., methyleneoxy, ethyleneoxy);
(30) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;
(31) a $C_{3-10}$ cycloalkoxy group (e.g., cyclopropoxy, cyclopentyloxy) optionally substituted by 1 to 3 substituents selected from
   (a) a halogen atom (e.g., a fluorine atom), and
   (b) a $C_{1-6}$ alkoxy group (e.g., methoxy) and the like. When the number of the substituents is not less than 2, the respective substituents may be the same or different.

The $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group and $C_{8-13}$ arylalkenyl group which are exemplified as the above-mentioned "hydrocarbon group" optionally have 1 to 3 substituents at substitutable positions.

Examples of the substituent include
(1) the groups exemplified as the substituents for the above-mentioned $C_{1-10}$ alkyl group and the like;
(2) a $C_{1-6}$ alkyl group optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group, and
   (f) an amino group optionally mono- or di-substituted by $C_{1-6}$ alkyl group(s);
(3) a $C_{2-6}$ alkenyl group (e.g., ethenyl, 1-propenyl) optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group, and
   (f) an amino group optionally mono- or di-substituted by $C_{1-6}$ alkyl group(s);
(4) a $C_{7-13}$ aralkyl group (e.g., benzyl) optionally substituted by 1 to
3 substituents selected from
   (a) a $C_{1-6}$ alkyl group optionally substituted by 1 to 3 halogen atoms,
   (b) a hydroxy group,
   (c) a $C_{1-6}$ alkoxy group, and
   (d) a halogen atom;
and the like. When the number of the substituents is not less than 2, the respective substituents may be the same or different.

Examples of the "heterocyclic group" of the above-mentioned "optionally substituted heterocyclic group" for $R^A$, $R^{A'}$ or $R^{B'}$ include an "aromatic heterocyclic group" and a "non-aromatic heterocyclic group".

Examples of the aromatic heterocyclic group include a 4- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, and the like.

Preferable examples of the aromatic heterocyclic group include monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like; fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl), pyridopyridinyl (e.g., pyrido[2,3-b]pyridin-3-yl), thienopyridyl (e.g., thieno[2,3-b]pyridin-3-yl) and the like; and the like.

Examples of the non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, a group wherein the above-mentioned group is partially saturated, and the like.

Preferable examples of the non-aromatic heterocyclic group include monocyclic non-aromatic heterocyclic groups such as pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like; fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like; and the like.

The "heterocyclic group" of the "optionally substituted heterocyclic group" for $R^A$, $R^{A'}$ or $R^{B'}$ optionally has 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group" for $R^A$, $R^{A'}$ or $R^{B'}$ optionally has. When the heterocyclic group is a "non-aromatic heterocyclic group", the substituent further includes an oxo group. When the number of the substituents is not less than 2, the respective substituents may be the same or different.

Examples of the "nitrogen-containing heterocycle" of the "optionally substituted nitrogen-containing heterocycle" formed by $R^{A1}$ and $R^{B1}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiamorpholine and the like.

The nitrogen-containing heterocycle optionally has 1 to 3 substituents at substitutable positions. Examples of the substituent include those similar to the substituents that the e "heterocyclic group" of the "optionally substituted heterocyclic group" for $R^A$, $R^{A'}$ or $R^{B'}$ optionally has. When the number of the substituents is not less than 2, the respective substituents may be the same or different.

Preferable examples of the "acyl group" include
(1) a formyl group;
(2) a carboxy group;
(3) a alkyl-carbonyl group optionally substituted by 1 to 3 substituents selected from
  (i) a halogen atom,
  (ii) an amino group,
  (iii) a carboxyl group,
  (iv) a $C_{1-6}$ alkoxy-carbonyl group,
  (v) a $C_{6-14}$ aryl group (e.g., phenyl), and
  (vi) a $C_{1-6}$ alkoxy group;
(4) a $C_{1-6}$ alkoxy-carbonyl group optionally substituted by 1 to 3 substituents selected from
  (i) a halogen atom,
  (ii) a $C_{6-14}$ aryl group (e.g., phenyl), and
  (iii) a $C_{1-6}$ alkoxy group;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl) optionally substituted by 1 to 3 halogen atoms;
(7) a carbamoyl group optionally mono- or di-substituted by substituent(s) selected from
  (i) a alkyl group optionally substituted by 1 to 3 substituents selected from
    (a) a halogen atom,
    (b) a $C_{1-6}$ alkoxy-carbonyl group,
    (c) a $C_{6-14}$ aryl group (e.g., phenyl),
    (d) a $C_{1-6}$ alkoxy group, and
    (e) an aromatic heterocyclic group (e.g., furyl),
  (ii) a $C_{3-10}$ cycloalkyl group (e.g., cyclopentyl, cyclohexyl),
  (iii) a $C_{6-14}$ aryl group (e.g., phenyl) optionally substituted by 1 to 3 substituents selected from
    (a) a halogen atom,
    (b) a $C_{1-6}$ alkyl group optionally substituted by 1 to 3 halogen atoms, and
    (c) a $C_{1-6}$ alkoxy group,
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups;
(8) a $C_{1-6}$ alkylsulfonyl group (e.g., methylsulfonyl, ethylsulfonyl, isopropylsulfonyl) optionally substituted by 1 to 3 substituents selected from
  (i) a halogen atom, and
  (ii) a $C_{6-16}$ aryl group (e.g., phenyl);
(9) a $C_{6-14}$ arylsulfonyl group (e.g., benzenesulfonyl) optionally substituted by 1 to 3 substituents selected from
  (i) a halogen atom, and
  (ii) a $C_{1-6}$ alkyl group;
(10) a $C_{3-10}$ cycloalkylsulfonyl group (e.g., cyclopropylsulfonyl);
(11) a sulfamoyl group optionally mono- or di-substituted by substituent(s) selected from (i) a $C_{1-6}$ alkyl group optionally substituted by 1 to 3 substituents selected from
  (a) a halogen atom, and
  (b) a non-aromatic heterocyclic group (e.g., pyrrolidinyl) optionally substituted by oxo group(s);
(12) a thiocarbamoyl group optionally mono- or di-substituted by substituent(s) selected from a $C_{1-6}$ alkyl group optionally substituted by 1 to 3 halogen atoms;
(13) an aromatic heterocyclylcarbonyl group (e.g., furylcarbonyl, thienylcarbonyl, pyrazolylcarbonyl, pyridylcarbonyl, isooxazolylcarbonyl, thiazolylcarbonyl) optionally substituted by 1 to 3 substituents selected from a $C_{1-6}$ alkyl group optionally substituted by 1 to 3 halogen atoms;
(14) a non-aromatic heterocyclylcarbonyl group (e.g., tetrahydrofurylcarbonyl, tetrahydropyranylcarbonyl) optionally substituted by 1 to 3 substituents selected from a $C_{1-6}$ alkyl group optionally substituted by 1 to 3 halogen atoms;
and the like.

The "acyl group" for A is preferably
(1) a $C_{1-6}$ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy);
(2) a $C_{1-6}$ alkoxy-carbonyl group (e.g., tert-butoxycarbonyl);
(3) a $C_{3-10}$ cycloalkyl-carbonyl group (e.g., cyclopropylcarbonyl, cyclopentylcarbonyl);
(4) a $C_{6-14}$ aryl-carbonyl group (e.g., benzoyl);
(5) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl);
(6) a $C_{1-6}$ alkylsulfonyl group (e.g., methylsulfonyl) optionally substituted by 1 to 3 $C_{6-14}$ aryl groups (e.g., phenyl);
(7) a $C_{6-14}$ arylsulfonyl group (e.g., benzenesulfonyl) optionally substituted by 1 to 3 $C_{1-6}$ alkyl groups (e.g., methyl);
(8) a $C_{3-10}$ cycloalkylsulfonyl group (e.g., cyclopropylsulfonyl);
(9) an aromatic heterocyclylcarbonyl group (e.g., furylcarbonyl, pyrazolylcarbonyl, pyridylcarbonyl, isooxazolylcarbonyl, thiazolylcarbonyl) optionally substituted by 1 to 3 substituents selected from a $C_{1-6}$ alkyl group optionally substituted by 1 to 3 halogen atoms (e.g., a fluorine atom);
(10) an non-aromatic heterocyclylcarbonyl group (e.g., tetrahydropyranylcarbonyl);
or the like.

Examples of the "5- or 6-membered aromatic ring group" of the "optionally substituted 5- or 6-membered aromatic ring group" for A include phenyl; pyrrolyl, pyrazolyl, imidazolyl, triazolyl (1,2,3-triazolyl, 1,2,4-triazolyl, 1,3,4-triazolyl), tetrazolyl, oxazolyl, isoxazolyl, thiazolyl, isothiazolyl, oxadiazolyl, thiadiazolyl, furyl, thienyl, pyridyl, pyridazinyl, pyrimidinyl, pyrazinyl, triazinyl and the like.

The "5- or 6-membered aromatic ring group" is preferably phenyl or a 5-membered aromatic heterocyclic group, more preferably a 5-membered aromatic heterocyclic group, particularly preferably pyrazolyl, oxazolyl, isoxazolyl, thiazolyl, isothiazolyl, thiadiazolyl or the like.

The "5- or 6-membered aromatic ring group" of the "optionally substituted 5- or 6-membered aromatic ring group" for A optionally has 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group" for $R^A$, $R^{A'}$ or $R^{B'}$ optionally has.

The "optionally substituted 5- or 6-membered aromatic ring group" for A is preferably phenyl or a 5-membered aromatic heterocyclic group (e.g., pyrazolyl, oxazolyl, isoxazolyl, thiazolyl, isothiazolyl, thiadiazolyl), each of which is optionally substituted by 1 to 3 substituents selected from
  (1) a $C_{1-6}$ alkyl-carbonyl group optionally substituted by 1 to 3 halogen atoms;
  (2) a $C_{1-6}$ alkoxy-carbonyl group optionally substituted by 1 to 3 substituents selected from
    (a) a halogen atom,
    (b) a $C_{1-6}$ alkoxy group, and
    (c) a $C_{6-14}$ aryl group (e.g., phenyl);
  (3) a carbamoyl group optionally mono- or di-substituted by $C_{1-6}$ alkyl group(s) optionally substituted by 1 to 3 halogen atoms;
  (4) a carboxy group;
  (5) a hydroxy group;
  (6) a halogen atom;
  (7) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy group;
and the like.

A is preferably
(1) a $C_{1-6}$ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy);
(2) a $C_{1-6}$ alkoxy-carbonyl group (e.g., tert-butoxycarbonyl);
(3) a $C_{3-10}$ cycloalkyl-carbonyl group (e.g., cyclopropylcarbonyl, cyclopentylcarbonyl);
(4) a $C_{6-14}$ aryl-carbonyl group (e.g., benzoyl);
(5) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl);
(6) a $C_{1-6}$ alkylsulfonyl group (e.g., methylsulfonyl) optionally substituted by 1 to 3 $C_{6-14}$ aryl groups (e.g., phenyl);
(7) a $C_{6-14}$ arylsulfonyl group (e.g., benzenesulfonyl) optionally substituted by 1 to 3 $C_{1-6}$ alkyl groups (e.g., methyl);
(8) a $C_{3-10}$ cycloalkylsulfonyl group (e.g., cyclopropylsulfonyl);

(9) an aromatic heterocyclylcarbonyl group (e.g., furylcarbonyl, pyrazolylcarbonyl, pyridylcarbonyl, isooxazolylcarbonyl, thiazolylcarbonyl) optionally substituted by 1 to 3 substituents selected from a $C_{1-6}$ alkyl group optionally substituted by 1 to 3 halogen atoms (e.g., a fluorine atom);
(10) an non-aromatic heterocyclylcarbonyl group (e.g., tetrahydropyranylcarbonyl);
(11) phenyl or a 5-membered aromatic heterocyclic group (e.g., pyrazolyl, oxazolyl, isoxazolyl, thiazolyl, isothiazolyl, thiadiazolyl), each of which is optionally substituted by 1 to 3 substituents selected from
  (i) a $C_{1-6}$ alkyl-carbonyl group optionally substituted by 1 to 3 halogen atoms,
  (ii) a $C_{1-6}$ alkoxy-carbonyl group optionally substituted by 1 to 3 substituents selected from
    (a) a halogen atom,
    (b) a alkoxy group, and
    (c) a $C_{6-14}$ aryl group (e.g., phenyl),
  (iii) a carbamoyl group optionally mono- or di-substituted by $C_{1-6}$ alkyl group(s) optionally substituted by 1 to 3 halogen atoms,
  (iv) a carboxy group,
  (v) a hydroxy group,
  (vi) a halogen atom,
  (vii) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy group
and the like;
or the like.
A is more preferably
(1) a $C_{1-6}$ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy);
(2) a $C_{1-6}$ alkoxy-carbonyl group (e.g., tert-butoxycarbonyl);
(3) a carbamoyl group optionally mono- or di-substituted by 10 substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{2-6}$ alkyl groups (e.g., methyl);
(4) phenyl or a 5-membered aromatic heterocyclic group (e.g., pyrazolyl, oxazolyl, isoxazolyl, thiazolyl, isothiazolyl, thiadiazolyl), each of which is optionally substituted by 1 to 3 substituents selected from (i) a halogen atom and (ii) a $C_{1-6}$ alkyl group;
or the like.
A is particularly preferably
(1) a $C_{1-6}$ alkyl-carbonyl group, or
(2) a 5-membered aromatic heterocyclic group (e.g., pyrazolyl, oxazolyl, isoxazolyl, thiazolyl, isothiazolyl, thiadiazolyl) optionally substituted by 1 to 3 substituents selected from (i) a halogen atom and (ii) a $C_{1-6}$ alkyl group.

A is neither
(a) α-aminoisobutyloyl group, nor
(b) a 5- or 6-membered aromatic ring group substituted by a group represented by the formula: —CO—$(CH_2)_3$—COOR$^{41}$ wherein R$^{41}$ is a hydrogen atom or a $C_{1-6}$ alkyl group, or a group represented by the formula: —CO—NR$^{42}$—CR$^{42}$R$^{44}$—CR$^{45}$R$^{46}$—COOR$^{47}$ wherein R$^{42}$, R$^{43}$, R$^{44}$, R$^{45}$ and R$^{47}$ are independently a hydrogen atom or a $C_{1-6}$ alkyl group; and R$^{46}$ is a hydrogen atom, a $C_{1-6}$ alkyl group or a hydroxy group.

Ring M is an optionally fused 5- to 7-membered ring which is optionally further substituted.

Examples of the "5- to 7-membered ring" of the "optionally fused 5- to 7-membered ring which is optionally further substituted" for ring M include benzene, a $C_{5-7}$ cycloalkane, a $C_{5-7}$ cycloalkene, a cycloalkadiene, a 5- to 7-membered aromatic heterocycle and a 5- to 7-membered non-aromatic heterocycle.

Examples of the $C_{5-7}$ cycloalkane include cyclopentane, cyclohexane and cycloheptane.

Examples of the $C_{5-7}$ cycloalkene include 1-cyclopentene, 1-cyclohexene and 1-cyclopentene.

Examples of the $C_{5-7}$ cycloalkadiene include 1,3-cyclopentadiene, 1,3-cyclohexadiene, 1,4-cyclohexadiene, 1,3-cycloheptadiene and 1,4-cycloheptadiene.

Examples of the 5- to 7-membered aromatic heterocycle include a 5- to 7-membered heterocycle, from among the corresponding ring to the monocyclic aromatic heterocyclic group exemplified as the "heterocyclic group" of the "optionally substituted heterocyclic group" for R$^A$, R$^{A1}$ or R$^{B1}$.

Specific examples thereof include pyrrole, pyrazole, imidazole, triazole (1,2,3-triazole, 1,2,4-triazole, 1,3,4-triazole), tetrazole, oxazole, isoxazole, thiazole, isothiazole, oxadiazole, thiadiazole, furan, thiophene, pyridine, pyridazine, pyrimidine, pyrazine, triazine and the like.

Examples of the 5- to 7-membered non-aromatic heterocycle include a 5- to 7-membered heterocycle, from among the corresponding ring to the monocyclic non-aromatic heterocyclic group exemplified as the "heterocyclic group" of the "optionally substituted heterocyclic group" for R$^A$, R$^{A1}$ or R$^{B1}$. Specific examples thereof include pyrroline, pyrrolidine, piperidine, piperazine, morpholine, thiomorpholine, pyrazoline, pyrazolidine, imidazoline, imidazolidine, triazoline (1,2,3-triazoline, 1,2,4-triazoline, 1,3,4-triazoline), triazolidine (1,2,3-triazolidine, 1,2,4-triazolidine, 1,3,4-triazolidine), tetrazoline, tetrazolidine, oxazoline, oxazolidine, isoxazoline, isoxazolidine, thiazoline, triazolidine, isothiazoline, isothiazolidine, oxadiazoline, oxadiazolidine, thiadiazoline, thiadiazolidine, dihydrofuran, tetrahydrofuran, dihydrothiophene, tetrahydrothiophene, dihydropyridine, tetrahydropyridine, dihydropyridazine, tetrahydropyridazine, dihydropyrimidine, tetrahydropyrimidine, dihydropyrazine, tetrahydropyrazine, dihydrotriazine, tetrahydrotriazine, pyran, dihydropyran, tetrahydropyran, thiopyran, dihydrothiopyran, tetrahydrothiopyran, dioxane, dioxolane, dioxole, azepane, azepine, oxazepane, oxazepine, thiazepane, thiazepine, diazepane, diazepine and the like.

The "5- to 7-membered ring" is optionally condensed, and examples thereof include a ring wherein the "5- to 7-membered ring" and a ring selected from a 5- to 7-membered monocyclic aromatic heterocycle, benzene and a partially saturated ring thereof are condensed.

Examples of the 5- to 7-membered monocyclic aromatic heterocycle include a 5- to 7-membered heterocycle, from among the corresponding ring to the monocyclic aromatic heterocyclic group exemplified as the "heterocyclic group" of the "optionally substituted heterocyclic group" for R$^A$, R$^{A1}$ or $R^{B'}$. Specific examples thereof include pyrrole, pyrazole, imidazole, triazole (1,2,3-triazole, 1,2,4-triazole, 1,3,4-triazole), tetrazole, oxazole, isoxazole, thiazole, isothiazole, oxadiazole, thiadiazole, furan, thiophene, pyridine, pyridazine, pyrimidine, pyrazine, triazine and the like.

Specific examples of the "optionally fused 5- to 7-membered ring" include indole, isoindole, indazole, benzimidazole, benzotriazole, benzoxazole, benzisoxazole, benzothiazole, benzoisothiazole, benzofuran, benzothiophene, quinoline, isoquinoline, quinazoline, quinoxaline, cinnoline, phthalazine, pyrrolopyridine, imidazopyridine, thienopyridine, pyrazolopyridine, pyridopyridine, pyrrolopyrimidine, imidazopyrimidine, thienopyrimidine, pyrazolopyrimidine, pyridopyrimidine, pyrrolopyridazine, imidazopyridazine, thienopyridazine, pyrazolopyridazine, pyridopyridazine, pyrrolopyrazine, imidazopyrazine, thienopyrazine, pyrazolopyrazine, pyridopyrazine, dihydroindole, dihydroisoindole, dihydrobenzofuran, tetrahydrobenzofuran, dihydrobenzothiophene, tetrahydrobenzothiophene, dihydrobenzodioxine, dihydrobenzodioxepine, chromene, dihydrochromene, dihydroquinoline, tetrahydroquinoline, dihydroisoquinoline, tetrahydroisoquinoline, dihydrophthalazine and the like.

The "optionally fused 5- to 7-membered ring" is preferably benzene, pyridine, dihydrobenzofuran, benzoxazole or the like, more preferably benzene, pyridine or the like.

The "optionally fused 5- to 7-membered ring" optionally has, besides group $L^2$, 1 to 3 substituents at substitutable positions. Examples of the substituent include those similar to the substituents that the "heterocyclic group" of the "optionally substituted heterocyclic group" for $R^A$, $R^{A'}$ or $R^{B'}$ optionally has. When the number of the substituents is not less than 2, the respective substituents may be the same or different.

Preferable examples of the substituent include
(1) a halogen atom (e.g., a fluorine atom, a chlorine atom, a bromine atom),
(2) a $C_{1-6}$ alkyl group (e.g., methyl, propyl),
(3) a $C_{1-6}$ alkoxy group (e.g., methoxy, ethoxy, propoxy, isopropoxy, butoxy, isobutoxy) optionally substituted by 1 to 3 substituents selected from
  (i) a halogen atom (e.g., a fluorine atom),
  (ii) a $C_{1-6}$ alkoxy group (e.g., methoxy),
  (iii) a $C_{3-10}$ cycloalkyl group (e.g., cyclopropyl, cyclobutyl, cyclohexyl),
  (iv) a heterocyclic group (e.g., tetrahydrofuryl),
  (v) a $C_{6-14}$ aryl group (e.g., phenyl), and
  (vi) a $C_{1-6}$ alkylthio group (e.g., methylthio),
(4) a $C_{1-6}$ alkylthio group (e.g., ethylthio),
(5) a $C_{1-6}$ alkyl-carbonyloxy group (e.g., acetyloxy),
(6) an aromatic heterocyclic group (e.g., pyrazolyl),
(7) a $C_{3-10}$ cycloalkoxy group (e.g., cyclopropoxy, cyclopentyloxy) optionally substituted by 1 to 3 substituents selected from
  (i) a halogen atom (e.g., a fluorine atom), and
  (ii) a $C_{1-6}$ alkoxy group (e.g., methoxy),
(8) a hydroxy group,
(9) a $C_{3-10}$ cycloalkyl group (e.g., cyclopropyl),
(10) an aromatic heterocyclyloxy group (e.g., pyridyloxy),
(11) a $C_{1-3}$ alkylenedioxy group (e.g., methylenedioxy) and the like.

Ring M is preferably benzene, pyridine, dihydrobenzofuran, benzoxazole or the like, each of which is optionally substituted by 1 to 3 substituents selected from
(1) a halogen atom (e.g., a fluorine atom, a chlorine atom, a bromine atom),
(2) a $C_{1-6}$ alkyl group (e.g., methyl, propyl),
(3) a $C_{1-6}$ alkoxy group (e.g., methoxy, ethoxy, propoxy, isopropoxy, butoxy, isobutoxy) optionally substituted by 1 to 3 substituents selected from
  (i) a halogen atom (e.g., a fluorine atom),
  (ii) a $C_{1-6}$ alkoxy group (e.g., methoxy),
  (iii) a $C_{3-10}$ cycloalkyl group (e.g., cyclopropyl, cyclobutyl, cyclohexyl),
  (iv) a heterocyclic group (e.g., tetrahydrofuryl),
  (v) a $C_{6-14}$ aryl group (e.g., phenyl), and
  (vi) a $C_{1-6}$ alkylthio group (e.g., methylthio),
(4) a $C_{1-6}$ alkylthio group (e.g., ethylthio),
(5) a $C_{1-6}$ alkyl-carbonyloxy group (e.g., acetyloxy),
(6) an aromatic heterocyclic group (e.g., pyrazolyl),
(7) a $C_{3-10}$ cycloalkoxy group (e.g., cyclopropoxy, cyclopentyloxy) optionally substituted by 1 to 3 substituents selected from
  (i) a halogen atom (e.g., a fluorine atom), and
  (ii) a $C_{1-6}$ alkoxy group (e.g., methoxy),
(8) a hydroxy group,
(9) a $C_{3-10}$ cycloalkyl group (e.g., cyclopropyl),
(10) an aromatic heterocyclyloxy group (e.g., pyridyloxy),
(11) a $C_{1-3}$ alkylenedioxy group (e.g., methylenedioxy) and the like.

Ring M is more preferably benzene, pyridine or the like, each of which is optionally substituted by 1 to 3 substituents selected from
(1) a halogen atom (e.g., a fluorine atom, a chlorine atom, a bromine atom),
(2) a $C_{1-6}$ alkyl group (e.g., methyl, propyl),
(3) a $C_{1-6}$ alkoxy group (e.g., methoxy, ethoxy, propoxy, isopropoxy, butoxy, isobutoxy) optionally substituted by 1 to 3 substituents selected from
  (i) a halogen atom (e.g., a fluorine atom),
  (ii) a $C_{1-6}$ alkoxy group (e.g., methoxy),
  (iii) a $C_{3-10}$ cycloalkyl group (e.g., cyclopropyl, cyclobutyl, cyclohexyl),
  (iv) a heterocyclic group (e.g., tetrahydrofuryl),
  (v) a $C_{6-14}$ aryl group (e.g., phenyl) and
  (vi) a $C_{1-6}$ alkylthio group (e.g., methylthio),
(4) a $C_{3-10}$ cycloalkoxy group (e.g., cyclopropoxy, cyclopentyloxy) optionally substituted by 1 to 3 substituents selected from
  (i) a halogen atom (e.g., a fluorine atom), and
  (ii) a $C_{1-6}$ alkoxy group (e.g., methoxy),
(5) a hydroxy group,
(6) a $C_{3-10}$ cycloalkyl group (e.g., cyclopropyl),
(7) an aromatic heterocyclyloxy group (e.g., pyridyloxy),
(8) a $C_{1-3}$ alkylenedioxy group (e.g., methylenedioxy) and the like.

Ring M is more preferably benzene, pyridine or the like, each of which is optionally substituted by 1 to 3 substituents selected from
(1) a halogen atom (e.g., a fluorine atom, a chlorine atom, a bromine atom),
(2) a $C_{1-6}$ alkyl group (e.g., methyl, propyl),
(3) a $C_{1-6}$ alkoxy group (e.g., methoxy, ethoxy, propoxy, isopropoxy, butoxy, isobutoxy) optionally substituted by 1 to 3 substituents selected from
  (i) a halogen atom (e.g., a fluorine atom),
  (ii) a $C_{1-6}$ alkoxy group (e.g., methoxy),
  (iii) a $C_{3-10}$ cycloalkyl group (e.g., cyclopropyl, cyclobutyl, cyclohexyl),
  (iv) a heterocyclic group (e.g., tetrahydrofuryl), and
  (v) a $C_{6-14}$ aryl group (e.g., phenyl),
(4) a $C_{3-10}$ cycloalkoxy group (e.g., cyclopropoxy, cyclopentyloxy) optionally substituted by 1 to 3 substituents selected from (i) a halogen atom (e.g., a fluorine atom), and (ii) a $C_{1-6}$ alkoxy group (e.g., methoxy), (5) a hydroxy group and the like.

As to ring P and ring Q, (1) ring P is optionally further substituted 5-membered heterocycle, ring Q is optionally further substituted 6-membered ring, and ring P and ring Q are condensed to form an optionally further substituted bicyclic aromatic heterocycle, or (2) ring P is an optionally further substituted 5-membered non-aromatic ring, ring Q is an optionally substituted 6-membered aromatic ring, and ring P and ring Q are condensed to form an optionally further substituted bicyclic non-aromatic ring.

When the ring P and ring Q are: "(1) ring P is optionally further substituted 5-membered heterocycle, ring Q is optionally further substituted 6-membered ring, and ring P and ring Q are condensed to form an optionally further substituted bicyclic aromatic heterocycle".

Examples of the "5-membered heterocycle" of the "optionally further substituted 5-membered heterocycle" for ring P include pyrrole, pyrazole, imidazole, triazole (1,2,3-triazole, 1,2,4-triazole, 1,3,4-triazole), tetrazole, oxazole, isoxazole, thiazole, isothiazole, oxadiazole, thiadiazole, furan, thiophene and the like.

The "5-membered heterocycle" of the "optionally further substituted 5-membered heterocycle" for ring P optionally has, besides the group —$CH(R^1)NH$-A, 1 or 2 substituents at substitutable positions. Examples of the substituent include those similar to the substituents that the $C_{3-10}$ cycloalkyl group and the like exemplified as the "hydrocarbon group" of the "optionally substituted hydrocarbon group" for $R^A$, $R^{A'}$ or $R^{B'}$ optionally has.

Preferable examples of the additional substituent for the "5-membered heterocycle" of the "optionally further substituted 5-membered heterocycle" for ring P include (1) a halogen atom (e.g., a chlorine atom), (2) a $C_{1-6}$ alkyl group (e.g., methyl)

and the like.

Examples of the "6-membered ring" of the "optionally further substituted 6-membered ring" for ring Q include benzene, pyridine, tetrahydropyridine, pyridazine, pyrimidine, pyrazine, triazine and the like.

The "6-membered ring" of the "optionally further substituted 6-membered ring" for ring Q optionally has, besides the group $L^1$, 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group" for $R^A$, $R^{A'}$ or $R^{B'}$ optionally has.

Preferable examples of the additional substituent for the "6-membered ring" of the "optionally further substituted 6-membered ring" for ring Q include (1) a halogen atom (e.g., a chlorine atom), (2) a $C_{1-6}$ alkyl group (e.g., methyl)

and the like.

Specific examples of the "bicyclic aromatic heterocycle" of the "optionally further substituted bicyclic aromatic heterocycle" formed by the condensation of ring P and ring Q include

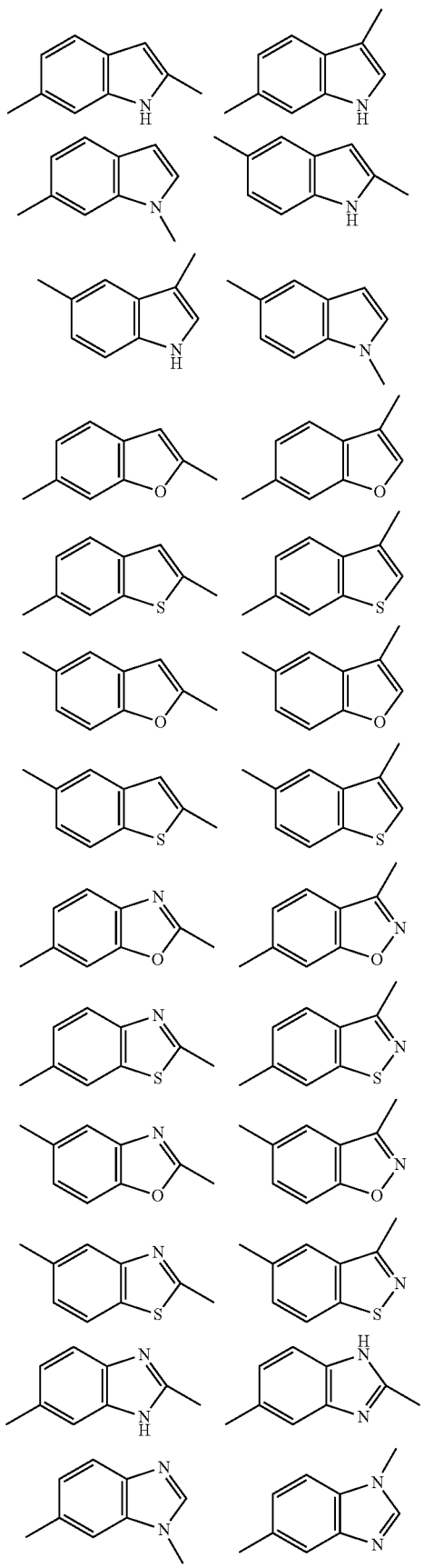

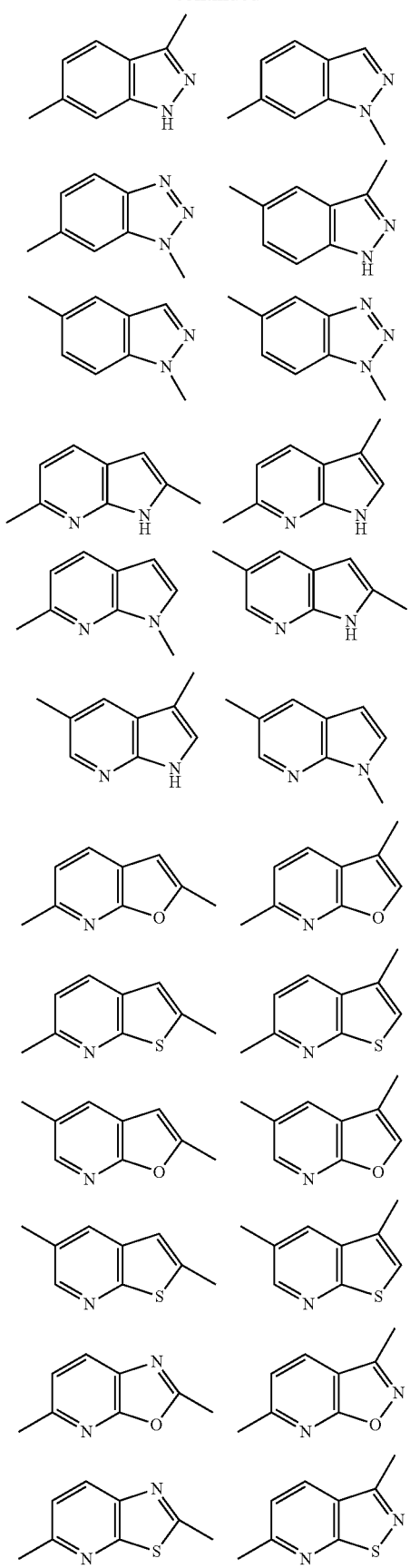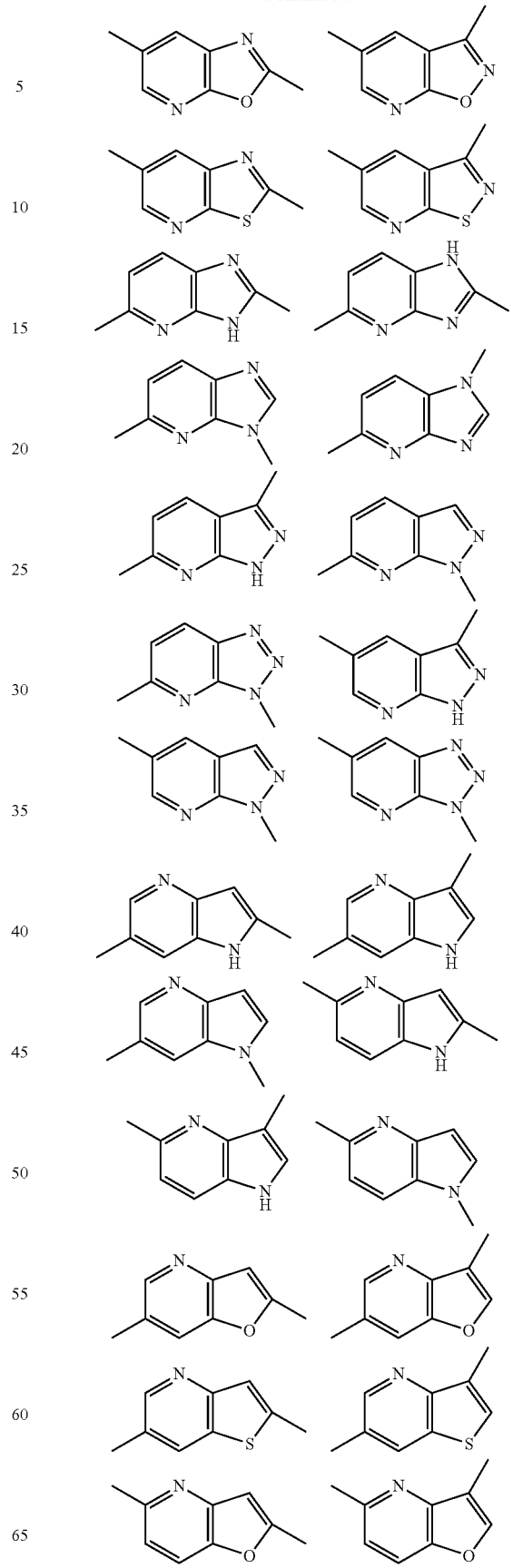

27
-continued
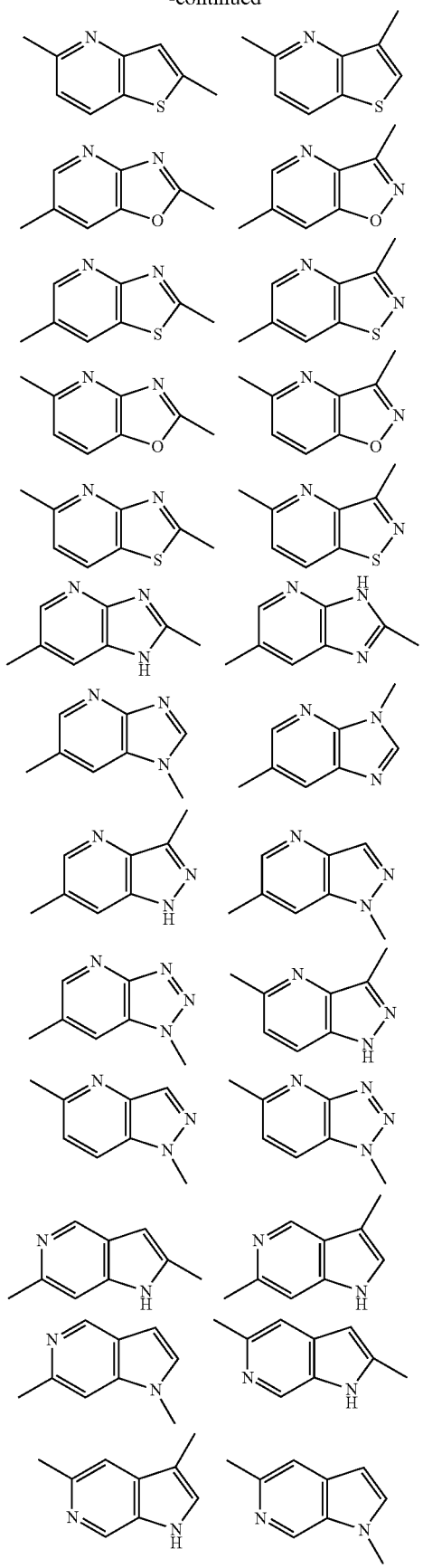
28
-continued
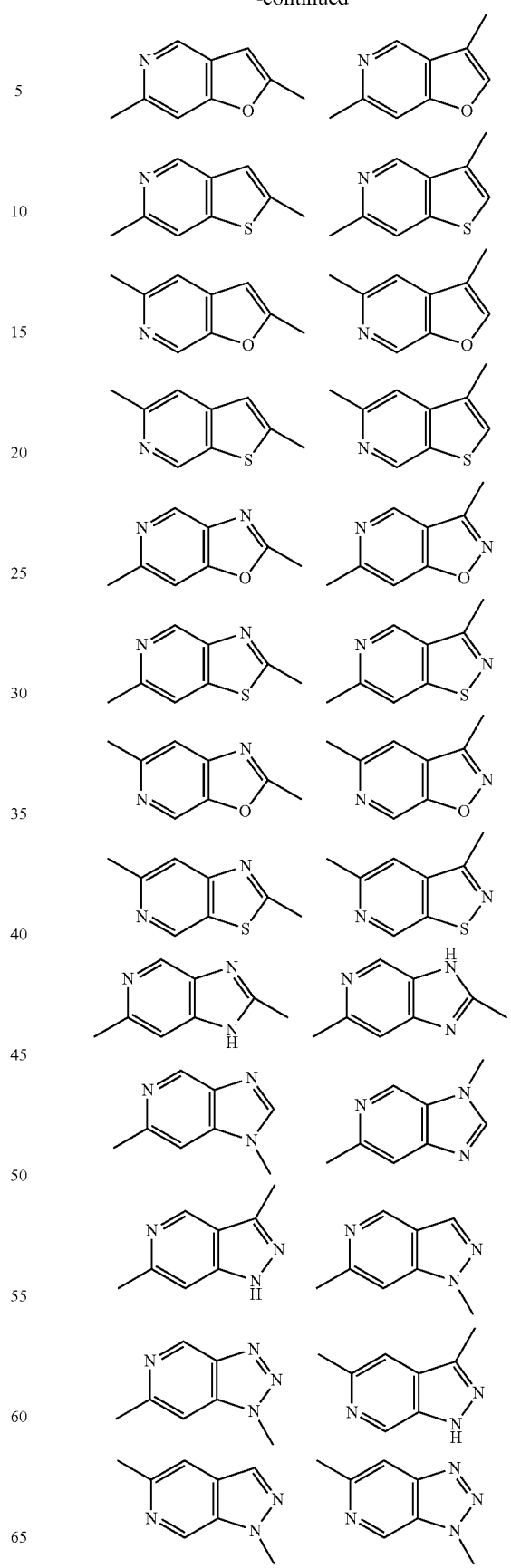

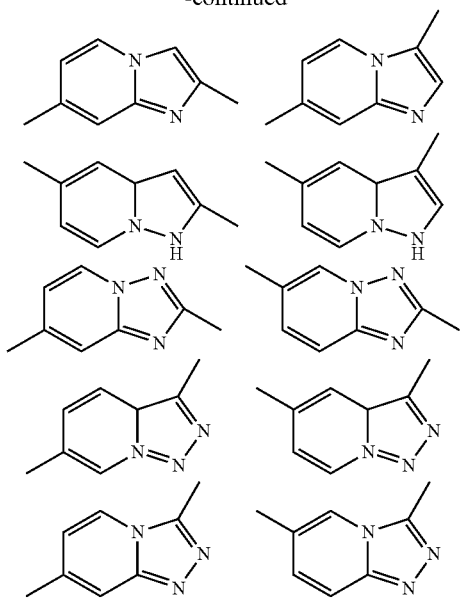

and the like.

The "bicyclic aromatic heterocycle" of the "optionally further substituted bicyclic aromatic heterocycle" formed by the condensation of ring P and ring Q optionally has, besides the group —CH(R$^1$)NH-A and the group L$^1$, 1 to 3 substituents at substitutable position. Examples of the substituent include those similar to the substituents that the C$_{3\text{-}10}$ cycloalkyl group and the like exemplified as the "hydrocarbon group" of the "optionally substituted hydrocarbon group" for R$^A$, R$^{A\prime}$ or R$^{B\prime}$ optionally has.

Preferable examples of the additional substituent for the "bicyclic aromatic heterocycle" of the "optionally further substituted bicyclic aromatic heterocycle" formed by the condensation of ring P and ring Q include
(1) a halogen atom (e.g., a chlorine atom),
(2) a C$_{1\text{-}6}$ alkyl group (e.g., methyl)
and the like.

The "optionally further substituted bicyclic aromatic heterocycle" formed by the condensation of ring P and ring Q is preferably

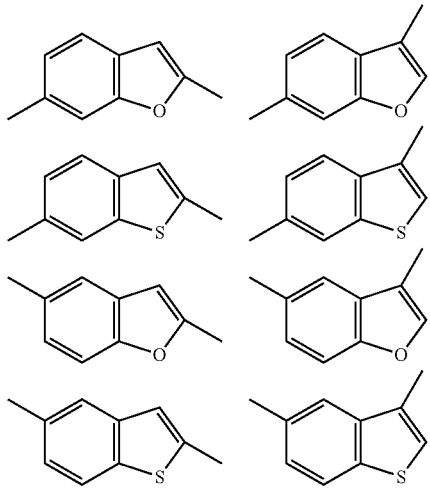

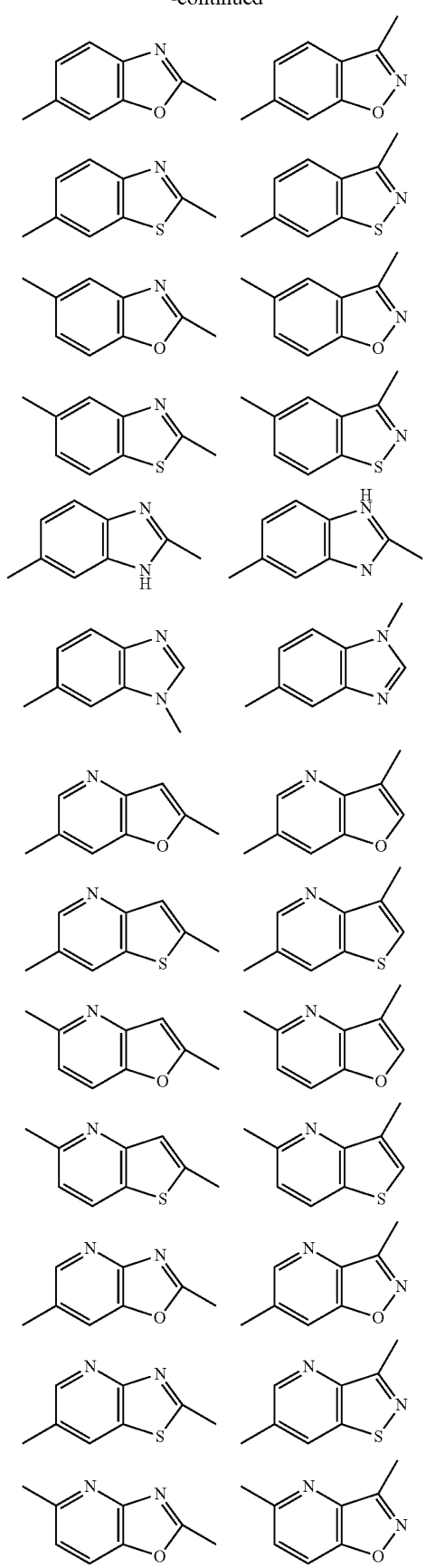

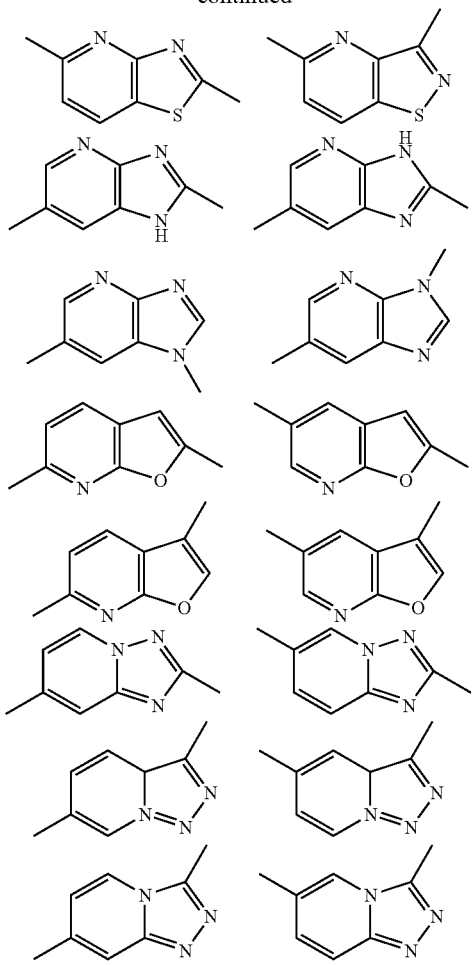

or the like, each of which is optionally substituted by 1 to 3 substituents selected from (1) a halogen atom (e.g., a chlorine atom),
(2) a $C_{1-6}$ alkyl group (e.g., methyl)
and the like.

When ring P and ring Q are: "(2) ring P is an optionally further substituted 5-membered non-aromatic ring, ring Q is an optionally substituted 6-membered aromatic ring, and ring P and ring Q are condensed to form an optionally further substituted bicyclic non-aromatic ring"

Examples of the "5-membered non-aromatic ring" of the "optionally further substituted 5-membered non-aromatic ring" for ring P include cyclopentene, dihydrofuran, dihydrothiophene, dihydropyrrole, dihydroimidazole, dihydropyrazole, dihydrotriazole, dihydrooxazole, dihydrothiazole, dihydroisoxazole, dihydroisothiazole and the like.

The "5-membered non-aromatic ring" of the "optionally further substituted 5-membered non-aromatic ring" for ring P optionally has, besides the group —CH($R^1$)NH-A, 1 or 2 substituents at substitutable positions. Examples of the substituent include those similar to the substituents that the $C_{3-10}$ cycloalkyl group and the like exemplified as the "hydrocarbon group" of the "optionally substituted hydrocarbon group" for $R^A$, $R^{A'}$ or $R^{3'}$ optionally has.

Preferable examples of the additional substituent for the "5-membered non-aromatic ring" of the "optionally further substituted 5-membered non-aromatic ring" for ring P include (1) a halogen atom (e.g., a chlorine atom),
(2) a $C_{1-6}$ alkyl group (e.g., methyl)
and the like.

Examples of the "6-membered aromatic ring" of the "optionally further substituted 6-membered aromatic ring" for ring Q include benzene, pyridine, pyridazine, pyrimidine, pyrazine, triazine and the like.

The "6-membered aromatic ring" of the "optionally further substituted 6-membered aromatic ring" for ring Q optionally has, besides the group $L^1$, 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group" for $R^A$, $R^{A'}$ or $R^{B'}$ optionally has.

Preferable examples of the additional substituent for the "6-membered aromatic ring" of the "optionally further substituted 6-membered aromatic ring" for ring Q include (1) a halogen atom (e.g., a chlorine atom),
(2) a $C_{1-6}$ alkyl group (e.g., methyl)
and the like.

Specific examples of the "bicyclic non-aromatic ring" of the "optionally further substituted bicyclic non-aromatic ring" formed by the condensation of ring P and ring Q include

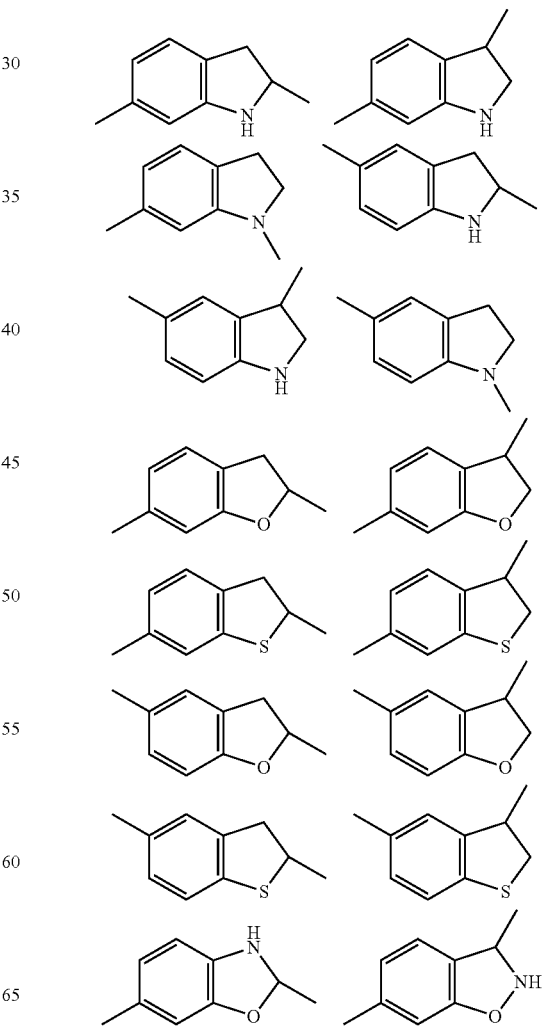

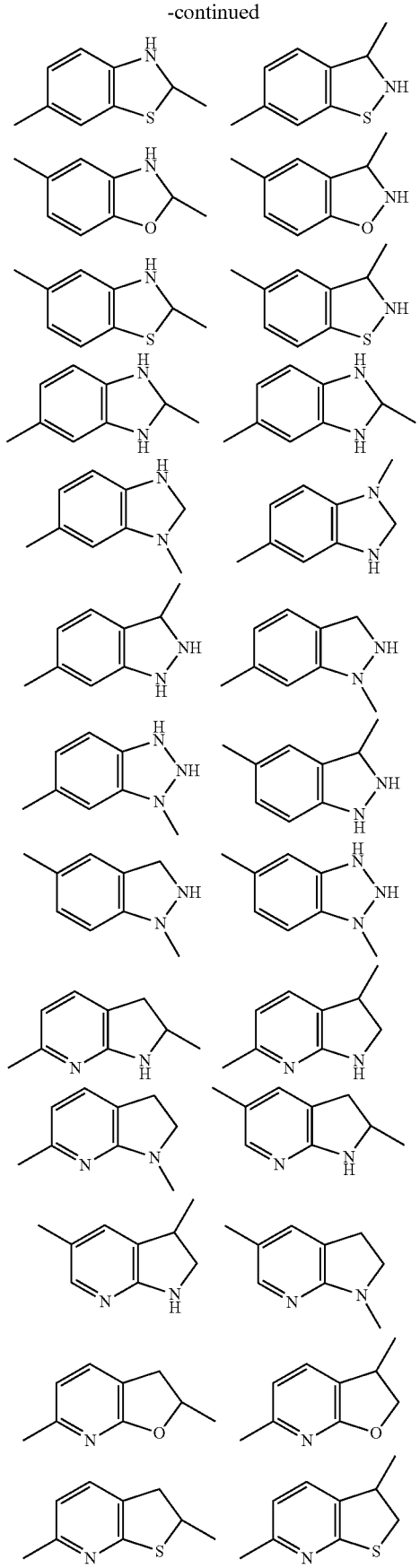
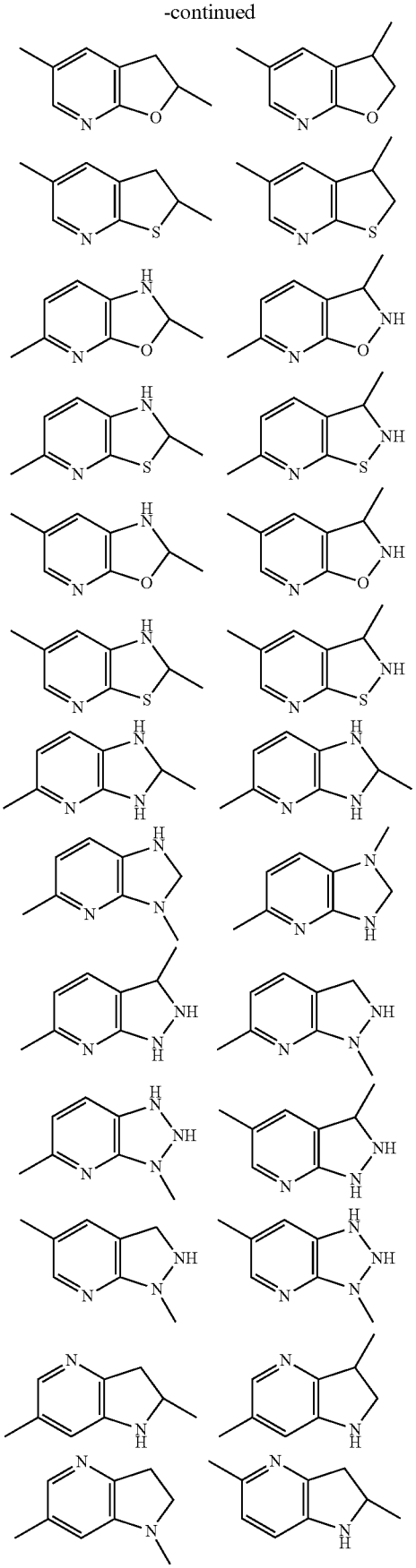

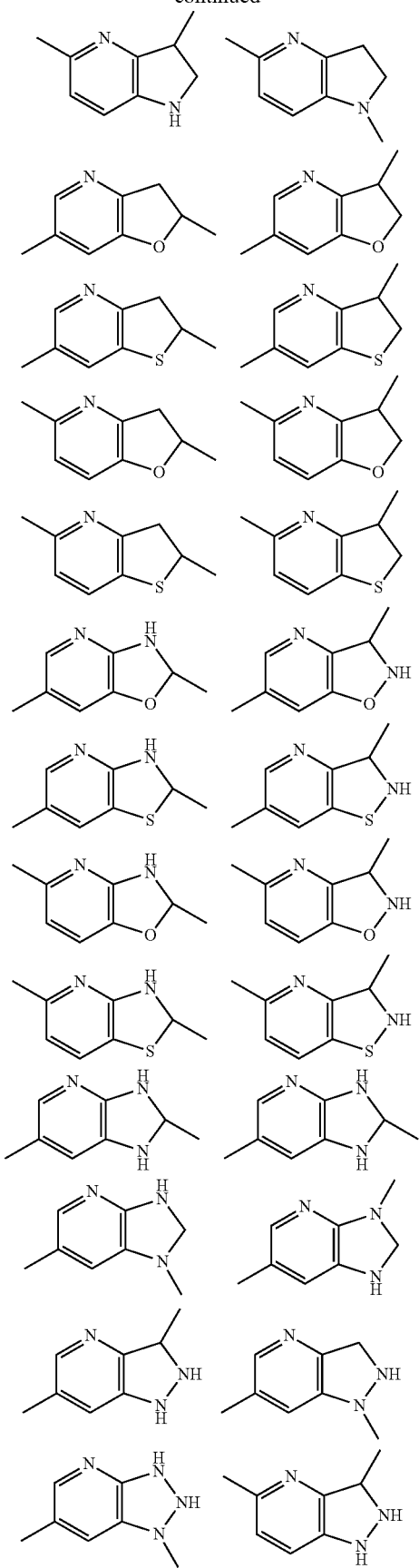
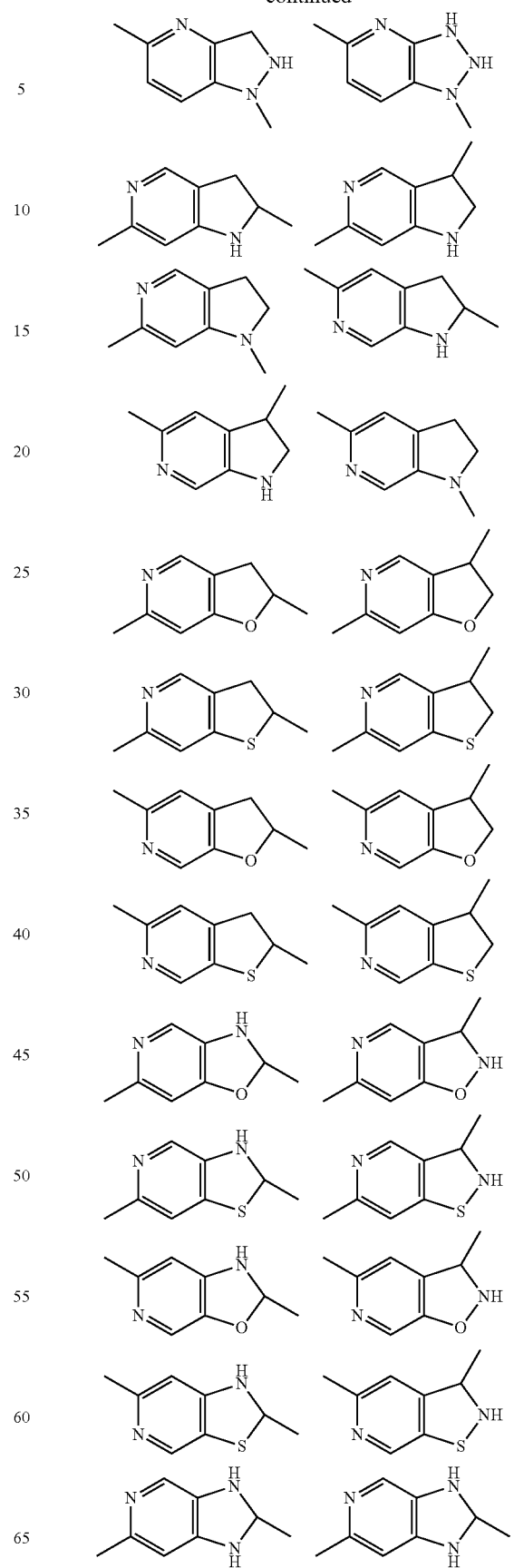

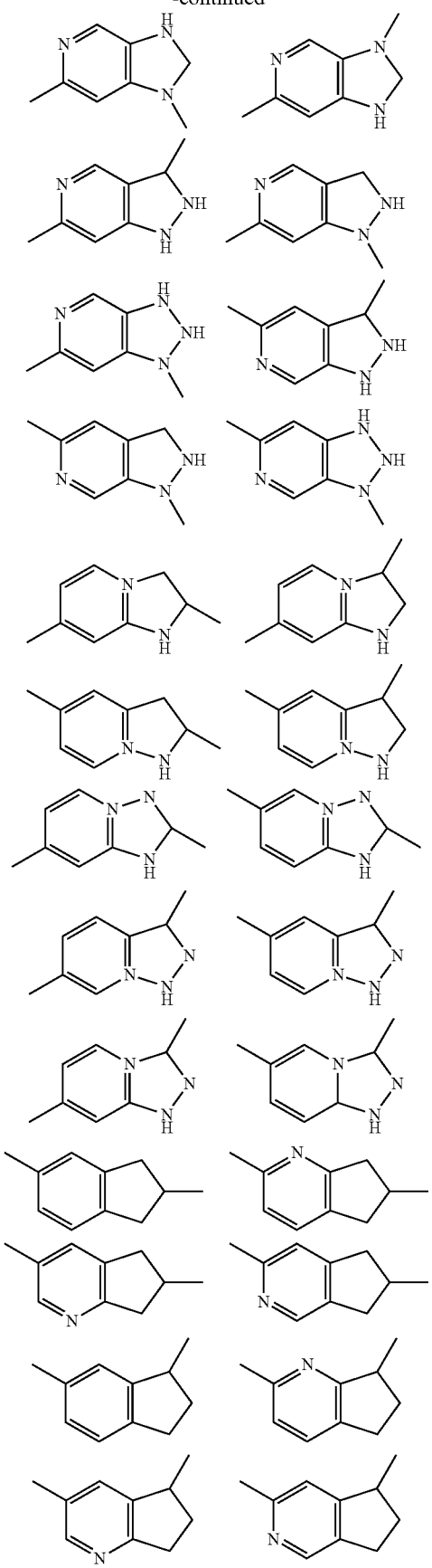

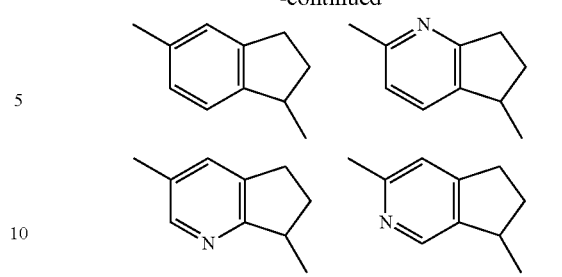

and the like.

The "bicyclic non-aromatic ring" of the "optionally further substituted bicyclic non-aromatic ring" formed by the condensation of ring P and ring Q optionally has, besides the group —CH($R^1$)NH-A and the group $L^1$, 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group" for $R^A$, $R^{A'}$ or $R^{B'}$ optionally has.

Preferable examples of the additional substituent for the "bicyclic non-aromatic ring" of the "optionally further substituted bicyclic non-aromatic ring" formed by the condensation of ring P and ring Q include (1) a halogen atom (e.g., a chlorine atom), (2) a $C_{1-6}$ alkyl group (e.g., methyl)

and the like.

The "optionally further substituted bicyclic non-aromatic ring" formed by the condensation of ring P and ring Q is preferably

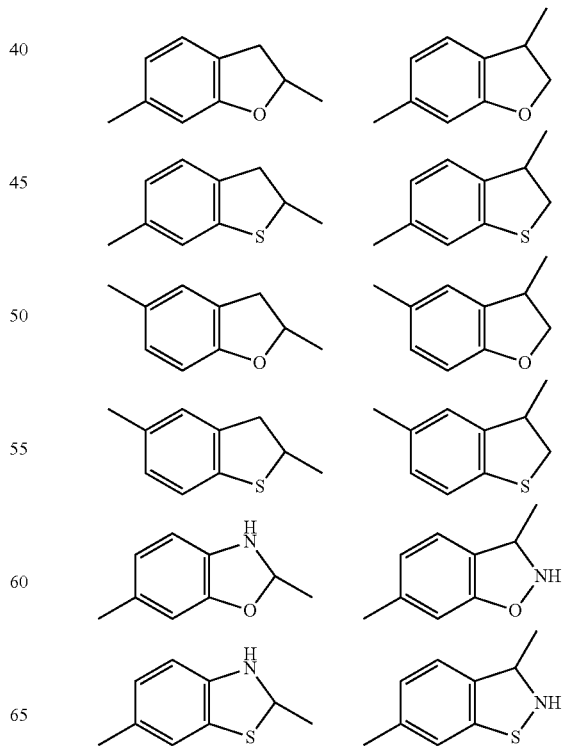

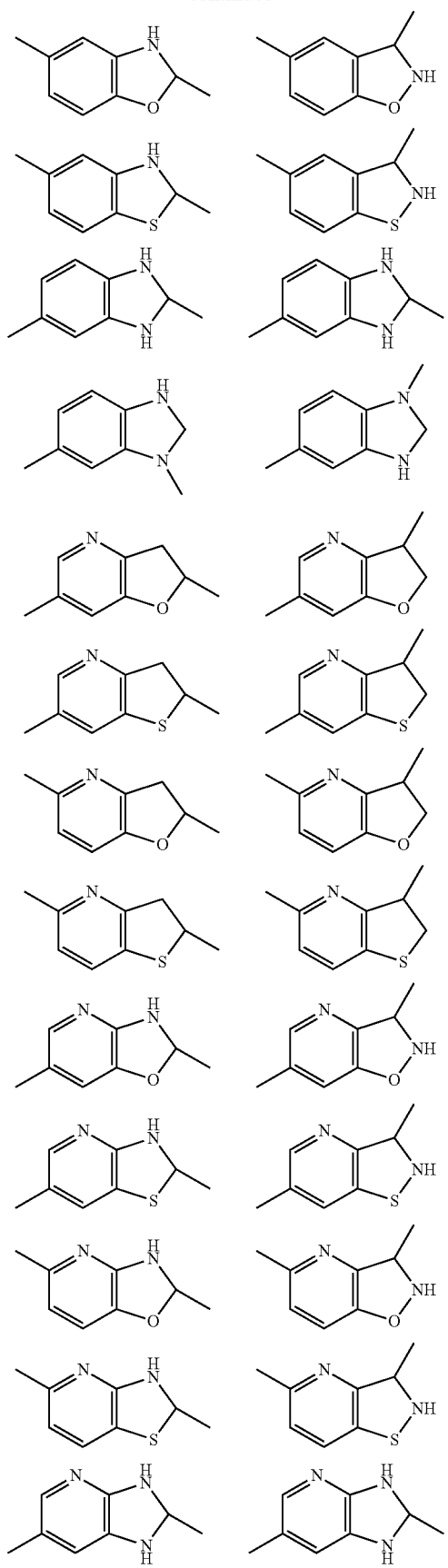
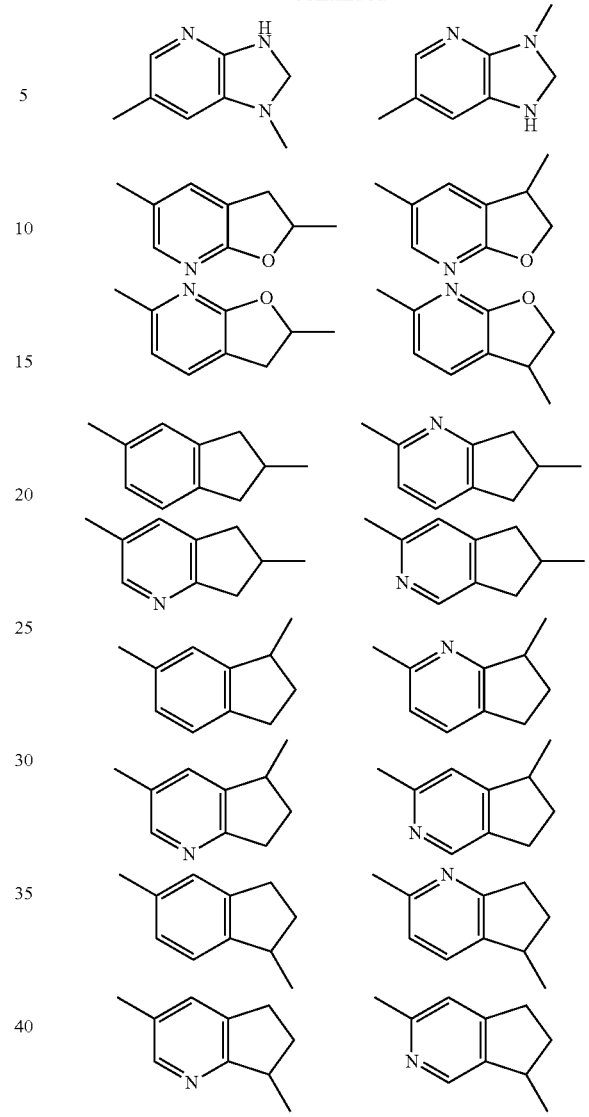
or the like, each of which is optionally substituted by 1 to 3 substituents selected from
(1) a halogen atom (e.g., a chlorine atom),
(2) a $C_{1-6}$ alkyl group (e.g., methyl)
and the like.
The "optionally further substituted bicyclic aromatic heterocycle" and the "optionally further substituted bicyclic non-aromatic ring" formed by the condensation of ring P and ring Q is preferably
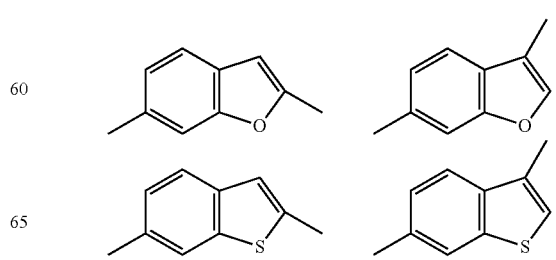

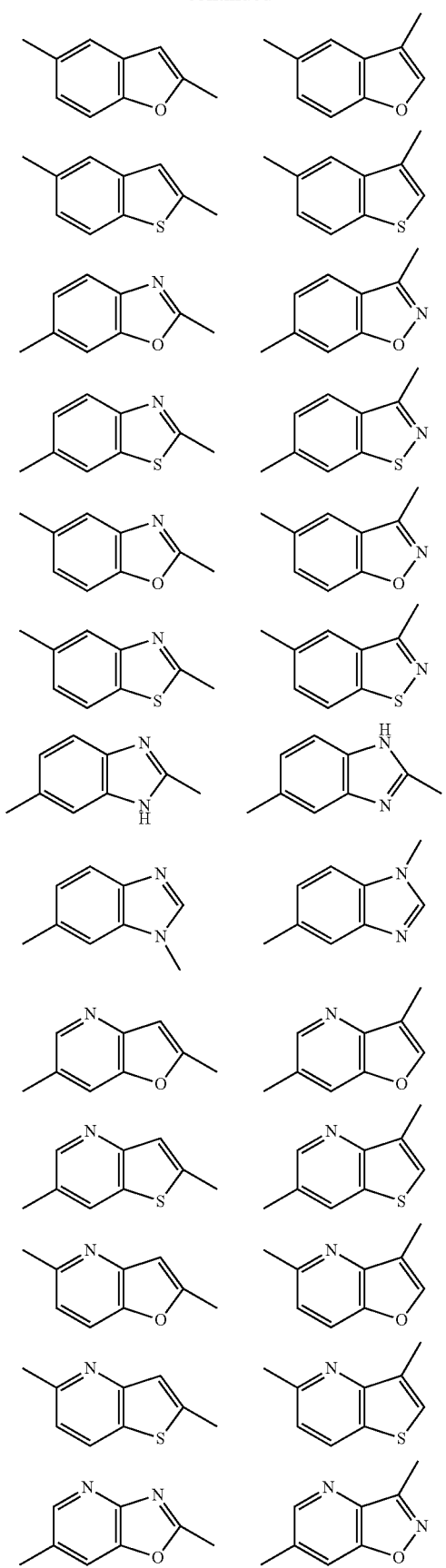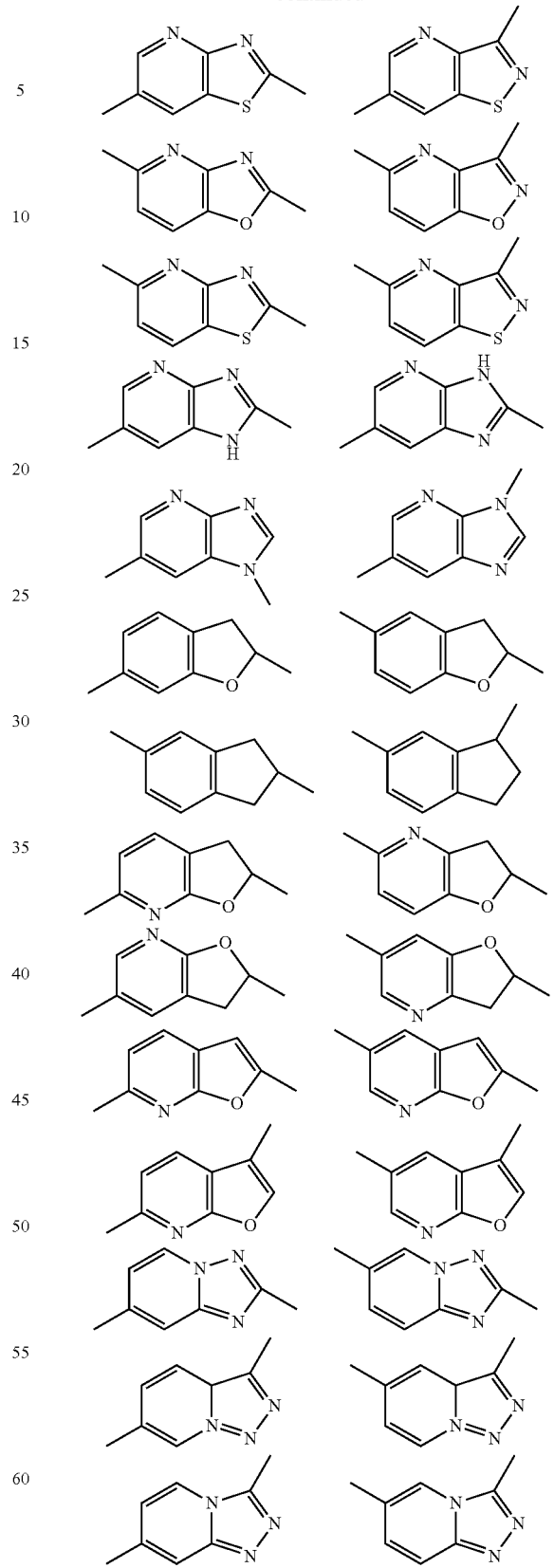
or the like, each of which is optionally substituted by 1 to 3 substituents selected from (1) a halogen atom (e.g., a chlorine atom),
(2) a $C_{1-6}$ alkyl group (e.g., methyl)
and the like.

The "optionally further substituted bicyclic aromatic heterocycle" and the "optionally further substituted bicyclic non-aromatic ring" formed by the condensation of ring P and ring Q is more preferably

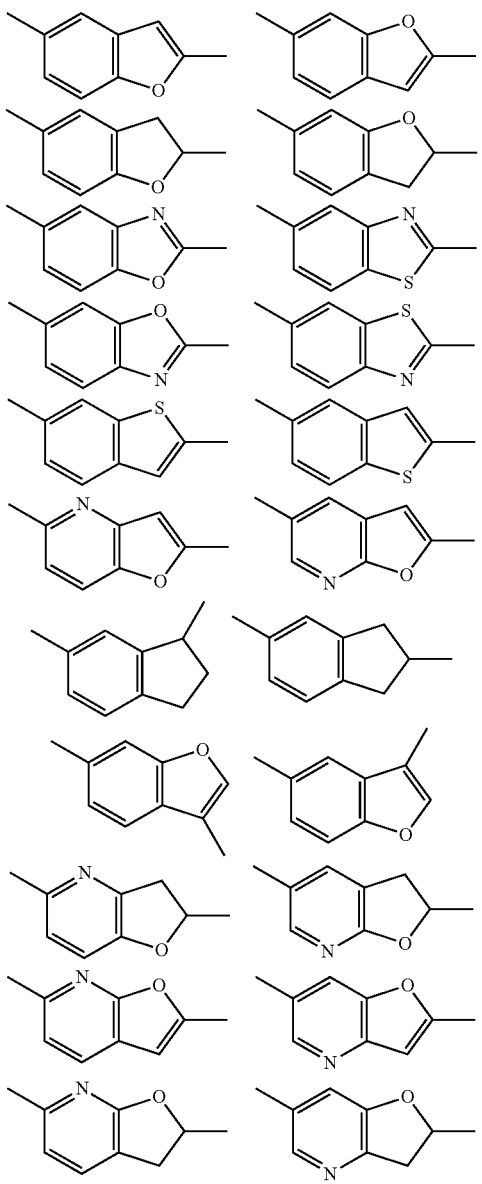

or the like, each of which is optionally substituted by 1 to 3 substituents selected from
(1) a halogen atom (e.g., a chlorine atom),
(2) a $C_{1-6}$ alkyl group (e.g., methyl)
and the like.

The "optionally further substituted bicyclic aromatic heterocycle" and the "optionally further substituted bicyclic non-aromatic ring" formed by the condensation of ring P and ring Q is further more preferably

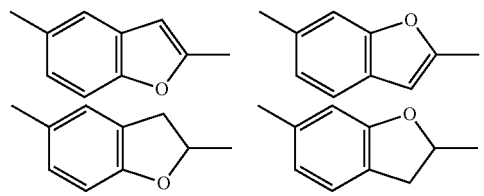

or the like, each of which is optionally substituted by 1 to 3 substituents selected from
(1) a halogen atom (e.g., a chlorine atom),
(2) a $C_{1-6}$ alkyl group (e.g., methyl)
and the like.

The "optionally further substituted bicyclic aromatic heterocycle" and the "optionally further substituted bicyclic non-aromatic ring" formed by the condensation of ring P and ring Q is still more preferably

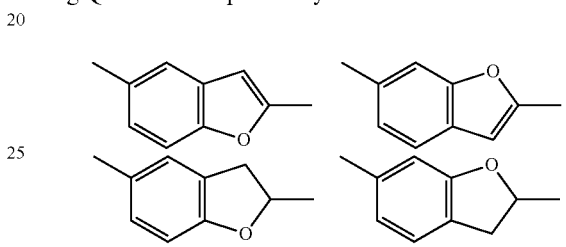

or the like.

$R^1$ is an optionally substituted $C_{1-6}$ alkyl group or an optionally substituted $C_{3-6}$ cycloalkyl group.

The "$C_{1-6}$ alkyl group" of the "optionally substituted $C_{1-6}$ alkyl group" for $R^1$ optionally has 1 to 3 substituents at substitutable positions. Examples of the substituent include those similar to the substituents that the $C_{1-6}$ alkyl group and the like exemplified as the "hydrocarbon group" of the "optionally substituted hydrocarbon group" for $R^A$, $R^{A'}$ or $R^{B'}$ optionally has.

Examples of the "$C_{3-6}$ cycloalkyl group" of the "optionally substituted $C_{3-6}$ cycloalkyl group" for $R^1$ include cyclopropyl, cyclobutyl, cyclopentyl and cyclohexyl.

The "$C_{3-6}$ cycloalkyl group" of the "optionally substituted $C_{3-6}$ cycloalkyl group" for $R^1$ optionally has 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group" for $R^A$, $R^{A'}$ or $R^{B'}$ optionally has.

$R^1$ is preferably a $C_{1-6}$ alkyl group or a $C_{3-6}$ cycloalkyl group, more preferably a $C_{1-6}$ alkyl group.

As to $L^1$ and $L^2$,
(1) $L^1$ and $L^2$ are independently optionally substituted methylene, O, S, SO or $SO_2$, or
(2) $L^1$ and $L^2$ in combination form optionally substituted vinylene, or ethynylene.

When $L^1$ and $L^2$ are: "(1) $L^1$ and $L^2$ are independently optionally substituted methylene, O, S, SO or $SO_2$"

The "methylene" of the "optionally substituted methylene" for $L^1$ or $L^2$ optionally has 1 or 2 substituents at substitutable positions. Examples of the substituent include those similar to the substituents that the $C_{1-6}$ alkyl group and the like exemplified as the "hydrocarbon group" of the "optionally substituted hydrocarbon group" for $R^A$, $R^{A'}$ or $R^{B'}$ optionally has.

$L^1$ is preferably methylene, O, S, SO or $SO_2$.
$L^2$ is preferably methylene or O.

When $L^1$ and $L^2$ are: "(2) $L^1$ and $L^2$ in combination form optionally substituted vinylene, or ethynylene"

The "vinylene" of the "optionally substituted vinylene" formed by $L^1$ and $L^2$ optionally has 1 or 2 substituents at substitutable positions. Examples of the substituent include those similar to the substituents that the $C_{1-6}$ alkyl group and the like exemplified as the "hydrocarbon group" of the "optionally substituted hydrocarbon group" for $R^A$, $R^{A'}$ or $R^{B'}$ optionally has.

Preferably, $L^1$ and $L^2$ in combination form vinylene or ethynylene.

As to $L^1$ and $L^2$, preferably
(1) $L^1$ is methylene, O, S, SO or $SO_2$, and $L^2$ is methylene or O, or
(2) $L^1$ and $L^2$ in combination form vinylene or ethynylene.

As to $L^1$ and $L^2$, more preferably
(1) $L^1$ and $L^2$ are independently methylene or O, or
(2) $L^1$ and $L^2$ in combination form vinylene or ethynylene.

Preferable examples of compound (I) include the following compounds.

[Compound A0]

Compound (I) wherein

A is
(1) a $C_{1-6}$ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy),
(2) a $C_{1-6}$ alkoxy-carbonyl group (e.g., tert-butoxycarbonyl),
(3) a $C_{3-10}$ cycloalkyl-carbonyl group (e.g., cyclopropylcarbonyl, cyclopentylcarbonyl),
(4) a $C_{6-14}$ aryl-carbonyl group (e.g., benzoyl),
(5) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl);
(6) a $C_{1-6}$ alkylsulfonyl group (e.g., methylsulfonyl) optionally substituted by 1 to 3 $C_{6-14}$ aryl groups (e.g., phenyl),
(7) a $C_{6-14}$ arylsulfonyl group (e.g., benzenesulfonyl) optionally substituted by 1 to 3 $C_{1-6}$ alkyl groups (e.g., methyl),
(8) a $C_{3-10}$ cycloalkylsulfonyl group (e.g., cyclopropylsulfonyl),
(9) an aromatic heterocyclylcarbonyl group (e.g., furylcarbonyl, pyrazolylcarbonyl, pyridylcarbonyl, isooxazolylcarbonyl, thiazolylcarbonyl) optionally substituted by 1 to 3 substituents selected from a $C_{1-6}$ alkyl group optionally substituted by 1 to 3 halogen atoms (e.g., a fluorine atom),
(10) a non-aromatic heterocyclylcarbonyl group (e.g., tetrahydropyranylcarbonyl), or
(11) a 5-membered aromatic ring group (e.g., pyrazolyl, oxazolyl, isoxazolyl, thiazolyl, isothiazolyl) optionally substituted by 1 to 3 substituents selected from
  (i) a $C_{1-6}$ alkyl-carbonyl group optionally substituted by 1 to 3 halogen atoms;
  (ii) a $C_{1-6}$ alkoxy-carbonyl group optionally substituted by 1 to 3 substituents selected from
    (a) a halogen atom,
    (b) a $C_{1-6}$ alkoxy group, and
    (c) a $C_{6-14}$ aryl group (e.g., phenyl);
  (iii) a carbamoyl group optionally mono- or di-substituted by $C_{1-6}$ alkyl group(s) optionally substituted by 1 to 3 halogen atoms;
  (iv) a carboxy group;
  (v) a hydroxy group;
  (vi) a halogen atom; and
  (vii) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy group;

ring M is benzene, pyridine or dihydrobenzofuran, each of which is optionally substituted by 1 to 3 substituents selected from
(1) a halogen atom (e.g., a fluorine atom, a chlorine atom),
(2) a $C_{1-6}$ alkyl group (e.g., propyl),
(3) a $C_{1-6}$ alkoxy group (e.g., methoxy, ethoxy, propoxy, isopropoxy, butoxy) optionally substituted by 1 to 3 substituents selected from
  (i) a halogen atom (e.g., a fluorine atom),
  (ii) a $C_{1-6}$ alkoxy group (e.g., methoxy),
  (iii) a $C_{3-10}$ cycloalkyl group (e.g., cyclopropyl, cyclohexyl),
  (iv) a heterocyclic group (e.g., tetrahydrofuryl), and
  (v) a $C_{6-14}$ aryl group (e.g., phenyl),
(4) a $C_{1-6}$ alkylthio group (e.g., ethylthio),
(5) a $C_{1-6}$ alkyl-carbonyloxy group (e.g., acetyloxy),
(6) an aromatic heterocyclic group (e.g., pyrazolyl),
(7) a $C_{3-10}$ cycloalkoxy group (e.g., cyclopropoxy, cyclopentyloxy) optionally substituted by 1 to 3 substituents selected from
  (i) a halogen atom (e.g., a fluorine atom), and
  (ii) a $C_{1-6}$ alkoxy group (e.g., methoxy), and
(8) a hydroxy group;

ring P and ring Q are condensed to form

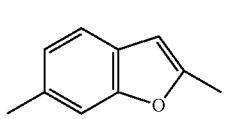 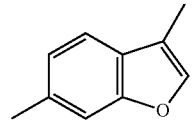

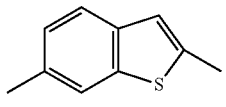 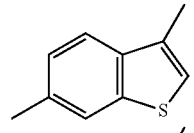

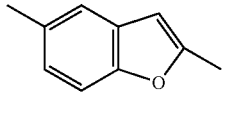 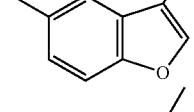

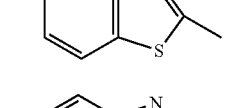 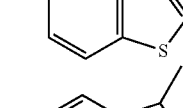

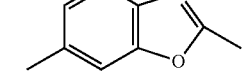 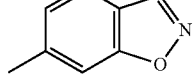

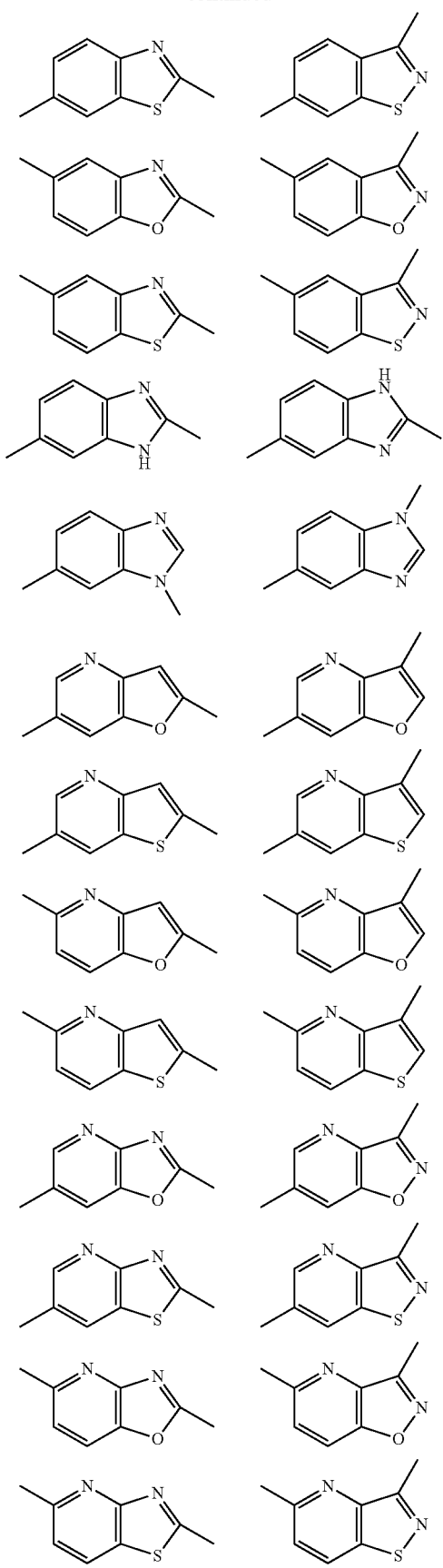
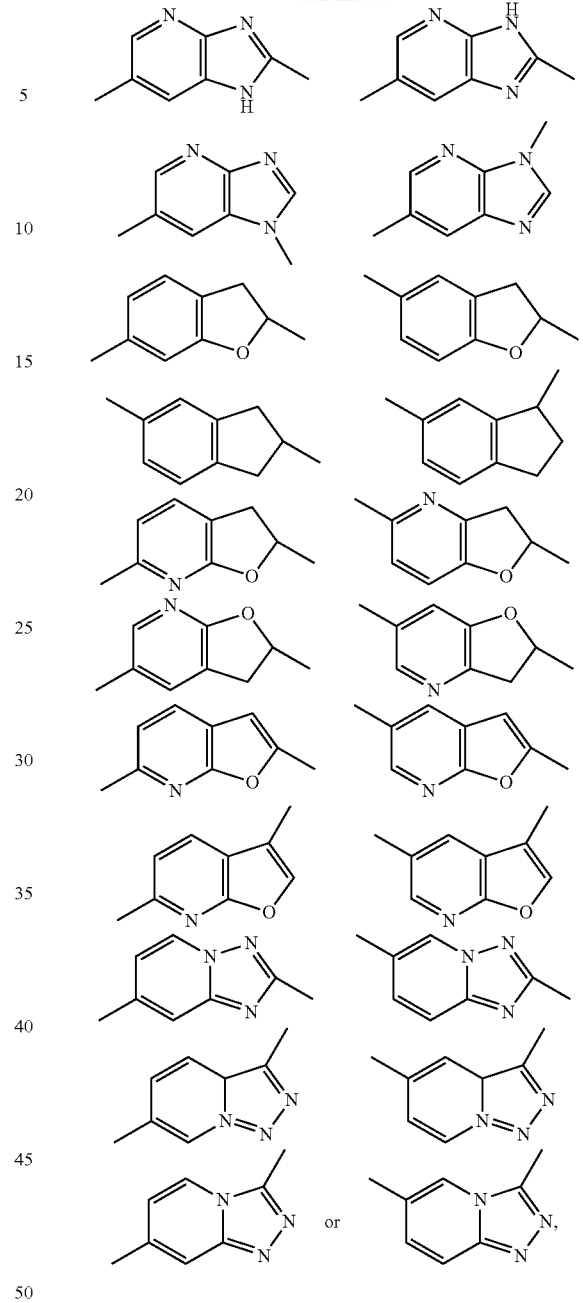

each of which is optionally substituted by 1 to 3 substituents selected from
(1) a halogen atom (e.g., a chlorine atom), and
(2) a $C_{1-6}$ alkyl group (e.g., methyl);
$R^1$ is a $C_{1-6}$ alkyl group or a $C_{3-6}$ cycloalkyl group (preferably a $C_{1-6}$ alkyl group); and
as to $L^1$ and $L^2$,
(1) $L^1$ is methylene, O, S, SO or $SO_2$, and $L^2$ is methylene or O, or
(2) $L^1$ and $L^2$ in combination form ethynylene or vinylene.

[Compound A]
Compound (I) wherein
ring M is benzene, pyridine or dihydrobenzofuran, each of which is optionally substituted by substituent(s) selected from (1) a halogen atom (e.g., a fluorine atom, a chlorine atom),
(2) a $C_{1-6}$ alkyl group (e.g., propyl),
(3) a $C_{1-6}$ alkoxy group (e.g., methoxy, ethoxy, propoxy, isopropoxy, butoxy) optionally substituted by 1 to 3 substituents selected from
  (i) a halogen atom (e.g., a fluorine atom),
  (ii) a $C_{1-6}$ alkoxy group (e.g., methoxy),
  (iii) a $C_{3-10}$ cycloalkyl group (e.g., cyclohexyl), and
  (iv) heterocyclic group (e.g., tetrahydrofuryl),
(4) a $C_{1-6}$ alkylthio group (e.g., ethylthio),
(5) a $C_{1-6}$ alkyl-carbonyloxy group (e.g., acetyloxy),
(6) an aromatic heterocyclic group (e.g., pyrazolyl), and
(7) a $C_{3-10}$ cycloalkoxy group (e.g., cyclopropoxy, cyclopentyloxy) optionally substituted by 1 to 3 substituents selected from
  (i) a halogen atom (e.g., a fluorine atom), and
  (ii) a $C_{1-6}$ alkoxy group (e.g., methoxy);
ring P and ring Q are condensed to form

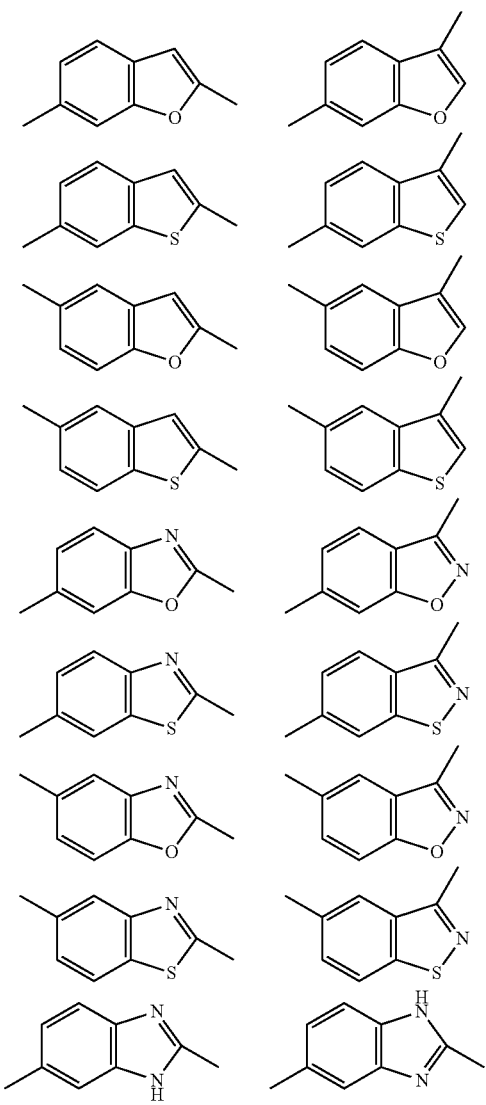

-continued

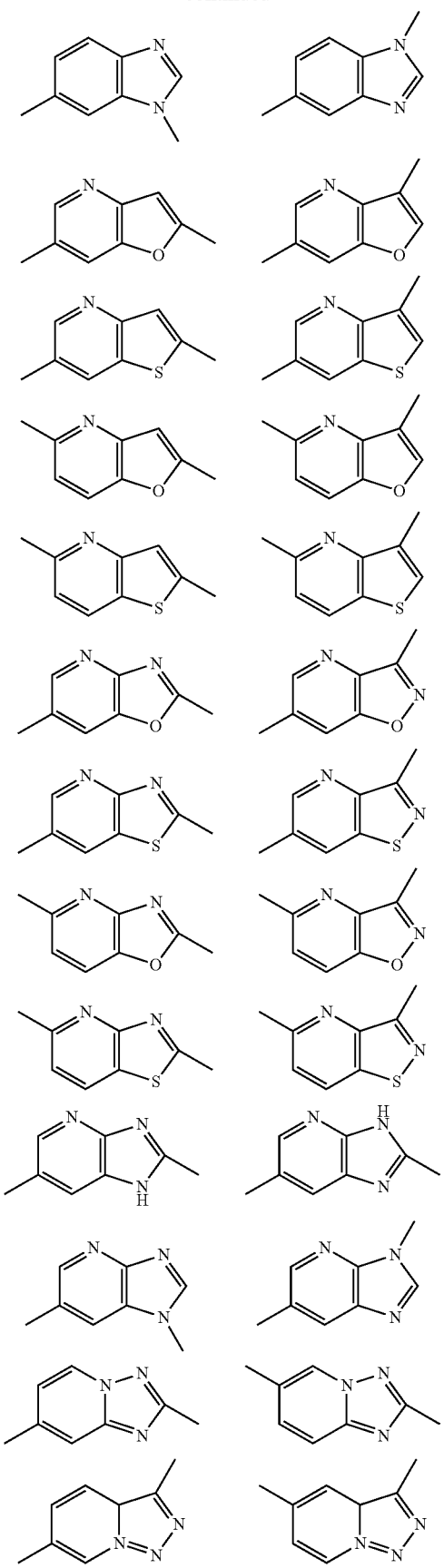

each of which is optionally substituted by 1 to 3 substituents selected from
(1) a halogen atom (e.g., a chlorine atom), and
(2) a $C_{1-6}$ alkyl group (e.g., methyl);

$R^1$ is a $C_{1-6}$ alkyl group or a $C_{3-6}$ cycloalkyl group (preferably a $C_{1-6}$ alkyl group);

A is an acyl group
(preferably
(1) a $C_{1-6}$ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy);
(2) a $C_{1-6}$ alkoxy-carbonyl group (e.g., tert-butoxycarbonyl);
(3) a $C_{3-10}$ cycloalkyl-carbonyl group (e.g., cyclopropylcarbonyl, cyclopentylcarbonyl);
(4) a $C_{6-14}$ aryl-carbonyl group (e.g., benzoyl);
(5) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl);
(6) a $C_{1-6}$ alkylsulfonyl group (e.g., methylsulfonyl) optionally substituted by 1 to 3 $C_{6-14}$ aryl groups (e.g., phenyl),
(7) a $C_{6-14}$ arylsulfonyl group (e.g., benzenesulfonyl) optionally substituted by 1 to 3 alkyl groups (e.g., methyl);
(8) a $C_{3-10}$ cycloalkylsulfonyl group (e.g., cyclopropylsulfonyl);
(9) an aromatic heterocyclylcarbonyl group (e.g., furylcarbonyl, pyrazolylcarbonyl, pyridylcarbonyl, isooxazolylcarbonyl, thiazolylcarbonyl) optionally substituted by 1 to 3 substituents selected from a $C_{1-6}$ alkyl group optionally substituted by 1 to 3 halogen atoms (e.g., a fluorine atom); or
(10) a non-aromatic heterocyclylcarbonyl group (e.g., tetrahydropyranylcarbonyl));

$L^1$ is methylene, O, S, SO or $SO_2$; and
$L^2$ is methylene or O.

[Compound B]
Compound (I) wherein
A is
(1) a $C_{1-6}$ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy), (2) a $C_{1-6}$ alkoxy-carbonyl group (e.g., tert-butoxycarbonyl),
(3) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl), or
(4) a 5-membered aromatic ring group (e.g., pyrazolyl, oxazolyl, isoxazolyl, thiazolyl, isothiazolyl);

ring M is benzene or pyridine, each of which is optionally substituted by 1 to 3 substituents selected from
(1) a halogen atom (e.g., a fluorine atom, a chlorine atom),
(2) a $C_{1-6}$ alkyl group (e.g., propyl),
(3) a $C_{1-6}$ alkoxy group (e.g., methoxy, ethoxy, propoxy, isopropoxy, butoxy) optionally substituted by 1 to 3 substituents selected from
  (i) a halogen atom (e.g., a fluorine atom),
  (ii) a alkoxy group (e.g., methoxy),
  (iii) a $C_{3-10}$ cycloalkyl group (e.g., cyclopropyl, cyclohexyl),
  (iv) a heterocyclic group (e.g., tetrahydrofuryl), and
  (v) a $C_{6-14}$ aryl group (e.g., phenyl),
(4) a $C_{3-10}$ cycloalkoxy group (e.g., cyclopropoxy, cyclopentyloxy) optionally substituted by 1 to 3 substituents selected from
  (i) a halogen atom (e.g., a fluorine atom), and
  (ii) a $C_{1-6}$ alkoxy group (e.g., methoxy), and
(5) a hydroxy group;

ring P and ring Q are condensed to form

-continued

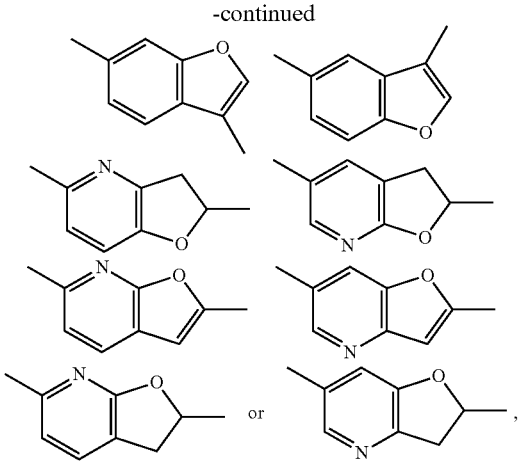

each of which is optionally substituted by 1 to 3 substituents selected from
(1) a halogen atom (e.g., a chlorine atom), and
(2) a $C_{1-6}$ alkyl group (e.g., methyl);
$R^1$ is a $C_{1-6}$ alkyl group or a $C_{3-6}$ cycloalkyl group (preferably a $C_{1-6}$ alkyl group); and
as to $L^1$ and $L^2$,
(1) $L^1$ and $L^2$ independently methylene or O, or
(2) $L^1$ and $L^2$ in combination form ethynylene or vinylene.

[Compound C]
Compound (I) wherein
A is
(1) a $C_{1-6}$ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy),
(2) a $C_{1-6}$ alkoxy-carbonyl group (e.g., tert-butoxycarbonyl),
(3) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl), or
(4) a 5-membered aromatic ring group (e.g., pyrazolyl, oxazolyl, isoxazolyl, thiazolyl, isothiazolyl); ring M is benzene or pyridine, each of which is optionally 15 substituted by 1 to 3 substituents selected from
(1) a halogen atom (e.g., a fluorine atom, a chlorine atom),
(2) a $C_{1-6}$ alkyl group (e.g., propyl),
(3) a $C_{1-6}$ alkoxy group (e.g., methoxy, ethoxy, propoxy, isopropoxy, butoxy) optionally substituted by 1 to 3 substituents selected from
  (i) a halogen atom (e.g., a fluorine atom),
  (ii) a $C_{1-6}$ alkoxy group (e.g., methoxy),
  (iii) a $C_{3-10}$ cycloalkyl group (e.g., cyclopropyl, cyclohexyl), (iv) a heterocyclic group (e.g., tetrahydrofuryl), and
(v) a $C_{6-14}$ aryl group (e.g., phenyl),
(4) a $C_{3-10}$ cycloalkoxy group (e.g., cyclopropoxy, cyclopentyloxy) optionally substituted by 1 to 3 substituents selected from
  (i) a halogen atom (e.g., a fluorine atom), and
  (ii) a $C_{1-6}$ alkoxy group (e.g., methoxy), and
(5) a hydroxy group;
ring P and ring Q are condensed to form

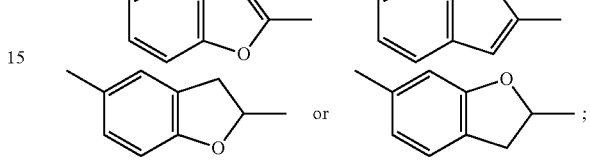

$R^1$ is a $C_{1-6}$ alkyl group or a $C_{3-6}$ cycloalkyl group (preferably a $C_{1-6}$ alkyl group); and
as to $L^1$ and $L^2$,
(1) $L^1$ and $L^2$ independently methylene or O, or
(2) $L^1$ and $L^2$ in combination form ethynylene or vinylene.

[Compound D]
Compound (I) wherein
A is
(1) a $C_{1-6}$ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy),
(2) a $C_{1-6}$ alkoxy-carbonyl group (e.g., tert-butoxycarbonyl),
(3) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl), or
(4) phenyl or a 5-membered aromatic heterocyclic group (e.g., pyrazolyl, oxazolyl, isoxazolyl, thiazolyl, isothiazolyl, thiadiazolyl), each of which is optionally substituted by 1 to 3 substituents selected from (i) a halogen atom and (ii) a $C_{1-6}$ alkyl group;
ring M is benzene or pyridine, each of which is optionally substituted by 1 to 3 substituents selected from
(1) a halogen atom (e.g., a fluorine atom, a chlorine atom, a bromine atom),
(2) a $C_{1-6}$ alkyl group (e.g., methyl, propyl),
(3) a $C_{1-6}$ alkoxy group (e.g., methoxy, ethoxy, propoxy, isopropoxy, butoxy, isobutoxy) optionally substituted by 1 to 3 substituents selected from
  (i) a halogen atom (e.g., a fluorine atom),
  (ii) a $C_{1-6}$ alkoxy group (e.g., methoxy),
  (iii) a $C_{3-10}$ cycloalkyl group (e.g., cyclopropyl, cyclobutyl, cyclohexyl), (iv) a heterocyclic group (e.g., tetrahydrofuryl),
(v) a $C_{6-14}$ aryl group (e.g., phenyl), and
(vi) a $C_{1-6}$ alkylthio group (e.g., methylthio),
(4) a $C_{3-10}$ cycloalkoxy group (e.g., cyclopropoxy, cyclopentyloxy) optionally substituted by 1 to 3 substituents selected from
(i) a halogen atom (e.g., a fluorine atom), and
(ii) a $C_{1-6}$ alkoxy group (e.g., methoxy), and
(5) a hydroxy group,
(6) a $C_{3-10}$ cycloalkyl group (e.g., cyclopropyl),
(7) an aromatic heterocyclyloxy group (e.g., pyridyloxy),
(8) a $C_{1-3}$ alkylenedioxy group (e.g., methylenedioxy);
ring P and ring Q are condensed to form

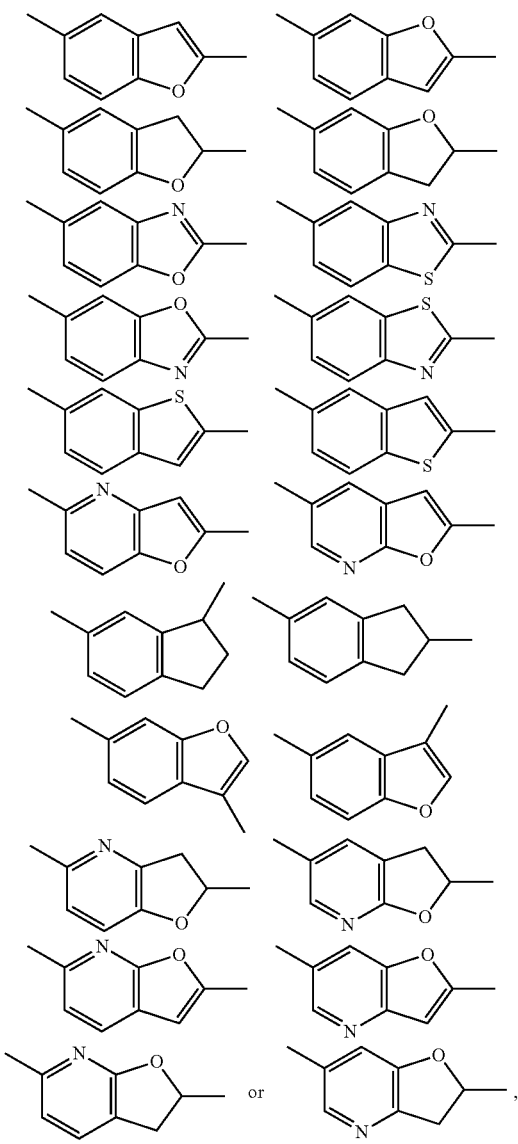

each of which is optionally substituted by 1 to 3 substituents selected from
(1) a halogen atom (e.g., a chlorine atom), and
(2) a $C_{1-6}$ alkyl group (e.g., methyl);
$R^1$ is a $C_{1-6}$ alkyl group or a $C_{3-6}$ cycloalkyl group (preferably a $C_{1-6}$ alkyl group); and
as to $L^1$ and $L^2$, (1) $L^1$ and $L^2$ independently methylene or O, or
(2) $L^1$ and $L^2$ in combination form ethynylene or vinylene.
[Compound E]
Compound (I) wherein
A is
(1) a $C_{1-6}$ alkyl-carbonyl group (e.g., acetyl, propionyl, butyryl, isobutyryl, isoamyl) optionally substituted by 1 to 3 substituents selected from
(i) an amino group,
(ii) a carboxyl group,
(iii) a $C_{1-6}$ alkoxy-carbonyl group (e.g., methoxycarbonyl, ethoxycarbonyl),
(iv) a $C_{6-14}$ aryl group (e.g., phenyl), and
(v) a $C_{1-6}$ alkoxy group (e.g., methoxy),
(2) a $C_{1-6}$ alkoxy-carbonyl group (e.g., tert-butoxycarbonyl),
(3) a carbamoyl group optionally mono- or di-substituted by substituent(s) selected from
(i) a $C_{1-6}$ alkyl group (e.g., methyl, ethyl, propyl, isopropyl) optionally substituted by 1 to 3 $C_{6-14}$ aryl groups (e.g., phenyl),
(ii) a $C_{6-14}$ aryl group (e.g., phenyl),
(iii) a $C_{3-10}$ cycloalkyl group (e.g., cyclopentyl, cyclohexyl),
(iv) a $C_{1-6}$ alkylsulfonyl group (e.g., methylsulfonyl), and
(v) an aromatic heterocyclic group (e.g., pyridyl) optionally substituted by 1 to 3 $C_{1-6}$ alkyl groups (e.g., methyl), or
(4) phenyl or a 5-membered aromatic heterocyclic group (e.g., pyrazolyl, oxazolyl, isoxazolyl, thiazolyl, isothiazolyl, thiadiazolyl), each of which is optionally substituted by 1 to 3 substituents selected from (i) a halogen atom and (ii) a $C_{1-6}$ alkyl group;
ring M is benzene or pyridine, each of which is optionally substituted by 1 to 3 substituents selected from
(1) a halogen atom (e.g., a fluorine atom, a chlorine atom, a bromine atom),
(2) a $C_{1-6}$ alkyl group (e.g., methyl, propyl),
(3) a $C_{1-6}$ alkoxy group (e.g., methoxy, ethoxy, propoxy, isopropoxy, butoxy, isobutoxy) optionally substituted by 1 to 3 substituents selected from
(i) a halogen atom (e.g., a fluorine atom),
(ii) a $C_{1-6}$ alkoxy group (e.g., methoxy),
(iii) a $C_{3-10}$ cycloalkyl group (e.g., cyclopropyl, cyclobutyl, cyclohexyl),
(iv) a heterocyclic group (e.g., tetrahydrofuryl),
(v) a $C_{6-14}$ aryl group (e.g., phenyl), and
(vi) a $C_{1-6}$ alkylthio group (e.g., methylthio),
(4) a $C_{3-10}$ cycloalkoxy group (e.g., cyclopropoxy, cyclopentyloxy) optionally substituted by 1 to 3 substituents selected from
(i) a halogen atom (e.g., a fluorine atom), and
(ii) a $C_{1-6}$ alkoxy group (e.g., methoxy), and
(5) a hydroxy group,
(6) a $C_{3-10}$ cycloalkyl group (e.g., cyclopropyl),
(7) an aromatic heterocyclyloxy group (e.g., pyridyloxy),
(8) a $C_{1-3}$ alkylenedioxy group (e.g., methylenedioxy);
ring P and ring Q are condensed to form

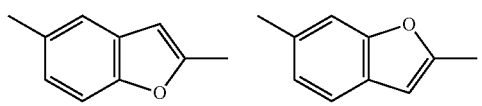

-continued

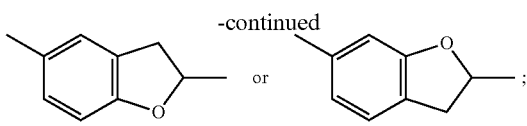

R$^1$ is a C$_{1-6}$ alkyl group or a C$_{3-6}$ cycloalkyl group (preferably a C$_{1-6}$ alkyl group); and
as to L$^1$ and L$^2$,
(1) L$^1$ and L$^2$ independently methylene or O, or
(2) L$^1$ and L$^2$ in combination form ethynylene or vinylene.
[Compound F]
Compound (I) wherein
A is
(1) a C$_{1-6}$ alkyl-carbonyl group, or
(2) a 5-membered aromatic heterocyclic group (e.g., pyrazolyl, oxazolyl, isoxazolyl, thiazolyl, isothiazolyl, thiadiazolyl) optionally substituted by 1 to 3 substituents selected from (i) a halogen atom and (ii) a C$_{1-6}$ alkyl group;
ring M is benzene or pyridine, each of which is optionally substituted by 1 to 3 substituents selected from
 (1) a halogen atom (e.g., a fluorine atom, a chlorine atom, a bromine atom),
 (2) a C$_{1-6}$ alkyl group (e.g., methyl, propyl),
 (3) a C$_{1-6}$ alkoxy group (e.g., methoxy, ethoxy, propoxy, isopropoxy, butoxy, isobutoxy) optionally substituted by 1 to 3 substituents selected from
  (i) a halogen atom (e.g., a fluorine atom),
  (ii) a C$_{1-6}$ alkoxy group (e.g., methoxy),
  (iii) a C$_{3-10}$ cycloalkyl group (e.g., cyclopropyl, cyclobutyl, cyclohexyl),
  (iv) a heterocyclic group (e.g., tetrahydrofuryl), and
  (v) a C$_{6-14}$ aryl group (e.g., phenyl),
 (4) a C$_{3-10}$ cycloalkoxy group (e.g., cyclopropoxy, cyclopentyloxy) optionally substituted by 1 to 3 substituents selected from
  (i) a halogen atom (e.g., a fluorine atom), and
  (ii) a C$_{1-6}$ alkoxy group (e.g., methoxy), and
 (5) a hydroxy group;
ring P and ring Q are condensed to form

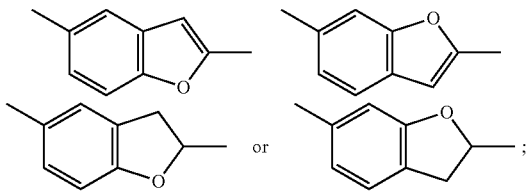

R$^1$ is a C$_{1-6}$ alkyl group; and
as to L$^1$ and L$^2$,
(1) L$^1$ and L$^2$ independently methylene or O, or
(2) L$^1$ and L$^2$ in combination form ethynylene or vinylene.
[Compound G]
N-{(1S)-1-[(2S)-6-{[4-(cyclopropylmethoxy)-2-fluorobenzyl]oxy}-2,3-dihydro-1-benzofuran-2-yl]ethyl}acetamide or a salt thereof.
N-[1-(5-{[6-(cyclopropylmethoxy)-4-fluoropyridin-3-yl]methoxy}-1-benzofuran-2-yl)ethyl]acetamide or a salt thereof.
N-(1-{6-[2-(4-ethoxyphenyl)ethyl]-1-benzofuran-2-yl}ethyl)acetamide or a salt thereof.
N-[1-(5-{[4-(cyclopropylmethoxy)benzyl]oxy}-1-benzofuran -2-yl)ethyl]acetamide or a salt thereof.

As a salt of the compound represented by the formula (I), a pharmacologically acceptable salt is preferable. Examples of such salt include salts with inorganic base, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt and the like; aluminum salt: ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

A prodrug of compound (I) means a compound which is converted to compound (I) with a reaction due to an enzyme, an gastric acid, etc. under the physiological condition in the living body, that is, a compound which is converted to compound (I) by oxidation, reduction, hydrolysis, etc. according to an enzyme; a compound which is converted to compound (I) by hydrolysis etc. due to gastric acid, etc.

Examples of the prodrug of compound (I) include a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methyl amidation etc.) and the like. These compounds can be produced from compound (I) according to a method known per se.

A prodrug for compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

In addition, compound (I) may be labeled with an isotope (e.g., $^3$H, $^{14}$C, $^{35}$S, $^{125}$I) and the like.

Compound (I) may be a non-solvate (e.g., anhydride) or a solvate (e.g., hydrate).

Compound (I) also encompasses a deuterium conversion form wherein $^1$H is converted to $^2$H(D).

Compound (I) or a prodrug thereof (hereinafter sometimes to be abbreviated simply as the compound of the present invention) has low toxicity, and can be used as an agent for the prophylaxis or treatment of various diseases mentioned below in a mammal (e.g., human, mouse, rat, rabbit, dog, cat, bovine, horse, swine, monkey) directly or in the form of a pharmaceutical composition by admixing with a pharmacologically acceptable carrier and the like.

Here, examples of the pharmacologically acceptable carrier include various organic or inorganic carrier substances conventionally used as preparation materials, which are added as excipient, lubricant, binder or disintegrant for solid dosage forms; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethylstarch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include paraoxybenzoates, chlorobutanol, benzyl alcohol, phenethyl alcohol, dehydroacetic acid and sorbic acid.

Preferable examples of the antioxidant include sulfite, ascorbate and the like.

Preferable examples of the colorant include aqueous food tar colors (e.g., food colors such as Food Red No. 2 and No. 3, Food Yellow No. 4 and No. 5, Food Blue No. 1 and No. 2, etc.), water insoluble lake dye (e.g., aluminum salt of the above-mentioned aqueous food tar color) and natural dye (e.g., β-carotene, chlorophyll, ferric oxide red).

Preferable examples of the sweetening agent include sodium saccharin, dipotassium glycyrrhizinate, aspartame and stevia.

Examples of the dosage form of the above-mentioned pharmaceutical composition include oral preparations such as tablets (inclusive of sugar-coated tablets, film-coated tablets, sublingual tablets, orally disintegrating tablets), capsules (inclusive of soft capsules, microcapsules), granules, powders, troches, syrups, emulsions, suspensions, films (e.g., orally disintegrable films) and the like; and parenteral agents such as injections (e.g., subcutaneous injections, intravenous injections, intramuscular injections, intraperitoneal injections, drip infusions), external preparations (e.g., dermal preparations, ointments), suppository (e.g., rectal suppositories, vaginal suppositories), pellets, nasal preparations, pulmonary preparations (inhalants), eye drops and the like. These may be safely administered orally or parenterally (e.g., topically, rectally, intravenously administered).

These preparations may be release control preparations (e.g., sustained-release microcapsule) such as immediate-release preparation, sustained-release preparation and the like.

A pharmaceutical composition can be produced by a method conventionally used in the technical field of pharmaceutical preparation, for example, the method described in the Japanese Pharmacopoeia and the like.

While the content of the compound of the present invention in the pharmaceutical composition varies depending on the dosage form, dose of the compound of the present invention, and the like, it is, for example, about 0.1 to 100 wt %.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, cardiotoxicity, carcinogenicity and the like) and a few side effects. Therefore, it can be used as an agent for the prophylaxis or treatment or a diagnostic of various diseases in a mammal (e.g., human, bovine, horse, dog, cat, monkey, mouse, rat).

The compound of the present invention has a superior ACC (acetyl-CoA carboxylase) inhibitory action. Examples of ACC include liver, adipose tissue or pancreas-specific isozyme (ACC1); and muscle specific isozyme (ACC2). The compound of the present invention particularly has a selective inhibitory action on ACC2 as compared to ACC1.

The compound of the present invention is superior in the metabolism stability and has advantages such as long half-life of compound, difficult in vivo metabolism and the like.

Moreover, the compound of the present invention is superior in the in vivo kinetics (e.g., oral absorbability, bioavailability).

The compound of the present invention can be used as an agent for the prophylaxis or treatment of obesity, diabetes (e.g., type 1 diabetes, type 2 diabetes, gestational diabetes, obese diabetes), hyperlipidemia (e.g., hypertriglyceridemia, hypercholesterolemia, high LDL-cholesterolemia, hypo-HDL-emia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (pathology having three or more selected from hypertriglyceridemia (TG), low HDL cholesterol (HDL-C), hypertension, abdomen obesity and impaired glucose tolerance), sarcopenia, cancer and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 hr level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 hr level (glucose concentration of intravenous plasma) of less than 140 mg/dl" (normal type) is called a "borderline type".

In addition, ADA (American Diabetes Association) in 1997 and WHO in 1998 reported new diagnostic criteria of diabetes.

According to these reports, diabetes is a condition showing a fasting blood glucose level (glucose concentration of intravenous plasma) of not less than 126 mg/dl and a 75 g oral glucose tolerance test 2 hr level (glucose concentration of intravenous plasma) of not less than 200 mg/dl.

According to the above-mentioned reports, impaired glucose tolerance is a condition showing fasting blood sugar level (glucose concentration of intravenous plasma) of less than 126 mg/dl and a 75 g oral glucose tolerance test 2 hr level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 hr level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention can also be used, for example, as an agent for the prophylaxis or treatment of osteoporosis, cachexia (e.g., carcinomatous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrosis syndrome, hypertensive nephrosclerosis, terminal renal disorder), muscular dystrophy, myocardial infarction, angina pectoris, cerebrovascular disorder (e.g., cerebral infarction, cerebral apoplexy), Alzheimer's disease, Parkinson's disease, anxiety, dementia, insulin resistance syndrome, syndrome X, hyperinsulinemia, sensory abnormality in hyperinsulinemia, irritable bowel syndrome, acute or chronic diarrhea, inflammatory disease (e.g., rheumatoid arthritis, spondylitis deformans, osteoarthritis, lumbago, gout, postoperative or posttraumatic inflammation, swelling, neuralgia, pharyngolaryngitis, cystitis, hepatitis (including nonalcoholic steatohepatitis), pneumonia, pancreatitis, enteritis, inflammatory bowel disease (including inflammatory colitis), ulcerative colitis, stomach mucosainjury (including stomach mucosainjury caused by aspirin)), small intestine mucosainjury, malabsorption, testis dysfunction, visceral obesity syndrome or sarcopenia.

In addition, the compound of the present invention can also be used as an agent for the prophylaxis or treatment of various carcinomas (particularly breast cancer (e.g., invasive ductal carcinoma, ductal carcinoma in situ, inflammatory breast cancer and the like), prostate cancer (e.g., hormone-dependent prostate cancer, non-hormone dependent prostate cancer and the like), pancreatic cancer (e.g., pancreatic duct cancer and the like), gastric cancer (e.g., papillary adenocarcinoma, mucinous adenocarcinoma, adenosquamous carcinoma and the like), lung cancer (e.g., non-small cell lung cancer, small cell lung cancer, malignant mesothelioma and the like), colorectal cancer (e.g., gastrointestinal stromal tumor and the like), rectal cancer (e.g., gastrointestinal stromal tumor and the like), colorectal cancer (e.g., familial colorectal cancer, hereditary nonpolyposis colorectal cancer, gastrointestinal stromal tumor and the like), small intestinal cancer (e.g., non-Hodgkin lymphoma, gastrointestinal stromal tumor and the like), esophagus cancer, duodenal cancer, cancer of the tongue, pharyngeal cancer (e.g., nasopharyngeal cancer, mesopharyngeal cancer, hypopharyngeal cancer and the like), salivary gland cancer, brain tumor (e.g., pineal astrocytoma, pilocytic astrocytoma, diffuse astrocytoma, anaplastic astrocytoma and the like), schwannoma, liver cancer (e.g., primary liver cancer, Extrahepatic Bile Duct Cancer and the like), kidney cancer (e.g., renal cell carcinoma, transitional carcinoma of kidney pelvis and urinary duct, and the like), biliary tract cancer, endometrial carcinoma, cervical cancer, ovarian cancer (e.g., ovarian epithelial carcinoma, extragonadal germ cell tumor ovarian germ cell tumor ovarian low malignant potential tumor and the like), urinary bladder cancer, urinary tract cancer, skin cancer (e.g., intraocular (ocular) melanoma, Merkel cell carcinoma and the like), Hemangioma, malignant lymphoma, malignant melanoma, thyroid cancer (e.g., medullary thyroid carcinoma and the like), parathyroid cancer, nasal cavity cancer, paranasal sinus cancer, bone tumor (e.g., osteosarcoma, Ewing's tumor uterus sarcoma, soft tissue sarcoma and the like), vascular fibroma, retinoblastoma, penile cancer, testis tumor solid cancer in childhood (e.g., Wilms' tumor childhood kidney tumor and the like), Kaposi's sarcoma, Kaposi's sarcoma derived from AIDS, maxillary tumor fibrous histiocytoma, leiomyosarcoma, rhabdomyosarcoma, leukemia (e.g., acute myeloid leukemia, acute lymphoblastic leukemia and the like) etc.).

The compound of the present invention can also be used for secondary prevention or suppression of progression of the above-mentioned various diseases (e.g., cardiovascular events such as myocardial infarction and the like).

While the dose of the compound of the present invention varies depending on the subject of administration, administration route, target disease, symptom and the like, for example, for oral administration to an adult diabetic patient, it is generally about 0.01 to 100 mg/kg body weight, preferably 0.05 to 30 mg/kg body weight, more preferably 0.1 to 10 mg/kg body weight for one dose, which is desirably administered once to 3 times a day.

With the aim of enhancing the action of the compound of the present invention or decreasing the dose of the compound and the like, the compound can be used in combination with medicaments such as therapeutic agents for diabetes, therapeutic agents for diabetic complications, therapeutic agents for hyperlipidemia, antihypertensive agents, antiobesity agents, diuretics, antithrombotic agents and the like (hereinafter to be abbreviated as concomitant drug). The time of administration of the compound of the present invention and that of the concomitant drug are not limited, and these concomitant drugs may be low-molecular-weight compounds or high-molecular-weight protein, polypeptide, antibody, vaccine and the like. They may be administered simultaneously or in a staggered manner to the administration subject. In addition, the compound of the present invention and the concomitant drug may be administered as two kinds of preparations containing respective active ingredients or a single preparation containing both active ingredients.

The dose of the concomitant drug can be appropriately determined based on the dose employed clinically. In addition, the mixing ratio of the compound of the present invention and the concomitant drug can be appropriately determined according to the administration subject, administration route, target disease, condition, combination, and the like. For example, when the administration subject is a human, the concomitant drug may be used in an amount of 0.01 to 100 parts by weight per 1 part by weight of the compound of the present invention.

Examples of the therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO 2007/013694, WO 2007/018314, WO 2008/093639 or WO 2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Alogliptin, Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compound described in WO 2004/041266, WO 2004/106276, WO 2005/063729, WO 2005/063725, WO 2005/087710, WO 2005/095338, WO 2007/013689 or WO 2008/001931), GLP-1 receptor agonists [e.g., GLP-1, GLP-1MR, Liraglutide, Exenatide, AVE-0010, BIM-51077, Aib(8,35)hGLP-1(7,37)NH$_2$, CJC-1131, Albiglutide], amylin agonists (e.g., pramlintide), phosphotyrosine phosphatase inhibitors (e.g., sodium vanadate), gluconeogenesis inhibitors (e.g., glycogen phosphorylase inhibitors glucose-6-phosphatase inhibitors, glucagon antagonists, FBPase inhibitors), SGLT2(sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498), adiponectin or an agonist thereof, IKK inhibitors (e.g., AS-2868), leptin resistance improving drugs, somatostatin receptor agonists, glucokinase activators (e.g., Piragliatin, AZD1656, AZD6370, TTP-355, compound described in WO 2006/112549, WO 2007/028135, WO 2008/047821, WO 2008/050821, WO 2008/136428 or WO 2008/156757), GIP (Glucose-dependent insulinotropic peptide) and the like.

Examples of the therapeutic agents for diabetic complications include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF, neurotrophic factors and increasing drugs thereof (e.g., 4-(4-chlorophenyl)-2-(2-methyl-1-imidazolyl)-5-[3-(2-methylphenoxy)propyl]oxazole) described in WO01/14372, a compound described in WO 2004/039365), nerve regeneration promoter (e.g., Y-128), PKC inhibitors (e.g., ruboxistaurin mesylate), AGE inhibitors (e.g., ALT946, pyratoxanthine, N-phenacylthiazolium bromide (ALT766), ALT-711, EXO-226, Pyridorin, pyridoxamine), GABA receptor agonists (e.g., gabapentin, Pregabalin), serotonin noradrenaline re-uptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1(ASK-1) inhibitors and the like.

Examples of the therapeutic agent for hyperlipidemia include statin compounds (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., a compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterols (e.g., soysterol), γ-oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the antihypertensive agent include angiotensin converting enzyme inhibitors (e.g., captopril, enalapril, delapril etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, amlodipine, cilnidipine and the like), β blockers (e.g., metoprolol, atenolol, propranolol, carvedilol, pindolol), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor GABA modulator regulator ?(e.g., topiramate), MCH receptor antagonists (e.g., SB-568849; SNAP-7941; compound described in WO 01/82925 or WO 01/87834), neuropeptide Y antagonists (e.g., velneperit), cannabinoid receptor antagonists (e.g., rimonabant, taranabant), ghrelinant agonists, ghrelin receptor antagonists, ghrelinacylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1(DGAT1) inhibitors, acetylCoAcarboxylase (ACC) inhibitors, stearic acid CoA desaturated enzyme inhibitors microsomal triglyceride transfer protein inhibitors (e.g., R-256918), Na-glucose cotransporter inhibitors (e.g., JNJ-28431754, remogliflozin), NFκ inhibitory (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1(GLP-1) preparations (e.g., animal GLP-1 preparations extracted from the pancreas of bovine and pig; human GLP-1 preparations genetically synthesized using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide TM-30339, TM-30335), oxyntomodulin preparations: FGF21 preparations (e.g., animal FGF21 preparations extracted from the pancreas of bovine and pig; human FGF21 preparations genetically synthesized using *Escherichia coli* or yeast; fragments or derivatives of FGF21)), anorexigenic agents (e.g., P-57) and the like.

Examples of the diuretics include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide, furosemide and the like.

Examples of the antithrombotic agent include heparins (e.g., heparin sodium, heparin calcium, enoxaparin sodium, dalteparin sodium), warfarins (e.g., warfarin potassium), anti-thrombin drugs (e.g., argatroban, dabigatran), thrombolytic agents (e.g., urokinase, tisokinase, alteplase, nateplase, monteplase, pamiteplase), platelet aggregation inhibitors (e.g., ticlopidine hydrochloride, clopidogrel, E5555, SHC530348, cilostazol, ethyl icosapentate, beraprost sodium, sarpogrelate hydrochloride, prasugrel, E5555, SHC530348), FXa inhibitors (e.g., rivaroxaban, apixaban, edoxaban, YM150, compound described in WO 02/06234, WO 2004/048363, WO 2005/030740, WO 2005/058823 or WO 2005/113504) and the like.

The administration time of the aforementioned concomitant drug is not limited, and the compound of the present invention and the concomitant drug may be administered to an administration subject simultaneously, or may be administered at different times. The dosage of the concomitant drug may be determined according to the dosage clinically used, and can be appropriately selected depending on the administration subject, administration route, diseases, combination thereof and the like.

The administration mode of the concomitant drug is not particularly limited, and the compound of the present invention and the concomitant drug only need to be combined on administration. Examples of such administration mode include the following (1) administration of a single preparation obtained by simultaneously processing the compound of the present invention and the concomitant drug,
(2) simultaneous administration of two kinds of preparations of the compound of the present invention and the concomitant drug, which have been separately produced, by the same administration route,
(3) administration of two kinds of preparations of the compound of the present invention and the concomitant drug, which have been separately produced, by the same administration route in a staggered manner,
(4) simultaneous administration of two kinds of preparations of the compound of the present invention and the concomitant drug, which have been separately produced, by different administration routes,
(5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug can be appropriately selected depending on the administration subject, administration route, diseases and the like.

The production method of compound (I) is explained in the following. compound (I) can be produced by, for example, Reaction Schemes 1 to 43 to be described in detail in the following or a method according thereto.

In the following Reaction Schemes 1 to 43, the compound used as a starting compound may be each in the form of a salt. Examples of the salt include those exemplified as the salt of compound (I).

In each reaction of the following Reaction Schemes 1 to 43, the product can be used for the next reaction as the reaction mixture or as a crude product, or can also be isolated according to a conventional method from the reaction mixture, and can also be easily purified according to a conventional separation means (e.g., recrystallization, distillation, chromatography).

When alkylation reaction, hydrolysis, amination reaction, esterification reaction, amidation reaction, esterification reaction, etherification reaction, oxidation reaction, reduction reaction and the like are to be performed in the following Reaction Schemes 1 to 43, these reactions are performed according to a method known per se. Examples of such method include the methods described in ORGANIC FUNCTIONAL GROUP PREPARATIONS, 2nd ed., ACADEMIC PRESS, INC., 1989; Comprehensive Organic Transformations, VCH Publishers Inc., 1989 and the like, and the like.

The following are explanations of the solvents in generic terms, which are used for the following reactions.

Examples of the "nitrile solvents" include acetonitrile, propionitrile and the like.

Examples of the "amide solvents" include N,N-dimethylformamide (DMF), N,N-dimethylacetamide, N-methylpyrrolidone and the like.

Examples of the "halogenated hydrocarbon solvents" include dichloromethane, chloroform, 1,2-dichloroethane, carbon tetrachloride and the like.

Examples of the "ether solvents" include diethyl ether, diisopropyl ether, tert-butyl methyl ether, tetrahydrofuran (THF), 1,4-dioxane, 1,2-dimethoxyethane and the like.

Examples of the "aromatic solvents" include benzene, toluene, xylene, pyridine and the like.

Examples of the "aliphatic hydrocarbon solvents" include hexane, pentane, cyclohexane and the like.

Examples of the "sulfoxide solvents" include dimethyl sulfoxide (DMSO) and the like.

Examples of the "alcohol solvents" include methanol, ethanol, propanol, 2-propanol, butanol, isobutanol, tert-butanol and the like.

Examples of the "ester solvents" include methyl acetate, ethyl acetate, n-butyl acetate, tert-butyl acetate and the like.

Examples of the "ketone solvents" include acetone, methyl ethyl ketone and the like.

Examples of the "organic acid solvents" include formic acid, acetic acid, propionic acid, trifluoroacetic acid, methanesulfonic acid and the like.

The following are explanations of the bases in generic terms, which are used for the following reactions.

Examples of the "inorganic bases" include sodium hydroxide, potassium hydroxide, lithium hydroxide, barium hydroxide and the like.

Examples of the "basic salt" include sodium carbonate, potassium carbonate, cesium carbonate, sodium hydrogen carbonate, potassium hydrogen carbonate and the like.

Examples of the "aromatic amines" include pyridine, imidazole, 2,6-lutidine and the like.

Examples of the "tertiary amines" include triethylamine, diisopropylethylamine, N-methylmorpholine, DBU (1,8-diazabicyclo[5.4.0]undec-7-ene), DBN (1,5-diazabicyclo[4.3.0]non-5-ene) and the like.

Examples of the "hydrides of alkali metal or alkaline earth metal" include lithium hydride, sodium hydride, potassium hydride, calcium hydride and the like.

Examples of the "metal amides" include lithium amide, sodium amide, lithium diisopropylamide, lithium dicyclohexylamide, lithium hexamethyldisilazide, sodium hexamethyldisilazide, potassium hexamethyldisilazide and the like.

Examples of the "alkyl metals" include n-butyllithium, sec-butyllithium, tert-butyllithium, methylmagnesium bromide and the like.

Examples of the "aryl metals" include phenyllithium, phenylmagnesium bromide and the like.

Examples of the "metal alkoxides" include sodium methoxide, sodium ethoxide, potassium tert-butoxide and the like.

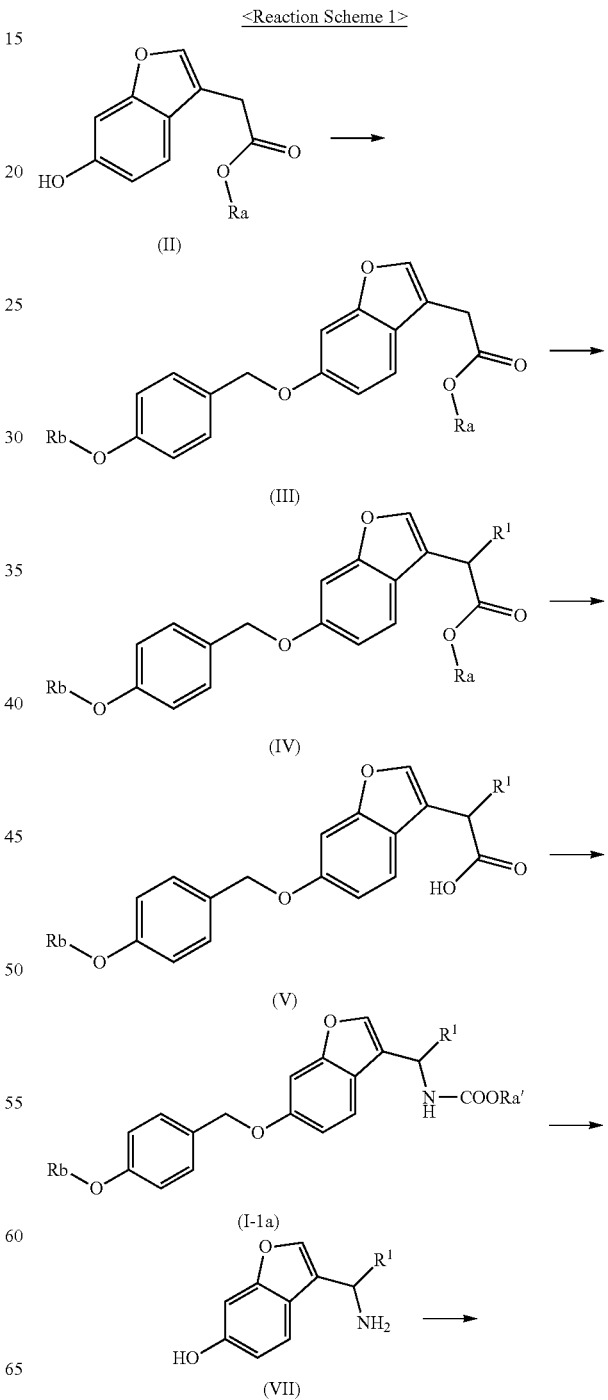

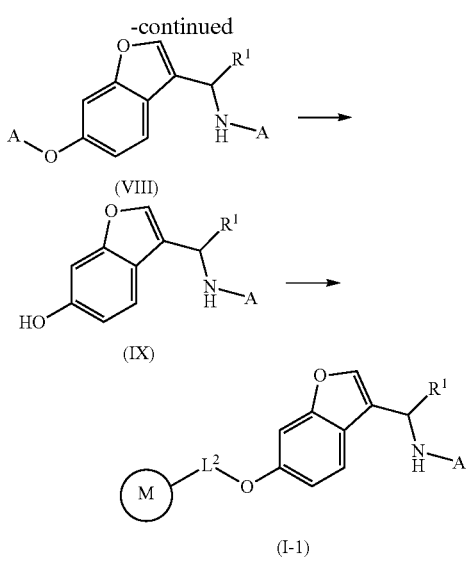

wherein M, $R^1$, A and $L^2$ are independently as defined above, and Ra, Ra' and Rb are independently an optionally substituted $C_{1-6}$ alkyl group or an optionally substituted $C_{7-12}$ aralkyl group.

Compound (II) may be easily commercially available, or can also be produced according to a method known per se, for example, the method described in Bioorganic Medicinal Chemistry Letters, pages 3630-3635, 2007 or the like, or a method analogous thereto.

Compound (III) can be produced, for example, by subjecting compound (II) to an alkylation reaction.

Examples of the alkylation reaction include the following "method using a base and an alkyl halide", "method employing the Mitsunobu reaction" and the like.

The "method using a base and an alkyl halide" can be carried out according to a method known per se, for example, the method described in Journal of Chemical Society, pages 1530-1534, 1937 or the like, or a method analogous thereto.

This reaction is carried out by reacting compound (II) with a 4-substituted benzyl halide in the presence of a base, in an inert solvent.

Examples of the above-mentioned "4-substituted benzyl halide" include 4-$C_{1-6}$ alkoxybenzyl chloride, 4-$C_{1-6}$ alkoxybenzyl bromide, 4-$C_{7-12}$ aralkyloxybenzyl chloride, 4-$C_{7-12}$ aralkyloxybenzyl bromide and the like. The amount of the "4-substituted benzyl halide" to be used is generally 1 to 5 equivalents, preferably 1 to 1.5 equivalents, relative to compound (II).

Examples of the above-mentioned "base" include "inorganic bases", "basic salts", "aromatic amines", "hydrides of alkali metal or alkaline earth metal", "alkyl metals", "aryl metals", "metal alkoxides" and the like. The amount of the "base" to be used is generally 1 to 10 equivalents, preferably 1 to 3 equivalents, relative to compound (II).

Examples of the inert solvent include nitrile solvents, amide solvents, halogenated hydrocarbon solvents, ether solvents and the like. These solvents may be used in a mixture of two or more kinds thereof at an appropriate ratio. Of those, THF, DMF and the like are preferable.

The reaction temperature is generally −100° C. to 150° C., preferably 0° C. to 100° C.

The reaction time is generally 5 min to 48 hr, preferably 30 min to 24 hr.

The "method employing the Mitsunobu reaction" can be carried out according to a method known per se, for example, the method described in Tetrahedron Letters, pages 769-770, 1980 or the like, or a method analogous thereto.

This reaction is carried out by reacting compound (II) with a (4-substituted phenyl)methanol in the presence of a hydroxyl group-activator in an inert solvent.

Examples of the above-mentioned "(4-substituted phenyl)methanol" include (4-$C_{1-6}$ alkoxyphenyl)methanols such as (4-methoxyphenyl)methanol, (4-ethoxyphenyl)methanol and the like; (4-$C_{7-12}$ aralkyloxyphenyl)methanols such as (4-benzyloxyphenyl)methanol and the like, and the like. The amount of the "(4-substituted phenyl)methanol" to be used is generally 1 to 10 equivalents, preferably 1 to 5 equivalents, relative to compound (II).

Examples of the above-mentioned "hydroxyl group-activator" include cyanomethylenetri-n-butylphosphorane, a combination of diethyl azodicarboxylate (DEAD) and triphenylphosphine, and the like. The amount of the "hydroxyl group-activator" to be used is generally 1 to 10 equivalents, preferably 1 to 1.5 equivalents, relative to compound (II).

Examples of the above-mentioned "inert solvent" include aromatic solvents, aliphatic hydrocarbon solvents, ether solvents, ester solvents, amide solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

Compound (IV) can be produced, for example, by subjecting compound (III) to an alkylation reaction (when $R^1$=$C_{1-6}$ alkyl group).

The alkylation reaction can be carried out according to a method known per se, for example, the method described in Journal of Medicinal Chemistry (J. Med. Chem.) pages 2439-2441, 1998 or the like, or a method analogous thereto.

This reaction is carried out by reacting compound (III) with an alkylating agent in the presence of a base, in an inert solvent.

Examples of the above-mentioned "alkylating agent" include iodomethane, iodoethane and the like. The amount of the "alkylating agent" to be used is generally 1 to 5 equivalents, preferably 1 to 1.5 equivalents, relative to compound (III).

Examples of the inert solvent include ether solvents, aromatic solvents, aliphatic hydrocarbon solvents and the like. These solvents may be used in a mixture of two or more kinds thereof at an appropriate ratio. Of those, ether solvents and the like are preferable.

Examples of the base include "hydrides of alkali metal or alkaline earth metal", "metal amides", "alkyl metals", "aryl metals" and the like. The amount of the base to be used is generally 1 to 10 equivalents, preferably 1 to 1.5 equivalents, relative to compound (III).

The reaction temperature is generally −100° C. to 150° C., preferably −78° C. to 100° C.

The reaction time is generally 5 min to 48 hr, preferably 30 min to 24 hr.

Compound (V) can be produced, for example, by subjecting compound (IV) to hydrolysis in the presence of a base.

Examples of the above-mentioned "base" include "inorganic bases", "basic salts" and the like. The amount of the "base" to be used is generally 1 to 10 equivalents, preferably 1 to 5 equivalents, relative to compound (IV).

Examples of the solvent to be used for the hydrolysis include alcohol solvents, nitrile solvents, aromatic solvents, aliphatic hydrocarbon solvents, ether solvents, amide solvents, halogenated hydrocarbon solvents and the like. These solvents are preferably used in a mixture with water at an appropriate ratio. Of those, alcohol solvents containing water are preferable.

The reaction temperature is generally −78° C. to 150° C., preferably −20° C. to 100° C.

The reaction time is generally 5 min to 100 hr, preferably 30 min to 24 hr.

Compound (I-1a) can be produced, for example, by subjecting compound (V) directly, or after conversion to a reactive derivative thereof (e.g., an acid halide, an acid amide, an acid anhydride, an ester etc.) and the like, to a rearrangement reaction.

Examples of the above-mentioned "rearrangement reaction" include Curtius rearrangement, Hofmann rearrangement, Schmidt rearrangement and the like.

The Curtius rearrangement reaction using diphenylphosphoryl azide is exemplified in the following.

The amount of the diphenylphosphoryl azide to be used is generally 1 to 3 equivalents, preferably 1 to 1.5 equivalents, relative to compound (V).

This reaction is carried out in the presence of a base, as necessary.

Examples of the above-mentioned "base" include "aromatic amines", "tertiary amines" and the like.

Examples of the above-mentioned "inert solvent" include ether solvents, alcohol solvents and the like. When a solvent other than alcohol solvent is used, the corresponding alkoxycarbonyl compound can be produced by adding an alcohol solvent after the progress of the rearrangement.

The reaction time is generally about 10 min to about 48 hr, preferably about 15 min to about 24 hr.

The reaction temperature is generally −20° C. to 200° C., preferably 0° C. to 150° C.

The method described in "Jikken Kagaku Kouza (The Chemical Society of Japan ed.), 4th Edition, vol. 20, pages 304 and 477-479, a method analogous thereto and the like are employed as other reaction conditions.

Compound (VII) can be produced, for example, by subjecting compound (I-1a) to deprotection. The deprotection can be carried out according to a method known per se, for example, the method described in Protective Groups in Organic Synthesis, John Wiley and Sons (1980) or the like.

Compound (VIII) can be produced, for example, by subjecting compound (VII) to an acylation reaction.

Examples of the "acylation reaction" include the following "method using a dehydration-condensation agent", "method using a reactive derivative of carboxylic acid or a reactive derivative of sulfonic acid" and the like.

The "method using a dehydration-condensation agent" is carried out by reacting compound (VII) with a substituted carboxylic acid in the presence of a dehydration-condensation agent, in an inert solvent. This reaction may be carried out in the presence of a base, a catalytic amount to 5 equivalents of 1-hydroxybenzotriazole (HOBt), and the like, as necessary.

The amount of the above-mentioned "substituted carboxylic acid" to be used is generally 0.5 to 5 equivalents, preferably 0.8 to 1.5 equivalents, relative to compound (VII).

Examples of the above-mentioned "dehydration-condensation agent" include dicyclohexylcarbodiimide (DCC), 1-ethyl-3-(3-dimethylaminopropyl)carbodiimide hydrochloride (EDC.HCl) and the like. Of these, EDC.HCl is preferable. The amount of the dehydration-condensation agent to be used is generally 1 to 10 equivalents, preferably 1 to 5 equivalents, relative to compound (VII).

Examples of the above-mentioned "inert solvent" include nitrile solvents, amide solvents, halogenated hydrocarbon solvents, ether solvents and the like. These may be used in a mixture of two or more kinds thereof at an appropriate ratio. Of these, amide solvents are preferable.

Examples of the above-mentioned "base" include aromatic amines, tertiary amines and the like. The amount of the "base" to be used is generally 1 to 20 equivalents, preferably 1 to 5 equivalents, relative to compound (VII).

The reaction temperature is generally −70 to 150° C., preferably −20 to 100° C.

The reaction time is generally 0.1 to 100 hr, preferably 1 to 48 hr.

The "method using a reactive derivative of carboxylic acid or a reactive derivative of sulfonic acid" is carried out by reacting compound (VII) with a reactive derivative of carboxylic acid or a reactive derivative of sulfonic acid in an inert solvent. This reaction may be carried out in the presence of a base, as necessary.

Examples of the above-mentioned "reactive derivative of carboxylic acid" include acid anhydrides, acid halides (e.g., acid chlorides, acid bromides), mixed acid anhydrides (e.g., acid anhydrides with a $C_{1-6}$ alkyl-carboxylic acid, a $C_{6-10}$ aryl-carboxylic acid, a $C_{1-6}$ alkyl-carbonic acid or the like), activated ester (e.g., esters with a phenol optionally having substituent(s), HOBt, N-hydroxysuccinimide or the like) and the like. The amount of the "reactive derivative of carboxylic acid" to be used is generally 1 to 20 equivalents, preferably 1 to 5 equivalents, relative to compound (VII).

Examples of the above-mentioned "reactive derivative of sulfonic acid" include substituted sulfonyl chlorides and the like. The amount of the "reactive derivative of sulfonic acid" to be used is generally 1 to 20 equivalents, preferably 1 to 5 equivalents, relative to compound (VII).

Examples of the above-mentioned "inert solvent" include ester solvents, ether solvents, halogenated hydrocarbon solvents, aromatic solvents, aliphatic hydrocarbon solvents, nitrile solvents, amide solvents, ketone solvents, sulfoxide solvents, water and the like. These may be used in a mixture of two or more kinds thereof at an appropriate ratio. Of these, ethyl acetate, acetonitrile, THF, dichloromethane, chloroform and the like are preferable.

Examples of the above-mentioned "base" include "aromatic amines", "tertiary amines" and the like. The amount of the "base" to be used is generally 1 to 20 equivalents, preferably 1 to 5 equivalents, relative to compound (VII).

The reaction temperature is generally −20 to 100° C., preferably −20° C. to 50° C.

The reaction time is generally 5 min to 40 hr, preferably 30 min to 18 hr.

Compound (IX) can be produced, for example, by subjecting compound (VIII) to deprotection. The deprotection can be carried out according to a method known per se, for example, the method described in Protective Groups in Organic Synthesis, John Wiley and Sons (1980) or the like.

Compound (I-1) can be produced, for example, by subjecting compound (IX) to an alkylation reaction (when $L^2$ is methylene).

Examples of the alkylation reaction include the following "method using a base and an alkyl halide", "method employing the Mitsunobu reaction", "method using a sulfonate" and the like.

The "method using a base and an alkyl halide" can be carried out according to a method known per se, for example, the method described in Journal of Chemical Society, pages 1530-1534, 1937 or the like, or a method analogous thereto.

This reaction is carried out by reacting compound (IX) with an alkyl halide in the presence of a base, in an inert solvent.

Examples of the above-mentioned "base" include "inorganic bases", "basic salts", "aromatic amines", "hydrides of alkali metal or alkaline earth metal", "alkyl metals", "aryl metals", "metal alkoxides" and the like. The amount of the "base" to be used is generally 1 to 10 equivalents, preferably 1 to 5 equivalents, relative to compound (IX).

Examples of the above-mentioned "inert solvent" include nitrile solvents, amide solvents, halogenated hydrocarbon solvents, ether solvents and the like. These may be used in a mixture of two or more kinds thereof at an appropriate ratio. Of these, THF, DMF and the like are preferable.

The reaction temperature is generally −100° C. to 150° C., preferably 0° C. to 100° C.

The reaction time is generally 5 min to 48 hr, preferably 30 min to 24 hr.

Examples of the above-mentioned "alkyl halide" include halomethanes having optionally fused 5- to 7-membered cyclic group(s) which is(are) optionally substituted, such as 4-alkoxybenzyl chlorides and the like, and the like. Alternatively, the alkyl halide can also be produced according to a method known per se, for example, the method described in Journal of Medicinal Chemistry, pages 2146-2163, 1998, Synlett, pages 2130-2134, 2005 or the like, or a method analogous thereto. The amount of the "alkyl halide" to be used is generally 1 to 10 equivalents, preferably 1 to 5 equivalents, relative to compound (IX).

The above-mentioned "alkyl halide" can be produced by reacting an alcohol having substituent(s) in the presence of a halogenating agent, in an inert solvent.

Examples of the above-mentioned "alcohol having substituent(s)" include the alcohols produced in Reaction Schemes 40 to 43 mentioned below, methyl alcohols having optionally fused 5- to 7-membered cyclic group(s) which is(are) optionally substituted, and the like. Specific examples thereof include (4-methoxyphenyl)methanol, (4-ethoxyphenyl)methanol and the like.

Examples of the above-mentioned "halogenating agent" include thionyl chloride, a combination of carbon tetrabromide and triphenylphosphine, and the like. The amount of the "halogenating agent" to be used is generally 1 to 10 equivalents, preferably 1 to 2 equivalents, relative to the alcohol having substituent(s).

Examples of the above-mentioned "inert solvent" include nitrile solvents, halogenated hydrocarbon solvents, ether solvents, aromatic solvents and the like. These may be used in a mixture of two or more kinds thereof at an appropriate ratio. Of these, toluene, THF and the like are preferable.

The "method employing the Mitsunobu reaction" can be carried out according to a method known per se, for example, the method described in Tetrahedron Letters, pages 769-770, 1980 or the like, or a method analogous thereto.

This reaction is carried out by reacting compound (IX) with an alcohol having substituent(s) in the presence of a hydroxyl group-activator in an inert solvent.

Examples of the above-mentioned "alcohol having substituent(s)" include methyl alcohols having optionally fused 5- to 7-membered cyclic group(s) which is(are) optionally substituted, and the like. Specific examples thereof include (4-methoxyphenyl)methanol, (4-ethoxyphenyl)methanol and the like. The amount of the "alcohol having substituent (s)" to be used is generally 1 to 10 equivalents, preferably 1 to 5 equivalents, relative to compound (IX).

Examples of the above-mentioned "hydroxyl group-activator" include cyanomethylenetri-n-butylphosphorane, a combination of DEAD and triphenylphosphine, and the like. The amount of the "hydroxyl group-activator" to be used is generally 1 to 10 equivalents, preferably 1 to 1.5 equivalents, relative to compound (IX).

Examples of the above-mentioned "inert solvent" include aromatic solvents, aliphatic hydrocarbon solvents, ether solvents, ester solvents, amide solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

The "method using a sulfonate" can be carried out using compound (IX) and a sulfonate prepared from an alcohol having substituent(s), according to method known per se, for example, the method described in Journal of Medicinal Chemistry, pages 3108-3120, 1994 or the like, or a method analogous thereto.

This reaction can be carried out by reacting compound (IX) with a "sulfonate prepared from an alcohol having substituent (s)" in the presence of a base, in an inert solvent.

Examples of the above-mentioned "base" include "inorganic bases", "basic salts", "aromatic amines", "tertiary amines", "hydrides of alkali metal or alkaline earth metal" and the like. The amount of the "base" to be used is generally 1 to 10 equivalents, preferably 1 to 2 equivalents, relative to compound (IX).

Examples of the above-mentioned "inert solvent" include nitrile solvents, amide solvents, halogenated hydrocarbon solvents, ether solvents, aromatic solvents and the like. Of these, DMF, N,N-dimethylacetamide is preferable. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

The above-mentioned "sulfonate prepared from an alcohol having substituent(s)" can be produced by reacting an alcohol having substituent(s) with a sulfonating agent in the presence of a base, in an inert solvent. The amount of the "sulfonate prepared from an alcohol having substituent(s)" to be used is generally 1 to 10 equivalents, preferably 1 to 2 equivalents, relative to compound (IX).

Examples of the above-mentioned "alcohol having substituent(s)" include the alcohols produced in Reaction Schemes 40 to 43 mentioned below, methyl alcohols having optionally fused 5- to 7-membered cyclic group(s) which is(are) optionally substituted, and the like. Specific examples thereof include (4-methoxyphenyl)methanol, (4-ethoxyphenyl)methanol and the like.

Examples of the above-mentioned "sulfonating agent" include methanesulfonyl chloride, p-toluenesulfonyl chloride and the like. The amount of the "sulfonating agent" to be used is generally 1 to 10 equivalents, preferably 1 to 2 equivalents, relative to the alcohol having substituent(s).

Examples of the above-mentioned "base" include "inorganic bases", "basic salts", "aromatic amines", "tertiary amines", "hydrides of alkali metal or alkaline earth metal" and the like. The amount of the "base" to be used is generally 1 to 10 equivalents, preferably 1 to 2 equivalents, relative to the alcohol having substituent(s).

Examples of the above-mentioned "inert solvent" include nitrile solvents, amide solvents, halogenated hydrocarbon solvents, ether solvents, aromatic solvents and the like. These may be used in a mixture of two or more kinds thereof at an appropriate ratio.

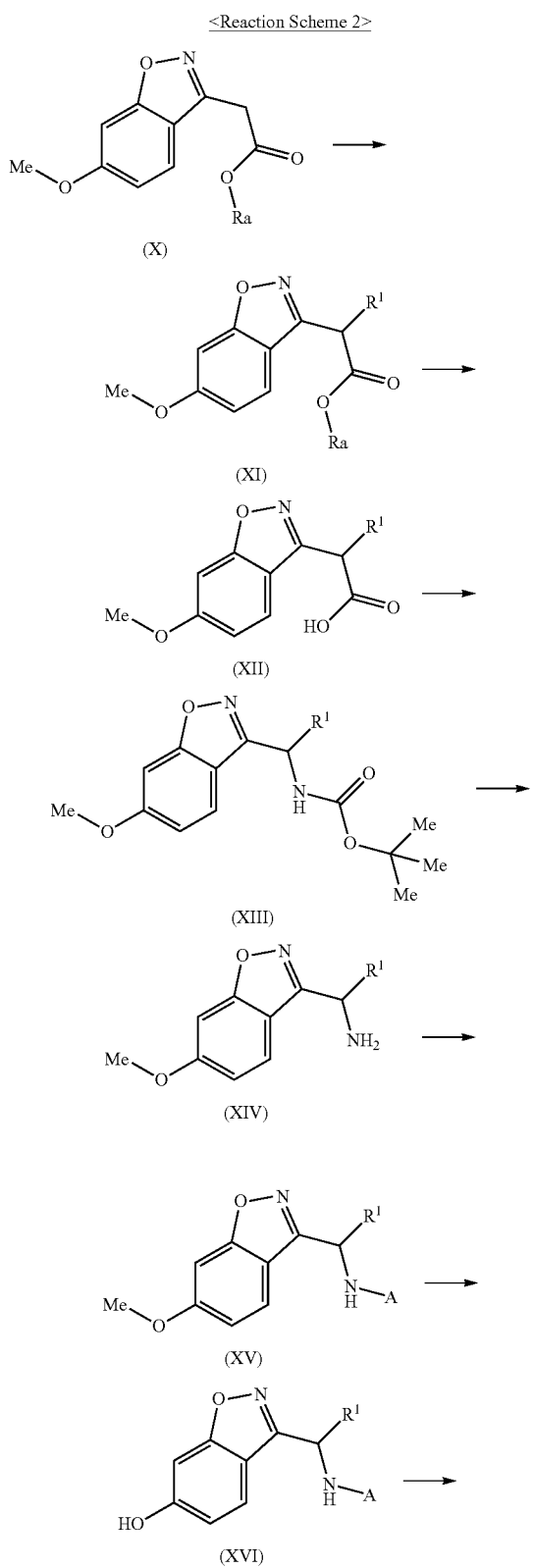

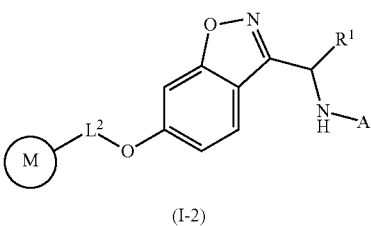

(I-2)

wherein M, $R^1$, A, $L^2$ and Ra are independently as defined above.

Compound (X) may be easily commercially available, or can also be produced according to a method known per se, for example, the method described in PhotoChemistry, pages 539-544, 1971, or a method analogous thereto.

Compound (XI) can be produced, for example, from compound (X), by a method similar to the alkylation reaction of compound (III) in the aforementioned Reaction Scheme 1.

Compound (XII) can be produced, for example, from compound (XI) by a method similar to hydrolysis of compound (IV) in the aforementioned Reaction Scheme 1.

Compound (XIII) can be produced, for example, from compound (XII) by a method similar to the Curtiusre arrangement reaction of compound (V) in the aforementioned Reaction Scheme 1.

Compound (XIV) can be produced, for example, by subjecting compound (XIII) to deprotection. The deprotection can be carried out according to a method known per se, for example, the method described in Protective Groups in Organic Synthesis, John Wiley and Sons (1980) or the like.

Compound (XV) can be produced, for example, from compound (XIV) by a method similar to the acylation reaction of compound (VII) in the aforementioned Reaction Scheme 1.

Compound (XVI) can be produced, for example, by subjecting compound (XV) to deprotection. The deprotection can be carried out according to a method known per se, for example, the method described in Protective Groups in Organic Synthesis, John Wiley and Sons (1980) or the like.

Compound (I-2) can be produced, for example, from compound (XVI) by a method similar to the alkylation reaction of compound (IX) in the aforementioned Reaction Scheme 1.

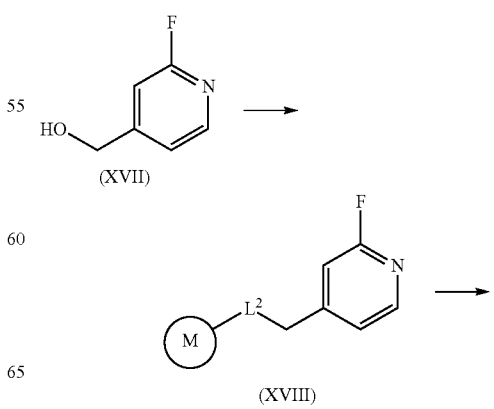

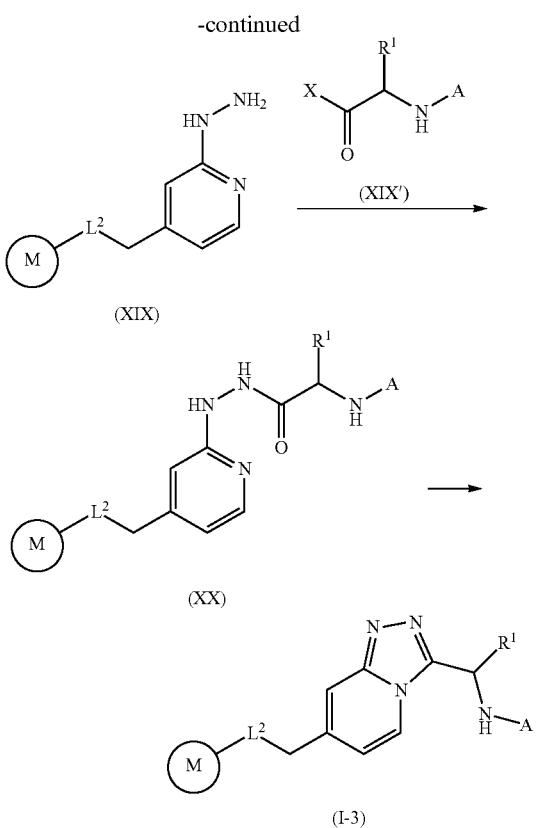

wherein M, R$^1$, A and L$^2$ are independently as defined above, and X is a leaving group.

Compound (XVII) may be easily commercially available, or can also be produced according to a method known per se or a method analogous thereto.

Compound (XVIII) can be produced, for example, by subjecting compound (XVII) to a substitution reaction.

Examples of the substitution reaction include the following "method using a base and a 5- to 7-membered cyclic halide", "method employing the Mitsunobu reaction" and the like.

The "method using a base and a 5- to 7-membered cyclic halide" can be carried out according to a method known per se, for example, the method described in Journal of Chemical Society, pages 1530-1534, 1937 or the like, or a method analogous thereto.

This reaction is carried out by reacting compound (XVII) with a 5- to 7-membered cyclic halide in the presence of a base, in an inert solvent.

Examples of the above-mentioned "5- to 7-membered cyclic halide" include optionally fused 5- to 7-membered cyclic halides which is(are) optionally substituted, such as 2-chloro-5-ethoxypyridine and the like, and the like. The amount of the "5- to 7-membered cyclic halide" to be used is generally 1 to 10 equivalents, preferably 1 to 5 equivalents, relative to compound (XVII).

Examples of the above-mentioned "base" include "inorganic bases", "basic salts", "aromatic amines", "hydrides of alkali metal or alkaline earth metal", "alkyl metals", "aryl metals", "metal alkoxides" and the like. The amount of the "base" to be used is generally 1 to 10 equivalents, preferably 1 to 5 equivalents, relative to compound (XVII).

Examples of the above-mentioned "inert solvent" include nitrile solvents, amide solvents, halogenated hydrocarbon solvents, ether solvents and the like. These may be used in a mixture of two or more kinds thereof at an appropriate ratio. Of these, THF, DMF and the like are preferable.

The reaction temperature is generally −100° C. to 250° C., preferably 0° C. to 100° C.

The reaction time is generally 5 min to 48 hr, preferably 30 min to 24 hr.

The "method employing the Mitsunobu reaction" can be carried out according to a method known per se, for example, the method described in Tetrahedron Letters, pages 769-770, 1980 or the like, or a method analogous thereto.

This reaction is carried out by reacting compound (XVII) a 5- to 7-membered cyclic alcohol or thiol and the like in the presence of a hydroxyl group-activator in an inert solvent.

Examples of the above-mentioned "5- to 7-membered cyclic alcohol or thiol" include optionally fused 5- to 7-membered cyclic alcohols or thiols which is(are) optionally substituted, and the like. Specific examples thereof include 4-methoxyphenol, 4-ethoxyphenol and the like. The amount of the "5- to 7-membered cyclic alcohol or thiol" to be used is generally 1 to 10 equivalents, preferably 1 to 5 equivalents, relative to compound (XVII).

Examples of the above-mentioned "hydroxyl group-activator" include cyanomethylenetri-n-butylphosphorane, a combination of DEAD and triphenylphosphine, and the like. The amount of the "hydroxyl group-activator" to be used is generally 1 to 10 equivalents, preferably 1 to 1.5 equivalents, relative to compound (XVII).

Examples of the above-mentioned "inert solvent" include aromatic solvents, aliphatic hydrocarbon solvents, ether solvents, ester solvents, amide solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

Compound (XIX) can be produced, for example, by subjecting compound (XVIII) to a substitution reaction.

The substitution reaction can be carried out according to a method known per se, for example, the method described in Journal of Organic Chemistry, pages 2494-2502, 2005 or the like, or a method analogous thereto.

This reaction is carried out by reacting compound (XVIII) with hydrazine in an inert solvent.

Examples of the above-mentioned "hydrazine" include hydrazine monohydrate. The amount of the "hydrazine" to be used is generally 1 to 10 equivalents, preferably 1 to 5 equivalents, relative to compound (XVIII).

Examples of the above-mentioned "inert solvent" include aromatic solvents, aliphatic hydrocarbon solvents, ether solvents, ester solvents, amide solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

Compound (XX) can be produced, for example, by subjecting compound (XIX) to a condensation reaction with compound (XIX'), by a method similar to the acylation reaction of compound (VII) in the aforementioned Reaction Scheme 1.

Compound (XIX') may be an optically active form or a racemate. Specific examples thereof include N-acetyl-DL-alanine, N-tert-butoxycarbonylalanine or reactive derivatives thereof, and the like. The amount of compound (XIX') to be used is generally 1 to 5 equivalents, preferably 1 to 1.5 equivalents, relative to compound (XIX).

Compound (I-3) can be produced, for example, by subjecting compound (XX) to a cyclization reaction.

The cyclization reaction can be carried out according to a method known per se, for example, the method described in Tetrahedron, pages 5177-5186, 1990 or the like, or a method analogous thereto.

This reaction is carried out by reacting compound (XX) in an inert solvent. An acid, an anhydride, a dehydrating agent, an activator and the like may be used, as necessary.

Examples of the above-mentioned "acid, anhydride, dehydrating agent or activator" include sulfuric acid, hydrochloric acid, methanesulfonic acid, pyridinium methanesulfonate, acetic acid, trifluoroacetic acid, acetic anhydride, polyphosphoric acid, diphosphorus pentoxide, phosphoryl chloride, triphenylphosphine, DEAD and the like. In addition, azido (trimethyl)silane may be added as an additive. The amount of the "acid, anhydride, dehydrating agent or activator" to be used is generally 0.01 to 20 equivalents, preferably 1 to 5 equivalents, relative to compound (XX). Excess amount thereof may be used as a solvent.

Examples of the above-mentioned "inert solvent" include aromatic solvents, halogenated hydrocarbon solvents, nitrile solvents, alcohol solvents, ketone solvents aromatic solvents, aliphatic hydrocarbon solvents, ether solvents, ester solvents, amide solvents and the like. These may be used in a mixture of two or more kinds thereof at an appropriate ratio.

The reaction temperature is generally −70 to 250° C., preferably −20 to 200° C.

The reaction time is generally 0.1 to 100 hr, preferably 0.1 to 40 hr.

<Reaction Scheme 4>

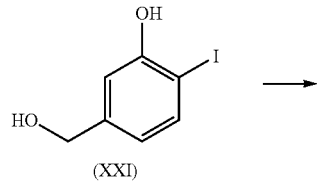

(XXI)

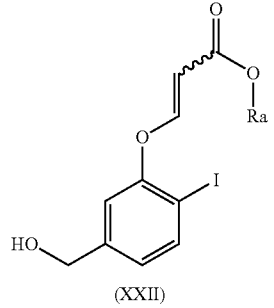

(XXII)

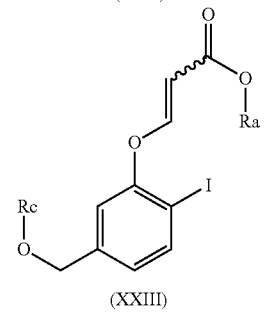

(XXIII)

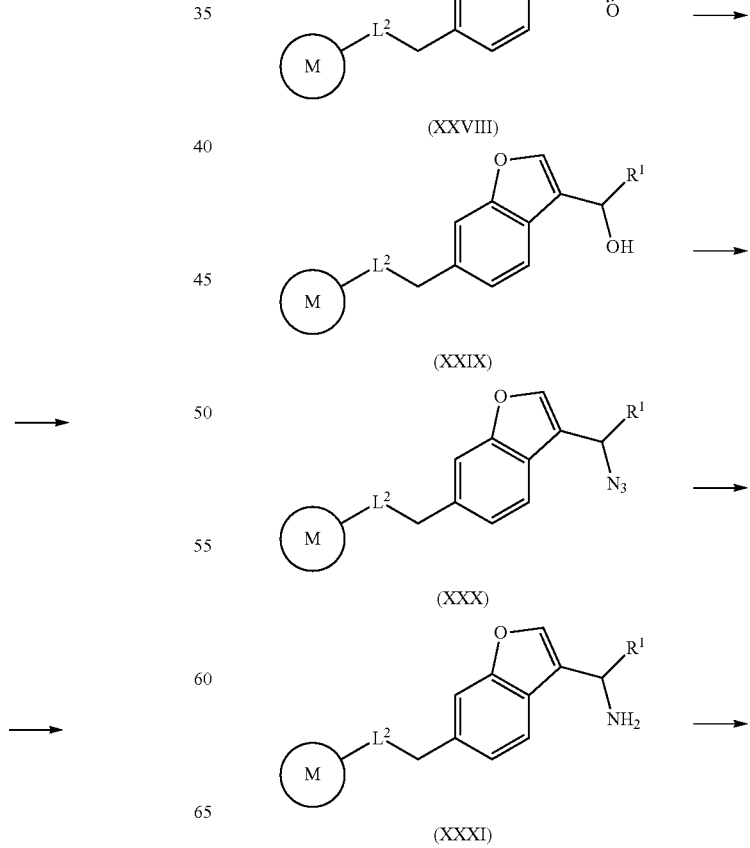

-continued

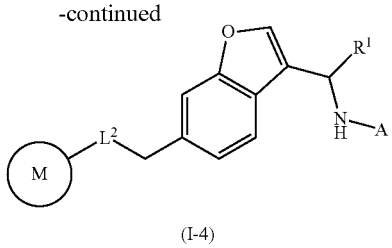

(I-4)

wherein M, $R^1$, A, $L^2$ and Ra are independently as defined above, and Rc is a hydroxy-protecting group generally used in organic chemistry and the like.

Compound (XXI) may be easily commercially available, or can also be produced according to a method known per se or a method analogous thereto.

Compound (XXII) can be produced, for example, by subjecting compound (XXI) to the Michael addition reaction.

The Michael addition reaction can be carried out according to a method known per se, for example, the method described in Organic Letters, pages 5661-5664, 2006 or the like, or a method analogous thereto.

This reaction is carried out by reacting compound (XXI) with a propiolate in the presence of a base, in an inert solvent.

Examples of the above-mentioned "base" include "aromatic amines", "tertiary amines" and the like. The amount of the "base" to be used is generally 0.1 to 20 equivalents, preferably 1 to 5 equivalents, relative to compound (XXI).

Examples of the above-mentioned "inert solvent" include alcohol solvents, aromatic solvents, aliphatic hydrocarbon solvents, ether solvents, ester solvents, amide solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

Compound (XXIII) can be produced, for example, by subjecting compound (XXII) to a protection reaction. The protection reaction can be carried out according to a method known per se, for example, the method described in Protective Groups in Organic Synthesis, John Wiley and Sons (1980) or the like.

Compound (XXIV) can be produced, for example, by subjecting compound (XXIII) to the Heck reaction.

The Heck reaction can be carried out according to a method known per se, for example, the method described in Organic Letters, pages 5661-5664, 2006 or the like, or a method analogous thereto.

This reaction is carried out by reacting compound (XXIII) in the presence of a transition metal catalyst, a ligand and a base, in an inert solvent, under an inert gas atmosphere.

Examples of the above-mentioned "transition metal catalyst" include palladium catalysts, nickel catalysts, iron catalysts, cobalt catalysts and the like. Examples of the palladium catalyst include palladium acetate, dichlorobis(benzonitrile) palladium and the like. The amount of the "transition metal catalyst" to be used is generally 0.01 to 20 equivalents, preferably 0.01 to 0.2 equivalents, relative to compound (XXIII).

Examples of the above-mentioned "ligand" include phosphine ligands. Examples of the phosphine ligand include triphenylphosphine and the like. The amount of the "ligand" to be used is generally 0.01 to 20 equivalents, preferably 0.01 to 0.2 equivalents, relative to compound (XXIII).

Examples of the above-mentioned "base" include "aromatic amines", "tertiary amines" and the like. The amount of the "base" to be used is generally 0.1 to 20 equivalents, preferably 1 to 5 equivalents, relative to compound (XXIII).

Examples of the above-mentioned "inert solvent" include alcohol solvents, aromatic solvents, aliphatic hydrocarbon solvents, ether solvents, ester solvents, amide solvents and the like. These may be used in a mixture of two or more kinds thereof at an appropriate ratio.

Examples of the above-mentioned "inert gas" include nitrogen, argon and the like.

The reaction temperature is generally −70 to 150° C., preferably −20 to 150° C.

The reaction time is generally 0.1 to 100 hr, preferably 0.1 to 40 hr.

Compound (XXV) can be produced, for example, by subjecting compound (XXIV) to an amidation reaction.

The amidation reaction can be carried out according to a method known per se, for example, the method described in European Journal of Organic Chemistry, pages 2609-2622, 1999 or the like, or a method analogous thereto.

This reaction is carried out by reacting compound (XXIV) with N,O-dimethylhydroxylamine or a salt thereof in the presence of a base, in an inert solvent.

The amount of the N,O-dimethylhydroxylamine or a salt thereof to be used is generally 1 to 10 equivalents, preferably 1 to 5 equivalents, relative to compound (XXIV).

Examples of the above-mentioned "base" include "alkyl metals" and the like. When N,O-dimethylhydroxylamine is used, the amount of the "base" to be used is generally 1 to 10 equivalents, preferably 1 to 5 equivalents, relative to compound (XXIV). When a salt of N,O-dimethylhydroxylamine is used, the amount of the "base" to be used is generally 2 to 20 equivalents, preferably 2 to 10 equivalents, relative to compound (XXIV).

Examples of the above-mentioned "inert solvent" include aromatic solvents, aliphatic hydrocarbon solvents, ether solvents, amide solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

Compound (XXVI) can be produced, for example, by subjecting compound (XXV) to a substitution reaction.

The substitution reaction can be carried out according to a method known per se, for example, the method described in Tetrahedron Letters, pages 3309-3312, 1994 or the like, or a method analogous thereto.

This reaction is carried out by reacting compound (XXV) with an "alkyl metals" in an inert solvent.

Examples of the above-mentioned "alkyl metals" include methyl magnesium bromide and the like. The amount of the "alkyl metals" to be used is generally 1 to 10 equivalents, preferably 1 to 5 equivalents, relative to compound (XXV).

Examples of the above-mentioned "inert solvent" include ether solvents and the like. Ether solvents may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

Compound (XXVII) can be produced, for example, by subjecting compound (XXVI) to deprotection. The deprotection can be carried out according to a method known per se, for example, the method described in Protective Groups in Organic Synthesis, John Wiley and Sons (1980) or the like.

Compound (XXVIII) can be produced, for example, from compound (XXVII) by a method similar to the substitution reaction of compound (XVII) in the aforementioned Reaction Scheme 3.

Compound (XXIX) can be produced, for example, by subjecting compound (XXVIII) to a reduction reaction.

The reduction reaction can be carried out according to a method known per se, for example, the method described in Bioorganic and Medicinal Chemistry, pages 2945-2952, 1999 or the like, or a method analogous thereto.

This reaction is carried out by reacting compound (XXVIII) in the presence of a reducing agent, in an inert solvent.

Examples of the above-mentioned "reducing agent" include metal hydride compounds (e.g., sodium bis(2-methoxyethoxy)aluminum hydride, diisobutylaluminum hydride), metal hydride complex compounds (e.g., sodium borohydride, sodium cyanoborohydride, lithium aluminum hydride, sodium aluminum hydride) and the like. The amount of the "reducing agent" to be used is generally 0.1 to 20 equivalents, preferably 1 to 5 equivalents, relative to compound (XXVIII).

Examples of the above-mentioned "inert solvent" include alcohol solvents, aromatic solvents, aliphatic hydrocarbon solvents, ether solvents, ester solvents, amide solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

Compound (XXX) can be produced, for example, by subjecting compound (XXIX) to a substitution reaction.

Examples of the substitution reaction include "two step method" which is carried out by preparing the sulfonate and subjecting the sulfonate to an azidation, and "method using an azide ester reagent".

The "two step method" can be carried out according to a method known per se, for example, the method described in Journal of Organic Chemistry, pages 1663-1671, 1992 or the like, or a method analogous thereto.

This reaction is carried out by reacting compound (XXIX) with a substituted sulfonyl chloride in the presence of a base, in an inert solvent, and then reacting the resulting substituted sulfonate corresponding to compound (XXIX) with an azide compound.

Examples of the above-mentioned "substituted sulfonyl chloride" include methanesulfonyl chloride and the like. The amount of the "substituted sulfonyl chloride" to be used is generally 1 to equivalents, preferably 1 to 5 equivalents, relative to compound (XXIX).

Examples of the above-mentioned "base" include "aromatic amines", "tertiary amines" and the like. The amount of the "base" to be used is generally 1 to 20 equivalents, preferably 1 to 5 equivalents, relative to compound (XXIX).

Examples of the above-mentioned "inert solvent" include aromatic solvents, aliphatic hydrocarbon solvents, ether solvents, ester solvents, amide solvents and the like. These may be used in a mixture of two or more kinds thereof at an appropriate ratio.

Examples of the above-mentioned "azide compound" include sodium azide and the like. The amount of the "azide compound" to be used is generally 1 to 20 equivalents, preferably 1 to 5 equivalents, relative to compound (XXIX).

The reaction temperature is generally −70 to 150° C., preferably −20 to 100° C.

The reaction time is generally 0.1 to 100 hr, preferably 0.1 to 40 hr.

The "method using an azide ester reagent" can be carried out according to a method known per se, for example, the method described in Journal of Organic Chemistry, pages 5886-5888, 1993 or the like, or a method analogous thereto.

This reaction is carried out by reacting compound (XXIX) with an azide ester reagent in the presence of a base, in an inert solvent.

Examples of the above-mentioned "azide ester reagent" include diphenyl azidophosphate and the like. The amount of the "azide ester reagent" to be used is generally 1 to 20 equivalents, preferably 1 to 5 equivalents, relative to compound (XXIX).

Examples of the above-mentioned "base" include "aromatic amines", "tertiary amines" and the like. The amount of the "base" to be used is generally 1 to 20 equivalents, preferably 1 to 5 equivalents, relative to compound (XXIX).

Examples of the above-mentioned "inert solvent" include aromatic solvents, aliphatic hydrocarbon solvents, ether solvents, ester solvents, amide solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

Compound (XXXI) can be produced, for example, by subjecting compound (XXX) to a reduction reaction.

The substitution reaction can be carried out according to a method known per se, for example, the method described in Journal of Organic Chemistry, pages 4892-4897, 1990 or the like, or a method analogous thereto.

This reaction is carried out by reacting compound (XXX) with a phosphine compound in the presence of water, in an inert solvent.

Examples of the above-mentioned "phosphine compound" include triphenylphosphine and the like. The amount of the "phosphine compound" to be used is generally 1 to 20 equivalents, preferably 1 to 5 equivalents, relative to compound (XXX).

Examples of the above-mentioned "inert solvent" include aromatic solvents, aliphatic hydrocarbon solvents, ether solvents, ester solvents, amide solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

Compound (I-4) can be produced, for example, from compound (XXXI) by a method similar to the acylation reaction of compound (VII) in the aforementioned Reaction Scheme 1.

<Reaction Scheme 5>

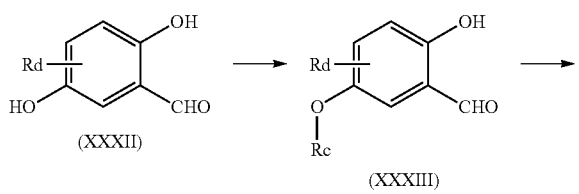

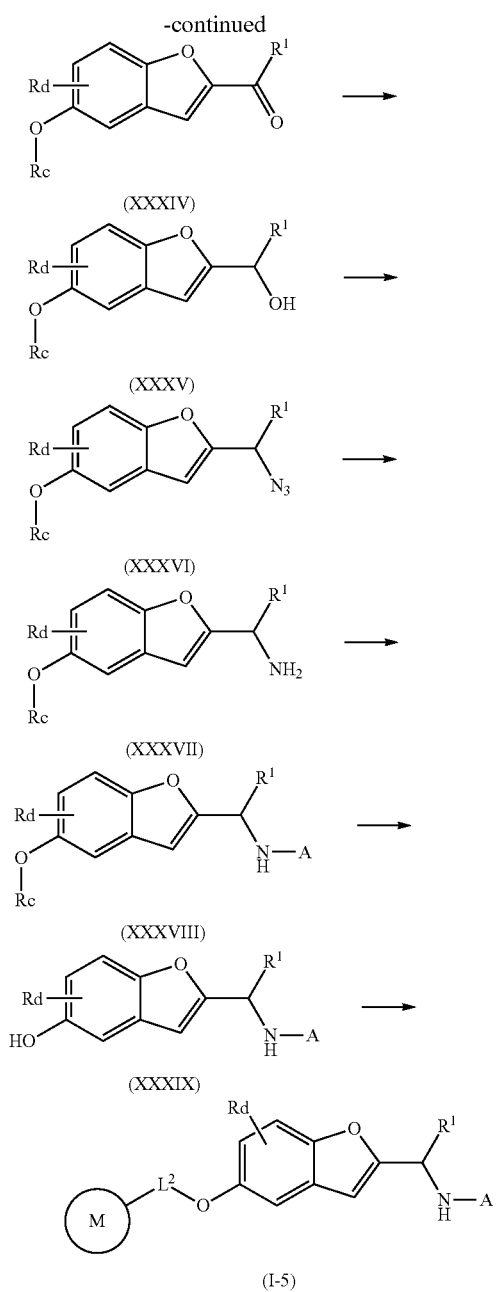

(I-5)

wherein M, $R^1$, A, $L^2$, Rc are independently as defined above, and Rd is an optionally substituted $C_{1-6}$ alkyl group or an optionally substituted benzyl group, or a halogen atom.

Compound (XXXII) may be easily commercially available, or can also be produced according to a method known per se or a method analogous thereto.

Compound (XXXIII) can be produced, for example, by subjecting compound (XXXII) to a protection reaction or an alkylation reaction.

The above-mentioned "protection reaction" can be carried out according to a method known per se, for example, the method described in Protective Groups in Organic Synthesis, John Wiley and Sons (1980) or the like.

The alkylation reaction can be carried out, for example, by a method similar to the alkylation reaction of compound (IX) in the aforementioned Reaction Scheme 1.

Compound (XXXIV) can be produced, for example, by subjecting compound (XXXIII) to a cyclization reaction.

The cyclization reaction can be carried out according to a method known per se, for example, the method described in Tetrahedron, pages 7663-7666, 1990 or the like, or a method analogous thereto.

This reaction is carried out by reacting compound (XXXIII) with an α-halocarbonyl compound in the presence of a base, in an inert solvent.

Examples of the above-mentioned "α-halocarbonyl compound" include 1-bromopropan-2-one and the like. The amount of the "α-halocarbonyl compound" to be used is generally 1 to 20 equivalents, preferably 1 to 5 equivalents, relative to compound (XXXIII).

Examples of the above-mentioned "base" include "inorganic bases", "basic salts", "hydrides of alkali metal or alkaline earth metal", "metal alkoxides" and the like. The amount of the "base" to be used is generally 2 to 10 equivalents, preferably 2 to 5 equivalents, relative to compound (XXXIII).

Examples of the above-mentioned "inert solvent" include nitrile solvents, alcohol solvents, ketone solvents aromatic solvents, aliphatic hydrocarbon solvents, ether solvents, ester solvents, amide solvents and the like. These may be used in a mixture of two or more kinds thereof at an appropriate ratio. Of these, acetonitrile, ethanol is preferable.

The reaction temperature is generally −70 to 150° C., preferably −20 to 100° C.

The reaction time is generally 0.1 to 100 hr, preferably 0.1 to 40 hr.

Compound (XXXV) can be produced, for example, from compound (XXXIV) by a method similar to the reduction reaction of compound (XXVIII) in the aforementioned Reaction Scheme 4.

Compound (XXXVI) can be produced, for example, from compound (XXXV) by a method similar to the substitution reaction of compound (XXIX) in the aforementioned Reaction Scheme 4.

Compound (XXXVII) can be produced, for example, from compound (XXXVI) by a method similar to the reduction reaction of compound (XXX) in the aforementioned Reaction Scheme 4.

Compound (XXXVIII) can be produced, for example, from compound (XXXVII) by a method similar to the acylation reaction of compound (VII) in the aforementioned Reaction Scheme 1.

Compound (XXXIX) can be produced, for example, by subjecting compound (XXXVIII) to deprotection. The deprotection can be carried out according to a method known per se, for example, the method described in Protective Groups in Organic Synthesis, John Wiley and Sons (1980) or the like.

Compound (I-5) can be produced, for example, from compound (XXXIX) by a method similar to the alkylation reaction of compound (IX) in the aforementioned Reaction Scheme 1.

<Reaction Scheme 6>

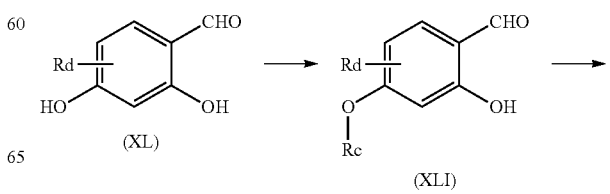

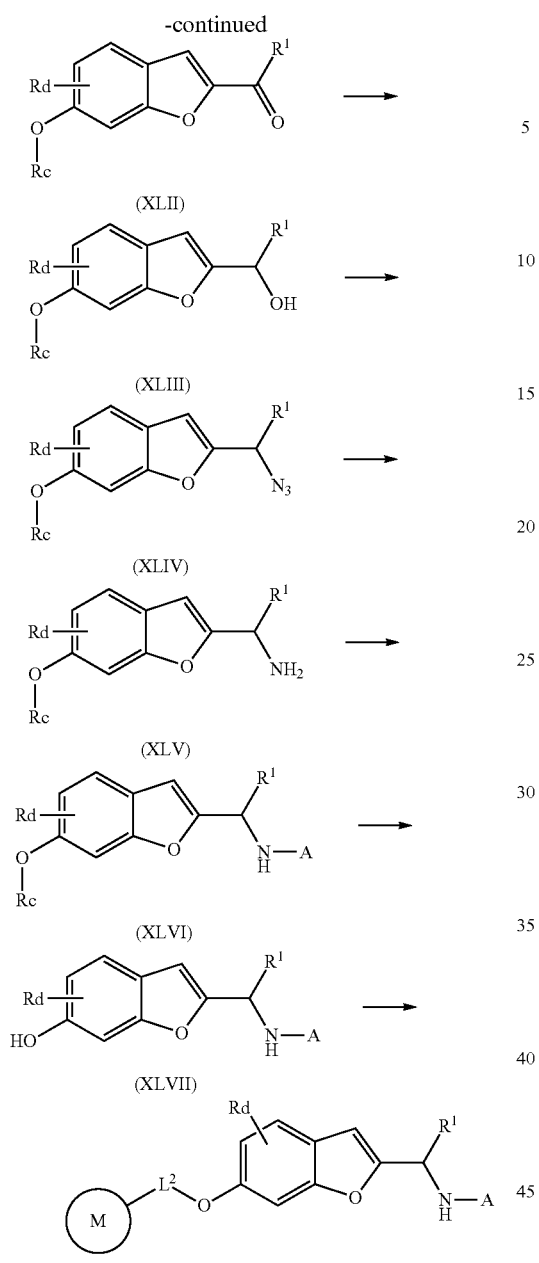

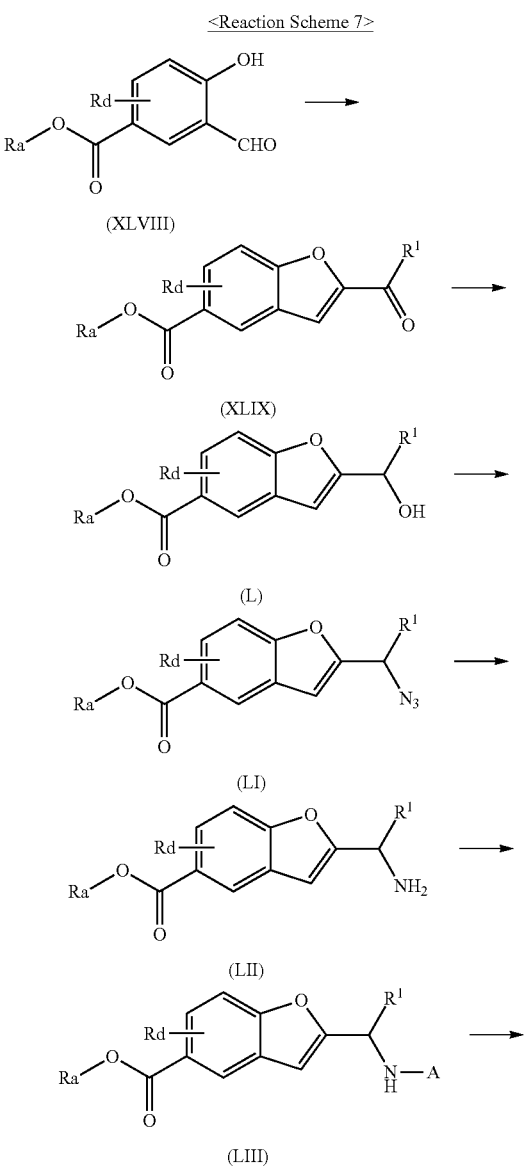

Compound (XLIV) can be produced, for example, from compound (XLIII) by a method similar to the substitution reaction of compound (XXIX) in the aforementioned Reaction Scheme 4.

Compound (XLV) can be produced, for example, from compound (XLIV) by a method similar to the reduction reaction of compound (XXX) in the aforementioned Reaction Scheme 4.

Compound (XLVI) can be produced, for example, from compound (XLV) by a method similar to the acylation reaction of compound (VII) in the aforementioned Reaction Scheme 1.

Compound (XLVII) can be produced, for example, by subjecting compound (XLVI) to deprotection. The deprotection can be carried out according to a method known per se, for example, the method described in Protective Groups in Organic Synthesis, John Wiley and Sons (1980) or the like.

Compound (I-6) can be produced, for example, from compound (XLVII) by a method similar to the alkylation reaction of compound (IX) in the aforementioned Reaction Scheme 1.

wherein M, R$^1$, A, L$^2$, Rc and Rd are independently as defined above.

Compound (XL) may be easily commercially available, or can also be produced according to a method known per se or a method analogous thereto.

Compound (XLI) can be produced, for example, from compound (XL) by a method similar to the protection reaction or alkylation reaction of the compound (XXXII) in aforementioned Reaction Scheme 5.

Compound (XLII) can be produced, for example, from compound (XLI) by a method similar to the cyclization reaction of compound (XXXIII) in the aforementioned Reaction Scheme 5.

Compound (XLIII) can be produced, for example, from compound (XLII) by a method similar to the reduction reaction of compound (XXVIII) in the aforementioned Reaction Scheme 4.

-continued

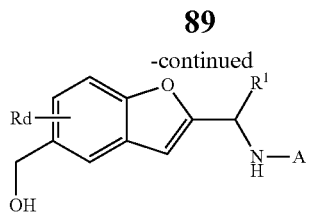

(LIV)

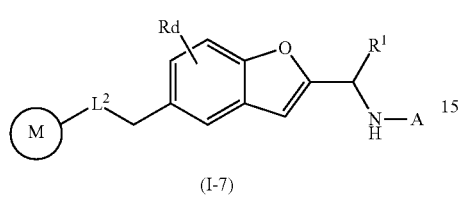

(I-7)

wherein M, $R^1$, A, $L^2$, Ra and Rd are independently as defined above.

Compound (XLVIII) may be easily commercially available, or can also be produced according to a method known per se or a method analogous thereto.

Compound (XLIX) can be produced, for example, from compound (XLVIII) by a method similar to the cyclization reaction of compound (XXXIII) in the aforementioned Reaction Scheme 5.

Compound (L) can be produced, for example, from compound (XLIX) by a method similar to the reduction reaction of compound (XXVIII) in the aforementioned Reaction Scheme 4.

Compound (LI) can be produced, for example, from compound (L) by a method similar to the substitution reaction of compound (XXIX) in the aforementioned Reaction Scheme 4.

Compound (LII) can be produced, for example, from compound (LI) by a method similar to the reduction reaction of compound (XXX) in the aforementioned Reaction Scheme 4.

Compound (LIII) can be produced, for example, from compound (LII) by a method similar to the acylation reaction of compound (VII) in the aforementioned Reaction Scheme 1.

Compound (LIV) can be produced, for example, from compound (LIII) by a method similar to the reduction reaction of compound (XXVIII) in the aforementioned Reaction Scheme 4.

Compound (I-7) can be produced, for example, from compound (LIV) by a method similar to the substitution reaction of compound (XVII) in the aforementioned Reaction Scheme 3.

<Reaction Scheme 8>

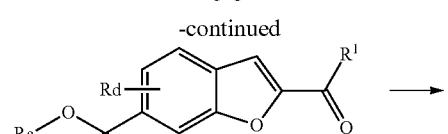

(LV)

-continued

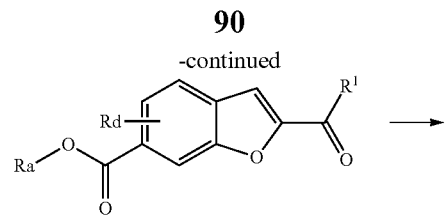

(LVI)

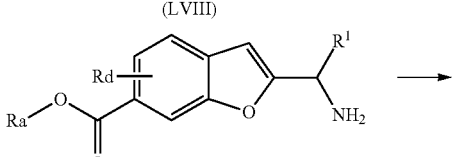

(LVII)

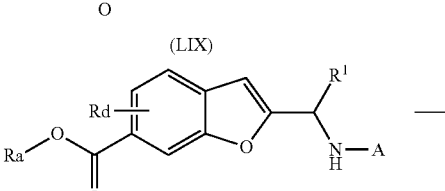

(LVIII)

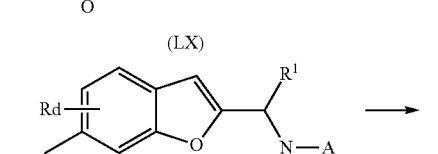

(LIX)

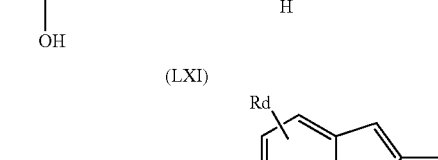

(LX)

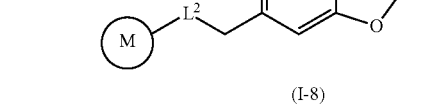

(LXI)

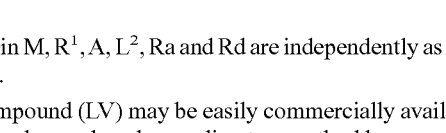

(I-8)

wherein M, $R^1$, A, $L^2$, Ra and Rd are independently as defined above.

Compound (LV) may be easily commercially available, or can also be produced according to a method known per se or a method analogous thereto.

Compound (LVI) can be produced, for example, from compound (LV) by a method similar to the cyclization reaction of compound (XXXIII) in the aforementioned Reaction Scheme 5.

Compound (LVII) can be produced, for example, from compound (LVI) by a method similar to the reduction reaction of compound (XXVIII) in the aforementioned Reaction Scheme 4.

Compound (LVIII) can be produced, for example, from compound (LVII) by a method similar to the substitution reaction of compound (XXIX) in the aforementioned Reaction Scheme 4.

Compound (LIX) can be produced, for example, from compound (LVIII) by a method similar to the reduction reaction of compound (XXX) in the aforementioned Reaction Scheme 4.

Compound (LX) can be produced, for example, from compound (LIX) by a method similar to the acylation reaction of compound (VII) in the aforementioned Reaction Scheme 1.

Compound (LXI) can be produced, for example, from compound (LX) by a method similar to the reduction reaction of compound (XXVIII) in the aforementioned Reaction Scheme 4.

Compound (I-8) can be produced, for example, from compound (LXI) by a method similar to the substitution reaction of compound (XVII) in the aforementioned Reaction Scheme 3.

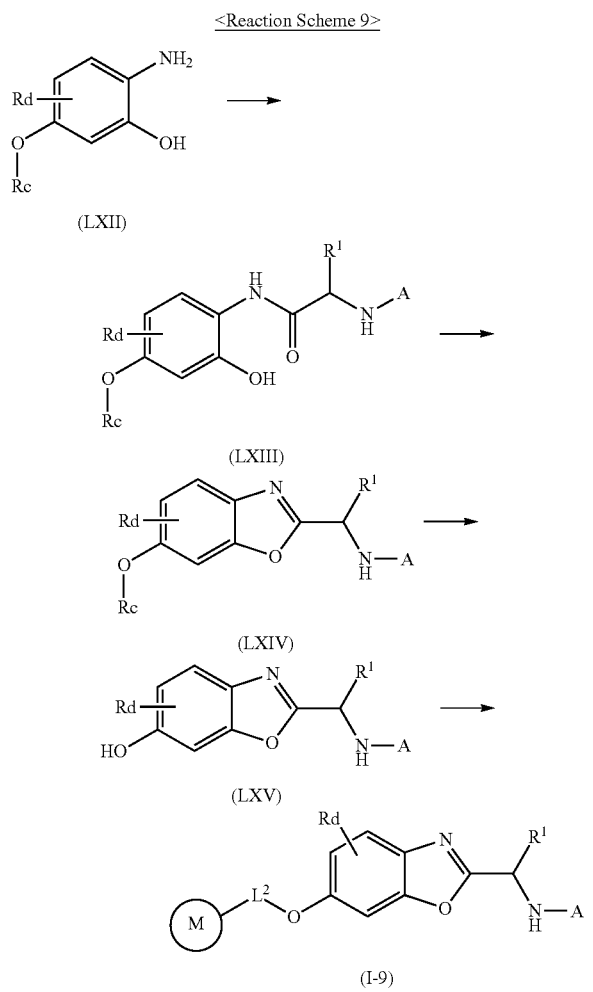

wherein M, $R^1$, A, $L^2$, Rc and Rd are independently as defined above.

Compound (LXII) may be easily commercially available, or can also be produced according to a method known per se or a method analogous thereto.

Compound (LXIII) can be produced, for example, from compound (LXII) by a method similar to the condensation reaction of compound (XIX) with compound (XIX') in the aforementioned Reaction Scheme 3.

Compound (LXIV) can be produced, for example, from compound (LXIII) by a method similar to the cyclization reaction of compound (XX) in the aforementioned Reaction Scheme 3.

Compound (LXV) can be produced, for example, by subjecting compound (LXIV) to deprotection. The deprotection can be carried out according to a method known per se, for example, the method described in Protective Groups in Organic Synthesis, John Wiley and Sons (1980) or the like.

Compound (I-9) can be produced, for example, from compound (LXV) by a method similar to the alkylation reaction of compound (IX) in the aforementioned Reaction Scheme 1.

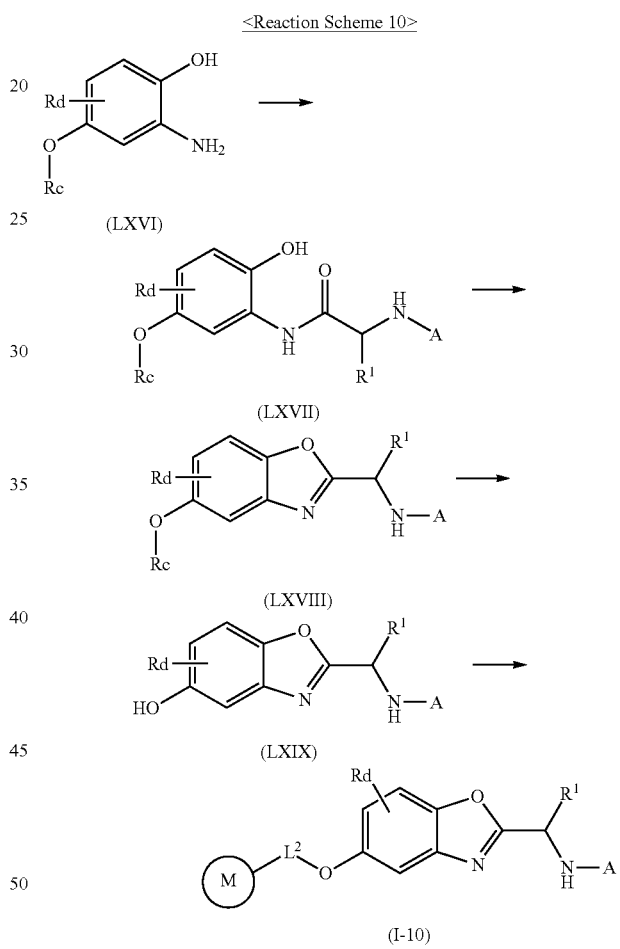

wherein M, $R^1$, A, $L^2$, Rc and Rd are independently as defined above.

Compound (LXVI) may be easily commercially available, or can also be produced according to a method known per se or a method analogous thereto.

Compound (LXVII) can be produced, for example, from compound (LXVI) by a method similar to the condensation reaction of compound (XIX) with compound (XIX') in the aforementioned Reaction Scheme 3.

Compound (LXVIII) can be produced, for example, from compound (LXVII) by a method similar to the cyclization reaction of compound (XX) in the aforementioned Reaction Scheme 3.

Compound (LXIX) can be produced, for example, by subjecting compound (LXVIII) to deprotection. The deprotection can be carried out according to a method known per se, for example, the method described in Protective Groups in Organic Synthesis, John Wiley and Sons (1980) or the like.

Compound (I-10) can be produced, for example, from compound (LXIX) by a method similar to the alkylation reaction of compound (IX) in the aforementioned Reaction Scheme 1.

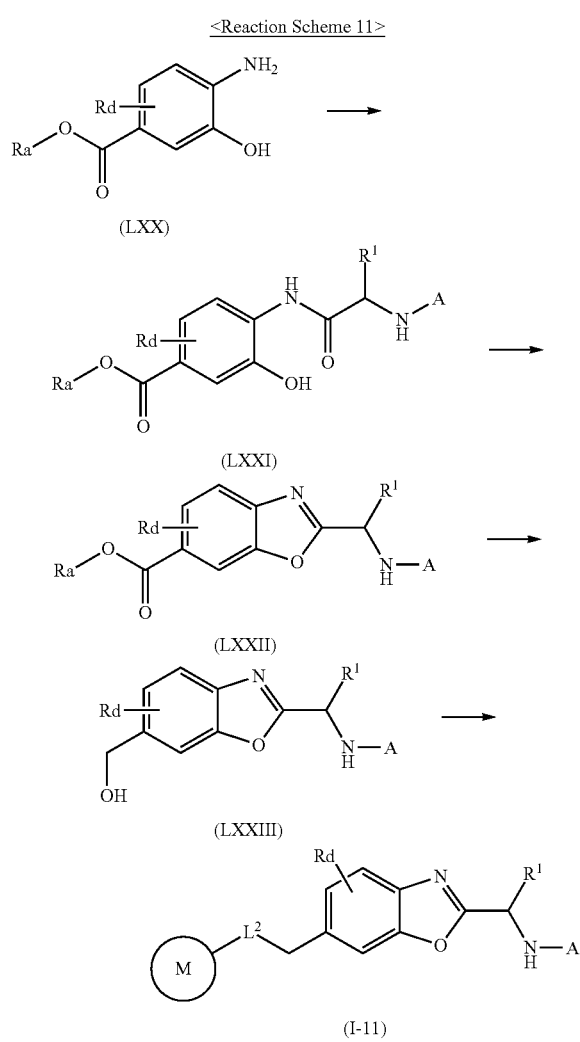

wherein M, R¹, A, L², Ra, Rd are independently as defined above.

Compound (LXX) may be easily commercially available, or can also be produced according to a method known per se or a method analogous thereto.

Compound (LXXI) can be produced, for example, from compound (LXX) by a method similar to the condensation reaction of compound (XIX) with compound (XIX') in the aforementioned Reaction Scheme 3.

Compound (LXXII) can be produced, for example, from compound (LXXI) by a method similar to the cyclization reaction of compound (XX) in the aforementioned Reaction Scheme 3.

Compound (LXXIII) can be produced, for example, from compound (LXXII) y a method similar to the reduction reaction of compound (XXVIII) in the aforementioned Reaction Scheme 4.

Compound (I-11) can be produced, for example, from compound (LXXIII) by a method similar to the substitution reaction of compound (XVII) in the aforementioned Reaction Scheme 3.

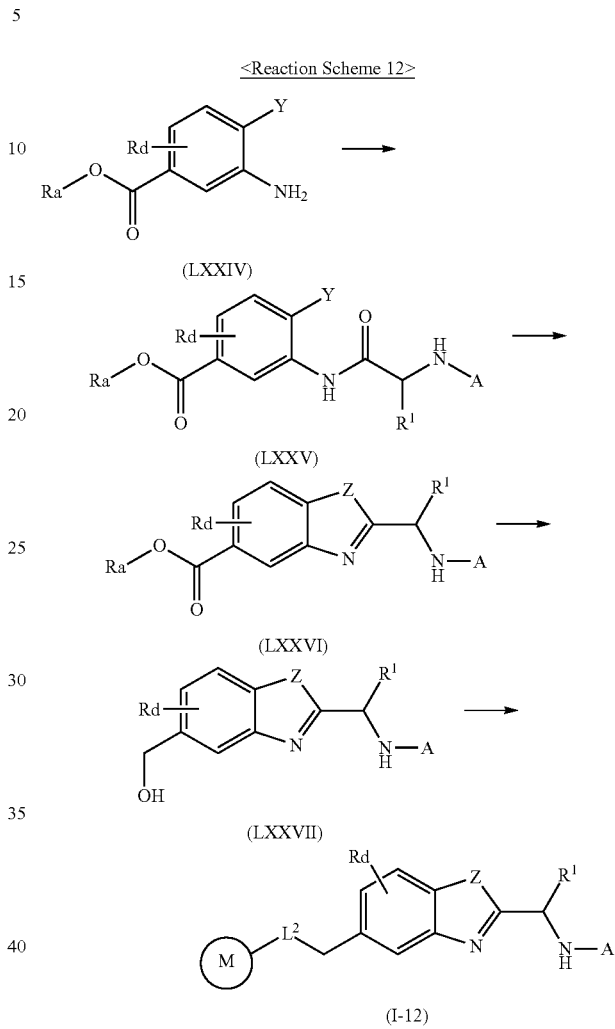

wherein M, R¹, A, L², Ra and Rd are independently as defined above, Y is OH or $NH_2$, and Z is O or NH.

Compound (LXXIV) may be easily commercially available, or can also be produced according to a method known per se or a method analogous thereto.

Compound (LXXV) can be produced, for example, from compound (LXXIV) by a method similar to the condensation reaction of compound (XIX) with compound (XIX') in the aforementioned Reaction Scheme 3.

Compound (LXXVI) can be produced, for example, from compound (LXXV) by a method similar to the cyclization reaction of compound (XX) in the aforementioned Reaction Scheme 3.

Compound (LXXVII) can be produced, for example, from compound (LXXVI) by a method similar to the reduction reaction of compound (XXVIII) in the aforementioned Reaction Scheme 4.

Compound (I-12) can be produced, for example, from compound (LXXVII) by a method similar to the substitution reaction of compound (XVII) in the aforementioned Reaction Scheme 3.

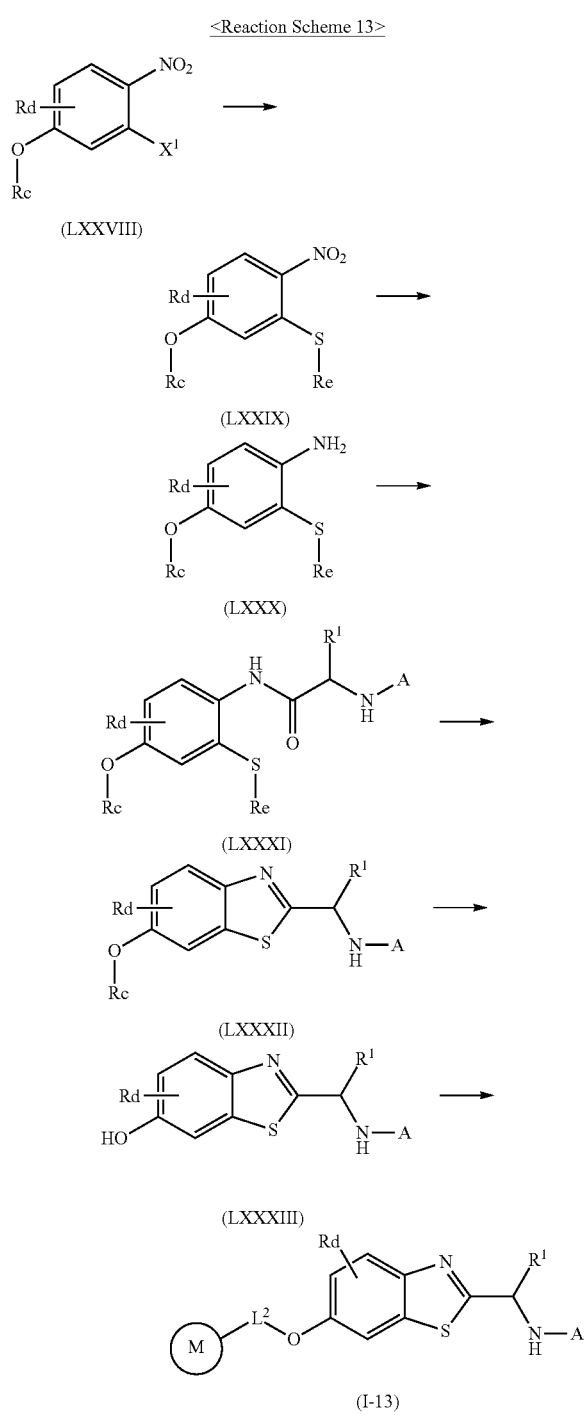

<Reaction Scheme 13>

(LXXVIII)
(LXXIX)
(LXXX)
(LXXXI)
(LXXXII)
(LXXXIII)
(I-13)

wherein M, $R^1$, A, $L^2$, Rc and Rd are independently as defined above, Re is a mercapto-protecting group generally used in organic chemistry and the like, and $X^1$ is a halogen atom.

Compound (LXXVIII) may be easily commercially available, or can also be produced according to a method known per se or a method analogous thereto.

Compound (LXXIX) can be produced, for example, by subjecting compound (LXXVIII) to an ipso substitution reaction or a cross coupling reaction using a transition metal catalyst.

The above-mentioned "ipso substitution reaction" can be carried out according to a method known per se, for example, the method described in Synlett, pages 1255-1259, 2006 or the like, or a method analogous thereto.

This reaction is carried out by reacting compound (LXXVIII) with a substituted thiol in the presence of a base, in an inert solvent.

Examples of the above-mentioned "substituted thiol" include thiols having a removable protecting group as a substituent. Specific examples thereof include 2-ethylhexyl 3-mercaptopropionate and the like. The amount of the "substituted thiol" to be used is generally 1 to 20 equivalents, preferably 1 to 5 equivalents, relative to compound (LXXVIII).

Examples of the above-mentioned "base" include "inorganic bases", "basic salts", "aromatic amines", "tertiary amines", "hydrides of alkali metal or alkaline earth metal" and the like. The amount of the "base" to be used is generally 1 to 20 equivalents, preferably 1 to 5 equivalents, relative to compound (LXXVIII).

Examples of the above-mentioned "inert solvent" include amide solvents, sulfoxide solvents, alcohol solvents, aromatic solvents, aliphatic hydrocarbon solvents, ether solvents, ester solvents and the like. These may be used in a mixture of two or more kinds thereof at an appropriate ratio.

The reaction temperature is generally −70 to 250° C., preferably −20 to 200° C.

The reaction time is generally 0.1 to 100 hr, preferably 0.1 to 40 hr.

The above-mentioned "cross coupling reaction using a transition metal catalyst" can be carried out according to a method known per se, for example, the method described in Tetrahedron, pages 5253-5260, 2005 or the like, or a method analogous thereto.

This reaction is carried out by reacting compound (LXXVIII) with a substituted thiol in the presence of a transition metal catalyst, a ligand and a base, in an inert solvent, under an inert gas atmosphere.

Examples of the above-mentioned "substituted thiol" include thiols having a removable protecting group as a substituent. Specific examples thereof include 2-ethylhexyl 3-mercaptopropionate and the like. The amount of the "substituted thiol" to be used is generally 1 to 20 equivalents, preferably 1 to 5 equivalents, relative to compound (LXXVIII).

Examples of the above-mentioned "transition metal catalyst" include palladium catalysts, nickel catalysts, iron catalysts, cobalt catalysts and the like. Examples of the palladium catalyst include tris(dibenzylideneacetone)dipalladium(0) and the like. The amount of the "transition metal catalyst" to be used is generally 0.01 to 20 equivalents, preferably 0.01 to 0.1 equivalents, relative to compound (LXXVIII).

Examples of the above-mentioned "ligand" include phosphine ligands and the like. Examples of the phosphine ligand include (9,9-dimethyl-9H-xanthene-4,5-diyl)bis(diphenylphosphane)(Xantophos) and the like. The amount of the "ligand" to be used is generally 0.01 to equivalents, preferably 0.01 to 0.1 equivalents, relative to compound (LXXVIII).

Examples of the above-mentioned "base" include "inorganic bases", "basic salts", "aromatic amines", "tertiary amines" and the like. The amount of the "base" to be used is generally 0.1 to 20 equivalents, preferably 1 to 5 equivalents, relative to compound (LXXVIII).

Examples of the above-mentioned "inert solvent" include alcohol solvents, aromatic solvents, aliphatic hydrocarbon solvents, ether solvents, ester solvents, amide solvents and the like. These may be used in a mixture of two or more kinds thereof at an appropriate ratio.

Examples of the above-mentioned "inert gas" include nitrogen, argon and the like.

The reaction temperature is generally −70 to 150° C., preferably −20 to 150° C.

The reaction time is generally 0.1 to 100 hr, preferably 0.1 to 40 hr.

Compound (LXXX) can be produced, for example, by subjecting compound (LXXIX) to a reduction reaction.

The reduction reaction can be carried out according to a method known per se, for example, the method described in Journal of American Chemical Society, pages 2084-2085, 1938 or the like, or a method analogous thereto.

This reaction is carried out by reacting compound (LXXIX) in the presence of a reducing agent in an inert solvent. In addition, an acid may be added or used as a solvent, as necessary.

Examples of the above-mentioned "reducing agent" include zinc powder, iron powder, tin(II) chloride and the like. The amount of the "reducing agent" to be used is generally 1 to 20 equivalents, preferably 1 to 10 equivalents, relative to compound (LXXIX).

Examples of the above-mentioned "inert solvent" include acetic acid, alcohol solvents, aromatic solvents, aliphatic hydrocarbon solvents, ether solvents, ester solvents, amide solvents and the like. These may be used in a mixture of two or more kinds thereof at an appropriate ratio. These may be used in a mixture with water at an appropriate ratio.

Examples of the above-mentioned "acid" include hydrochloric acid and the like. The amount of the "acid" to be used is generally 0.1 to 20 equivalents, preferably 1 to 10 equivalents, relative to compound (LXXIX).

The reaction temperature is generally −70 to 150° C., preferably −20 to 100° C.

The reaction time is generally 0.1 to 100 hr, preferably 0.1 to 40 hr.

In addition, this reaction can also be carried out by reacting compound (LXXIX) in the presence of a metal catalyst and a hydrogen source in an inert solvent.

Examples of the metal catalyst include palladium-carbon, palladium black, palladium chloride, platinum oxide, platinum black, platinum-palladium, Raney-nickel, Raney-cobalt and the like. The amount of the "metal catalyst" to be used is generally 0.001 to 1000 equivalents, preferably 0.01 to 100 equivalents, relative to compound (LXXIX).

Examples of the hydrogen source include hydrogen gas, formic acid, amine salts of formic acid, phosphinates, hydrazine and the like.

Examples of the above-mentioned "inert solvent" include acetic acid, alcohol solvents, aromatic solvents, aliphatic hydrocarbon solvents, ether solvents, ester solvents, amide solvents and the like. These may be used in a mixture of two or more kinds thereof at an appropriate ratio. These may be used in a mixture with water at an appropriate ratio.

The reaction temperature is generally −70 to 150° C., preferably −20 to 100° C.

The reaction time is generally 0.1 to 100 hr, preferably 0.1 to 40 hr.

Compound (LXXXI) can be produced, for example, from compound (LXXX) by a method similar to the condensation reaction of compound (XIX) with compound (XIX') in the aforementioned Reaction Scheme 3.

Compound (LXXXII) can be produced, for example, by subjecting compound (LXXXI) to deprotection and subsequent cyclization reaction.

The deprotection can be carried out according to a method known per se, for example, the method described in Protective Groups in Organic Synthesis, John Wiley and Sons (1980) or the like.

When Re is a 2-(alkoxycarbonyl)ethyl group, the deprotection can be carried out according to a method known per se, for example, the method described in Journal of Organic Chemistry, pages 5758-5761, 2003 or the like, or a method analogous thereto.

This reaction is carried out by reacting compound (LXXXI) in the presence of a base, in an inert solvent.

Examples of the above-mentioned "base" include "metal alkoxides" and the like. The amount of the "base" to be used is generally 1 to 20 equivalents, preferably 1 to 5 equivalents, relative to compound (LXXXI).

Examples of the above-mentioned "inert solvent" include alcohol solvents, ether solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

The subsequent cyclization reaction can be produced by a method similar to the cyclization reaction of compound (XX) in the aforementioned Reaction Scheme 3.

Compound (LXXXIII) can be produced, for example, by subjecting compound (LXXXII) to deprotection. The deprotection can be carried out according to a method known per se, for example, the method described in Protective Groups in Organic Synthesis, John Wiley and Sons (1980) or the like.

Compound (I-13) can be produced, for example, from compound (LXXXIII) by a method similar to the alkylation reaction of compound (IX) in the aforementioned Reaction Scheme 1.

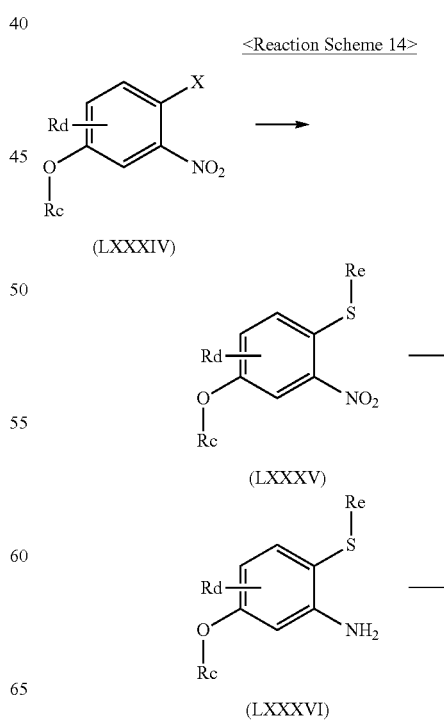

<Reaction Scheme 14>

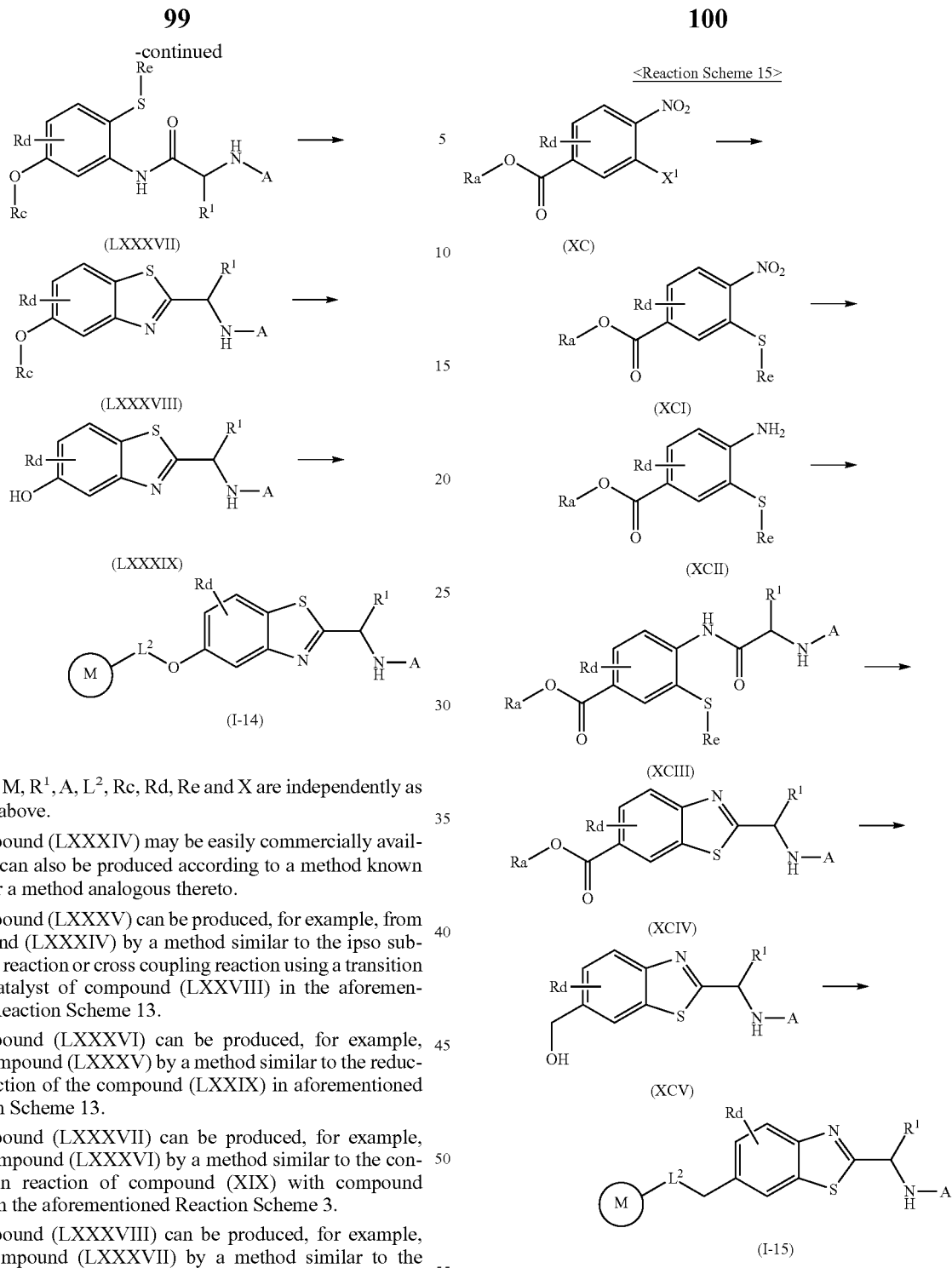

wherein M, $R^1$, A, $L^2$, Rc, Rd, Re and X are independently as defined above.

Compound (LXXXIV) may be easily commercially available, or can also be produced according to a method known per se or a method analogous thereto.

Compound (LXXXV) can be produced, for example, from compound (LXXXIV) by a method similar to the ipso substitution reaction or cross coupling reaction using a transition metal catalyst of compound (LXXVIII) in the aforementioned Reaction Scheme 13.

Compound (LXXXVI) can be produced, for example, from compound (LXXXV) by a method similar to the reduction reaction of the compound (LXXIX) in aforementioned Reaction Scheme 13.

Compound (LXXXVII) can be produced, for example, from compound (LXXXVI) by a method similar to the condensation reaction of compound (XIX) with compound (XIX') in the aforementioned Reaction Scheme 3.

Compound (LXXXVIII) can be produced, for example, from compound (LXXXVII) by a method similar to the deprotection and cyclization reaction of the compound (LXXXI) in aforementioned Reaction Scheme 13.

Compound (LXXXIX) can be produced, for example, by subjecting compound (LXXXVIII) to deprotection. The deprotection can be carried out according to a method known per se, for example, the method described in Protective Groups in Organic Synthesis, John Wiley and Sons (1980) or the like.

Compound (I-14) can be produced, for example, from compound (LXXXIX) by a method similar to the alkylation reaction of compound (IX) in the aforementioned Reaction Scheme 1.

wherein M, $R^1$, A, $L^2$, Ra, Rd, Re and $X^1$ are independently as defined above.

Compound (XC) may be easily commercially available, or can also be produced according to a method known per se or a method analogous thereto.

Compound (XCI) can be produced, for example, from compound (XC) by a method similar to the ipso substitution reaction or cross coupling reaction using a transition metal catalyst of compound (LXXVIII) in the aforementioned Reaction Scheme 13.

Compound (XCII) can be produced, for example, from compound (XCI) by a method similar to the reduction reaction of compound (LXXIX) in the aforementioned Reaction Scheme 13.

Compound (XCIII) can be produced, for example, from compound (XCII) by a method similar to the condensation reaction of compound (XIX) with compound (XIX') in the aforementioned Reaction Scheme 3.

Compound (XCIV) can be produced, for example, from compound (XCIII) by a method similar to the deprotection and cyclization reaction of compound (LXXXI) in the aforementioned Reaction Scheme 13.

Compound (XCV) can be produced, for example, from compound (XCIV) by a method similar to the reduction reaction of compound (XXVIII) in the aforementioned Reaction Scheme 4.

Compound (I-15) can be produced, for example, from compound (XCV) by a method similar to the substitution reaction of compound (XVII) in the aforementioned Reaction Scheme 3.

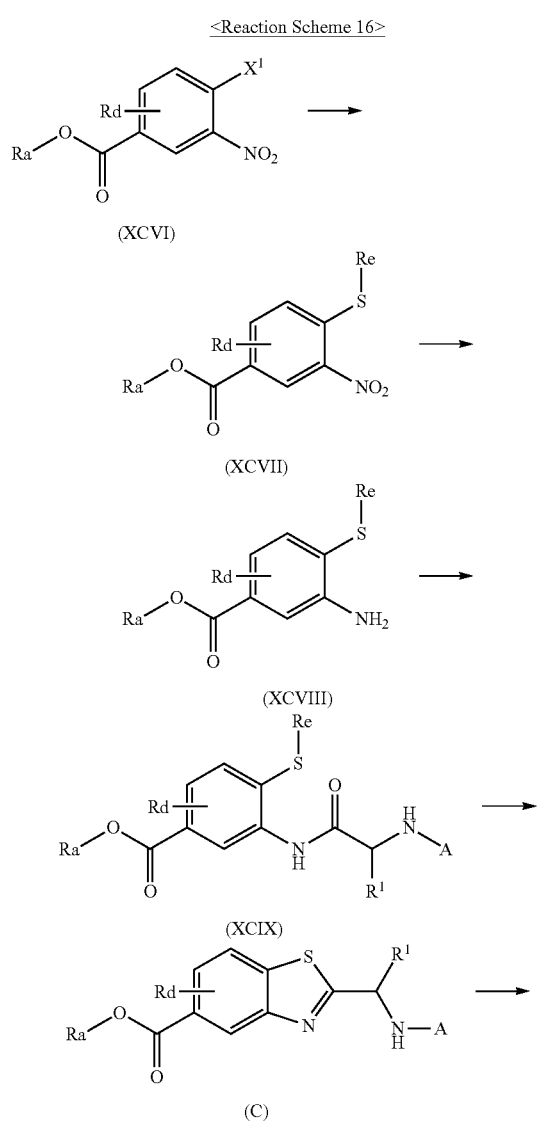

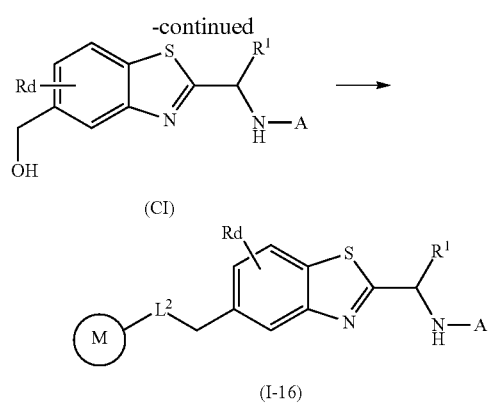

wherein M, $R^1$, A, $L^2$, Ra, Rd, Re and $X^1$ are independently as defined above.

Compound (XCVI) may be easily commercially available, or can also be produced according to a method known per se or a method analogous thereto.

Compound (XCVII) can be produced, for example, from compound (XCVI) by a method similar to the ipso substitution reaction or cross coupling reaction using a transition metal catalyst of compound (LXXVIII) in the aforementioned Reaction Scheme 13.

Compound (XCVIII) can be produced, for example, from compound (XCVII) by a method similar to the reduction reaction of compound (LXXIX) in the aforementioned Reaction Scheme 13.

Compound (XCIX) can be produced, for example, from compound (XCVIII) by a method similar to the condensation reaction of compound (XIX) with compound (XIX') in the aforementioned Reaction Scheme 3.

Compound (C) can be produced, for example, from compound (XCIX) by a method similar to the deprotection and cyclization reaction of compound (LXXXI) in the aforementioned Reaction Scheme 13.

Compound (CI) can be produced, for example, from compound (C) by a method similar to the reduction reaction of compound (XXVIII) in the aforementioned Reaction Scheme 4.

Compound (I-16) can be produced, for example, from compound (CI) by a method similar to the substitution reaction of compound (XVII) in the aforementioned Reaction Scheme 3.

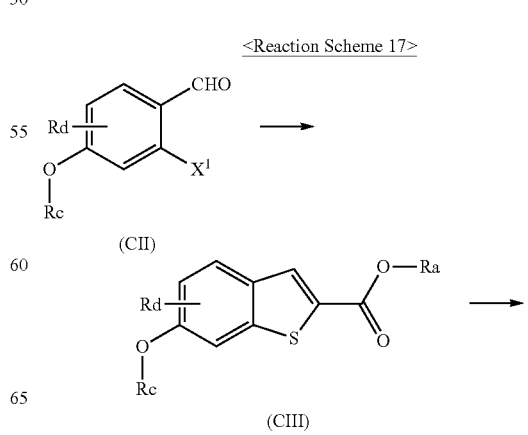

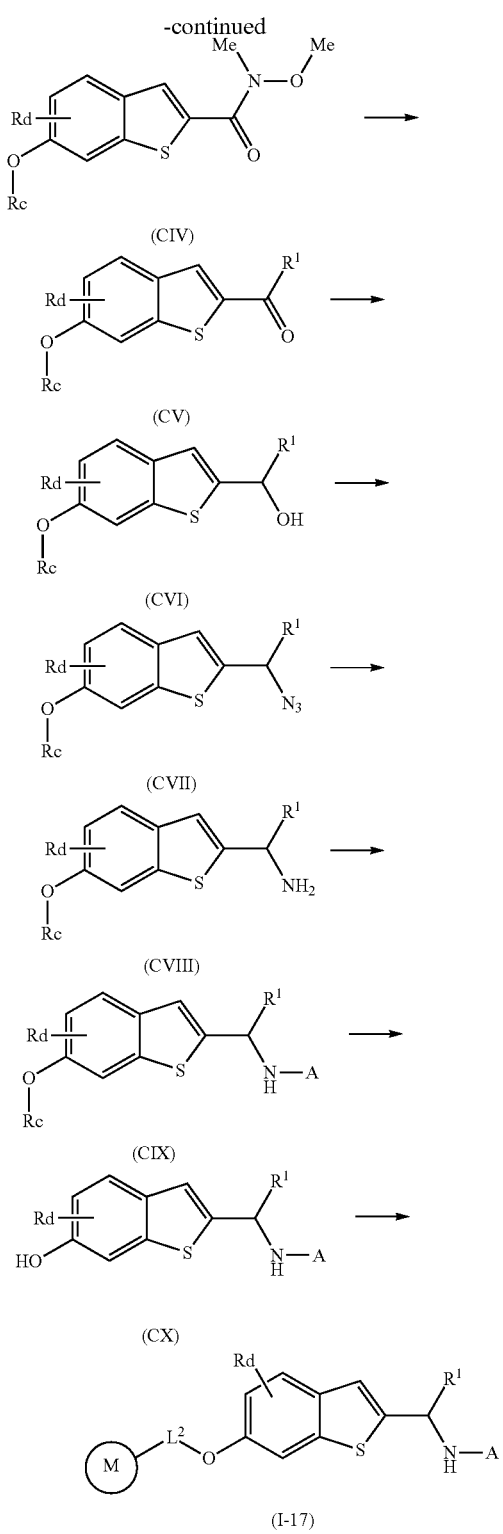

wherein M, R¹, A, L², Ra, Rc, Rd, Re and X¹ are independently as defined above.

Compound (CII) may be easily commercially available, or can also be produced according to a method known per se or a method analogous thereto.

Compound (CIII) can be produced, for example, by subjecting compound (CII) to a cyclization reaction.

The cyclization reaction can be carried out according to a method known per se, for example, the method described in Bioorganic and Medicinal Chemistry Letters, pages 2998-3001, 2005 or the like, or a method analogous thereto.

This reaction is carried out by reacting compound (CII) with a mercaptoacetate in the presence of a base, in an inert solvent.

Examples of the above-mentioned "mercaptoacetate" include ethyl mercaptoacetate and the like. The amount of the "mercaptoacetate" to be used is generally 1 to 20 equivalents, preferably 1 to 5 equivalents, relative to compound (CII).

Examples of the above-mentioned "base" include "inorganic bases", "basic salts", "aromatic amines", "tertiary amines", "hydrides of alkali metal or alkaline earth metal" and the like. The amount of the "base" to be used is generally 1 to 20 equivalents, preferably 1 to 5 equivalents, relative to compound (CII).

Examples of the above-mentioned "inert solvent" include amide solvents, sulfoxide solvents, alcohol solvents, aromatic solvents, aliphatic hydrocarbon solvents, ether solvents, ester solvents, nitrile solvents and the like. These may be used in a mixture of two or more kinds thereof at an appropriate ratio.

The reaction temperature is generally −70 to 250° C., preferably −20 to 200° C.

The reaction time is generally 0.1 to 100 hr, preferably 0.1 to 40 hr.

Compound (CIV) can be produced, for example, from compound (CIII) by a method similar to the amidation reaction of compound (XXIV) in the aforementioned Reaction Scheme 4.

Compound (CV), can be produced for example, from compound (CIV) by a method similar to the substitution reaction of compound (XXV) in the aforementioned Reaction Scheme 4.

Compound (CVI) can be produced, for example, from compound (CV) by a method similar to the reduction reaction of compound (XXVIII) in the aforementioned Reaction Scheme 4.

Compound (CVII) can be produced, for example, from compound (CVI) by a method similar to the substitution reaction of compound (XXIX) in the aforementioned Reaction Scheme 4.

Compound (CVIII) can be produced, for example, from compound (CVII) by a method similar to the reduction reaction of compound (XXX) in the aforementioned Reaction Scheme 4.

Compound (CIX) can be produced, for example, from compound (CVIII) by a method similar to the acylation reaction of compound (VII) in the aforementioned Reaction Scheme 1.

Compound (CX) can be produced, for example, by subjecting compound (CIX) to deprotection. The deprotection can be carried out according to a method known per se, for example, the method described in Protective Groups in Organic Synthesis, John Wiley and Sons (1980) or the like.

Compound (I-17) can be produced, for example, from compound (CX) by a method similar to the alkylation reaction of compound (IX) in the aforementioned Reaction Scheme 1.

<Reaction Scheme 18>

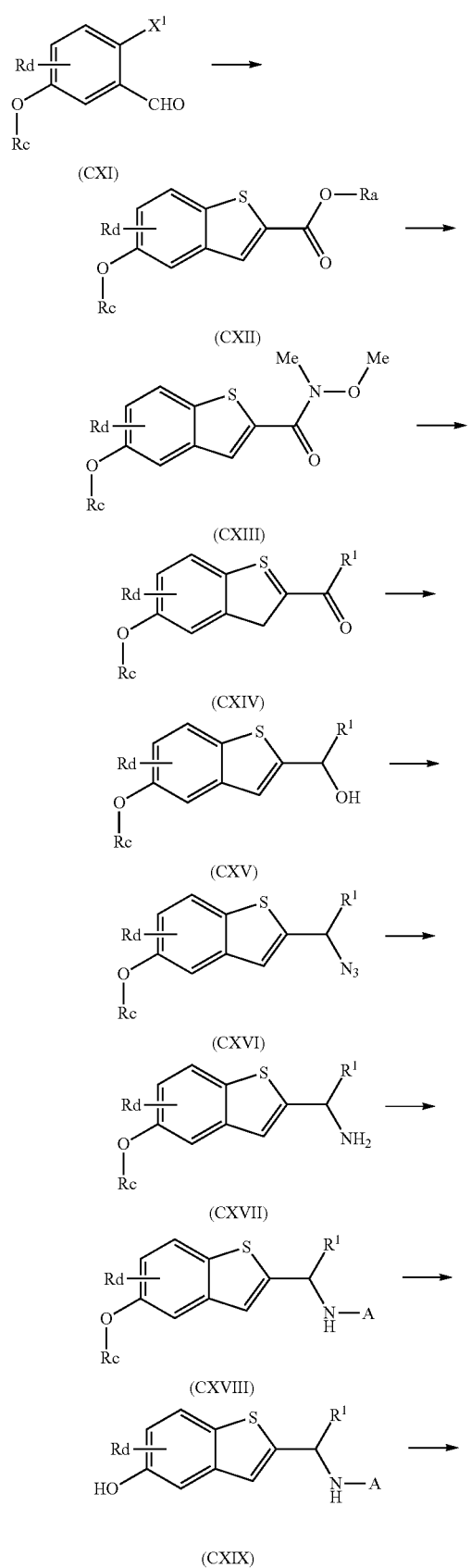

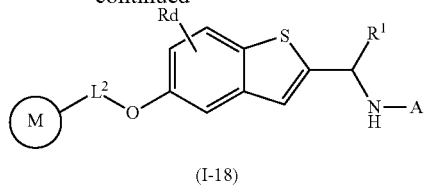

(I-18)

wherein M, $R^1$, A, $L^2$, Ra, Rc, Rd, Re and $X^1$ are independently as defined above.

Compound (CXI) may be easily commercially available, or can also be produced according to a method known per se or a method analogous thereto.

Compound (CXII) can be produced, for example, from compound (CXI) by a method similar to the substitution reaction of compound (CII) in the aforementioned Reaction Scheme 17.

Compound (CXIII) can be produced, for example, from compound (CXII) by a method similar to the amidation reaction of compound (XXIV) in the aforementioned Reaction Scheme 4.

Compound (CXIV) can be produced, for example, from compound (CXIII) by a method similar to the substitution reaction of compound (XXV) in the aforementioned Reaction Scheme 4.

Compound (CXV) can be produced, for example, from compound (CXIV) by a method similar to the reduction reaction of compound (XXVIII) in the aforementioned Reaction Scheme 4.

Compound (CXVI) can be produced, for example, from compound (CXV) by a method similar to the substitution reaction of compound (XXIX) in the aforementioned Reaction Scheme 4.

Compound (CXVII) can be produced, for example, from compound (CXVI) by a method similar to the reduction reaction of compound (XXX) in the aforementioned Reaction Scheme 4.

Compound (CXVIII) can be produced, for example, from compound (CXVII) by a method similar to the acylation reaction of compound (VII) in the aforementioned Reaction Scheme 1.

Compound (CXIX) can be produced, for example, by subjecting compound (CXVIII) to deprotection. The deprotection can be carried out according to a method known per se, for example, the method described in Protective Groups in Organic Synthesis, John Wiley and Sons (1980) or the like.

Compound (I-18) can be produced, for example, from compound (CXIX) by a method similar to the alkylation reaction of compound (IX) in the aforementioned Reaction Scheme 1.

<Reaction Scheme 19>

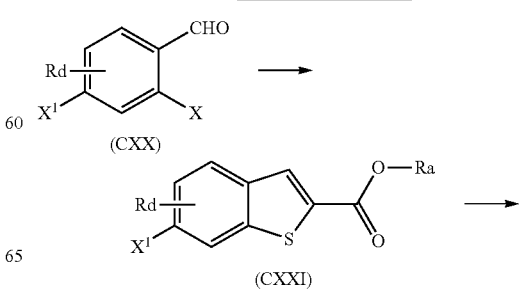

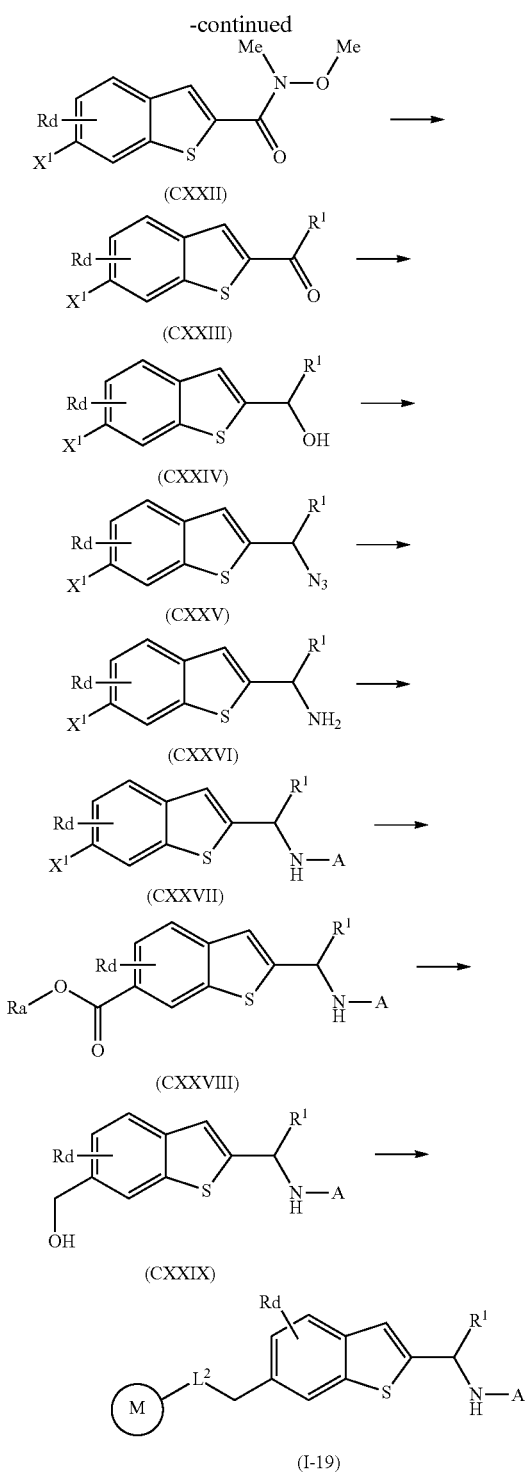

wherein M, $R^1$, A, $L^2$, Ra, Rd, X and $X^1$ are independently as defined above.

Compound (CXX) may be easily commercially available, or can also be produced according to a method known per se or a method analogous thereto.

Compound (CXXI) can be produced, for example, from compound (CXX) by a method similar to the cyclization reaction of compound (CII) in the aforementioned Reaction Scheme 17.

Compound (CXXII) can be produced, for example, from compound (CXXI) by a method similar to the amidation reaction of compound (XXIV) in the aforementioned Reaction Scheme 4.

Compound (CXXIII) can be produced, for example, from compound (CXXII) by a method similar to the substitution reaction of compound (XXV) in the aforementioned Reaction Scheme 4.

Compound (CXXIV) can be produced, for example, from compound (CXXIII) by a method similar to the reduction reaction of compound (XXVIII) in the aforementioned Reaction Scheme 4.

Compound (CXXV) can be produced, for example, from compound (CXXIV) by a method similar to the substitution reaction of compound (XXIX) in the aforementioned Reaction Scheme 4.

Compound (CXXVI) can be produced, for example, from compound (CXXV) by a method similar to the reduction reaction of compound (XXX) in the aforementioned Reaction Scheme 4.

Compound (CXXVII) can be produced, for example, from compound (CXXVI) by a method similar to the acylation reaction of compound (VII) in the aforementioned Reaction Scheme 1.

Compound (CXXVIII) can be produced, for example, an "alkoxycarbonylation reaction using a transition metal catalyst" of compound (CXXVII), a "method of reacting an activated compound (obtained from compound (CXXVII) and an alkyl metal or an aryl metal) with carbon dioxide, and then subjecting the resulting carboxylic acid derivative to an esterification reaction" and the like.

The above-mentioned "alkoxycarbonylation reaction using a transition metal catalyst" can be carried out according to a method known per se, for example, the method described in Tetrahedron: Asymmetry, pages 1793-1804, 1994 or the like, or a method analogous thereto.

This reaction is carried out by reacting compound (CXXVII) in the presence of a transition metal catalyst, a ligand, an alcohol and a base, in an inert solvent, under carbon monooxide gas atmosphere.

Examples of the above-mentioned "transition metal catalyst" include palladium catalysts, nickel catalysts, iron catalysts, cobalt catalysts and the like. Examples of the palladium catalyst include dichlorobis(triphenylphosphine)palladium and the like. The amount of the "transition metal catalyst" to be used is generally 0.01 to 20 equivalents, preferably 0.01 to 1 equivalents, relative to compound (CXXVII).

Examples of the above-mentioned "ligand" include phosphine ligands. Examples of the phosphine ligand include triphenylphosphine and the like. The amount of the "ligand" to be used is generally 0.01 to 20 equivalents, preferably 0.01 to 1 equivalents, relative to compound (CXXVII).

Examples of the above-mentioned "alcohol" include methanol, ethanol and the like. The amount of the "alcohol" to be used is generally 1 to 20 equivalents, preferably 1 to 10 equivalents, relative to compound (CXXVII).

Examples of the above-mentioned "base" include "aromatic amines", "tertiary amines" and the like. The amount of the "base" to be used is generally 0.1 to 20 equivalents, preferably 1 to 5 equivalents, relative to compound (CXXVII).

Examples of the above-mentioned "inert solvent" include alcohol solvents, aromatic solvents, aliphatic hydrocarbon solvents, ether solvents, ester solvents, amide solvents and the like. These may be used in a mixture of two or more kinds thereof at an appropriate ratio.

The pressure of the above-mentioned "carbon monooxide gas" is generally 1 to 100 pressure, preferably 1 to 10 pressure.

The reaction temperature is generally −70 to 150° C., preferably −20 to 150° C.

The reaction time is generally 0.1 to 100 hr, preferably 0.1 to 40 hr.

The above-mentioned "method of reacting an activated compound (obtained from compound (CXXVII) and an alkyl metal or an aryl metal) with carbon dioxide, and then subjecting the resulting carboxylic acid derivative to an esterification reaction" can be carried out according to a method known per se, for example, the method described in Tetrahedron: Asymmetry, pages 689-692, 2003 or the like, or a method analogous thereto.

The amount of the above-mentioned "alkyl metals" or "aryl metals" to be used is generally 1 to 2 equivalents, preferably 1 to 1.5 equivalents, relative to compound (CXXVII).

Carbon dioxide is generally used in an excess amount.

This carboxylation reaction is advantageously in a solvent inert to the reaction. The solvent is not particularly limited as long as the reaction proceeds, and preferable examples thereof include aromatic solvents, aliphatic hydrocarbon solvents, ether solvents, mixtures thereof and the like.

The reaction time is generally 10 min to 48 hr, preferably 15 min to 24 hr.

The reaction temperature is generally −78° C. to 100° C., preferably −78° C. to 50° C.

The subsequent esterification can be carried out according to a method known per se, for example, the method described in Protective Groups in Organic Synthesis, John Wiley and Sons (1980) or the like.

Compound (CXXIX) can be produced, for example, from compound (CXXVIII) by a method similar to the reduction reaction of compound (XXVIII) in the aforementioned Reaction Scheme 4.

Compound (I-19) can be produced, for example, from compound (CXXIX) by a method similar to the substitution reaction of compound (XVII) in the aforementioned Reaction Scheme 3.

<Reaction Scheme 20>

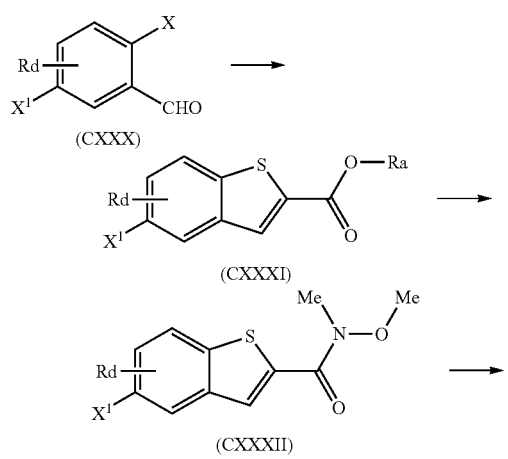

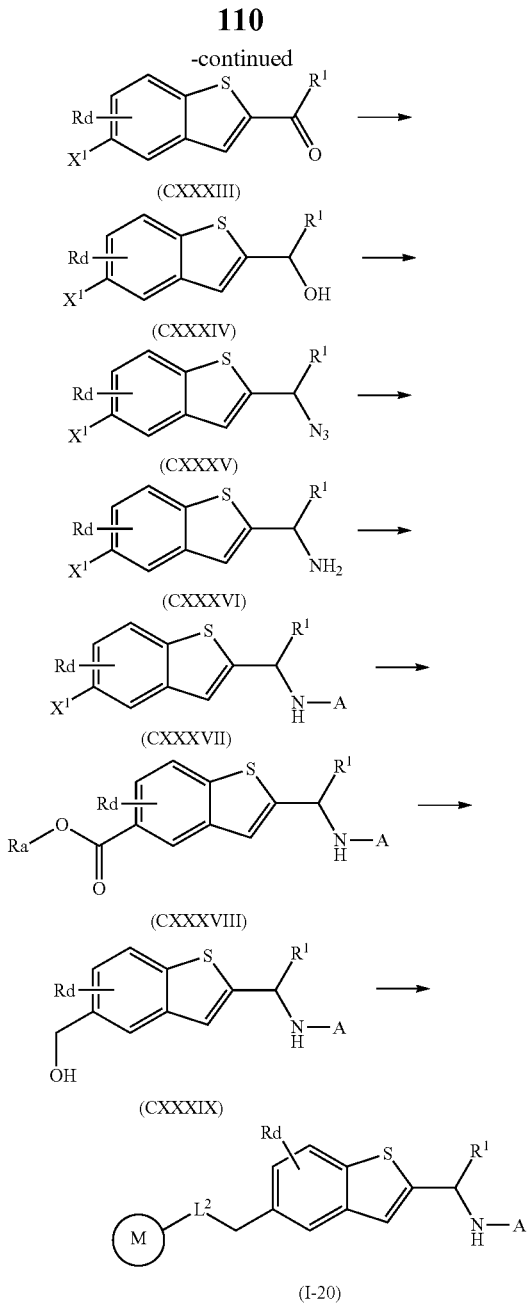

wherein M, $R^1$, A, $L^2$, Ra, Rd, X and $X^1$ are independently as defined above.

Compound (CXXX) may be easily commercially available, or can also be produced according to a method known per se or a method analogous thereto.

Compound (CXXXI) can be produced, for example, from compound (CXXX) by a method similar to the cyclization reaction of compound (CII) in the aforementioned Reaction Scheme 17.

Compound (CXXXII) can be produced, for example, from compound (CXXXI) by a method similar to the amidation reaction of compound (XXIV) in the aforementioned Reaction Scheme 4.

Compound (CXXXIII) can be produced, for example, from compound (CXXXII) by a method similar to the substitution reaction of compound (XXV) in the aforementioned Reaction Scheme 4.

Compound (CXXXIV) can be produced, for example, from compound (CXXXIII) by a method similar to the reduction reaction of compound (XXVIII) in the aforementioned Reaction Scheme 4.

Compound (CXXXV) can be produced, for example, from compound (CXXXIV) by a method similar to the substitution reaction of compound (XXIX) in the aforementioned Reaction Scheme 4.

Compound (CXXXVI), can be produced for example, from compound (CXXXV) by a method similar to the reduction reaction of compound (XXX) in the aforementioned Reaction Scheme 4.

Compound (CXXXVII) can be produced, for example, from compound (CXXXVI) by a method similar to the acylation reaction of compound (VII) in the aforementioned Reaction Scheme 1.

Compound (CXXXVIII) can be produced, for example, from compound (CXXXVII) by the "alkoxycarbonylation reaction using a transition metal catalyst" of compound (CXXVII), the "method of reacting an activated compound (obtained from compound (CXXVII) and an alkyl metal or an aryl metal) with carbon dioxide, and then subjecting the resulting carboxylic acid derivative to an esterification reaction" and the like in the aforementioned Reaction Scheme 19.

Compound (CXXXIX) can be produced, for example, from compound (CXXXVIII) by a method similar to the reduction reaction of compound (XXVIII) in the aforementioned Reaction Scheme 4.

Compound (I-20) can be produced, for example, from compound (CXXXIX) by a method similar to the substitution reaction of compound (XVII) in the aforementioned Reaction Scheme 3.

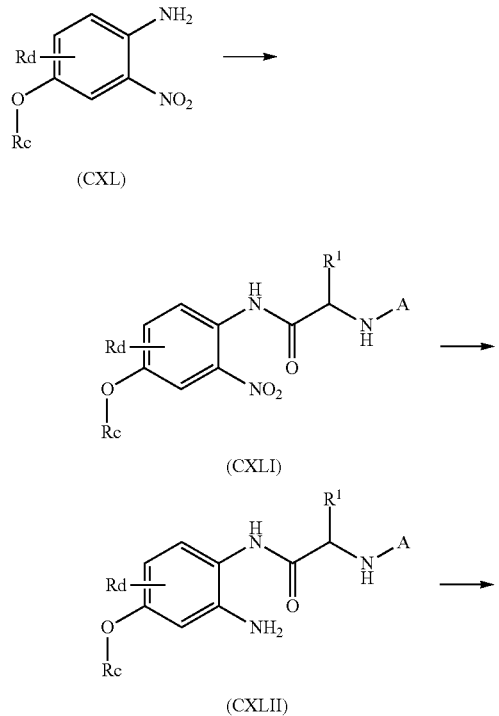

wherein M, $R^1$, A, $L^2$, Rc and Rd are independently as defined above.

Compound (CXL) may be easily commercially available, or can also be produced according to a method known per se or a method analogous thereto.

Compound (CXLI) can be produced, for example, from compound (CXL) by a method similar to the condensation reaction of compound (XIX) with compound (XIX') in the aforementioned Reaction Scheme 3.

Compound (CXLII) can be produced, for example, from compound (CXLI) by a method similar to the reduction reaction of compound (LXXIX) in the aforementioned Reaction Scheme 13.

Compound (CXLIII) can be produced, for example, from compound (CXLII) by a method similar to the cyclization reaction of compound (XX) in the aforementioned Reaction Scheme 3.

Compound (CXLIV) can be produced, for example, by subjecting compound (CXLIII) to deprotection. The deprotection can be carried out according to a method known per se, for example, the method described in Protective Groups in Organic Synthesis, John Wiley and Sons (1980) or the like.

Compound (I-21) can be produced, for example, from compound (CXLIV) by a method similar to the alkylation reaction of compound (IX) in the aforementioned Reaction Scheme 1.

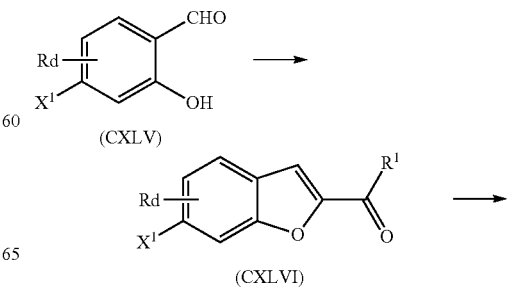

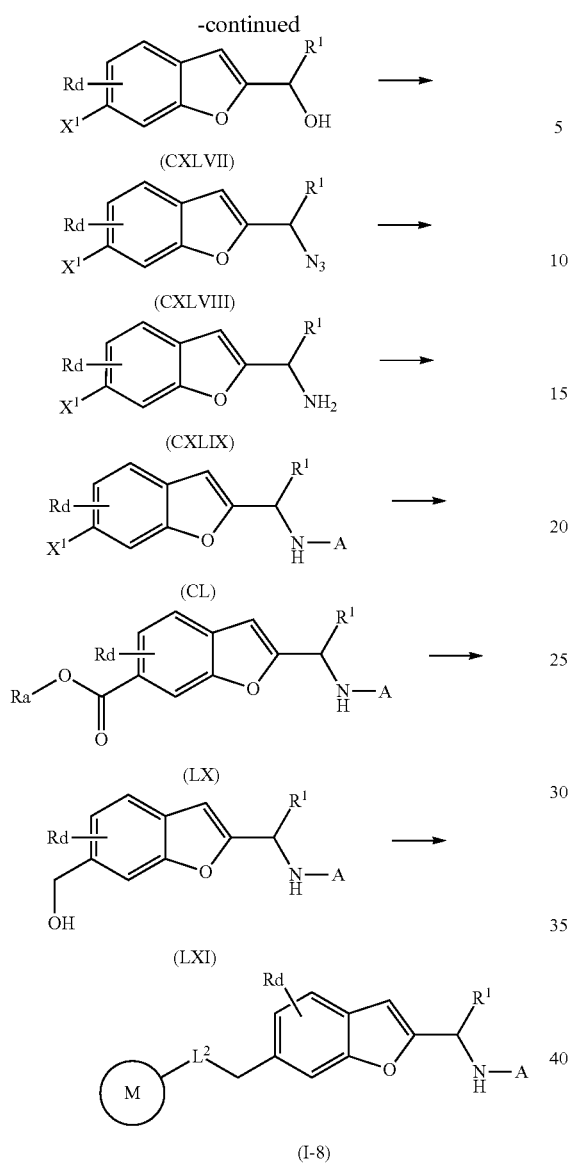

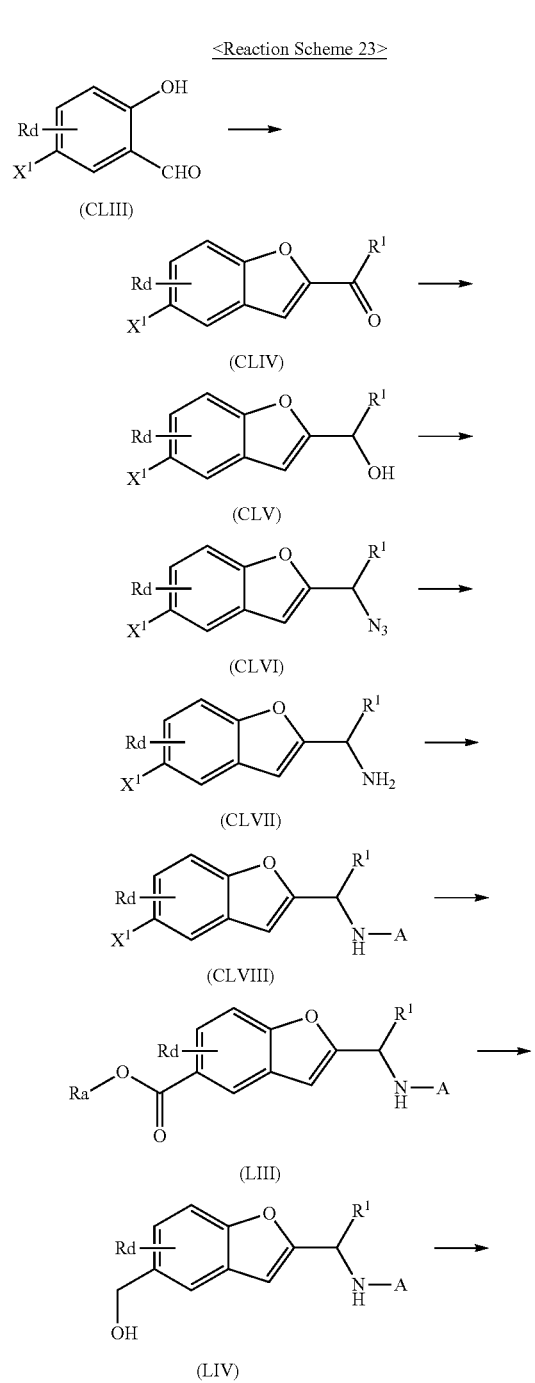

wherein M, R$^1$, A, L$^2$, Rd and X$^1$ are independently as defined above.

Compound (CXLV) may be easily commercially available, or can also be produced according to a method known per se or a method analogous thereto.

Compound (CXLVI) can be produced, for example, from compound (CXLV) by a method similar to the cyclization reaction of compound (XXXIII) in the aforementioned Reaction Scheme 5.

Compound (CXLVII) can be produced, for example, from compound (CXLVI) by a method similar to the reduction reaction of compound (XXVIII) in the aforementioned Reaction Scheme 4.

Compound (CXLVIII) can be produced, for example, from compound (CXLVII) by a method similar to the substitution reaction of compound (XXIX) in the aforementioned Reaction Scheme 4.

Compound (CXLIX) can be produced, for example, from compound (CXLVIII) by a method similar to the reduction reaction of compound (XXX) in the aforementioned Reaction Scheme 4.

Compound (CL) can be produced, for example, from compound (CXLIX) by a method similar to the acylation reaction of compound (VII) in the aforementioned Reaction Scheme 1.

Compound (LX) can also be produced, for example, from compound (CL) by the "alkoxycarbonylation reaction using a transition metal catalyst" of compound (CXXVII), the "method of reacting an activated compound (obtained from compound (CXXVII) and an alkyl metal or an aryl metal) with carbon dioxide, and then subjecting the resulting carboxylic acid derivative to an esterification reaction" and the like in the aforementioned Reaction Scheme 19.

<Reaction Scheme 23>

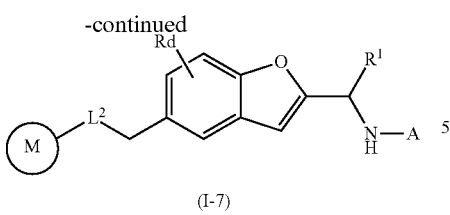

(I-7)

wherein M, R¹, A, L², Rd and X¹ are independently as defined above.

Compound (CLIII) may be easily commercially available, or can also be produced according to a method known per se or a method analogous thereto.

Compound (CLIV) can be produced, for example, from compound (CLIII) by a method similar to the cyclization reaction of compound (XXXIII) in the aforementioned Reaction Scheme 5.

Compound (CLV) can be produced, for example, from compound (CLIV) by a method similar to the reduction reaction of compound (XXVIII) in the aforementioned Reaction Scheme 4.

Compound (CLVI) can be produced, for example, from compound (CLV) by a method similar to the substitution reaction of compound (XXIX) in the aforementioned Reaction Scheme 4.

Compound (CLVII) can be produced, for example, from compound (CLVI) by a method similar to the reduction reaction of compound (XXX) in the aforementioned Reaction Scheme 4.

Compound (CLVIII) can be produced, for example, from compound (CLVII) by a method similar to the acylation reaction of compound (VII) in the aforementioned Reaction Scheme 1.

Compound (LIII) can also be produced, for example, from compound (CLVIII) by the "alkoxycarbonylation reaction using a transition metal catalyst" of compound (CXXVII), the "method of reacting an activated compound (obtained from compound (CXXVII) and an alkyl metal or an aryl metal) with carbon dioxide, and then subjecting the resulting carboxylic acid derivative to an esterification reaction" and the like in the aforementioned Reaction Scheme 19.

<Reaction Scheme 24>

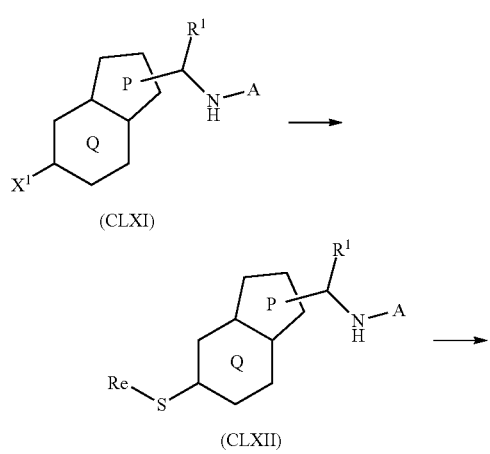

(CLXI)

(CLXII)

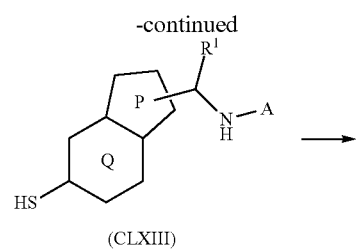

(CLXIII)

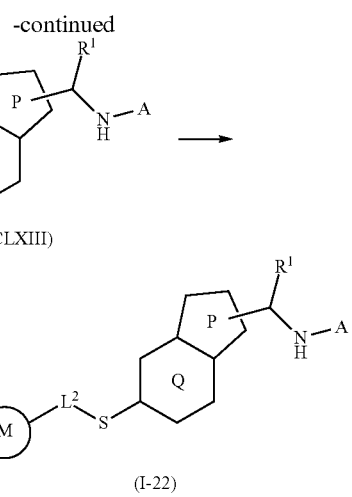

(I-22)

wherein M, Q, P, R¹, A, L², Re and X¹ are independently as defined above.

Compound (CLXI) can be produced according to synthesis methods of compound (CXXVII), (CXXXVII), (CL) and (CLVIII), and the like.

Compound (CLXII) can be produced, for example, from compound (CLXI) by a method similar to the ipso substitution reaction or cross coupling reaction using a transition metal catalyst of compound (LXXVIII) in the aforementioned Reaction Scheme 13.

Compound (CLXIII) can be produced, for example, from compound (CLXII) by a method similar to the deprotection and cyclization reaction of compound (LXXXI) in the aforementioned Reaction Scheme 13.

Compound (I-22) can be produced, for example, from compound (CLXIII) by a method similar to the alkylation reaction of compound (IX) in the aforementioned Reaction Scheme 1.

<Reaction Scheme 25>

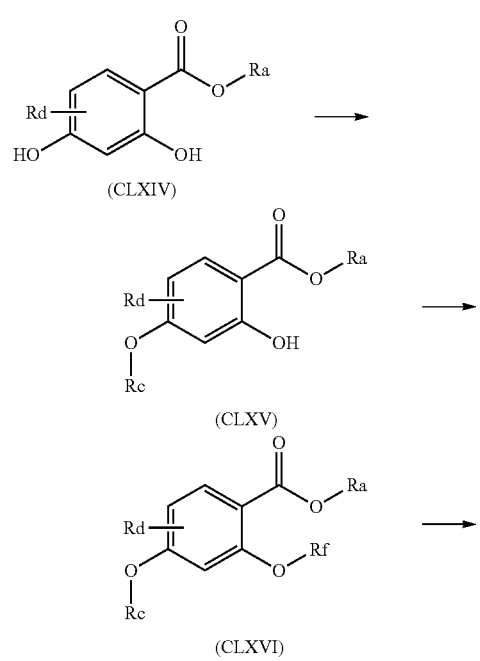

(CLXIV)

(CLXV)

(CLXVI)

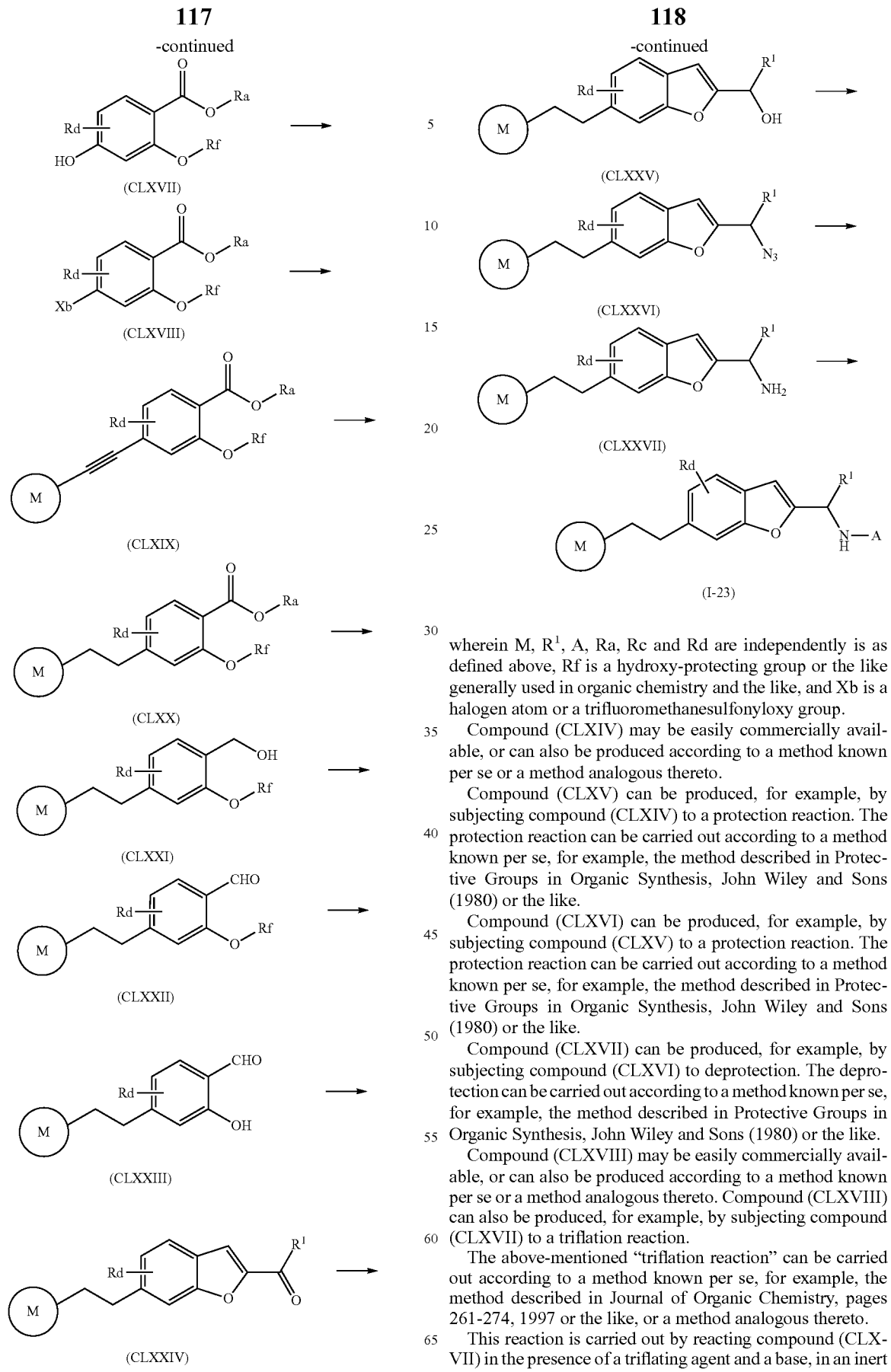

wherein M, $R^1$, A, Ra, Rc and Rd are independently is as defined above, Rf is a hydroxy-protecting group or the like generally used in organic chemistry and the like, and Xb is a halogen atom or a trifluoromethanesulfonyloxy group.

Compound (CLXIV) may be easily commercially available, or can also be produced according to a method known per se or a method analogous thereto.

Compound (CLXV) can be produced, for example, by subjecting compound (CLXIV) to a protection reaction. The protection reaction can be carried out according to a method known per se, for example, the method described in Protective Groups in Organic Synthesis, John Wiley and Sons (1980) or the like.

Compound (CLXVI) can be produced, for example, by subjecting compound (CLXV) to a protection reaction. The protection reaction can be carried out according to a method known per se, for example, the method described in Protective Groups in Organic Synthesis, John Wiley and Sons (1980) or the like.

Compound (CLXVII) can be produced, for example, by subjecting compound (CLXVI) to deprotection. The deprotection can be carried out according to a method known per se, for example, the method described in Protective Groups in Organic Synthesis, John Wiley and Sons (1980) or the like.

Compound (CLXVIII) may be easily commercially available, or can also be produced according to a method known per se or a method analogous thereto. Compound (CLXVIII) can also be produced, for example, by subjecting compound (CLXVII) to a triflation reaction.

The above-mentioned "triflation reaction" can be carried out according to a method known per se, for example, the method described in Journal of Organic Chemistry, pages 261-274, 1997 or the like, or a method analogous thereto.

This reaction is carried out by reacting compound (CLXVII) in the presence of a triflating agent and a base, in an inert solvent.

Examples of the above-mentioned "triflating agent" include trifluoromethanesulfonic anhydride and the like. The amount of the "triflating agent" to be used is generally 1 to 20 equivalents, preferably 1 to 2 equivalents, relative to compound (CLXVII).

Examples of the above-mentioned "base" include "aromatic amines", "tertiary amines" and the like. The amount of the "base" to be used is generally 1 to 20 equivalents, preferably 1 to 5 equivalents, relative to compound (CLXVII).

Examples of the above-mentioned "inert solvent" include halogenated hydrocarbon solvents, aromatic solvents, aliphatic hydrocarbon solvents, ether solvents, ester solvents, amide solvents and the like. These may be used in a mixture of two or more kinds thereof at an appropriate ratio.

The reaction temperature is generally −70 to 150° C., preferably −20 to 150° C.

The reaction time is generally 0.1 to 100 hr, preferably 0.1 to 40 hr.

Compound (CLXIX) can be produced, for example, by subjecting compound (CLXVIII) to the Sonogashira reaction.

The Sonogashira reaction can be carried out according to a method known per se, for example, the method described in Tetrahedron Letters, pages 2581-2584, 1989 or the like, or a method analogous thereto.

This reaction is carried out by reacting compound (CLXVIII) in the presence of an alkyne derivative having the substituent M, a transition metal catalyst, a ligand and a base, in an inert solvent, under an inert gas atmosphere.

Examples of the above-mentioned "alkyne derivative having the substituent M" include acetylenes having an optionally fused 5- to 7-membered ring which is optionally substituted, as a substituent, such as 1-ethoxy-4-ethynylbenzene and the like. The amount of the "alkyne derivative having the substituent M" to be used is generally 1 to 20 equivalents, preferably 1 to 5 equivalents, relative to compound (CLXVIII).

Examples of the above-mentioned "transition metal catalyst" include palladium catalysts, nickel catalysts, iron catalysts, cobalt catalysts and the like. Examples of the palladium catalyst include dichlorobis(triphenylphosphine)palladium and the like. The amount of the "transition metal catalyst" to be used is generally 0.001 to 1 equivalents, preferably 0.01 to 0.1 equivalents, relative to compound (CLXVIII). In addition, a copper catalyst and the like may be added as a cocatalyst. Examples of the copper catalyst include copper iodide and the like. The amount of the "cocatalyst" to be used is generally 0.001 to 1 equivalents, preferably 0.01 to 0.1 equivalents, relative to compound (CLXVIII).

Examples of the above-mentioned "ligand" include phosphine ligands. Examples of the phosphine ligand include triphenylphosphine and the like. The amount of the "ligand" to be used is generally 0.01 to 20 equivalents, preferably 0.01 to 1 equivalents, relative to compound (CLXVIII).

Examples of the above-mentioned "base" include "aromatic amines", "tertiary amines" and the like. The amount of the "base" to be used is generally 0.1 to 20 equivalents, preferably 1 to 5 equivalents, relative to compound (CLXVIII). In addition, the base may be used as a solvent.

Examples of the above-mentioned "inert solvent" include amide solvents, aromatic solvents, aliphatic hydrocarbon solvents, ether solvents, ester solvents and the like. These may be used in a mixture of two or more kinds thereof at an appropriate ratio.

Examples of the above-mentioned "inert gas" include nitrogen, argon and the like.

The reaction temperature is generally −70 to 150° C., preferably −20 to 150° C.

The reaction time is generally 0.1 to 100 hr, preferably 0.1 to 40 hr.

Compound (CLXX) can be produced, for example, by subjecting compound (CLXIX) to a hydrogenation reaction.

The hydrogenation reaction can be carried out according to a method known per se, for example, the method described in European Journal of Medicinal Chemistry, pages 7-18, 1992 or the like, or a method analogous thereto.

This reaction can be carried out, for example, by reacting compound (CLXIX) in the presence of a metal catalyst and a hydrogen source, in an inert solvent.

Examples of the above-mentioned "metal catalyst" include palladium carbon, palladium black, palladium chloride, platinum oxide, platinum black, platinum palladium, Raney-nickel, Raney-cobalt and the like. The amount of the "metal catalyst" to be used is generally 0.001 to 1000 equivalents, preferably 0.01 to 100 equivalents, relative to compound (CLXIX).

Examples of the above-mentioned "hydrogen source" include hydrogen gas, formic acid, formic acid amine salt, phosphinates, hydrazine and the like.

Examples of the above-mentioned "inert solvent" include alcohol solvents, nitrile solvents, aromatic solvents, aliphatic hydrocarbon solvents, ether solvents, amide solvents, halogenated hydrocarbon solvents and the like. These solvents may be used in a mixture with water at an appropriate ratio. Of these, alcohol solvents are preferable.

The reaction temperature is generally −70 to 150° C., preferably −20 to 100° C.

The reaction time is generally 0.1 to 100 hr, preferably 0.1 to 40 hr.

Compound (CLXXI) can be produced, for example, from compound (CLXX) by a method similar to the reduction reaction of compound (XXVIII) in the aforementioned Reaction Scheme 4.

Compound (CLXXII) can be produced, for example, by subjecting compound (CLXXI) to an oxidization reaction.

The oxidation reaction can be carried out according to a method known per se, for example, the method described in Journal of Medicinal Chemistry, pages 5282-5290, 2006 or the like, or a method analogous thereto.

This reaction is carried out by reacting compound (CLXXI) with an oxidant in an inert solvent.

Examples of the above-mentioned "oxidant" include manganese dioxide, tetrapropylammonium perruthenate, chromium trioxide, Dess-Martin reagent and the like. The amount of the "oxidant" to be used is generally 1 to 5 equivalents, preferably 1 to 1.5 equivalents, relative to compound (CLXXI).

Examples of the above-mentioned "inert solvent" include alcohol solvents, nitrile solvents, amide solvents, halogenated hydrocarbon solvents, ether solvents, aromatic solvents and the like. These may be used in a mixture of two or more kinds thereof at an appropriate ratio. Of these, halogenated hydrocarbon solvents are preferable.

The reaction temperature is generally −100° C. to 50° C., preferably −78° C. to 0° C.

The reaction time is generally 5 min to 48 hr, preferably 30 min to 24 hr.

Compound (CLXXIII) can be produced, for example, by subjecting compound (CLXXII) to deprotection. The deprotection can be carried out according to a method known per se, for example, the method described in Protective Groups in Organic Synthesis, John Wiley and Sons (1980) or the like.

Compound (CLXXIV) can be produced, for example, from compound (CLXXIII) by a method similar to the cyclization reaction of compound (XXXIII) in the aforementioned Reaction Scheme 5. Compound (CLXXV) can be produced, for example, from compound (CLXXIV) by a method similar to the reduction reaction of compound (XXVIII) in the aforementioned Reaction Scheme 4.

Compound (CLXXVI) can be produced, for example, from compound (CLXXV) by a method similar to the substitution reaction of compound (XXIX) in the aforementioned Reaction Scheme 4.

Compound (CLXXVII) can be produced, for example, from compound (CLXXVI) by a method similar to the reduction reaction of compound (XXX) in the aforementioned Reaction Scheme 4.

Compound (I-23) can be produced, for example, from compound (CLXXVII) by a method similar to the acylation reaction of compound (VII) in the aforementioned Reaction Scheme 1.

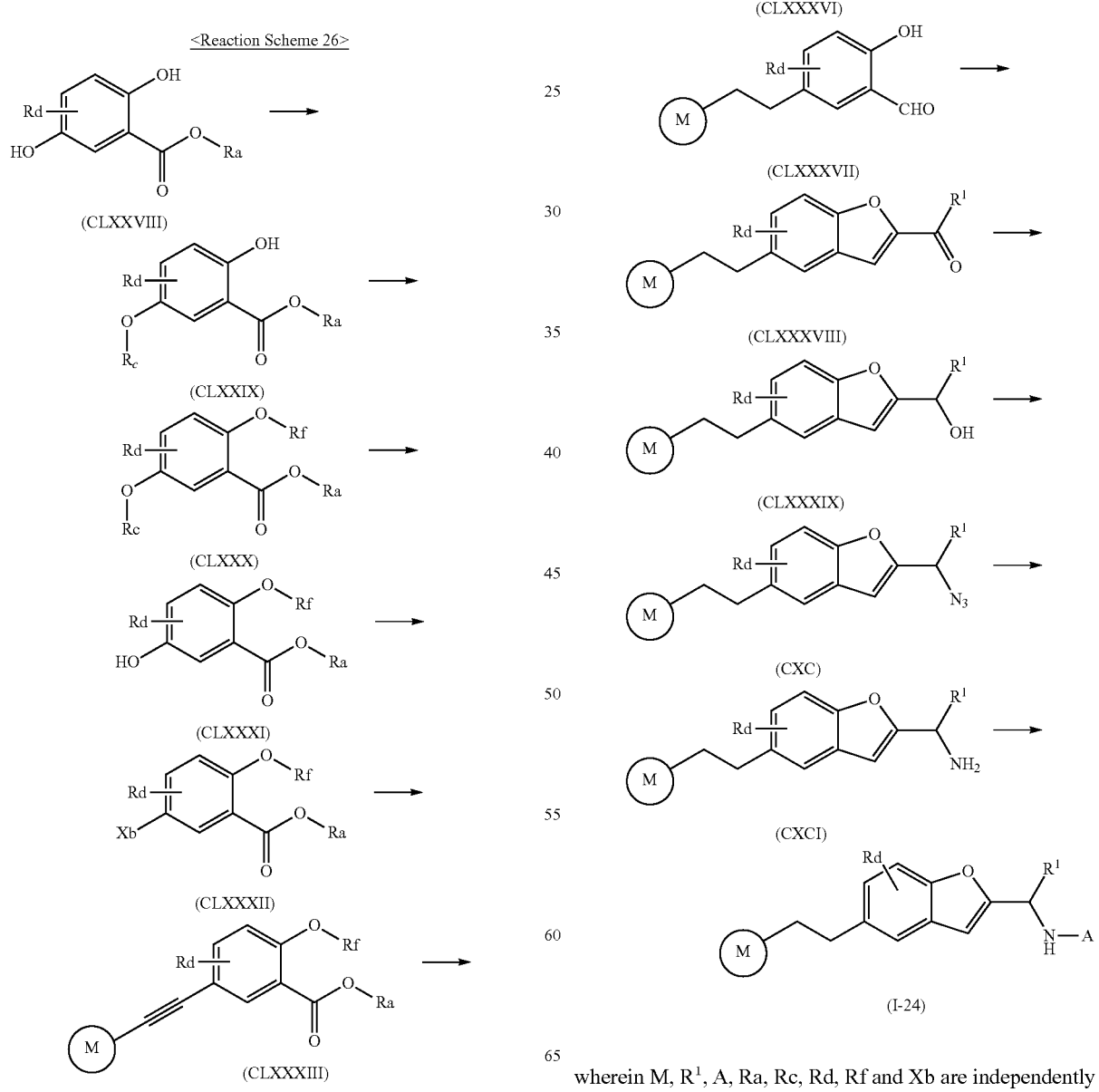

wherein M, $R^1$, A, Ra, Rc, Rd, Rf and Xb are independently as defined above.

Compound (CLXXVIII) may be easily commercially available, or can also be produced according to a method known per se or a method analogous thereto.

Compound (CLXXIX) can be produced, for example, by subjecting compound (CLXXVIII) to a protection reaction. The protection reaction can be carried out according to a method known per se, for example, the method described in Protective Groups in Organic Synthesis, John Wiley and Sons (1980) or the like.

Compound (CLXXX) can be produced, for example, by subjecting compound (CLXXIX) to a protection reaction. The protection reaction can be carried out according to a method known per se, for example, the method described in Protective Groups in Organic Synthesis, John Wiley and Sons (1980) or the like.

Compound (CLXXXI) can be produced, for example, by subjecting compound (CLXXX) to deprotection. The deprotection can be carried out according to a method known per se, for example, the method described in Protective Groups in Organic Synthesis, John Wiley and Sons (1980) or the like.

Compound (CLXXXII) may be easily commercially available, or can also be produced according to a method known per se or a method analogous thereto. Alternatively, compound (CLXXXII) can be produced, for example, from compound (CLXXXI) by a method similar to the triflation reaction of compound (CLXVII) in the aforementioned Reaction Scheme 25.

Compound (CLXXXIII) can be produced, for example, from compound (CLXXXII) by a method similar to the Sonogashira reaction of the compound (CLXIX) in aforementioned Reaction Scheme 25.

Compound (CLXXXIV) can be produced, for example, from compound (CLXXXIII) by a method similar to the hydrogenation reaction of compound (CLXVIII) in the aforementioned Reaction Scheme 25.

Compound (CLXXXV) can be produced, for example, from compound (CLXXXIV) by a method similar to the reduction reaction of compound (XXVIII) in the aforementioned Reaction Scheme 4.

Compound (CLXXXVI) can be produced, for example, from compound (CLXXXV) by a method similar to the oxidization reaction of compound (CLXXI) in the aforementioned Reaction Scheme 25.

Compound (CLXXXVII) can be produced, for example, by subjecting compound (CLXXXVI) to deprotection. The deprotection can be carried out according to a method known per se, for example, the method described in Protective Groups in Organic Synthesis, John Wiley and Sons (1980) or the like.

Compound (CLXXXVIII) can be produced, for example, from compound (CLXXXVII) by a method similar to the cyclization reaction of compound (XXXIII) in the aforementioned Reaction Scheme 5.

Compound (CLXXXIX) can be produced, for example, from compound (CLXXXVIII) by a method similar to the reduction reaction of compound (XXVIII) in the aforementioned Reaction Scheme 4.

Compound (CXC) can be produced, for example, from compound (CLXXXIX) by a method similar to the substitution reaction of compound (XXIX) in the aforementioned Reaction Scheme 4.

Compound (CXCI) can be produced, for example, from compound (CXC) by a method similar to the reduction reaction of compound (XXX) in the aforementioned Reaction Scheme 4.

Compound (I-24) can be produced, for example, from compound (CXCI) by a method similar to the acylation reaction of compound (VII) in the aforementioned Reaction Scheme 1.

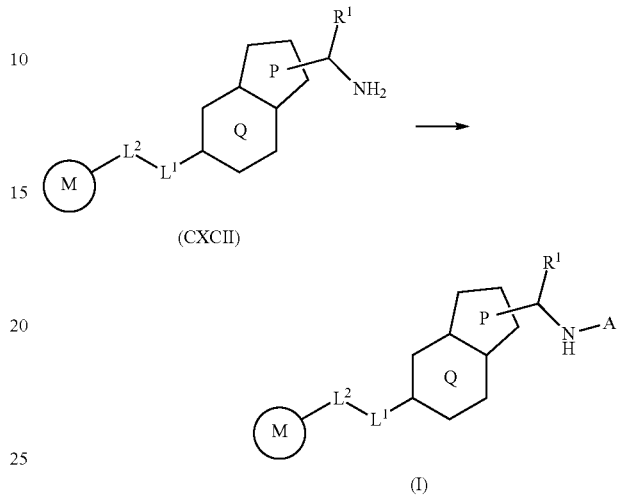

wherein M, P, Q, $R^1$, A, $L^1$ and $L^2$ are independently as defined above.

Compound (CXCII) can be produced, for example, according to a method known per se or according to the aforementioned Reaction Schemes 1 to 26.

Compound (I) can be produced, for example, from compound (CXCII) by a method similar to the acylation reaction of compound (VII) in the aforementioned Reaction Scheme 1.

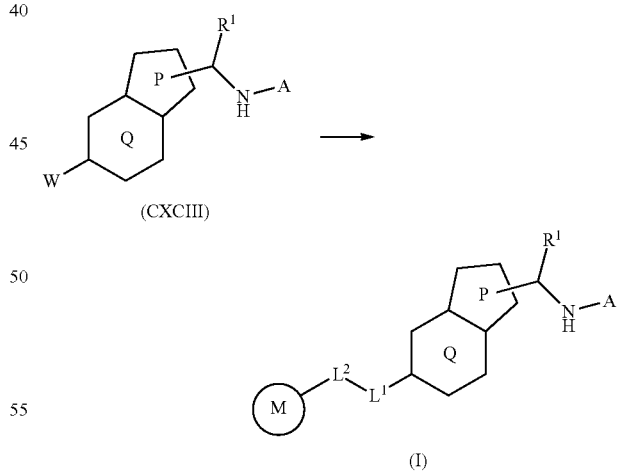

wherein M, P, Q, $R^1$, A, $L^1$ and $L^2$ are independently as defined above, and W is a hydroxy group, a mercapto group or a hydroxymethyl group.

Compound (CXCIII) can be produced, for example, according to a method known per se, or according to the aforementioned Reaction Schemes 1 to 43 mentioned above or below.

Compound (I) can also be produced, for example, from compound (CXCIII) by a method similar to the alkylation reaction of compound (IX) in the aforementioned Reaction Scheme 1 or the substitution reaction of compound (XVII) in the aforementioned Reaction Scheme 3.

<Reaction Scheme 29>

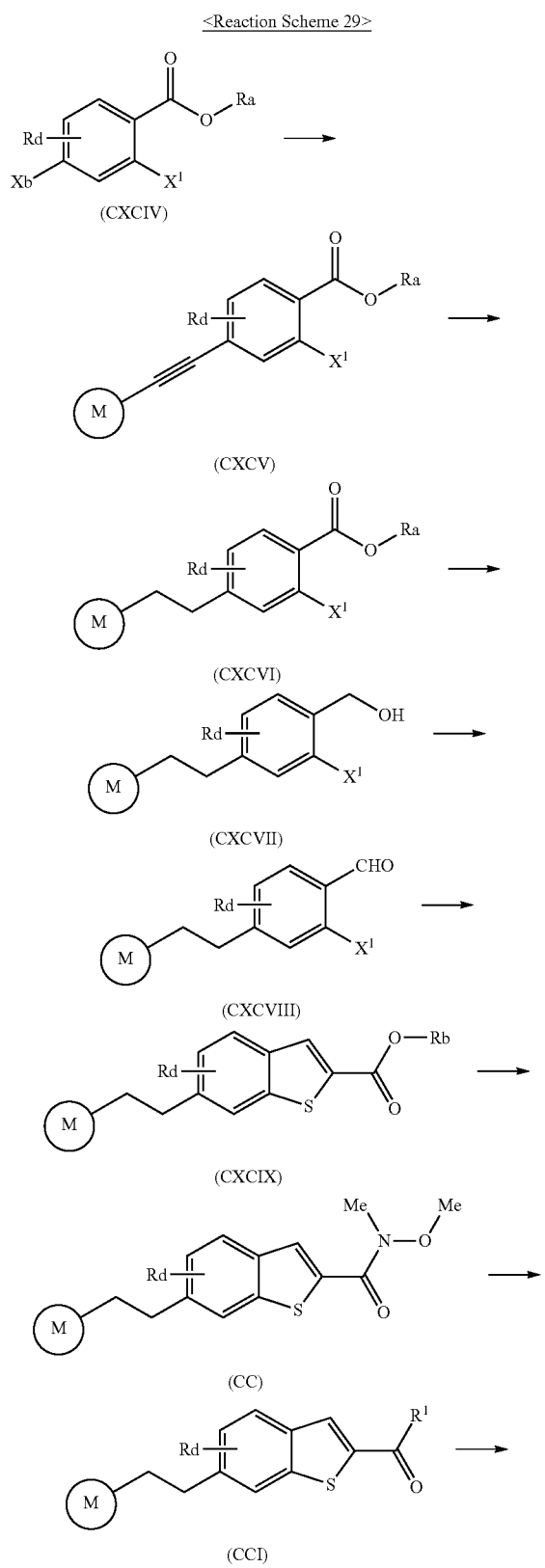

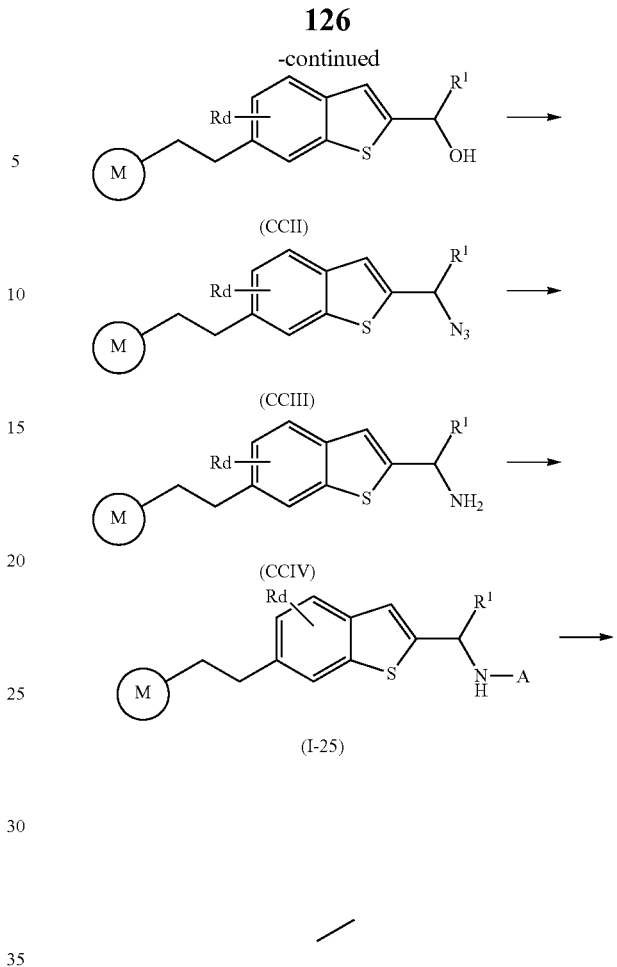

wherein M, $R^1$, A, Ra, Rb, Rd, $X^1$ and Xb are independently as defined above.

Compound (CXCIV) may be easily commercially available, or can also be produced according to a method known per se or a method analogous thereto.

Compound (CXCV) can be produced, for example, from compound (CXCIV) by a method similar to the Sonogashira reaction of compound (CLXVIII) in the aforementioned Reaction Scheme 25.

Compound (CXCVI) can be produced, for example, from compound (CXCV) by a method similar to the hydrogenation reaction of compound (CLXIX) in the aforementioned Reaction Scheme 25.

Compound (CXCVII) can be produced, for example, from compound (CXCVI) by a method similar to the reduction reaction of compound (XXVIII) in the aforementioned Reaction Scheme 4.

Compound (CXCVIII) can be produced, for example, from compound (CXCVII) by a method similar to the oxidization reaction of compound (CLXXI) in the aforementioned Reaction Scheme 25.

Compound (CXCIX) can be produced, for example, from compound (CXCVIII) by a method similar to the cyclization reaction of compound (CII) in the aforementioned Reaction Scheme 17.

Compound (CC) can be produced, for example, from compound (CXCIX) by a method similar to the amidation reaction of compound (XXIV) in the aforementioned Reaction Scheme 4.

Compound (CCI) can be produced, for example, from compound (CC) by a method similar to the substitution reaction of compound (XXV) in the aforementioned Reaction Scheme 4.

Compound (CCII) can be produced, for example, from compound (CCI) by a method similar to the reduction reaction of compound (XXVIII) in the aforementioned Reaction Scheme 4.

Compound (CCIII) can be produced, for example, from compound (CCII) by a method similar to the substitution reaction of compound (XXIX) in the aforementioned Reaction Scheme 4.

Compound (CCIV) can be produced, for example, from compound (CCIII) by a method similar to the reduction reaction of compound (XXX) in the aforementioned Reaction Scheme 4.

Compound (I-25) can be produced, for example, from compound (CCIV) by a method similar to the acylation reaction of compound (VII) in the aforementioned Reaction Scheme 1.

<Reaction Scheme 30>

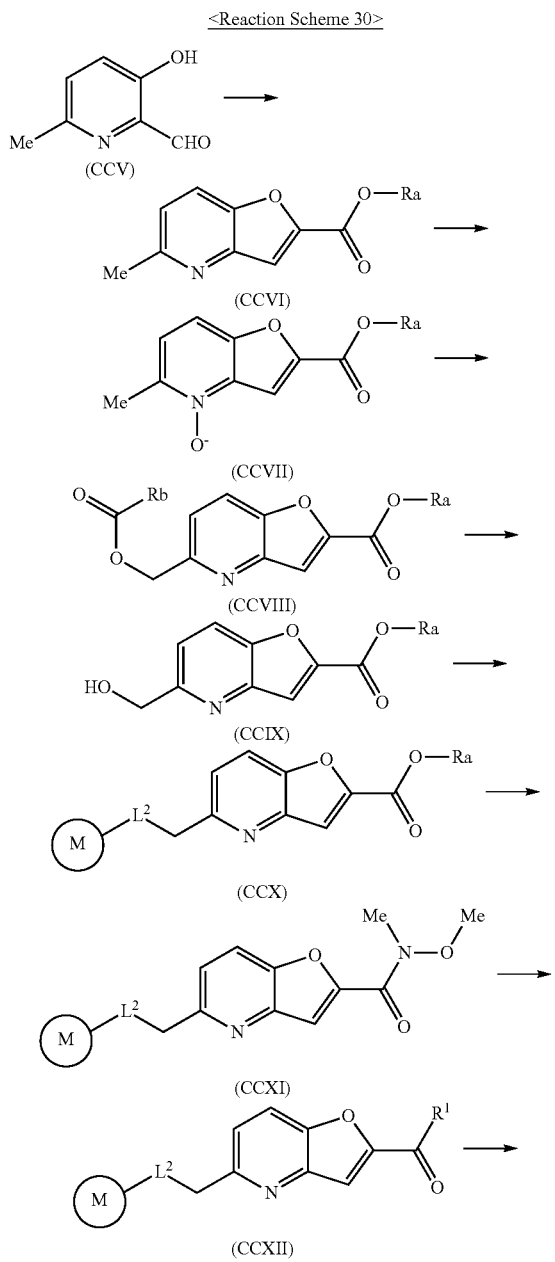

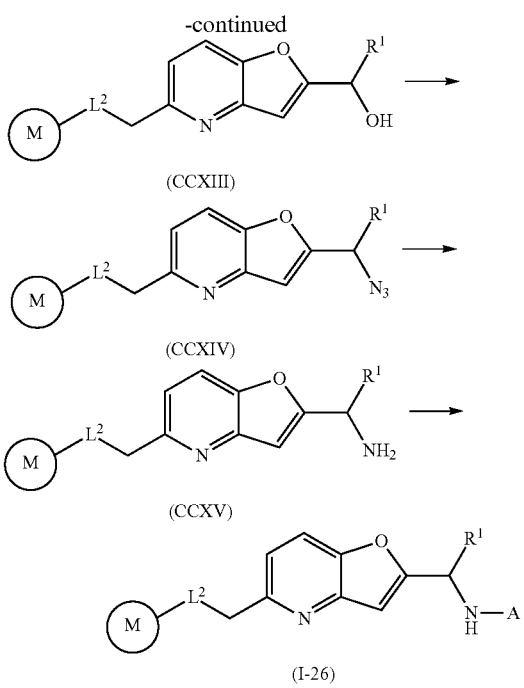

wherein M, $R^1$, A, $L^2$, Ra and Rb are independently as defined above.

Compound (CCV) may be easily commercially available, or can also be produced according to a method known per se, for example, the method described in Journal of Medicinal Chemistry, pages 2703-2705, 1993 or the like, or a method analogous thereto.

Compound (CCVI) can be produced, for example, by subjecting compound (CCV) to a cyclization reaction.

The cyclization reaction can be carried out according to a method known per se, for example, the method described in Bulletin of Chemical Society Japan, page 2762-2767, 1983 or the like, or a method analogous thereto.

This reaction is carried out by reacting compound (CCV) with a α-haloester compound in the presence of a base, in an inert solvent.

Examples of the above-mentioned "α-haloester compound" include ethyl 1-bromoacetate and the like. The amount of the "α-haloester compound" to be used is generally 1 to 20 equivalents, preferably 1 to 5 equivalents, relative to compound (CCV).

Examples of the above-mentioned "base" include "inorganic bases", "basic salts", "hydrides of alkali metal or alkaline earth metal", "metal alkoxides" and the like. The amount of the "base" to be used is generally 2 to 10 equivalents, preferably 2 to 5 equivalents, relative to compound (CCV).

Examples of the above-mentioned "inert solvent" include nitrile solvents, alcohol solvents, ketone solvents aromatic solvents, aliphatic hydrocarbon solvents, ether solvents, ester solvents, amide solvents and the like. These may be used in a mixture of two or more kinds thereof at an appropriate ratio. Of these, acetonitrile, ethanol is preferable.

The reaction temperature is generally –70 to 150° C., preferably –20 to 100° C.

The reaction time is generally 0.1 to 100 hr, preferably 0.1 to 40 hr.

Compound (CCVII) can be produced, for example, by subjecting compound (CCVI) to an oxidization reaction.

The oxidation reaction can be carried out according to a method known per se, for example, the method described in Journal of Heterocyclic Chemistry, pages 1051-1056, 1996 or the like, or a method analogous thereto.

This reaction is carried out by reacting compound (CCVI) in the presence of an oxidant, in an inert solvent.

Examples of the above-mentioned "oxidant" include hydrogen peroxide, m-chloroperbenzoic acid and the like. The amount of the "oxidant" to be used is generally 1 to 20 equivalents, preferably 1 to 5 equivalents, relative to compound (CCVI).

Examples of the above-mentioned "inert solvent" include halogenated hydrocarbon solvents, aromatic solvents, aliphatic hydrocarbon solvents, ester solvents, amide solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

Compound (CCVIII) can be produced, for example, by subjecting compound (CCVII) to a rearrangement reaction.

The rearrangement reaction can be carried out according to a method known per se, for example, the method described in Journal of American Chemical Society, pages 1286-1289, 1954 or the like, or a method analogous thereto.

This reaction is carried out by reacting compound (CCVII) in the presence of a carboxylic anhydride, in an inert solvent or without in a solvent.

Examples of the above-mentioned "carboxylic anhydride" include acetic anhydride, trifluoroacetic acid anhydride and the like. The amount of the "carboxylic anhydride" to be used is generally 1 to 20 equivalents, preferably 1 to 5 equivalents, relative to compound (CCVII).

Examples of the above-mentioned "inert solvent" include halogenated hydrocarbon solvents, aromatic solvents, aliphatic hydrocarbon solvents and the like. These may be used in a mixture of two or more kinds thereof at an appropriate ratio.

The reaction temperature is generally −70 to 250° C., preferably −20 to 200° C.

The reaction time is generally 0.1 to 100 hr, preferably 0.1 to 40 hr.

Compound (CCIX) can be produced, for example, from compound (CCVIII) by a method similar to the aforementioned hydrolysis of compound (IV) in Reaction Scheme 1.

Compound (CCX) can be produced, for example, from compound (CCIX) by a method similar to the substitution reaction of compound (XVII) in the aforementioned Reaction Scheme 3.

Compound (CCXI) can be produced, for example, from compound (CCX) by a method similar to the amidation reaction of compound (XXIV) in the aforementioned Reaction Scheme 4.

Compound (CCXII) can be produced, for example, from compound (CCXI) by a method similar to the substitution reaction of compound (XXV) in the aforementioned Reaction Scheme 4.

Compound (CCXIII) can be produced, for example, from compound (CCXII) by a method similar to the reduction reaction of compound (XXVIII) in the aforementioned Reaction Scheme 4.

Compound (CCXIV) can be produced, for example, from compound (CCXIII) by a method similar to the substitution reaction of compound (XXIX) in the aforementioned Reaction Scheme 4.

Compound (CCXV) can be produced, for example, from compound (CCXIV) by a method similar to the reduction reaction of compound (XXX) in the aforementioned Reaction Scheme 4.

Compound (I-26), can be produced for example, from compound (CCXV) by a method similar to the acylation reaction of compound (VII) in the aforementioned Reaction Scheme 1.

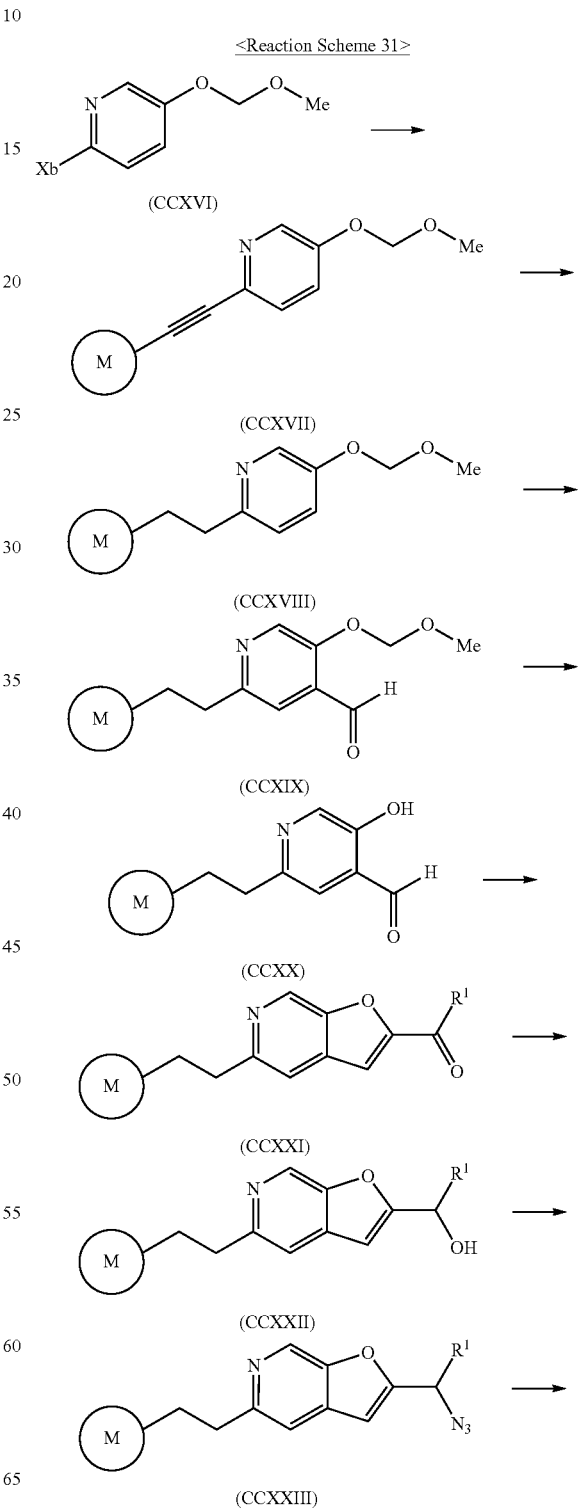

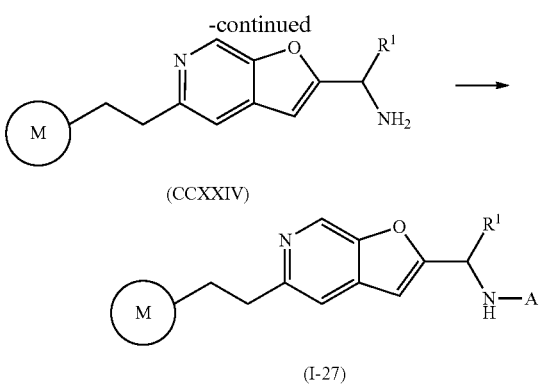

wherein M, R¹, A and Xb are independently as defined above.

Compound (CCXVI) may be easily commercially available, or can also be produced according to a method known per se, for example, the method described in Journal of Medicinal Chemistry, pages 8378-8383, 2006 or the like, or a method analogous thereto.

Compound (CCXVII) can be produced, for example, from compound (CCXVI) by a method similar to the Sonogashira reaction of compound (CLXVIII) in the aforementioned Reaction Scheme 25.

Compound (CCXVIII) can be produced, for example, from compound (CCXVII) by a method similar to the hydrogenation reaction of compound (CLXIX) in the aforementioned Reaction Scheme 25.

Compound (CCXIX) can be produced, for example, by subjecting compound (CCXVIII) to a formylation reaction. The formylation reaction can be carried out according to a method known per se, for example, the method described in Synlett, pages 1908-1912, 2006 or the like, or a method analogous thereto.

This reaction can be carried out by reacting compound (CCXVIII) in the presence of a base, in an inert solvent, and then adding a formylating agent.

Examples of the above-mentioned "formylating agent" include amide solvents having a formyl group such as DMF and the like, formates and the like. The amount of the "formylating agent" to be used is generally 1 to 20 equivalents, preferably 1 to 5 equivalents, relative to compound (CCXVIII).

Examples of the above-mentioned "base" include "hydrides of alkali metal or alkaline earth metal", "metal amides", "alkyl metals", "aryl metals" and the like. The amount of the "base" to be used is generally 1 to 20 equivalents, preferably 1 to 5 equivalents, relative to compound (CCXVIII). In this case, a "tertiary amine" such as tetramethylethylenediamine and the like may be added.

Examples of the above-mentioned "inert solvent" include ether solvents, aromatic solvents, aliphatic hydrocarbon solvents and the like. These may be used in a mixture of two or more kinds thereof at an appropriate ratio.

The reaction temperature is generally −100 to 100° C., preferably −80 to 100° C.

The reaction time is generally 0.1 to 100 hr, preferably 0.1 to 8 hr.

Compound (CCXX) can be produced, for example, by subjecting compound (CCXIX) to deprotection. The deprotection can be carried out according to a method known per se, for example, the method described in Protective Groups in Organic Synthesis, John Wiley and Sons (1980) or the like.

Compound (CCXXI) can be produced, for example, from compound (CCXX) by a method similar to the cyclization reaction of compound (XXXIII) in the aforementioned Reaction Scheme 5.

Compound (CCXXII) can be produced, for example, from compound (CCXXI) by a method similar to the reduction reaction of compound (XXVIII) in the aforementioned Reaction Scheme 4.

Compound (CCXXIII) can be produced, for example, from compound (CCXXII) by a method similar to the substitution reaction of compound (XXIX) in the aforementioned Reaction Scheme 4.

Compound (CCXXIV) can be produced, for example, from compound (CCXXIII) by a method similar to the reduction reaction of compound (XXX) in the aforementioned Reaction Scheme 4.

Compound (I-27) can be produced, for example, from compound (CCXXIV) by a method similar to the acylation reaction of compound (VII) in the aforementioned Reaction Scheme 1.

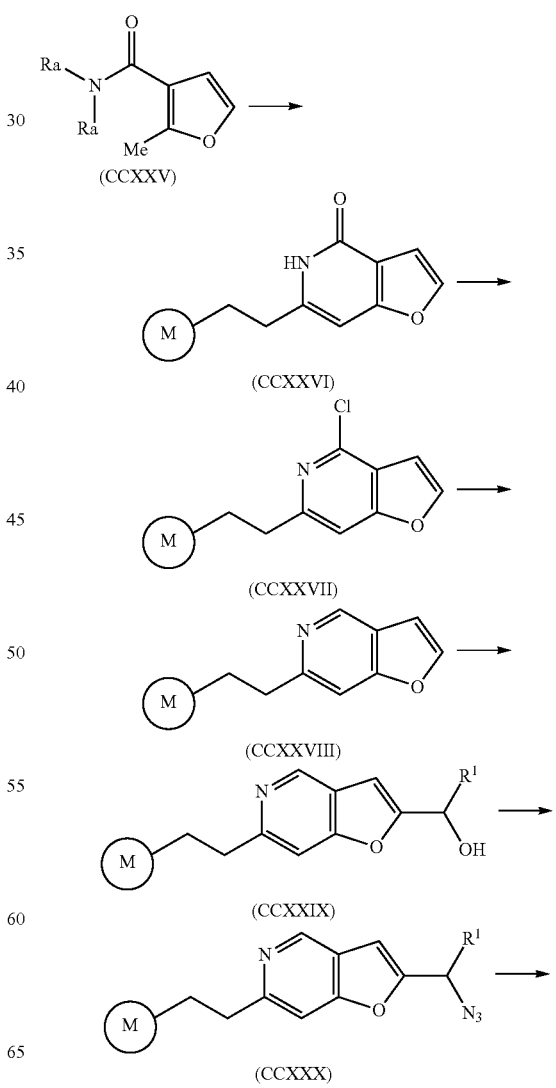

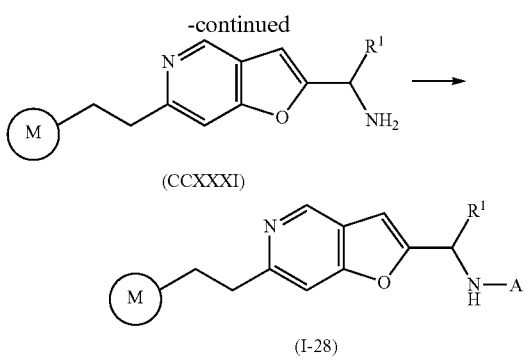

wherein M, R¹, A and Ra are independently as defined above.

Compound (CCXXV) may be easily commercially available, or can also be produced according to a method known per se, for example, the method described in Russian Journal of General Chemistry, pages 542-547, 1998 or the like, or a method analogous thereto.

Compound (CCXXVI) can be produced, for example, by subjecting compound (CCXXV) to a cyclization reaction.

The cyclization reaction can be carried out according to a method known per se, for example, the method described in U.S. Pat. No. 4,808,595 and the like, or a method analogous thereto.

This reaction is carried out by reacting compound (CCXXV) in the presence of a base, in an inert solvent, and then adding a nitrile compound.

Examples of the above-mentioned "nitrile compound" include alkyl cyanides and the like. The amount of the "nitrile compound" to be used is generally 1 to 20 equivalents, preferably 1 to 5 equivalents, relative to compound (CCXXV).

Examples of the above-mentioned "base" include "hydrides of alkali metal or alkaline earth metal", "metal amides", "alkyl metals", "aryl metals" and the like. The amount of the "base" to be used is generally 1 to 20 equivalents, preferably 1 to 5 equivalents, relative to compound (CCXXV).

Examples of the above-mentioned "inert solvent" include ether solvents, aromatic solvents, aliphatic hydrocarbon solvents and the like. These may be used in a mixture of two or more kinds thereof at an appropriate ratio.

The reaction temperature is generally −100 to 100° C., preferably −80 to 100° C.

The reaction time is generally 0.1 to 100 hr, preferably 0.1 to 8 hr.

Compound (CCXXVII) can be produced, for example, by subjecting compound (CCXXVI) to a chlorination reaction.

The chlorination reaction can be carried out according to a method known per se, for example, the method described in Journal of Heterocyclic Chemistry, pages 281-284, 1989 or the like, or a method analogous thereto.

This reaction is carried out by reacting compound (CCXXVI) in the presence of a chlorinating agent, in an inert solvent or without in a solvent.

Examples of the above-mentioned "chlorinating agent" include oxyphosphorus trichloride, phosphorus pentachloride and the like. The amount of the "chlorinating agent" to be used is generally 1 to equivalents, preferably 1 to 5 equivalents, relative to compound (CCXXVI).

Examples of the above-mentioned "inert solvent" include halogenated hydrocarbon solvents, ether solvents, aromatic solvents, aliphatic hydrocarbon solvents and the like. These may be used in a mixture of two or more kinds thereof at an appropriate ratio.

The reaction temperature is generally −100 to 200° C., preferably 0 to 120° C.

The reaction time is generally 0.1 to 100 hr, preferably 0.1 to 24 hr.

Compound (CCXXVIII) can be produced, for example, by subjecting compound (CCXXVII) to a reduction reaction.

The reduction reaction can be carried out according to a method known per se, for example, the method described in Journal of Heterocyclic Chemistry, pages 57-60, 1971 or the like, or a method analogous thereto.

This reaction is carried out by reacting compound (CCXXVII) in the presence of zinc, in an organic acid solvent.

The amount of the above-mentioned "zinc" to be used is generally 1 to 20 equivalents, preferably 1 to 5 equivalents, relative to compound (CCXXVII).

The reaction temperature is generally −100 to 200° C., preferably 0 to 120° C.

The reaction time is generally 0.1 to 100 hr, preferably 0.1 to 24 hr.

Compound (CCXXIX) can be produced, for example, by subjecting compound (CCXXVIII) to an addition reaction.

The addition reaction can be carried out according to a method known per se, for example, the method described in Journal of Medicinal Chemistry, pages 1293-1310, 2000 or the like, or a method analogous thereto.

This reaction is carried out by reacting compound (CCXXVIII) in the presence of a base, in an inert solvent, and then adding a formyl compound.

Examples of the above-mentioned "formyl compound" include aldehydes such as acetoaldehyde and the like. The amount of the "formyl compound" to be used is generally 1 to 20 equivalents, preferably 1 to 5 equivalents, relative to compound (CCXXVIII).

Examples of the above-mentioned "base" include "hydrides of alkali metal or alkaline earth metal", "metal amides", "alkyl metals", "aryl metals" and the like. The amount of the "base" to be used is generally 1 to 20 equivalents, preferably 1 to 5 equivalents, relative to compound (CCXXVIII).

Examples of the above-mentioned "inert solvent" include ether solvents, aromatic solvents, aliphatic hydrocarbon solvents and the like. These may be used in a mixture of two or more kinds thereof at an appropriate ratio.

The reaction temperature is generally −100 to 100° C., preferably −80 to 100° C.

The reaction time is generally 0.1 to 100 hr, preferably 0.1 to 8 hr.

Compound (CCXXX) can be produced, for example, from compound (CCXXIX) by a method similar to the substitution reaction of compound (XXIX) in the aforementioned Reaction Scheme 4.

Compound (CCXXXI) can be produced, for example, from compound (CCXXX) by a method similar to the reduction reaction of compound (XXX) in the aforementioned Reaction Scheme 4.

Compound (I-28) can be produced, for example, from compound (CCXXXI) by a method similar to the acylation reaction of compound (VII) in the aforementioned Reaction Scheme 1.

<Reaction Scheme 33>

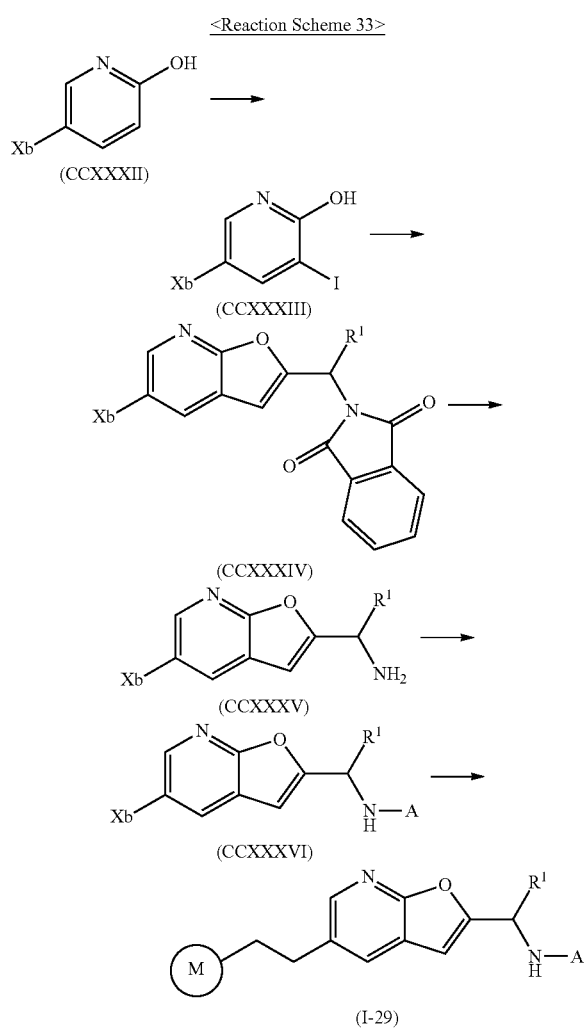

wherein M, R¹, A and Xb are independently as defined above.

Compound (CCXXXII) may be easily commercially available, or can also be produced according to a method known per se or a method analogous thereto.

Compound (CCXXXIII) can be produced, for example, by subjecting compound (CCXXXII) to an iodination reaction.

The iodination reaction can be carried out according to a method known per se, for example, the method described in Synlett, 1678-1682, 2003 or the like, or a method analogous thereto.

This reaction is carried out by reacting compound (CCXXXII) in the presence of an iodinating agent, in an inert solvent. In addition, this reaction may be carried out in the presence of a base.

Examples of the above-mentioned "iodinating agent" include N-iodosuccinimide, iodine and the like. The amount of the "iodinating agent" to be used is generally 1 to 20 equivalents, preferably 1 to 5 equivalents, relative to compound (CCXXXII).

Examples of the above-mentioned "inert solvent" include nitrile solvents, amide solvents, ether solvents, aromatic solvents, aliphatic hydrocarbon solvents, water and the like. These may be used in a mixture of two or more kinds thereof at an appropriate ratio.

Examples of the above-mentioned "base" include "basic salts", "aromatic amines", "tertiary amines", "hydrides of alkali metal or alkaline earth metal", "metal amides", "alkyl metals", "aryl metals", "metal alkoxides" and the like. The amount of the "base" to be used is generally 0.1 to 20 equivalents, preferably 1 to 5 equivalents, relative to compound (CCXXXII). In addition, the base may be used as a solvent.

The reaction temperature is generally −100 to 100° C., preferably −80 to 100° C.

The reaction time is generally 0.1 to 100 hr, preferably 0.1 to 8 hr.

Compound (CCXXXIV) can be produced, for example, by subjecting compound (CCXXXIII) to a cyclization reaction.

The cyclization reaction can be carried out according to a method known per se, for example, the method described in Synthesis, pages 749-751, 1986 or the like, or a method analogous thereto.

This reaction is carried out by reacting compound (CCXXXIII) in the presence of 2-(1-methylpropan-2-yn-1-yl)-1H-isoindole-1,3(2H)-dione, a transition metal catalyst and a base, in an inert solvent, under an inert gas atmosphere. In addition, a ligand may be added in this reaction, as necessary.

The amount of the 2-(1-methylpropan-2-yn-1-yl)-1H-isoindole-1,3(2H)-dione to be used is generally 1 to 20 equivalents, preferably 1 to 5 equivalents, relative to compound (CCXXXIII).

Examples of the above-mentioned "transition metal catalyst" include palladium catalysts, nickel catalysts, iron catalysts, cobalt catalysts and the like. Examples of the palladium catalyst include dichlorobis(triphenylphosphine)palladium and the like. The amount of the "transition metal catalyst" to be used is generally 0.001 to 1 equivalents, preferably 0.01 to 0.1 equivalents, relative to compound (CCXXXIII). In addition, a copper catalyst and the like may be added as a cocatalyst. Examples of the copper catalyst include copper iodide and the like. The amount of the "cocatalyst" to be used is generally 0.001 to 1 equivalents, preferably 0.01 to 0.1 equivalents, relative to compound (CCXXXIII).

Examples of the above-mentioned "ligand" include phosphine ligands. Examples of the phosphine ligand include triphenylphosphine and the like. The amount of the "ligand" to be used is generally 0 to 20 equivalents, preferably 0 to 1 equivalents, relative to compound (CCXXXIII).

Examples of the above-mentioned "base" include "aromatic amines", "tertiary amines" and the like. The amount of the "base" to be used is generally 0.1 to 20 equivalents, preferably 1 to 5 equivalents, relative to compound (CCXXXIII). In addition, the based may be used as a solvent.

Examples of the above-mentioned "inert solvent" include amide solvents, aromatic solvents, aliphatic hydrocarbon solvents, ether solvents, ester solvents and the like. These may be used in a mixture of two or more kinds thereof at an appropriate ratio.

Examples of the above-mentioned "inert gas" include nitrogen, argon and the like.

The reaction temperature is generally −70 to 150° C., preferably −20 to 150° C.

The reaction time is generally 0.1 to 100 hr, preferably 0.1 to 40 hr.

Compound (CCXXXV) can be produced, for example, by subjecting compound (CCXXXIV) to deprotection. The deprotection can be carried out according to a method known per se, for example, the method described in Protective Groups in Organic Synthesis, John Wiley and Sons (1980) or the like.

Compound (CCXXXVI) can be produced, for example, from compound (CCXXXV) by a method similar to the acylation reaction of compound (VII) in the aforementioned Reaction Scheme 1. Alternatively, compound (CCXXXVI) can be produced from an alkyne derivative having substituent A instead of 2-(1-methylpropan-2-yn-1-yl)-1H-isoindole-1,3(2H)-dione by a method similar to the above-mentioned cyclization reaction of compound (CCXXXIII). Examples of the alkyne derivative having substituent A include a propan-2-yn-1-amine having an acyl group or an optionally substituted 5- or 6-membered aromatic ring group on the nitrogen atom and having an optionally substituted $C_{1-6}$ alkyl group or an optionally substituted $C_{3-6}$ cycloalkyl group on the 1-position, such as N-(1-methylpropan-2-yn-1-yl)acetamide and the like.

Compound (I-29) can be produced, for example, by subjecting compound (CCXXXVI) to a cross coupling reaction.

The cross coupling reaction can be carried out according to a method known per se, for example, the method described in Journal of American Chemical Society, pages 158-163, 1984 or the like, or a method analogous thereto.

This reaction is carried out by reacting compound (CCXXXVI) in the presence of a Grignard reagent and a transition metal catalyst, in an inert solvent, under an inert gas atmosphere. In addition, a ligand may be added in this reaction, as necessary.

Examples of the above-mentioned "Grignard reagent" include 4-alkoxyphenylethylmagnesium bromide and the like. The amount of the "Grignard reagent" to be used is generally 2 to 10 equivalents, preferably 2 to 5 equivalents, relative to compound (CCXXXVI).

Examples of the above-mentioned "transition metal catalyst" include palladium catalysts, nickel catalysts, iron catalysts, cobalt catalysts and the like. Examples of the palladium catalyst include dichloro{bis(triphenylphosphino)ferrocene}palladium, dichlorobis(triphenylphosphine)palladium and the like. The amount of the "transition metal catalyst" to be used is generally 0.001 to 1 equivalents, preferably 0.01 to 0.1 equivalents, relative to compound (CCXXXVI).

Examples of the above-mentioned "ligand" include phosphine ligands. Examples of the phosphine ligand include triphenylphosphine and the like. The amount of the "ligand" to be used is generally 0 to 20 equivalents, preferably 0 to 1 equivalents, relative to compound (CCXXXVI).

Examples of the above-mentioned "inert solvent" include amide solvents, aromatic solvents, aliphatic hydrocarbon solvents, ether solvents and the like. These may be used in a mixture of two or more kinds thereof at an appropriate ratio.

Examples of the above-mentioned "inert gas" include nitrogen, argon and the like.

The reaction temperature is generally −70 to 150° C., preferably −20 to 150° C.

The reaction time is generally 0.1 to 100 hr, preferably 0.1 to 40 hr.

<Reaction Scheme 34>

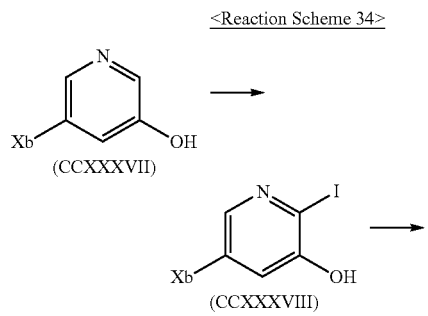

(CCXXXVII)

(CCXXXVIII)

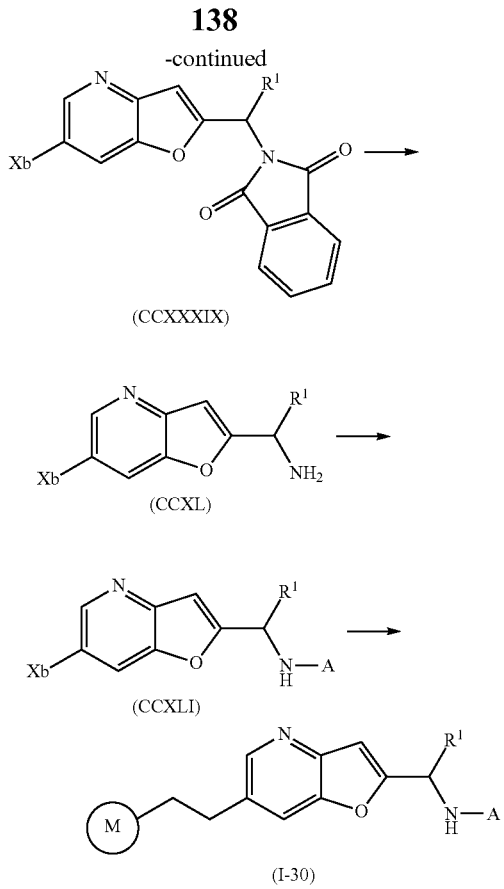

(CCXXXIX)

(CCXL)

(CCXLI)

(I-30)

wherein M, $R^1$, A and Xb are independently as defined above.

Compound (CCXXXVII) may be easily commercially available, or can also be produced according to a method known per se or a method analogous thereto.

Compound (CCXXXVIII) can be produced, for example, from compound (CCXXXVII) by a method similar to the iodination reaction of compound (CCXXXII) in the aforementioned Reaction Scheme 3.

Compound (CCXXXIX) can be produced, for example, from compound (CCXXXVIII) by a method similar to the cyclization reaction of compound (CCXXXIII) in the aforementioned Reaction Scheme 33.

Compound (CCXL) can be produced, for example, by subjecting compound (CCXXXIX) to deprotection. The deprotection can be carried out according to a method known per se, for example, the method described in Protective Groups in Organic Synthesis, John Wiley and Sons (1980) or the like.

Compound (CCXLI) can be produced, for example, from compound (CCXL) by a method similar to the acylation reaction of compound (VII) in the aforementioned Reaction Scheme 1. Alternatively, compound (CCXLI) can be produced from an alkyne derivative having substituent A instead of 2-(1-methylpropan-2-yn-1-yl)-1H-isoindole-1,3(2H)-dione by a method similar to the above-mentioned cyclization reaction of compound (CCXXXVIII).

Compound (I-30) can be produced, for example, from compound (CCXLI) by a method similar to the cross coupling reaction of compound (CCXXXVI) in the aforementioned Reaction Scheme 33.

<Reaction Scheme 35>

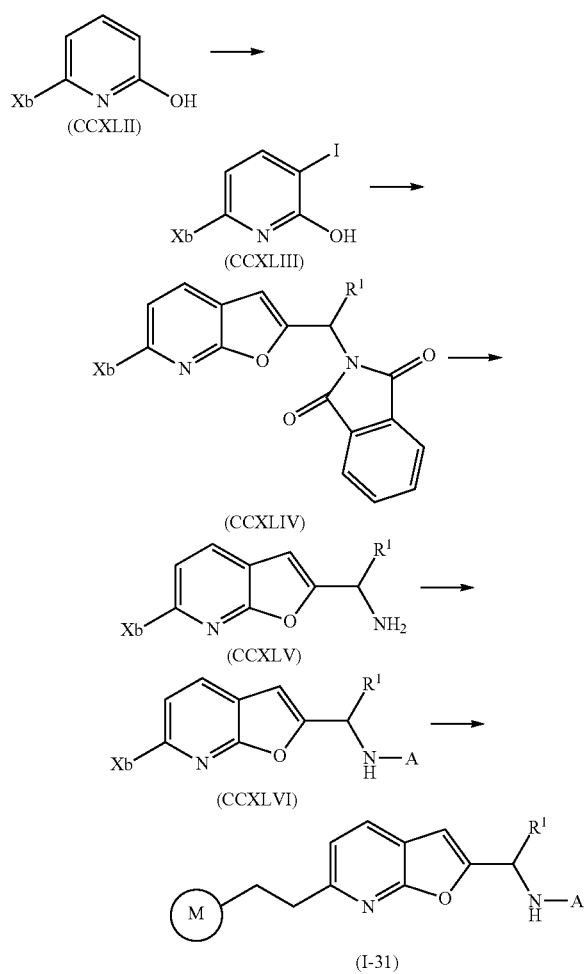

(I-31)

wherein M, $R^1$, A and Xb are independently as defined above.

Compound (CCXLII) may be easily commercially available, or can also be produced according to a method known per se or a method analogous thereto.

Compound (CCXLIII) can be produced, for example, from compound (CCXLII) by a method similar to the iodination reaction of compound (CCXXXII) in the aforementioned Reaction Scheme 3.

Compound (CCXLIV) can be produced, for example, from compound (CCXLIII) by a method similar to the cyclization reaction of compound (CCXXXIII) in the aforementioned Reaction Scheme 33.

Compound (CCXLV) can be produced, for example, by subjecting compound (CCXLIV) to deprotection. The deprotection can be carried out according to a method known per se, for example, the method described in Protective Groups in Organic Synthesis, John Wiley and Sons (1980) or the like.

Compound (CCXLVI) can be produced, for example, from compound (CCXLV) by a method similar to the acylation reaction of compound (VII) in the aforementioned Reaction Scheme 1. Alternatively, compound (CCXLVI) can be produced from an alkyne derivative having substituent A instead of 2-(1-methylpropan-2-yn-1-yl)-1H-isoindole-1,3(2H)-dione by a method similar to the above-mentioned cyclization reaction of compound (CCXLIII).

Compound (I-31) can be produced, for example, from compound (CCXLVI) by a method similar to the cross coupling reaction of compound (CCXXXVI) in the aforementioned Reaction Scheme 33.

<Reaction Scheme 36>

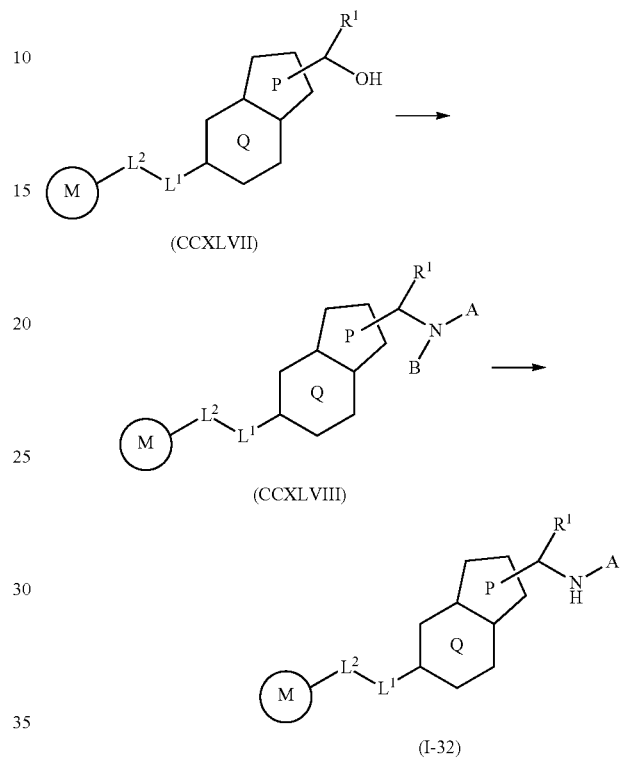

(I-32)

wherein M, P, Q, $R^1$, A, $L^1$ and $L^2$ are independently as defined above, and B is a nitrogen atom-protecting group generally used in organic chemistry and the like.

Compound (CCXLVII) can be produced, for example, according to a method known per se or the aforementioned Reaction Schemes 1 to 35.

Compound (CCXLVIII) can be produced, for example, by subjecting compound (CCXLVII) to the Mitsunobu reaction.

The Mitsunobu reaction can be carried out according to a method known per se, for example, the method described in Bioorganic and Medicinal Chemical Letters, pages 1803-1807, 2007 or the like, or a method analogous thereto.

This reaction is carried out by reacting compound (CCXLVII) with a sulfonamide derivative in the presence of a hydroxyl group-activator in an inert solvent.

Examples of the above-mentioned "sulfonamide derivative" include sulfonamides activated by a nitrobenzenesulfonyl group and the like, such as N-(isoxazol-3-yl)-4-nitrobenzenesulfonamide, and the like. The amount of the "sulfonamide derivative" to be used is generally 1 to 10 equivalents, preferably 1 to 5 equivalents, relative to compound (CCXLVII).

Examples of the above-mentioned "hydroxyl group-activator" include cyanomethylenetri-n-butylphosphorane; a combination of diethyl azodicarboxylate (DEAD) and triphenylphosphine, and the like. The amount of the "hydroxyl group-activator" to be used is generally 1 to 10 equivalents, preferably 1 to 1.5 equivalents, relative to compound (CCXLVII).

Examples of the above-mentioned "inert solvent" include aromatic solvents, aliphatic hydrocarbon solvents, ether solvents, ester solvents, amide solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

Compound (I-32) can be produced, for example, by subjecting compound (CCXLVIII) to deprotection. The deprotection can be carried out according to a method known per se, for example, the method described in Protective Groups in Organic Synthesis, John Wiley and Sons (1980) or the like.

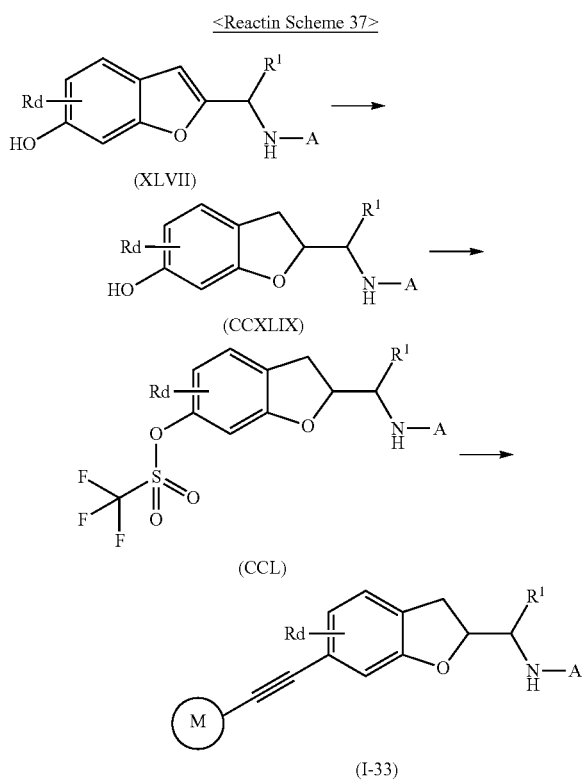

wherein M, $R^1$, A and Rd are independently as defined above.

Compound (CCXLIX) can be produced, for example, by subjecting compound (XLVII) to a hydrogenation reaction.

The hydrogenation reaction can be carried out according to a method known per se, for example, the method described in Journal of Chemical Society, pages 3362-3369, 1959 or the like, or a method analogous thereto.

This reaction can be carried out, for example, by reacting compound (XLVII) in the presence of a metal catalyst and a hydrogen source, in an inert solvent.

Examples of the above-mentioned "metal catalyst" include palladium carbon, palladium black, palladium chloride, platinum oxide, platinum black, platinum palladium, Raney-nickel, Raney-cobalt and the like. The amount of the "metal catalyst" to be used is generally 0.001 to 1000 equivalents, preferably 0.01 to 100 equivalents, relative to compound (XLVII).

Examples of the above-mentioned "hydrogen source" include hydrogen gas, formic acid, formic acid amine salt, phosphinate, hydrazine and the like.

Examples of the above-mentioned "inert solvent" include alcohol solvents, nitrile solvents, aromatic solvents, aliphatic hydrocarbon solvents, ether solvents, amide solvents, halogenated hydrocarbon solvents and the like. These solvents are preferably used in a mixture with water at an appropriate ratio. Of these, alcohol solvents are preferable.

The reaction temperature is generally −70 to 150° C., preferably −20 to 100° C.

The reaction time is generally 0.1 to 100 hr, preferably 0.1 to 40 hr.

Compound (CCL) can be produced, for example, from compound (CCXLIX) by a method similar to the triflation reaction of compound (CLXVII) in the aforementioned Reaction Scheme 25.

Compound (I-33) can be produced, for example, from compound (CCL) by a method similar to the Sonogashira reaction of compound (CLXVIII) in the aforementioned Reaction Scheme 25.

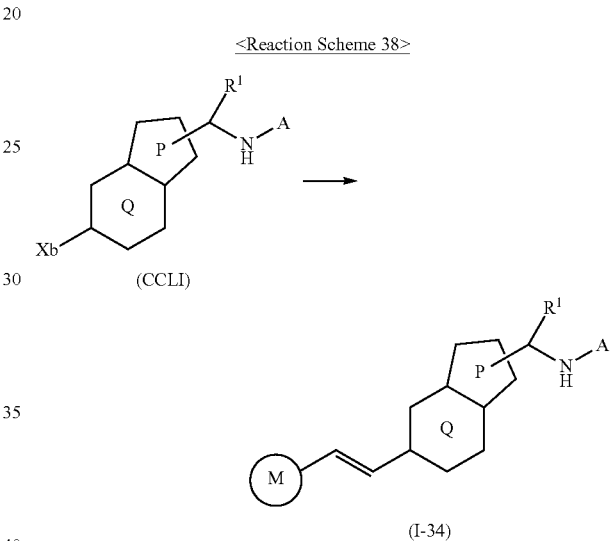

wherein M, P, Q, $R^1$, A and Xb are independently as defined above.

Compound (CCLI) can be produced, for example, according to a method known per se or the aforementioned Reaction Schemes 1 to 37.

Compound (I-34) can be produced, for example, by subjecting compound (CCLI) to the Heck reaction.

The Heck reaction can be carried out according to a method known per se, for example, the method described in Journal of Medicinal Chemistry, pages 2085-2101, 1997 or the like, or a method analogous thereto.

This reaction is carried out by reacting compound (CCLI) with a vinyl compound in the presence of a transition metal catalyst, a ligand and a base, in an inert solvent, under an inert gas atmosphere.

Examples of the above-mentioned "vinyl compound" include styrene derivatives. The amount of the "vinyl compound" to be used is generally 1 to 20 equivalents, preferably 1 to 10 equivalents, relative to compound (CCLI).

Examples of the above-mentioned "transition metal catalyst" include palladium catalysts, nickel catalysts, iron catalysts, cobalt catalysts and the like. Examples of the palladium catalyst include palladium acetate, dichlorobis(benzonitrile) palladium and the like. The amount of the "transition metal catalyst" to be used is generally 0.01 to 20 equivalents, preferably 0.01 to 0.2 equivalents, relative to compound (CCLI).

Examples of the above-mentioned "ligand" include phosphine ligands. Examples of the phosphine ligand include triphenylphosphine and the like. The amount of the "ligand" to be used is generally 0.01 to 20 equivalents, preferably 0.01 to 0.2 equivalents, relative to compound (CCLI).

Examples of the above-mentioned "base" include "aromatic amines", "tertiary amines" and the like. The amount of the "base" to be used is generally 0.1 to 20 equivalents, preferably 1 to 5 equivalents, relative to compound (CCLI).

Examples of the above-mentioned "inert solvent" include alcohol solvents, aromatic solvents, aliphatic hydrocarbon solvents, ether solvents, ester solvents, amide solvents and the like. These may be used in a mixture of two or more kinds thereof at an appropriate ratio.

Examples of the above-mentioned "inert gas" include nitrogen, argon and the like.

The reaction temperature is generally −70 to 150° C., preferably −20 to 150° C.

The reaction time is generally 0.1 to 100 hr, preferably 0.1 to 40 hr.

<Reaction Scheme 39>

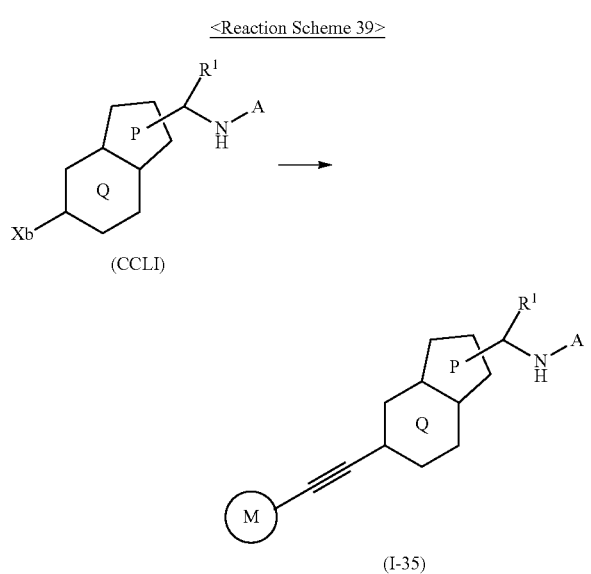

(CCLI)

(I-35)

wherein M, P, Q, $R^1$, A and Xb are independently as defined above.

Compound (I-35) can be produced, for example, from compound (CCLI) by a method similar to the Sonogashira reaction of compound (CLXVIII) in the aforementioned Reaction Scheme 25.

<Reaction Scheme 40>

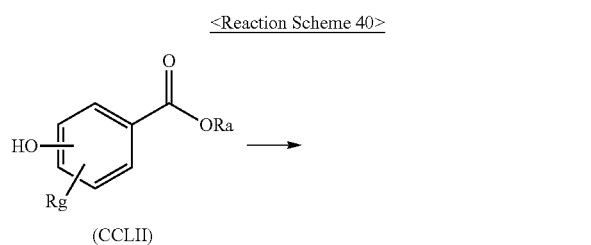

(CCLII)

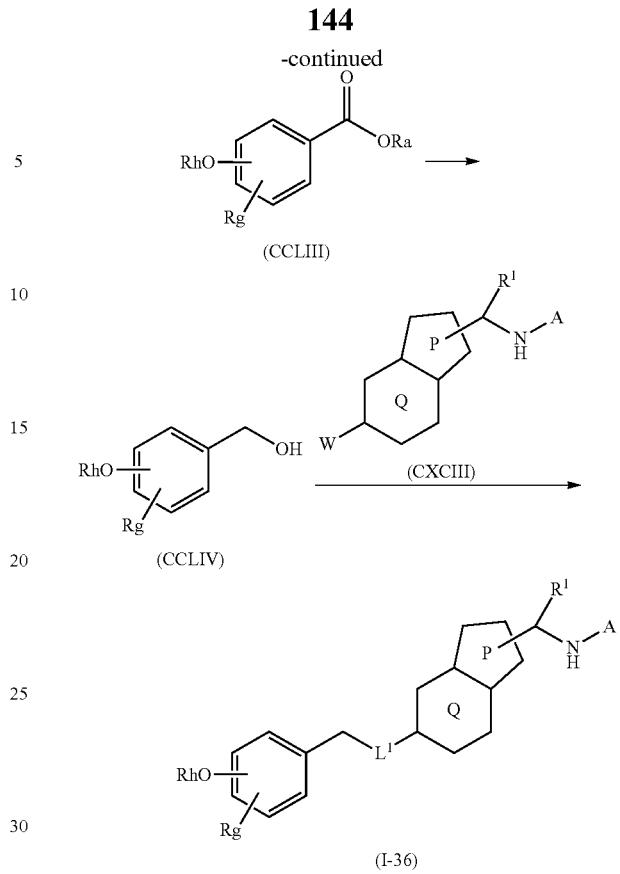

(CCLIII)

(CCLIV)

(I-36)

wherein Rg is a hydrogen atom, an optionally substituted hydrocarbon group or an optionally substituted heterocyclic group, Rh is an optionally substituted $C_{1-6}$ alkyl group or a $C_{7-12}$ aralkyl group, and P, Q, $R^1$, $L^1$, A, Ra and W are independently is as defined above. Examples of the "optionally substituted hydrocarbon group" and "optionally substituted heterocyclic group" for Rg include those similar to the "optionally substituted hydrocarbon group" and "optionally substituted heterocyclic group" for $R^A$, $R^{A'}$ or $R^{B'}$.

Compound (CCLII) may be easily commercially available, or can be produced, for example, according to a method known per se.

Compound (CCLIII) can be produced, for example, by subjecting compound (CCLII) to an alkylation reaction.

Examples of the alkylation reaction include the following "method using a base and alkyl halide 2", "method employing the Mitsunobu reaction", and the like.

The "method using a base and alkyl halide 2" can be carried out according to a method known per se, for example, the method described in Journal of Chemical Society, pages 1530-1534, 1937 or the like, or a method analogous thereto.

This reaction is carried out by reacting compound (CCLII) with alkyl halide 2 in the presence of a base, in an inert solvent.

Examples of the above-mentioned "alkyl halide 2" include halide compounds such as bromopropane, 2-iodopropane, (bromomethyl)cyclopropane and the like, and the like. The amount of the "alkyl halide 2" to be used is generally 1 to 10 equivalents, preferably 1 to 5 equivalents, relative to compound (CCLII).

Examples of the above-mentioned "base" include "inorganic bases", "basic salts", "aromatic amines", "hydrides of alkali metal or alkaline earth metal", "alkyl metals", "aryl metals", "metal alkoxides" and the like. The amount of the "base" to be used is generally 1 to 10 equivalents, preferably 1 to 5 equivalents, relative to compound (CCLII).

Examples of the above-mentioned "inert solvent" include nitrile solvents, amide solvents, halogenated hydrocarbon solvents, ether solvents and the like. These may be used in a mixture of two or more kinds thereof at an appropriate ratio. Of these, THF, DMF and the like are preferable.

The reaction temperature is generally −100° C. to 150° C., preferably 0° C. to 100° C.

The reaction time is generally 5 min to 48 hr, preferably 30 min to 24 hr.

The "method employing the Mitsunobu reaction" can be carried out according to a method known per se, for example, the method described in Tetrahedron Letters, pages 769-770, 1980 or the like, or a method analogous thereto.

This reaction is carried out by reacting compound (CCLII) with alcohol 2 having substituent(s) in the presence of a hydroxyl group-activator in an inert solvent.

Examples of the above-mentioned "alcohol 2 having substituent(s)" include alcohols such as tetrahydrofuran-2-yl-methanol and the like. The amount of the "alcohol 2 having substituent(s)" to be used is generally 1 to 10 equivalents, preferably 1 to 5 equivalents, relative to compound (CCLII).

Examples of the above-mentioned "hydroxyl group-activator" include cyanomethylenetri-n-butylphosphorane, a combination of DEAD and triphenylphosphine and the like. The amount of the "hydroxyl group-activator" to be used is generally 1 to 10 equivalents, preferably 1 to 1.5 equivalents, relative to compound (CCLII).

Examples of the above-mentioned "inert solvent" include aromatic solvents, aliphatic hydrocarbon solvents, ether solvents, ester solvents, amide solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

Compound (CCLIV) can be produced, for example, from compound (CCLIII) by a method similar to the reduction reaction of compound (XXVIII) in the aforementioned Reaction Scheme 4.

Compound (I-36) can be produced, for example, from compound (CCLIV) and compound (CXCIII) according to a method known per se, or by a method similar to the synthetic method of compound (I-1) in the aforementioned Reaction Scheme 1.

<Reaction Scheme 41>

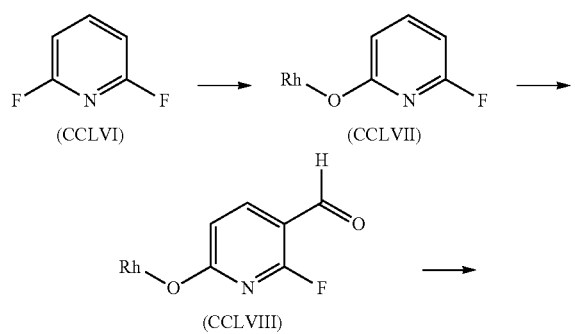

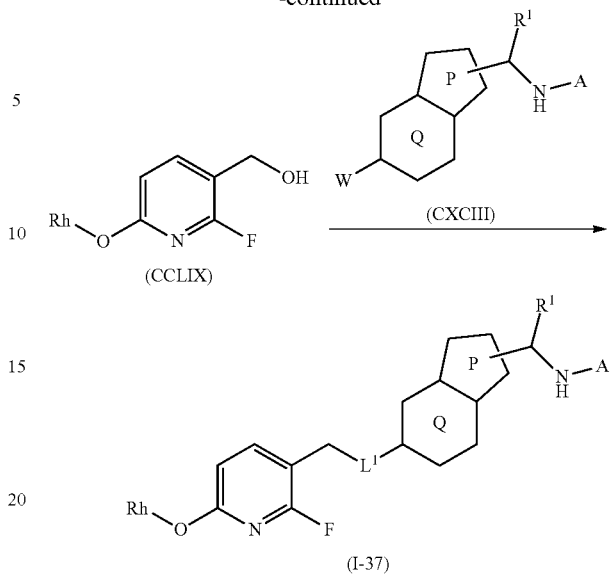

wherein P, Q, $R^1$, $L^1$, A, W and Rh are independently as defined above.

Compound (CCLVI) may be easily commercially available.

Compound (CCLVII) can be produced, for example, by subjecting compound (CCLVI) to a substitution reaction.

The substitution reaction can be carried out according to a method known per se, for example, the method described in Journal of Fluorine Chemistry, pages 135-146, 2001 or the like, or a method analogous thereto.

This reaction is carried out by reacting compound (CCLVI) with alcohol 2 having substituent(s) in the presence of a base, in an inert solvent.

Examples of the above-mentioned "alcohol 2 having substituent(s)" include alcohols such as cyclopropylmethanol, tetrahydrofuran-2-ylmethanol and the like. The amount of the "alcohol 2 having substituent(s)" to be used is generally 1 to 10 equivalents, preferably 1 to 5 equivalents, relative to compound (CCLVI).

Examples of the above-mentioned "base" include "inorganic bases", "basic salts", "aromatic amines", "tertiary amines", "hydrides of alkali metal or alkaline earth metal", "metal alkoxide" and the like. The amount of the "base" to be used is generally 1 to 10 equivalents, preferably 1 to 2 equivalents, relative to compound (CCLVI).

Examples of the above-mentioned "inert solvent" include aromatic solvents, aliphatic hydrocarbon solvents, ether solvents, ester solvents, amide solvents and the like. These may be used in a mixture of two or more kinds thereof at an appropriate ratio.

The reaction temperature is generally −70 to 150° C., preferably −20 to 100° C.

The reaction time is generally 0.1 to 100 hr, preferably 0.1 to 40 hr.

Compound (CCLVIII) can be produced, for example, by subjecting compound (CCLVII) to a substitution reaction.

The substitution reaction can be carried out according to a method known per se, for example, the method described in Journal of Organic Chemistry, pages 565-573, 1992 or the like, or a method analogous thereto.

This reaction is carried out by reacting compound (CCLVII) in the presence of a base, in an inert solvent, and then adding a formylating agent.

Examples of the above-mentioned "base" include "hydrides of alkali metal or alkaline earth metal", "metal amides", "alkyl metals", "aryl metals" and the like. The amount of the "base" to be used is generally 1 to 20 equivalents, preferably 1 to 5 equivalents, relative to compound (CCLVII).

Examples of the above-mentioned "inert solvent" include ether solvents, aromatic solvents, aliphatic hydrocarbon solvents and the like. These may be used in a mixture of two or more kinds thereof at an appropriate ratio.

Examples of the above-mentioned "formylating agent" include ethyl formate, DMF and the like. The amount of the "formylating agent" to be used is generally 1 to 20 equivalents, preferably 1 to 5 equivalents, relative to compound (CCLVII).

The reaction temperature is generally −100 to 100° C., preferably −80 to 100° C.

The reaction time is generally 0.1 to 100 hr, preferably 0.1 to 8 hr.

Compound (CCLIX) can be produced, for example, from compound (CCLVIII) by a method similar to the reduction reaction of compound (XXVIII) in the aforementioned Reaction Scheme 4.

Compound (I-37) can be produced, for example, from compound (CCLIX) and compound (CXCIII) according to a method known per se, or by a method similar to the synthetic method of compound (I-1) in the aforementioned Reaction Scheme 1.

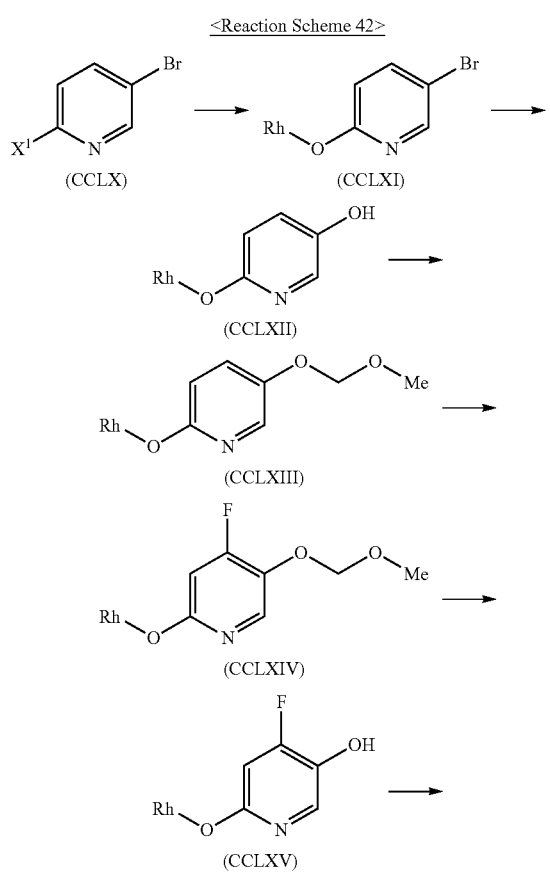

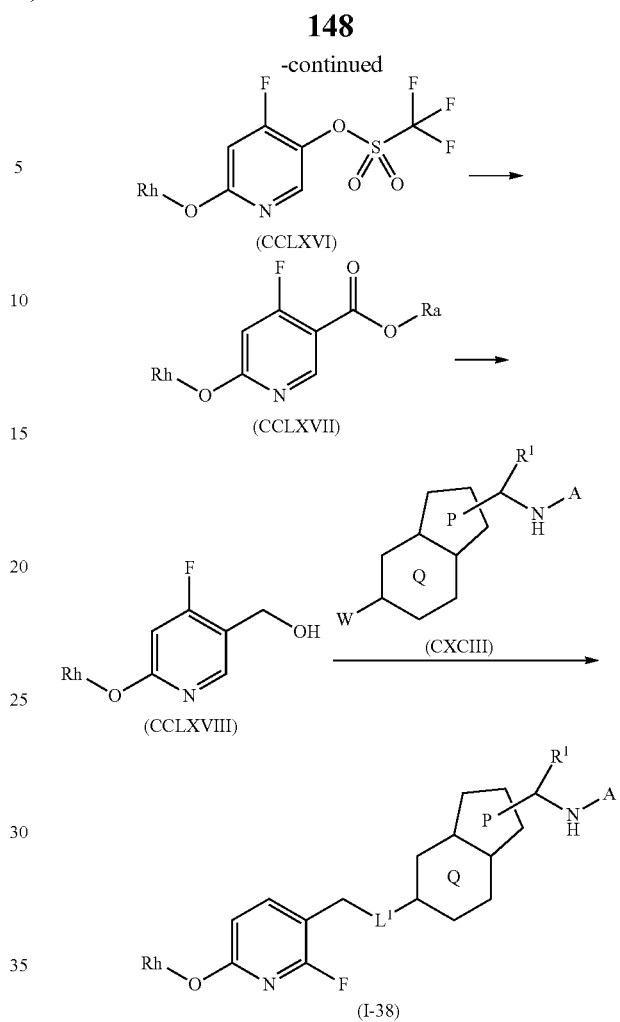

wherein P, Q, $R^1$, $L^1$, A, Ra, W, Rh and $X^1$ are independently as defined above.

Compound (CCLXI) can be produced, for example, from compound (CCLX) by a method similar to the substitution reaction of compound (CCLVI) in the aforementioned Reaction Scheme 41.

Compound (CCLXII) can be produced, for example, by subjecting compound (CCLXI) to an oxidization reaction.

The oxidation reaction can be carried out according to a method known per se, for example, the method described in Synthetic Communications, pages 969-978, 1981 or the like, or a method analogous thereto.

This reaction is carried out by reacting compound (CCLXI) in the presence of a base, in an inert solvent, and then adding successively a trialkyloxyborane and a peroxide.

Examples of the above-mentioned "base" include "alkyl metals", "aryl metals" and the like. The amount of the "base" to be used is generally 1 to 20 equivalents, preferably 1 to 2 equivalents, relatively compound (CCLXI).

Examples of the above-mentioned "inert solvent" include ether solvents, aromatic solvents, aliphatic hydrocarbon solvents and the like. These may be used in a mixture of two or more kinds thereof at an appropriate ratio.

Examples of the above-mentioned "trialkyloxyborane" include trimethoxyborane, tributyloxyborane and the like. The amount of the "trialkyloxyborane" to be used is generally 1 to 20 equivalents, preferably 1 to 2 equivalents, relatively compound (CCLXI).

Examples of the above-mentioned "peroxide" include aqueous hydrogen peroxide, m-chloroperbenzoic acid and the like. The amount of the "peroxide" to be used is generally 1 to 20 equivalents, preferably 1 to 10 equivalents, relatively compound (CCLXI). In this case, an aqueous "inorganic base" solution is generally simultaneously added. The amount of the aqueous "inorganic base" solution to be used is generally 1 to 20 equivalents, preferably 1 to 10 equivalents, relatively compound (CCLXI).

The reaction temperature is generally −100 to 100° C., preferably −80 to 100° C.

The reaction time is generally 0.1 to 100 hr, preferably 0.1 to 8 hr.

Compound (CCLXIII) can be produced, for example, by subjecting compound (CCLXII) to an alkoxyalkylation reaction. The alkoxyalkylation reaction can be carried out according to a method known per se, for example, the method described in Protective Groups in Organic Synthesis, John Wiley and Sons (1980) or the like.

Compound (CCLXIV) can be produced, for example, by subjecting compound (CCLXIII) to a fluorating reaction.

The fluorating reaction can be carried out according to a method known per se, for example, the method described in U.S. Pat. No. 6,355,660 and the like, or a method analogous thereto.

This reaction is carried out by reacting compound (CCLXIII) in the presence of a base, in an inert solvent, and then adding a fluorating agent.

Examples of the above-mentioned "base" include "alkyl metals", "aryl metals" and the like. The amount of the "base" to be used is generally 1 to 20 equivalents, preferably 1 to 2 equivalents, relative to compound (CCLXIII).

Examples of the above-mentioned "inert solvent" include ether solvents, aromatic solvents, aliphatic hydrocarbon solvents and the like. These may be used in a mixture of two or more kinds thereof at an appropriate ratio.

Examples of the above-mentioned "fluorating agent" include N-fluorobenzenesulfonamide and the like. The amount of the "fluorating agent" to be used is generally 1 to 20 equivalents, preferably 1 to 2 equivalents, relative to compound (CCLXIII).

The reaction temperature is generally −100 to 100° C., preferably −80 to 100° C.

The reaction time is generally 0.1 to 100 hr, preferably 0.1 to 8 hr.

Compound (CCLXV) can be produced, for example, by subjecting compound (CCLXIV) to deprotection. The deprotection can be carried out according to a method known per se, for example, the method described in Protective Groups in Organic Synthesis, John Wiley and Sons (1980) or the like.

Compound (CCLXVI) can be produced, for example, from compound (CCLXV) by a method similar to the triflation reaction of compound (CLXVII) in the aforementioned Reaction Scheme 25.

Compound (CCLXVII) can be produced, for example, from compound (CCLXVI) by a method similar to the "alkoxycarbonylation reaction using a transition metal catalyst" of compound (CXXVII) in the aforementioned Reaction Scheme 19.

Compound (CCLXVIII) can be produced, for example, from compound (CCLXVII) by a method similar to the reduction reaction of compound (XXVIII) in the aforementioned Reaction Scheme 4.

Compound (I-38) can be produced, for example, from compound (CXCIII) and compound (CCLXVIII) according to a method known per se, or by a method similar to the synthetic method of compound (I-1) in the aforementioned Reaction Scheme 1.

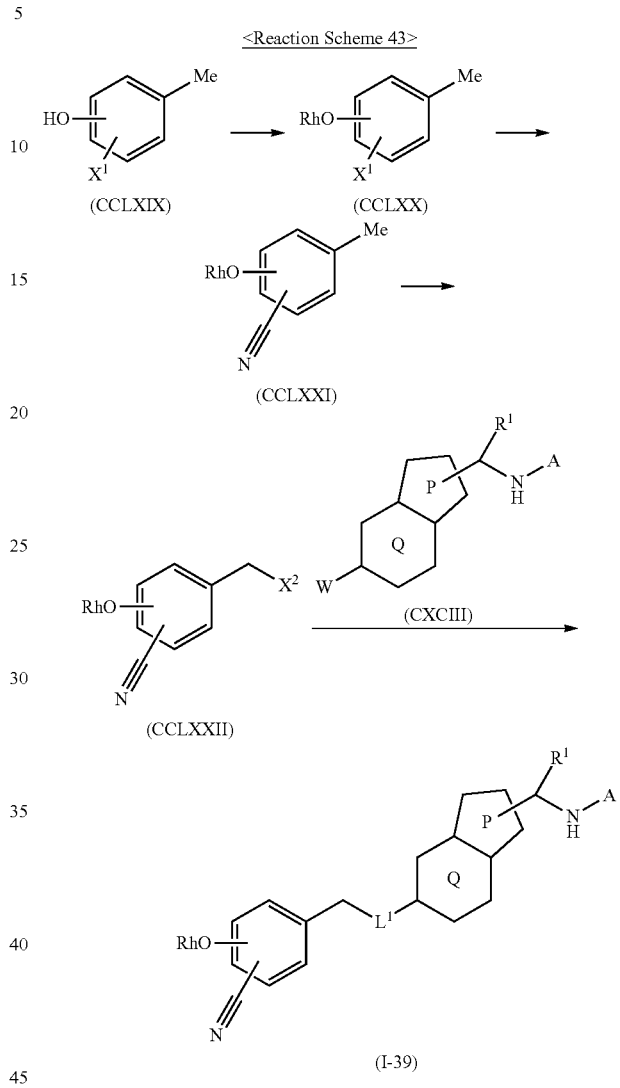

wherein $X^2$ is halogen, and P, Q, $R^1$, $L^1$, A, W, Rh and $X^1$ are independently as defined above.

Compound (CCLXIX) may be easily commercially available, or can be produced according to a method known per se or a method analogous thereto.

Compound (CCLXX) can be produced, for example, from compound (CCLXIX) by a method similar to the alkylation reaction of compound (CCLII) in the aforementioned Reaction Scheme 40.

Compound (CCLXXI) can be produced, for example, by subjecting compound (CCLXX) to a cyanation reaction.

The cyanation reaction can be carried out according to a method known per se, for example, the method described in Journal of Medicinal Chemistry, pages 1158-1162, 1978 or the like, or a method analogous thereto.

This reaction is carried out by reacting compound (CCLXX) in the presence of a cyanating agent, in an inert solvent.

Examples of the above-mentioned "cyanating agent" include copper(I) cyanide, zinc(II) cyanide and the like. The amount of the "cyanating agent" to be used is generally 1 to 20 equivalents, preferably 1 to 2 equivalents, relative compound (CCLXX). In this case, a transition metal catalyst may be used.

Examples of the above-mentioned "inert solvent" include amide solvents, sulfoxide solvents, nitrile solvents, ester solvents, ether solvents, aromatic solvents, aliphatic hydrocarbon solvents, aromatic amines and the like. These may be used in a mixture of two or more kinds thereof at an appropriate ratio.

The reaction temperature is generally −100 to 300° C., preferably 20 to 200° C.

The reaction time is generally 0.1 to 500 hr, preferably 0.1 to 48 hr.

Compound (CCLXXII) can be produced, for example, by subjecting compound (CCLXXI) to halogenation.

The halogenation can be carried out according to a method known per se, for example, the method described in Synthetic Communications, pages 3435-3454, 2003 or the like, or a method analogous thereto.

This reaction is carried out by reacting compound (CCLXXI) in the presence of halogenating agent 2, in an inert solvent.

Examples of the above-mentioned "halogenating agent 2" include N-bromosuccinimide, N-chlorosuccinimide and the like. The amount of the "halogenating agent 2" to be used is generally 1 to 20 equivalents, preferably 1 to 1.2 equivalents, relative to compound (CCLXXI). In addition, a radical initiator such as 2,2'-azobisisobutyronitrile and the like may be used.

Examples of the above-mentioned "inert solvent" include halogenated hydrocarbon solvents, amide solvents, sulfoxide solvents, nitrile solvents, ester solvents, ether solvents, aromatic solvents, aliphatic hydrocarbon solvents and the like. These may be used in a mixture of two or more kinds thereof at an appropriate ratio.

The reaction temperature is generally −100 to 200° C., preferably 20 to 100° C.

The reaction time is generally 0.1 to 100 hr, preferably 0.1 to 24 hr.

Compound (I-39) can be produced, for example, from compound (CXCIII) and compound (CCLXXII) according to a method known per se or by a method similar to the synthetic method of compound (I-1) in the aforementioned Reaction Scheme 1.

<Reaction Scheme 44>

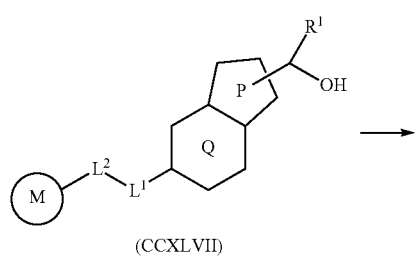

(CCXLVII)

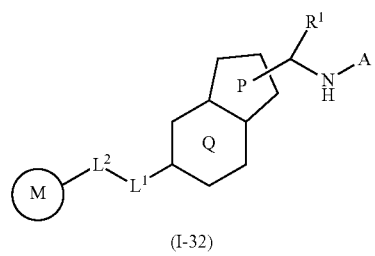

(I-32)

wherein M, P, Q, R$^1$, A, L$^1$ and L$^2$ are independently as defined above.

Compound (I-32) can be produced, for example, by subjecting compound (CCXLVII) to an amination reaction.

The amination reaction can be carried out according to a method known per se, for example, the method described in US 2004/87600 A1 and the like, or a method analogous thereto.

This reaction is carried out by reacting an alkyl halide prepared from compound (CCXLVII) with an amine corresponding to A (A=an optionally substituted 5- or 6-membered aromatic ring group) in the presence of a base, in an inert solvent.

The above-mentioned "alkyl halide prepared from compound (CCXLVII)" can be produced, for example, by a method similar to the production of the alkyl halide in the synthesis of compound (I-1).

Examples of the above-mentioned "amine corresponding to A" include heteroarylamines such as aniline, isoxazol-3-amine and the like, and the like. The amount of the "amine corresponding to A" to be used is generally 1 to 10 equivalents, preferably 1 to 5 equivalents, relative to the alkyl halide prepared from compound (CCXLVII).

Examples of the above-mentioned "base" include "inorganic bases", "basic salts", "aromatic amines", "hydrides of alkali metal or alkaline earth metal", "alkyl metals", "aryl metals", "metal alkoxides" and the like. The amount of the "base" to be used is generally 0 to 10 equivalents, preferably 0 to 5 equivalents, relative to the alkyl halide prepared from compound (CCXLVII). In addition, sodium iodide and the like may be added as an additive. The amount of the "additive" to be used is generally 1 to 10 equivalents, preferably 1 to 5 equivalents, relative to the alkyl halide prepared from compound (CCXLVII).

Examples of the above-mentioned "inert solvent" include nitrile solvents, amide solvents, halogenated hydrocarbon solvents, ether solvents and the like. These may be used in a mixture of two or more kinds thereof at an appropriate ratio. Of these, THF, DMF and the like are preferable.

The reaction temperature is generally −100° C. to 150° C., preferably 0° C. to 100° C.

The reaction time is generally 5 min to 48 hr, preferably 30 min to 24 hr.

<Reaction Scheme 45>

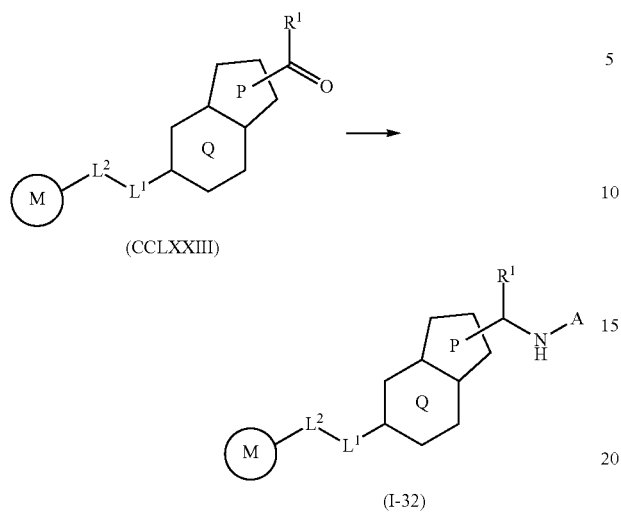

(CCLXXIII)

(I-32)

wherein M, P, Q, R¹, A, L¹ and L² are independently as defined above.

Compound (CCLXXIII) can be produced, for example, according to a method known per se or the aforementioned Reaction Schemes 1 to 43.

Compound (I-32) can be produced, for example, by subjecting compound (CCLXXIII) to a reductive amination reaction.

The reductive amination reaction can be carried out according to a method known per se, for example, the method described in EP 1179532A1 and the like, or a method analogous thereto.

This reaction is carried out by reacting compound (CCLXXIII) with an amine corresponding to A (A=an optionally substituted 5- or 6-membered aromatic ring group) in the presence of reducing agent 2, in an inert solvent.

Examples of the above-mentioned "amine corresponding to A" include heteroarylamines such as aniline, isoxazol-3-amine and the like, and the like. The amount of the "amine corresponding to A" to be used is generally 1 to 10 equivalents, preferably 1 to 5 equivalents, relative to compound (CCLXXIII).

Examples of the above-mentioned "reducing agent 2" include decaborane, sodium triacetoxyborohydride and the like. The amount of the "reducing agent 2" to be used is generally 1 to 10 equivalents, preferably 1 to 5 equivalents, relative to compound (CCLXXIII).

Before adding the "reducing agent 2", compound (CCLXXIII) and an amine corresponding to A may be reacted with a dehydrating agent. Examples of the above-mentioned "dehydrating agent" include titanium tetraisopropoxide and the like. The amount of the "dehydrating agent" to be used is generally 1 to 10 equivalents, preferably 1 to 5 equivalents, relative to compound (CCLXXIII).

Examples of the above-mentioned "inert solvent" include alcohol solvents, aromatic solvents, nitrile solvents, amide solvents, halogenated hydrocarbon solvents, ether solvents and the like. These may be used in a mixture of two or more kinds thereof at an appropriate ratio. Of these, methanol, THF and the like are preferable.

The reaction temperature is generally −100° C. to 150° C., preferably 0° C. to 100° C.

The reaction time is generally 5 min to 48 hr, preferably 30 min to 24 hr.

<Reaction Scheme 46>

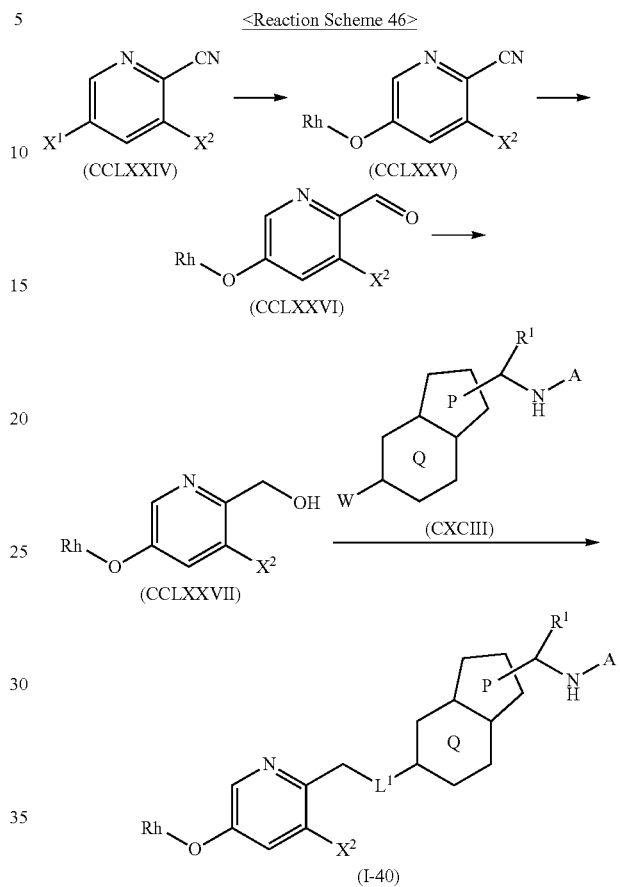

(CCLXXIV)

(CCLXXV)

(CCLXXVI)

(CCLXXVII)

(I-40)

wherein P, Q, R¹, A, L¹, W, Rh, X¹ and X² are independently as defined above.

Compound (CCLXXIV) can be easily synthesized according to a method known to literatures or may be easily commercially available.

Compound (CCLXXV) can be produced, for example, from compound (CCLXXIV) by a method similar to the substitution reaction of compound (CCLVI) in the aforementioned Reaction Scheme 41.

Compound (CCLXXVI) can be produced, for example, by subjecting compound (CCLXXV) to a reduction reaction.

The reduction reaction can be carried out according to a method known per se, for example, the method described in Journal of American Chemical Society, pages 2844-2845, 2005 or the like, or a method analogous thereto.

This reaction is carried out by reacting compound (CCLXXV) in the presence of reducing agent 3, in an inert solvent.

Examples of the above-mentioned "reducing agent 3" include diisobutylaluminum hydride and the like. The amount of the "reducing agent 3" to be used is generally 1 to 10 equivalents, preferably 1 to 5 equivalents, relative to compound (CCLXXV).

Examples of the above-mentioned "inert solvent" include halogenated hydrocarbon solvents, aromatic solvents, ether solvents and the like. These may be used in a mixture of two or more kinds thereof at an appropriate ratio. Of these, dichloromethane, toluene and the like are preferable.

The reaction temperature is generally −100° C. to 150° C., preferably −100° C. to 30° C.

The reaction time is generally 5 min to 48 hr, preferably 30 min to 24 hr.

Compound (CCLXXVII) can be produced, for example, from compound (CCLXXVI) by a method similar to the reduction reaction of compound (XXVIII) in the aforementioned Reaction Scheme 4.

Compound (I-40) can be produced, for example, from compound (CXCIII) and compound (CCLXXVII) according to a method known per se, or by a method similar to the synthetic method of compound (I-1) in the aforementioned Reaction Scheme 1.

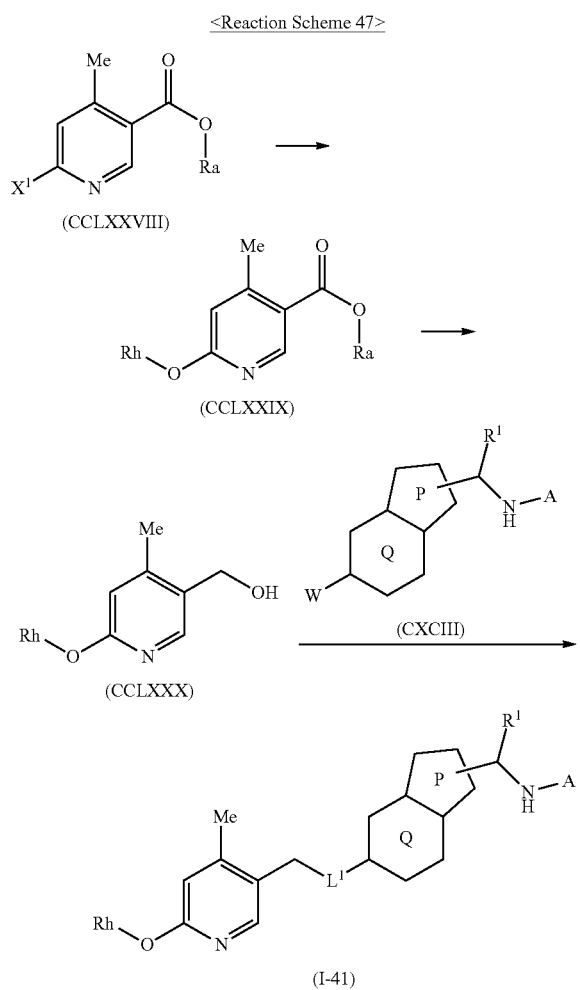

wherein P, Q, $R^1$, A, $L^1$, W, Ra, Rh and $X^1$ are independently as defined above.

Compound (CCLXXVIII) can be easily synthesized according to a method known to literatures, or may be easily commercially available.

Compound (CCLXXIX) can be produced, for example, from compound (CCLXXVIII) by a method similar to the substitution reaction compound (CCLVI) of the aforementioned Reaction Scheme 41.

Compound (CCLXXX) can be produced, for example, from compound (CCLXXIX) by a method similar to the reduction reaction of compound (XXVIII) in the aforementioned Reaction Scheme 4.

Compound (I-41) can be produced, for example, from compound (CXCIII) and compound (CCLXXX) according to a method known per se, or by a method similar to the synthetic method of compound (I-1) in the aforementioned Reaction Scheme 1.

In compound (I) thus obtained, a functional group within a molecule can also be converted to a desired functional group by a combination of chemical reactions known per se. Examples of the chemical reaction here include oxidation reaction, reduction reaction, alkylation reaction, acylation reaction, ureation reaction, hydrolysis reaction, amination reaction, esterification reaction, aryl coupling reaction, deprotection reaction and the like.

In the above-mentioned production methods, when the starting compound has an amino group, a carboxyl group, a hydroxy group, a carbonyl group or a mercapto group as a substituent, a protecting group generally used in peptide chemistry and the like may be introduced into these groups. By removing the protecting group as necessary after the reaction, the object compound can be obtained.

Examples of the amino-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, a N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-10}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group and a nitro group.

Examples of the carbonyl-protecting group include a cyclic acetal (e.g., 1,3-dioxane), a non-cyclic acetal (e.g., a di-$C_{1-6}$ alkylacetal) and the like.

Examples of the mercapto-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmathoxycarbonyl), a 2-tetrahydropyranyl group, a $C_{1-6}$ alkylamino-carbonyl group (e.g., methylaminocarbonyl, ethylaminocarbonyl), and the like. These groups are optionally substituted by 1 to 3 substituents selected from a halogen atom, a $C_{1-6}$ alkyl group, a $C_{1-6}$ alkoxy group and a nitro group.

The above-mentioned protecting group can be removed according to deprotection known per se.

Compound (I) obtained by the above-mentioned production methods can be isolated and purified by a known means, for example, solvent extraction, liquid conversion, phase transfer, crystallization, recrystallization, chromatography and the like.

When compound (I) contains an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced by a method known per se.

Compound (I) may be a crystal.

Crystals of compound (I) (hereinafter sometimes to be abbreviated as the crystals of the present invention) can be produced by crystallization according to crystallization methods known per se.

In the present specification, the melting point means that measured using, for example, a micromelting point apparatus (Yanako, MP-500D or Buchi, B-545), a DSC (differential scanning calorimetry) device (SEIKO, EXSTAR6000) or the like.

In general, the melting points vary depending on the measurement apparatuses, the measurement conditions and the like. The crystal in the present specification may show different values from the melting point described in the present specification, as long as they are within each of a general error range.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

EXAMPLES

The present invention is explained in detail in the following by referring to Reference Examples, Examples, Experimental Examples and Formulation Examples, which are not to be construed as limitative, and the invention may be changed within the scope of the present invention.

In the following Reference Examples and Examples, "%" means, unless otherwise specified, mol/mol % for yield and wt % for others. The "room temperature" means 1-30° C. unless otherwise specified.

The basic silica gel column chromatography is Fuji Silysia Chemical Ltd. NH silica gel plate, and preparative silica gel TLC is Merck silica gel 60 F254 plate.

Reference Example 1 methyl {6-[(4-ethoxybenzyl)oxy]-1-benzofuran-3-yl}acetate

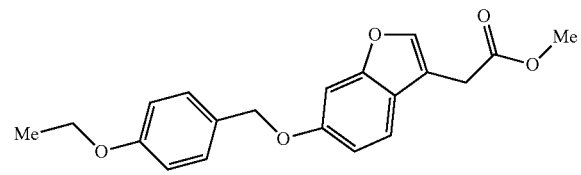 [SMILES: CCOc1ccc(COc2ccc3c(CC(=O)OC)coc3c2)cc1]

To a solution of methyl (6-hydroxy-1-benzofuran-3-yl)acetate (10.0 g, 48.5 mmol) in DMF (100 mL) were added 1-(chloromethyl)-4-ethoxybenzene (12.4 g, 72.7 mmol) and potassium carbonate (13.5 g, 97.0 mmol), and the mixture was stirred at room temperature for 3 hr. Water was added to the reaction mixture, and the mixture was extracted with ethyl acetate. The extract was washed twice with saturated brine, and dried over anhydrous magnesium sulfate. The solvent was evaporated under reduced pressure and the residue was washed with diethyl ether and hexane to give the title compound (15.8 g, yield 96%) as a white solid.

$^1$H NMR (CDCl$_3$) δ 1.41 (t, J=7.0 Hz, 3H), 3.67 (s, 2H), 3.72 (s, 3H), 4.04 (q, J=6.8 Hz, 2H), 5.02 (s, 2H), 6.90 (d, J=8.7 Hz, 2H), 6.96 (dd, J=8.7, 2.3 Hz, 1H), 7.07 (d, J=2.3 Hz, 1H), 7.36 (d, J=8.7 Hz, 2H), 7.41 (d, J=8.7 Hz, 1H), 7.52 (s, 1H).

Reference Example 2 methyl 2-{6-[(4-ethoxybenzyl)oxy]-1-benzofuran-3-yl}propanoate

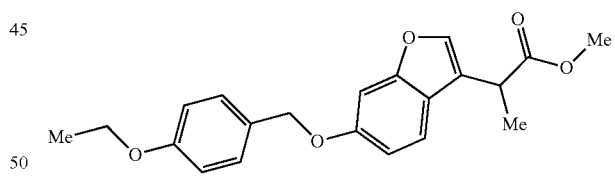

To a solution of methyl {6-[(4-ethoxybenzyl)oxy]-1-benzofuran-3-yl}acetate (15.8 g, 46.4 mmol) obtained in Reference Example 1 in THF (150 mL) was added dropwise 1.0 M lithium bis(trimethylsilyl)amide THF solution (55.0 mL, 55.0 mmol) at −78° C. The reaction mixture was stirred at the same temperature for 30 min, methyl iodide (3.47 mL, 55.7 mmol) was added thereto and the mixture was stirred at room temperature for 10 min. To the reaction mixture was added saturated aqueous ammonium chloride solution, and the mixture was extracted with ethyl acetate. The extract was washed with saturated brine, and dried over anhydrous magnesium sulfate. The solvent was evaporated under reduced pressure, and the obtained residue was purified by silica gel column chromatography (hexane:ethyl acetate=19:1 to 3:7) to give the title compound (15.3 g, yield 93%) as an oil.

¹H NMR (CDCl₃) δ 1.41 (t, J=7.0 Hz, 3H), 1.59 (d, J=7.2 Hz, 3H), 3.69 (s, 3H), 3.84-3.91 (m, 1H), 4.04 (q, J=7.0 Hz, 2H), 5.01 (s, 2H), 6.89-6.97 (m, 4H), 7.05-7.07 (1H, m), 7.36 (d, J=8.7 Hz, 2H), 7.46 (s, 1H).

Reference Example 3

2-{6-[(4-ethoxybenzyl)oxy]-1-benzofuran-3-yl}propanoic acid

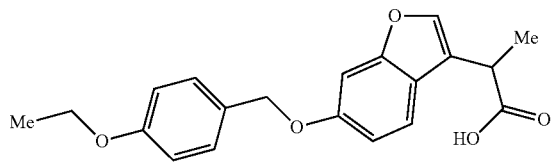 [SMILES: CCOc1ccc(COc2ccc3c(C(C)C(=O)O)coc3c2)cc1]

To a solution of methyl 2-{6-[(4-ethoxybenzyl)oxy]-1-benzofuran-3-yl}propanoate (15.3 g, 43.2 mmol) obtained in Reference Example 2 in a mixed solvent of THF (100 mL)-methanol (40 mL) was added 1N aqueous sodium hydroxide solution (66.0 mL, 66.0 mmol), and the mixture was stirred at room temperature for 1 hr. The reaction mixture was acidified with 1N hydrochloric acid and extracted three times with ethyl acetate. The combined organic layer was washed with saturated brine and dried over anhydrous magnesium sulfate. The solvent was evaporated under reduced pressure and the obtained residue (14.2 g, yield 97%) was used for the next reaction without further purification.

Reference Example 4

N-[1-(6-hydroxy-1-benzofuran-3-yl)ethyl]acetamide

To a solution of 2-{6-[(4-ethoxybenzyl)oxy]-1-benzofuran-3-yl}propanoic acid (14.2 g, 41.7 mmol) obtained in Reference Example 3 in tert-butanol (120 mL) were added diphenyl azidophosphate (10.8 mL, 50.0 mmol) and triethylamine (8.70 mL, 62.6 mmol). The reaction mixture was stirred with heating under reflux for 15 hr. The solvent was evaporated under reduced pressure, and the obtained residue was purified by basic silica gel column chromatography (ethyl acetate) to give an oil. A solution (30 mL) of this oil in 4N hydrogen chloride-ethyl acetate was stirred at room temperature for 30 min. The solvent was evaporated under reduced pressure, the obtained residue was dissolved in acetic anhydride (15 mL)-pyridine (15 mL), and the mixture was stirred at room temperature for 30 min. The solvent was evaporated under reduced pressure, and the obtained solid was washed with diethyl ether and hexane. The solid was dissolved in methanol (20 mL), potassium carbonate (1.36 g, 9.79 mmol) was added thereto and the mixture was stirred at room temperature for 15 min. The reaction mixture was neutralized with 1N hydrochloric acid and extracted four times with ethyl acetate. The combined organic layer was washed with saturated brine, and dried over anhydrous magnesium sulfate. The solvent was evaporated under reduced pressure and the obtained residue was purified by silica gel column chromatography (hexane:ethyl acetate=1:4 to ethyl acetate) to give the title compound (1.04 g, yield 11%) as a white solid.

¹H NMR (DMSO-d₆) δ 1.43 (d, J=6.8 Hz, 3H), 1.83 (s, 3H), 5.06-5.16 (m, 1H), 6.73 (dd, J=8.4, 2.1 Hz, 1H), 6.87 (d, J=8.4 Hz, 1H), 7.38 (d, J=8.4 Hz, 1H), 7.64 (d, J=2.1 Hz, 1H), 8.19 (d, J=8.4 Hz, 1H), 9.49 (s, 1H).

Reference Example 5

4-propylbenzyl methanesulfonate

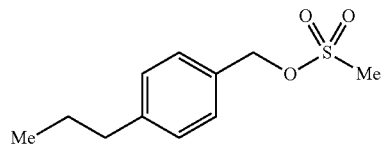 [SMILES: CCCc1ccc(COS(C)(=O)=O)cc1]

To a solution of (4-propylphenyl)methanol (116 mg, 0.770 mmol) in THF (5 mL) were added triethylamine (0.220 mL, 1.54 mmol) and methanesulfonyl chloride (89.0 mL, 1.16 mmol), and the mixture was stirred at room temperature for 15 min. Water was added to the reaction mixture, and the mixture was extracted twice with ethyl acetate. The extract was washed with saturated brine, and dried over anhydrous magnesium sulfate. The solvent was evaporated under reduced pressure to give the title compound (176 mg, quantitative). This was used for the next step without purification.

Reference Example 6 methyl 2-(6-methoxy-1,2-benzisoxazol-3-yl)propanoate

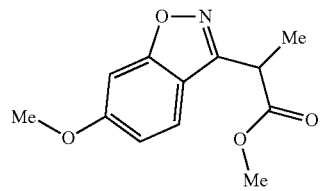 [SMILES: COC(=O)C(C)c1noc2cc(OC)ccc12]

To a solution of methyl (6-methoxy-1,2-benzisoxazol-3-yl)acetate (3.00 g, 13.6 mmol) in anhydrous THF (70 mL) was added 60% sodium hydride (544 mg, 13.6 mmol) under ice-cooling. After stirring for 30 min, methyl iodide (0.929 mL, 14.9 mmol) in THF (4 mL) was added dropwise thereto, and the mixture was stirred for 1 hr. Water was added to the reaction mixture, and the mixture was extracted with ethyl acetate. The extract was washed with 10% aqueous potassium carbonate solution and saturated brine, and dried over anhydrous sodium sulfate. This solution was applied to basic silica gel column chromatography (ethyl acetate) to give the title compound (3.19 g, quantitative) as an oil.

$^1$H NMR (CDCl$_3$) δ 1.70 (d, J=7.5 Hz, 3H), 3.71 (s, 3H), 3.88 (s, 3H), 4.21 (q, J=7.5 Hz, 1H), 6.89 (dd, J=1.8, 8.7 Hz, 1H), 6.98 (d, J=1.8 Hz, 1H), 7.54 (d, J=8.7 Hz, 1H).

Reference Example 7

2-(6-methoxy-1,2-benzisoxazol-3-yl)propanoic acid

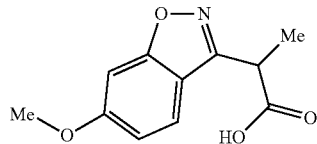 [SMILES: COc1ccc2c(C(C)C(=O)O)noc2c1]

To a solution of methyl 2-(6-methoxy-1,2-benzisoxazol-3-yl)propanoate (3.19 g, 13.6 mmol) obtained in Reference Example 6 in methanol (60 mL) was added 2N aqueous sodium hydroxide solution (10.2 mL, 20.3 mmol) under ice-cooling. The mixture was stirred for 2 hr, concentrated under reduced pressure, and partitioned between water and diisopropyl ether. To the aqueous layer was added 1N hydrochloric acid (30 mL), and the mixture was extracted with ethyl acetate. The extract was washed with saturated brine, and dried over anhydrous sodium sulfate. The solvent was evaporated under reduced pressure, and the residue was solidified with hexane to give the title compound (3.00 g, quantitative). This was used for the next step without purification.

Reference Example 8 tert-butyl [1-(6-methoxy-1,2-benzisoxazol-3-yl)ethyl]carbamate

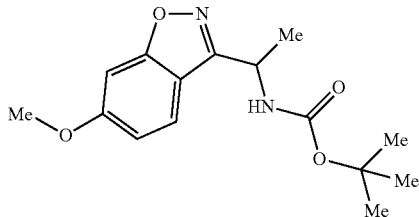 [SMILES: COc1ccc2c(C(C)NC(=O)OC(C)(C)C)noc2c1]

To a solution of 2-(6-methoxy-1,2-benzisoxazol-3-yl)propanoic acid (3.00 g, 13.6 mmol) obtained in Reference Example 7 in tert-butanol (60 mL) were added diisopropylethylamine (3.54 mL, 20.3 mmol) and diphenyl azidophosphate (3.21 mL, 14.9 mmol), and the mixture was stirred at room temperature for 30 min, and then stirred with heating at 90° C. for 16 hr under nitrogen. The reaction mixture was allowed to cool to room temperature. The solvent was evaporated under reduced pressure, and the residue was dissolved in ethyl acetate. The organic layer was washed with 0.5N hydrochloric acid, 10% aqueous potassium carbonate solution and saturated brine, and dried over anhydrous sodium sulfate. This solution was applied to basic silica gel column chromatography (ethyl acetate). The solvent was evaporated under reduced pressure, the obtained residue was purified by silica gel column chromatography (hexane:ethyl acetate=3:1 to ethyl acetate), and the residue was solidified with hexane to give the title compound (1.87 g, yield 47%).

$^1$H NMR (CDCl$_3$) δ 1.45 (s, 9H), 1.65 (d, J=6.9 Hz, 3H), 3.88 (s, 3H), 5.17 (m, 1H), 5.28 (m, 1H), 6.88 (dd, J=2.1, 8.7 Hz, 1H), 6.97 (d, J=2.1 Hz, 1H), 7.57 (d, J=8.7 Hz, 1H).

Reference Example 9

N-[1-(6-methoxy-1,2-benzisoxazol-3-yl)ethyl]acetamide

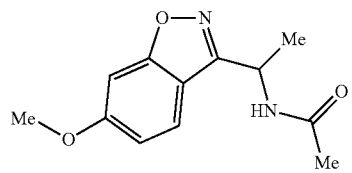

To tert-butyl [1-(6-methoxy-1,2-benzisoxazol-3-yl)ethyl]carbamate (1.87 g, 6.40 mmol) obtained in Reference Example 8 was added 4N hydrogen chloride-ethyl acetate solution (30 mL), and the mixture was concentrated under reduced pressure 1 hr later. To the obtained residue was added pyridine (15 mL), acetic anhydride (0.907 mL, 9.59 mmol) was added dropwise thereto, and the mixture was stirred at room temperature for 3 hr. The solvent was evaporated under reduced pressure and the residue was dissolved in ethyl acetate. The organic layer was washed with 1N hydrochloric acid, 10% aqueous potassium carbonate solution and saturated brine, and dried over anhydrous sodium sulfate. The solvent was evaporated under reduced pressure and the obtained residue was triturated with diisopropyl ether to give the title compound (1.24 g, yield 83%).

$^1$H NMR (CDCl$_3$) δ 1.66 (d, J=6.9 Hz, 3H), 2.05 (s, 3H), 3.88 (s, 3H), 5.61 (m, 1H), 6.23 (d, J=7.5 Hz, 1H), 6.90 (dd, J=2.1, 8.7 Hz, 1H), 6.97 (d, J=2.1 Hz, 1H), 7.57 (d, J=8.7 Hz, 1H).

Reference Example 10

N-[1-(6-hydroxy-1,2-benzisoxazol-3-yl)ethyl]acetamide

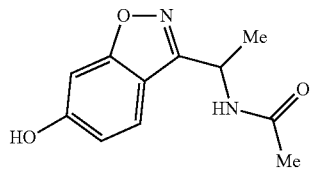

To a suspension of N-[1-(6-methoxy-1,2-benzisoxazol-3-yl)ethyl]acetamide (500 mg, 2.13 mmol) obtained in Reference Example 9 in toluene (10 mL) was added 1 M boron tribromide methylene chloride solution (6.40 mL, 6.40 mmol) under ice-cooling and, under a nitrogen atmosphere, the mixture was stirred at room temperature for 1 hr. Methylene chloride (5 mL) and 1 M boron tribromide methylene chloride solution (5.00 mL, 5.00 mmol) were added thereto at room temperature, and the mixture was stirred under heating at 50° C. for 16 hr. To the reaction mixture was added ethyl acetate, and the mixture was washed with saturated brine, and dried over anhydrous sodium sulfate. The solvent was evaporated under reduced pressure to give the title compound (470 mg, quantitative) as an oil. This was used for the next step without purification.

Reference Example 11

4-[(4-ethoxyphenoxy)methyl]-2-fluoropyridine

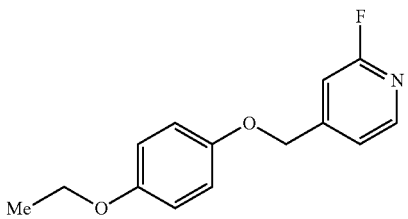 [SMILES: CCOc1ccc(OCc2ccnc(F)c2)cc1]

To a solution of (2-fluoropyridin-4-yl)methanol (5.06 g, 39.8 mmol) in DMF (100 mL) were added triethylamine (8.30 mL, 59.7 mmol) and methanesulfonyl chloride (3.08 mL, 39.8 mmol) under ice-cooling. After stirring for 30 min, 4-ethoxyphenol (5.77 g, 41.8 mmol) and potassium carbonate (5.50 g, 39.8 mmol) were added thereto and the mixture was stirred at room temperature for 16 hr. To the reaction mixture was added ethyl acetate, and the mixture was washed with water, 10% aqueous potassium carbonate solution and saturated brine, and dried over anhydrous sodium sulfate. The solvent was evaporated under reduced pressure, and the obtained residue was purified by silica gel column chromatography (hexane:ethyl acetate=9:1 to 7:3). A mixture of the obtained product and 4-ethoxyphenol (starting material) was purified again by basic silica gel column chromatography (hexane:ethyl acetate=9:1 to 7:3) to give the title compound (822 mg, yield 8.4%).

$^1$H NMR (CDCl$_3$) δ 1.39 (t, J=6.9 Hz, 3H), 3.98 (q, J=6.9 Hz, 2H), 5.05 (s, 2H), 6.81-6.89 (m, 4H), 7.01-7.02 (m, 1H), 7.19-7.25 (m, 1H), 8.19 (d, J=5.5 Hz, 1H).

Reference Example 12

4-[(4-ethoxyphenoxy)methyl]-2-hydrazinopyridine

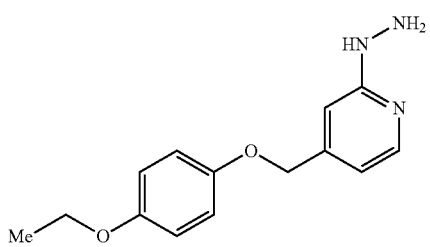 [SMILES: CCOc1ccc(OCc2ccnc(NN)c2)cc1]

To a solution of 4-[(4-ethoxyphenoxy)methyl]-2-fluoropyridine (822 mg, 3.32 mmol) obtained in Reference Example 11 in 2-ethoxyethanol (5 mL) was added hydrazine monohydrate (1.61 mL, 33.2 mmol) under a nitrogen atmosphere, and the mixture was stirred under heating at 150° C. for 16 hr. The reaction mixture was allowed to cool to room temperature, and diluted with ethyl acetate, and the mixture was washed with 10% aqueous potassium carbonate solution and saturated brine, and dried over anhydrous sodium sulfate. The solvent was evaporated under reduced pressure, and the obtained residue was triturated with diisopropyl ether to give the title compound (726 mg, yield 84%).

$^1$H NMR (CDCl$_3$) δ 1.39 (t, J=7.2 Hz, 3H), 3.82 (br, 2H), 3.97 (q, J=7.2 Hz, 2H), 4.95 (s, 2H), 5.84 (s, 1H), 6.69-6.71 (m, 1H), 6.77 (s, 1H), 6.79-6.89 (m, 4H), 8.10 (d, J=5.1 Hz, 1H).

Reference Example 13

N-[2-(2-{4-[(4-ethoxyphenoxy)methyl]pyridin-2-yl}hydrazino)-1-methyl-2-oxoethyl]acetamide

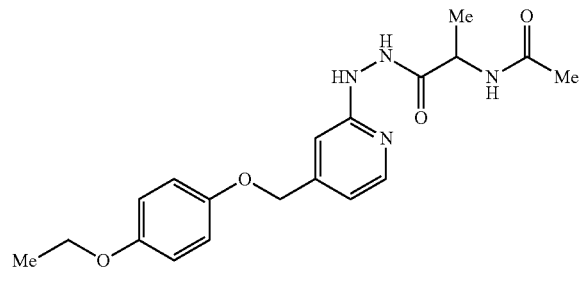 [SMILES: CCOc1ccc(OCc2ccnc(NNC(=O)C(C)NC(C)=O)c2)cc1]

To a solution of 4-[(4-ethoxyphenoxy)methyl]-2-hydrazinopyridine (300 mg, 1.16 mmol) obtained in Reference Example 12, N-acetyl-D,L-alanine (167 mg, 1.27 mmol) and 1-hydroxybenzotriazole (172 mg, 1.27 mmol) in DMF (5 mL) was added 1-ethyl-3-(3-dimethylaminopropyl)carbodiimide hydrochloride (244 mg, 1.27 mmol), and the mixture was stirred at room temperature for 1 day. The reaction mixture was diluted with ethyl acetate, and the mixture was washed with 10% aqueous potassium carbonate solution and saturated brine, and dried over anhydrous sodium sulfate. The solvent was evaporated under reduced pressure, and the obtained residue was triturated with diisopropyl ether to give the title compound (319 mg, yield 74%).

$^1$H NMR (DMSO-d$_6$) δ 1.23-1.31 (m, 6H), 1.84 (s, 3H), 3.93 (q, J=6.9 Hz, 2H), 4.35 (m, 1H), 4.96 (s, 2H), 6.62 (s, 1H), 6.69 (d, J=5.4 Hz, 1H), 6.82 (d, J=9.3 Hz, 2H), 6.90 (d, J=9.3 Hz, 2H), 8.00 (d, J=5.4 Hz, 1H), 8.09 (d, J=7.8 Hz, 1H), 8.28 (d, J=1.5 Hz, 1H), 9.82 (d, J=1.5 Hz, 1H).

Reference Example 14

5-(hydroxymethyl)-2-iodophenol

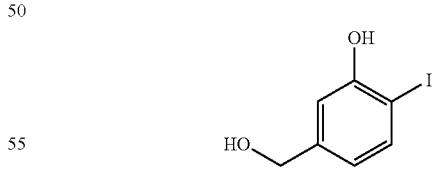

To a solution of 3-hydroxy-4-iodobenzoic acid (20.9 g, 79.3 mmol) in anhydrous THF (160 mL) was added 1 M borane THF solution (240 mL, 240 mmol) by small portions, and the mixture was stirred at 60° C. for 2 hr. Water was added to the reaction mixture, and the mixture was extracted twice with ethyl acetate. The extract was washed with saturated brine, and dried over anhydrous sodium sulfate. The solvent was evaporated under reduced pressure, and the residue was washed with diisopropyl ether and hexane to give the title compound (17.4 g, yield 88%) as a white solid.

¹H NMR (CDCl₃) δ 1.69 (br, 1H), 4.64 (s, 2H), 5.33 (s, 1H), 6.70 (dd, J=7.8, 1.5 Hz, 1H), 7.01 (d, J=1.5 Hz, 1H), 7.63 (d, J=7.8 Hz, 1H).

Reference Example 15 ethyl 3-[5-(hydroxymethyl)-2-iodophenoxy]prop-2-enoate

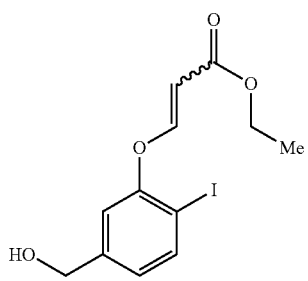 [SMILES: CCOC(=O)C=COc1cc(CO)ccc1I]

A solution of 5-(hydroxymethyl)-2-iodophenol (7.2 g, 28.7 mmol) obtained in Reference Example 14 and N-methylmorpholine (1.3 mL, 11.5 mmol) in anhydrous THF (20 mL) was added dropwise to a solution of ethyl propiolate (3.94 g, 40.2 mmol) in anhydrous THF (20 mL) at 0° C. The reaction mixture was stirred at room temperature overnight. Thereafter, the solvent was evaporated under reduced pressure, and the obtained residue was purified by silica gel column chromatography (hexane to hexane:ethyl acetate=3:2) to give the title compound (4.00 g, yield 40%) as an oil.

¹H NMR (CDCl₃) δ 1.25 (t, J=7.2 Hz, 3H), 1.86 (t, J=5.8 Hz, 1H), 4.20 (q, J=7.2 Hz, 2H), 4.69 (d, J=5.8 Hz, 2H), 5.52 (d, J=12.1 Hz, 1H), 6.95 (dd, J=8.1, 1.7 Hz, 1H), 7.10 (d, J=1.7 Hz, 1H), 7.70 (d, J=12.1 Hz, 1H), 7.80 (d, J=8.1 Hz, 1H).

Reference Example 16 ethyl 3-[5-({[tert-butyl(dimethyl)silyl]oxy}methyl)-2-iodophenoxy]prop-2-enoate

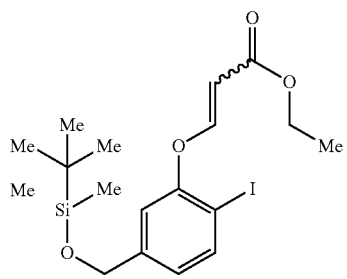

To a solution of ethyl 3-[5-(hydroxymethyl)-2-iodophenoxy]prop-2-enoate (4.00 g, 11.5 mmol) obtained in Reference Example 15 in DMF (12 mL) were added tert-butyldimethylchlorosilane (1.89 g, 12.6 mmol) and imidazole (1.17 g, 17.3 mmol), and the mixture was stirred at room temperature for 1 hr. To the reaction mixture was added brine, and the mixture was extracted with ethyl acetate. The extract was washed with saturated brine, and dried over anhydrous magnesium sulfate. The solvent was evaporated under reduced pressure, and the obtained residue was purified by silica gel column chromatography (hexane to hexane:ethyl acetate=4:1) to give the title compound (4.68 g, yield 88%) as an oil.

¹H NMR (CDCl₃) δ 0.10 (s, 6H), 0.94 (s, 9H), 1.28 (t, J=7.2 Hz, 3H), 4.19 (q, J=7.2 Hz, 2H), 4.70 (s, 2H), 5.50 (d, J=12.2 Hz, 1H), 6.87-6.95 (m, 1H), 7.01-7.08 (m, 1H), 7.70 (d, J=12.2 Hz, 1H), 7.76 (d, J=8.1 Hz, 1H).

Reference Example 17 ethyl 6-({[tert-butyl(dimethyl)silyl]oxy}methyl)-1-benzofuran-3-carboxylate

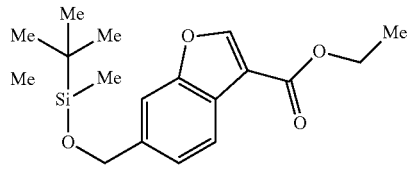

To a solution of ethyl 3-[5-({[tert-butyl(dimethyl)silyl]oxy}methyl)-2-iodophenoxy]prop-2-enoate (4.68 g, 10.1 mmol) obtained in Reference Example 16 in acetonitrile (20 mL) were added palladium acetate (216 mg, 1.01 mmol), triphenylphosphine (264 mg, 1.01 mmol) and triethylamine (7.5 mL, 51 mmol), and the mixture was refluxed under a nitrogen atmosphere overnight. Water was added to the reaction mixture, and the mixture was extracted twice with ethyl acetate. The extract was washed with saturated brine, and dried over anhydrous magnesium sulfate. The solvent was evaporated under reduced pressure, and the obtained residue was purified by silica gel column chromatography (hexane to hexane:ethyl acetate=9:1) to give the title compound (2.76 g, yield 82%) as an oil.

¹H NMR (CDCl₃) δ 0.12 (s, 6H), 0.98 (s, 9H), 1.42 (t, J=7.2 Hz, 3H), 4.41 (q, J=7.2 Hz, 2H), 4.86 (s, 2H), 7.23-7.33 (m, 1H), 7.55 (d, J=0.8 Hz, 1H), 7.99 (d, J=8.1 Hz, 1H), 8.23 (s, 1H).

Reference Example 18

6-({[tert-butyl(dimethyl)silyl]oxy}methyl)-N-methoxy-N-methyl-1-benzofuran-3-carboxamide

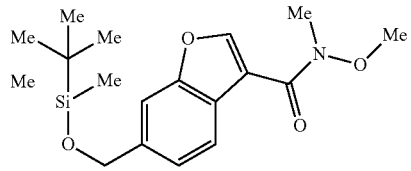

A solution of ethyl 6-({[tert-butyl(dimethyl)silyl]oxy}methyl)-1-benzofuran-3-carboxylate (2.76 g, 8.26 mmol) obtained in Reference Example 17 in anhydrous THF (8 mL) was added dropwise to a solution of N,O-dimethylhydroxylamine hydrochloride (4.03 g, 41.3 mmol) and 1.6 M n-butyllithium hexane solution (51 mL, 83 mmol) in anhydrous THF (50 mL) at 0° C., and the mixture was stirred at 0° C. for 1 hr. Water was added to the reaction mixture, and the mixture was extracted twice with ethyl acetate. The extract was washed with saturated brine, and dried over anhydrous magnesium sulfate. The solvent was evaporated under reduced pressure, and the obtained residue was purified by silica gel column chromatography (hexane to hexane:ethyl acetate=3:2) to give the title compound (1.38 g, yield 48%) as an oil.

$^1$H NMR (CDCl$_3$) δ 0.12 (s, 6H), 0.96 (s, 9H), 3.39 (s, 3H), 3.74 (s, 3H), 4.87 (s, 2H), 7.21-7.29 (m, 1H), 7.54 (s, 1H), 8.19 (d, J=8.3 Hz, 1H), 8.27 (s, 1H).

Reference Example 19

1-[6-({[tert-butyl(dimethyl)silyl]oxy}methyl)-1-benzofuran-3-yl]ethanone

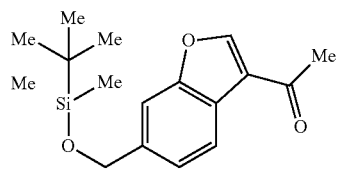

A solution of 6-({[tert-butyl(dimethyl)silyl]oxy}methyl)-N-methoxy-N-methyl-1-benzofuran-3-carboxamide (1.38 mg, 3.95 mmol) obtained in Reference Example 18 in anhydrous THF (3 mL) was added to a solution of 1.6 M methylmagnesium bromide THF solution (5.0 mL, 8.0 mmol) in anhydrous THF (8 mL), and the mixture was stirred at room temperature for 1 hr. To the reaction mixture was added aqueous saturated ammonium chloride, and the mixture was extracted twice with ethyl acetate. The extract was washed with saturated brine, and dried over anhydrous magnesium sulfate. The solvent was evaporated under reduced pressure, to give the title compound (1.19 g, quantitative) as an oil.

$^1$H NMR (CDCl$_3$) δ 0.10 (s, 6H), 0.94 (s, 9H), 2.56 (s, 3H), 4.83 (s, 2H), 7.36 (d, J=8.0 Hz, 1H), 7.58 (s, 1H), 8.21 (d, J=8.0 Hz, 1H), 8.24 (s, 1H).

Reference Example 20

1-{6-[(4-ethoxyphenoxy)methyl]-1-benzofuran-3-yl}ethanone

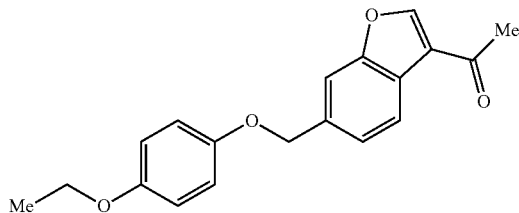 [SMILES: CCOc1ccc(OCc2ccc3c(C(C)=O)coc3c2)cc1]

To a solution of 1-[6-({[tert-butyl(dimethyl)silyl]oxy}methyl)-1-benzofuran-3-yl]ethanone (1.19 g, 3.91 mmol) obtained in Reference Example 19 in THF (6 mL) was added 1 M tetrabutylammonium fluoride THF solution (7.82 mL, 7.82 mmol). The mixture was stirred at room temperature for 2 hr. To the reaction mixture was added aqueous saturated ammonium chloride, and the mixture was extracted twice with ethyl acetate. The extract was washed with saturated brine, and dried over anhydrous magnesium sulfate, and the solution was passed through silica gel. The solvent was evaporated under reduced pressure to give an alcohol form (965 mg). To a solution of the obtained alcohol form (965 mg), triphenylphosphine (1.54 g, 5.88 mmol) and p-ethoxyphenol (825 mg, 5.88 mmol) in anhydrous THF (8 mL) was added dropwise 40% diethyl azodicarboxylate-toluene solution (2.7 mL, 5.88 mmol) and the mixture was stirred at room temperature for 10 min. The solvent was evaporated under reduced pressure, and the obtained residue was purified by silica gel column chromatography (hexane to hexane:ethyl acetate=7:3) to give the title compound (117 mg, yield from 1-[6-({[tert-butyl(dimethyl)silyl]oxy}methyl)-1-benzofuran-3-yl]ethanone 10%) as an oil.

$^1$H NMR (CDCl$_3$) δ 1.38 (t, J=7.2 Hz, 3H), 2.56 (s, 3H), 3.97 (q, J=7.1 Hz, 2H), 5.14 (s, 2H), 6.72-6.94 (m, 4H), 7.43 (s, 1H), 7.62 (s, 1H), 8.21 (s, 1H), 8.24 (s, 1H).

Reference Example 21

1-{6-[(4-ethoxyphenoxy)methyl]-1-benzofuran-3-yl}ethanol

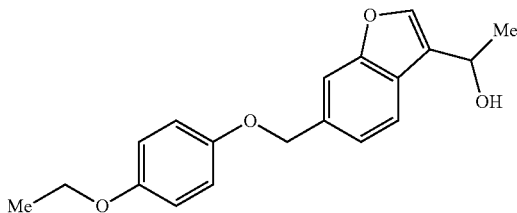 [SMILES: CCOc1ccc(OCc2ccc3c(C(C)O)coc3c2)cc1]

To a solution of 1-{6-[(4-ethoxyphenoxy)methyl]-1-benzofuran-3-yl}ethanone (117 mg, 0.377 mmol) obtained in Reference Example 20 in methanol (3 mL) was added sodium borohydride (28.6 mg, 0.755 mmol) and the mixture was stirred at room temperature for 1 hr. To the reaction mixture was added brine, and the mixture was extracted twice with ethyl acetate. The extract was washed with saturated brine, and dried over anhydrous magnesium sulfate. The solvent was evaporated under reduced pressure to give the title compound (101 mg, yield 85%) as an oil.

$^1$H NMR (CDCl$_3$) δ 1.39 (q, J=6.7 Hz, 3H), 1.66 (d, J=6.6 Hz, 3H), 1.80 (s, 1H), 4.01 (q, J=6.7 Hz, 2H), 5.12 (s, 2H), 5.14 (br, 1H), 6.71-6.96 (m, 4H), 7.31 (dd, J=7.9, 1.3 Hz, 1H), 7.53-7.62 (m, 2H), 7.70 (d, J=7.9 Hz, 1H).

Reference Example 22

3-(1-azidoethyl)-6-[(4-ethoxyphenoxy)methyl]-1-benzofuran

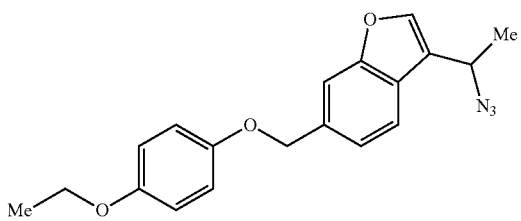 [SMILES: CCOc1ccc(OCc2ccc3c(C(C)N=[N+]=[N-])coc3c2)cc1]

To a solution of 1-{6-[(4-ethoxyphenoxy)methyl]-1-benzofuran-3-yl}ethanol (101 mg, 0.322 mmol) obtained in Reference Example 21 in DMF (1.1 mL) were successively added dropwise methanesulfonyl chloride (0.038 mL, 0.483 mmol) and triethylamine (0.096 mL, 0.644 mmol) at 0° C., and the mixture was stirred at 0° C. for 30 min. Sodium azide (104 mg, 1.61 mmol) was added, and the mixture was stirred at room temperature overnight. To the reaction mixture was added brine, and the mixture was extracted twice with ethyl acetate. The extract was washed with saturated brine, and dried over anhydrous magnesium sulfate. The solvent was evaporated under reduced pressure to give the title compound (114 mg, quantitative) as an oil.

$^1$H NMR (CDCl$_3$) δ 1.35-1.41 (m, 3H), 1.68 (d, J=6.8 Hz, 3H), 3.93-4.01 (m, 2H), 4.79 (q, J=7.1 Hz, 1H), 5.13 (s, 2H), 6.80-6.95 (m, 4H), 7.32-7.36 (m, 1H), 7.56-7.61 (m, 2H), 7.63-7.71 (m, 1H).

Reference Example 23

1-[6-(benzyloxy)-1-benzofuran-2-yl]ethanol

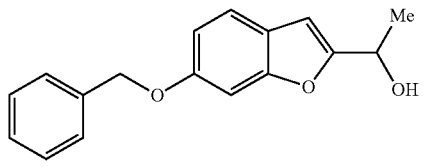 [SMILES: CC(O)c1cc2ccc(OCc3ccccc3)cc2o1]

To a solution of 1-[6-(benzyloxy)-1-benzofuran-2-yl]ethanone (25.7 g, 96.6 mmol) in methanol (300 mL) was added sodium borohydride (3.67 g, 96.6 mmol) by small portions, and the mixture was stirred at room temperature for 1 hr. Water was added to the reaction mixture, and the solvent was evaporated. Ethyl acetate was added thereto, and the mixture was washed with water and saturated brine, and dried over anhydrous sodium sulfate. The solvent was evaporated under reduced pressure, and the obtained residue was purified by silica gel column chromatography (petroleum ether:ethyl acetate=5:1) to give the title compound (18.3 g, yield 71%).

$^1$H NMR (CDCl$_3$) δ 1.62 (d, J=6.6 Hz, 3H), 2.06 (d, J=5.1 Hz, 1H), 4.96-4.99 (m, 1H), 5.10 (s, 2H), 6.53 (s, 1H), 6.93 (dd, J=8.7, 2.4 Hz, 1H), 7.06 (dd, J=8.7, 2.1 Hz, 1H), 7.33-7.47 (m, 6H).

Reference Example 24

2-(1-azidoethyl)-6-(benzyloxy)-1-benzofuran

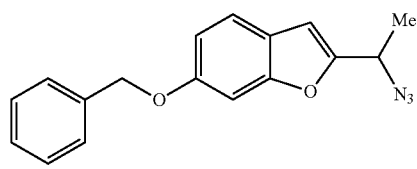 [SMILES: CC(N=[N+]=[N-])c1cc2ccc(OCc3ccccc3)cc2o1]

To a solution of 1-[6-(benzyloxy)-1-benzofuran-2-yl]ethanol (18.3 g, 68.3 mmol) obtained in Reference Example 23 in toluene (350 mL) were successively added dropwise diphenyl azidophosphate (20.7 mL, 95.6 mmol) and DBU (14.2 mL, 95.6 mmol) at 0° C. The mixture was stirred while gradually allowed to warm to room temperature for 3 hr. Ethyl acetate was added thereto, and the mixture was washed with water, and dried over anhydrous sodium sulfate. The solvent was evaporated under reduced pressure, and the obtained residue was purified by silica gel column chromatography (petroleum ether:ethyl acetate=20:1) to give the title compound (18.0 g, yield 90%) as an oil.

$^1$H NMR (CDCl$_3$) δ 1.63 (d, J=6.9 Hz, 3H), 4.64 (q, J=6.9 Hz, 1H), 5.10 (s, 2H), 6.59 (s, 1H), 6.95 (dd, J=10.8, 5.1 Hz, 1H), 7.09 (d, J=5.1 Hz, 1H), 7.33-7.48 (m, 6H).

Reference Example 25

1-[6-(benzyloxy)-1-benzofuran-2-yl]ethanamine

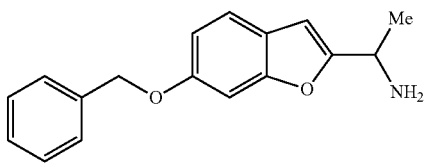 [SMILES: CC(N)c1cc2ccc(OCc3ccccc3)cc2o1]

To a solution of 2-(1-azidoethyl)-6-(benzyloxy)-1-benzofuran (18.0 g, 61.4 mmol) obtained in Reference Example 24 in THF (400 mL) were added triphenylphosphine (20.9 g, 79.8 mmol) and water (40 mL), and the mixture was refluxed overnight. After evaporation of the solvent, the obtained residue was purified by silica gel column chromatography (petroleum ether:ethyl acetate=5:1 to 2:1, then methylene chloride:methanol=19:1) to give the title compound (18.0 g, yield 90%).

$^1$H NMR (CDCl$_3$) δ 1.50 (d, J=6.6 Hz, 3H), 1.88 (br, 2H), 4.17 (q, J=6.6 Hz, 1H), 5.10 (s, 2H), 6.41 (s, 1H), 6.92 (dd, J=8.7, 2.1 Hz, 1H), 7.05 (d, J=2.1 Hz, 1H), 7.32-7.48 (m, 6H).

Reference Example 27

N-[1-(6-hydroxy-1-benzofuran-2-yl)ethyl]acetamide

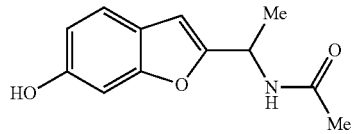 [SMILES: CC(=O)NC(C)c1cc2ccc(O)cc2o1]

To a solution of N-{1-[6-(benzyloxy)-1-benzofuran-2-yl]ethyl}acetamide (7.62 g, 24.7 mmol) obtained in the below-mentioned Example 101 in methanol (200 mL) was added 10% palladium carbon (50% water-containing product, 200 mg), and the mixture was stirred at room temperature under a hydrogen atmosphere for 5 hr. Palladium carbon was removed through silica gel, and the solvent was evaporated. The obtained residue was purified by silica gel column chromatography (methylene chloride:methanol=20:1) to give the title compound (2.60 g, yield 48%) as a white solid.

¹H NMR (DMSO-d₆) δ 1.40 (d, J=6.6 Hz, 3H), 1.84 (s, 3H), 5.02-5.07 (m, 1H), 6.54 (s, 1H), 6.69 (dd, J=8.7, 2.1 Hz, 1H), 6.86 (t, J=0.9 Hz, 1H), 7.32 (d, J=8.1 Hz, 1H), 8.32 (d, J=7.5 Hz, 1H), 9.43 (s, 1H).

Reference Example 28 methyl 2-(1-azidoethyl)-1-benzofuran-6-carboxylate

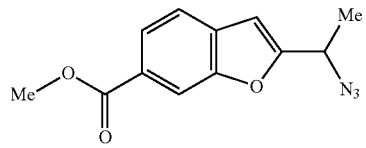 [SMILES: COC(=O)c1ccc2cc(C(C)N=[N+]=[N-])oc2c1]

To a solution of methyl 2-(1-hydroxyethyl)-1-benzofuran-6-carboxylate (1.10 g, 4.99 mmol) in toluene (20 mL) were added diphenyl azidophosphate (1.62 mL, 7.50 mmol) and DBU (1.50 mL, 9.98 mmol), and the mixture was stirred at room temperature for 2.5 hr. Ethyl acetate was added thereto, and the mixture was washed with water, and dried over anhydrous magnesium sulfate. The solvent was evaporated under reduced pressure, and the obtained residue was purified by silica gel column chromatography (hexane:ethyl acetate=20:1 to 2:3) to give the title compound (1.22 g, yield 88%) as an oil.

¹H NMR (CDCl₃) δ 1.68 (d, J=6.8 Hz, 3H), 3.95 (s, 3H), 4.72 (q, J=6.8 Hz, 1H), 6.72 (s, 1H), 7.59 (d, J=8.3 Hz, 1H), 7.96 (dd, J=8.3, 1.3 Hz, 1H), 8.17 (s, 1H).

Reference Example 29 methyl 2-{1-[(tert-butoxycarbonyl)amino]ethyl}-1-benzofuran-6-carboxylate

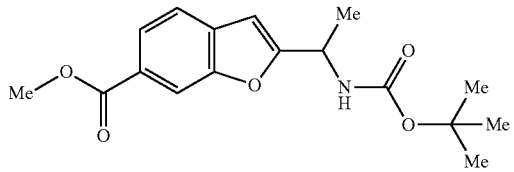 [SMILES: COC(=O)c1ccc2cc(C(C)NC(=O)OC(C)(C)C)oc2c1]

To a solution of methyl 2-(1-azidoethyl)-1-benzofuran-6-carboxylate (1.22 g, 4.97 mmol) obtained in Reference Example 28 in THF (20 mL) was added triphenylphosphine (1.51 g, 5.75 mmol), and the mixture was stirred at 60° C. for 30 min. To the reaction mixture was added water (0.5 mL), and the mixture was stirred at 60° C. for 15 hr. The reaction mixture was allowed to cool to room temperature, saturated aqueous sodium hydrogen carbonate solution (1 mL) and di-/o tert-butyl bicarbonate (1.37 mL, 5.96 mmol) were added thereto, and the mixture was stirred at room temperature for 15 min. To the reaction mixture was added saturated brine, and the mixture was extracted twice with ethyl acetate. The extract was dried over anhydrous magnesium sulfate. The solvent was evaporated under reduced pressure, and the obtained residue was purified by silica gel column chromatography (hexane:ethyl acetate=19:1 to 3:2) to give the title compound (1.33 g, yield 87%) as an oil.

¹H NMR (CDCl₃) δ 1.46 (s, 9H), 1.57 (d, J=6.8 Hz, 3H), 3.94 (s, 3H), 4.86-4.94 (m, 1H), 4.98-5.09 (m, 1H), 6.60 (s, 1H), 7.54 (d, J=8.1 Hz, 1H), 7.92 (dd, J=8.1, 1.3 Hz, 1H), 8.12 (s, 1H).

Reference Example 30 tert-butyl {1-[6-(hydroxymethyl)-1-benzofuran-2-yl]ethyl}carbamate

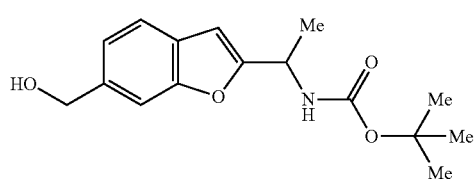 [SMILES: CC(NC(=O)OC(C)(C)C)c1cc2ccc(CO)cc2o1]

To a solution of methyl 2-{1-[(tert-butoxycarbonyl)amino]ethyl}-1-benzofuran-6-carboxylate (1.37 g, 4.31 mmol) obtained in Reference Example 29 in THF (20 mL) was added 1.5 M diisobutylaluminum hydride toluene solution (11.5 mL, 17.2 mmol) at 0° C., and the mixture was stirred at the same temperature for 10 min. To the reaction mixture was added sodium sulfate decahydrate (5.55 g, 17.2 mmol), and the mixture was stirred at room temperature for 30 min. The reaction mixture was filtered. The solvent was evaporated under reduced pressure and the obtained residue was purified by silica gel column chromatography (hexane:ethyl acetate=7:3 to 2:3) to give the title compound (0.870 g, yield 69%) as a white solid.

¹H NMR (CDCl₃) δ 1.46 (s, 9H), 1.55 (d, J=6.8 Hz, 3H), 4.78 (d, J=5.7 Hz, 2H), 4.83-4.91 (m, 1H), 4.96-5.06 (m, 1H), 6.53 (s, 1H), 7.21 (dd, J=8.0, 1.5 Hz, 1H), 7.46 (s, 1H), 7.49 (d, J=8.1 Hz, 1H).

Reference Example 31

N$^{\alpha}$-acetyl-N-(2-hydroxy-4-methoxyphenyl) alaninamide

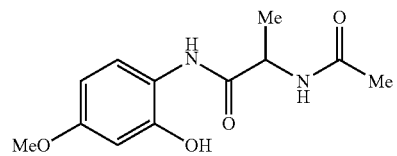 [SMILES: COc1ccc(NC(=O)C(C)NC(C)=O)c(O)c1]

To a solution of 2-amino-5-methoxyphenol hydrochloride (5.24 g, 29.8 mmol), N-acetyl-D,L-alanine (3.91 g, 29.8 mmol) and 1-hydroxybenzotriazole (4.03 g, 29.8 mmol) in DMF (5 mL) were added triethylamine (4.15 mL, 29.8 mmol) and 1-ethyl-3-(3-dimethylaminopropyl)carbodiimide hydrochloride (5.72 g, 29.8 mmol), and the mixture was stirred at room temperature for 3 days. The reaction mixture was diluted with ethyl acetate, and the mixture was washed with 1N hydrochloric acid, 10% aqueous potassium carbonate solution and saturated brine, and dried over anhydrous sodium sulfate. The solvent was evaporated under reduced pressure, and the obtained residue was purified by basic silica gel column chromatography (ethyl acetate to methanol:ethyl acetate=1:4), and triturated with ethyl acetate to give the title compound (740 mg, yield 9.8%).

$^1$H NMR (CDCl$_3$) δ 1.46 (d, J=6.9 Hz, 3H), 2.07 (s, 3H), 3.76 (s, 3H), 4.74 (m, 1H), 6.08 (d, J=7.2 Hz, 1H), 6.41 (dd, J=2.7, 8.7 Hz, 1H), 6.54 (d, J=2.7 Hz, 1H), 6.91 (d, J=8.7 Hz, 1H), 8.91 (s, 1H), 8.93 (br, 1H).

Reference Example 32

N-[1-(6-methoxy-1,3-benzoxazol-2-yl)ethyl]acetamide

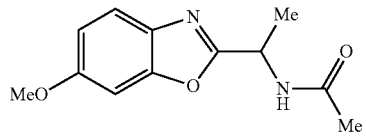 [SMILES: COc1ccc2nc(C(C)NC(C)=O)oc2c1]

A suspension of N$^α$-acetyl-N-(2-hydroxy-4-methoxyphenyl)alaninamide (740 mg, 2.93 mmol) obtained in Reference Example 31 and p-toluenesulfonic acid monohydrate (55.8 mg, 0.293 mmol) in o-xylene (15 mL) was stirred under heating under a nitrogen atmosphere at 140° C. for 16 hr. The reaction mixture was diluted with ethyl acetate, and the mixture was washed with 10% aqueous potassium carbonate solution and saturated brine, and dried over anhydrous sodium sulfate. The solvent was evaporated under reduced pressure, and the obtained residue was purified by basic silica gel column chromatography (hexane:ethyl acetate=1:1 to ethyl acetate), and triturated with diisopropyl ether to give the title compound (225 mg, yield 33%).

$^1$H NMR (CDCl$_3$) δ 1.63 (d, J=6.9 Hz, 3H), 2.08 (s, 3H), 3.85 (s, 3H), 5.39 (m, 1H), 6.27 (d, J=6.9 Hz, 1H), 6.92 (dd, J=2.4, 9.0 Hz, 1H), 7.03 (d, J=2.4 Hz, 1H), 7.54 (d, J=9.0 Hz, 1H).

Reference Example 33

N-[1-(6-hydroxy-1,3-benzoxazol-2-yl)ethyl]acetamide

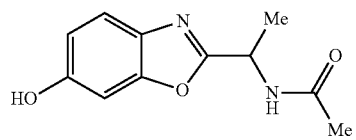 [SMILES: CC(=O)NC(C)c1nc2ccc(O)cc2o1]

To a solution of N-[1-(6-methoxy-1,3-benzoxazol-2-yl)ethyl]acetamide (223 mg, 0.952 mmol) obtained in Reference Example 32 in methylene chloride (4 mL) was added 1 M boron tribromide methylene chloride solution (3.80 mL, 3.80 mmol) under ice-cooling, and the mixture was stirred at room temperature for 4 hr. To the reaction mixture was added ice, and the mixture was extracted with ethyl acetate. The extract was washed with saturated brine, and dried over anhydrous sodium sulfate. This solution was applied to basic silica gel column chromatography (THF), and the obtained residue was triturated with diisopropyl ether to give the title compound (104 mg, yield 50%). This was used for the next step without purification.

Reference Example 34

1-(5-{[tert-butyl(dimethyl)silyl]oxy}-1-benzofuran-2-yl)ethanone

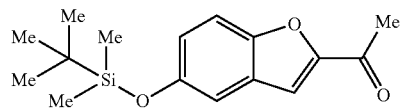 [SMILES: CC(=O)c1cc2cc(O[Si](C)(C)C(C)(C)C)ccc2o1]

Using 1-(5-hydroxy-1-benzofuran-2-yl)ethanone (1.15 g, 6.53 mmol), DMF (10 mL), tert-butyldimethylchlorosilane (1.07 g, 7.18 mmol) and imidazole (666 mg, 9.80 mmol), an operation in the same manner as in Reference Example 16 was performed to give the title compound (1.76 g, yield 98%).

$^1$H NMR (CDCl$_3$) δ 0.19-0.25 (m, 6H), 0.97-0.04 (m, 9H), 2.59 (s, 3H), 7.00 (dd, J=8.9, 2.4 Hz, 1H), 7.09 (d, J=2.3 Hz, 1H), 7.38-7.46 (m, 2H).

To a solution of 1-(5-hydroxy-1-benzofuran-2-yl)ethanone (1.15 g, 6.53 mmol) in DMF (10 mL) were added tert-butyldimethylchlorosilane (1.07 g, 7.18 mmol) and imidazole (666 mg, 9.80 mmol), and the mixture was stirred at room temperature overnight. To the reaction mixture was added brine, and the mixture was extracted with ethyl acetate. The extract was washed with saturated brine, and dried over anhydrous magnesium sulfate. The solvent was evaporated under reduced pressure, and the obtained residue was purified by silica gel column chromatography (hexane:ethyl acetate=19:1 to 7:3) to give the title compound (1.76 g, yield 98%).

$^1$H NMR (CDCl$_3$) δ 0.21 (s, 6H), 1.00 (s, 9H), 2.59 (s, 3H), 7.00 (dd, J=8.9, 2.5 Hz, 1H), 7.09 (d, J=2.5 Hz, 1H), 7.39-7.45 (m, 2H).

Reference Example 35

1-(5-{[tert-butyl(dimethyl)silyl]oxy}-1-benzofuran-2-yl)ethanol

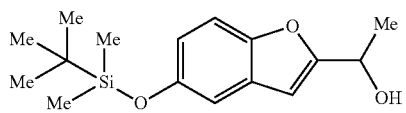

Using 1-(5-{[tert-butyl(dimethyl)silyl]oxy}-1-benzofuran-2-yl)ethanone (1.76 g, 6.37 mmol) obtained in Reference Example 34, methanol (18 mL) and sodium borohydride (484 mg, 12.7 mmol), an operation in the same manner as in Reference Example 23 was performed to give the title compound (1.60 g, yield 90%).

$^1$H NMR (CDCl$_3$) δ 0.20 (s, 6H), 1.02 (s, 9H), 1.55 (d, J=7.2 Hz, 3H), 2.04 (s, 1H), 4.89-5.07 (m, 1H), 6.51 (s, 1H), 6.77 (dd, J=8.8, 2.3 Hz, 1H), 6.96 (d, J=2.3 Hz, 1H), 7.21-7.32 (m, 1H).

To a solution of 1-(5-{[tert-butyl(dimethyl)silyl]oxy}-1-benzofuran-2-yl)ethanone (1.76 g, 6.37 mmol) obtained in Reference Example 34 in methanol (18 mL) was added sodium borohydride (484 mg, 12.7 mmol) by small portions, and the mixture was stirred at room temperature for 1.5 hr. Water was added to the reaction mixture, and the solvent was evaporated. Ethyl acetate was added thereto, and the mixture was washed with water and saturated brine, and dried over anhydrous magnesium sulfate. The solvent was evaporated under reduced pressure to give the title compound (1.60 g, yield 90%) as an oil.

$^1$H NMR (CDCl$_3$) δ 0.19 (s, 6H), 1.00 (s, 9H), 1.62 (d, J=7.2 Hz, 3H), 2.04 (s, 1H), 4.96-5.02 (m, 1H), 6.51 (s, 1H), 6.77 (dd, J=8.8, 2.3 Hz, 1H), 6.96 (d, J=2.3 Hz, 1H), 7.25-7.33 (m, 1H).

Reference Example 36

{[2-(1-azidoethyl)-1-benzofuran-5-yl]oxy}(tert-butyl)dimethylsilane

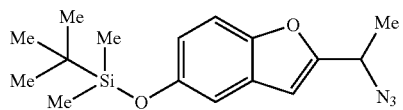

To a solution of 1-(5-{[tert-butyl(dimethyl)silyl]oxy}-1-benzofuran-2-yl)ethanol (1.60 g, 5.76 mmol) obtained in Reference Example 35 in anhydrous DMF (5.8 mL) were successively added dropwise methanesulfonyl chloride (0.665 mL, 8.64 mmol) and triethylamine (1.71 mL, 11.5 mmol) at 0° C., and the mixture was stirred at the same temperature for 30 min. Sodium azide (1.87 g, 28.8 mmol) was added thereto, and the mixture was further stirred at room temperature overnight. To the reaction mixture was added brine, and the mixture was extracted twice with ethyl acetate. The extract was washed with saturated brine, and dried over anhydrous magnesium sulfate. The solvent was evaporated under reduced pressure, and the obtained residue was purified by silica gel column chromatography (hexane to hexane:ethyl acetate=4:1) to give the title compound (1.12 g, yield 61%) as an oil.

$^1$H NMR (CDCl$_3$) δ 0.19 (s, 6H), 1.00 (s, 9H), 1.64 (d, J=6.8 Hz, 3H), 4.65 (q, J=6.8 Hz, 1H), 6.56 (s, 1H), 6.80 (dd, J=9.0, 2.5 Hz, 1H), 6.97 (d, J=2.5 Hz, 1H), 7.30 (d, J=9.0 Hz, 1H).

Reference Example 37

N-[1-(5-{[tert-butyl(dimethyl)silyl]oxy}-1-benzofuran-2-yl)ethyl]acetamide

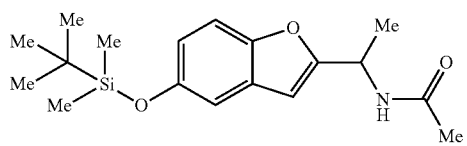

To a solution of {[2-(1-azidoethyl)-1-benzofuran-5-yl]oxy}(tert-butyl)dimethylsilane (1.12 g, 3.53 mmol) obtained in Reference Example 36 in THF (7 mL) and water (1 mL) was added triphenylphosphine (1.38 g, 5.29 mmol), and the mixture was stirred at 50° C. overnight. To the reaction mixture was added brine, and the mixture was extracted with ethyl acetate. The extract was dried over anhydrous magnesium sulfate. The solvent was evaporated under reduced pressure, and the obtained residue was directly used for the next reaction. To the obtained residue were added ethyl acetate (5 mL) and acetic anhydride (0.67 mL, 7.1 mmol) and the mixture was stirred at room temperature for 10 min. The solvent was evaporated under reduced pressure, and the obtained residue was purified by basic silica gel column chromatography (hexane:ethyl acetate=9:1 to 1:4) to give the title compound (931 mg, yield 79%).

$^1$H NMR (CDCl$_3$) δ 0.18 (s, 6H), 0.99 (s, 9H), 1.55 (d, J=7.0 Hz, 3H), 2.01 (s, 3H), 5.24-5.38 (m, 1H), 5.81 (br, 1H), 6.47 (s, 1H), 6.77 (dd, J=8.8, 2.4 Hz, 1H), 6.93 (d, J=2.4 Hz, 1H), 7.23-7.28 (m, 1H).

Reference Example 38

N-[1-(5-hydroxy-1-benzofuran-2-yl)ethyl]acetamide

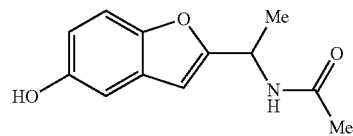 [SMILES: CC(=O)NC(C)c1cc2cc(O)ccc2o1]

To a solution of N-[1-(5-{[tert-butyl(dimethyl)silyl]oxy}-1-benzofuran-2-yl)ethyl]acetamide (931 mg, 2.79 mmol) obtained in Reference Example 37 in THF (5 mL) was added 1 M tetrabutylammonium fluoride THF solution (3.63 mL, 3.63 mmol) and the mixture was stirred at room temperature for 2 hr. To the reaction mixture was added aqueous saturated ammonium chloride, and the mixture was extracted twice with ethyl acetate. The extract was washed with aqueous saturated ammonium chloride and saturated brine, dried over anhydrous sodium sulfate, and the solution was passed through silica gel. The solvent was evaporated under reduced pressure, and the obtained white solid was washed with diisopropyl ether to give the title compound (525 mg, yield 86%).

$^1$H NMR (CDCl$_3$) δ 1.55 (d, J=7.0 Hz, 3H), 2.01 (s, 3H), 4.77 (s, 1H), 5.24-5.42 (m, 1H), 5.76 (br, 1H), 6.47 (s, 1H), 6.77 (dd, J=8.8, 2.5 Hz, 1H), 6.92 (d, J=2.5 Hz, 1H), 7.24-7.31 (m, 1H).

Reference Example 39 ethyl 6-hydroxy-1-benzothiophene-2-carboxylate

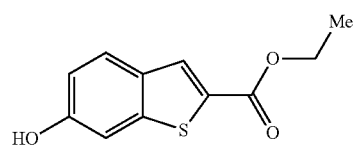 [SMILES: CCOC(=O)c1cc2ccc(O)cc2s1]

To a solution of ethyl 6-methoxy-1-benzothiophene-2-carboxylate (5.58 g, 23.6 mmol) in methylene chloride (50 mL) was added dropwise 1 M boron tribromide methylene chloride solution (71 mL, 70.8 mmol) at −20° C., and the mixture was stirred at room temperature for 3 hr. The reaction mixture was poured into ice, and the mixture was extracted twice with ethyl acetate. The extract was washed with saturated brine and dried over anhydrous sodium sulfate. The solvent was evaporated under reduced pressure, and the obtained residue was purified by silica gel column chromatography (hexane to hexane:ethyl acetate=3:2) to give the title compound (1.76 g, yield 34%) as a white solid.

¹H NMR (CDCl₃) δ 1.41 (t, J=7.1 Hz, 3H), 4.39 (q, J=7.1 Hz, 2H), 5.48 (s, 1H), 6.96 (dd, J=8.7, 2.3 Hz, 1H), 7.25-7.30 (m, 1H), 7.73 (d, J=8.7 Hz, 1H), 7.97 (s, 1H).

Reference Example 40 ethyl 6-{[tert-butyl(dimethyl)silyl]oxy}-1-benzothiophene-2-carboxylate

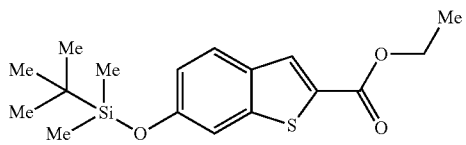 [SMILES: CCOC(=O)c1cc2ccc(O[Si](C)(C)C(C)(C)C)cc2s1]

Using ethyl 6-hydroxy-1-benzothiophene-2-carboxylate (1.76 g, 7.93 mmol) obtained in Reference Example 39, DMF (8 mL), tert-butyldimethylchlorosilane (1.31 g, 8.72 mmol) and imidazole (809 mg, 11.9 mmol), an operation in the same manner as in Reference Example 16 was performed to give the title compound (2.54 g, yield 95%).

¹H NMR (CDCl₃) δ 0.21 (s, 6H), 1.00 (s, 9H), 1.40 (t, J=7.2 Hz, 3H), 4.39 (q, J=7.2 Hz, 2H), 6.93 (dd, J=8.7, 2.1 Hz, 1H), 7.26 (s, 1H), 7.71 (d, J=8.7 Hz, 1H), 7.96 (d, J=0.75 Hz, 1H).

Reference Example 41

6-{[tert-butyl(dimethyl)silyl]oxy}-N-methoxy-N-methyl-1-benzothiophene-2-carboxamide

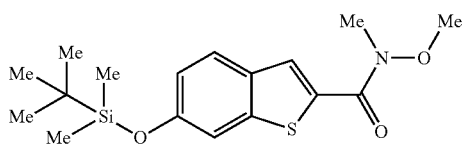 [SMILES: CON(C)C(=O)c1cc2ccc(O[Si](C)(C)C(C)(C)C)cc2s1]

Using ethyl 6-{[tert-butyl(dimethyl)silyl]oxy}-1-benzothiophene-2-carboxylate (2.54 g, 7.55 mmol) obtained in Reference Example 40, anhydrous THF (46 mL), N,O-dimethylhydroxylamine hydrochloride (3.66 g, 37.8 mmol) and 1.6 M n-butyllithium hexane solution (48 mL, 75.6 mmol), an operation in the same manner as in Reference Example 18 was performed to give the title compound (2.65 g, quantitative).

¹H NMR (CDCl₃) δ 0.23 (s, 6H), 1.00 (s, 9H), 3.41 (s, 3H), 3.82 (s, 3H), 6.93 (dd, J=8.7, 2.3 Hz, 1H), 7.21-7.29 (m, 1H), 7.72 (d, J=8.7 Hz, 0.1H), 8.11 (s, 1H).

Reference Example 42

1-(6-{[tert-butyl(dimethyl)silyl]oxy}-1-benzothiophen-2-yl)ethanone

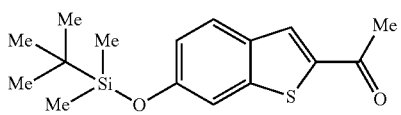

Using 6-{[tert-butyl(dimethyl)silyl]oxy}-N-methoxy-N-methyl-1-benzothiophene-2-carboxamide (2.65 g, 7.55 mmol) obtained in Reference Example 41, anhydrous THF (16 mL) and 1 M methylmagnesium bromide THF solution (15.1 mL, 15.1 mmol), an operation in the same manner as in Reference Example 19 was performed to give the title compound (1.19 g, yield 52%).

¹H NMR (CDCl₃) δ 0.25 (s, 6H), 1.03 (s, 9H), 2.62 (s, 3H), 6.94 (dd, J=8.7, 2.2 Hz, 1H), 7.22-7.32 (m, 1H), 7.73 (d, J=8.7 Hz, 1H), 7.85 (s, 1H).

Reference Example 43

1-(6-{[tert-butyl(dimethyl)silyl]oxy}-1-benzothiophen-2-yl)ethanol

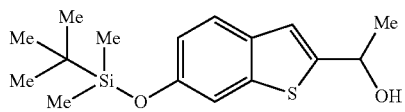 [SMILES: CC(O)c1cc2ccc(O[Si](C)(C)C(C)(C)C)cc2s1]

Using 1-(6-{[tert-butyl(dimethyl)silyl]oxy}-1-benzothiophen-2-yl)ethanone (1.19 g, 3.89 mmol) obtained in Reference Example 42, methanol (7 mL) and sodium borohydride (294 mg, 7.76 mmol), an operation in the same manner as in Reference Example 21 was performed to give the title compound (950 mg, yield 79%).

¹H NMR (CDCl₃) δ 0.20 (s, 6H), 1.00 (s, 9H), 1.64 (d, J=6.4 Hz, 3H), 2.00 (d, J=4.7 Hz, 1H), 5.09-5.24 (m, 1H), 6.87 (dd, J=8.7, 2.3 Hz, 1H), 7.09 (s, 1H), 7.23-7.28 (m, 1H), 7.55 (d, J=8.5 Hz, 1H).

Reference Example 44

{[2-(1-azidoethyl)-1-benzothiophen-6-yl]oxy}(tert-butyl)dimethylsilane

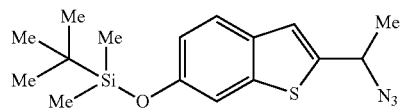 [SMILES: CC(N=[N+]=[N-])c1cc2ccc(O[Si](C)(C)C(C)(C)C)cc2s1]

Using 1-(6-{[tert-butyl(dimethyl)silyl]oxy}-1-benzothiophen-2-yl)ethanol (101 mg, 0.322 mmol) obtained in Reference Example 43, DMF (1.1 mL), methanesulfonyl chloride (0.356 mL, 4.63 mmol), triethylamine (0.915 mL, 6.16 mmol) and sodium azide (1.00 mg, 15.4 mmol), an operation in the same manner as in Reference Example 22 was performed to give the title compound (759 mg, yield 74%) as an oil.

¹H NMR (CDCl₃) δ 0.22 (s, 6H), 1.00 (s, 9H), 1.65 (d, J=6.8 Hz, 3H), 4.84 (q, J=6.8 Hz, 1H), 6.89 (dd, J=8.7, 2.3 Hz, 1H), 7.14 (s, 1H), 7.23-7.28 (m, 1H), 7.57 (d, J=8.3 Hz, 1H).

Reference Example 45

N-[1-(6-{[tert-butyl(dimethyl)silyl]oxy}-1-benzothiophen-2-yl)ethyl]acetamide

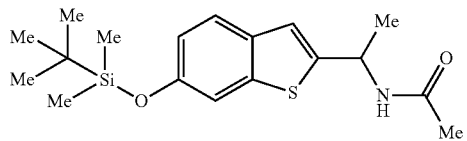 [SMILES: CC(=O)NC(C)c1cc2ccc(O[Si](C)(C)C(C)(C)C)cc2s1]

Using {[2-(1-azidoethyl)-1-benzothiophen-6-yl]oxy}(tert-butyl)dimethylsilane (759 mg, 2.27 mmol) obtained in Reference Example 44, THF (5 mL), water (1 mL), triphenylphosphine (894 mg, 3.41 mmol), ethyl acetate (5 mL) and acetic anhydride (0.42 mL, 4.54 mmol) and an operation in the same manner as in Reference Example 37 was performed to give the title compound (765 mg, yield 97%).

¹H NMR (CDCl₃) δ 0.22 (s, 6H), 1.00 (s, 9H), 1.62 (d, J=6.8 Hz, 3H), 2.01 (s, 3H), 5.33-5.50 (m, 1H), 5.73 (br, 1H), 6.87 (dd, J=8.6, 2.3 Hz, 1H), 7.09 (s, 1H), 7.22 (d, J=2.3 Hz, 1H), 7.50-7.56 (m, 1H).

Reference Example 46

N-[1-(6-hydroxy-1-benzothiophen-2-yl)ethyl]acetamide

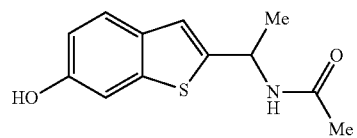 [SMILES: CC(=O)NC(C)c1cc2ccc(O)cc2s1]

Using N-[1-(6-{[tert-butyl(dimethyl)silyl]oxy}-1-benzothiophen-2-yl)ethyl]acetamide (765 mg, 2.19 mmol) obtained in Reference Example 45, THF (2.2 mL) and 1 M tetrabutylammonium fluoride THF solution (2.85 mL, 2.85 mmol) and an operation in the same manner as in Reference Example 38 was performed to give the title compound (373 mg, yield 72%) as a white solid.

¹H NMR (CDCl₃) δ 1.62 (d, J=6.8 Hz, 3H), 2.02 (s, 3H), 5.16 (s, 1H), 5.39-5.52 (m, 1H), 5.72 (br, 1H), 6.88 (dd, J=8.5, 2.5 Hz, 1H), 7.08 (s, 1H), 7.26 (s, 1H), 7.55 (d, j=8.5 Hz, 1H).

Reference Example 47 methyl 4-[(4-ethoxyphenyl)ethynyl]-2-(methoxymethoxy)benzoate

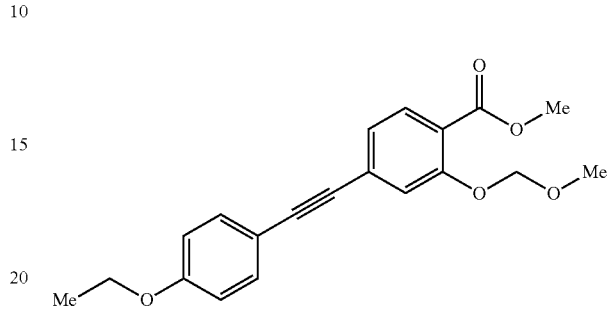

To a solution of methyl 2-hydroxy-4-iodobenzoate (1.00 g, 3.60 mmol) and 1-ethoxy-4-ethynylbenzene (789 mg, 5.40 mmol) and copper(I) iodide (68.6 mg, 0.360 mmol) in triethylamine (9 mL) was added bis(triphenylphosphine)palladium (II) chloride (253 mg, 0.360 mmol), and the mixture was stirred under an argon stream at room temperature for 15 min. The reaction mixture was diluted with ethyl acetate, and the mixture was washed with water, and dried over anhydrous magnesium sulfate. The solvent was evaporated under reduced pressure and the obtained residue was dissolved in DMF (10 mL). Potassium carbonate (2.59 g, 18.8 mmol) and chloromethyl methyl ether (1.07 mL, 14.0 mmol) were added thereto, and the mixture was stirred at room temperature for 20 min. Water was added to the reaction mixture, and the mixture was extracted with ethyl acetate. The extract was washed twice with saturated brine, and dried over anhydrous magnesium sulfate. The solvent was evaporated under reduced pressure and the obtained residue was purified by silica gel column chromatography (hexane:ethyl acetate=9:1 to 1:1) to give the title compound (623 mg, yield 51%) as a yellow solid.

¹H NMR (CDCl₃) δ 1.43 (t, J=7.0 Hz, 3H), 3.54 (s, 3H), 3.89 (s, 3H), 4.05 (q, J=7.0 Hz, 2H), 5.28 (s, 2H), 6.87 (d, J=8.9 Hz, 2H), 7.17 (dd, J=8.0, 1.4 Hz, 1H), 7.33 (d, J=1.4 Hz, 1H), 7.47 (d, J=8.9 Hz, 2H), 7.76 (d, J=8.0 Hz, 1H).

Reference Example 48

{4-[2-(4-ethoxyphenyl)ethyl]-2-(methoxymethoxy)phenyl}methanol

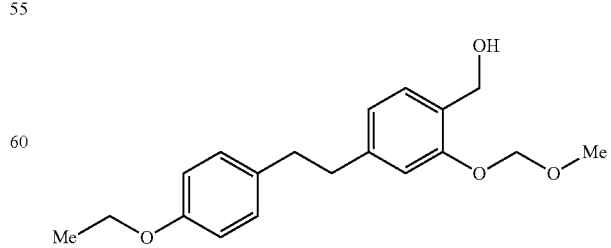

A solution of methyl 4-[(4-ethoxyphenyl)ethynyl]-2-(methoxymethoxy)benzoate (623 mg, 1.83 mmol) obtained in Reference Example 47 and 10% palladium carbon (50% water-containing product, 1.00 g) in ethanol (5 mL)-THF (1 mL) was stirred under a hydrogen atmosphere (normal pressure) for 30 min. After filtration, the filtrate was concentrated under reduced pressure, a solution of the obtained residue in THF (5 mL) was added to a suspension of lithium aluminum hydride (100 mg, 2.63 mmol) in THF (5 mL), and the mixture was stirred at room temperature for 15 min. To the reaction mixture were successively added water (0.10 mL), 15% aqueous sodium hydroxide solution (0.10 mL) and water (0.30 mL), and the mixture was stirred at room temperature for 15 min. After filtration, the filtrate was concentrated under reduced pressure, and the obtained residue was purified by silica gel column chromatography (hexane:ethyl acetate=4:1 to 2:3) to give the title compound (415 mg, yield 71%) as an oil.

$^1$H NMR (CDCl$_3$) δ 1.40 (t, J=7.0 Hz, 3H), 2.21 (t, J=6.5 Hz, 1H), 2.82-2.89 (m, 4H), 3.49 (s, 3H), 4.01 (q, J=7.0 Hz, 2H), 4.67 (d, J=6.5 Hz, 2H), 5.20 (s, 2H), 6.79-6.84 (m, 3H), 6.89 (d, J=1.3 Hz, 1H), 7.07 (d, J=8.7 Hz, 2H), 7.20 (d, J=7.5 Hz, 1H).

Reference Example 49

4-[2-(4-ethoxyphenyl)ethyl]-2-(methoxymethoxy)benzaldehyde

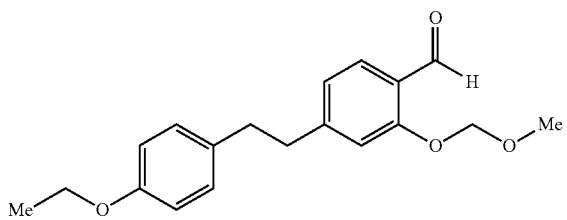 [SMILES: CCOc1ccc(CCc2ccc(C=O)c(OCOC)c2)cc1]

To a solution of {4-[2-(4-ethoxyphenyl)ethyl]-2-(methoxymethoxy)phenyl}methanol (415 mg, 1.32 mmol) obtained in Reference Example 48 in acetonitrile (10 mL) were added molecular sieves 4A (powder, 0.75 g), 4-methylmorpholine N-oxide (232 mg, 1.98 mmol) and tetrapropylammonium perruthenate (23.1 mg, 0.0656 mmol), and the mixture was stirred at room temperature for 15 min. The reaction mixture was filtered. The solvent was evaporated under reduced pressure, and the obtained residue was purified by silica gel column chromatography (hexane:ethyl acetate=19:1 to 3:2) to give the title compound (345 mg, yield 83%) as an oil.

$^1$H NMR (CDCl$_3$) δ 1.40 (t, J=7.0 Hz, 3H), 2.83-2.95 (m, 4H), 3.51 (s, 3H), 4.01 (q, J=7.0 Hz, 2H), 5.24 (s, 2H), 6.81 (d, J=8.7 Hz, 2H), 6.89 (d, J=7.9 Hz, 1H), 6.94 (d, J=1.1 Hz, 1H), 7.04 (d, J=8.7 Hz, 2H), 7.75 (d, J=7.9 Hz, 1H), 10.43 (d, J=0.6 Hz, 1H).

Reference Example 50

4-[2-(4-ethoxyphenyl)ethyl]-2-hydroxybenzaldehyde

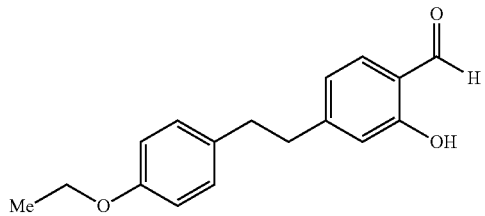 [SMILES: CCOc1ccc(CCc2ccc(C=O)c(O)c2)cc1]

To a solution of 4-[2-(4-ethoxyphenyl)ethyl]-2-(methoxymethoxy)benzaldehyde (345 mg, 1.10 mmol) obtained in Reference Example 49 in THF (5 mL) was added 6N hydrochloric acid (2 mL) and the mixture was stirred at 60° C. for 2 hr. The reaction mixture was neutralized with saturated aqueous sodium hydrogen carbonate solution, and the mixture was extracted twice with ethyl acetate. The extract was dried over anhydrous magnesium sulfate. The solvent was evaporated under reduced pressure and the obtained residue was purified by silica gel column chromatography (hexane:ethyl acetate=19:1 to 7:13) to give the title compound (255 mg, yield 86%) as a white solid.

$^1$H NMR (CDCl$_3$) δ 1.40 (t, J=7.0 Hz, 3H), 2.83-2.94 (m, 4H), 4.01 (q, J=7.0 Hz, 2H), 6.78-6.83 (m, 4H), 7.05 (d, J=8.7 Hz, 2H), 7.43 (d, J=8.3 Hz, 1H), 9.83 (s, 1H), 11.03 (s, 1H).

Reference Example 51

1-{6-[2-(4-ethoxyphenyl)ethyl]-1-benzofuran-2-yl}ethanone

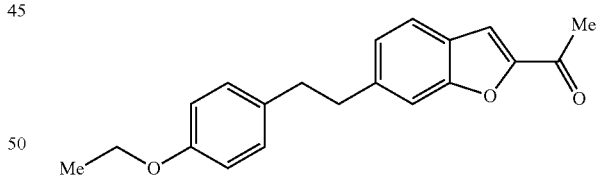

To a solution of 4-[2-(4-ethoxyphenyl)ethyl]-2-hydroxybenzaldehyde (255 mg, 0.943 mmol) obtained in Reference Example 50 in acetonitrile (10 mL) were added potassium carbonate (262 mg, 1.89 mmol) and bromoacetone (0.120 mL, 1.42 mmol), and the mixture was stirred at 80° C. for 13 hr. Water was added to the reaction mixture, and the mixture was extracted twice with ethyl acetate, and the combined organic layer was dried over anhydrous magnesium sulfate. The solvent was evaporated and the obtained residue was purified by silica gel column chromatography (hexane:ethyl acetate=19:1 to 3:2) to give the title compound (234 mg, yield 80%) as a white solid.

$^1$H NMR (CDCl$_3$) δ 1.40 (t, J=7.0 Hz, 3H), 2.59 (s, 3H), 2.88-2.93 (m, 2H), 3.01-3.06 (m, 2H), 4.01 (q, J=7.0 Hz, 2H), 6.80 (d, J=8.7 Hz, 2H), 7.06 (d, J=8.7 Hz, 2H), 7.13 (dd, J=8.1, 1.3 Hz, 1H), 7.34 (s, 1H), 7.47 (d, J=1.3 Hz, 1H), 7.59 (d, J=8.1 Hz, 1H).

Reference Example 52

1-{6-[2-(4-ethoxyphenyl)ethyl]-1-benzofuran-2-yl}ethanol

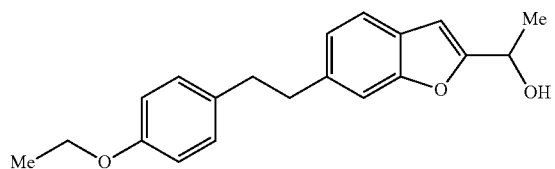

To a solution of 1-{6-[2-(4-ethoxyphenyl)ethyl]-1-benzofuran-2-yl}ethanone (234 mg, 0.759 mmol) obtained in Reference Example 51 in THF (2 mL)-methanol (5 mL) was added sodium borohydride (28.8 mg, 0.759 mmol), and the mixture was stirred at room temperature for 10 min. To the reaction mixture was added aqueous ammonium chloride solution, and the mixture was extracted twice with ethyl acetate. The combined organic layer was dried over anhydrous magnesium sulfate. The solvent was evaporated and the obtained residue was purified by silica gel column chromatography (hexane:ethyl acetate=4:1 to 1:1) to give the title compound (229 mg, yield 97%) as an oil.

$^1$H NMR (CDCl$_3$) δ 1.26 (t, J=7.0 Hz, 3H), 1.63 (d, J=6.4 Hz, 3H), 2.86-2.92 (m, 2H), 2.96-3.02 (m, 2H), 4.01 (q, J=7.0 Hz, 2H), 4.96-5.04 (m, 1H), 6.56 (s, 1H), 6.81 (d, J=8.7 Hz, 2H), 7.03 (dd, J=8.1, 1.5 Hz, 1H), 7.08 (d, J=8.7 Hz, 2H), 7.42 (d, J=8.1 Hz, 1H).

Reference Example 53

2-(1-azidoethyl)-6-[2-(4-ethoxyphenyl)ethyl]-1-benzofuran

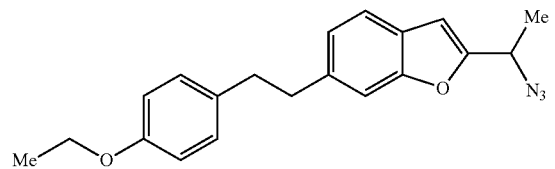

Using 1-{6-[2-(4-ethoxyphenyl)ethyl]-1-benzofuran-2-yl}ethanol (230 mg, 0.741 mmol) obtained in Reference Example 52, an operation in the same manner as in Reference Example 28 was performed to give the title compound (237 mg, yield 95%) as an oil.

$^1$H NMR (CDCl$_3$) δ 1.40 (t, J=7.0 Hz, 3H), 1.65 (d, J=6.8 Hz, 3H), 2.86-2.92 (m, 2H), 2.97-3.02 (m, 2H), 4.01 (q, J=7.0 Hz, 2H), 4.67 (q, J=6.8 Hz, 1H), 6.62 (s, 1H), 6.81 (d, J=8.7 Hz, 2H), 7.04-7.10 (m, 3H), 7.28 (s, 1H), 7.44 (d, J=8.0 Hz, 1H).

Reference Example 54

4-[(4-ethoxybenzyl)oxy]-2-hydroxy-3-methylbenzaldehyde

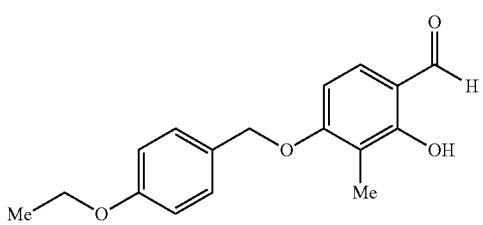 [SMILES: CCOc1ccc(COc2ccc(C=O)c(O)c2C)cc1]

To a solution of 2,4-dihydroxy-3-methylbenzaldehyde (1.00 g, 6.57 mmol) in DMF (20 mL) were added potassium carbonate (1.36 g, 9.86 mmol) and 1-(chloromethyl)-4-ethoxybenzene (1.23 g, 7.23 mmol), and the mixture was stirred at room temperature for 15 hr. Water was added to the reaction mixture, and the mixture was extracted with ethyl acetate. The organic layer was washed twice with saturated brine, and dried over anhydrous magnesium sulfate. The solvent was evaporated under reduced pressure and the obtained residue was purified by silica gel column chromatography (hexane:ethyl acetate=9:1 to 3:2) to give the title compound (336 mg, yield 18%) as a white solid.

$^1$H NMR (CDCl$_3$) δ 1.42 (t, J=7.0 Hz, 3H), 2.13 (s, 3H), 4.05 (q, J=7.0 Hz, 2H), 5.10 (s, 2H), 6.61 (d, J=8.7 Hz, 1H), 6.92 (d, J=8.7 Hz, 2H), 7.32-7.36 (m, 3H), 9.71 (s, 1H), 11.45 (s, 1H).

Reference Example 55

1-[6-[(4-ethoxybenzyl)oxy]-7-methyl-1-benzofuran-2-yl]ethanone

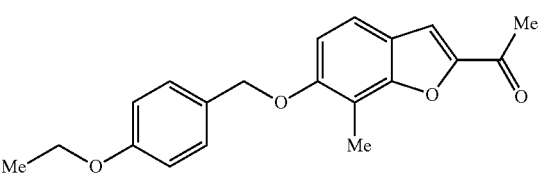 [SMILES: CCOc1ccc(COc2ccc3cc(C(C)=O)oc3c2C)cc1]

Using 4-[(4-ethoxybenzyl)oxy]-2-hydroxy-3-methylbenzaldehyde (336 mg, 1.17 mmol) obtained in Reference Example 54, an operation in the same manner as in Reference Example 51 was performed to give the title compound (326 mg, yield 85%) as a yellow solid.

¹H NMR (CDCl₃) δ 1.42 (t, J=7.0 Hz, 3H), 2.44 (s, 3H), 2.58 (s, 3H), 4.05 (q, J=7.0 Hz, 2H), 5.09 (s, 2H), 6.91 (d, J=8.7 Hz, 2H), 7.01 (d, J=8.7 Hz, 1H), 7.35 (d, J=8.7 Hz, 2H), 7.44-7.46 (m, 2H)

Reference Example 56

1-{6-[(4-ethoxybenzyl)oxy]-7-methyl-1-benzofuran-2-yl}ethanol

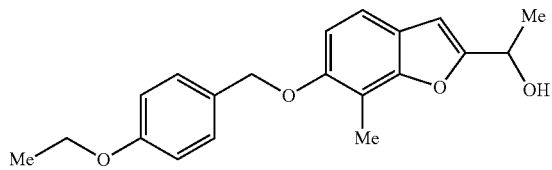 [SMILES: CCOc1ccc(COc2ccc3cc(C(C)O)oc3c2C)cc1]

Using 1-{6-[(4-ethoxybenzyl)oxy]-7-methyl-1-benzofuran-2-yl}ethanone (326 mg, 1.00 mmol) obtained in Reference Example 55, an operation in the same manner as in Reference Example 52 was performed to give the title compound (285 mg, yield 88%) as an oil.

¹H NMR (CDCl₃) δ 1.42 (t, J=7.0 Hz, 3H), 1.63 (d, J=6.6 Hz, 3H), 2.40 (s, 3H), 4.04 (q, J=7.0 Hz, 2H), 5.04 (s, 2H), 6.52 (d, J=0.6 Hz, 1H), 6.89-6.91 (m, 3H), 7.25-7.27 (m, 1H), 7.36 (d, J=8.7 Hz, 2H).

Reference Example 57

2-(1-azidoethyl)-6-[(4-ethoxybenzyl)oxy]-7-methyl-1-benzofuran

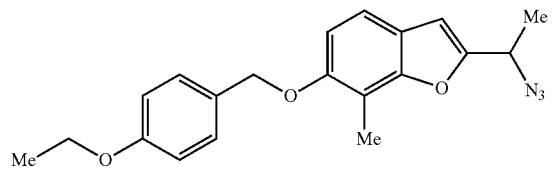 [SMILES: CCOc1ccc(COc2ccc3cc(C(C)N=[N+]=[N-])oc3c2C)cc1]

Using 1-{6-[(4-ethoxybenzyl)oxy]-7-methyl-1-benzofuran-2-yl}ethanol (285 mg, 0.873 mmol) obtained in Reference Example 56, an operation in the same manner as in Reference Example 28 was performed to give the title compound (227 mg, yield 74%) as an oil.

¹H NMR (CDCl₃) δ 0.89-0.91 (m, 3H), 1.64 (d, J=7.0 Hz, 3H), 2.40 (s, 3H), 4.04 (q, J=7.0 Hz, 2H), 5.04 (s, 2H), 6.58 (d, J=0.6 Hz, 1H), 6.89-6.93 (m, 3H), 7.23-7.29 (m, 1H), 7.36 (d, J=8.7 Hz, 2H).

Reference Example 58

1-(5-bromo-1-benzothiophen-2-yl)ethanol

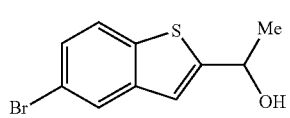

Using 1-(5-bromo-1-benzothiophen-2-yl)ethanone (1.29 g, 5.06 mmol), an operation in the same manner as in Reference Example 52 was performed to give the title compound (1.17 g, yield 90%) as an oil.

¹H NMR (CDCl₃) δ 1.65 (d, J=6.4 Hz, 3H), 2.08 (d, J=4.7 Hz, 1H), 5.16-5.24 (m, 1H), 7.12 (s, 1H), 7.39 (dd, J=8.5, 1.9 Hz, 1H), 7.66 (d, J=8.5 Hz, 1H), 7.85 (d, J=1.9 Hz, 1H).

Reference Example 59

2-(1-azidoethyl)-5-bromo-1-benzothiophene

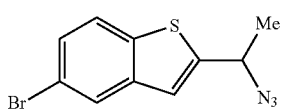 [SMILES: CC(N=[N+]=[N-])c1cc2cc(Br)ccc2s1]

Using 1-(5-bromo-1-benzothiophen-2-yl)ethanol (1.17 g, 4.55 mmol) obtained in Reference Example 58, an operation in the same manner as in Reference Example 28 was performed to give the title compound (1.23 g, yield 95%) as an oil.

¹H NMR (CDCl₃) δ 1.67 (d, J=6.8 Hz, 3H), 4.88 (q, J=6.8 Hz, 1H), 7.16 (s, 1H), 7.43 (dd, J=8.7, 1.9 Hz, 1H), 7.67 (d, J=8.7 Hz, 1H), 7.88 (d, J=1.9 Hz, 1H).

Reference Example 60 tert-butyl [1-(5-bromo-1-benzothiophen-2-yl)ethyl]carbamate

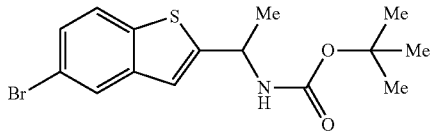 [SMILES: CC(NC(=O)OC(C)(C)C)c1cc2cc(Br)ccc2s1]

Using 2-(1-azidoethyl)-5-bromo-1-benzothiophene (1.23 g, 4.36 mmol) obtained in Reference Example 59, an operation in the same manner as in Reference Example 29 was performed to give the title compound (1.13 g, yield 72%) as a white solid.

¹H NMR (CDCl₃) δ 1.46 (s, 9H), 1.60 (d, J=6.8 Hz, 3H), 4.86 (br, 1H), 5.12 (br, 1H), 7.08 (s, 1H), 7.38 (dd, J=8.7, 1.9 Hz, 1H), 7.63 (d, J=8.7 Hz, 1H), 7.83 (d, J=1.9 Hz, 1H).

Reference Example 61 methyl 2-{1-[(tert-butoxycarbonyl)amino]ethyl}-1-benzothiophene-5-carboxylate

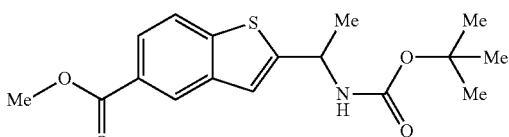

To a solution of tert-butyl [1-(5-bromo-1-benzothiophen-2-yl)ethyl]carbamate (1.13 g, 3.18 mmol) obtained in Reference Example 60 in DMF (10 mL)-methanol (6 mL) were added triethylamine (0.887 mL, 6.36 mmol) and [1,1'-bis(diphenylphosphino)ferrocene]palladium(II) dichloride dichloromethane complex (1:1) (260 mg, 0.318 mmol), and the mixture was stirred under a carbon monooxide atmosphere (normal pressure) at 80° C. for 15 hr. The reaction mixture was diluted with ethyl acetate, and the mixture was washed three times with saturated brine, and dried over anhydrous magnesium sulfate. The solvent was evaporated under reduced pressure and the obtained residue was purified by silica gel column chromatography (hexane:ethyl acetate=17:3 to 1:1) to give the title compound (854 mg, yield 80%) as a white solid.

$^1$H NMR (CDCl$_3$) δ 1.46 (s, 9H), 1.62 (d, J=6.8 Hz, 3H), 3.95 (s, 3H), 4.89 (br, 1H), 5.14 (br, 1H), 7.22 (s, 1H), 7.81 (d, J=8.3 Hz, 1H), 7.95 (dd, J=8.3, 1.5 Hz, 1H), 8.40 (d, J=1.5 Hz, 1H).

Reference Example 62 tert-butyl {1-[5-(hydroxymethyl)-1-benzothiophen-2-yl]ethyl}carbamate

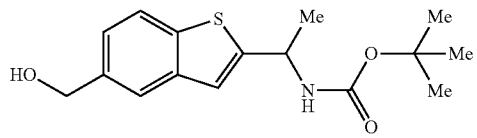 [SMILES: CC(NC(=O)OC(C)(C)C)c1cc2cc(CO)ccc2s1]

Using methyl 2-{1-[(tert-butoxycarbonyl)amino]ethyl}-1-benzothiophene-5-carboxylate (854 mg, 2.55 mmol) obtained in Reference Example 61, an operation in the same manner as in Reference Example 30 was performed to give the title compound (534 mg, yield 68%).

$^1$H NMR (CDCl$_3$) δ 1.46 (s, 9H), 1.60 (d, J=6.8 Hz, 3H), 4.78 (d, J=5.7 Hz, 2H), 4.87 (br, 1H), 5.12 (br, 1H), 7.14 (s, 1H), 7.30 (d, J=8.3 Hz, 1H), 7.69 (s, 1H), 7.76 (d, J=8.3 Hz, 1H).

Reference Example 63

1-(5-bromo-4-methyl-1-benzofuran-2-yl)ethanone

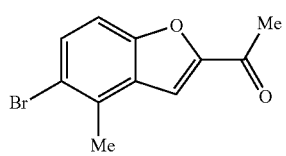 [SMILES: CC(=O)c1cc2c(C)c(Br)ccc2o1]

Using 3-bromo-6-hydroxy-2-methylbenzaldehyde (560 mg, 2.60 mmol), an operation in the same manner as in Reference Example 51 was performed to give the title compound (425 mg, yield 65%) as a yellow solid.

$^1$H NMR (CDCl$_3$) δ 2.59 (s, 3H), 2.62 (s, 3H), 7.30 (d, J=8.7 Hz, 1H), 7.52 (s, 1H), 7.61 (d, J=8.7 Hz, 1H).

Reference Example 64

1-(5-bromo-4-methyl-1-benzofuran-2-yl)ethanol

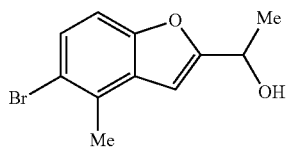 [SMILES: Cc1c(Br)ccc2oc(C(C)O)cc12]

Using 1-(5-bromo-4-methyl-1-benzofuran-2-yl)ethanone (425 mg, 1.68 mmol) obtained in Reference Example 63, an operation in the same manner as in Reference Example 52 was performed to give the title compound (359 mg, yield 83%) as an oil.

$^1$H NMR (CDCl$_3$) δ 1.64 (d, J=6.6 Hz, 3H), 2.53 (s, 3H), 4.97-5.05 (m, 1H), 6.63 (s, 1H), 7.17 (d, J=8.7 Hz, 1H), 7.41 (d, J=8.7 Hz, 1H).

Reference Example 65

2-(1-azidoethyl)-5-bromo-4-methyl-1-benzofuran

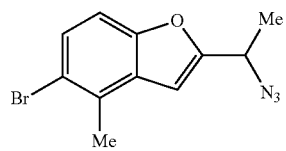 [SMILES: Cc1c(Br)ccc2oc(C(C)N=[N+]=[N-])cc12]

Using 1-(5-bromo-4-methyl-1-benzofuran-2-yl)ethanol (359 mg, 1.41 mmol) obtained in Reference Example 64, an operation in the same manner as in Reference Example 28 was performed to give the title compound (342 mg, yield 87%) as an oil.

$^1$H NMR (CDCl$_3$) δ 1.66 (d, J=6.8 Hz, 3H), 2.54 (s, 3H), 4.69 (q, J=6.8 Hz, 1H), 6.67 (s, 1H), 7.19 (d, J=8.7 Hz, 1H), 7.44 (d, J=8.7 Hz, 1H).

Reference Example 66 tert-butyl [1-(5-bromo-4-methyl-1-benzofuran-2-yl)ethyl]carbamate

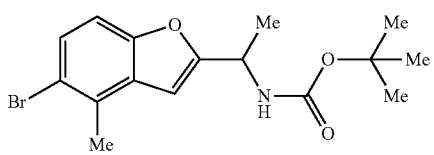 [SMILES: Cc1c(Br)ccc2oc(C(C)NC(=O)OC(C)(C)C)cc12]

Using 2-(1-azidoethyl)-5-bromo-4-methyl-1-benzofuran (342 mg, 1.22 mmol) obtained in Reference Example 65, an operation in the same manner as in Reference Example 29 was performed to give the title compound (392 mg, yield 90%) as an oil.

¹H NMR (CDCl₃) δ 1.46 (s, 9H), 1.55 (d, J=6.8 Hz, 3H), 2.51 (s, 3H), 4.87 (br, 1H), 4.99 (br, 1H), 6.55 (s, 1H), 7.14 (d, J=8.7 Hz, 1H), 7.39 (d, J=8.7 Hz, 1H).

Reference Example 67 methyl 2-{1-[(tert-butoxycarbonyl)amino]ethyl}-4-methyl-1-benzofuran-5-carboxylate

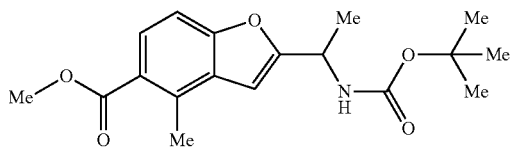 [SMILES: COC(=O)c1ccc2oc(C(C)NC(=O)OC(C)(C)C)cc2c1C]

Using tert-butyl [1-(5-bromo-4-methyl-1-benzofuran-2-yl)ethyl]carbamate (392 mg, 1.11 mmol) obtained in Reference Example 66, an operation in the same manner as in Reference Example 61 was performed to give the title compound (370 mg, quantitative) as an oil.

¹H NMR (CDCl₃) δ 1.46 (s, 9H), 1.56 (d, J=6.8 Hz, 3H), 2.74 (s, 3H), 3.90 (s, 3H), 4.89 (br, 1H), 5.02 (br, 1H), 6.66 (s, 1H), 7.26-7.30 (m, 1H), 7.88 (d, J=8.7 Hz, 1H).

Reference Example 68 tert-butyl {1-[5-(hydroxymethyl)-4-methyl-1-benzofuran-2-yl]ethyl}carbamate

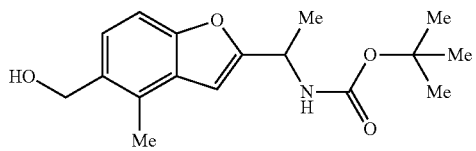 [SMILES: Cc1c(CO)ccc2oc(C(C)NC(=O)OC(C)(C)C)cc12]

Using methyl 2-{1-[(tert-butoxycarbonyl)amino]ethyl}-4-methyl-1-benzofuran-5-carboxylate (377 mg, 1.14 mmol) obtained in Reference Example 67, an operation in the same manner as in Reference Example was performed to give the title compound (177 mg, yield 51%) as an oil.

¹H NMR (CDCl₃) δ 1.46 (s, 9H), 1.55 (d, J=5.3 Hz, 3H), 2.51 (s, 3H), 4.77 (d, J=5.7 Hz, 2H), 4.89 (br, 1H), 5.01 (br, 1H), 6.58 (s, 1H), 7.22-7.28 (m, 2H).

Reference Example 69 methyl 5-[(4-ethoxyphenyl)ethynyl]-2-(methoxymethoxy)benzoate

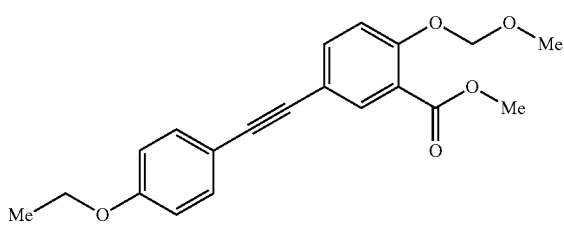 [SMILES: CCOc1ccc(C#Cc2ccc(OCOC)c(C(=O)OC)c2)cc1]

Using methyl 2-hydroxy-5-iodobenzoate (2.78 g, 10.0 mmol), an operation in the same manner as in Reference Example 47 was performed to give the title compound (880 mg, yield 26%) as a yellow solid.

¹H NMR (CDCl₃) δ 1.42 (t, J=7.0 Hz, 3H), 3.52 (s, 3H), 3.90 (s, 3H), 4.05 (q, J=7.0 Hz, 2H), 5.27 (s, 2H), 6.86 (d, J=8.7 Hz, 2H), 7.17 (d, J=8.7 Hz, 1H), 7.43 (d, J=8.7 Hz, 2H), 7.56 (dd, J=8.7, 2.3 Hz, 1H), 7.94 (d, J=2.3 Hz, 1H).

Reference Example 70

{5-[2-(4-ethoxyphenyl)ethyl]-2-(methoxymethoxy)phenyl}methanol

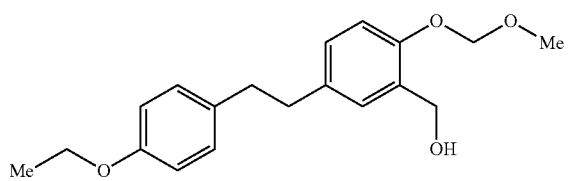 [SMILES: CCOc1ccc(CCc2ccc(OCOC)c(CO)c2)cc1]

Using methyl 5-[(4-ethoxyphenyl)ethynyl]-2-(methoxymethoxy)benzoate (880 mg, 2.59 mmol) obtained in Reference Example 69, an operation in the same manner as in Reference Example 48 was performed to give the title compound (756 mg, yield 92%) as an oil.

¹H NMR (CDCl₃) δ 1.40 (t, J=7.0 Hz, 3H), 2.79-2.85 (m, 4H), 3.49 (s, 3H), 4.01 (q, J=7.0 Hz, 2H), 4.68 (d, J=6.6 Hz, 2H), 5.21 (s, 2H), 6.81 (d, J=8.7 Hz, 2H), 6.99-7.14 (m, 5H).

Reference Example 71

5-[2-(4-ethoxyphenyl)ethyl]-2-(methoxymethoxy)benzaldehyde

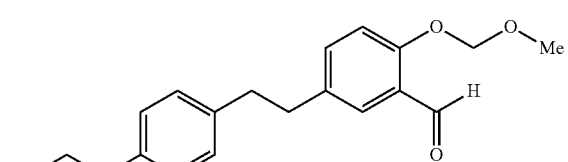

Using {5-[2-(4-ethoxyphenyl)ethyl]-2-(methoxymethoxy)phenyl}methanol (756 mg, 2.39 mmol) obtained in Reference Example 70, an operation in the same manner as in Reference Example 49 was performed to give the title compound (580 mg, yield 77%) as an oil.

¹H NMR (CDCl₃) δ 1.40 (t, J=7.0 Hz, 3H), 2.80-2.88 (m, 4H), 3.52 (s, 3H), 4.01 (q, J=7.0 Hz, 2H), 5.27 (s, 2H), 6.81 (d,

J=8.7 Hz, 2H), 7.06 (d, J=8.7 Hz, 2H), 7.11 (d, J=1.1 Hz, 1H), 7.29 (dd, J=8.7, 2.3 Hz, 1H), 7.67 (d, J=2.3 Hz, 1H), 10.48 (d, J=0.6 Hz, 1H)

Reference Example 72

5-[2-(4-ethoxyphenyl)ethyl]-2-hydroxybenzaldehyde

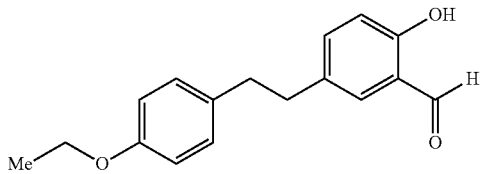 [SMILES: CCOc1ccc(CCc2ccc(O)c(C=O)c2)cc1]

Using 5-[2-(4-ethoxyphenyl)ethyl]-2-(methoxymethoxy)benzaldehyde (580 mg, 1.85 mmol) obtained in Reference Example 71, an operation in the same manner as in Reference Example 50 was performed to give the title compound (492 mg, yield 98%) as a white solid.

$^1$H NMR (CDCl$_3$) δ 1.40 (t, J=7.0 Hz, 3H), 2.80-2.91 (m, 4H), 4.00 (q, J=7.0 Hz, 2H), 6.80 (d, J=8.7 Hz, 2H), 6.89 (d, J=8.3 Hz, 1H), 7.02 (d, J=8.7 Hz, 2H), 7.25-7.31 (m, 2H), 9.82 (s, 1H), 10.86 (s, 1H).

Reference Example 73

1-{5-[2-(4-ethoxyphenyl)ethyl]-1-benzofuran-2-yl}ethanone

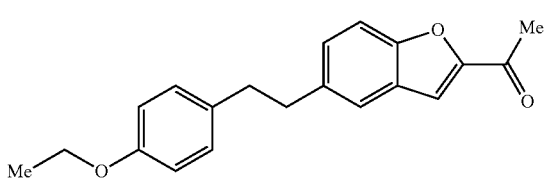 [SMILES: CCOc1ccc(CCc2ccc3oc(C(C)=O)cc3c2)cc1]

Using 5-[2-(4-ethoxyphenyl)ethyl]-2-hydroxybenzaldehyde (492 mg, 1.82 mmol) obtained in Reference Example 72, an operation in the same manner as in Reference Example 51 was performed to give the title compound (480 mg, yield 85%) as a yellow solid.

$^1$H NMR (CDCl$_3$) δ 1.40 (t, J=7.0 Hz, 3H), 2.60 (s, 3H), 2.86-2.92 (m, 2H), 2.96-3.02 (m, 2H), 4.01 (q, J=7.0 Hz, 2H), 6.80 (d, J=8.7 Hz, 2H), 7.05 (d, J=8.7 Hz, 2H), 7.25-7.29 (m, 1H), 7.43-7.49 (m, 3H)

Reference Example 74

1-{5-[2-(4-ethoxyphenyl)ethyl]-1-benzofuran-2-yl}ethanol

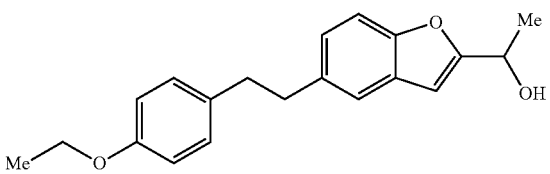

Using 1-{5-[2-(4-ethoxyphenyl)ethyl]-1-benzofuran-2-yl}ethanone (480 mg, 1.56 mmol) obtained in Reference Example 73, an operation in the same manner as in Reference Example 52 was performed to give the title compound (369 mg, yield 76%) as an oil.

$^1$H NMR (CDCl$_3$) δ 1.40 (t, J=7.0 Hz, 3H), 1.63 (d, J=6.4 Hz, 3H), 2.03 (br, 1H), 2.84-2.90 (m, 2H), 2.93-2.99 (m, 2H), 4.01 (q, J=7.0 Hz, 2H), 5.00 (br, 1H), 6.54 (s, 1H), 6.80 (d, J=8.7 Hz, 2H), 7.05-7.10 (m, 3H), 7.31 (d, J=1.5 Hz, 1H), 7.35 (d, J=8.3 Hz, 1H).

Reference Example 75

2-(1-azidoethyl)-5-[2-(4-ethoxyphenyl)ethyl]-1-benzofuran

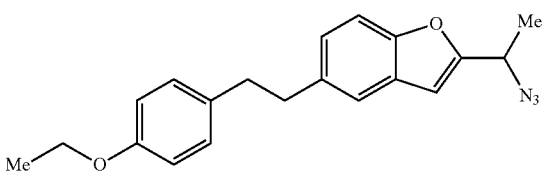

Using 1-{5-[2-(4-ethoxyphenyl)ethyl]-1-benzofuran-2-yl}ethanol (369 mg, 1.19 mmol) obtained in Reference Example 74, an operation in the same manner as in Reference Example 28 was performed to give the title compound (400 mg, quantitative) as an oil.

$^1$H NMR (CDCl$_3$) δ 1.40 (t, J=7.0 Hz, 3H), 1.65 (d, J=7.0 Hz, 3H), 2.85-2.90 (m, 2H), 2.94-3.00 (m, 2H), 4.01 (q, J=7.0 Hz, 2H), 4.67 (q, J=7.0 Hz, 1H), 6.60 (s, 1H), 6.81 (d, J=8.7 Hz, 2H), 7.06-7.11 (m, 3H), 7.32 (d, J=1.3 Hz, 1H), 7.37 (d, J=8.7 Hz, 1H).

Reference Example 76

2-ethylhexyl 3-{[4-(benzyloxy)-2-nitrophenyl]sulfanyl}propanoate

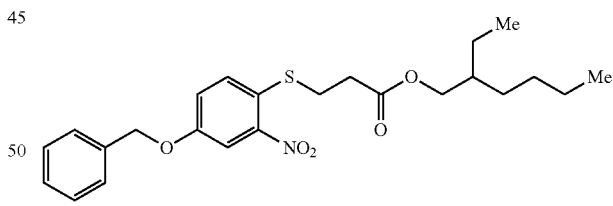

A suspension of 4-(benzyloxy)-1-chloro-2-nitrobenzene (5.00 g, 19.0 mmol), 2-ethylhexyl 3-sulfanylpropanoate (4.55 g, 20.9 mmol) and potassium carbonate (3.93 g, 28.4 mmol) in DMF (20 mL) was stirred under heating at 60° C. for 16 hr. The reaction mixture was diluted with ethyl acetate, and the mixture was washed with water, 10% aqueous potassium carbonate solution and saturated brine, and dried over anhydrous sodium sulfate. The solvent was evaporated under reduced pressure, and the obtained residue was purified by silica gel column chromatography (hexane:ethyl acetate=19:1 to 3:1) to give the title compound (5.67 g, yield 67%) as an oil.

$^1$H NMR (CDCl$_3$) δ 0.86-0.91 (m, 6H), 1.23-1.40 (m, 8H), 1.55-1.59 (m, 1H), 2.67 (t, J=7.5 Hz, 2H), 3.20 (t, J=7.5 Hz,

2H), 4.02 (m, 2H), 5.10 (s, 2H), 7.20 (dd, J=2.7 9.0 Hz, 1H), 7.33-7.43 (m, 6H), 7.73 (d, J=2.7 Hz, 1H).

Reference Example 77

2-ethylhexyl 3-{[2-amino-4-(benzyloxy)phenyl]sulfanyl}propanoate

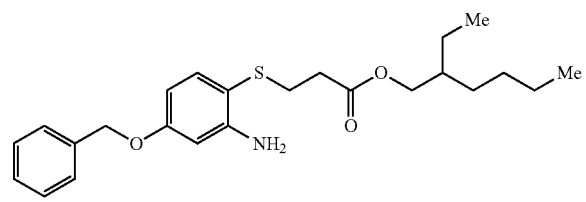 [SMILES: CCCCC(CC)COC(=O)CCSc1ccc(OCc2ccccc2)cc1[N+](=O)[O-]]

A solution of 2-ethylhexyl 3-{[4-(benzyloxy)-2-nitrophenyl]sulfanyl}propanoate (5.66 g, 12.7 mmol) obtained in Reference Example 76 in acetic acid (10 mL) was added dropwise under ice-cooling to a solution (66 mL) of zinc powder (8.31 g, 127 mmol) in 90% aqueous acetic acid over 30 min, and the mixture was stirred for 1 hr. The reaction mixture was filtered through celite, and the filtrate was concentrated under reduced pressure. The obtained residue was diluted with ethyl acetate, and the mixture was washed with 10% aqueous potassium carbonate solution and saturated brine, and dried over anhydrous sodium sulfate. The solution was applied to basic silica gel column chromatography (ethyl acetate) to give the title compound (5.28 g, quantitative) as an oil.

$^1$H NMR (CDCl$_3$) δ 0.86-0.91 (m, 6H), 1.23-1.40 (m, 8H), 1.54-1.58 (m, 1H), 2.53 (t, J=7.2 Hz, 2H), 2.89 (t, J=7.2 Hz, 2H), 3.99 (m, 2H), 4.42 (s, 2H), 5.01 (s, 2H), 6.31-6.35 (m, 2H), 7.26-7.42 (m, 6H).

Reference Example 78

2-ethylhexyl 3-({2-[(N-acetylalanyl)amino]-4-(benzyloxy)phenyl}sulfanyl)propanoate

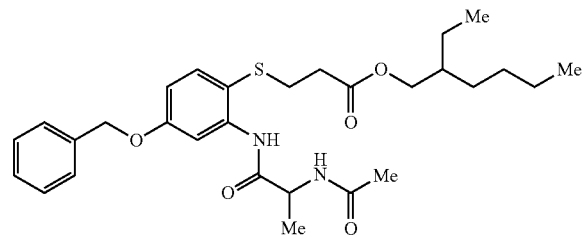 [SMILES: CCCCC(CC)COC(=O)CCSc1ccc(OCc2ccccc2)cc1NC(=O)C(C)NC(C)=O]

To a solution of 2-ethylhexyl 3-{[2-amino-4-(benzyloxy)phenyl]sulfanyl}propanoate (1.00 g, 2.41 mmol) obtained in Reference Example 77, N-acetyl-D,L-alanine (347 mg, 2.65 mmol), 1-hydroxybenzotriazole (358 mg, 2.65 mmol) and 4,4-dimethylaminopyridine (294 mg, 2.65 mmol) in DMF (3 mL) was added 1-ethyl-3-(3-dimethylaminopropyl)carbodiimide hydrochloride (507 mg, 2.65 mmol), and the mixture was stirred at room temperature for 16 hr. The reaction mixture was diluted with ethyl acetate, and the mixture was washed with 1N hydrochloric acid, 10% aqueous potassium carbonate solution and saturated brine, and dried over anhydrous sodium sulfate. This solution was applied to basic silica gel column chromatography (ethyl acetate). The solvent was evaporated under reduced pressure, and the obtained residue was purified by silica gel column chromatography (hexane:ethyl acetate=3:1 to 1:3) to give the title compound (812 mg, yield 64%) as an oil.

$^1$H NMR (CDCl$_3$) δ 0.86-0.91 (m, 6H), 1.28-1.40 (m, 8H), 1.50-1.59 (m, 4H), 2.07 (s, 3H), 2.52 (t, J=6.9 Hz, 2H), 2.89 (t, J=6.9 Hz, 2H), 4.01 (d, J=5.7 Hz, 2H), 4.75 (m, 1H), 5.07 (s, 2H), 6.36 (br, 1H), 6.68 (dd, J=2.7, 8.4 Hz, 1H), 7.32-7.45 (m, 6H), 8.24 (d, J=2.7 Hz, 1H), 9.22 (s, 1H).

Reference Example 80

N-[1-(5-hydroxy-1,3-benzothiazol-2-yl)ethyl]acetamide

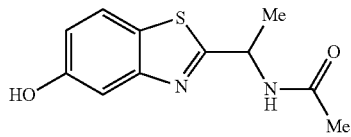

A suspension of N-{1-[5-(benzyloxy)-1,3-benzothiazol-2-yl]ethyl}acetamide (257 mg, 0.787 mmol) obtained in the below-mentioned Example 102 and 10% palladium carbon (50% water-containing product, 500 mg) in THF (7 mL) was stirred under a hydrogen atmosphere for 1 hr. The reaction mixture was filtered through celite. The solvent was evaporated under reduced pressure, 10% palladium carbon (50% water-containing product, 2.0 g) and THF (30 mL) were added again thereto, and the mixture was stirred under a hydrogen atmosphere for 16 hr. The reaction mixture was filtered through celite. The solvent was evaporated under reduced pressure, and the obtained residue was purified by silica gel column chromatography (hexane:ethyl acetate=1:1 to ethyl acetate), and triturated with ethyl acetate to give the title compound (10.5 mg, yield 5.6%).

$^1$H NMR (DMSO-d$_6$) δ 1.52 (d, J=6.9 Hz, 3H), 1.90 (s, 3H), 5.19 (m, 1H), 6.89 (dd, J=2.1, 8.7 Hz, 1H), 7.25 (d, J=2.1 Hz, 1H), 7.77 (d, J=8.7 Hz, 1H), 8.70 (d, J=7.2 Hz, 1H), 9.63 (s, 1H).

Reference Example 81 methyl 3-({3-[(2-ethylhexyl)oxy]-3-oxopropyl}sulfanyl)-4-nitrobenzoate

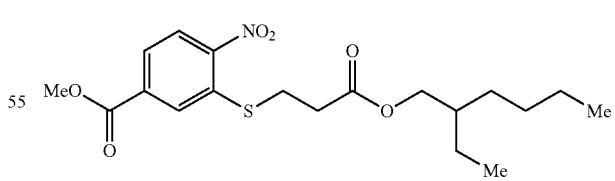

Methyl 3-fluoro-4-nitrobenzoate (8.72 g, 43.8 mmol) was added to a suspension of 2-ethylhexyl 3-sulfanylpropanoate (10.5 g, 48.2 mmol) and potassium carbonate (9.08 g, 65.7 mmol) in DMF (50 mL) at room temperature, and the mixture was stirred for 16 hr. The reaction mixture was diluted with ethyl acetate, and the mixture was washed with water, 10% aqueous potassium carbonate solution and saturated brine, and dried over anhydrous sodium sulfate. The solvent was evaporated under reduced pressure, and the obtained residue was purified by silica gel column chromatography (hexane:ethyl acetate=9:1 to 7:3) to give the title compound (14.4 g, yield 83%).

¹H NMR (CDCl₃) δ 0.87-0.92 (m, 6H), 1.24-1.38 (m, 8H), 1.57-1.59 (m, 1H), 2.75 (t, J=7.2 Hz, 2H), 3.33 (t, J=7.2 Hz, 2H), 3.98 (s, 3H), 4.06 (m, 2H), 7.88 (dd, J=1.8 8.4 Hz, 1H), 8.09 (d, J=1.8 Hz, 1H), 8.22 (d, J=8.4 Hz, 1H).

Reference Example 82 methyl 4-amino-3-({3-[(2-ethylhexyl)oxy]-3-oxopropyl}sulfanyl)benzoate

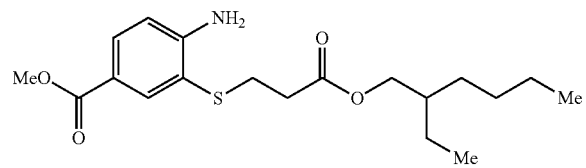 [SMILES: CCCCC(CC)COC(=O)CCSc1cc(C(=O)OC)ccc1N]

Using methyl 3-({3-[(2-ethylhexyl)oxy]-3-oxopropyl}sulfanyl)-4-nitrobenzoate (13.4 g, 33.7 mmol) obtained in Reference Example 81 and zinc powder (22.1 g, 337 mmol) and in the same manner as in Reference Example 77, the title compound (12.4 g, quantitative) was obtained.

¹H NMR (CDCl₃) δ 0.86-0.91 (m, 6H), 1.23-1.40 (m, 8H), 1.53-1.63 (m, 1H), 2.56 (t, J=7.2 Hz, 2H), 2.99 (t, J=7.2 Hz, 2H), 3.85 (s, 3H), 3.99 (m, 2H), 4.87 (s, 2H), 6.69 (d, J=8.4 Hz, 1H), 7.80 (dd, J=1.8, 8.4 Hz, 1H), 8.08 (d, J=1.8 Hz, 1H).

Reference Example 83 methyl 4-[(N-acetylalanyl)amino]-3-({3-[(2-ethylhexyl)oxy]-3-oxopropyl}sulfanyl)benzoate

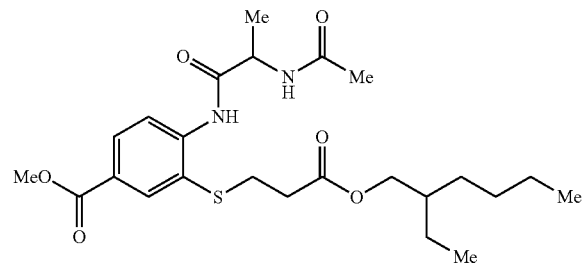 [SMILES: CCCCC(CC)COC(=O)CCSc1cc(C(=O)OC)ccc1NC(=O)C(C)NC(C)=O]

To a solution of N-(tert-butoxycarbonyl)-D,L-alanine (1.70 g, 8.98 mmol) and triethylamine (1.25 mL, 8.98 mmol) in THF (10 mL) was added 2-methylpropyl chlorocarbonate (1.16 mL, 8.98 mmol) under ice-cooling, and the mixture was stirred for 30 min. To this solution was added a solution of methyl 4-amino-3-({3-[(2-ethylhexyl)oxy]-3-oxopropyl}sulfanyl)benzoate (3.00 g, 8.16 mmol) obtained in Reference Example 82 in THF (4 mL) under a nitrogen atmosphere, and the mixture was heated under reflux at 80° C. for 16 hr. After being allowed to cool to room temperature, the reaction mixture was diluted with ethyl acetate, and the mixture was washed with 0.5N hydrochloric acid, 10% aqueous potassium carbonate solution and saturated brine, and dried over anhydrous sodium sulfate. This solution was applied to basic silica gel column chromatography (ethyl acetate). The solvent was evaporated under reduced pressure, and the obtained residue was purified by silica gel column chromatography (hexane:ethyl acetate=19:1 to 7:3) to give methyl 4-{[N-(tert-butoxycarbonyl)alanyl]amino}-3-({3-[(2-ethylhexyl)oxy]-3-oxopropyl}sulfanyl)benzoate (1.66 g). To the obtained oil (1.66 g, 3.08 mmol) was added trifluoroacetic acid (15 mL), and the mixture was stirred for 10 min. The reaction mixture was concentrated under reduced pressure. Ethyl acetate was added to the residue, and the mixture was washed with 10% aqueous potassium carbonate solution and saturated brine, and dried over anhydrous sodium sulfate. The solvent was evaporated under reduced pressure to give methyl 4-(alanylamino)-3-({3-[(2-ethylhexyl)oxy]-3-oxopropyl}sulfanyl)benzoate (1.32 g). To a solution of this oil (1.32 g, 3.01 mmol) in ethyl acetate (15 mL) was added acetic anhydride (0.437 mL, 4.62 mmol) at room temperature and the mixture was stirred for 30 min. The solvent was evaporated under reduced pressure, and the residue was dissolved in ethyl acetate. The solution was purified by basic silica gel column chromatography (ethyl acetate) and the obtained residue was triturated with hexane to give the title compound (1.04 g, yield 70%).

¹H NMR (CDCl₃) δ 0.87-0.91 (m, 6H), 1.28-1.40 (m, 8H), 1.51-1.58 (m, 4H), 2.08 (s, 3H), 2.57 (t, J=6.9 Hz, 2H), 3.01 (t, J=6.9 Hz, 2H), 3.90 (s, 3H), 4.02 (m, 2H), 4.77 (m, 1H), 6.33 (d, J=8.1 Hz, 1H), 8.01 (dd, J=2.1, 8.7 Hz, 1H), 8.22 (d, J=2.1 Hz, 1H), 8.52 (d, J=8.7 Hz, 1H), 9.39 (s, 1H).

Reference Example 84 methyl 2-[1-(acetylamino)ethyl]-1,3-benzothiazole-6-carboxylate

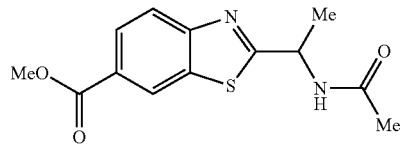

Using methyl 4-[(N-acetylalanyl)amino]-3-({3-[(2-ethylhexyl)oxy]-3-oxopropyl}sulfanyl)benzoate (1.03 g, 2.14 mmol) obtained in Reference Example 83, a method in the same manner as in the below-mentioned Example 102 was performed, and the obtained residue was triturated with diisopropyl ether to give the title compound (477 mg, yield 79%).

¹H NMR (CDCl₃) δ 1.69 (d, J=8.1 Hz, 3H), 2.10 (s, 3H), 3.96 (s, 3H), 5.51 (m, 1H), 6.39 (d, J=6.6 Hz, 1H), 7.99 (d, J=8.4 Hz, 1H), 8.14 (dd, J=1.8, 8.4 Hz, 1H), 8.57 (d, J=1.8 Hz, 1H).

Reference Example 85

N-{1-[6-(hydroxymethyl)-1,3-benzothiazol-2-yl]ethyl}acetamide

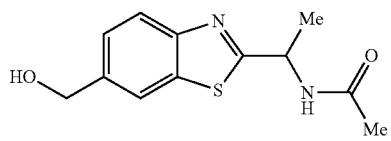

To a suspension of lithium aluminum hydride (59.6 mg, 1.57 mmol) in THF (7 mL) was added dropwise a solution of methyl 2-[1-(acetylamino)ethyl]-1,3-benzothiazole-6-carboxylate (220 mg, 0.785 mmol) obtained in Reference Example 84 in THF (5 mL) under ice-cooling, and the mixture was stirred for 30 min. After completion of the reaction, sodium sulfate decahydrate (760 mg) was slowly added thereto, and the mixture was filtered through celite. The filtrate was concentrated under reduced pressure, and the obtained residue was triturated with diisopropyl ether to give the title compound (142 mg, yield 73%).

$^1$H NMR (DMSO-$d_6$) δ 1.54 (d, J=7.2 Hz, 3H), 1.91 (s, 3H), 4.61 (d. J=5.7 Hz, 2H), 5.24 (m, 1H), 5.32 (t, J=5.7 Hz, 1H), 7.41 (dd, J=1.8, 8.4 Hz, 1H), 7.88 (d, J=8.4 Hz, 1H), 7.95 (d, J=1.8 Hz, 1H), 8.74 (d, J=8.1 Hz, 1H).

Reference Example 86 ethyl 2-acetyl-1-benzofuran-5-carboxylate

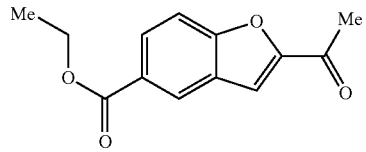 [SMILES: CCOC(=O)c1ccc2oc(C(C)=O)cc2c1]

To a solution of ethyl 3-formyl-4-hydroxybenzoate (4.00 g, 11.5 mmol) in acetonitrile (85 mL) were added bromoacetone (9.68 g, 64.1 mmol) and potassium carbonate (14.7 g, 106 mmol), and the mixture was stirred at 70° C. overnight. Water was added to the reaction mixture, and the mixture was extracted twice with ethyl acetate. The extract was washed with saturated brine, and dried over anhydrous magnesium sulfate. The solution was passed through silica gel. The solvent was evaporated under reduced pressure, and the obtained solid was washed with diisopropyl ether to give the title compound (6.59 g, yield 67%).

$^1$H NMR (CDCl$_3$) δ 1.43 (t, J=7.2 Hz, 3H), 2.64 (s, 3H), 4.42 (q, J=7.2 Hz, 2H), 7.56 (d, J=0.8 Hz, 1H), 7.62 (d, J=8.8 Hz, 1H), 8.20 (dd, J=8.8, 1.7 Hz, 1H), 8.47 (d, J=1.7 Hz, 1H).

Reference Example 87 ethyl 2-(1-hydroxyethyl)-1-benzofuran-5-carboxylate

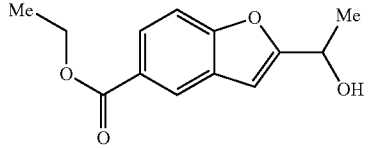 [SMILES: CCOC(=O)c1ccc2oc(C(C)O)cc2c1]

Using ethyl 2-acetyl-1-benzofuran-5-carboxylate (6.59 g, 28.4 mmol) obtained in Reference Example 86, methanol (56 mL) and sodium borohydride (2.09 g, 56.8 mmol), an operation in the same manner as in Reference Example 21 was performed to give the title compound (5.52 g, yield 83%).

$^1$H NMR (CDCl$_3$) δ 1.42 (t, J=7.1 Hz, 3H), 1.66 (d, J=6.6 Hz, 3H), 2.05-2.18 (m, 1H), 4.40 (q, J=7.2 Hz, 2H), 4.94-5.12 (m, 1H), 6.68 (s, 1H), 7.47 (d, J=8.7 Hz, 1H), 8.01 (dd, J=8.7, 1.7 Hz, 1H), 8.28 (d, J=1.7 Hz, 1H).

Reference Example 88 ethyl 2-(1-azidoethyl)-1-benzofuran-5-carboxylate

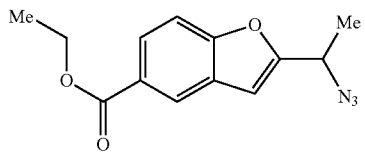 [SMILES: CCOC(=O)c1ccc2oc(C(C)N=[N+]=[N-])cc2c1]

Using ethyl 2-(1-hydroxyethyl)-1-benzofuran-5-carboxylate (5.52 g, 23.5 mmol) obtained in Reference Example 87, DMF (4.6 mL), methanesulfonyl chloride (2.7 mL, 35.3 mmol), triethylamine (6.9 mL, 47.0 mmol) and sodium azide (7.64 g, 117 mmol), an operation in the same manner as in Reference Example 22 was performed to give the title compound (4.34 g, yield 72%).

$^1$H NMR (CDCl$_3$) δ 1.42 (t, J=7.2 Hz, 3H), 1.68 (d, J=6.8 Hz, 3H), 4.40 (q, J=7.2 Hz, 2H), 4.71 (q, J=6.8 Hz, 1H), 6.73 (s, 1H), 7.50 (d, J=8.7 Hz, 1H), 8.04 (dd, J=8.7, 1.9 Hz, 1H), 8.31 (d, J=1.9 Hz, 1H).

Reference Example 89 ethyl 2-[1-(acetylamino)ethyl]-1-benzofuran-5-carboxylate

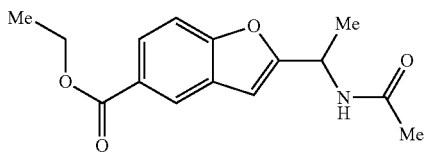 [SMILES: CCOC(=O)c1ccc2oc(C(C)NC(C)=O)cc2c1]

Using ethyl 2-(1-azidoethyl)-1-benzofuran-5-carboxylate (4.34 g, 16.7 mmol) obtained in Reference Example 88, THF (17 mL), water (1.7 mL); triphenylphosphine (6.58 g, 25.1 mmol), ethyl acetate (5 mL) and acetic anhydride (2.4 mL, 25.1 mmol), an operation in the same manner as in Reference Example 37 was performed to give the title compound (2.42 g, yield 53%).

$^1$H NMR (CDCl$_3$) δ 1.41 (t, J=7.2 Hz, 3H), 1.58 (d, J=7.0 Hz, 3H), 2.04 (s, 3H), 4.39 (q, J=7.2 Hz, 2H), 5.29-5.48 (m,

1H), 5.82 (br, 1H), 6.63 (s, 1H), 7.45 (d, J=8.7 Hz, 1H), 8.00 (dd, J=8.7, 1.7 Hz, 1H), 8.25 (d, J=1.7 Hz, 1H).

Reference Example 90

N-{1-[5-(hydroxymethyl)-1-benzofuran-2-yl]ethyl}acetamide

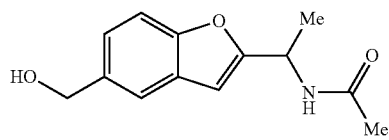

To a solution of ethyl 2-[1-(acetylamino)ethyl]-1-benzofuran-5-carboxylate (2.22 g, 9.52 mmol) obtained in Reference Example 89 in THF (32 mL) was added lithium aluminum hydride (722 mg, 19.0 mmol) at 0° C. After stirring at room temperature for 1 hr, water (0.056 mL), 15% aqueous sodium hydroxide solution (0.056 mL), water (0.17 mL) and celite were successively added, and the mixture was further stirred for 30 min at room temperature. The precipitate was removed by filtration, and the filtrate was concentrated under reduced pressure. The obtained solid was washed with diethyl ether to give the title compound (1.56 g, yield 70%).

$^1$H NMR (CDCl$_3$) δ 1.57 (d, J=7.0 Hz, 3H), 1.69 (br, 1H), 2.03 (s, 3H), 4.76 (s, 2H), 5.28-5.44 (m, 1H), 5.80 (br, 1H), 6.55 (s, 1H), 7.23-7.31 (m, 1H), 7.42 (d, J=8.5 Hz, 1H), 7.52 (d, J=1.1 Hz, 1H).

Reference Example 91 ethyl 5-methylfuro[3,2-b]pyridine-2-carboxylate

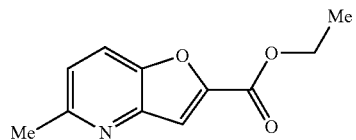 [SMILES: CCOC(=O)c1cc2nc(C)ccc2o1]

To a solution of 3-hydroxy-6-methylpyridine-2-carbaldehyde (4.92 mmol, 35.9 mmol) in DMF (70 mL) were added potassium carbonate (9.93 g, 71.8 mmol) and ethyl bromoacetate (5.97 mL, 53.9 mmol), and the mixture was stirred at 100° C. for 30 min. Water was added to the reaction mixture, and the mixture was extracted with ethyl acetate. The organic layer was washed with saturated brine, and dried over anhydrous magnesium sulfate. The solvent was evaporated and the obtained residue was purified by silica gel column chromatography (hexane:ethyl acetate=19:1 to 3:2) to give the title compound (2.36 g, yield 32%) as an oil.

$^1$H NMR (CDCl$_3$) δ 1.41-1.47 (m, 3H), 2.88-2.89 (m, 3H), 4.43-4.51 (m, 2H), 7.22-7.25 (m, 1H), 7.60 (br, 1H), 7.75-7.78 (m, 1H).

Reference Example 92 methyl 5-(hydroxymethyl)furo[3,2-b]pyridine-2-carboxylate

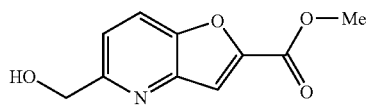 [SMILES: COC(=O)c1cc2nc(CO)ccc2o1]

To a solution of ethyl 5-methylfuro[3,2-b]pyridine-2-carboxylate (690 mg, 3.37 mmol) obtained in Reference Example 91 in methylene chloride (5 mL) was added 75% m-chloroperbenzoic acid (930 mg, 4.03 mmol), and the mixture was stirred at room temperature for 30 min. The reaction mixture was directly applied to basic silica gel chromatography (ethyl acetate), and the obtained crude product was dissolved in acetic anhydride (5 mL). This solution was stirred at 110° C. for 20 min. The solvent was evaporated under reduced pressure and the obtained residue was dissolved in methanol (10 mL), and potassium carbonate (932 mg, 6.73 mmol) was added thereto. The reaction mixture was stirred at room temperature for 15 min. Water was added thereto, and the mixture was extracted twice with ethyl acetate. The combined organic layer was dried over anhydrous magnesium sulfate. The solvent was evaporated and the obtained residue was purified by silica gel column chromatography (ethyl acetate) to give the title compound (242 mg, yield 35%) as a white solid.

$^1$H NMR (CDCl$_3$) δ 4.04 (s, 3H), 4.90 (s, 2H), 7.35 (d, J=8.7 Hz, 1H), 7.66 (s, 1H), 7.88 (d, J=8.7 Hz, 1H).

Reference Example 93 methyl 5-[(4-ethoxyphenoxy)methyl]furo[3,2-b]pyridine-2-carboxylate

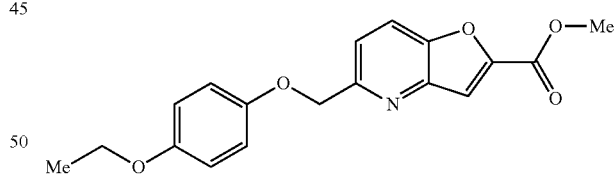

To a solution of methyl 5-(hydroxymethyl)furo[3,2-b]pyridine-2-carboxylate (242 mg, 1.17 mmol) obtained in Reference Example 92 in THF (10 mL) were added triethylamine (0.327 mL, 2.34 mmol) and methanesulfonyl chloride (0.136 mL, 1.75 mmol), and the mixture was stirred at room temperature for 10 min. To the reaction mixture was added saturated aqueous sodium hydrogen carbonate solution, the mixture was extracted with ethyl acetate, and the organic layer was dried over anhydrous magnesium sulfate. The solvent was evaporated, to a solution of the obtained residue in DMF (5 mL) were added 4-ethoxyphenol (242 mg, 1.75 mmol) and potassium carbonate (324 mg, 2.34 mmol), and the mixture was stirred at 60° C. for 30 min. Water was added to the reaction mixture, and the mixture was extracted with ethyl acetate. The extract was washed twice with saturated brine, and dried over anhydrous magnesium sulfate. The solvent was evaporated and the obtained residue was purified by silica gel column chromatography (ethyl acetate) to give the title compound (200 mg, yield 52%) as a white solid.

$^1$H NMR (CDCl$_3$) δ 1.38 (t, J=7.0 Hz, 3H), 3.97 (q, J=7.0 Hz, 2H), 4.02 (s, 3H), 5.26 (s, 2H), 6.81-6.85 (m, 2H), 6.90-6.95 (m, 2H), 7.64 (d, J=8.7 Hz, 1H), 7.67 (d, J=0.8 Hz, 1H), 7.89 (d, J=8.7 Hz, 1H).

Reference Example 94

5-[(4-ethoxyphenoxy)methyl]-N-methoxy-N-methyl-furo[3,2-b]pyridine-2-carboxamide

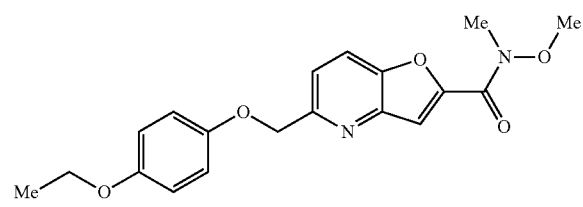 [SMILES: CCOc1ccc(OCc2ccc3oc(C(=O)N(C)OC)cc3n2)cc1]

To a solution of methyl 5-[(4-ethoxyphenoxy)methyl]furo[3,2-b]pyridine-2-carboxylate (200 mg, 0.611 mmol) obtained in Reference Example 93 in THF (5 mL)-methanol (3 mL) was added 1N aqueous sodium hydroxide solution (1.20 mL, 1.20 mmol), and the mixture was stirred at room temperature for 15 min. The reaction mixture was acidified with 1N hydrochloric acid, and the mixture was extracted twice with ethyl acetate, and the combined organic layer was dried over anhydrous magnesium sulfate. The solvent was evaporated, to a solution of the obtained residue in DMF (10 mL) were added N,O-dimethylhydroxylamine hydrochloride (89.4 mg, 0.917 mmol) and 1-ethyl-3-(3-dimethylaminopropyl)carbodiimide hydrochloride (176 mg, 0.917 mmol), triethylamine (0.128 mL, 0.917 mmol) and 4-dimethylaminopyridine (7.50 mg, 0.0611 mmol), and the mixture was stirred at room temperature for 2 hr. Water was added to the reaction mixture, and the mixture was extracted with ethyl acetate. The organic layer was washed twice with saturated brine and dried over anhydrous magnesium sulfate. The solvent was evaporated and the obtained residue was purified by silica gel column chromatography (hexane:ethyl acetate=3:2 to ethyl acetate) to give the title compound (178 mg, yield 82%) as a white solid.

$^1$H NMR (CDCl$_3$) δ 1.38 (t, J=7.0 Hz, 3H), 3.44 (s, 3H), 3.84 (3H, s), 3.97 (q, J=7.0 Hz, 2H), 5.26 (s, 2H), 6.81-6.85 (m, 2H), 6.90-6.94 (m, 2H), 7.61 (d, J=8.7 Hz, 1H), 7.66 (d, J=0.8 Hz, 1H), 7.90 (d, J=8.7 Hz, 1H).

Reference Example 95

1-{5-[(4-ethoxyphenoxy)methyl]furo[3,2-b]pyridin-2-yl}ethanol

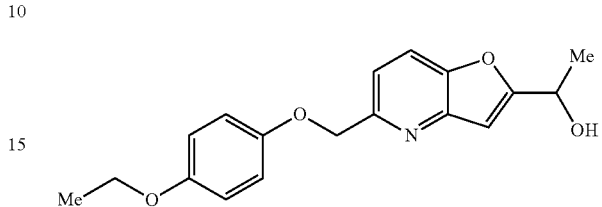

To a solution of 5-[(4-ethoxyphenoxy)methyl]-N-methoxy-N-methylfuro[3,2-b]pyridine-2-carboxamide (178 mg, 0.499 mmol) obtained in Reference Example 94 in THF (5 mL) was added 1.0 M methylmagnesium bromide THF solution (0.750 mL, 0.750 mmol), and the mixture was stirred at room temperature for 15 min. To the reaction mixture was added saturated aqueous ammonium solution, and the mixture was extracted twice with ethyl acetate. The combined organic layer was dried over anhydrous magnesium sulfate, the solvent was evaporated and the obtained residue was dissolved in THF (5 mL)-methanol (3 mL). To this solution was added sodium borohydride (18.9 mg, 0.449 mmol), and the mixture was stirred at room temperature for 15 min. To the reaction mixture was added saturated aqueous ammonium solution, and the mixture was extracted twice with ethyl acetate. The combined organic layer was dried over anhydrous magnesium sulfate, and the solvent was evaporated. The obtained residue was purified by silica gel column chromatography (hexane:ethyl acetate=7:3 to 1:4) to give the title compound (110 mg, yield 70%) as an oil.

$^1$H NMR (CDCl$_3$) δ 1.38 (t, J=7.0 Hz, 3H), 1.66 (d, J=6.4 Hz, 3H), 3.97 (q, J=7.0 Hz, 2H), 5.01-5.10 (m, 1H), 5.23 (s, 2H), 6.80-6.84 (m, 3H), 6.89-6.93 (m, 2H), 7.44 (d, J=8.7 Hz, 1H), 7.71 (d, J=8.7 Hz, 1H).

Reference Example 96

2-(1-azidoethyl)-5-[(4-ethoxyphenoxy)methyl]furo[3,2-b]pyridine

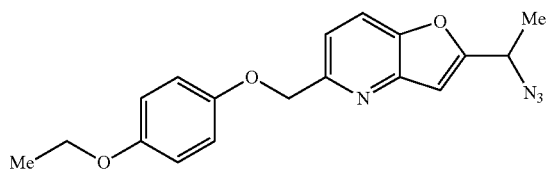 [SMILES: CCOc1ccc(OCc2ccc3oc(C(C)N=[N+]=[N-])cc3n2)cc1]

Using 1-{5-[(4-ethoxyphenoxy)methyl]furo[3,2-b]pyridin-2-yl}ethanol (110 mg, 0.351 mmol) obtained in Reference Example 95, an operation in the same manner as in Reference Example 28 was performed to give the title compound (118 mg, quantitative) as an oil.

$^1$H NMR (CDCl$_3$) δ 1.38 (t, J=7.0 Hz, 3H), 1.69 (d, J=6.8 Hz, 3H), 3.97 (q, J=7.2 Hz, 2H), 4.74 (q, J=6.9 Hz, 1H), 5.24

(s, 2H), 6.80-6.85 (m, 3H), 6.89-6.94 (m, 2H), 7.47 (d, J=8.7 Hz, 1H), 7.75 (d, J=8.7 Hz, 1H).

Reference Example 97 methyl 2-(methoxymethoxy)-4-[(4-propoxyphenyl)ethynyl]benzoate

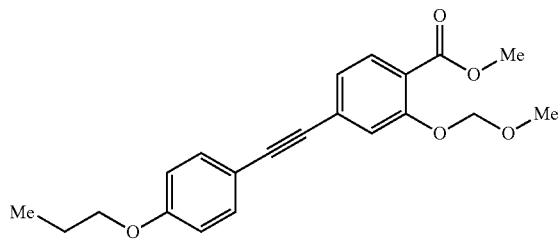 [SMILES: CCCOc1ccc(C#Cc2ccc(C(=O)OC)c(OCOC)c2)cc1]

Using methyl 2-hydroxy-4-iodobenzoate (4.63 g, 16.6 mmol) and 1-ethynyl-4-propoxybenzene (3.20 g, 20.0 mmol), an operation in the same manner as in Reference Example 47 was performed to give the title compound (5.85 g, yield 99%) as a yellow solid.

$^1$H NMR (CDCl$_3$) δ 1.04 (t, J=7.4 Hz, 3H), 1.76-1.88 (m, 2H), 3.54 (s, 3H), 3.90 (s, 3H), 3.94 (t, J=6.6 Hz, 2H), 5.28 (s, 2H), 6.88 (d, J=8.7 Hz, 2H), 7.17 (dd, J=8.1, 1.3 Hz, 1H), 7.33 (d, J=1.3 Hz, 1H), 7.46 (d, J=8.7 Hz, 2H), 7.76 (d, J=8.1 Hz, 1H).

Reference Example 98

{2-(methoxymethoxy)-4-[2-(4-propoxyphenyl)ethyl]phenyl}methanol

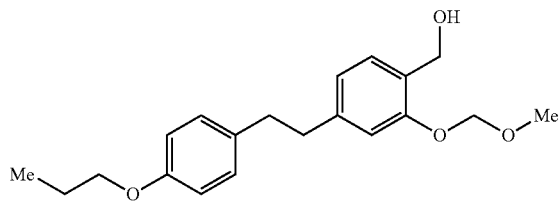 [SMILES: CCCOc1ccc(CCc2ccc(CO)c(OCOC)c2)cc1]

Using methyl 2-(methoxymethoxy)-4-[(4-propoxyphenyl)ethynyl]benzoate (5.85 g, 16.5 mmol) obtained in Reference Example 97, an operation in the same manner as in Reference Example 48 was performed to give the title compound (4.42 g, yield 81%) as a white solid.

$^1$H NMR (CDCl$_3$) δ 1.03 (t, J=7.4 Hz, 3H), 1.73-1.85 (m, 2H), 2.81-2.88 (m, 4H), 3.48 (s, 3H), 3.89 (t, J=6.6 Hz, 2H), 4.67 (d, J=6.4 Hz, 2H), 5.19 (s, 2H), 6.80-6.84 (m, 3H), 6.89 (d, J=1.1 Hz, 1H), 7.07 (d, J=8.7 Hz, 2H), 7.20 (d, J=7.6 Hz, 1H).

Reference Example 99

2-(methoxymethoxy)-4-[2-(4-propoxyphenyl)ethyl]benzaldehyde

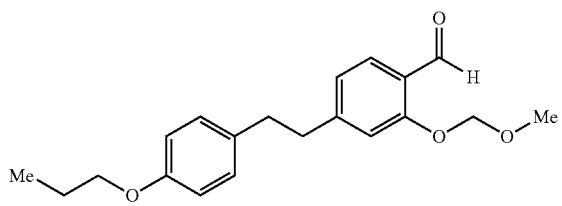 [SMILES: CCCOc1ccc(CCc2ccc(C=O)c(OCOC)c2)cc1]

Using {2-(methoxymethoxy)-4-[2-(4-propoxyphenyl)ethyl]phenyl}methanol (4.42 g, 13.4 mmol) obtained in Reference Example 98, an operation in the same manner as in Reference Example 49 was performed to give the title compound (3.90 g, yield 89%) as an oil.

$^1$H NMR (CDCl$_3$) δ 1.03 (t, J=7.0 Hz, 3H), 1.74-1.85 (m, 2H), 2.82-2.95 (m, 4H), 3.51 (s, 3H), 3.89 (t, J=6.6 Hz, 2H), 5.24 (s, 2H), 6.81 (d, J=8.7 Hz, 2H), 6.89 (d, J=7.9 Hz, 1H), 6.94 (d, J=1.1 Hz, 1H), 7.04 (d, J=8.7 Hz, 2H), 7.75 (d, J=7.9 Hz, 1H), 10.43 (d, J=0.6 Hz, 1H).

Reference Example 100

2-hydroxy-4-[2-(4-propoxyphenyl)ethyl]benzaldehyde

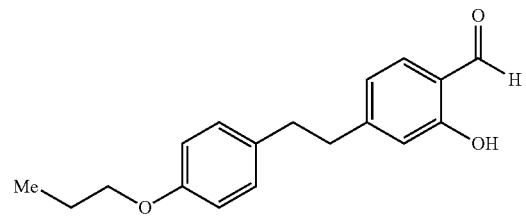 [SMILES: CCCOc1ccc(CCc2ccc(C=O)c(O)c2)cc1]

Using 2-(methoxymethoxy)-4-[2-(4-propoxyphenyl)ethyl]benzaldehyde (3.90 g, 11.9 mmol) obtained in Reference Example 99, an operation in the same manner as in Reference Example 50 was performed to give the title compound (3.21 g, yield 95%) as a yellow solid.

¹H NMR (CDCl₃) δ 1.03 (t, J=7.4 Hz, 3H), 1.74-1.85 (m, 2H), 2.82-2.94 (m, 4H), 3.89 (t, J=6.6 Hz, 2H), 6.78-6.84 (m, 4H), 7.05 (d, J=8.7 Hz, 2H), 7.43 (d, J=8.3 Hz, 1H), 9.83 (s, 1H), 11.03 (s, 1H).

Reference Example 101

1-{6-[2-(4-propoxyphenyl)ethyl]-1-benzofuran-2-yl}ethanone

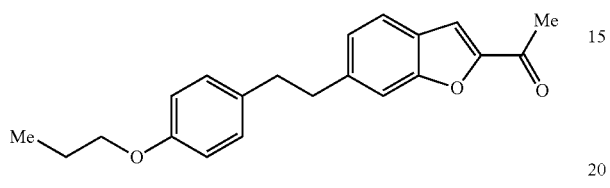

Using 2-hydroxy-4-[2-(4-propoxyphenyl)ethyl]benzaldehyde (3.21 g, 11.3 mmol) obtained in Reference Example 100, an operation in the same manner as in Reference Example 51 was performed to give the title compound (3.64 g, quantitative) as a yellow solid.

¹H NMR (CDCl₃) δ 1.03 (t, J=7.4 Hz, 3H), 1.74-1.85 (m, 2H), 2.59 (s, 3H), 2.88-2.94 (m, 2H), 3.00-3.05 (m, 2H), 3.89 (t, J=6.6 Hz, 2H), 6.81 (d, J=8.3 Hz, 2H), 7.06 (d, J=8.3 Hz, 2H), 7.13 (dd, J=8.1, 1.3 Hz, 1H), 7.34 (s, 1H), 7.46 (d, J=1.3 Hz, 1H), 7.59 (d, J=8.1 Hz, 1H).

Reference Example 102

1-[6-[2-(4-propoxyphenyl)ethyl]-1-benzofuran-2-yl]ethanol

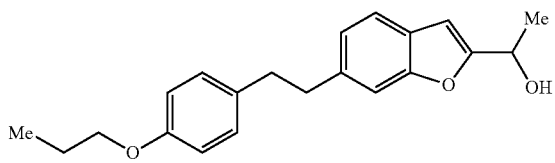

Using 1-[6-[2-(4-propoxyphenyl)ethyl]-1-benzofuran-2-yl]ethanone (3.64 g, 11.3 mmol) obtained in Reference Example 101, an operation in the same manner as in Reference Example 52 was performed to give the title compound (2.98 g, yield 81%) as a white solid.

¹H NMR (CDCl₃) δ 1.03 (t, J=7.4 Hz, 3H), 1.63 (d, J=6.6 Hz, 3H), 1.74-1.86 (m, 2H), 2.86-2.92 (m, 2H), 2.96-3.02 (m, 2H), 3.90 (t, J=6.6 Hz, 2H), 4.96-5.04 (m, 1H), 6.56 (s, 1H), 6.81 (d, J=8.7 Hz, 2H), 7.04 (dd, J=8.0, 1.4 Hz, 1H), 7.08 (d, J=8.7 Hz, 2H), 7.42 (d, J=8.0 Hz, 1H).

Reference Example 103

2-(1-azidoethyl)-6-[2-(4-propoxyphenyl)ethyl]-1-benzofuran

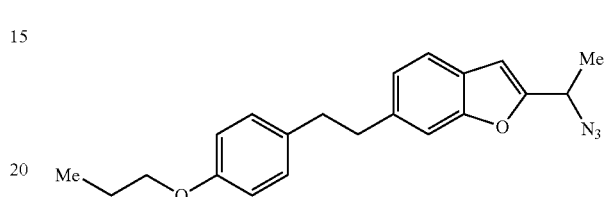

Using 1-{6-[2-(4-propoxyphenyl)ethyl]-1-benzofuran-2-yl}ethanol (1.08 g, 3.33 mmol) obtained in Reference Example 102, an operation in the same manner as in Reference Example 28 was performed to give the title compound (1.16 g, quantitative) as an oil.

¹H NMR (CDCl₃) δ 1.03 (t, J=7.4 Hz, 3H), 1.65 (d, J=6.8 Hz, 3H), 1.74-1.85 (m, 2H), 2.86-2.92 (m, 2H), 2.97-3.02 (m, 2H), 3.90 (t, J=6.6 Hz, 2H), 4.67 (q, J=6.8 Hz, 1H), 6.62 (s, 1H), 6.82 (d, J=8.3 Hz, 2H), 7.04-7.10 (m, 3H), 7.29 (s, 1H), 7.44 (d, J=8.0 Hz, 1H).

Reference Example 104

1-{6-[2-(4-propoxyphenyl)ethyl]-1-benzofuran-2-yl}ethanamine

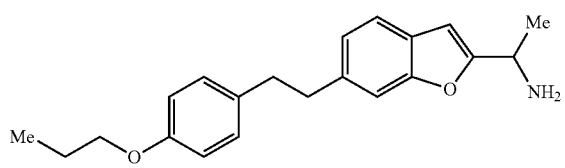 [SMILES: CCCOc1ccc(CCc2ccc3cc(C(C)N)oc3c2)cc1]

To a solution of 2-(1-azidoethyl)-6-[2-(4-propoxyphenyl)ethyl]-1-benzofuran (462 mg, 1.32 mmol) obtained in Reference Example 103 in THF (10 mL) was added triphenylphosphine (416 mg, 1.58 mmol), and the mixture was stirred at 60° C. for 30 min. To the reaction mixture was added water (0.5 mL), and the mixture was stirred at 60° C. for 15 hr. The solvent was evaporated under reduced pressure and the obtained residue was purified by basic silica gel column chromatography (hexane:ethyl acetate=4:1 to 2:3) to give the title compound (391 mg, yield 91%) as a white solid.

¹H NMR (CDCl₃) δ 1.03 (t, J=7.4 Hz, 3H), 1.51 (d, J=6.4 Hz, 3H), 1.74-1.85 (m, 2H), 2.86-2.91 (m, 2H), 2.96-3.01 (m, 2H), 3.90 (t, J=6.4 Hz, 2H), 4.18 (q, J=6.4 Hz, 1H), 6.44 (s,

1H), 6.81 (d, J=8.7 Hz, 2H), 7.02 (dd, J=8.0, 1.1 Hz, 1H), 7.09 (d, J=8.7 Hz, 2H), 7.24 (s, 1H), 7.39 (d, J=8.0 Hz, 1H).

Reference Example 105 methyl 3-{[N-(tert-butoxycarbonyl)alanyl]amino}-4-hydroxybenzoate

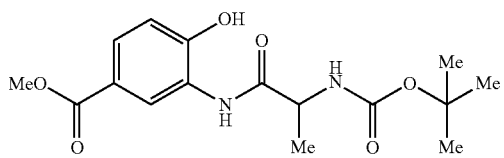

To a solution of N-(tert-butoxycarbonyl)-D,L-alanine (3.40 g, 17.9 mmol) and triethylamine (2.50 mL, 17.9 mmol) in THF (20 mL) was added 2-methylpropyl chlorocarbonate (2.33 mL, 17.9 mmol) under ice-cooling, and the mixture was stirred for 1 hr. To this solution was added dropwise a solution of methyl 3-amino-4-hydroxybenzoate (3.00 g, 17.9 mmol) in THF (10 mL) under a nitrogen atmosphere, and the mixture was stirred at room temperature for 3 days. The reaction mixture was diluted with ethyl acetate, and the mixture was washed with 0.5N hydrochloric acid and saturated brine, and dried over anhydrous sodium sulfate. The solvent was evaporated under reduced pressure, and the obtained residue was triturated with hexane-chloroform (1:1) to give the title compound (2.57 g, yield 42%).

$^1$H NMR (CDCl$_3$) δ 1.46-1.49 (m, 12H), 3.87 (s, 3H), 4.42 (m, 1H), 4.95 (d, J=7.2 Hz, 1H), 7.01 (d, J=8.4 Hz, 1H), 7.70 (d, J=1.8 Hz, 1H), 7.80 (dd, J=1.8, 8.4 Hz, 1H), 8.87 (br, 1H), 9.68 (s, 1H).

Reference Example 106 methyl 3-(alanylamino)-4-hydroxybenzoate hydrochloride

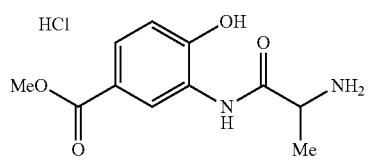 [SMILES: COC(=O)c1ccc(O)c(NC(=O)C(C)N)c1 ; Cl]

To methyl 3-{[N-(tert-butoxycarbonyl)alanyl]amino}-4-hydroxybenzoate (2.56 g, 7.57 mmol) obtained in Reference Example 105 was added 4N hydrogen chloride-ethyl acetate solution (40 mL), and the mixture was concentrated under reduced pressure 1 hr later. The obtained residue was triturated with diisopropyl ether to give the title compound (2.08 g, quantitative). This was used for the next step without purification.

Reference Example 107 methyl 3-[(N-acetylalanyl)amino]-4-hydroxybenzoate

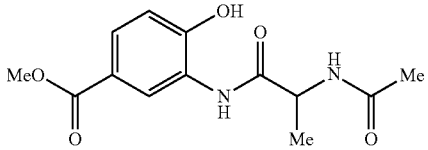 [SMILES: COC(=O)c1ccc(O)c(NC(=O)C(C)NC(C)=O)c1]

To a solution of methyl 3-(alanylamino)-4-hydroxybenzoate hydrochloride (2.08 g, 7.57 mmol) obtained in Reference Example 106 in DMF (20 mL) were added triethylamine (1.26 mL, 9.08 mmol) and acetic anhydride (0.715 mL, 7.57 mmol) under ice-cooling, and the mixture was stirred for 1 hr. The reaction mixture was diluted with ethyl acetate, and the mixture was washed with 1N hydrochloric acid saturated with sodium chloride and saturated brine, and dried over anhydrous sodium sulfate. The solvent was evaporated under reduced pressure, and the obtained residue was triturated with diisopropyl ether to give the title compound (1.82 g, yield 86%).

$^1$H NMR (CDCl$_3$) δ 1.49 (d, J=7.2 Hz, 3H), 2.12 (s, 3H), 3.87 (s, 3H), 4.83 (m, 1H), 6.12 (br, 1H), 7.00 (d, J=8.4 Hz, 1H), 7.79 (dd, J=2.1, 8.4 Hz, 1H), 7.84 (d, J=1.8 Hz, 1H), 9.36 (s, 1H), 9.73 (s, 1H).

Reference Example 108 methyl 2-[1-(acetylamino)ethyl]-1,3-benzoxazole-5-carboxylate

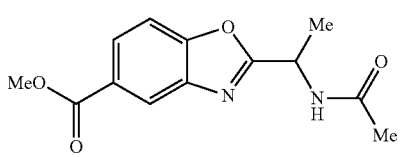 [SMILES: COC(=O)c1ccc2oc(C(C)NC(C)=O)nc2c1]

Using methyl 3-[(N-acetylalanyl)amino]-4-hydroxybenzoate (1.80 g, 6.42 mmol) obtained in Reference Example 107, a method in the same manner as in Reference Example 32 was performed, and the obtained residue was triturated with diisopropyl ether to give the title compound (269 mg, yield 16%).

¹H NMR (CDCl₃) δ 1.66 (d, J=6.9 Hz, 3H), 2.10 (s, 3H), 3.95 (s, 3H), 5.44 (m, 1H), 6.27 (d, J=7.2 Hz, 1H), 7.54 (d, J=8.4 Hz, 1H), 8.09 (dd, J=1.8, 8.4 Hz, 1H), 8.37 (d, J=1.8 Hz, 1H).

Reference Example 109

N-{1-[5-(hydroxymethyl)-1,3-benzoxazol-2-yl]ethyl}acetamide

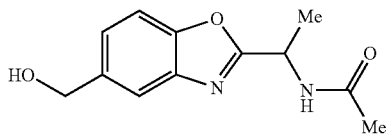 [SMILES: CC(=O)NC(C)c1nc2cc(CO)ccc2o1]

Using methyl 2-[1-(acetylamino)ethyl]-1,3-benzoxazole-5-carboxylate (267 mg, 1.02 mmol) obtained in Reference Example 108, a method in the same manner as in Reference Example 85 was performed, and the obtained residue was purified by preparative silica gel TLC (ethyl acetate) and triturated with diisopropyl ether to give the title compound (25.4 mg, yield 11%).

¹H NMR (DMSO-d₆) δ 1.50 (d, J=7.2 Hz, 3H), 1.88 (s, 3H), 4.58 (d, J=5.4 Hz, 2H), 5.16 (m, 1H), 5.27 (t, J=5.4 Hz, 1H), 7.31 (d, J=8.4 Hz, 1H), 7.60-7.63 (m, 2H), 8.60 (d, J=8.4 Hz, 1H).

Reference Example 110 methyl 4-({3-[(2-ethylhexyl)oxy]-3-oxopropyl}sulfanyl)-3-nitrobenzoate

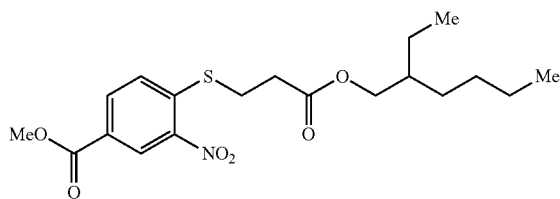 [SMILES: CCCCC(CC)COC(=O)CCSc1ccc(C(=O)OC)cc1[N+](=O)[O-]]

To a suspension of methyl 4-fluoro-3-nitrobenzoate (10.0 g, 50.2 mmol) and potassium carbonate (13.9 g, 100 mmol) in DMF (120 mL) was added dropwise under ice-cooling 2-ethylhexyl 3-sulfanylpropanoate (12.1 g, 55.2 mmol), and the mixture was stirred at room temperature for 3 hr. The reaction mixture was diluted with ethyl acetate, and the mixture was washed with water, 10% aqueous potassium carbonate solution and saturated brine, and dried over anhydrous sodium sulfate. This solution was applied to basic silica gel column chromatography (ethyl acetate). The solvent was evaporated under reduced pressure, and the obtained residue was purified by silica gel column chromatography (hexane:ethyl acetate=19:1 to 3:1) to give the title compound (20.0 g, quantitative).

¹H NMR (CDCl₃) δ 0.86-0.91 (m, 6H), 1.23-1.40 (m, 8H), 1.56-1.60 (m, 1H), 2.76 (t, J=7.5 Hz, 2H), 3.30 (t, J=7.5 Hz, 2H), 3.96 (s, 3H), 4.06 (m, 2H), 7.48 (d, J=8.4 Hz, 1H), 8.18 (m, 1H), 8.84 (m, 1H).

Reference Example 111 methyl 3-amino-4-({3-[(2-ethylhexyl)oxy]-3-oxopropyl}sulfanyl)benzoate

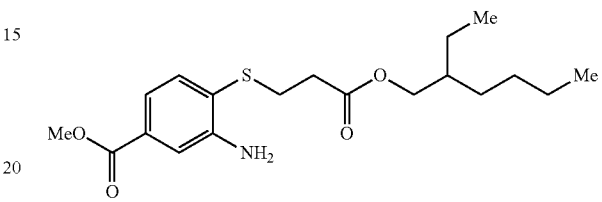

Using methyl 4-({3-[(2-ethylhexyl)oxy]-3-oxopropyl}sulfanyl)-3-nitrobenzoate (20.0 g, 50.2 mmol) obtained in Reference Example 110 and zinc powder (32.8 g, 502 mmol) and in the same manner as in Reference Example 77, the title compound (17.8 g, yield 96%) was obtained.

¹H NMR (CDCl₃) δ 0.86-0.91 (m, 6H), 1.24-1.40 (m, 8H), 1.52-1.58 (m, 1H), 2.56 (t, J=7.2 Hz, 2H), 3.06 (t, J=7.2 Hz, 2H), 3.88 (s, 3H), 3.98 (m, 2H), 4.42 (s, 2H), 7.31-7.40 (m, 3H).

Reference Example 112 methyl 3-[(N-acetylalanyl)amino]-4-({3-[(2-ethylhexyl)oxy]-3-oxopropyl}sulfanyl)benzoate

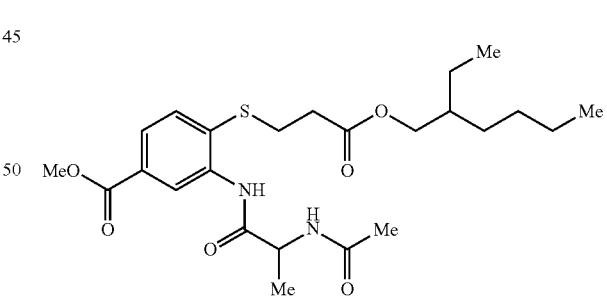

Using methyl 3-amino-4-({3-[(2-ethylhexyl)oxy]-3-oxopropyl}sulfanyl)benzoate (3.00 g, 8.16 mmol) obtained in Reference Example 111, a method in the same manner as in Reference Example 83 was performed, and the obtained residue was triturated with diisopropyl ether to give the title compound (2.88 g, yield from methyl 3-amino-4-({3-[(2-ethylhexyl)oxy]-3-oxopropyl}sulfanyl)benzoate 74%).

¹H NMR (CDCl₃) δ 0.86-0.91 (m, 6H), 1.28-1.39 (m, 8H), 1.50-1.59 (m, 4H), 2.08 (s, 3H), 2.58 (t, J=6.9 Hz, 2H), 3.07 (t, J=6.9 Hz, 2H), 3.91 (s, 3H), 4.02 (m, 2H), 4.75 (m, 1H), 6.25 (d, J=7.5 Hz, 1H), 7.56 (d, J=8.1 Hz, 1H), 7.75 (dd, J=1.8, 8.1 Hz, 1H), 8.52 (d, J=1.8 Hz, 1H), 8.98 (s, 1H).

Reference Example 113 methyl 2-[1-(acetylamino)ethyl]-1,3-benzothiazole-5-carboxylate

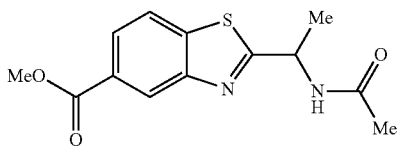

Using methyl 3-[(N-acetylalanyl)amino]-4-({3-[(2-ethylhexyl)oxy]-3-oxopropyl}sulfanyl)benzoate (2.87 g, 5.97 mmol) obtained in Reference Example 112, a method in the same manner as in the below-mentioned Example 102 was performed, and the obtained residue was triturated with diisopropyl ether to give the title compound (1.42 g, yield 85%).

$^1$H NMR (DMSO-$d_6$) δ 1.56 (d, J=7.2 Hz, 3H), 1.93 (s, 3H), 3.90 (s, 3H), 5.26 (m, 1H), 7.97 (dd, J=1.8, 8.1 Hz, 1H), 8.21 (d, J=8.1 Hz, 1H), 8.44 (d, J=1.8 Hz, 1H), 8.82 (d, J=7.2 Hz, 1H).

Reference Example 114

N-{1-[5-(hydroxymethyl)-1,3-benzothiazol-2-yl]ethyl}acetamide

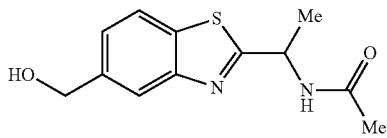

Using methyl 2-[1-(acetylamino)ethyl]-1,3-benzothiazole-5-carboxylate (500 mg, 1.80 mmol) obtained in Reference Example 113, a method in the same manner as in Reference Example 85 was performed, and the obtained residue was triturated with ethyl acetate to give the title compound (307 mg, yield 68%).

$^1$H NMR (DMSO-$d_6$) δ 1.54 (d, J=7.2 Hz, 3H), 1.91 (s, 3H), 4.62 (d, J=5.7 Hz, 2H), 5.23 (m, 1H), 5.31 (t, J=5.7 Hz, 1H), 7.36 (dd, J=1.5, 8.4 Hz, 1H), 7.85 (d, J=1.5 Hz, 1H), 7.97 (d, J=8.4 Hz, 1H), 8.75 (d, J=7.5 Hz, 1H).

Reference Example 115 ethyl 4-(benzyloxy)-2-(methoxymethoxy)-6-methylbenzoate

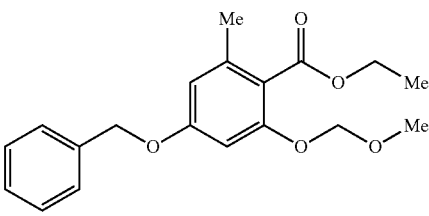 [SMILES: CCOC(=O)c1c(C)cc(OCc2ccccc2)cc1OCOC]

To a solution of ethyl 4-(benzyloxy)-2-hydroxy-6-methylbenzoate (15.0 g, 52.4 mmol) in DMF (100 mL) were added potassium carbonate (14.5 g, 105 mmol) and bromomethyl methyl ether (6.40 mL, 78.5 mmol), and the mixture was stirred at room temperature for 20 min. Water was added to the reaction mixture, and the mixture was extracted with ethyl acetate. The extract was washed twice with saturated brine, and dried over anhydrous magnesium sulfate. The solvent was evaporated under reduced pressure and the obtained residue was purified by silica gel column chromatography (hexane:ethyl acetate=19:1 to 4:1) to give the title compound (14.9 g, yield 86%) as a yellow solid.

$^1$H NMR (CDCl$_3$) δ 1.36 (t, J=7.4 Hz, 3H), 2.29 (s, 3H), 3.46 (s, 3H), 4.36 (q, J=7.2 Hz, 2H), 5.04 (s, 2H), 5.13 (s, 2H), 6.47 (d, J=2.2 Hz, 1H), 6.64 (d, J=2.2 Hz, 1H), 7.28-7.43 (m, 5H).

Reference Example 116 ethyl 4-hydroxy-2-(methoxymethoxy)-6-methylbenzoate

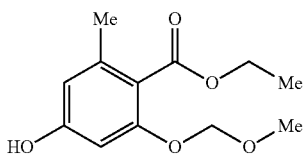 [SMILES: CCOC(=O)c1c(C)cc(O)cc1OCOC]

To a solution of ethyl 4-(benzyloxy)-2-(methoxymethoxy)-6-methylbenzoate (14.9 g, 45.1 mmol) obtained in Reference Example 115 in ethanol (100 mL) was added 10% palladium carbon (50% water-containing product, 13.0 g), and the mixture was stirred under a hydrogen atmosphere (normal pressure) for 30 min. After filtration, the solvent was evaporated under reduced pressure, and the obtained solid was washed with diethyl ether and hexane to give the title compound (8.09 g, yield 75%) as a white solid.

¹H NMR (CDCl₃) δ 1.36 (t, J=7.0 Hz, 3H), 2.26 (s, 3H), 3.46 (s, 3H), 4.37 (q, J=7.0 Hz, 2H), 5.13 (s, 2H), 6.31 (s, 1H), 6.48 (s, 1H).

Reference Example 117 ethyl 2-(methoxymethoxy)-6-methyl-4-{[(trifluoromethyl)sulfonyl]oxy}benzoate

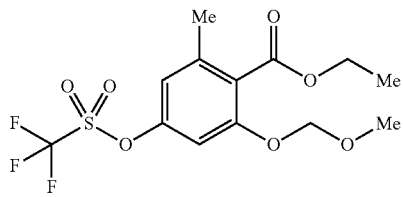 [SMILES: CCOC(=O)c1c(C)cc(OS(=O)(=O)C(F)(F)F)cc1OCOC]

To a solution of ethyl 4-hydroxy-2-(mathoxymethoxy)-6-methylbenzoate (3.00 g, 12.5 mmol) obtained in Reference Example 116 in THF (50 mL) were added triethylamine (3.50 mL, 25.0 mmol) and N-phenylbis(trifluoromethanesulfonimide) (7.70 g, 18.7 mmol), and the mixture was stirred at room temperature for 2 hr. The solvent was evaporated under reduced pressure and the obtained residue was purified by silica gel column chromatography (hexane:ethyl acetate=9:1 to 3:2) to give the title compound (4.33 g, yield 93%) as an oil.

¹H NMR (CDCl₃) δ 1.38 (t, J=7.2 Hz, 3H), 2.34 (s, 3H), 3.47 (s, 3H), 4.41 (q, J=7.2 Hz, 2H), 5.18 (s, 2H), 6.78 (d, J=1.9 Hz, 1H), 6.94 (d, J=1.9 Hz, 1H).

Reference Example 118 ethyl 4-[(4-ethoxyphenyl)ethynyl]-2-(methoxymethoxy)-6-methylbenzoate

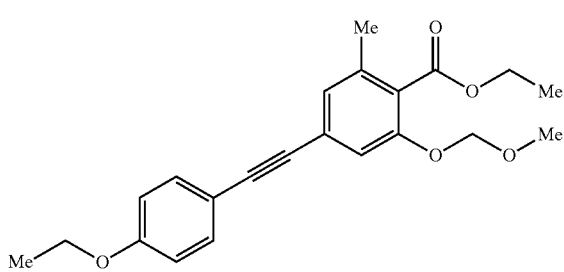 [SMILES: CCOC(=O)c1c(C)cc(C#Cc2ccc(OCC)cc2)cc1OCOC]

To a solution of ethyl 2-(methoxymethoxy)-6-methyl-4-{[(trifluoromethyl)sulfonyl]oxy}benzoate (2.17 g, 5.82 mmol) obtained in Reference Example 117, 1-ethoxy-4-ethynylbenzene (1.30 mL, 8.73 mmol) and copper(I) iodide (111 mg, 0.582 mmol) in triethylamine (14 mL) was added bis(triphenylphosphine)palladium(II) chloride (409 mg, 0.582 mmol), and the mixture was stirred under an argon stream 60° C. for 15 min. The reaction mixture was diluted with ethyl acetate, and the mixture was washed with water, and dried over anhydrous magnesium sulfate. The solvent was evaporated under reduced pressure and the obtained residue was purified by silica gel column chromatography (hexane:ethyl acetate=9:1 to 3:2) to give the title compound (1.89 g, yield 88%) as an oil.

¹H NMR (CDCl₃) δ 1.26 (t, J=7.2 Hz, 3H), 1.38 (t, J=7.2 Hz, 3H), 2.29 (s, 3H), 3.48 (s, 3H), 4.12 (q, J=7.2 Hz, 2H), 4.40 (q, J=7.2 Hz, 2H), 5.19 (s, 2H), 6.86 (d, J=8.9 Hz, 2H), 7.02 (s, 1H), 7.12 (s, 1H), 7.45 (d, J=8.9 Hz, 2H).

Reference Example 119

{4-[2-(4-ethoxyphenyl)ethyl]-2-(methoxymethoxy)-6-methylphenyl}methanol

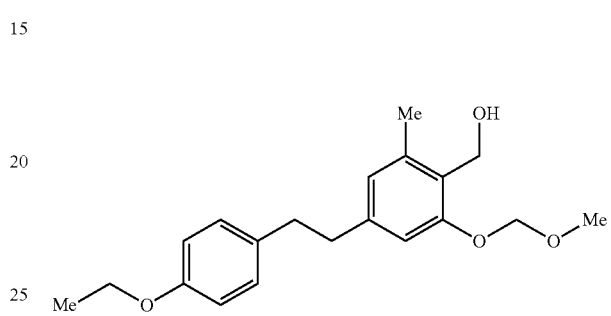

Using ethyl 4-[(4-ethoxyphenyl)ethynyl]-2-(methoxymethoxy)-6-methylbenzoate (1.89 g, 5.13 mmol) obtained in Reference Example 118, an operation in the same manner as in Reference Example 48 was performed to give the title compound (1.23 g, yield 72%) as an oil.

¹H NMR (CDCl₃) δ 1.40 (t, J=7.0 Hz, 3H), 2.38 (s, 3H), 2.79-2.85 (m, 4H), 3.49 (s, 3H), 4.01 (q, J=7.0 Hz, 2H), 4.72 (d, J=4.5 Hz, 2H), 5.17 (s, 2H), 6.72 (s, 1H), 6.75 (s, 1H), 6.81 (d, J=8.7 Hz, 2H), 7.08 (d, J=8.7 Hz, 2H).

Reference Example 120

4-[2-(4-ethoxyphenyl)ethyl]-2-(methoxymethoxy)-6-methylbenzaldehyde

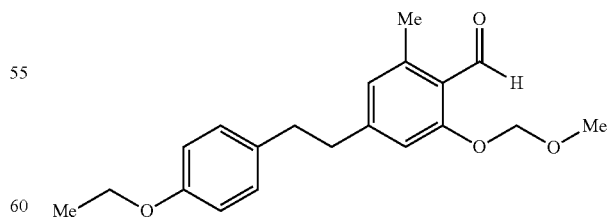

Using {4-[2-(4-ethoxyphenyl)ethyl]-2-(methoxymethoxy)-6-methylphenyl}methanol (1.23 g, 3.72 mmol) obtained in Reference Example 119, an operation in the same manner as in Reference Example 49 was performed to give the title compound (1.07 g, yield 87%) as an oil.

¹H NMR (CDCl₃) δ 1.40 (t, J=7.0 Hz, 3H), 2.55 (s, 3H), 2.81-2.87 (m, 4H), 3.50 (s, 3H), 4.01 (q, J=7.0 Hz, 2H), 5.21 (s, 2H), 6.69 (s, 1H), 6.80-6.84 (m, 3H), 7.06 (d, J=8.7 Hz, 2H), 10.61 (s, 1H).

Reference Example 121

4-[2-(4-ethoxyphenyl)ethyl]-2-hydroxy-6-methyl-benzaldehyde

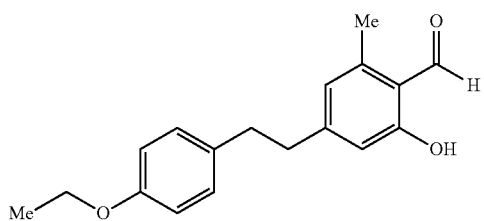 [SMILES: CCOc1ccc(CCc2cc(C)c(C=O)c(O)c2)cc1]

Using 4-[2-(4-ethoxyphenyl)ethyl]-2-(methoxymethoxy)-6-methylbenzaldehyde (1.07 g, 3.26 mmol) obtained in Reference Example 120, an operation in the same manner as in Reference Example 50 was performed to give the title compound (849 mg, yield 92%) as an oil.

¹H NMR (CDCl₃) δ 1.40 (t, J=7.0 Hz, 3H), 2.56 (s, 3H), 2.78-2.89 (m, 4H), 4.01 (q, J=7.0 Hz, 2H), 6.53 (s, 1H), 6.64 (s, 1H), 6.81 (d, J=8.7 Hz, 2H), 7.07 (d, J=8.7 Hz, 2H), 10.25 (s, 1H), 11.93 (s, 1H).

Reference Example 122

1-{6-[2-(4-ethoxyphenyl)ethyl]-4-methyl-1-benzofuran-2-yl}ethanone

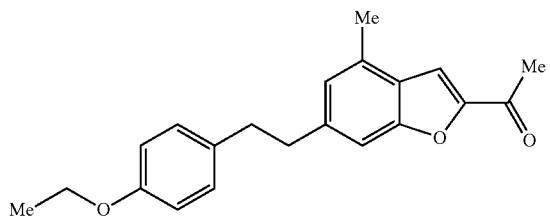 [SMILES: CCOc1ccc(CCc2cc(C)c3cc(C(C)=O)oc3c2)cc1]

Using 4-[2-(4-ethoxyphenyl)ethyl]-2-hydroxy-6-methylbenzaldehyde (849 mg, 2.99 mmol) obtained in Reference Example 121, an operation in the same manner as in Reference Example 51 was performed to give the title compound (964 mg, quantitative) as a yellow solid.

¹H NMR (CDCl₃) δ 1.40 (t, J=7.0 Hz, 3H), 2.52 (s, 3H), 2.59 (s, 3H), 2.86-2.92 (m, 2H), 2.95-3.01 (m, 2H), 4.01 (q, J=7.0 Hz, 2H), 6.80 (d, J=8.7 Hz, 2H), 6.94 (s, 1H), 7.07 (d, J=8.7 Hz, 2H), 7.17 (s, 1H), 7.50 (d, J=0.8 Hz, 1H).

Reference Example 123

1-{6-[2-(4-ethoxyphenyl)ethyl]-4-methyl-1-benzofuran-2-yl}ethanol

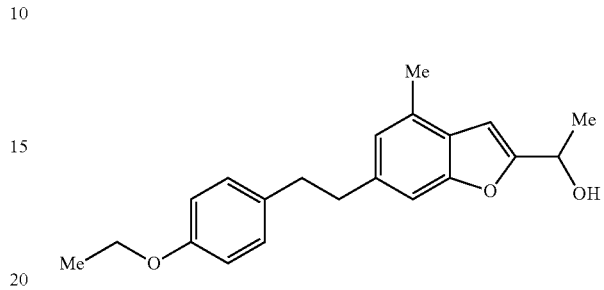

Using 1-{6-[2-(4-ethoxyphenyl)ethyl]-4-methyl-1-benzofuran-2-yl}ethanone (964 mg, 2.99 mmol) obtained in Reference Example 122, an operation in the same manner as in Reference Example 52 was performed to give the title compound (899 mg, yield 79%) as an oil.

¹H NMR (CDCl₃) δ 1.40 (t, J=7.0 Hz, 3H), 1.63 (d, J=6.4 Hz, 3H), 2.46 (s, 3H), 2.84-2.90 (m, 2H), 2.92-2.98 (m, 2H), 4.12 (q, J=7.0 Hz, 2H), 4.96-5.04 (m, 1H), 6.58 (s, 1H), 6.81 (d, J=8.3 Hz, 2H), 6.86 (s, 1H), 7.08-7.11 (m, 3H).

Reference Example 124

2-(1-azidoethyl)-6-[2-(4-ethoxyphenyl)ethyl]-4-methyl-1-benzofuran

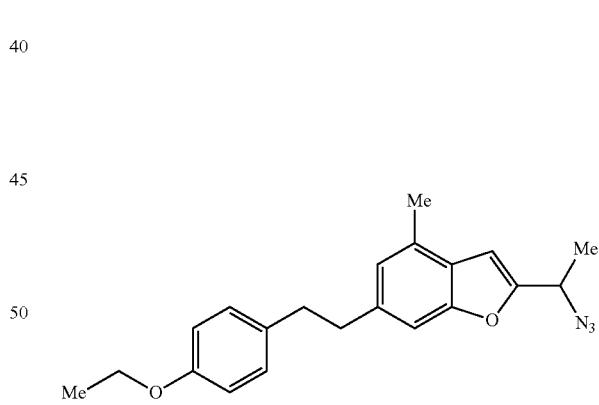

Using 1-{6-[2-(4-ethoxyphenyl)ethyl]-4-methyl-1-benzofuran-2-yl}ethanol (899 mg, 2.77 mmol) obtained in Reference Example 123, an operation in the same manner as in Reference Example 28 was performed to give the title compound (816 mg, yield 84%) as an oil.

¹H NMR (CDCl₃) δ 1.40 (t, J=7.0 Hz, 3H), 1.65 (d, J=6.8 Hz, 3H), 2.47 (s, 3H), 2.84-2.90 (m, 2H), 2.93-2.98 (m, 2H), 4.01 (q, J=7.0 Hz, 2H), 4.67 (q, J=7.0 Hz, 1H), 6.63 (s, 1H), 6.82 (d, J=8.5 Hz, 2H), 6.88 (s, 1H), 7.10 (d, J=8.7 Hz, 2H), 7.12 (s, 1H).

Reference Example 125 ethyl 5-hydroxy-1-benzothiophene-2-carboxylate

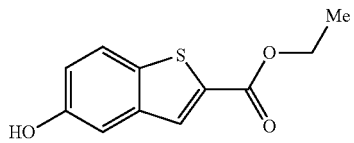 [SMILES: CCOC(=O)c1cc2cc(O)ccc2s1]

To a solution of ethyl 5-methoxy-1-benzothiophene-2-carboxylate (1.77 g, 7.49 mmol) in methylene chloride (15 mL) was added dropwise 1 M boron tribromide methylene chloride solution (22.5 mL, 22.5 mmol) at −20° C., and the mixture was stirred at the same temperature for 2 hr. The reaction mixture was poured into ice, and the mixture was extracted twice with ethyl acetate. The extract was washed with saturated brine, dried over anhydrous sodium sulfate, and the solution was passed through silica gel. The solvent was evaporated under reduced pressure, and the obtained solid was washed with hexane to give the title compound (1.53 g, yield 92%).

$^1$H NMR (CDCl$_3$) δ 1.41 (t, J=7.2 Hz, 3H), 4.40 (q, J=7.2 Hz, 2H), 5.01 (s, 1H), 7.05 (dd, J=8.8, 2.4 Hz, 1H), 7.22-7.33 (m, 1H), 7.71 (d, J=8.8 Hz, 1H), 7.93 (s, 1H).

Reference Example 126 ethyl 5-{[tert-butyl(dimethyl)silyl]oxy}-1-benzothiophene-2-carboxylate

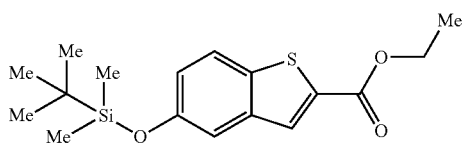 [SMILES: CCOC(=O)c1cc2cc(O[Si](C)(C)C(C)(C)C)ccc2s1]

Using ethyl 5-hydroxy-1-benzothiophene-2-carboxylate (1.53 g, 6.88 mmol) obtained in Reference Example 125, DMF (7 mL), tert-butyldimethylchlorosilane (1.35 g, 9.63 mmol) and imidazole (839 mg, 12.3 mmol), an operation in the same manner as in Reference Example 16 was performed to give the title compound (1.80 g, yield 78%).

$^1$H NMR (CDCl$_3$) δ 0.22 (s, 6H), 1.04 (s, 9H), 1.41 (t, J=7.2 Hz, 3H), 4.40 (q, J=7.2 Hz, 2H), 7.02 (dd, J=8.7, 2.5 Hz, 1H), 7.23-7.33 (m, 1H), 7.68 (d, J=8.7 Hz, 1H), 7.94 (s, 1H).

Reference Example 127

5-{[tert-butyl(dimethyl)silyl]oxy}-N-methoxy-N-methyl-1-benzothiophene-2-carboxamide

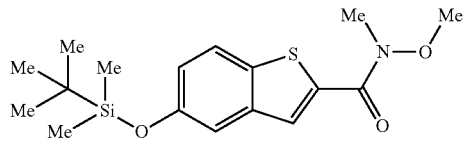 [SMILES: CON(C)C(=O)c1cc2cc(O[Si](C)(C)C(C)(C)C)ccc2s1]

Using ethyl 5-{[tert-butyl(dimethyl)silyl]oxy}-1-benzothiophene-2-carboxylate (1.80 g, 5.35 mmol) obtained in Reference Example 126, anhydrous THF (50 mL), N,O-dimethylhydroxylamine hydrochloride (2.61 g, 26.7 mmol) and 1.6 M n-butyllithium hexane solution (33 mL, 53.5 mmol), an operation in the same manner as in Reference Example 18 was performed to give the title compound (2.13 g, quantitative).

$^1$H NMR (CDCl$_3$) δ 0.23 (s, 6H), 1.03 (s, 9H), 3.41 (s, 3H), 3.82 (s, 3H), 7.00 (dd, J=8.7, 2.3 Hz, 1H), 7.29 (d, J=2.3 Hz, 1H), 7.68 (d, J=8.7 Hz, 1H), 8.08 (s, 1H).

Reference Example 128

1-(5-{[tert-butyl(dimethyl)silyl]oxy}-1-benzothiophen-2-yl)ethanone

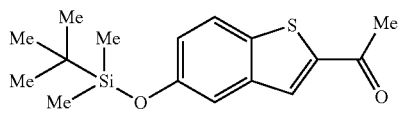

Using 5-{[tert-butyl(dimethyl)silyl]oxy}-N-methoxy-N-methyl-1-benzothiophene-2-carboxamide (2.13 g, 5.35 mmol) obtained in Reference Example 127, anhydrous THF (13 mL) and 1 M methylmagnesium bromide THF solution (10.7 mL, 10.7 mmol), an operation in the same manner as in Reference Example 19 was performed to give the title compound (2.54 g, quantitative).

$^1$H NMR (CDCl$_3$) δ 0.23 (s, 6H), 1.01 (s, 9H), 2.64 (s, 3H), 7.03 (dd, J=8.7, 2.3 Hz, 1H), 7.30 (d, J=2.3 Hz, 1H), 7.70 (d, J=8.7 Hz, 1H), 7.83 (s, 1H).

Reference Example 129

1-(5-{[tert-butyl(dimethyl)silyl]oxy}-1-benzothiophen-2-yl)ethanol

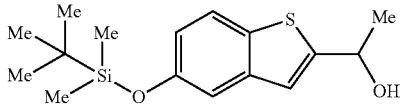 [SMILES: CC(O)c1cc2cc(O[Si](C)(C)C(C)(C)C)ccc2s1]

Using 1-(5-{[tert-butyl(dimethyl)silyl]oxy}-1-benzothiophen-2-yl)ethanone (2.54 g, 5.35 mmol) obtained in Reference Example 128, methanol (10.6 mL) and sodium borohydride (406 mg, 10.7 mmol), an operation in the same manner as in Reference Example 21 was performed to give the title compound (1.46 g, yield 89%).

$^1$H NMR (CDCl$_3$) δ 0.20 (s, 6H), 1.00 (s, 9H), 1.65 (d, J=6.4 Hz, 3H), 2.01 (d, J=4.7 Hz, 1H), 5.11-5.25 (m, 1H), 6.86 (dd, J=8.7, 2.3 Hz, 1H), 7.08 (s, 1H), 7.15 (d, J=2.3 Hz, 1H), 7.62 (d, J=8.7 Hz, 1H).

Reference Example 130

{[2-(1-azidoethyl)-1-benzothiophen-5-yl]oxy}(tert-butyl)dimethylsilane

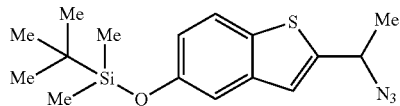

Using 1-(5-{[tert-butyl(dimethyl)silyl]oxy}-1-benzothiophen-2-yl)ethanol (1.46 g, 4.74 mmol) obtained in Reference Example 129, DMF (10 mL), methanesulfonyl chloride (0.547 mL, 7.11 mmol), triethylamine (1.41 mL, 9.48 mmol) and sodium azide (1.54 mg, 23.7 mmol), an operation in the same manner as in Reference Example 22 was performed to give the title compound (2.10 g) as an oil.

$^1$H NMR (CDCl$_3$) δ 0.21 (s, 6H), 1.00 (s, 9H), 1.66 (d, J=6.7 Hz, 3H), 4.86 (q, J=6.7 Hz, 1H), 6.86-6.93 (m, 1H), 7.12 (s, 1H), 7.17 (d, J=2.3 Hz, 1H), 7.63 (d, J=8.7 Hz, 1H).

Reference Example 131

N-[1-(5-{[tert-butyl(dimethyl)silyl]oxy}-1-benzothiophen-2-yl)ethyl]acetamide

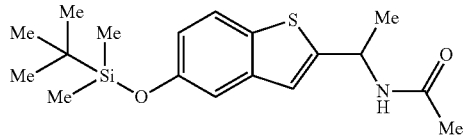 [SMILES: CC(=O)NC(C)c1cc2cc(O[Si](C)(C)C(C)(C)C)ccc2s1]

To a solution of {[2-(1-azidoethyl)-1-benzothiophen-5-yl]oxy}(tert-butyl)dimethylsilane (2.10 g, 4.74 mmol) obtained in Reference Example 130 in THF (10 mL) and water (1 mL) was added triphenylphosphine (polystyrene-supported, 1.84 mmol/g, 3.09 g, 5.68 mmol), and the mixture was heated under reflux overnight. The resin was filtered off, and the solvent was evaporated under reduced pressure. To the obtained residue were added ethyl acetate (5 mL) and acetic anhydride (0.42 mL, 4.54 mmol), and the mixture was stirred at room temperature for 10 min. The solvent was evaporated under reduced pressure, and the obtained residue was purified by silica gel column chromatography (hexane to hexane:ethyl acetate=3:7) to give the title compound (857 mg, yield from {[2-(1-azidoethyl)-1-benzothiophen-5-yl]oxy}(tert-butyl)dimethylsilane 52%) as an oil.

$^1$H NMR (CDCl$_3$) δ 0.20 (s, 6H), 1.00 (s, 9H), 1.56-1.66 (m, 3H), 1.98-2.03 (m, 3H), 5.32-5.55 (m, 1H), 5.75 (d, J=7.6 Hz, 1H), 6.86 (dd, J=8.7, 2.3 Hz, 1H), 7.04-7.10 (m, 1H), 7.13 (d, J=2.3 Hz, 1H), 7.59 (d, J=8.7 Hz, 1H).

Reference Example 132

N-[1-(5-hydroxy-1-benzothiophen-2-yl)ethyl]acetamide

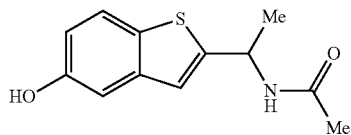

Using N-[1-(5-{[tert-butyl(dimethyl)silyl]oxy}-1-benzothiophen-2-yl)ethyl]acetamide (857 mg, 2.45 mmol) obtained in Reference Example 131, THF (5.0 mL) and 1M tetrabutylammonium fluoride THF solution (3.7 mL, 3.68 mmol) and an operation in the same manner as in Reference Example 38 was performed to give the title compound (412 mg, yield 72%) as a white solid.

$^1$H NMR (CDCl$_3$) δ 1.62 (d, J=6.8 Hz, 3H), 2.03 (s, 3H), 5.24 (br, 1H), 5.40-5.53 (m, 1H), 5.73 (br, 1H), 6.87 (dd, J=8.5, 2.5 Hz, 1H), 7.05 (s, 1H), 7.12 (d, J=2.7 Hz, 1H), 7.60 (d, J=8.5 Hz, 1H).

Reference Example 133

2-ethylhexyl 3-{[5-(benzyloxy)-2-nitrophenyl]sulfanyl}propanoate

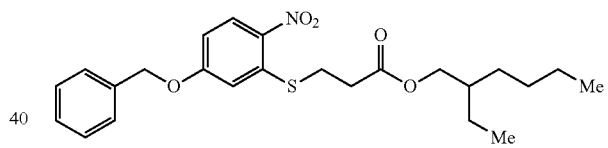

Using 4-(benzyloxy)-2-fluoro-1-nitrobenzene (10.3 g, 41.6 mmol) and 2-ethylhexyl 3-sulfanylpropanoate (10.0 g, 45.8 mmol) and in the same manner as in Reference Example 81, the title compound (18.6 g, quantitative) was obtained as an oil.

$^1$H NMR (CDCl$_3$) δ 0.86-0.91 (m, 6H), 1.23-1.40 (m, 8H), 1.54-1.60 (m, 1H), 2.70 (t, J=7.5 Hz, 2H), 3.16 (t, J=7.5 Hz, 2H), 4.05 (m, 2H), 5.17 (s, 2H), 6.79 (dd, J=2.4 9.3 Hz, 1H), 6.87 (d, J=2.4 Hz, 1H), 7.34-7.44 (m, 5H), 8.25 (d, J=9.3 Hz, 1H).

Reference Example 134

2-ethylhexyl 3-{[2-amino-5-(benzyloxy)phenyl]sulfanyl}propanoate

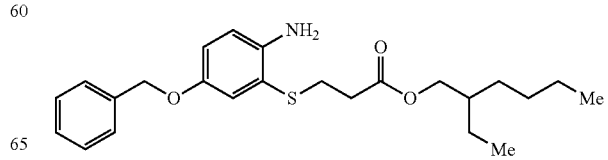

Using obtained in Reference Example 133 2-ethylhexyl 3-{([5-(benzyloxy)-2-nitrophenyl]sulfanyl}propanoate (18.6 g, 41.6 mmol) and zinc powder (27.2 g, 416 mmol) and in the same manner as in Reference Example 77, the title compound (14.5 g) was obtained as an oil. This was used for the next step without purification.

Reference Example 135

2-ethylhexyl 3-({2-[(N-acetylalanyl)amino]-5-(benzyloxy)phenyl}sulfanyl)propanoate

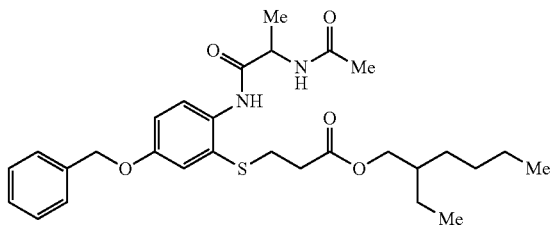 [SMILES: CCCCC(CC)COC(=O)CCSc1cc(OCc2ccccc2)ccc1NC(=O)C(C)NC(C)=O]

Using obtained in Reference Example 134 2-ethylhexyl 3-{[2-amino-5-(benzyloxy)phenyl]sulfanyl}propanoate (4.00 g, 9.62 mmol) and N-acetyl-D,L-alanine (1.26 g, 9.62 mmol) and in the same manner as in Reference Example 13, the title compound (2.24 g, yield 45%) was obtained as a solid.

$^1$H NMR (CDCl$_3$) δ 0.86-0.91 (m, 6H), 1.26-1.40 (m, 8H), 1.49-1.57 (m, 4H), 2.07 (s, 3H), 2.53 (t, J=6.9 Hz, 2H), 2.98 (t, J=6.9 Hz, 2H), 4.01 (m, 2H), 4.72 (m, 1H), 5.04 (s, 2H), 6.33 (br, 1H), 6.96 (dd, J=2.7, 9.0 Hz, 1H), 7.13 (d, J=2.7 Hz, 1H), 7.29-7.42 (m, 1H), 8.21 (d, J=9.0 Hz, 1H), 8.80 (s, 1H).

Reference Example 137

N-[1-(6-hydroxy-1,3-benzothiazol-2-yl)ethyl]acetamide

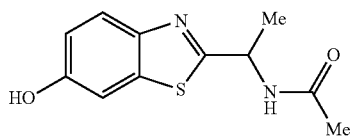

To a solution of N-{1-[6-(benzyloxy)-1,3-benzothiazol-2-yl]ethyl}acetamide (150 mg, 0.460 mmol) obtained in the below-mentioned Example 103 in trifluoroacetic acid (2 mL) was added thioanisole (0.2 mL), and the mixture was stirred under heating at 55° C. for 16 hr. The reaction mixture was concentrated under reduced pressure, and the obtained residue was purified by silica gel column chromatography (hexane:ethyl acetate=1:1 to ethyl acetate), and triturated with diisopropyl ether to give the title compound (76.0 mg, yield 70%).

$^1$H NMR (DMSO-d$_6$) δ 1.51 (d, J=7.2 Hz, 3H), 1.89 (s, 3H), 5.18 (m, 1H), 6.92 (dd, J=2.1, 8.7 Hz, 1H), 7.31 (d, J=2.1 Hz, 1H), 7.71 (d, J=8.7 Hz, 1H), 8.67 (d, J=7.8 Hz, 1H), 9.70 (s, 1H).

Reference Example 138 tert-butyl {2-[(2-hydroxy-5-methoxyphenyl)amino]-1-methyl-2-oxoethyl}carbamate

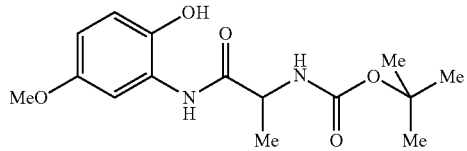 [SMILES: COc1ccc(O)c(NC(=O)C(C)NC(=O)OC(C)(C)C)c1]

Using 2-amino-4-methoxyphenol (3.00 g, 21.6 mmol) and N-(tert-butoxycarbonyl)-D,L-alanine (4.08 g, 21.6 mmol), a method in the same manner as in Reference Example 13 was performed, and the obtained residue was triturated with ethyl acetate to give the title compound (5.42 g, yield 81%).

$^1$H NMR (CDCl$_3$) δ 1.45-1.48 (m, 12H), 3.73 (s, 3H), 4.38 (m, 1H), 4.97 (m, 1H), 6.67-6.70 (m, 2H), 6.91 (d, J=9.3 Hz, 1H), 7.89 (s, 1H), 8.73 (br, 1H).

Reference Example 139

N-(2-hydroxy-5-methoxyphenyl)alaninamide hydrochloride

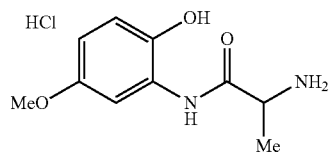 [SMILES: Cl ; COc1ccc(O)c(NC(=O)C(C)N)c1]

Using tert-butyl {2-[(2-hydroxy-5-methoxyphenyl)amino]-1-methyl-2-oxoethyl}carbamate (5.42 g, 17.5 mmol) obtained in Reference Example 138 and in the same manner as in Reference Example 20106, the title compound (4.31 g, quantitative) was obtained. This was used for the next step without purification.

Reference Example 140

N$^\alpha$-acetyl-N-(2-hydroxy-5-methoxyphenyl)alaninamide

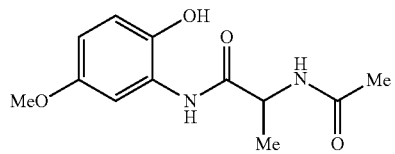 [SMILES: COc1ccc(O)c(NC(=O)C(C)NC(C)=O)c1]

Using N-(2-hydroxy-5-methoxyphenyl)alaninamide hydrochloride (4.31 g, 17.5 mmol) obtained in Reference Example 139 and acetic anhydride (1.65 mL, 17.5 mmol), a method in the same manner as in Reference Example 107 was performed, and the obtained residue was triturated with ethyl acetate to give the title compound (2.61 g, yield 59%).

¹H NMR (CDCl₃) δ 1.27 (d, J=6.9 Hz, 3H), 1.88 (s, 3H), 3.64 (s, 3H), 4.45 (m, 1H), 6.50 (dd, J=3.0, 8.7, 1H), 6.75 (d, J=8.7 Hz, 1H), 7.61 (d, J=3.0 Hz, 1H), 8.31 (d, J=7.2 Hz, 1H), 9.06 (s, 1H), 9.37 (s, 1H).

Reference Example 141

N-[1-(5-methoxy-1,3-benzoxazol-2-yl)ethyl]acetamide

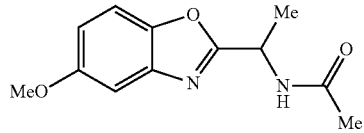 [SMILES: COc1ccc2oc(C(C)NC(C)=O)nc2c1]

Using N^α-acetyl-N-(2-hydroxy-5-methoxyphenyl)alaninamide (1.00 g, 3.96 mmol) obtained in Reference Example 140, a method in the same manner as in Reference Example 32 was performed, and the obtained residue was triturated with diisopropyl ether-hexane (1:1) to give the title compound (462 mg, yield 50%).

¹H NMR (CDCl₃) δ 1.63 (d, J=6.9 Hz, 3H), 2.09 (s, 3H), 3.84 (s, 3H), 5.39 (m, 1H), 6.26 (br, 1H), 6.93 (dd, J=2.4, 8.7 Hz, 1H), 7.16 (d, J=2.4 Hz, 1H), 7.39 (d, J=8.7 Hz, 1H).

Reference Example 142

N-[1-(5-hydroxy-1,3-benzoxazol-2-yl)ethyl]acetamide

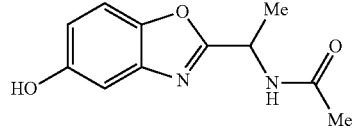

Using N-[1-(5-methoxy-1,3-benzoxazol-2-yl)ethyl]acetamide (250 mg, 1.07 mmol) obtained in Reference Example 141, a method in the same manner as in Reference Example 33 was performed, and the obtained residue was triturated with diisopropyl ether to give the title compound (195 mg, yield 83%).

¹H NMR (DMSO-d₆) δ 1.48 (d, J=6.9 Hz, 3H), 1.87 (s, 3H), 5.12 (m, 1H), 6.78 (dd, J=2.1, 9.0, 1H), 6.99 (d, J=2.1 Hz, 1H), 7.45 (d, J=9.0 Hz, 1H), 8.56 (d, J=8.1 Hz, 1H), 9.43 (s, 1H).

Reference Example 143 methyl 2-(methoxymethoxy)-4-{[4-(trifluoromethoxy)phenyl]ethynyl}benzoate

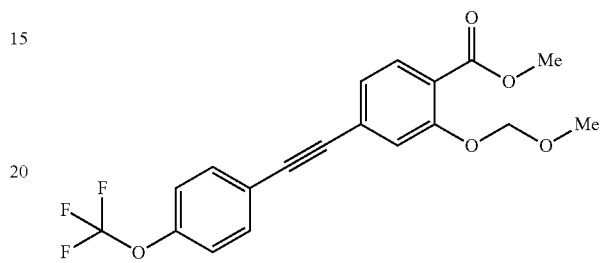

Using methyl 2-hydroxy-4-iodobenzoate (1.36 g, 4.88 mmol) and 1-ethynyl-4-(trifluoromethoxy)benzene (1.00 g, 5.37 mmol), an operation in the same manner as in Reference Example 47 was performed to give the title compound (1.82 g, yield 98%) as a yellow solid.

¹H NMR (CDCl₃) δ 3.55 (s, 3H), 3.91 (s, 3H), 5.29 (s, 2H), 7.18-7.23 (m, 3H), 7.36 (d, J=1.3 Hz, 1H), 7.57 (d, J=8.9 Hz, 2H), 7.78 (d, J=8.1 Hz, 1H).

Reference Example 144

[2-(methoxymethoxy)-4-{2-[4-(trifluoromethoxy)phenyl]ethyl]phenyl}methanol

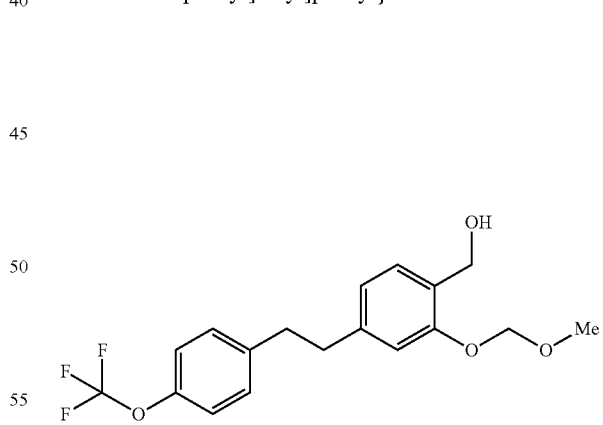

Using methyl 2-(methoxymethoxy)-4-{[4-(trifluoromethoxy)phenyl]ethynyl}benzoate (1.82 g, 4.79 mmol) obtained in Reference Example 143, an operation in the same manner as in Reference Example 48 was performed to give the title compound (1.39 g, yield 89%) as an oil.

¹H NMR (CDCl₃) δ 2.86-2.93 (m, 4H), 3.48 (s, 3H), 4.67 (d, J=6.1 Hz, 2H), 5.17 (s, 2H), 6.80-6.83 (m, 3H), 6.85 (s, 1H), 7.09-7.18 (m, 4H), 7.21 (d, J=7.6 Hz, 1H).

Reference Example 145

2-(methoxymethoxy)-4-{2-[4-(trifluoromethoxy)phenyl]ethyl}benzaldehyde

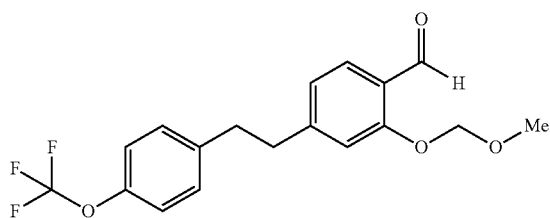 [SMILES: COCOc1cc(CCc2ccc(OC(F)(F)F)cc2)ccc1C=O]

Using [2-(methoxymethoxy)-4-{2-[4-(trifluoromethoxy)phenyl]ethyl]phenyl}methanol (1.39 g, 3.90 mmol) obtained in Reference Example 144, an operation in the same manner as in Reference Example 49 was performed to give the title compound (1.20 g, yield 87%) as an oil.
¹H NMR (CDCl₃) δ 2.92-2.98 (m, 4H), 3.50 (s, 3H), 5.22 (s, 2H), 6.89-6.91 (m, 2H), 7.10-7.16 (m, 4H), 7.77 (d, J=8.3 Hz, 1H), 10.43 (s, 1H).

Reference Example 146

2-hydroxy-4-{2-[4-(trifluoromethoxy)phenyl]ethyl}benzaldehyde

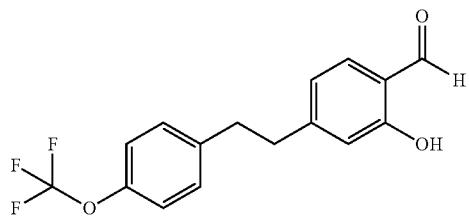 [SMILES: O=Cc1ccc(CCc2ccc(OC(F)(F)F)cc2)cc1O]

Using 2-(methoxymethoxy)-4-{2-[4-(trifluoromethoxy)phenyl]ethyl}benzaldehyde (1.20 g, 3.39 mmol) obtained in Reference Example 145, an operation in the same manner as in Reference Example 50 was performed to give the title compound (966 mg, yield 92%) as an oil.
¹H NMR (CDCl₃) δ 2.91-2.96 (m, 4H), 6.77-6.80 (m, 2H), 7.11-7.18 (m, 4H), 7.45 (d, J=7.7 Hz, 1H), 9.84 (s, 1H), 11.04 (s, 1H).

Reference Example 147

1-(6-{2-[(4-(trifluoromethoxy)phenyl]ethyl}-1-benzofuran-2-yl)ethanone

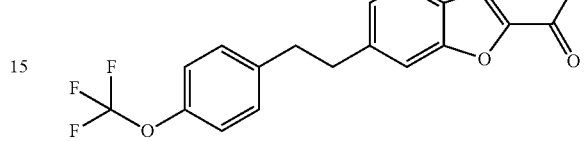

Using 2-hydroxy-4-{2-[4-(trifluoromethoxy)phenyl]ethyl}benzaldehyde (966 mg, 3.11 mmol) obtained in Reference Example 146, an operation in the same manner as in Reference Example 51 was performed to give the title compound (1.08 g, quantitative) as an oil.
¹H NMR (CDCl₃) δ 2.59 (s, 3H), 2.95-3.00 (m, 2H), 3.04-3.09 (In, 2H), 7.10-7.18 (m, 5H), 7.35 (s, 1H), 7.47 (d, J=0.9 Hz, 1H), 7.60 (d, J=8.1 Hz, 1H).

Reference Example 148

1-(6-{2-[4-(trifluoromethoxy)phenyl]ethyl}-1-benzofuran-2-yl)ethanol

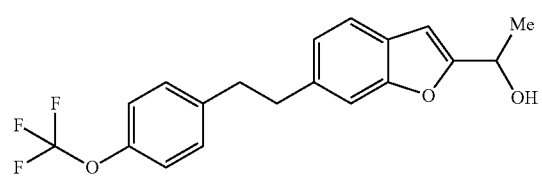 [SMILES: CC(O)c1cc2ccc(CCc3ccc(OC(F)(F)F)cc3)cc2o1]

Using 1-(6-{2-[4-(trifluoromethoxy)phenyl]ethyl}-1-benzofuran-2-yl)ethanone (1.08 g, 3.11 mmol) obtained in Reference Example 147, an operation in the same manner as in Reference Example 52 was performed to give the title compound (833 mg, yield 70%) as an oil.
¹H NMR (CDCl₃) δ 1.63 (d, J=6.6 Hz, 3H), 2.92-3.05 (m, 4H), 4.96-5.04 (m, 1H), 6.57 (s, 1H), 7.01 (dd, J=8.0, 1.4 Hz, 1H), 7.09-7.19 (m, 4H), 7.25 (s, 1H), 7.43 (d, J=7.9 Hz, 1H).

Reference Example 149

2-(1-azidoethyl)-6-{2-[4-(trifluoromethoxy)phenyl]ethyl}-1-benzofuran

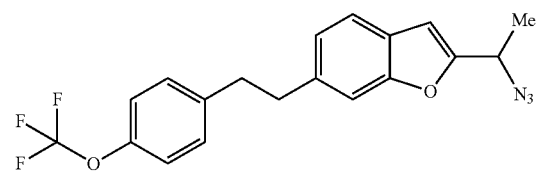 [SMILES: CC(N=[N+]=[N-])c1cc2ccc(CCc3ccc(OC(F)(F)F)cc3)cc2o1]

Using 1-(6-{2-[4-(trifluoromethoxy)phenyl]ethyl}-1-benzofuran-2-yl)ethanol (833 mg, 2.38 mmol) obtained in Reference Example 148, an operation in the same manner as in Reference Example 28 was performed to give the title compound (825 mg, yield 92%) as an oil.

$^1$H NMR (CDCl$_3$) δ 1.65 (d, J=7.0 Hz, 3H), 2.93-3.06 (m, 4H), 4.68 (d, J=7.0 Hz, 1H), 6.63 (s, 1H), 7.03 (dd, J=7.9, 1.3 Hz, 1H), 7.10-7.20 (m, 4H), 7.28 (s, 1H), 7.45 (d, J=7.9 Hz, 1H).

Reference Example 150 methyl 4-[(4-butoxyphenyl)ethynyl]-2-(methoxymethoxy)benzoate

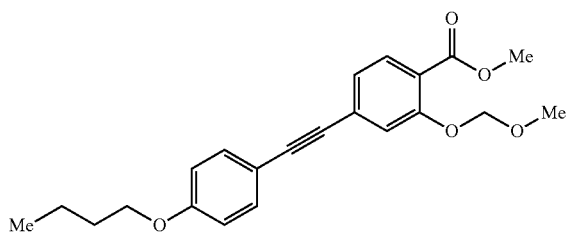 [SMILES: CCCCOc1ccc(C#Cc2ccc(C(=O)OC)c(OCOC)c2)cc1]

Using methyl 2-hydroxy-4-iodobenzoate (1.45 g, 5.22 mmol) and 1-butoxy-4-ethynylbenzene (1.00 g, 5.74 mmol), an operation in the same manner as in Reference Example 47 was performed to give the title compound (1.92 g, yield 99%) as an oil.

$^1$H NMR (CDCl$_3$) δ 0.98 (t, J=7.4 Hz, 3H), 1.44-1.56 (m, 2H), 1.73-1.83 (m, 2H), 3.52 (s, 3H), 3.90 (s, 3H), 3.98 (t, J=6.6 Hz, 2H), 5.28 (s, 2H), 6.87 (d, J=8.9 Hz, 2H), 7.17 (dd, J=8.1, 1.5 Hz, 1H), 7.33 (d, J=1.3 Hz, 1H), 7.46 (d, J=8.9 Hz, 2H), 7.76 (d, J=8.1 Hz, 1H).

Reference Example 151

{4-[2-(4-butoxyphenyl)ethyl]-2-(methoxymethoxy)phenyl}methanol

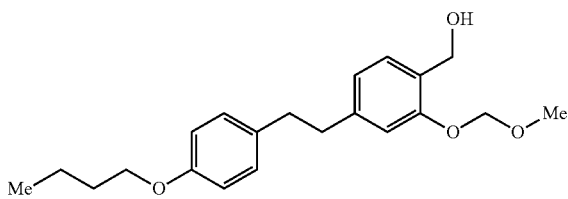 [SMILES: CCCCOc1ccc(CCc2ccc(CO)c(OCOC)c2)cc1]

Using methyl 4-[(4-butoxyphenyl)ethynyl]-2-(methoxymethoxy)benzoate (1.92 g, 5.22 mmol) obtained in Reference Example 150, an operation in the same manner as in Reference Example 48 was performed to give the title compound (1.15 g, yield 64%) as an oil.

$^1$H NMR (CDCl$_3$) δ 0.97 (t, J=7.4 Hz, 3H), 1.42-1.55 (m, 2H), 1.71-1.80 (m, 2H), 2.83-2.88 (m, 4H), 3.49 (s, 3H), 3.94 (t, J=6.6 Hz, 2H), 4.67 (d, J=6.2 Hz, 2H), 5.20 (s, 2H), 6.80-6.84 (m, 3H), 6.89 (d, J=1.3 Hz, 1H), 7.07 (d, J=8.7 Hz, 2H), 7.20 (d, J=7.7 Hz, 1H).

Reference Example 152

4-[2-(4-butoxyphenyl)ethyl]-2-(methoxymethoxy)benzaldehyde

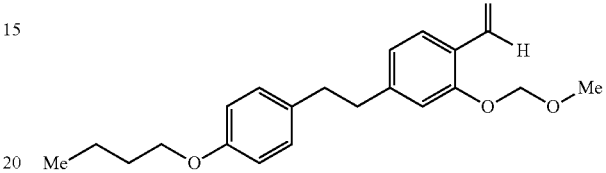

Using {4-[2-(4-butoxyphenyl)ethyl]-2-(methoxymethoxy)phenyl}methanol (1.15 g, 3.34 mmol) obtained in Reference Example 151, an operation in the same manner as in Reference Example 49 was performed to give the title compound (1.00 g, yield 87%) as an oil.

$^1$H NMR (CDCl$_3$) δ 0.97 (t, J=7.4 Hz, 3H), 1.42-1.55 (m, 2H), 1.71-1.80 (m, 2H), 2.82-2.95 (m, 4H), 3.51 (s, 3H), 3.93 (t, J=6.5 Hz, 2H), 5.24 (s, 2H), 6.81 (d, J=8.1 Hz, 2H), 6.89 (d, J=8.1 Hz, 2H), 6.94 (s, 1H), 7.04 (d, J=8.7 Hz, 2H), 7.75 (d, J=7.9 Hz, 1H), 10.44 (s, 1H).

Reference Example 153

4-[2-(4-butoxyphenyl)ethyl]-2-hydroxybenzaldehyde

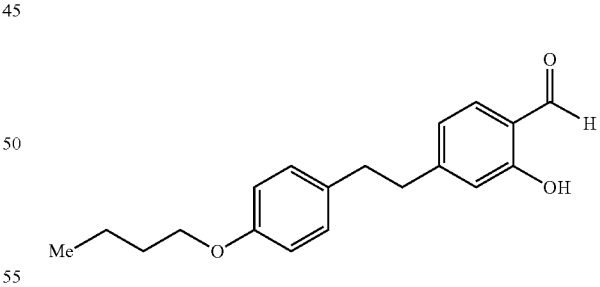

Using 4-[2-(4-butoxyphenyl)ethyl]-2-(methoxymethoxy)benzaldehyde (1.00 g, 2.92 mmol) obtained in Reference Example 152, an operation in the same manner as in Reference Example 50 was performed to give the title compound (862 mg, yield 99%) as an oil.

$^1$H NMR (CDCl$_3$) δ 0.97 (t, J=7.4 Hz, 3H), 1.42-1.52 (m, 2H), 1.71-1.80 (m, 2H), 2.83-2.94 (m, 4H), 3.93 (t, J=6.5 Hz,

2H), 6.78-6.83 (m, 4H), 7.05 (d, J=8.5 Hz, 2H), 7.44 (d, J=8.3 Hz, 1H), 9.83 (s, 1H), 11.03 (s, 1H).

Reference Example 154

1-[6-[2-(4-butoxyphenyl)ethyl]-1-benzofuran-2-yl]ethanone

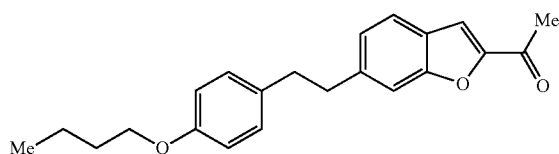 [SMILES: CCCCOc1ccc(CCc2ccc3cc(C(C)=O)oc3c2)cc1]

Using 4-[2-(4-butoxyphenyl)ethyl]-2-hydroxybenzaldehyde (862 mg, 2.89 mmol) obtained in Reference Example 153, an operation in the same manner as in Reference Example 51 was performed to give the title compound (829 mg, yield 85%) as an oil.

$^1$H NMR (CDCl$_3$) δ 0.97 (t, J=7.4 Hz, 3H), 1.43-1.53 (m, 2H), 1.71-1.80 (m, 2H), 2.60 (s, 3H), 2.87-2.93 (m, 2H), 3.01-3.06 (m, 2H), 3.93 (t, J=6.5 Hz, 2H), 6.80 (d, J=8.7 Hz, 2H), 7.06 (d, J=8.7 Hz, 2H), 7.13 (dd, J=8.1, 1.3 Hz, 1H), 7.34 (s, 1H), 7.47 (d, J=0.9 Hz, 1H), 7.59 (d, J=8.1 Hz, 1H).

Reference Example 155

1-{6-[2-(4-butoxyphenyl)ethyl]-1-benzofuran-2-yl}ethanol

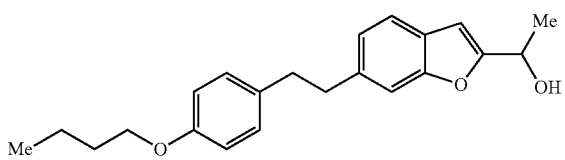 [SMILES: CCCCOc1ccc(CCc2ccc3cc(C(C)O)oc3c2)cc1]

Using 1-{6-[2-(4-butoxyphenyl)ethyl]-1-benzofuran-2-yl}ethanone (829 mg, 2.47 mmol) obtained in Reference Example 154, an operation in the same manner as in Reference Example 52 was performed to give the title compound (690 mg, yield 82%) as an oil.

$^1$H NMR (CDCl$_3$) δ 0.97 (t, J=7.4 Hz, 3H), 1.42-1.55 (m, 2H), 1.63 (d, J=6.8 Hz, 3H), 1.71-1.83 (m, 2H), 2.86-2.91 (m, 2H), 2.96-3.02 (m, 2H), 3.94 (t, J=6.4 Hz, 2H), 4.96-5.04 (m, 1H), 6.56 (s, 1H), 6.81 (d, J=8.3 Hz, 2H), 7.04 (d, J=8.0, 1.5 Hz, 1H), 7.08 (dd, J=8.3 Hz, 2H), 7.26 (s, 1H), 7.42 (d, J=8.0 Hz, 1H).

Reference Example 156

2-(1-azidoethyl)-6-[2-(4-butoxyphenyl)ethyl]-1-benzofuran

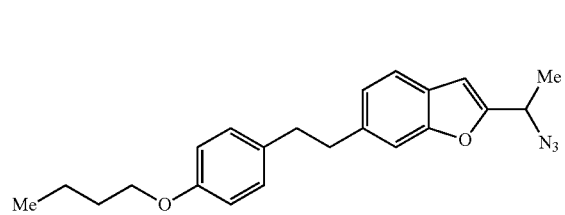 [SMILES: CCCCOc1ccc(CCc2ccc3cc(C(C)N=[N+]=[N-])oc3c2)cc1]

Using 1-{6-[2-(4-butoxyphenyl)ethyl]-1-benzofuran-2-yl}ethanol (690 mg, 2.04 mmol) obtained in Reference Example 155, an operation in the same manner as in Reference Example 28 was performed to give the title compound (553 mg, yield 75%) as an oil.

$^1$H NMR (CDCl$_3$) δ 0.97 (t, J=7.4 Hz, 3H), 1.43-1.52 (m, 2H), 1.65 (d, J=6.8 Hz, 3H), 1.71-1.80 (m, 2H), 2.86-2.92 (m, 2H), 2.97-3.02 (m, 2H), 3.94 (t, J=6.5 Hz, 2H), 4.67 (q, J=8.7 Hz, 1H), 6.62 (s, 1H), 6.81 (d, J=8.7 Hz, 2H), 7.04-7.10 (m, 3H), 7.29 (s, 1H), 7.44 (d, J=7.9 Hz, 1H).

Reference Example 157

1-(6-bromo-1-benzothiophen-2-yl)ethanol

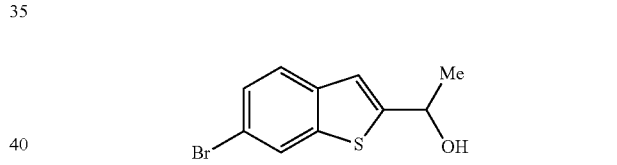

Using 1-(6-bromo-1-benzothiophen-2-yl)ethanone (1.91 g, 7.50 mmol), an operation in the same manner as in Reference Example 52 was performed to give the title compound (1.92 g, quantitative) as an oil.

$^1$H NMR (CDCl$_3$) δ 1.65 (d, J=6.4 Hz, 3H), 5.14-5.22 (m, 1H), 7.14 (s, 1H), 7.43 (dd, J=8.5, 1.7 Hz, 1H), 7.56 (d, J=8.5 Hz, 1H), 7.94 (s, 1H).

Reference Example 158

2-(1-azidoethyl)-6-bromo-1-benzothiophene

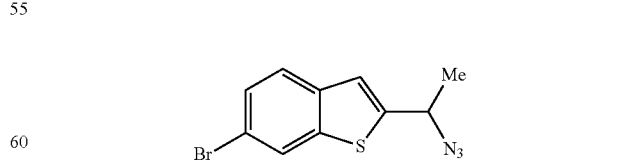

Using 1-(6-bromo-1-benzothiophen-2-yl)ethanol (1.92 g, 7.50 mmol) obtained in Reference Example 157, an operation in the same manner as in Reference Example 28 was performed to give the title compound (1.97 g, yield 93%) as an oil.

¹H NMR (CDCl₃) δ 1.67 (d, J=6.8 Hz, 3H), 4.87 (q, J=6.8 Hz, 1H), 7.19 (s, 1H), 7.46 (dd, J=8.5, 1.9 Hz, 1H), 7.59 (d, J=8.5 Hz, 1H), 7.95 (d, J=1.9 Hz, 1H).

Reference Example 159 tert-butyl [1-(6-bromo-1-benzothiophen-2-yl)ethyl]carbamate

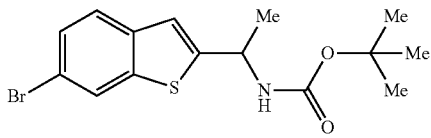 [SMILES: CC(NC(=O)OC(C)(C)C)c1cc2ccc(Br)cc2s1]

Using 2-(1-azidoethyl)-6-bromo-1-benzothiophene (1.97 g, 6.98 mmol) obtained in Reference Example 158, an operation in the same manner as in Reference Example 29 was performed to give the title compound (2.38 g, yield 95%) as an oil.
¹H NMR (CDCl₃) δ 1.46 (s, 9H), 1.60 (d, J=6.8 Hz, 3H), 4.86 (br, 1H), 7.11 (s, 1H), 7.42 (dd, J=8.5, 1.9 Hz, 1H), 7.54 (d, J=8.5 Hz, 1H), 7.91 (d, J=1.9 Hz, 1H).

Reference Example 160 methyl 2-{1-[(tert-butoxycarbonyl)amino]ethyl}-1-benzothiophene-6-carboxylate

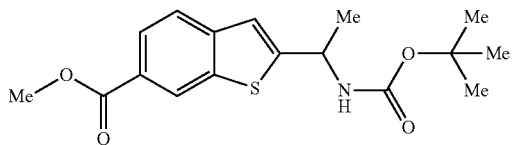 [SMILES: COC(=O)c1ccc2cc(C(C)NC(=O)OC(C)(C)C)sc2c1]

Using tert-butyl [1-(6-bromo-1-benzothiophen-2-yl)ethyl]carbamate (1.13 g, 3.18 mmol) obtained in Reference Example 159, an operation in the same manner as in Reference Example 61 was performed to give the title compound (914 mg, yield 85%) as an oil.
¹H NMR (CDCl₃) δ 1.46 (s, 9H), 1.62 (d, J=7.0 Hz, 3H), 3.95 (s, 3H), 4.90 (br, 1H), 5.15 (br, 1H), 7.21 (s, 1H), 7.72 (d, J=8.3 Hz, 1H), 7.99 (dd, J=8.3, 1.4 Hz, 1H), 8.50 (s, 1H).

Reference Example 161 tert-butyl {1-[6-(hydroxymethyl)-1-benzothiophen-2-yl]ethyl}carbamate

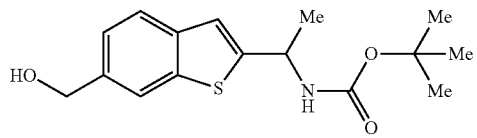 [SMILES: CC(NC(=O)OC(C)(C)C)c1cc2ccc(CO)cc2s1]

Using methyl 2-{1-[(tert-butoxycarbonyl)amino]ethyl}-1-benzothiophene-6-carboxylate (914 mg, 2.72 mmol) obtained in Reference Example 160, an operation in the same manner as in Reference Example 30 was performed to give the title compound (286 mg, yield 34%) as an oil.

¹H NMR (CDCl₃) δ 1.46 (s, 9H), 1.60 (d, J=6.8 Hz, 3H), 4.79 (d, J=5.8 Hz, 2H), 4.87 (br, 1H), 5.12 (br, 1H), 7.14 (s, 1H), 7.32 (dd, J=8.1, 1.3 Hz, 1H), 7.67 (d, J=8.1 Hz, 1H), 7.79 (s, 1H).

Reference Example 162

2-(1-azidoethyl)-5-bromo-1-benzofuran

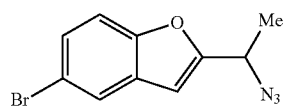

Using 1-(5-bromo-1-benzofuran-2-yl)ethanol (6.11 g, 25.4 mmol), DMF (50 mL), methanesulfonyl chloride (2.9 mL, 38.0 mmol), triethylamine (7.5 mL, 50.8 mmol) and sodium azide (8.64 g, 127 mmol), an operation in the same manner as in Reference Example 22 was performed to give the title compound 5.22 g as an oil. This was used for the next step without purification.

Reference Example 163

N-[1-(5-bromo-1-benzofuran-2-yl)ethyl]acetamide

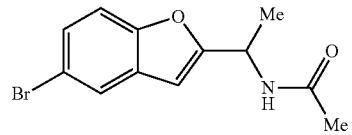 [SMILES: CC(=O)NC(C)c1cc2cc(Br)ccc2o1]

To a solution of 2-(1-azidoethyl)-5-bromo-1-benzofuran (5.22 g, 19.6 mmol) obtained in Reference Example 162 in THF (20 mL) and water (2 mL) was added triphenylphosphine (7.71 g, 294 mmol) and the mixture was refluxed for 4 hr. Ethyl acetate was added thereto, and the mixture was extracted twice with 1N hydrochloric acid. The extract was basified with 8N aqueous sodium hydroxide solution, and extracted twice with ethyl acetate. The extract was washed with saturated brine, and dried over magnesium sulfate. The solvent was evaporated under reduced pressure, and to the obtained residue were added ethyl acetate (10 mL) and acetic anhydride (2.75 mL, 29.4 mmol), and the mixture was stirred at room temperature for 3 min. The solvent was evaporated under reduced pressure, and the obtained solid was washed with diisopropyl ether to give the title compound (4.29 g, yield from 1-(5-bromo-1-benzofuran-2-yl)ethanol 78%).

¹H NMR (CDCl₃) δ 1.56 (d, J=6.8 Hz, 3H), 2.03 (s, 3H), 5.26-5.48 (m, 1H), 6.52 (s, 1H), 7.22-7.43 (m, 2H), 7.64 (s, 1H).

Reference Example 164

1-[5-chloro-6-(methoxymethoxy)-1-benzofuran-2-yl]ethanone

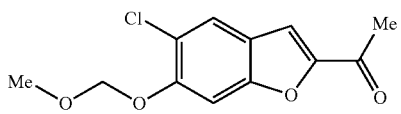

Using 5-chloro-2-hydroxy-4-(methoxymethoxy)benzaldehyde (1.50 g, 6.94 mmol), acetonitrile (14 mL), bromoacetone (1.57 g, 10.4 mmol) and potassium carbonate (2.87 g, 20.8 mmol), an operation in the same manner as in Reference Example 86 was performed to give the title compound (1.28 g, yield 72%).
¹H NMR (CDCl₃) δ 2.58 (s, 3H), 3.54 (s, 3H), 5.32 (s, 2H), 7.40 (s, 1H), 7.42 (s, 1H), 7.71 (s, 1H).

Reference Example 165

1-[5-chloro-6-(methoxymethoxy)-1-benzofuran-2-yl]ethanol

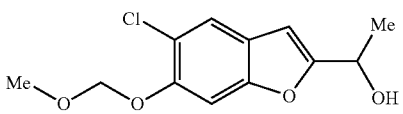 [SMILES: COCOc1cc2oc(C(C)O)cc2cc1Cl]

Using 1-[5-chloro-6-(methoxymethoxy)-1-benzofuran-2-yl]ethanone (1.28 g, 5.03 mmol) obtained in Reference Example 164, methanol (10 mL) and sodium borohydride (383 mg, 10.1 mmol), an operation in the same manner as in Reference Example 21 was performed to give the title compound (1.28 g, quantitative).
¹H NMR (CDCl₃) δ 1.61 (d, J=6.8 Hz, 3H), 2.03 (d, J=5.1 Hz, 1H), 3.54 (s, 3H), 4.91-5.05 (m, 1H), 5.27 (s, 2H), 6.51 (s, 1H), 7.34 (s, 1H), 7.52 (s, 1H).

Reference Example 166

2-(1-azidoethyl)-5-chloro-6-(methoxymethoxy)-1-benzofuran

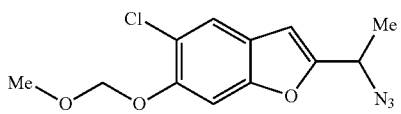

Using 1-[5-chloro-6-(methoxymethoxy)-1-benzofuran-2-yl]ethanol (1.28 g, 5.00 mmol) obtained in Reference Example 165, DMF (10 methanesulfonyl chloride (0.58 mL, 7.50 mmol), triethylamine (1.5 mL. 10.0 mmol) and sodium azide (1.70 g, 25.0 mmol), an operation in the same manner as in Reference Example 22 was performed to give the title compound (1.79 g, quantitative).

¹H NMR (CDCl₃) δ 1.64 (d, J=6.8 Hz, 3H), 3.55 (s, 3H), 4.65 (q, J=7.0 Hz, 1H), 5.28 (s, 2H), 6.56 (s, 1H), 7.36 (s, 1H), 7.54 (s, 1H).

Reference Example 167

1-[5-chloro-6-(methoxymethoxy)-1-benzofuran-2-yl]ethanamine

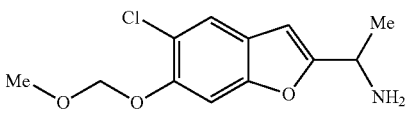 [SMILES: COCOc1cc2oc(C(C)N)cc2cc1Cl]

Using 2-(1-azidoethyl)-5-chloro-6-(methoxymethoxy)-1-benzofuran (1.79 g, 5.00 mmol) obtained in Reference Example 166, THF (5 mL), water (1 mL) and triphenylphosphine (1.96 g, 7.50 mmol), an operation in the same manner as in Reference Example 25 was performed to give the title compound (1.14 g, yield 81%).
¹H NMR (CDCl₃) δ 1.49 (d, J=6.8 Hz, 3H), 3.55 (s, 2H), 4.07-4.17 (m, 1H), 5.26 (s, 2H), 6.39 (s, 1H), 7.26 (s, 1H), 7.49 (s, 1H).

Reference Example 168

N-[1-(5-chloro-6-hydroxy-1-benzofuran-2-yl)ethyl]acetamide

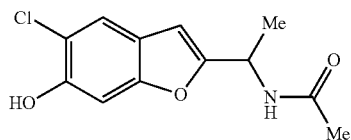

To a solution of 1-[5-chloro-6-(methoxymethoxy)-1-benzofuran-2-yl]ethanamine (1.14 g, 4.06 mmol) obtained in Reference Example 167 in THF (8 mL) was added acetic anhydride (0.42 mL, 4.46 mmol) and the mixture was stirred at room temperature for 10 min. 1N Hydrochloric acid (5 mL) and concentrated hydrochloric acid (2 mL) were added thereto, and the mixture was further stirred at 50° C. for 2 hr. Brine was added thereto, and the mixture was extracted twice with ethyl acetate. The extract was washed with saturated brine, and dried over anhydrous sodium sulfate. The solution was passed through silica gel. The solvent was evaporated under reduced pressure, and the obtained solid was washed with diethyl ether to give the title compound (766 mg, yield 74%) as a white solid.

¹H NMR (CDCl₃) δ 1.55 (d, J=6.8 Hz, 3H), 2.02 (s, 3H), 5.20-5.42 (m, 1H), 5.69-5.86 (m, 2H), 6.44 (s, 1H), 7.11 (d, J=0.8 Hz, 1H), 7.44 (s, 1H).

Reference Example 169 methyl 4-[(4-ethoxyphenyl)ethynyl]-2-fluorobenzoate

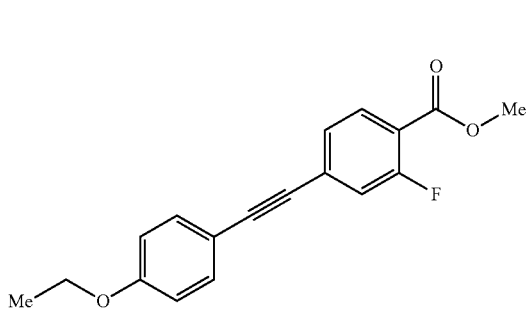 [SMILES: CCOc1ccc(C#Cc2ccc(C(=O)OC)c(F)c2)cc1]

To methyl 4-bromo-2-fluorobenzoate (1.29 g, 5.54 mmol) in THF (10 mL)-triethylamine (5 mL) solvent were added 1-ethoxy-4-ethynylbenzene (1.24 mL, 8.30 mmol), copper(I) iodide (106 mg, 0.544 mmol) and bis(triphenylphosphine)palladium(II) chloride (195 mg, 0.277 mmol), and the mixture was stirred under an argon stream at room temperature for 15 min. The reaction mixture was diluted with ethyl acetate, and the mixture was washed with water, and dried over anhydrous magnesium sulfate. The solvent was evaporated under reduced pressure and the obtained residue was purified by silica gel column chromatography (hexane:ethyl acetate=97:3 to 17:3) to give the title compound (1.38 g, yield 84%) as an oil.

¹H NMR (CDCl₃) δ 1.43 (t, J=7.0 Hz, 3H), 3.93 (s, 3H), 4.04 (q, J=7.0 Hz, 2H), 6.88 (d, J=8.7 Hz, 2H), 7.23-7.33 (m, 2H), 7.46 (d, J=8.7 Hz, 2H), 7.90 (t, J=8.0 Hz, 1H).

Reference Example 170

{4-[2-(4-ethoxyphenyl)ethyl]-2-fluorophenyl}methanol

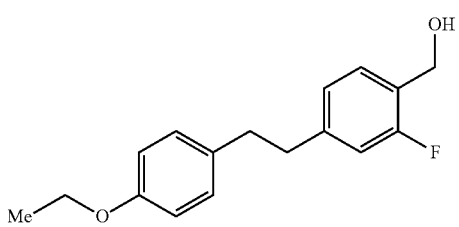 [SMILES: CCOc1ccc(CCc2ccc(CO)c(F)c2)cc1]

Using methyl 4-[(4-ethoxyphenyl)ethynyl]-2-fluorobenzoate (1.32 g, 4.43 mmol) obtained in Reference Example 169, an operation in the same manner as in Reference Example 48 was performed to give the title compound (1.14 g, yield 94%) as a white solid.

¹H NMR (CDCl₃) δ 1.40 (t, J=7.0 Hz, 3H), 2.80-2.91 (m, 4H), 4.01 (q, J=7.0 Hz, 2H), 4.72 (t, J=6.0 Hz, 2H), 6.81 (d, J=8.7 Hz, 2H), 6.86 (dd, J=11.1, 1.5 Hz, 1H), 6.93 (dd, J=7.7, 1.5 Hz, 1H), 7.05 (d, J=8.7 Hz, 2H), 7.29 (t, J=7.8 Hz, 1H).

Reference Example 171

4-[2-(4-ethoxyphenyl)ethyl]-2-fluorobenzaldehyde

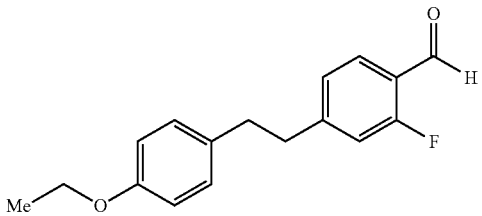 [SMILES: CCOc1ccc(CCc2ccc(C=O)c(F)c2)cc1]

Using {4-[2-(4-ethoxyphenyl)ethyl]-2-fluorophenyl}methanol (1.14 g, 4.16 mmol) obtained in Reference Example 170, an operation in the same manner as in Reference Example 49 was performed to give the title compound (886 mg, yield 78%) as an oil.

¹H NMR (CDCl₃) δ 1.40 (t, J=7.0 Hz, 3H), 2.84-2.90 (m, 2H), 2.92-2.98 (m, 2H), 4.01 (q, J=7.0 Hz, 2H), 6.81 (d, J=8.7 Hz, 2H), 6.93 (dd, J=11.4, 1.5 Hz, 1H), 7.00-7.07 (m, 3H), 7.76 (t, J=7.8 Hz, 1H), 10.30 (s, 1H).

Reference Example 172 ethyl 6-[2-(4-ethoxyphenyl)ethyl]-1-benzothiophene-2-carboxylate

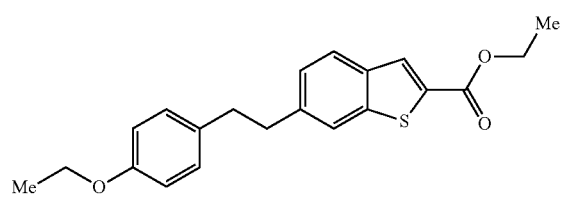 [SMILES: CCOC(=O)c1cc2ccc(CCc3ccc(OCC)cc3)cc2s1]

To a solution of ethyl mercaptoacetateester (0.450 mL, 4.07 mmol) in DMSO (10 mL) was added sodium hydride (60%, 196 mg, 4.89 mmol) and the mixture was stirred at room temperature for 10 min. To this reaction mixture was added 4-[2-(4-ethoxyphenyl)ethyl]-2-fluorobenzaldehyde (886 mg, 3.26 mmol) obtained in Reference Example 171, and the mixture was stirred at room temperature for 20 min. Water was added to the reaction mixture, and the mixture was extracted with ethyl acetate. The organic layer was washed twice with saturated brine, and dried over anhydrous magnesium sulfate. The solvent was evaporated under reduced pressure, and the obtained residue was purified by basic silica gel column chromatography (hexane:ethyl acetate=19:1 to 1:1) to give the title compound (723 mg, yield 63%) as an oil.

¹H NMR (CDCl₃) δ 1.38-1.43 (m, 6H), 2.88-2.94 (m, 2H), 2.99-3.05 (m, 2H), 4.01 (q, J=7.0 Hz, 2H), 4.40 (q, J=7.0 Hz,

2H), 6.80 (d, J=8.7 Hz, 2H), 7.06 (d, J=8.7 Hz, 2H), 7.21 (dd, J=8.2, 1.4 Hz, 2H), 7.62 (s, 1H), 7.77 (d, J=8.3 Hz, 1H), 8.01 (s, 1H).

Reference Example 173

6-[2-(4-ethoxyphenyl)ethyl]-N-methoxy-N-methyl-1-benzothiophene-2-carboxamide

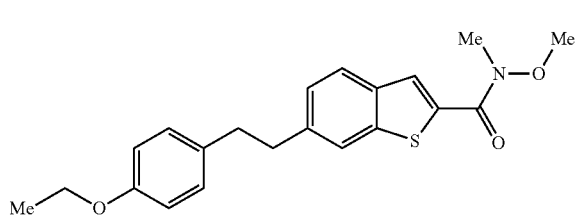 [SMILES: CCOc1ccc(CCc2ccc3cc(C(=O)N(C)OC)sc3c2)cc1]

Using ethyl 6-[2-(4-ethoxyphenyl)ethyl]-1-benzothiophene-2-carboxylate (723 mg, 2.04 mmol) obtained in Reference Example 172, an operation in the same manner as in Reference Example 94 was performed to give the title compound (254 mg, yield 34%) as an oil.

¹H NMR (CDCl₃) δ 1.40 (t, J=7.0 Hz, 3H), 2.89-2.94 (m, 2H), 3.00-3.05 (m, 2H), 3.42 (s, 3H), 3.82 (s, 3H), 4.01 (q, J=7.0 Hz, 2H), 6.81 (d, J=8.3 Hz, 2H), 7.08 (d, J=8.7 Hz, 2H), 7.21 (dd, J=8.3, 1.5 Hz, 1H), 7.62 (s, 1H), 7.78 (d, J=8.3 Hz, 1H), 8.16 (s, 1H).

Reference Example 174

1-{6-[2-(4-ethoxyphenyl)ethyl]-1-benzothiophen-2-yl}ethanol

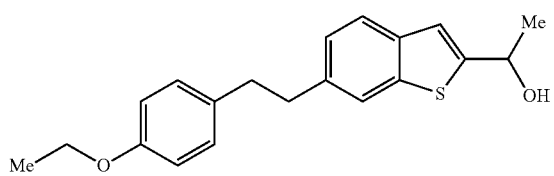

Using 6-[2-(4-ethoxyphenyl)ethyl]-N-methoxy-N-methyl-1-benzothiophene-2-carboxamide (254 mg, 0.688 mmol) obtained in Reference Example 173, an operation in the same manner as in Reference Example 95 was performed to give the title compound (172 mg, yield 77%) as a white solid.

¹H NMR (CDCl₃) δ 1.40 (t, J=7.0 Hz, 3H), 1.65 (d, J=6.4 Hz, 3H), 2.01 (d, J=4.7 Hz, 1H), 2.85-2.92 (m, 2H), 2.96-3.02 (m, 2H), 4.01 (q, J=7.0 Hz, 2H), 5.15-5.23 (m, 1H), 6.81 (d, J=8.7 Hz, 2H), 7.07 (d, J=8.5 Hz, 2H), 7.13-7.16 (m, 2H), 7.60-7.30 (m, 2H).

Reference Example 175

2-(1-azidoethyl)-6-[2-(4-ethoxyphenyl)ethyl]-1-benzothiophene

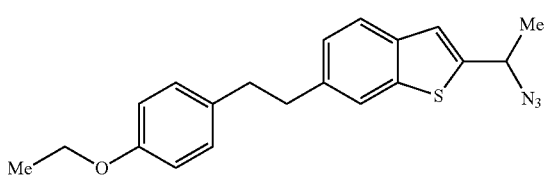 [SMILES: CCOc1ccc(CCc2ccc3cc(C(C)N=[N+]=[N-])sc3c2)cc1]

Using 1-{6-[2-(4-ethoxyphenyl)ethyl]-1-benzothiophen-2-yl}ethanol (172 mg, 0.527 mmol) obtained in Reference Example 174, an operation in the same manner as in Reference Example 28 was performed to give the title compound (168 mg, yield 90%) as an oil.

¹H NMR (CDCl₃) δ 1.40 (t, J=7.0 Hz, 3H), 1.66 (d, J=6.8 Hz, 3H), 2.85-2.93 (m, 2H), 2.97-3.02 (m, 2H), 4.01 (q, J=6.8 Hz, 2H), 4.87 (q, J=6.8 Hz, 1H), 6.81 (d, J=8.7 Hz, 2H), 7.08 (d, J=8.7 Hz, 2H), 7.17 (dd, J=8.3, 1.5 Hz, 1H), 7.19 (s, 1H), 7.60 (s, 1H), 7.64 (d, J=8.3 Hz, 1H).

Reference Example 176

2-ethoxy-5-ethynylpyridine

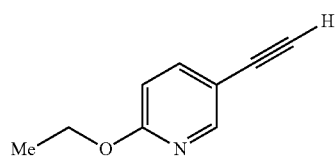 [SMILES: C#Cc1ccc(OCC)nc1]

To a solution of 5-bromo-2-ethoxypyridine (5.00 g, 24.8 mmol) in THF (50 mL)-triethylamine (25 mL) were added trimethylsilylacetylene (5.3 mL, 37.2 mmol), copper(I) iodide (237 mg, 1.24 mmol) and bis(triphenylphosphine)palladium(II) chloride (870 mg, 1.24 mmol), and the mixture was stirred under an argon stream at 60° C. for 1 hr. Water was added to the reaction mixture, the mixture was extracted twice with hexane, and the combined organic layer was dried over anhydrous magnesium sulfate. The solvent was evaporated under reduced pressure and the obtained residue was purified by silica gel column chromatography (hexane to hexane:ethyl acetate=19:1) to give an oil. To a solution of the oil in THF (50 mL) was added 1 M tetrabutylammonium fluoride THF solution (26.0 mL, 26.0 mmol), and the mixture was stirred at room temperature for 30 min. To the reaction mixture was added saturated aqueous sodium hydrogen carbonate solution, and the mixture was extracted twice with diethyl ether. The combined organic layer was dried over anhydrous magnesium sulfate. The solvent was evaporated under reduced pressure and the obtained residue was purified by silica gel column chromatography (hexane to hexane:ethyl acetate=19:1) to give the title compound (690 mg, yield 19%) as an oil.

¹H NMR (CDCl₃) δ 1.39 (t, J=7.0 Hz, 3H), 3.10 (s, 1H), 4.33-4.40 (m, 2H), 6.67 (dd, J=8.6, 0.7 Hz, 1H), 7.63 (dd, J=8.6, 2.1 Hz, 1H), 8.29 (d, J=2.1 Hz, 1H).

Reference Example 177 methyl 4-[(6-ethoxypyridin-3-yl)ethynyl]-2-(methoxymethoxy)benzoate

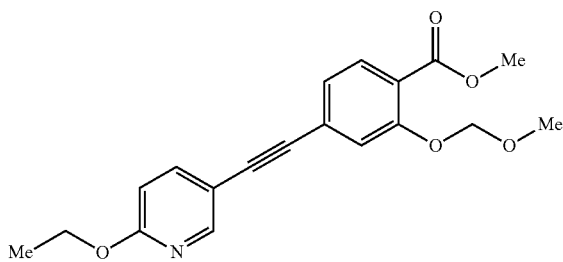

Using methyl 2-hydroxy-4-iodobenzoate (1.09 g, 3.91 mmol) and 2-ethoxy-5-ethynylpyridine (690 mg, 4.69 mmol) obtained in Reference Example 176, an operation in the same manner as in Reference Example 47 was performed to give the title compound (660 mg, yield 49%) as a yellow solid.

¹H NMR (CDCl₃) δ 1.40 (t, J=7.2 Hz, 3H), 3.55 (s, 3H), 3.90 (s, 3H), 4.39 (q, J=7.2 Hz, 2H), 5.28 (s, 2H), 6.72 (dd, J=8.7, 2.3 Hz, 1H), 7.18 (dd, J=8.0, 1.5 Hz, 1H), 7.34 (d, J=1.5 Hz, 1H), 7.68 (dd, J=8.7, 2.3 Hz, 2H), 7.77 (d, J=8.0 Hz, 1H).

Reference Example 178

{4-[2-(6-ethoxypyridin-3-yl)ethyl]-2-(methoxymethoxy)phenyl}methanol

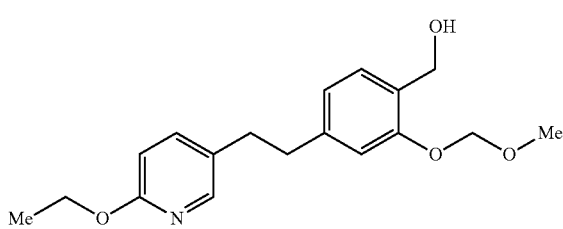 [SMILES: CCOc1ccc(CCc2ccc(CO)c(OCOC)c2)cn1]

Using methyl 4-[(6-ethoxypyridin-3-yl)ethynyl]-2-(methoxymethoxy)benzoate (660 mg, 1.94 mmol) obtained in Reference Example 177, an operation in the same manner as in Reference Example 48 was performed to give the title compound (425 mg, yield 69%) as an oil.

¹H NMR (CDCl₃) δ 1.38 (t, J=7.0 Hz, 3H), 2.78-2.89 (m, 4H), 3.48 (s, 3H), 4.31 (q, J=7.0 Hz, 2H), 4.67 (d, J=6.2 Hz, 2H), 5.20 (s, 2H), 6.64 (d, J=8.7 Hz, 1H), 6.80 (dd, J=7.6, 1.4 Hz, 1H), 6.87 (d, J=1.4 Hz, 1H), 7.21 (d, J=7.6 Hz, 1H), 7.34 (dd, J=8.7, 2.5 Hz, 1H), 7.90 (d, J=2.5 Hz, 1H).

Reference Example 179

4-[2-(6-ethoxypyridin-3-yl)ethyl]-2-(methoxymethoxy)benzaldehyde

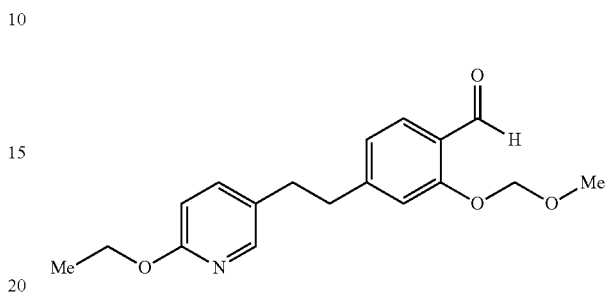

Using {4-[2-(6-ethoxypyridin-3-yl)ethyl]-2-(methoxymethoxy)phenyl}methanol (425 mg, 1.34 mmol) obtained in Reference Example 178, an operation in the same manner as in Reference Example 49 was performed to give the title compound (342 mg, yield 81%) as an oil.

¹H NMR (CDCl₃) δ 1.38 (t, J=7.0 Hz, 3H), 2.81-2.94 (m, 4H), 3.51 (s, 3H), 4.31 (q, J=7.0 Hz, 2H), 5.25 (s, 2H), 6.64 (d, J=8.7 Hz, 1H), 6.88 (d, J=8.0 Hz, 1H), 6.94 (s, 1H), 7.33 (dd, J=8.7, 2.5 Hz, 1H), 7.76 (d, J=8.0 Hz, 1H), 7.89 (d, J=2.5 Hz, 1H), 10.43 (s, 1H).

Reference Example 180

4-[2-(6-ethoxypyridin-3-yl)ethyl]-2-hydroxybenzaldehyde

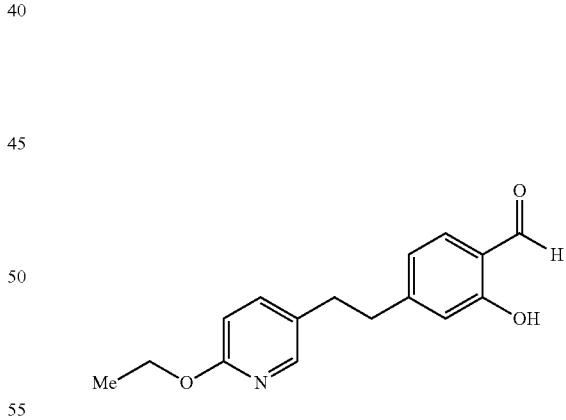

Using 4-[2-(6-ethoxypyridin-3-yl)ethyl]-2-(methoxymethoxy)benzaldehyde (342 mg, 1.08 mmol) obtained in Reference Example 179, an operation in the same manner as in Reference Example 50 was performed to give the title compound (274 mg, yield 94%) as an oil.

¹H NMR (CDCl₃) δ 1.38 (t, J=7.0 Hz, 3H), 2.82-2.93 (m, 4H), 4.31 (q, J=7.0 Hz, 2H), 6.64 (d, J=8.3 Hz, 1H), 6.77-6.79

(m, 2H), 7.34 (dd, J=8.5, 2.5 Hz, 1H), 7.45 (d, J=8.3 Hz, 1H), 7.90 (d, J=2.5 Hz, 1H), 9.84 (s, 1H), 11.03 (s, 1H).

Reference Example 181

1-{6-[2-(6-ethoxypyridin-3-yl)ethyl]-1-benzofuran-2-yl}ethanone

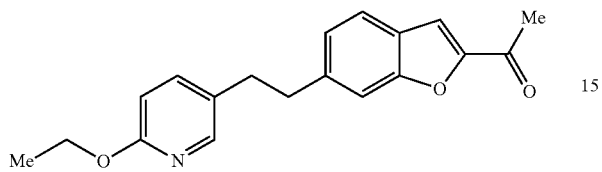

Using 4-[2-(6-ethoxypyridin-3-yl)ethyl]-2-hydroxybenzaldehyde (274 mg, 1.01 mmol) obtained in Reference Example 180, an operation in the same manner as in Reference Example 51 was performed to give the title compound (312 mg, quantitative) as an oil.

$^1$H NMR (CDCl$_3$) δ 1.38 (t, J=7.2 Hz, 3H), 2.59 (s, 3H), 2.87-2.92 (m, 2H), 3.00-3.05 (m, 2H), 4.31 (q, J=7.2 Hz, 2H), 6.63 (d, J=8.3 Hz, 1H), 7.11 (dd, J=8.3, 1.1 Hz, 1H), 7.31-7.35 (m, 2H), 7.46 (d, J=1.1 Hz, 1H), 7.60 (d, J=8.3 Hz, 1H), 7.89 (d, J=2.3 Hz, 1H).

Reference Example 182

1-{6-[2-(6-ethoxypyridin-3-yl)ethyl]-1-benzofuran-2-yl}ethanol

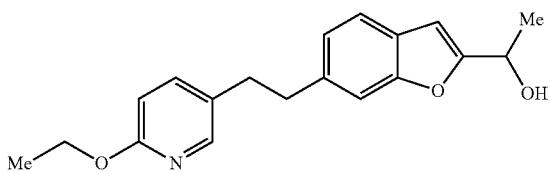

Using 1-{6-[2-(6-ethoxypyridin-3-yl)ethyl]-1-benzofuran-2-yl}ethanone (312 mg, 1.01 mmol) obtained in Reference Example 181, an operation in the same manner as in Reference Example 52 was performed to give the title compound (248 mg, yield 77%) as an oil.

$^1$H NMR (CDCl$_3$) δ 1.38 (t, J=7.0 Hz, 3H), 1.63 (d, J=6.8 Hz, 3H), 2.10 (d, J=4.5 Hz, 1H), 2.84-2.89 (m, 2H), 2.95-3.00 (m, 2H), 4.31 (q, J=7.0 Hz, 2H), 4.96-5.04 (m, 1H), 6.56 (s, 1H), 6.63 (d, J=8.3 Hz, 1H), 7.01 (dd, J=8.0, 1.5 Hz, 1H), 7.23 (s, 1H), 7.33 (dd, J=8.5, 2.5 Hz, 1H), 7.42 (d, J=8.0 Hz, 1H), 7.90 (d, J=2.5 Hz, 1H).

Reference Example 183

5-{2-[2-(1-azidoethyl)-1-benzofuran-6-yl]ethyl}-2-ethoxypyridine

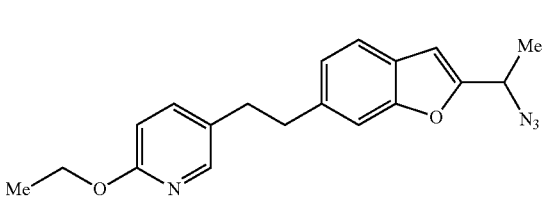

Using 1-{6-[2-(6-ethoxypyridin-3-yl)ethyl]-1-benzofuran-2-yl}ethanol (248 mg, 0.796 mmol) obtained in Reference Example 182, an operation in the same manner as in Reference Example 28 was performed to give the title compound (259 mg, yield 96%) as an oil.

$^1$H NMR (CDCl$_3$) δ 1.38 (t, J=7.0 Hz, 3H), 1.65 (d, J=6.8 Hz, 3H), 2.85-2.90 (m, 2H), 2.96-3.01 (m, 2H), 4.31 (q, J=7.0 Hz, 2H), 4.67 (q, J=6.8 Hz, 1H), 6.62-6.65 (m, 2H), 7.03 (dd, J=8.0, 1.1 Hz, 1H), 7.26-7.28 (m, 1H), 7.34 (dd, J=8.5, 2.5 Hz, 1H), 7.44 (d, J=8.0 Hz, 1H), 7.91 (d, J=2.5 Hz, 1H).

Reference Example 184

5-ethoxy-2-ethynylpyridine

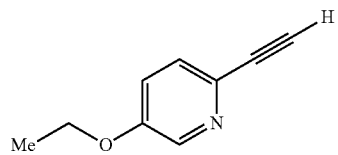 [SMILES: C#Cc1ccc(OCC)cn1]

Using 2-bromo-5-ethoxypyridine (5.00 g, 24.8 mmol), an operation in the same manner as in Reference Example 176 was performed to give the title compound (3.48 g, yield 95%) as a white solid.

¹H NMR (CDCl₃) δ 1.44 (t, J=7.0 Hz, 3H), 3.06 (s, 1H), 4.09 (q, J=7.0 Hz, 2H), 7.12 (dd, J=8.7, 3.0 Hz, 1H), 7.41 (d, J=8.6 Hz, 1H), 8.26 (d, J=3.0 Hz, 1H).

Reference Example 185 methyl 4-[(5-ethoxypyridin-2-yl)ethynyl]-2-(methoxymethoxy)benzoate

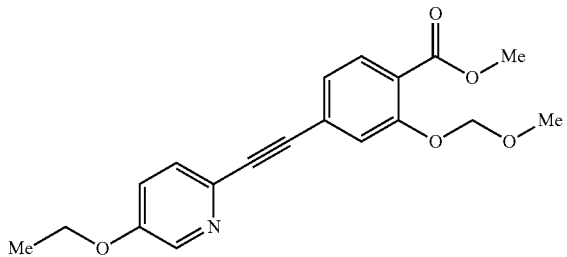

Using methyl 2-hydroxy-4-iodobenzoate (1.09 g, 3.91 mmol) and 5-ethoxy-2-ethynylpyridine (690 mg, 4.69 mmol) obtained in Reference Example 184, an operation in the same manner as in Reference Example 3047 was performed to give the title compound (918 mg, yield 69%) as a yellow solid.

¹H NMR (CDCl₃) δ 1.46 (t, J=7.0 Hz, 3H), 3.53 (s, 3H), 3.90 (s, 3H), 4.12 (q, J=7.0 Hz, 2H), 5.26 (s, 2H), 7.17 (dd, J=8.7, 3.0 Hz, 1H), 7.24 (dd, J=8.0, 1.4 Hz, 1H), 7.42 (d, J=1.4 Hz, 1H), 7.48 (d, J=8.7 Hz, 1H), 7.77 (d, J=8.0 Hz, 1H), 8.31 (d, J=3.0 Hz, 1H).

Reference Example 186

{4-[2-(5-ethoxypyridin-2-yl)ethyl]-2-(methoxymethoxy)phenyl}methanol

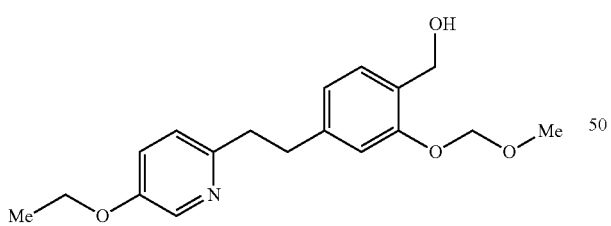

Using methyl 4-[(5-ethoxypyridin-2-yl)ethynyl]-2-(methoxymethoxy)benzoate (918 mg, 2.69 mmol) obtained in Reference Example 185, an operation in the same manner as in Reference Example 48 was performed to give the title compound (793 mg, yield 93%) as an oil.

¹H NMR (CDCl₃) δ 1.43 (t, J=7.0 Hz, 3H), 2.22 (t, J=6.3 Hz, 1H), 2.95-3.06 (m, 4H), 3.48 (s, 3H), 4.06 (q, J=7.0 Hz, 2H), 4.66 (d, J=6.2 Hz, 2H), 5.19 (s, 2H), 6.84 (dd, J=7.5, 1.5 Hz, 1H), 6.93 (d, J=1.5 Hz, 1H), 6.99 (d, J=8.1 Hz, 1H), 7.07-7.11 (m, 1H), 7.20 (d, J=7.5 Hz, 1H), 8.24 (d, J=3.0 Hz, 1H).

Reference Example 187

4-[2-(5-ethoxypyridin-2-yl)ethyl]-2-(methoxymethoxy)benzaldehyde

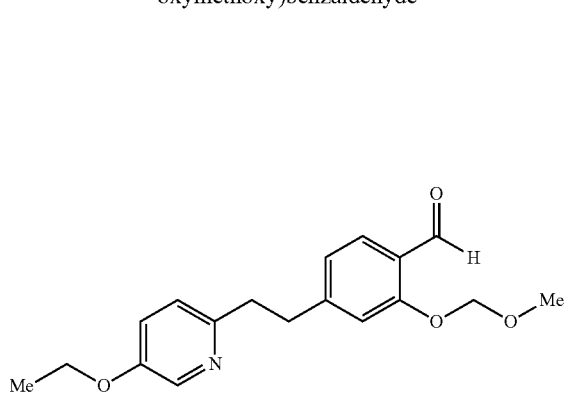

Using {4-[2-(5-ethoxypyridin-2-yl)ethyl]-2-(methoxymethoxy)phenyl}methanol (793 mg, 2.50 mmol) obtained in Reference Example 186, an operation in the same manner as in Reference Example 49 was performed to give the title compound (682 mg, yield 86%) as an oil.

¹H NMR (CDCl₃) δ 1.43 (t, J=7.0 Hz, 3H), 3.01-3.08 (m, 4H), 3.50 (s, 3H), 4.06 (q, J=7.0 Hz, 2H), 5.24 (s, 2H), 6.91 (d, J=8.0 Hz, 1H), 6.97 (d, J=8.3 Hz, 1H), 7.00 (d, J=1.1 Hz, 1H), 7.06-7.10 (m, 1H), 7.74 (d, J=8.0 Hz, 1H), 8.25 (s, 1H), 10.43 (s, 1H).

Reference Example 188

4-[2-(5-ethoxypyridin-2-yl)ethyl]-2-hydroxybenzaldehyde

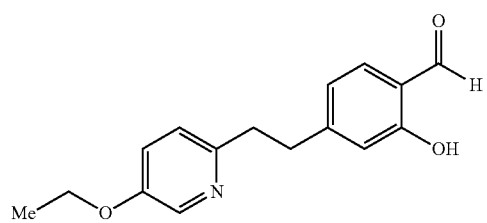 [SMILES: CCOc1ccc(CCc2ccc(C=O)c(O)c2)nc1]

Using 4-[2-(5-ethoxypyridin-2-yl)ethyl]-2-(methoxymethoxy)benzaldehyde (682 mg, 2.16 mmol) obtained in Reference Example 187, an operation in the same manner as in Reference Example 50 was performed to give the title compound (557 mg, yield 95%) as an oil.

¹H NMR (CDCl₃) δ 1.39 (t, J=7.0 Hz, 3H), 3.01-3.07 (m, 4H), 4.06 (q, J=7.0 Hz, 2H), 6.81-6.85 (m, 2H), 6.97 (d, J=8.5

Hz, 1H), 7.06-7.10 (m, 1H), 7.43 (d, J=7.9 Hz, 1H), 8.24 (d, J=2.6 Hz, 1H), 9.83 (s, 1H), 11.02 (s, 1H).

Reference Example 189

1-{6-[2-(5-ethoxypyridin-2-yl)ethyl]-1-benzofuran-2-yl}ethanone

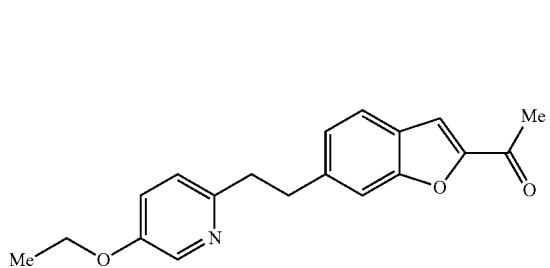 [SMILES: CCOc1ccc(CCc2ccc3cc(C(C)=O)oc3c2)nc1]

Using 4-[2-(5-ethoxypyridin-2-yl)ethyl]-2-hydroxybenzaldehyde (557 mg, 2.06 mmol) obtained in Reference Example 188, an operation in the same manner as in Reference Example 51 was performed to give the title compound (594 mg, yield 93%) as an oil.

$^1$H NMR (CDCl$_3$) δ 1.43 (t, J=7.0 Hz, 3H), 2.59 (s, 3H), 3.05-3.11 (m, 2H), 3.15-3.21 (m, 2H), 4.06 (q, J=7.0 Hz, 2H), 6.96 (d, J=8.35 Hz, 1H), 7.07 (dd, J=8.5, 3.0 Hz, 1H), 7.16 (dd, J=8.1, 1.3 Hz, 1H), 7.35 (s, 1H), 7.46 (d, J=1.3 Hz, 1H), 7.59 (d, J=8.1 Hz, 1H), 8.25 (d, J=3.0 Hz, 1H).

Reference Example 190

1-{6-[2-(5-ethoxypyridin-2-yl)ethyl]-1-benzofuran-2-yl}ethanol

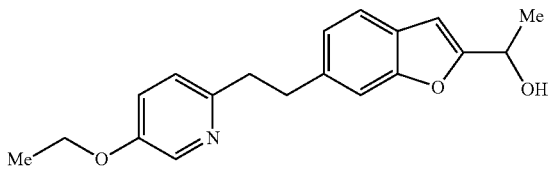 [SMILES: CCOc1ccc(CCc2ccc3cc(C(C)O)oc3c2)nc1]

Using 1-{6-[2-(5-ethoxypyridin-2-yl)ethyl]-1-benzofuran-2-yl}ethanone (594 mg, 1.92 mmol) obtained in Reference Example 189, an operation in the same manner as in Reference Example 52 was performed to give the title compound (525 mg, yield 88%) as an oil.

$^1$H NMR (CDCl$_3$) δ 1.42 (t, J=7.0 Hz, 3H), 1.63 (d, J=6.6 Hz, 3H), 3.03-3.16 (m, 4H), 4.05 (q, J=7.0 Hz, 2H), 4.96-5.03 (m, 1H), 6.55 (s, 1H), 6.97 (d, J=8.5 Hz, 1H), 7.03-7.09 (m, 2H), 7.26-7.28 (m, 1H), 7.41 (d, J=7.9 Hz, 1H), 8.25 (d, J=2.8 Hz, 1H).

Reference Example 191

2-{2-[2-(1-azidoethyl)-1-benzofuran-6-yl]ethyl}-5-ethoxypyridine

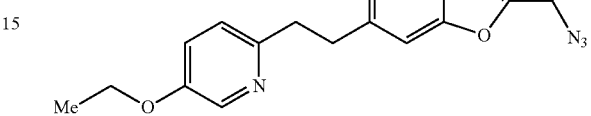

Using 1-{6-[2-(5-ethoxypyridin-2-yl)ethyl]-1-benzofuran-2-yl}ethanol (525 mg, 1.69 mmol) obtained in Reference Example 190, an operation in the same manner as in Reference Example 28 was performed to give the title compound (512 mg, yield 90%) as an oil.

$^1$H NMR (CDCl$_3$) δ 1.43 (t, J=7.0 Hz, 3H), 1.65 (d, J=6.6 Hz, 3H), 3.03-3.17 (m, 4H), 4.06 (q, J=7.0 Hz, 2H), 4.67 (q, J=6.8 Hz, 1H), 6.61 (s, 1H), 6.98 (d, J=8.3 Hz, 1H), 7.06-7.10 (m, 2H), 7.30 (s, 1H), 7.43 (d, J=8.0 Hz, 1H), 8.26 (d, J=2.5 Hz, 1H).

Reference Example 192 methyl 4-{[N-(tert-butoxycarbonyl)alanyl]amino}-3-hydroxybenzoate

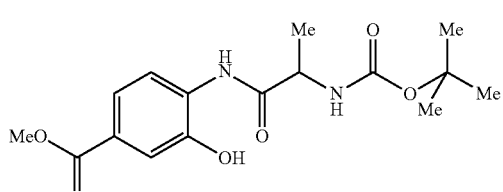

Using N-(tert-butoxycarbonyl)-D,L-alanine (3.74 g, 19.7 mmol), 2-methylpropyl chlorocarbonate (2.56 mL, 19.7 mmol) and methyl 4-amino-3-hydroxybenzoate (3.00 g, 19.7 mmol), a method in the same manner as in Reference Example 105 was performed, and the obtained residue was triturated with ethyl acetate to give the title compound (2.94 g, yield 48%).

¹H NMR (CDCl₃) δ 1.46-1.48 (m, 12H), 3.89 (s, 3H), 4.39 (m, 1H), 5.02 (br, 1H), 7.39 (m, 1H), 7.56 (dd, J=1.8, 8.4 Hz, 1H), 7.65 (d, J=1.8 Hz, 1H), 8.73 (br, 1H), 8.96 (br, 1H).

Reference Example 193 methyl 4-(alanylamino)-3-hydroxybenzoate hydrochloride

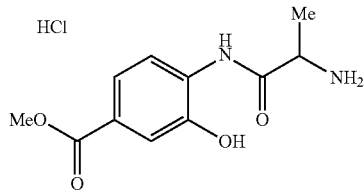 [SMILES: COC(=O)c1ccc(NC(=O)C(C)N)c(O)c1 ; Cl]

Using methyl 4-{[N-(tert-butoxycarbonyl)alanyl]amino}-3-hydroxybenzoate (2.93 g, 8.66 mmol) obtained in Reference Example 192, a method in the same manner as in Reference Example 106 was performed, and the obtained residue was triturated with diisopropyl ether to give the title compound (2.38 g, quantitative). This was used for the next step without purification.

Reference Example 194 methyl 4-[(N-acetylalanyl)amino]-3-hydroxybenzoate

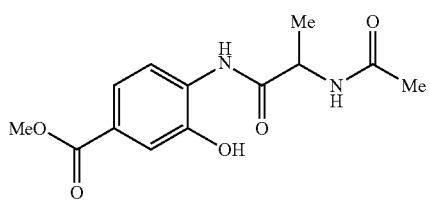 [SMILES: COC(=O)c1ccc(NC(=O)C(C)NC(C)=O)c(O)c1]

Using methyl 4-(alanylamino)-3-hydroxybenzoate hydrochloride (2.38 g, 8.66 mmol) obtained in Reference Example 193 and acetic anhydride (0.823 mL, 8.66 mmol), a method in the same manner as in Reference Example 107 was performed, and the obtained residue was triturated with ethyl acetate to give the title compound (1.70 g, yield from methyl 4-(alanylamino)-3-hydroxybenzoate hydrochloride 70%).

¹H NMR (DMSO-d₆) δ 1.28 (d, J=7.2 Hz, 3H), 1.88 (s, 3H), 3.80 (s, 3H), 4.50 (m, 1H), 7.39-7.44 (m, 2H), 8.15 (d, J=8.1 Hz, 1H), 8.34 (d, J=6.9 Hz, 1H), 9.23 (s, 1H), 10.43 (s, 1H).

Reference Example 195 methyl 2-[1-(acetylamino)ethyl]-1,3-benzoxazole-6-carboxylate

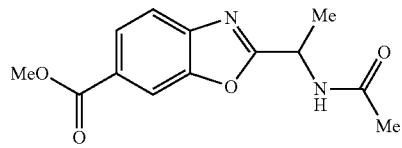 [SMILES: COC(=O)c1ccc2nc(C(C)NC(C)=O)oc2c1]

A solution of methyl 4-[(N-acetylalanyl)amino]-3-hydroxybenzoate (1.69 g, 6.03 mmol) obtained in Reference Example 194 and p-toluenesulfonic acid monohydrate (115 mg, 0.603 mmol) in toluene (30 mL) was heated under reflux using the Dean-Stark apparatus for 16 hr. After being allowed to cool to room temperature, the mixture was diluted with ethyl acetate and THF, and washed with 10% aqueous potassium carbonate solution and saturated brine. This solution was applied to basic silica gel column chromatography (ethyl acetate). The solvent was evaporated under reduced pressure, and the obtained residue was triturated with ethyl acetate-diisopropyl ether (1:2) to give the title compound (657 mg, yield 42%).

¹H NMR (CDCl₃) δ 1.67 (d, J=6.9 Hz, 3H), 2.10 (s, 3H), 3.96 (s, 3H), 5.45 (m, 1H), 6.25 (m, 1H), 7.69-7.72 (m, 1H), 8.05 (dd, J=1.5, 8.4 Hz, 1H), 8.21 (m, 1H).

Reference Example 196

N-{1-[6-(hydroxymethyl)-1,3-benzoxazol-2-yl]ethyl}acetamide

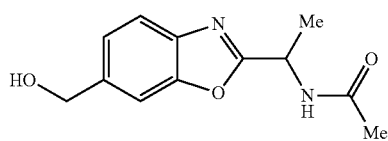 [SMILES: CC(=O)NC(C)c1nc2ccc(CO)cc2o1]

Using methyl 2-[1-(acetylamino)ethyl]-1,3-benzoxazole-6-carboxylate (300 mg, 1.14 mmol) obtained in Reference Example 195 and lithium aluminum hydride (86.8 mg, 2.29 mmol) and in the same manner as in Reference Example 109, the title compound (22.2 mg, yield 8.3%) as an oil.

¹H NMR (CDCl₃) δ 1.63 (d, J=6.9 Hz, 3H), 2.08 (s, 3H), 4.80 (s, 2H), 5.40 (m, 1H), 6.46 (br, 1H), 7.30 (m, 1H), 7.53 (s, 1H), 7.60 (d, J=8.4 Hz, 1H).

Reference Example 197 methyl 4-amino-3-{[N-(tert-butoxycarbonyl)alanyl]amino}benzoate

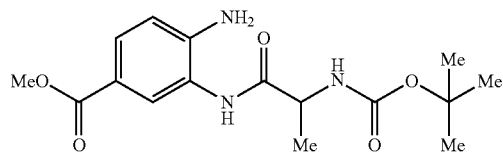 [SMILES: COC(=O)c1ccc(N)c(NC(=O)C(C)NC(=O)OC(C)(C)C)c1]

To a solution of N-(tert-butoxycarbonyl)-D,L-alanine (3.76 g, 19.9 mmol) and triethylamine (2.76 mL, 19.9 mmol) in THF (25 mL) was added 2-methylpropyl chlorocarbonate (2.58 mL, 19.9 mmol) under ice-cooling, and the mixture was stirred for 30 min. To this solution was added dropwise a solution of methyl 3,4-diaminobenzoate (3.00 g, 18.1 mmol) in THF (15 mL) under a nitrogen atmosphere, and the mixture was stirred at room temperature for 1 hr. The reaction mixture was diluted with ethyl acetate, and the mixture was washed with 10% aqueous potassium carbonate solution and saturated brine, and dried over anhydrous sodium sulfate. This solution was applied to basic silica gel column chromatography (ethyl acetate). The solvent was evaporated under reduced pressure, and the obtained residue was triturated with ethyl acetate to give the title compound (4.21 g, yield 69%).

¹H NMR (DMSO-d₆) δ 1.27 (d, J=7.2 Hz, 3H), 1.39 (s, 9H), 3.74 (s, 3H), 4.08 (m, 1H), 5.74 (br, 2H), 6.71 (d, J=8.4 Hz, 1H), 7.14 (d, J=6.3 Hz, 1H), 7.53 (dd, J=1.8, 8.4 Hz, 1H), 7.70 (s, 1H), 9.19 (s, 1H).

Reference Example 198 methyl 2-{1-[(tert-butoxycarbonyl)amino]ethyl}-1H-benzoimidazole-5-carboxylate

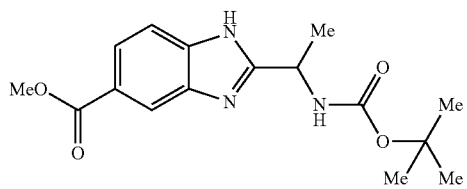 [SMILES: COC(=O)c1ccc2[nH]c(C(C)NC(=O)OC(C)(C)C)nc2c1]

A solution of methyl 4-amino-3-{[N-(tert-butoxycarbonyl)alanyl]amino}benzoate (4.20 g, 12.4 mmol) obtained in Reference Example 197 in acetic acid (30 mL) was stirred under heating at 80° C. for 16 hr. The reaction mixture was allowed to cool to room temperature, and concentrated under reduced pressure. The residue was dissolved in ethyl acetate, and the solution was washed with 10% aqueous potassium carbonate solution and saturated brine, and dried over anhydrous sodium sulfate. This solution was applied to basic silica gel column chromatography (ethyl acetate). The solvent was evaporated under reduced pressure, and the obtained residue was triturated with hexane to give the title compound (3.16 g, yield 79%).

¹H NMR (DMSO-d₆) δ 1.47 (sx2, 9H), 1.75 (d, J=6.9 Hz, 3H), 3.93 (sx2, 3H), 5.00 (m, 1H), 5.15 (m, 1H), 7.42, 7.73 (m, 1H), 7.93-7.99 (m, 1H), 8.15, 8.45 (m, 1H), 10.45 (m, 1H).

Reference Example 199 tert-butyl {1-[5-(hydroxymethyl)-1H-benzimidazol-2-yl]ethyl}carbamate

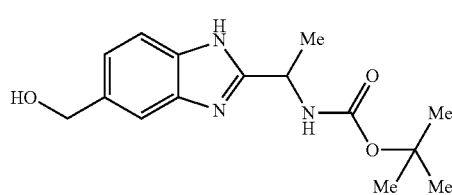 [SMILES: CC(NC(=O)OC(C)(C)C)c1nc2cc(CO)ccc2[nH]1]

Using methyl 2-{1-[(tert-butoxycarbonyl)amino]ethyl}-1H-benzoimidazole-5-carboxylate (500 mg, 1.57 mmol) obtained in Reference Example 198 and lithium aluminum hydride (119 mg, 3.13 mmol) and in the same manner as in Reference Example 85, the title compound (409 mg, yield 90%) was obtained as an oil.

¹H NMR (CDCl₃) δ 1.45 (sx2, 9H), 1.69 (m, 3H), 4.75 (s, 2H), 4.97 (m, 1H), 5.33 (br, 1H), 7.17-7.20 (m, 1H), 7.30-7.34 (m, 1H), 7.65 (m, 1H), 10.45 (m, 1H).

Reference Example 200

1-{5-[(4-ethoxyphenoxy)methyl]-1H-benzimidazol-2-yl}ethanamine dihydrochloride

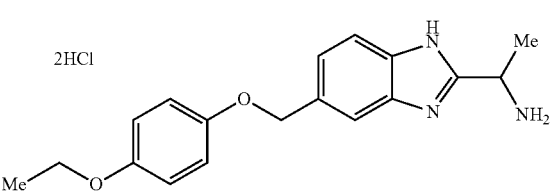 [SMILES: CCOc1ccc(OCc2ccc3[nH]c(C(C)N)nc3c2)cc1]

Using tert-butyl (1-{5-[(4-ethoxyphenoxy)methyl]-1H-benzimidazol-2-yl}ethyl)carbamate (86.9 mg, 0.211 mmol) obtained in Example 59, a method in the same manner as in Reference Example 106 was performed, and the obtained residue was triturated with ethyl acetate to give the title compound (56.9 mg, yield 70%). This was used for the next step without purification.

Reference Example 202

1-[5-(benzyloxy)-1H-benzimidazol-2-yl]ethanamine dihydrochloride

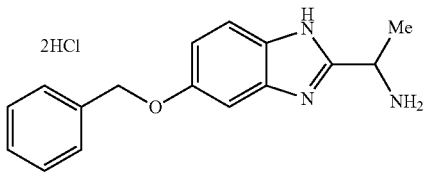 [SMILES: CC(N)c1nc2cc(OCc3ccccc3)ccc2[nH]1]

Using tert-butyl {1-[5-(benzyloxy)-1H-benzimidazol-2-yl]ethyl}carbamate (400 mg, 1.09 mmol) obtained in the below-mentioned Example 104, a method in the same manner as in Reference Example 106 was performed, and the obtained residue was triturated with diisopropyl ether to give the title compound (370 mg, quantitative). This was used for the next step without purification.

Reference Example 204

N-[1-(5-hydroxy-1H-benzimidazol-2-yl)ethyl]acetamide

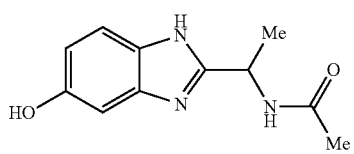 [SMILES: CC(=O)NC(C)c1nc2cc(O)ccc2[nH]1]

A solution of N-{1-[5-(benzyloxy)-1H-benzimidazol-2-yl]ethyl}acetamide (151 mg, 0.488 mmol) obtained in the below-mentioned Example 105 and 10% palladium carbon (50% water-containing product, 500 mg) in methanol (5 mL) was stirred under a hydrogen atmosphere for 16 hr. The reaction mixture was filtered through celite, and the solvent was evaporated under reduced pressure. The obtained residue was purified by basic silica gel column chromatography (methanol), and triturated with diisopropyl ether to give the title compound (98.6 mg, yield 92%).

$^1$H NMR (DMSO-$d_6$) δ 1.45 (d, J=7.2 Hz, 3H), 1.87 (s, 3H), 5.06 (m, 1H), 6.59 (dd, J=2.1, 8.4 Hz, 1H), 6.79 (d, J=2.1 Hz, 1H), 7.25 (d, J=8.4 Hz, 1H), 8.38 (d, J=7.8 Hz, 1H).

Reference Example 205

1-{5-[(4-ethoxybenzyl)oxy]-1-benzofuran-2-yl}ethanol

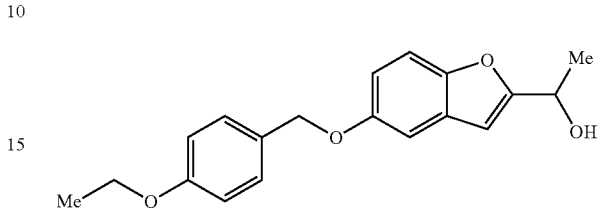

To a solution of 1-(5-hydroxy-1-benzofuran-2-yl)ethanone (2.40 g, 13.7 mmol) in anhydrous DMF (1 mL) were added 4-ethoxybenzyl chloride (2.81 g, 16.5 mmol) and potassium carbonate (3.78 g, 27.4 mmol) and the mixture was stirred at 50° C. overnight. Saturated brine was added thereto, and the mixture was extracted three times with ethyl acetate. The extract was washed with saturated brine, and dried over anhydrous magnesium sulfate. The solvent was evaporated under reduced pressure to give 1-{5-[(4-ethoxybenzyl)oxy]-1-benzofuran-2-yl}ethanone (6.95 g). This was directly used for the next reaction.

To a solution of the obtained 1-{5-[(4-ethoxybenzyl)oxy]-1-benzofuran-2-yl}ethanone (6.95 g) in methanol (50 mL) was added sodium borohydride (1.04 g, 27.4 mmol) by small portions, and the mixture was stirred at room temperature for 30 min. Water was added to the reaction mixture, and the solvent was evaporated. Ethyl acetate was added thereto, and the mixture was washed with water and saturated brine, and dried over anhydrous magnesium sulfate. The solvent was evaporated under reduced pressure, and the obtained residue was purified by silica gel column chromatography (hexane to hexane:ethyl acetate=3:2) to give the title compound (2.87 g, yield 67%).

$^1$H NMR (CDCl$_3$) δ 1.42 (t, J=7.0 Hz, 3H), 1.62 (d, J=6.6 Hz, 3H), 2.02 (d, J=5.1 Hz, 1H), 4.04 (q, J=7.0 Hz, 2H), 4.92-5.04 (m, 1H), 5.00 (s, 2H), 6.54 (s, 1H), 6.85-6.93 (m, 2H), 6.95 (d, J=2.5 Hz, 1H), 7.07 (d, J=2.6 Hz, 1H), 7.29-7.41 (m, 3H).

Reference Example 206

2-(1-azidoethyl)-5-[(4-ethoxybenzyl)oxy]-1-benzofuran

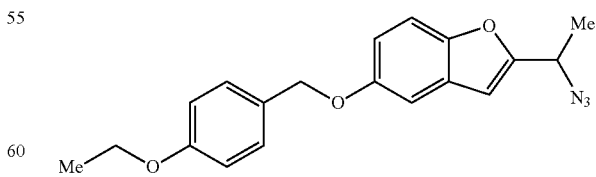

Using 1-{5-[(4-ethoxybenzyl)oxy]-1-benzofuran-2-yl}ethanol (2.87 g, 9.19 mmol) obtained in Reference Example 205, DMF (20 methanesulfonyl chloride (1.06 mL, 13.4 mmol) and triethylamine (2.73 mL, 18.4 mmol), an operation in the same manner as in Reference Example 22 was performed to give 2-(1-azidoethyl)-5-[(4-ethoxybenzyl)oxy]-1-benzofuran (4.62 g). This was used for the next reaction without purification.

Reference Example 207

1-{5-[(4-ethoxybenzyl)oxy]-1-benzofuran-2-yl}ethanamine

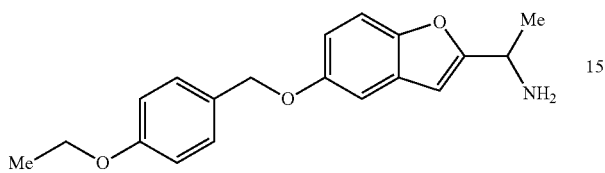

Using 2-(1-azidoethyl)-5-[(4-ethoxybenzyl)oxy]-1-benzofuran (4.62 g) obtained in Reference Example 206, THF (400 mL), triphenylphosphine (20.9 g, 79.8 mmol) and water (40 mL), an operation in the same manner as in Reference Example 25 was performed to give the title compound (1.42 g, yield 50%).

$^1$H NMR (CDCl$_3$) δ 1.42 (t, J=7.0 Hz, 3H), 1.50 (d, J=6.8 Hz, 3H), 4.04 (q, J=7.0 Hz, 2H), 4.17 (q, J=6.8 Hz, 1H), 5.00 (s, 2H), 6.42 (s, 1H), 6.86-6.94 (m, 3H), 7.05 (d, J=2.4 Hz, 2H), 7.31 (d, J=8.9 Hz, 1H), 7.36 (d, J=8.6 Hz, 2H).

Reference Example 208 methyl 4-(2,3-dihydro-1-benzofuran-5-ylethynyl)-2-(methoxymethoxy)benzoate

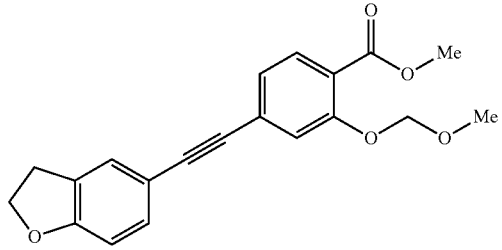 [SMILES: COCOc1cc(C#Cc2ccc3c(c2)CCO3)ccc1C(=O)OC]

Using methyl 2-hydroxy-4-iodobenzoate (1.52 g, 5.46 mmol) and 5-ethynyl-2,3-dihydro-1-benzofuran (944 mg, 6.55 mmol), an operation in the same manner as in Reference Example 47 was performed to give the title compound (1.13 g, yield 61%) as a yellow solid.

$^1$H NMR (CDCl$_3$) δ 3.22 (t, J=8.7 Hz, 2H), 3.54 (s, 3H), 3.89 (s, 3H), 4.61 (t, J=8.7 Hz, 2H), 5.28 (s, 2H), 6.76 (d, J=8.3 Hz, 1H), 7.16 (dd, J=8.0, 1.5 Hz, 1H), 7.31-7.38 (m, 3H), 7.76 (d, J=8.0 Hz, 1H).

Reference Example 209

{4-[2-(2,3-dihydro-1-benzofuran-5-yl)ethyl]-2-(methoxymethoxy)phenyl}methanol

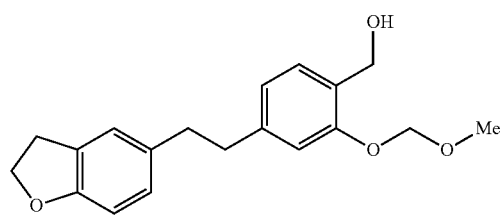 [SMILES: COCOc1cc(CCc2ccc3c(c2)CCO3)ccc1CO]

Using methyl 4-(2,3-dihydro-1-benzofuran-5-ylethynyl)-2-(methoxymethoxy)benzoate (1.13 g, 3.34 mmol) obtained in Reference Example 208, an operation in the same manner as in Reference Example 48 was performed to give the title compound (820 mg, yield 78%) as an oil.

$^1$H NMR (CDCl$_3$) δ 2.78-2.90 (m, 4H), 3.17 (t, J=8.7 Hz, 2H), 3.49 (s, 3H), 4.54 (t, J=8.7 Hz, 2H), 4.67 (d, J=6.8 Hz, 2H), 5.20 (s, 2H), 6.69 (d, J=8.0 Hz, 1H), 6.83 (dd, J=7.6, 1.1 Hz, 1H), 6.90-6.92 (m, 2H), 7.02 (s, 1H), 7.21 (d, J=7.6 Hz, 1H).

Reference Example 210

4-[2-(2,3-dihydro-1-benzofuran-5-yl)ethyl]-2-(methoxymethoxy)benzaldehyde

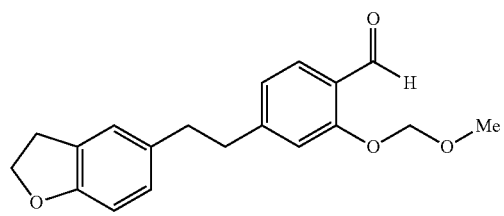 [SMILES: COCOc1cc(CCc2ccc3c(c2)CCO3)ccc1C=O]

Using {4-[2-(2,3-dihydro-1-benzofuran-5-yl)ethyl]-2-(methoxymethoxy)phenyl}methanol (820 mg, 2.61 mmol) obtained in Reference Example 209, an operation in the same manner as in Reference Example 49 was performed to give the title compound (767 mg, yield 93%) as an oil.

¹H NMR (CDCl₃) δ 2.81-2.94 (m, 4H), 3.17 (t, J=8.7 Hz, 2H), 3.51 (s, 3H), 4.54 (t, J=8.7 Hz, 2H), 5.25 (s, 2H), 6.89 (d, J=8.0 Hz, 1H), 6.86-6.91 (m, 2H), 6.95-6.99 (m, 2H), 7.75 (d, J=8.0 Hz, 1H), 10.44 (s, 1H).

Reference Example 211

4-[2-(2,3-dihydro-1-benzofuran-5-yl)ethyl]-2-hydroxybenzaldehyde

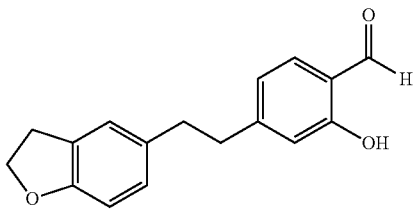 [SMILES: O=Cc1ccc(CCc2ccc3c(c2)CCO3)cc1O]

Using 4-[2-(2,3-dihydro-1-benzofuran-5-yl)ethyl]-2-(methoxymethoxy)benzaldehyde (767 mg, 2.45 mmol) obtained in Reference Example 210, an operation in the same manner as in Reference Example 50 was performed to give the title compound (457 mg, yield 69%) as a white solid.

¹H NMR (CDCl₃) δ 2.81-2.93 (m, 4H), 3.17 (t, J=8.7 Hz, 2H), 4.55 (t, J=8.7 Hz, 2H), 6.69 (d, J=8.1 Hz, 1H), 6.80-6.83 (m, 2H), 6.89 (dd, J=8.1, 1.7 Hz, 1H), 6.99 (s, 1H), 7.44 (d, J=8.3 Hz, 1H), 9.84 (s, 1H), 11.04 (s, 1H).

Reference Example 212

1-{6-[2-(2,3-dihydro-1-benzofuran-5-yl)ethyl]-1-benzofuran-2-yl}ethanone

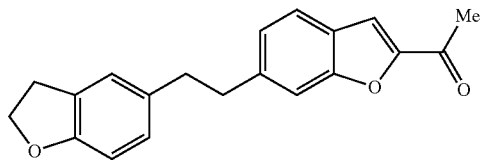 [SMILES: CC(=O)c1cc2ccc(CCc3ccc4c(c3)CCO4)cc2o1]

Using 4-[2-(2,3-dihydro-1-benzofuran-5-yl)ethyl]-2-hydroxybenzaldehyde (457 mg, 1.71 mmol) obtained in Reference Example 211, an operation in the same manner as in Reference Example 51 was performed to give the title compound (523 mg, quantitative) as an oil.

¹H NMR (CDCl₃) δ 2.61 (s, 3H), 2.87-2.92 (m, 2H), 3.00-3.05 (m, 2H), 3.17 (t, J=8.7 Hz, 2H), 4.55 (t, J=8.7 Hz, 2H), 6.69 (d, J=8.1 Hz, 1H), 6.89 (d, J=8.1 Hz, 1H), 7.01 (s, 1H), 7.14 (dd, J=8.1, 1.5 Hz, 1H), 7.34 (s, 1H), 7.47 (d, J=1.5 Hz, 1H), 7.60 (d, J=7.9 Hz, 1H).

Reference Example 213

1-{6-[2-(2,3-dihydro-1-benzofuran-5-yl)ethyl]-1-benzofuran-2-yl}ethanol

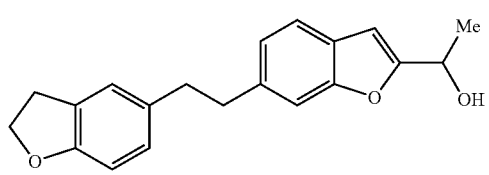 [SMILES: CC(O)c1cc2ccc(CCc3ccc4c(c3)CCO4)cc2o1]

Using 1-{6-[2-(2,3-dihydro-1-benzofuran-5-yl)ethyl]-1-benzofuran-2-yl}ethanone (523 mg, 1.71 mmol) obtained in Reference Example 212, an operation in the same manner as in Reference Example 52 was performed to give the title compound (452 mg, yield 86%) as an oil.

¹H NMR (CDCl₃) δ 1.63 (d, J=6.6 Hz, 3H), 2.85-2.91 (m, 2H), 2.95-3.01 (m, 2H), 3.18 (t, J=8.7 Hz, 2H), 4.55 (t, J=8.7 Hz, 2H), 4.97-5.05 (m, 1H), 6.57 (s, 1H), 6.70 (d, J=8.1 Hz, 1H), 6.92 (d, J=6.4 Hz, 1H), 7.03-7.06 (m, 2H), 7.26-7.27 (m, 1H), 7.43 (d, J=7.9 Hz, 1H).

Reference Example 214

2-(1-azidoethyl)-6-[2-(2,3-dihydro-1-benzofuran-5-yl)ethyl]-1-benzofuran

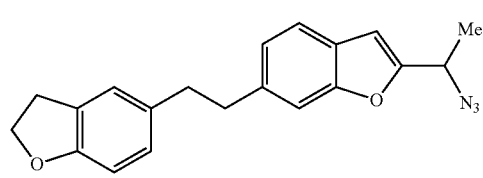 [SMILES: CC(N=[N+]=[N-])c1cc2ccc(CCc3ccc4c(c3)CCO4)cc2o1]

Using 1-{6-[2-(2,3-dihydro-1-benzofuran-5-yl)ethyl]-1-benzofuran-2-yl}ethanol (452 mg, 1.47 mmol) obtained in Reference Example 213, an operation in the same manner as in Reference Example 28 was performed to give the title compound (394 mg, yield 80%) as an oil.

¹H NMR (CDCl₃) δ 1.65 (d, J=6.8 Hz, 3H), 2.85-2.91 (m, 2H), 2.96-3.02 (m, 2H), 3.17 (t, J=8.7 Hz, 2H), 4.55 (t, J=8.7 Hz, 2H), 4.68 (q, J=6.8 Hz, 1H), 6.62 (s, 1H), 6.70 (d, J=8.1

Hz, 1H), 6.92 (d, J=8.3 Hz, 1H), 7.03 (s, 1H), 7.06 (dd, J=8.0, 1.2 Hz, 1H), 7.29 (s, 1H), 7.45 (d, J=7.9 Hz, 1H).

Reference Example 215 methyl 2-{[tert-butyl(dimethyl)silyl]oxy}-4-{[4-(methoxymethoxy)phenyl]ethynyl}benzoate

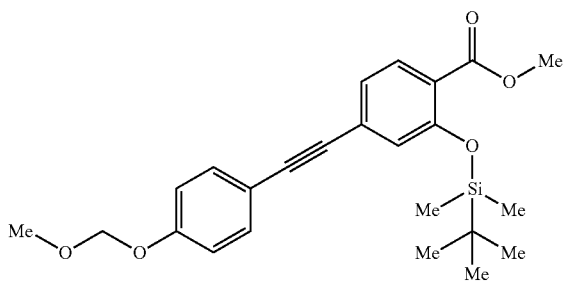 [SMILES: COCOc1ccc(C#Cc2ccc(C(=O)OC)c(O[Si](C)(C)C(C)(C)C)c2)cc1]

To a solution of methyl 2-hydroxy-4-iodobenzoate (6.55 g, 23.6 mmol), 1-ethynyl-4-(methoxymethoxy)benzene (4.58 g, 28.3 mmol) and copper(I) iodide (450 mg, 2.36 mmol) in triethylamine (50 mL) was added bis(triphenylphosphine)palladium(II) chloride (1.66 mg, 2.36 mmol), and the mixture was stirred under an argon stream at room temperature for 30 min. The reaction mixture was diluted with ethyl acetate, and the mixture was washed with water, and dried over anhydrous magnesium sulfate. The solvent was evaporated under reduced pressure and the obtained residue was dissolved in DMF (30 mL). Imidazole (2.42 g, 35.4 mmol) and tert-butyl(chloro)dimethylsilane (4.27 g, 28.3 mmol) were added thereto, and the mixture was stirred at room temperature for 1.5 hr. Water was added to the reaction mixture, and the mixture was extracted with ethyl acetate. The extract was washed twice with saturated brine, and dried over anhydrous magnesium sulfate. The solvent was evaporated under reduced pressure and the obtained residue was purified by silica gel column chromatography (hexane:ethyl acetate=19:1 to 3:2) to give the title compound (8.50 g, yield 84%) as an oil.

$^1$H NMR (CDCl$_3$) δ 0.28 (s, 6H), 1.03 (s, 9H), 3.50 (s, 3H), 3.87 (s, 3H), 5.21 (s, 2H), 6.99 (d, J=1.5 Hz, 1H), 7.03 (d, J=8.7 Hz, 2H), 7.13 (dd, J=8.3, 1.5 Hz, 1H), 7.49 (d, J=8.7 Hz, 2H), 7.74 (d, J=8.3 Hz, 1H).

Reference Example 216

2-(hydroxymethyl)-5-[2-[4-(methoxymethoxy)phenyl]ethyl]phenol

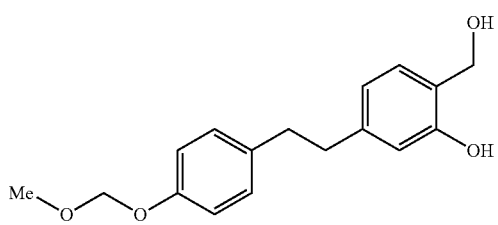 [SMILES: COCOc1ccc(CCc2ccc(CO)c(O)c2)cc1]

Using methyl 2-{[tert-butyl(dimethyl)silyl]oxy}-4-{[4-(methoxymethoxy)phenyl]ethynyl}benzoate (8.50 g, 20.0 mmol) obtained in Reference Example 215, an operation in the same manner as in Reference Example 48 was performed to give the title compound (890 mg, yield 14%) as a white solid.

$^1$H NMR (CDCl$_3$) δ 2.80-2.87 (m, 4H), 3.48 (s, 3H), 4.82-4.87 (m, 2H), 5.15 (s, 2H), 6.67 (dd, J=7.6, 1.9 Hz, 1H), 6.73 (s, 1H), 6.92-6.97 (m, 3H), 7.09 (d, J=8.7 Hz, 2H).

Reference Example 217

2-hydroxy-4-{2-[4-(methoxymethoxy)phenyl]ethyl}benzaldehyde

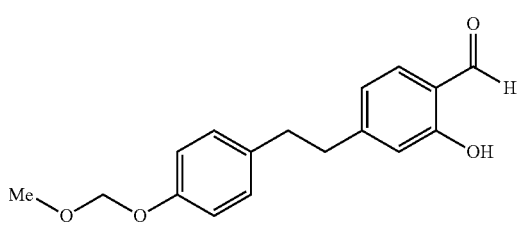

To a solution of 2-(hydroxymethyl)-5-{2-[4-(methoxymethoxy)phenyl]ethyl}phenol (890 mg, 3.09 mmol) obtained in Reference Example 216 in methylene chloride (20 mL) was added manganese dioxide (1.35 g, 15.5 mmol), and the mixture was stirred at room temperature for 30 min. The reaction mixture was filtered. The solvent was evaporated under reduced pressure and the obtained residue was purified by silica gel column chromatography (hexane:ethyl acetate-9:1 to 1:1) to give the title compound (514 mg, yield 58%) as an oil.

$^1$H NMR (CDCl$_3$) δ 2.86-2.95 (m, 4H), 3.48 (s, 3H), 5.15 (s, 2H), 6.77-6.85 (m, 2H), 6.95 (d, J=8.7 Hz, 2H), 7.07 (d, J=8.7 Hz, 2H), 7.44 (d, J=8.3 Hz, 1H), 9.84 (s, 1H), 11.03 (s, 1H).

Reference Example 218

1-(6-{2-[4-(methoxymethoxy)phenyl]ethyl}-1-benzofuran-2-yl)ethanol

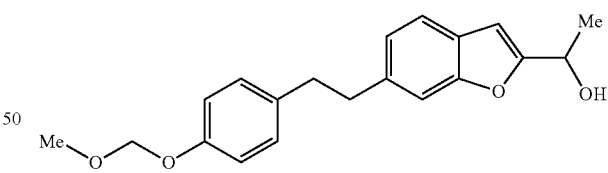

To a solution of 2-hydroxy-4-{2-[4-(methoxymethoxy)phenyl]ethyl}benzaldehyde (514 mg, 1.79 mmol) obtained in Reference Example 217 in acetonitrile (10 mL) were added potassium carbonate (495 mg, 3.58 mmol) and bromoacetone (0.227 mL, 2.69 mmol), and the mixture was stirred at 80° C. for 2 hr. Water was added to the reaction mixture, and the mixture was extracted twice with ethyl acetate, and the combined organic layer was dried over anhydrous magnesium sulfate. The solvent was evaporated and the obtained residue was purified by basic silica gel column chromatography (ethyl acetate) to give an oil. To a solution of the oil in methanol (10 mL) was added sodium borohydride (67.8 mg, 1.79 mmol), and the mixture was stirred at room temperature for 10 min. To the reaction mixture was added aqueous ammonium chloride solution, and the mixture was extracted twice with ethyl acetate. The combined organic layer was dried over anhydrous magnesium sulfate and the solvent was evaporated. The obtained residue was purified by silica gel column chromatography (hexane:ethyl acetate=4:1 to 1:4) to give the title compound (307 mg, yield 52%) as an oil.

$^1$H NMR (CDCl$_3$) δ 1.63 (d, J=6.4 Hz, 3H), 2.87-2.93 (m, 2H), 2.97-3.03 (m, 2H), 3.48 (s, 3H), 4.96-5.04 (m, 1H), 5.15 (s, 2H), 6.56 (s, 1H), 6.95 (d, J=8.7 Hz, 2H), 7.04 (dd, J=8.0, 1.1 Hz, 1H), 7.10 (d, J=8.7 Hz, 2H), 7.26-7.28 (m, 1H), 7.43 (d, J=8.0 Hz, 1H).

Reference Example 219

2-(1-azidoethyl)-6-{2-[4-(methoxymethoxy)phenyl]ethyl}-1-benzofuran

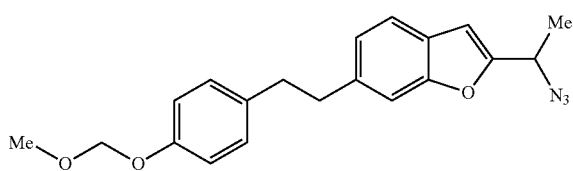 [SMILES: COCOc1ccc(CCc2ccc3cc(C(C)N=[N+]=[N-])oc3c2)cc1]

Using 1-(6-{2-[4-(methoxymethoxy)phenyl]ethyl}-1-benzofuran-2-yl)ethanol (307 mg, 0.941 mmol) obtained in Reference Example 218, an operation in the same manner as in Reference Example 28 was performed to give the title compound (263 mg, yield 79%) as an oil.

$^1$H NMR (CDCl$_3$) δ 1.65 (d, J=7.2 Hz, 3H), 2.87-2.93 (m, 2H), 2.97-3.03 (m, 2H), 3.48 (s, 3H), 4.67 (q, J=7.2 Hz, 1H), 5.15 (s, 2H), 6.82 (s, 1H), 6.96 (d, J=8.7 Hz, 2H), 7.06 (dd, J=8.0, 1.1 Hz, 1H), 7.11 (d, J=8.7 Hz, 2H), 7.29 (s, 1H), 7.44 (d, J=8.0 Hz, 1H).

Reference Example 220

5-bromo-3-iodopyridin-2-ol

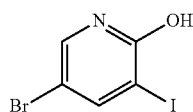

A solution of 5-bromopyridin-2-ol (5.22 g, 30.0 mmol) and N-iodosuccinimide (7.42 g, 33.0 mmol) in acetonitrile (150 mL) was heated under reflux under a nitrogen atmosphere for 1 hr. After being allowed to cool to room temperature, the resulting solid was collected and washed with acetonitrile to give the title compound (7.07 g, yield 79%).

Reference Example 221

2-[(1S)-1-(5-bromofuro[2,3-b]pyridin-2-yl)ethyl]-1H-isoindole-1,3(2H)-dione

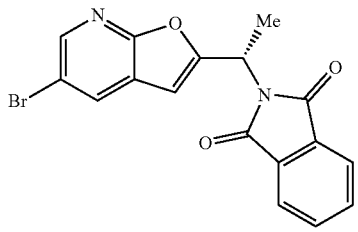 [SMILES: C[C@@H](c1cc2cc(Br)cnc2o1)N1C(=O)c2ccccc2C1=O]

To a solution of 5-bromo-3-iodopyridin-2-ol (1.00 g, 3.33 mmol) obtained in Reference Example 220, 2-((1S)-methylprop-2-yn-1-yl)-1H-isoindole-1,3(2H)-dione (664 mg, 3.33 mmol), copper(I) iodide (127 mg, 0.667 mmol) and triethylamine (0.464 mL, 3.33 mmol) in DMF (6 mL) was added bis(triphenylphosphine)palladium(II) chloride (117 mg, 0.167 mmol), and the mixture was deaerated, and stirred under a nitrogen atmosphere with heating at 60° C. for 16 hr. The reaction mixture was diluted with ethyl acetate, and the mixture was washed with water, 10% aqueous sodium carbonate solution and saturated brine, and dried over anhydrous sodium sulfate. The solution was purified by basic silica gel column chromatography (ethyl acetate). The solvent was evaporated under reduced pressure and the obtained residue was purified by silica gel column chromatography (hexane: ethyl acetate=3:1 to 1:1) to give the title compound (553 mg, yield 45%).

$^1$H NMR (CDCl$_3$) δ 1.93 (d, J=7.2 Hz, 3H), 5.67-5.75 (m, 1H), 6.79 (d, J=1.5 Hz, 1H), 7.58-7.88 (m, 4H), 7.97 (d, J=2.1 Hz, 1H), 8.27 (d, J=2.1 Hz, 1H).

Reference Example 222

N-[(1S)-1-(5-bromofuro[2,3-b]pyridin-2-yl)ethyl]acetamide

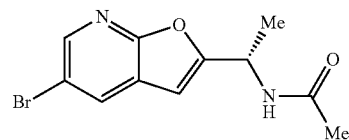

To a solution of 2-[(1S)-1-(5-bromofuro[2,3-b]pyridin-2-yl)ethyl]-1H-isoindole-1,3(2H)-dione (552 mg, 1.49 mmol) obtained in Reference Example 221 in methanol (15 mL) was added hydrazine monohydrate (0.443 mL, 8.92 mmol) and the mixture was stirred at 60° C. for 1 hr. The solvent was evaporated under reduced pressure, ethyl acetate was added thereto and the resulting solid was filtered off. The filtrate was concentrated under reduced pressure, ethyl acetate was added thereto and the resulting solid was filtered off again. The filtrate was concentrated under reduced pressure, and to the obtained residue were added ethyl acetate (13 mL) and acetic anhydride (0.17 mL, 1.78 mmol), and the mixture was stirred at room temperature for 1 hr. The solvent was evaporated under reduced pressure and the obtained solid was washed with diisopropyl ether to give the title compound (359 mg, yield 85%).

$^1$H NMR (CDCl$_3$) δ 1.58 (d, J=6.9 Hz, 3H), 2.02 (s, 3H), 5.32-5.37 (m, 1H), 5.94 (d, J=7.5 Hz, 1H), 6.54 (s, 1H), 7.95 (d, J=2.4 Hz, 1H), 8.30 (d, J=2.4 Hz, 1H).

Reference Example 223

5-bromo-2-iodopyridin-3-ol

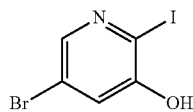

To a solution of 5-bromopyridin-3-ol (2.75 g, 15.8 mmol) and sodium carbonate (3.35 g, 31.6 mmol) in water (45 mL) was added iodine (4.01 g, 15.8 mmol), and the mixture was stirred at room temperature for 1 hr. 6N Hydrochloric acid (7 mL) was added thereto, and the mixture was weakly acidified with 1N hydrochloric acid (about 5 mL) (pH 4). The resulting solid was collected, washed with water and dissolved in ethyl acetate. The solution was washed with saturated brine, and dried over anhydrous sodium sulfate. The solvent was evaporated under reduced pressure and the obtained solid was washed with a small amount of acetonitrile to give the title compound (3.57 g, yield 75%).

$^1$H NMR (DMSO-d$_6$) δ 7.28 (d, J=2.1 Hz, 1H), 8.00 (d, J=2.1 Hz, 1H), 11.39 (br, 1H).

Reference Example 224

2-[(1S)-1-(6-bromofuro[3,2-b]pyridin-2-yl)ethyl]-1H-isoindole-1,3(2H)-dione

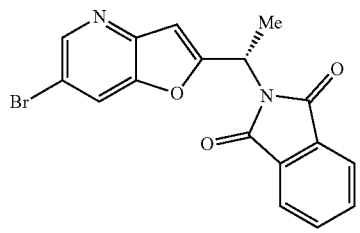 [SMILES: C[C@@H](c1cc2ncc(Br)cc2o1)N1C(=O)c2ccccc2C1=O]

Using 5-bromo-2-iodopyridin-3-ol (1.00 g, 3.33 mmol) obtained in Reference Example 223, 2-((1S)-methylprop-2-yn-1-yl)-1H-isoindole-1,3(2H)-dione (664 mg, 3.33 mmol), copper(I) iodide (127 mg, 0.667 mmol), triethylamine (0.464 mL, 3.33 mmol), DMF (6 mL) and bis(triphenylphosphine) palladium(II) chloride (117 mg, 0.167 mmol), an operation in the same manner as in Reference Example 221 was performed to give the title compound (334 mg, yield 27%).

$^1$H NMR (CDCl$_3$) δ 1.95 (d, J=7.2 Hz, 3H), 5.64-5.72 (m, 1H), 6.92 (m, 1H), 7.71-7.87 (m, 5H), 8.55 (d, J=1.8 Hz, 1H).

Reference Example 225

N-[(1S)-1-(6-bromofuro[3,2-b]pyridin-2-yl)ethyl]acetamide

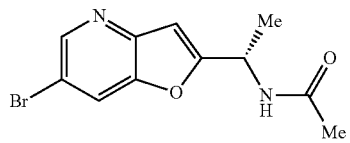 [SMILES: CC(=O)N[C@@H](C)c1cc2ncc(Br)cc2o1]

To a solution of 2-[(1S)-1-(6-bromofuro[3,2-b]pyridin-2-yl)ethyl]-1H-isoindole-1,3(2H)-dione (332 mg, 0.867 mmol) obtained in Reference Example 224 in methanol (9 mL) was added hydrazine monohydrate (0.252 mL, 5.20 mmol), and the mixture was stirred at 60° C. for 1 hr. The solvent was evaporated under reduced pressure, ethyl acetate was added thereto and the resulting solid was filtered off. The filtrate was concentrated under reduced pressure, ethyl acetate was added thereto and the resulting solid was filtered off again. The filtrate was concentrated under reduced pressure, and to the obtained residue were added ethyl acetate (9 mL) and acetic anhydride (0.098 mL, 1.04 mmol), and the mixture was stirred at room temperature for 2 hr. The solvent was evaporated under reduced pressure and the obtained solid was washed with diisopropyl ether to give the title compound (243 mg, yield 99%).

$^1$H NMR (DMSO-d$_6$) δ 1.46 (d, J=7.2 Hz, 3H), 1.88 (s, 3H), 5.08-5.27 (m, 1H), 6.93 (s, 1H), 8.39 (s, 1H), 8.47 (d, J=8.1 Hz, 1H), 8.57 (d, J=1.8 Hz, 1H).

Reference Example 226

2-chloro-4-(cyclopropylmethoxy)benzaldehyde

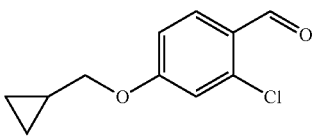 [SMILES: O=Cc1ccc(OCC2CC2)cc1Cl]

A solution of 2-chloro-4-hydroxybenzaldehyde (1.00 g, 6.39 mmol), bromomethylcyclopropane (0.93 mL, 9.58 mmol) and potassium carbonate (1.77 g, 12.8 mmol) in DMF (8 mL) was stirred under heating at 50° C. for 1 day. The reaction mixture was diluted with water, and the mixture was extracted with ethyl acetate. The extract was washed with saturated brine, and dried over anhydrous sodium sulfate. The solvent was evaporated under reduced pressure, and the obtained residue was purified by silica gel column chromatography (hexane:ethyl acetate=4:1 to 3:1) to give the title compound (1.08 g, yield 80%) as an oil.

Reference Example 227

[2-chloro-4-(cyclopropylmethoxy)phenyl]methanol

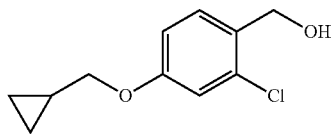 [SMILES: OCc1ccc(OCC2CC2)cc1Cl]

To a solution of 2-chloro-4-(cyclopropylmethoxy)benzaldehyde (1.07 g, 5.08 mmol) obtained in Reference Example 226 in a mixed solvent of methanol (6 mL) and THF (6 mL) was added sodium borohydride (192 mg, 5.08 mmol), and the mixture was stirred at room temperature for 30 min. The reaction mixture was diluted with water, and the mixture was extracted with ethyl acetate. The extract was washed with saturated brine, and dried over anhydrous sodium sulfate. The solvent was evaporated under reduced pressure, and the obtained residue was purified by silica gel column chromatography (hexane:ethyl acetate=9:1 to 7:3) to give the title compound (1.12 g, quantitative) as an oil.

$^1$H NMR (CDCl$_3$) δ 0.32-0.36 (m, 2H), 0.62-0.68 (m, 2H), 1.21-1.31 (m, 1H), 1.84-1.88 (m, 1H), 3.78 (d, J=6.9 Hz, 2H), 4.69 (d, J=6.0 Hz, 2H), 6.80 (dd, J=8.4, 2.7 Hz, 1H), 6.92 (d, J=2.7 Hz, 1H), 7.32 (d, J=8.4 Hz, 1H).

Reference Example 228

N-[1-(6-hydroxy-2,3-dihydro-1-benzofuran-2-yl)ethyl]acetamide

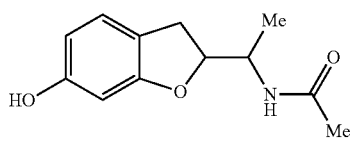

A solution of N-[1-(6-hydroxy-1-benzofuran-2-yl)ethyl]acetamide (3.52 g, 16.1 mmol) obtained in Reference Example 27 and 10% palladium carbon (50% water-containing product, 2.00 g) in THF (80 mL) was stirred under a hydrogen atmosphere (normal pressure) for 3 hr. After filtration, the filtrate was concentrated under reduced pressure, and the obtained residue was purified by silica gel column chromatography (ethyl acetate) to give the title compound (3.44 g, yield 97%) as an oil. This was used for the next reaction without purification.

Reference Example 229

1:1 mixture (less polar mixture) of (2R)-2-[(1R)-1-(acetylamino)ethyl]-2,3-dihydro-1-benzofuran-6-yl trifluoromethanesulfonate and (2S)-2-[(1S)-1-(acetylamino)ethyl]-2,3-dihydro-1-benzofuran-6-yl trifluoromethanesulfonate

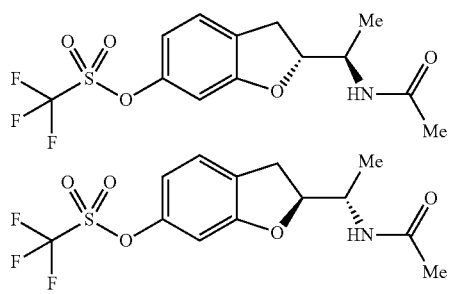

1:1 mixture (more polar mixture) of (2R)-2-[(1S)-1-(acetylamino)ethyl]-2,3-dihydro-1-benzofuran-6-yl trifluoromethanesulfonate and (2S)-2-[(1R)-1-(acetylamino)ethyl]-2,3-dihydro-1-benzofuran-6-yl trifluoromethanesulfonate

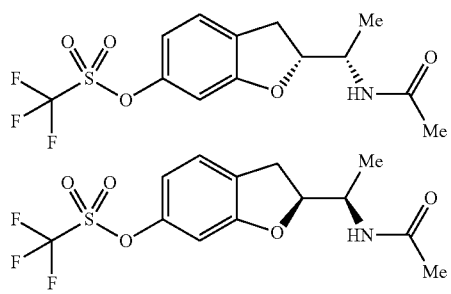

N-[1-(6-Hydroxy-2,3-dihydro-1-benzofuran-2-yl)ethyl] acetamide (3.43 g, 15.5 mmol) obtained in Reference Example 228, triethylamine (3.23 mL, 23.3 mmol) and N-phenylbis(trifluoromethanesulfonimide) (8.3.1 g, 23.3 mmol) in THF (40 mL) was stirred at room temperature for 16 hr. The reaction mixture was diluted with ethyl acetate, and the mixture was washed with 1N hydrochloric acid, 10% aqueous potassium carbonate solution and saturated brine, and dried over anhydrous sodium sulfate. The solution was purified by basic silica gel column chromatography (ethyl acetate). The solvent was evaporated under reduced pressure, and the residue was triturated with diisopropyl ether to give the title compound 1.59 g (less polar compound: yield 29%). The filtrate was purified by silica gel column chromatography (hexane:ethyl acetate=1:1 to ethyl acetate), and the obtained residue was triturated with hexane to give the title compound (2.31 g) (more polar compound: yield 42%).

less polar compound: $^1$H NMR (CDCl$_3$) δ 1.34 (d, J=6.9 Hz, 3H), 1.92 (s, 3H), 3.00-3.24 (m, 2H), 4.34-4.40 (m, 1H), 4.83-4.89 (m, 1H), 5.43 (d, J=10.2 Hz, 1H), 6.68 (d, J=2.1 Hz, 1H), 6.74 (dd, J=8.1, 2.1 Hz, 1H), 7.14 (d, J=8.1 Hz, 1H).

more polar compound: $^1$H NMR (CDCl$_3$) δ 1.12 (d, J=6.9 Hz, 3H), 2.02 (s, 3H), 2.95-3.03 (m, 1H), 3.27-3.36 (m, 1H), 4.20-4.27 (m, 1H), 4.90-4.96 (m, 1H), 5.66 (br, 1H), 6.67 (d, J=2.4 Hz, 1H), 6.74 (dd, J=8.1, 2.4 Hz, 1H), 7.16 (d, J=8.1 Hz, 1H).

Reference Example 230

[4-(cyclopropylmethoxy)-2-fluorophenyl]methanol

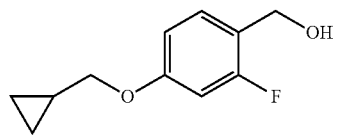 [SMILES: OCc1ccc(OCC2CC2)cc1F]

To a solution of 4-(cyclopropylmethoxy)-2-fluorobenzoic acid (5.00 g, 23.8 mmol) in THF (100 mL) was added dropwise 1 M borane-THF solution (54.7 mL, 54.7 mmol), and the mixture was stirred at room temperature for 3 hr. To the reaction mixture was slowly added dropwise water (100 mL). To this solution was further added water, and the mixture was extracted with ethyl acetate. The extract was washed with 10% aqueous potassium carbonate solution and saturated brine, and dried over anhydrous sodium sulfate. The solution was purified by basic silica gel column chromatography (ethyl acetate), and the obtained residue was triturated with hexane to give the title compound (4.08 g, yield 87%).

$^1$H NMR (CDCl$_3$) δ 0.32-0.37 (m, 2H), 0.62-0.67 (m, 2H), 1.21-1.31 (m, 1H), 1.66-1.70 (m, 1H), 3.77 (d, J=6.9 Hz, 2H), 4.66 (d, J=6.0 Hz, 2H), 6.58-6.69 (m, 2H), 7.23-7.29 (m, 1H).

Reference Example 231

(2S)-2-[(1S)-1-(acetylamino)ethyl]-2,3-dihydro-1-benzofuran-6-yl trifluoromethanesulfonate (retention time longer)

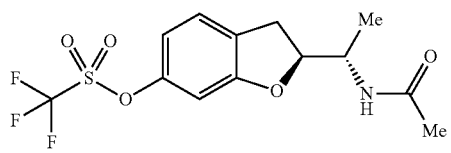 [SMILES: CC(=O)N[C@@H](C)[C@@H]1Cc2ccc(OS(=O)(=O)C(F)(F)F)cc2O1]

(2R)-2-[(1R)-1-(acetylamino)ethyl]-2,3-dihydro-1-benzofuran-6-yl trifluoromethanesulfonate (retention time shorter)

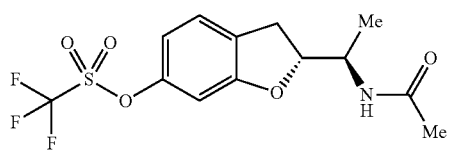 [SMILES: CC(=O)N[C@H](C)[C@H]1Cc2ccc(OS(=O)(=O)C(F)(F)F)cc2O1]

A 1:1 mixture (less polar mixture) (228 mg) (obtained in Reference Example 229) of (2R)-2-[(1R)-1-(acetylamino)ethyl]-2,3-dihydro-1-benzofuran-6-yl trifluoromethanesulfonate and (2S)-2-[(1S)-1-(acetylamino)ethyl]-2,3-dihydro-1-benzofuran-6-yl trifluoromethanesulfonate was optically resolved by high performance liquid chromatography (HPLC) under the following conditions to give two kinds of optically active forms of "retention time longer (110 mg)" and "retention time shorter (113 mg)".

<Preparative HPLC Conditions> column: CHIRALPAK AS (50 mmID×500 mL)

mobile phase: hexane:ethanol=1:1 flow rate: 60 mL/min column temperature: 25° C.

detection: UV 220 nm compound injection volume: 130 mg/40 mL

<HPLC Analysis Conditions> column: CHIRALPAK AS (4.6 mmID×250 mL)

mobile phase: hexane:ethanol=1:1 flow rate: 0.5 mL/min column temperature: 30° C.

detection: UV 220 nm retention time of "retention time longer": 8.8 min retention time of "retention time shorter": 7.1 min Reference Example 232

{[4-(cyclopropylmethoxy)phenyl]ethynyl}(trimethyl)silane

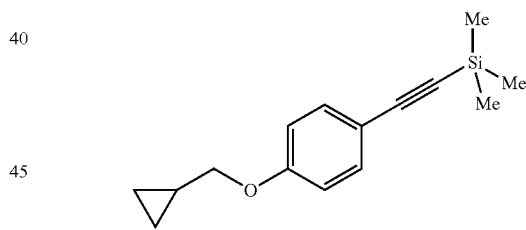

To a solution of 1-(cyclopropylmethoxy)-4-iodobenzene (2.49 g, 9.09 mmol) and copper(I) iodide (86.6 mg, 0.455 mmol) in a mixed solvent of THF-triethylamine (8 mL-2 mL) was added bis(triphenylphosphine)palladium(II) chloride (319 mg, 0.455 mmol), and the mixture was deaerated. Trimethylsilylacetylene (1.54 mL, 10.9 mmol) was added dropwise thereto, and the mixture was stirred under a nitrogen atmosphere for 30 min. The reaction mixture was diluted with ethyl acetate, and the mixture was washed with water and saturated brine, and dried over anhydrous sodium sulfate. The solution was purified by basic silica gel column chromatography (ethyl acetate), and the solvent was evaporated under reduced pressure. The obtained residue was purified by silica gel column chromatography (hexane to hexane:ethyl acetate=9:1) to give the title compound (1.52 g, yield 69%) as an oil.

$^1$H NMR (CDCl$_3$) δ 0.23 (s, 9H), 0.32-0.37 (m, 2H), 0.61-0.67 (m, 2H), 1.23-1.28 (m, 1H), 3.78 (d, J=6.9 Hz, 2H), 6.67-6.82 (m, 2H), 7.35-7.40 (m, 2H).

Reference Example 233

1-(cyclopropylmethoxy)-4-ethynylbenzene

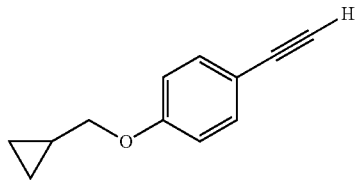 [SMILES: C#Cc1ccc(OCC2CC2)cc1]

To a solution of {[4-(cyclopropylmethoxy)phenyl]ethynyl}(trimethyl)silane (1.52 g, 6.22 mmol) obtained in Reference Example 232 in methanol (8 mL) was added potassium carbonate (1.72 g, 12.4 mmol), and the mixture was stirred at room temperature for 16 hr. The reaction mixture was diluted with ethyl acetate, and the mixture was washed with water and saturated brine, and dried over anhydrous sodium sulfate. The solution was purified by basic silica gel column chromatography (ethyl acetate) to give the title compound (1.07 g, quantitative) as an oil.

$^1$H NMR (CDCl$_3$) δ0.32-0.38 (m, 2H), 0.62-0.68 (m, 2H), 1.24-1.29 (m, 1H), 2.99 (s, 1H), 3.79 (d, J=6.9 Hz, 2H), 6.81-6.85 (m, 2H), 7.38-7.43 (m, 2H).

Reference Example 234

[3-chloro-4-(cyclopropylmethoxy)phenyl]methanol

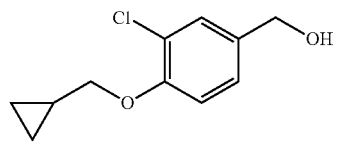 [SMILES: OCc1ccc(OCC2CC2)c(Cl)c1]

To a solution of methyl 3-chloro-4-(cyclopropylmethoxy) benzoate (2.42 g, 10.1 mmol) in THF (25 mL) was added dropwise 1.5 M diisobutylaluminum hydride-toluene solution (16.8 mL, 25.1 mmol) under ice-cooling and the mixture was stirred for 30 min. The reaction was quenched with water, and the mixture was extracted with ethyl acetate. The extract was washed with 1N hydrochloric acid, 10% aqueous potassium carbonate solution and saturated brine, and dried over anhydrous sodium sulfate. The solution was purified by basic silica gel column chromatography (ethyl acetate) to give the title compound (2.07 g, yield 97%) as an oil.

$^1$H NMR (CDCl$_3$) δ0.36-0.41 (m, 2H), 0.62-0.68 (m, 2H), 1.23-1.34 (m, 1H), 1.64 (m, 1H), 3.88 (d, J=6.6 Hz, 2H), 4.59 (d, J=5.7 Hz, 2H), 6.88 (d, J=8.7 Hz, 1H), 7.17 (dd, J=2.1, 8.7 Hz, 1H), 7.37 (d, J=2.1 Hz, 1H).

Reference Example 235

6-chloro-3-iodopyridin-2-ol

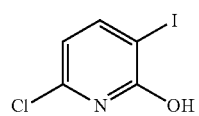

To a solution of 6-chloropyridin-2-ol (3.00 g, 23.2 mmol) and sodium carbonate (4.88 g, 46.4 mmol) in water (60 mL) was added iodine (5.84 g, 23.0 mmol), and the mixture was stirred at room temperature overnight. The resulting solid was collected by filtration, 1N hydrochloric acid was added to the obtained solid, and the mixture was extracted twice with ethyl acetate. The extract was washed with saturated brine, and dried over anhydrous sodium sulfate. The solvent was evaporated under reduced pressure, and to the obtained residue were added diisopropyl ether and hexane, and the resulting solid was collected by filtration to give the title compound (1.04 g, yield 18%).

$^1$H NMR (CDCl$_3$) δ 6.42 (d, J=8.0 Hz, 1H), 8.00 (d, J=8.0 Hz, 1H), 11.4 (br, 1H).

Reference Example 236

2-[1-(6-chlorofuro[2,3-b]pyridin-2-yl)ethyl]-1H-isoindole-1,3(2H)-dione

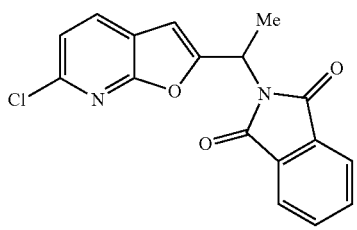 [SMILES: CC(c1cc2ccc(Cl)nc2o1)N1C(=O)c2ccccc2C1=O]

Using 6-chloro-3-iodopyridin-2-ol (500 mg, 1.96 mmol) obtained in Reference Example 235, 2-(1-methylprop-2-yn-1-yl)-1H-isoindole-1,3(2H)-dione (390 mg, 1.96 mmol), copper(I) iodide (18.6 mg, 0.0980 mmol), triethylamine (1.45 mL, 9.80 mmol), THF (6.5 mL) and bis(triphenylphosphine) palladium(II) chloride (68.7 mg, 0.0980 mmol), an operation in the same manner as in Reference Example 221 was performed to give the title compound (71.9 mg, yield 11%).

$^1$H NMR (CDCl$_3$) δ 1.93 (d, J=7.2 Hz, 3H), 5.58-5.80 (m, 1H), 6.74 (s, 1H), 7.16-7.43 (m, 1H), 7.68-7.93 (m, 5H).

Reference Example 237

N-[1-(6-chlorofuro[2,3-b]pyridin-2-yl)ethyl]acetamide

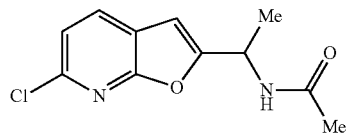 [SMILES: CC(=O)NC(C)c1cc2ccc(Cl)nc2o1]

To a solution of 2-[1-(6-chlorofuro[2,3-b]pyridin-2-yl)ethyl]-1H-isoindole-1,3(2H)-dione (71.9 mg, 0.221 mmol) obtained in Reference Example 236 in methanol (3 mL) was added hydrazine monohydrate (0.5 mL, 10.0 mmol), and the mixture was stirred at 50° C. for 30 min. The solvent was evaporated under reduced pressure, ethyl acetate was added thereto, and the resulting solid was filtered off. The solvent of the obtained filtrate was evaporated again under reduced pressure. Ethyl acetate was added thereto, and the resulting solid was filtered off. The solvent was evaporated under reduced pressure, and to the obtained residue were added ethyl acetate (3 mL) and acetic anhydride (0.100 mL, 1.05 mmol), and the mixture was stirred at room temperature for 5 min. The solvent was evaporated under reduced pressure, and the obtained solid was washed with diisopropyl ether to give the title compound (71.2 mg, quantitative).

$^1$H NMR (CDCl$_3$) δ 1.50-1.66 (m, 3H), 2.01 (s, 3H), 5.23-5.47 (m, 1H), 5.86 (br, 1H), 6.59 (s, 1H), 7.20-7.36 (m, 1H), 7.80 (d, J=8.3 Hz, 1H).

Reference Example 238

N-(1-{6-[2-(4-ethoxyphenyl)ethyl]-1-benzofuran-2-yl}ethyl)-N-(isoxazol-3-yl)-4-nitrobenzenesulfonamide

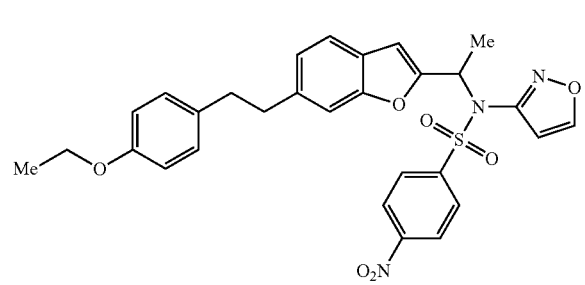 [SMILES: CCOc1ccc(CCc2ccc3cc(C(C)N(c4ccon4)S(=O)(=O)c4ccc([N+](=O)[O-])cc4)oc3c2)cc1]

To a solution of 1-[6-[2-(4-ethoxyphenyl)ethyl]-1-benzofuran-2-yl]ethanol (100 mg, 0.322 mmol) obtained in Reference Example 52, N-(isoxazol-3-yl)-4-nitrobenzenesulfonamide (104 mg, 0.387 mmol) and triphenylphosphine (109 mg, 0.418 mmol) in anhydrous THF (1.5 mL) was added 40% diethyl azodicarboxylate-toluene solution (0.190 mL, 0.418 mmol), and the mixture was stirred at room temperature for 2 days. The solvent was evaporated, and the obtained residue was purified by silica gel column chromatography (hexane to hexane:ethyl acetate=3:2) to give the title compound (127 mg, yield 70%) as a white solid.

$^1$H NMR (CDCl$_3$) δ 1.41 (t, J=7.2 Hz, 3H), 1.68 (d, J=7.3 Hz, 3H), 2.80-2.99 (m, 4H), 4.02 (q, J=7.2 Hz, 2H), 5.71 (q, J=7.3 Hz, 1H), 6.29 (d, J=1.9 Hz, 1H), 6.51 (s, 1H), 6.82 (d, J=8.7 Hz, 2H), 6.95 (s, 1H), 7.01 (d, J=7.9 Hz, 1H), 7.07 (d, J=8.7 Hz, 2H), 7.33 (d, J=7.8 Hz, 1H), 7.97 (d, J=9.0 Hz, 2H), 8.16-8.23 (m, 2H), 8.32-8.36 (m, 1H).

Reference Example 239

2-[1-(acetylamino)ethyl]-1-benzofuran-6-yl trifluoromethanesulfonate

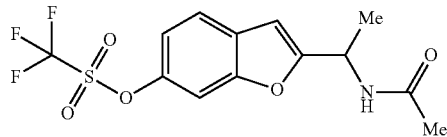 [SMILES: CC(=O)NC(C)c1cc2ccc(OS(=O)(=O)C(F)(F)F)cc2o1]

Using N-[1-(6-hydroxy-1-benzofuran-2-yl)ethyl]acetamide (2.21 g, 10.1 mmol) obtained in Reference Example 27, THF (20 mL), triethylamine (3.00 mL, 20.2 mmol) and N-phenylbis(trifluoromethanesulfonimide) (5.70 g, 15.2 mmol), an operation in the same manner as in Reference Example 117 was performed to give the title compound (3.13 g, yield 88%) as a white solid.

$^1$H NMR (CDCl$_3$) δ 1.58 (d, J=6.9 Hz, 3H), 2.03 (s, 3H), 5.32-5.42 (m, 1H), 5.79 (d, J=7.5 Hz, 1H), 6.61 (s, 1H), 7.15 (dd, J=8.3, 2.3 Hz, 1H), 7.41 (d, J=2.3 Hz, 1H), 7.55 (d, J=8.3 Hz, 1H).

Reference Example 240

N-[1-(6-{2-[4-(cyclopropylmethoxy)phenyl]ethyl}-1-benzofuran-2-yl)ethyl]-N-(3,4-dimethylisoxazol-5-yl)-4-nitrobenzenesulfonamide

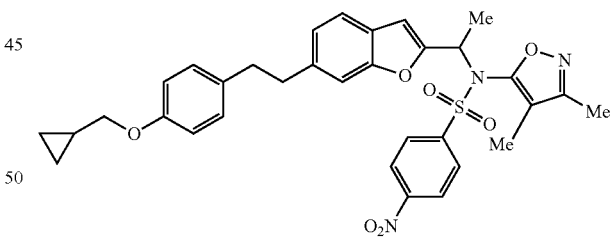

Using 1-{6-[2-(4-cyclopropylphenyl)ethyl]-1-benzofuran-2-yl}ethanol (500 mg, 1.48 mmol) obtained in Reference Example 52, N-(3,4-dimethylisoxazol-5-yl)-4-nitrobenzenesulfonamide (441 mg, 1.48 mmol), triphenylphosphine (426 mg, 1.63 mmol), anhydrous THF (3 mL) and 40% diethyl azodicarboxylate-toluene solution (0.740 mL, 1.63 mmol), an operation in the same manner as in Reference Example 238 was performed to give the title compound (125 mg, yield 16%) as a white solid.

$^1$H NMR (CDCl$_3$) δ 0.24-0.43 (m, 2H), 0.59-0.69 (m, 2H), 1.20-1.34 (m, 1H), 1.52 (d, J=7.2 Hz, 3H), 1.68 (s, 3H), 2.19 (s, 3H), 2.80-2.99 (m, 4H), 3.78 (d, J=7.2 Hz, 2H), 5.51 (q, J=7.2 Hz, 1H), 6.42 (s, 1H), 6.76-6.87 (m, 2H), 6.96-7.03 (m,

2H), 7.03-7.12 (m, 2H), 7.31 (d, J=8.3 Hz, 1H), 7.92-8.04 (m, 2H), 8.19-8.31 (d, J=9.0 Hz, 2H).

Reference Example 241

[4-(cyclopropylmethoxy)-3-fluorophenyl]methanol

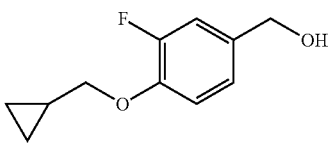 [SMILES: OCc1ccc(OCC2CC2)c(F)c1]

To a suspension of 2-fluoro-4-(hydroxymethyl)phenol (1.08 g, 7.61 mmol) and potassium carbonate (2.10 g, 15.2 mmol) in ethanol (15 mL) was added bromomethylcyclopropane (1.54 g, 11.4 mmol), and the mixture was stirred at 70° C. for 4 hr. Water was added thereto, and the mixture was extracted twice with ethyl acetate, and the extract was washed with saturated brine, and dried over anhydrous magnesium sulfate. The solvent was evaporated under reduced pressure, and the obtained residue was purified by silica gel column chromatography (hexane:ethyl acetate=19:1 to hexane:ethyl acetate=3:2) to give the title compound (777 mg, yield 52%) as a white solid.

$^1$H NMR (CDCl$_3$) δ 0.32-0.41 (m, 2H), 0.60-0.69 (m, 2H), 1.20-1.37 (m, 1H), 1.65 (br, 1H), 3.87 (d, J=6.8 Hz, 2H), 4.61 (s, 2H), 6.88-6.96 (m, 1H), 7.00-7.05 (m, 1H), 7.11 (dd, J=11.9, 1.8 Hz, 1H)

Reference Example 242

6-[2-(4-ethoxyphenyl)ethyl]furo[3,2-c]pyridin-4(5H)-one

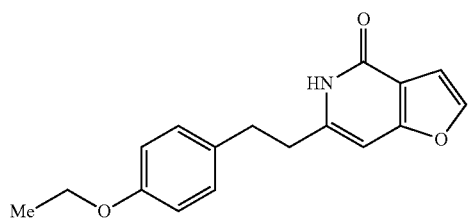 [SMILES: CCOc1ccc(CCc2cc3occc3c(=O)[nH]2)cc1]

To a solution of 2,2,6,6-tetramethylpiperidine (11.6 mL, 68.8 mmol) in THF (100 mL) was added 1.6 M n-butyllithium hexane solution (39.0 mL, 62.4 mmol) at −78° C., and the mixture was warmed to −20° C. and stirred at the same temperature for 10 min. To this solution was added a solution of N,N-diethyl-2-methylfuran-3-carboxamide (11.3 g, 62.5 mmol) in THF (10 mL), and the mixture was further stirred for 1 hr. To the solution was added 3-(4-ethoxyphenyl)propanenitrile (11.5 g, 65.6 mmol), and the mixture was stirred at room temperature for hr. 6N Hydrochloric acid was added thereto and the mixture was extracted twice with ethyl acetate. The combined organic layer was dried over anhydrous magnesium sulfate and the solvent was evaporated under reduced pressure. The obtained solid was washed with ethyl acetate to give the title compound (2.74 g, yield 15%) as a white solid.

$^1$H NMR (CDCl$_3$) δ 1.40 (t, J=7.0 Hz, 3H), 2.91-3.02 (m, 4H), 4.00 (q, J=7.0 Hz, 2H), 6.35 (s, 1H), 6.81 (d, J=8.7 Hz, 2H), 6.93-6.94 (m, 1H), 7.18 (d, J=8.7 Hz, 2H), 7.46 (d, J=1.9 Hz, 1H), 11.78 (br, 1H).

Reference Example 243

4-chloro-6-[2-(4-ethoxyphenyl)ethyl]furo[3,2-c]pyridine

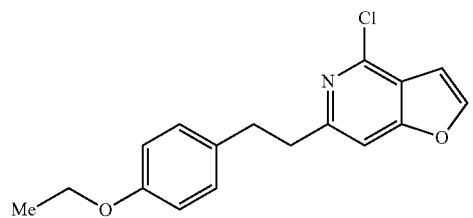 [SMILES: CCOc1ccc(CCc2cc3occc3c(Cl)n2)cc1]

6-[2-(4-Ethoxyphenyl)ethyl]furo[3,2-c]pyridin-4(5H)-one (2.74 g, 9.67 mmol) obtained in Reference Example 242 and phosphorus oxychloride (10 mL) were stirred at 110° C. for 30 min. The reaction mixture was neutralized with saturated aqueous sodium hydrogen carbonate, and the mixture was extracted twice with ethyl acetate, and the combined organic layer was dried over anhydrous magnesium sulfate. The solvent was evaporated under reduced pressure and the obtained residue was purified by silica gel column chromatography (hexane:ethyl acetate=19:1 to 13:7) to give the title compound (2.52 g, yield 86%) as an oil.

$^1$H NMR (CDCl$_3$) δ 1.39 (t, J=7.0 Hz, 3H), 2.99-3.05 (m, 2H), 3.10-3.16 (m, 2H), 4.00 (q, J=7.0 Hz, 2H), 6.80 (d, J=8.3 Hz, 2H), 6.83 (dd, J=2.3, 1.1 Hz, 1H), 7.09 (d, J=8.3 Hz, 2H), 7.13 (s, 1H), 7.61 (d, J=2.3 Hz, 1H).

Reference Example 244

6-[2-(4-ethoxyphenyl)ethyl]furo[3,2-c]pyridine

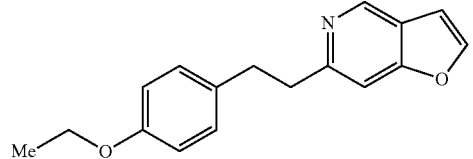 [SMILES: CCOc1ccc(CCc2cc3occc3cn2)cc1]

To a solution of 4-chloro-6-[2-(4-ethoxyphenyl)ethyl]furo[3,2-c]pyridine (2.52 g, 8.35 mmol) obtained in Reference Example 243 in acetic acid (25 mL) was added zinc powder (5.47 g, 83.5 mmol) and the mixture was stirred at 50° C. for 20 min. The reaction mixture was filtered, and the filtrate was concentrated. The obtained residue was neutralized with saturated aqueous sodium hydrogen carbonate and the mixture was extracted twice with ethyl acetate, and the combined organic layer was dried over anhydrous magnesium sulfate. The solvent was evaporated under reduced pressure and the obtained residue was purified by silica gel column chromatography (hexane:ethyl acetate=13:7 to 0:1) to give the title compound (2.00 g, yield 80%) as a white solid.

$^1$H NMR (CDCl$_3$) δ 1.39 (t, J=6.8 Hz, 3H), 3.00-3.08 (m, 2H), 3.14-3.20 (m, 2H), 4.00 (q, J=6.8 Hz, 2H), 6.76-6.82 (m, 3H), 7.11 (d, J=8.7 Hz, 2H), 7.22 (s, 1H), 7.58 (d, J=2.3 Hz, 1H), 8.87 (s, 1H).

Reference Example 245

1-{6-[2-(4-ethoxyphenyl)ethyl]furo[3,2-c]pyridin-2-yl}ethanol

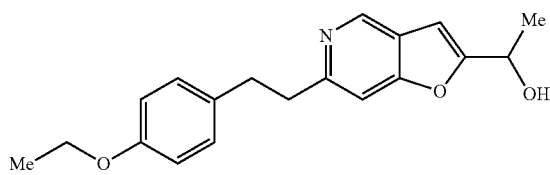 [SMILES: CCOc1ccc(CCc2cc3oc(C(C)O)cc3cn2)cc1]

To a solution of 6-[2-(4-ethoxyphenyl)ethyl]furo[3,2-c]pyridine (401 mg, 1.50 mmol) obtained in Reference Example 244 in THF (10 mL) was added 1.6 M n-butyllithium hexane solution (1.08 mL, 1.73 mmol) at −78° C., and the mixture was stirred at the same temperature for 15 min. To this solution was added acetoaldehyde (0.168 mL, 3.00 mmol) and the mixture was stirred at room temperature for 15 min. Water was added to the reaction mixture, and the mixture was extracted twice with ethyl acetate, and the combined organic layer was dried over anhydrous magnesium sulfate. The solvent was evaporated under reduced pressure and the obtained residue was purified by silica gel column chromatography (hexane:ethyl acetate=1:1 to 0:1) to give the title compound (399 mg, yield 85%) as an oil.

$^1$H NMR (CDCl$_3$) δ 1.39 (t, J=7.0 Hz, 3H), 1.64 (d, J=6.4 Hz, 3H), 2.99-3.05 (m, 2H), 3.13-3.19 (m, 2H), 4.00 (q, J=7.0 Hz, 2H), 4.98-5.07 (m, 1H), 6.64 (s, 1H), 6.80 (d, J=8.7 Hz, 2H), 7.10 (d, J=8.7 Hz, 2H), 7.16 (s, 1H), 8.79 (s, 1H).

Reference Example 246

2-(1-azidoethyl)-6-[2-(4-ethoxyphenyl)ethyl]furo[3,2-c]pyridine

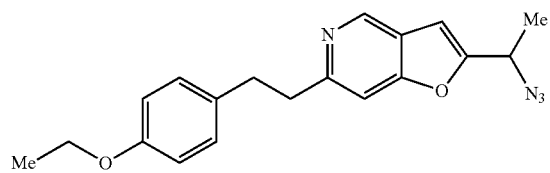

To a solution of 1-{6-[2-(4-ethoxyphenyl)ethyl]furo[3,2-c]pyridin-2-yl}ethanol (623 mg, 2.00 mmol) obtained in Reference Example 245 in toluene (10 mL) were added diphenyl azidophosphate (0.647 mL, 3.00 mmol) and DBU (0.598 mL, 4.00 mmol), and the mixture was stirred at room temperature for 2 hr. Ethyl acetate was added thereto, and the mixture was washed with water, and dried over anhydrous magnesium sulfate. The solvent was evaporated under reduced pressure, and the obtained residue was purified by silica gel column chromatography (hexane:ethyl acetate=17:3 to 2:3) to give the title compound (622 mg, yield 92%) as an oil.

$^1$H NMR (CDCl$_3$) δ 1.40 (t, J=7.0 Hz, 3H), 1.66 (d, J=7.0 Hz, 3H), 3.00-3.05 (m, 2H), 3.14-3.20 (m, 2H), 4.00 (q, J=7.0 Hz, 2H), 4.69 (q, J=6.0 Hz, 1H), 6.69 (s, 1H), 6.80 (d, J=8.3 Hz, 2H), 7.11 (d, J=8.3 Hz, 2H), 7.20 (s, 1H), 8.82 (d, J=0.7 Hz, 1H).

Reference Example 247

2-[(4-ethoxyphenyl)ethynyl]-5-(methoxymethoxy)pyridine

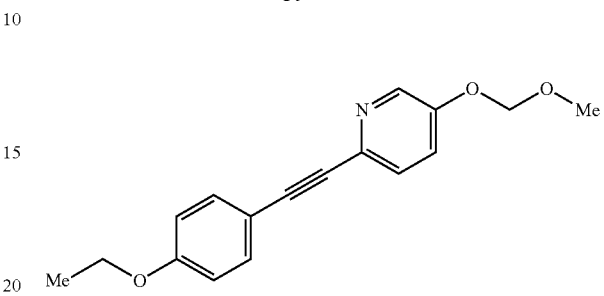

To a solution of 2-bromo-5-(methoxymethoxy)pyridine (2.50 g, 11.5 mmol), 1-ethoxy-4-ethynylbenzene (2.57 mL, 17.2 mmol) and copper(I) iodide (220 mg, 1.15 mmol) in a mixed solvent of THF-triethylamine (20 ml-10 mL) was added bis(triphenylphosphine)palladium(II) chloride (807 mg, 1.15 mmol), and the mixture was stirred under an argon stream at 60° C. for 15 min. The reaction mixture was diluted with ethyl acetate, and the mixture was washed with water, and dried over anhydrous magnesium sulfate. The solvent was evaporated under reduced pressure and the obtained residue was purified by silica gel column chromatography (hexane:ethyl acetate=4:1 to 3:7) to give the title compound (3.21 g, yield 98%) as a yellow solid.

$^1$H NMR (CDCl$_3$) δ 1.42 (t, J=7.0 Hz, 3H), 3.50 (s, 3H), 4.05 (q, J=7.0 Hz, 2H), 5.21 (s, 2H), 6.86 (d, J=8.7 Hz, 2H), 7.32-7.36 (111, 1H), 7.42-7.45 (m, 1H), 7.50 (d, J=8.7 Hz, 2H), 8.38 (d, J=2.3 Hz, 1H).

Reference Example 248

2-[2-(4-ethoxyphenyl)ethyl]-5-(methoxymethoxy)pyridine

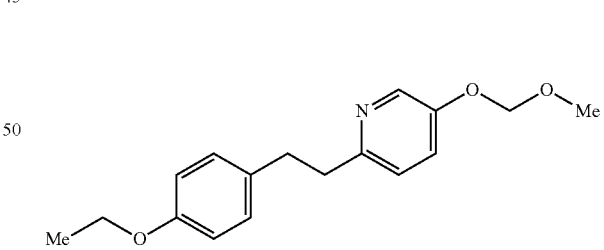

A solution of 2-[(4-ethoxyphenyl)ethynyl]-5-(methoxymethoxy)pyridine (3.21 g, 11.3 mmol) obtained in Reference Example 247 and 10% palladium carbon (50% water-containing product, 5.00 g) in ethanol (20 mL)-THF (10 mL) was stirred under a hydrogen atmosphere (normal pressure) for 30 min. After filtration, the filtrate was concentrated under reduced pressure, and the obtained residue was purified by silica gel column chromatography (hexane:ethyl acetate=4:1 to 3:7) to give the title compound (2.48 g, yield 76%) as an oil.

$^1$H NMR (CDCl$_3$) δ 1.40 (t, J=7.2 Hz, 3H), 2.91-3.04 (m, 4H), 3.49 (s, 3H), 4.00 (q, J=7.2 Hz, 2H), 5.17 (s, 2H), 6.80 (d,

J=8.3 Hz, 2H), 6.99 (d, J=8.3 Hz, 1H), 7.09 (d, J=8.3 Hz, 2H), 7.26 (dd, J=8.3, 3.0 Hz, 1H), 8.34 (d, J=3.0 Hz, 1H).

Reference Example 249

2-[2-(4-ethoxyphenyl)ethyl]-5-(methoxymethoxy)pyridine-4-carbaldehyde

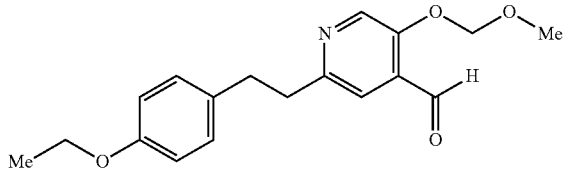 [SMILES: CCOc1ccc(CCc2cc(C=O)c(OCOC)cn2)cc1]

To a solution of 2-[2-(4-ethoxyphenyl)ethyl]-5-(methoxymethoxy)pyridine (2.48 g, 8.63 mmol) obtained in Reference Example 248 in THF (20 mL) was added 1.6 M n-butyllithium hexane solution (6.50 mL, 10.4 mmol) at −78° C., and the mixture was stirred at the same temperature for 30 min. To the solution was added DMF (1.00 mL, 12.9 mmol), and the mixture was stirred at 0° C. for 10 min. Water was added to the reaction mixture, and the mixture was extracted twice with ethyl acetate, and the combined organic layer was dried over anhydrous magnesium sulfate. The solvent was evaporated under reduced pressure and the obtained residue was purified by silica gel column chromatography (ethyl acetate) to give the title compound (2.72 g, quantitative) as an oil.

$^1$H NMR (CDCl$_3$) δ 1.39 (t, J=7.0 Hz, 3H), 2.93-2.99 (m, 2H), 3.04-3.10 (m, 2H), 3.55 (s, 3H), 4.00 (q, J=7.0 Hz, 2H), 5.34 (s, 2H), 6.80 (d, J=8.7 Hz, 2H), 7.10 (d, J=8.7 Hz, 2H), 7.42 (s, 1H), 8.67 (s, 1H), 10.49 (s, 1H).

Reference Example 250

2-[2-(4-ethoxyphenyl)ethyl]-5-hydroxypyridine-4-carbaldehyde

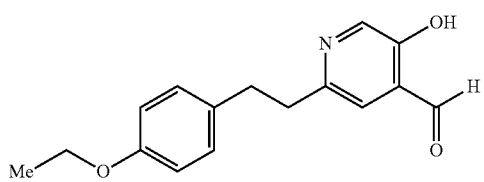 [SMILES: CCOc1ccc(CCc2cc(C=O)c(O)cn2)cc1]

To a solution of 2-[2-(4-ethoxyphenyl)ethyl]-5-(methoxymethoxy)pyridine-4-carbaldehyde (2.72 g, 8.63 mmol) obtained in Reference Example 249 in THF (30 mL) was added 6N hydrochloric acid (14 mL) and the mixture was stirred at 60° C. for 30 min. The reaction mixture was neutralized with saturated aqueous sodium hydrogen carbonate solution and extracted twice with ethyl acetate. The extract was dried over anhydrous magnesium sulfate, the solvent was evaporated under reduced pressure and the obtained residue was purified by silica gel column chromatography (hexane:ethyl acetate=4:1 to 3:7) to give the title compound (1.85 g, yield 79%) as a yellow solid.

$^1$H NMR (CDCl$_3$) δ 1.39 (t, J=7.0 Hz, 3H), 2.95-3.01 (m, 2H), 3.06-3.11 (m, 2H), 4.00 (q, J=7.0 Hz, 2H), 6.80 (d, J=8.7 Hz, 2H), 7.05 (d, J=8.7 Hz, 2H), 7.12 (s, 1H), 8.50 (s, 1H), 9.92 (s, 1H), 10.10 (s, 1H).

Reference Example 251

1-{5-[2-(4-ethoxyphenyl)ethyl]furo[2,3-c]pyridin-2-yl}ethanol

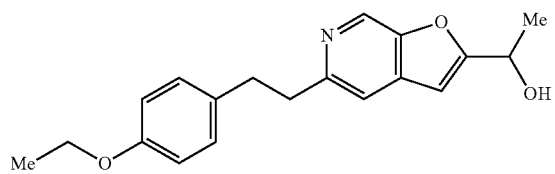 [SMILES: CCOc1ccc(CCc2cc3cc(C(C)O)oc3cn2)cc1]

To a solution of 2-[2-(4-ethoxyphenyl)ethyl]-5-hydroxypyridine-4-carbaldehyde (1.85 g, 6.82 mmol) obtained in Reference Example 250 in acetonitrile (30 mL) were added potassium carbonate (1.89 g, 13.7 mmol) and bromoacetone (0.688 mL, 8.18 mmol) and the mixture was stirred at 85° C. for 1 hr. Water was added to the reaction mixture, and the mixture was extracted with ethyl acetate, and the organic layer was dried over anhydrous magnesium sulfate. The solvent was evaporated and the obtained residue was purified by basic silica gel column chromatography (ethyl acetate) to give an oil. The obtained oil was dissolved in methanol (20 mL), sodium borohydride (258 mg, 6.82 mmol) was added thereto and the mixture was stirred at room temperature for 15 min. To the reaction mixture was added aqueous ammonium chloride solution, and the mixture was extracted twice with ethyl acetate, and the combined organic layer was dried over anhydrous magnesium sulfate. The solvent was evaporated. The obtained residue was purified by silica gel column chromatography (hexane:ethyl acetate=3:1 to 1:4) to give the title compound (1.12 g, yield 52%) as a yellow solid.

$^1$H NMR (CDCl$_3$) δ 1.39 (t, J=7.0 Hz, 3H), 1.65 (d, J=6.4 Hz, 3H), 2.98-3.04 (m, 2H), 3.09-3.15 (m, 2H), 4.00 (q, J=7.0 Hz, 2H), 4.99-5.08 (m, 1H), 6.57 (s, 1H), 6.79 (d, J=8.7 Hz, 2H), 7.09 (d, J=8.7 Hz, 2H), 7.23 (s, 1H), 8.75 (s, 1H).

Reference Example 252

2-(1-azidoethyl)-5-[2-(4-ethoxyphenyl)ethyl]furo[2,3-c]pyridine

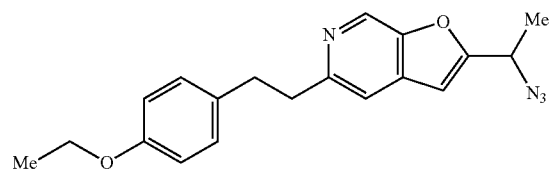 [SMILES: CCOc1ccc(CCc2cc3cc(C(C)N=[N+]=[N-])oc3cn2)cc1]

To a solution of 1-{5-[2-(4-ethoxyphenyl)ethyl]furo[2,3-c]pyridin-2-yl}ethanol (1.12 g, 3.60 mmol) obtained in Reference Example 251 in toluene (20 mL) was added diphenyl azidophosphate (1.17 mL, 5.39 mmol) and DBU (1.08 mL, 7.20 mmol), and the mixture was stirred at room temperature for 2.5 hr. Ethyl acetate was added thereto, and the mixture was washed with water, and dried over anhydrous magnesium sulfate. The solvent was evaporated under reduced pressure, and the obtained residue was purified by silica gel column chromatography (hexane:ethyl acetate=9:1 to 1:4) to give the title compound (1.20 g, yield 99%) as an oil.

$^1$H NMR (CDCl$_3$) δ 1.39 (t, J=7.0 Hz, 3H), 1.67 (d, J=7.0 Hz, 3H), 2.98-3.05 (m, 2H), 3.10-3.16 (m, 2H), 4.00 (q, J=7.0 Hz, 2H), 4.71 (q, J=7.0 Hz, 1H), 6.60 (s, 1H), 6.80 (d, J=8.7 Hz, 2H), 7.09 (d, J=8.7 Hz, 2H), 7.24 (s, 1H), 8.79 (s, 1H).

Reference Example 253

2-bromo-5-(cyclopropylmethoxy)pyridine

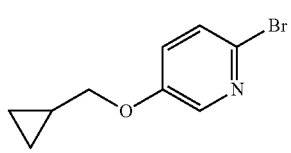 [SMILES: Brc1ccc(OCC2CC2)cn1]

To a solution of 6-bromopyridin-3-ol (5.00 g, 28.8 mmol) in DMF (50 mL) were added potassium carbonate (7.96 g, 55.6 mmol) and (bromomethyl)cyclopropane (4.18 mL, 43.1 mmol), and the mixture was stirred at 60° C. for 30 min. The reaction mixture was diluted with ethyl acetate, and the mixture was washed three times with saturated brine, and dried over anhydrous magnesium sulfate. The solvent was evaporated under reduced pressure, and the obtained residue was purified by silica gel column chromatography (hexane:ethyl acetate=19:1 to 1:1) to give the title compound (6.32 g, yield 96%) as an oil.

$^1$H NMR (CDCl$_3$) δ 0.34-0.39 (m, 2H), 0.64-0.70 (m, 2H), 1.20-1.33 (m, 1H), 3.83 (d, J=6.8 Hz, 2H), 7.09 (dd, J=8.7, 3.0 Hz, 1H), 7.35 (d, J=8.7 Hz, 1H), 8.05 (d, H=3.0 Hz, 1H).

Reference Example 254

5-(cyclopropylmethoxy)-2-ethynylpyridine

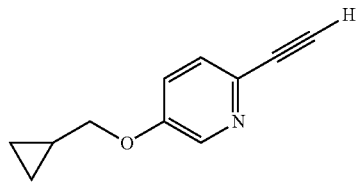 [SMILES: C#Cc1ccc(OCC2CC2)cn1]

Using 2-bromo-5-(cyclopropylmethoxy)pyridine (4.76 g, 20.9 mmol) obtained in Reference Example 253, an operation in the same manner as in Reference Example 176 was performed to give the title compound (3.53 g, yield 97%) as an oil.

$^1$H NMR (CDCl$_3$) δ 0.35-0.40 (m, 2H), 0.64-0.71 (m, 2H), 1.21-1.34 (m, 1H), 3.06 (s, 1H), 3.86 (d, J=6.8 Hz, 2H), 7.13 (dd, J=8.7, 3.0 Hz, 1H), 7.41 (d, J=8.7 Hz, 1H), 8.27 (d, H=3.0 Hz, 1H).

Reference Example 255

2-(cyclopropylmethoxy)-5-iodopyridine

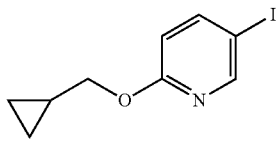 [SMILES: Ic1ccc(OCC2CC2)nc1]

To a solution of 5-iodopyridin-2-ol (5.32 g, 24.0 mmol) in DMF (50 mL) were added cesium carbonate (23.4 g, 72.0 mmol) and (bromomethyl)cyclopropane (4.67 mL, 48.2 mmol), and the mixture was stirred at 60° C. for 15 min. The reaction mixture was diluted with ethyl acetate, and the mixture was washed three times with saturated brine, and dried over anhydrous magnesium sulfate. The solvent was evaporated under reduced pressure, and the obtained residue was purified by silica gel column chromatography (hexane:ethyl acetate=4:1 to 1:4) to give the title compound (2.17 g, yield 32%) as an oil.

$^1$H NMR (CDCl$_3$) δ 0.34 (q, J=4.9 Hz, 2H), 0.58-0.64 (m, 2H), 1.19-1.33 (m, 1H), 4.09 (d, J=7.2 Hz, 2H), 6.61 (d, J=8.7 Hz, 1H), 7.77 (dd, J=8.7, 2.3 Hz, 1H), 8.30 (d, H=2.3 Hz, 1H).

Reference Example 256

2-(cyclopropylmethoxy)-5-ethynylpyridine

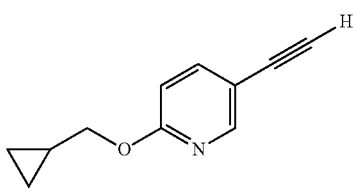 [SMILES: C#Cc1ccc(OCC2CC2)nc1]

Using 2-(cyclopropylmethoxy)-5-iodopyridine (2.17 g, 7.89 mmol) obtained in Reference Example 255, an operation in the same manner as in Reference Example 176 was performed to give the title compound (1.36 g, yield 99%) as an oil.

¹H NMR (CDCl₃) δ 0.32-0.37 (m, 2H), 0.58-0.65 (m, 2H), 1.21-1.34 (m, 1H), 3.10 (s, 1H), 4.14 (d, J=7.2 Hz, 2H), 6.72 (d, J=8.7 Hz, 1H), 7.64 (dd, J=8.7, 2.3 Hz, 1H), 8.28 (d, H=2.3 Hz, 1H).

Reference Example 257

N-[1-(5-hydroxy-1-benzofuran-2-yl)ethyl]acetamide

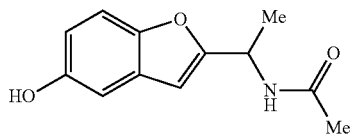 [SMILES: CC(=O)NC(C)c1cc2cc(O)ccc2o1]

N-[1-(5-hydroxy-1-benzofuran-2-yl)ethyl]acetamide (30 g) obtained in Reference Example 38 was optically resolved by supercritical chromatography (SFC) under the following conditions, and two kinds of optically active forms of "retention time longer (14.1 g)" and "retention time shorter (14.1 g)".
<Preparative HPLC Conditions>
  column: CHIRALPAK AD-H (4.6 mmID×250 mmL)
  mobile phase: CO₂: ethanol=7:3
  flow rate: 50 mL/min
  column temperature: 35° C.
  detection: UV 220 nm
  compound injection volume: 10 mg/ml (in ethanol), 4.0 mL
<HPLC Analysis Conditions>
  column: CHIRALPAK AD-H (4.6 mmID×250 mmL)
  mobile phase: CO₂:methanol=7:3
  pressure: 100 bar
  flow rate: 2.0 mL/min
  column temperature: 35° C.
  detection: UV 220 nm
  retention time of "retention time longer": 2.01 min
  retention time of "retention time shorter": 1.47 min Reference Example 258

N-[1-(5-hydroxy-2,3-dihydro-1-benzofuran-2-yl)ethyl]acetamide

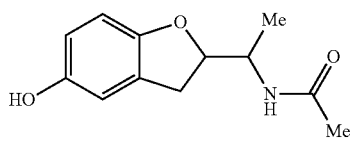 [SMILES: CC(=O)NC(C)C1Cc2cc(O)ccc2O1]

To a solution of N-[1-(5-hydroxy-1-benzofuran-2-yl)ethyl]acetamide (1.97 g, 8.99 mmol, retention time longer) obtained in Reference Example 257 in a mixed solvent of THF (30 mL)-ethanol (20 mL) was added 10% palladium carbon (50% water-containing product, 2.00 g), and the mixture was stirred under a hydrogen atmosphere at room temperature for 2 hr. Palladium carbon was filtered off, and the solvent was evaporated. The obtained residue (1.99 g, quantitatively) was directly used for the next reaction without purification.

Reference Example 259

N-{(1S)-1-[(2S)-6-hydroxy-2,3-dihydro-1-benzofuran-2-yl]ethyl}acetamide

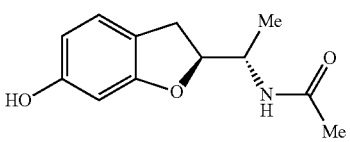 [SMILES: CC(=O)N[C@@H](C)[C@@H]1Cc2ccc(O)cc2O1]

To a solution (20 mL) of (2S)-2-[(1S)-1-(acetylamino)ethyl]-2,3-dihydro-1-benzofuran-6-yl trifluoromethanesulfonate (retention time longer) (2.81 g, 7.96 mmol) obtained in Reference Example 231 in THF was added 10% aqueous tetraethylammonium hydroxide solution (36 mL, 24 mmol), and the mixture was stirred at room temperature overnight. 1N Hydrochloric acid was added thereto, and the mixture was extracted twice with ethyl acetate. The organic layer was washed with saturated brine, and dried over anhydrous sodium sulfate. The solvent was evaporated under reduced pressure, and the obtained solid was washed with hexane to give the title compound (1.74 g, yield 99%) as a carnation solid.
¹H NMR (CDCl₃) δ 1.33 (d, J=6.8 Hz, 3H), 1.92 (s, 3H), 2.85-3.01 (m, 1H), 3.05-3.20 (m, 1H), 4.23-4.39 (m, 1H), 4.60-4.85 (m, 1H), 5.54 (br, 1H), 6.26-6.37 (m, 2H), 6.90-7.00 (m, 1H).

Reference Example 260

2-(cyclopropylmethoxy)-6-fluoropyridine

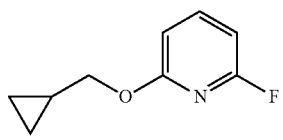 [SMILES: Fc1cccc(OCC2CC2)n1]

To a solution of cyclopropylmethanol (3.87 g, 47.7 mmol) in THF (50 mL) was added sodium hydride (oil, 60%, 2.08 g, 52.1 mmol), and the mixture was stirred at room temperature for 20 min. To this solution was added 2,6-difluoropyridine (5.00 g, 43.4 mmol) and the mixture was stirred at room temperature for 30 min. The reaction was quenched with water, and the mixture was extracted with ethyl acetate. The extract was dried over anhydrous magnesium sulfate. The solvent was evaporated under reduced pressure and the obtained residue was purified by silica gel column chromatography (hexane:ethyl acetate=99:1 to 4:1) to give the title compound (5.69 g, yield 78%) as an oil.

¹H NMR (CDCl₃) δ0.32-0.37 (m, 2H), 0.59-0.65 (m, 2H), 1.21-1.34 (m, 1H), 4.10 (d, J=7.2 Hz, 2H), 6.44 (dd, J=7.7, 2.5 Hz, 1H), 6.62 (dd, J=7.9, 1.5 Hz, 1H), 7.59-7.67 (m, 1H).

Reference Example 261

6-(cyclopropylmethoxy)-2-fluoropyridine-3-carbaldehyde

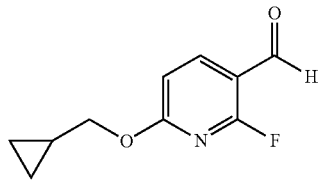 [SMILES: O=Cc1ccc(OCC2CC2)nc1F]

To a solution of 2-(cyclopropylmethoxy)-6-fluoropyridine (7.00 g, 41.9 mmol) obtained in Reference Example 260 in THF (100 mL) was added 2.0M lithiumdiisopropylamide-THF solution (25.0 mL, 50.2 mmol) at −78° C., and the mixture was stirred at the same temperature for 1 hr. To this solution was added ethyl formate (5.08 mL, 62.9 mmol), and the reaction mixture was stirred at room temperature for 30 min. The reaction was quenched with water, and the mixture was extracted with ethyl acetate. The extract was washed twice with saturated brine, and dried over anhydrous magnesium sulfate. The solvent was evaporated under reduced pressure and the obtained residue was purified by silica gel column chromatography (hexane:ethyl acetate=19:1 to 3:1) to give the title compound (4.66 g, yield 57%) as an oil.

¹H NMR (CDCl₃) δ0.34-0.40 (m, 2H), 0.58-0.68 (m, 2H), 1.23-1.36 (m, 1H), 4.21 (d, J=7.2 Hz, 2H), 6.73 (d, J=8.7 Hz, 1H), 8.13-8.19 (m, 1H), 10.2 (s, 1H).

Reference Example 262

[6-(cyclopropylmethoxy)-2-fluoropyridin-3-yl]methanol

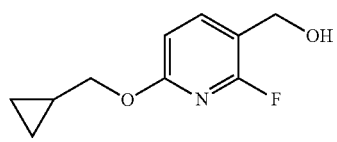 [SMILES: OCc1ccc(OCC2CC2)nc1F]

To a solution of 6-(cyclopropylmethoxy)-2-fluoropyridine-3-carbaldehyde (4.66 g, 23.9 mmol) obtained in Reference Example 261 in a mixed solvent of THF (50 mL)-methanol (20 mL) was added sodium borohydride (230 mg, 5.97 mmol) and the mixture was stirred at room temperature for 10 min. To the reaction mixture was added aqueous ammonium chloride solution, and the mixture was extracted twice with ethyl acetate, and the combined organic layer was dried over anhydrous magnesium sulfate. The solvent was evaporated under reduced pressure and the obtained residue was purified by silica gel column chromatography (hexane:ethyl acetate=4:1 to 1:4) to give the title compound (621 mg, yield 13%) as an oil.

¹H NMR (CDCl₃) δ0.32-0.40 (m, 2H), 0.58-0.65 (m, 2H), 1.20-1.33 (m, 1H), 4.09 (d, J=7.2 Hz, 2H), 4.65 (s, 2H), 6.64 (d, J=8.0 Hz, 1H), 7.69-7.75 (m, 1H).

Reference Example 263

3-(bromomethyl)-6-(cyclopropylmethoxy)-2-fluoropyridine

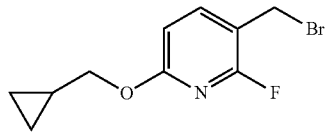 [SMILES: Fc1nc(OCC2CC2)ccc1CBr]

To a solution of [6-(cyclopropylmethoxy)-2-fluoropyridin-3-yl]methanol (200 mg, 1.01 mmol) obtained in Reference Example 262 and triphenylphosphine (345 mg, 1.31 mmol) in THF (5 mL) was added carbon tetrabromide (504 mg, 1.52 mmol), and the mixture was stirred at room temperature for 10 min. The solvent was evaporated under reduced pressure and the obtained residue was purified by silica gel column chromatography (hexane:ethyl acetate=9:1 to 1:1) to give the title compound (262 mg, quantitative) as an oil.

Reference Example 264

5-bromo-2-(cyclopropylmethoxy)pyridine

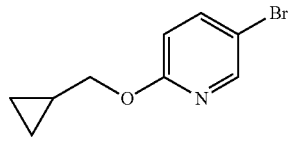 [SMILES: Brc1ccc(OCC2CC2)nc1]

To a solution of cyclopropylmethanol (0.890 mL, 11.0 mmol) in DMF (30 mL) was added sodium hydride (oil, 60%, 440 mg, 11.0 mmol), and the mixture was stirred at room temperature for 10 min. To this solution was added 2,5-dibromopyridine (2.00 g, 8.46 mmol) and the mixture was stirred at 70° C. for 1 hr. The reaction was quenched with water, and the mixture was extracted with ethyl acetate. The organic layer was washed twice with saturated brine, and dried over anhydrous magnesium sulfate. The solvent was evaporated under reduced pressure and the obtained residue was purified by silica gel column chromatography (hexane:ethyl acetate=49:1 to 17:3) to give the title compound (1.88 g, yield 97%) as an oil.

¹H NMR (CDCl₃) δ0.31-0.36 (m, 2H), 0.58-0.64 (m, 2H), 1.20-1.33 (m, 1H), 4.09 (d, J=7.2 Hz, 2H), 6.68 (d, J=9.5 Hz, 1H), 7.63 (dd, J=8.9, 2.5 Hz, 1H), 8.16 (d, J=2.3 Hz, 1H).

Reference Example 265

6-(cyclopropylmethoxy)pyridin-3-ol

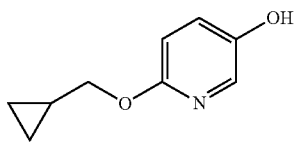 [SMILES: Oc1ccc(OCC2CC2)nc1]

To a solution of 5-bromo-2-(cyclopropylmethoxy)pyridine (1.88 g, 8.24 mmol) obtained in Reference Example 264 in THF (15 mL) was added 1.6 M n-butyllithium-hexane solution (7.25 mL, 11.6 mmol) at −78° C., and the mixture was stirred at the same temperature for 20 min. To this solution was added trimethylborane (1.29 mL, 11.6 mmol) and the mixture was stirred at −78° C. for 30 min. The reaction mixture was allowed to warm to 0° C., aqueous hydrogen peroxide (30%, 5 mL) and 8N aqueous sodium hydroxide solution (1.55 mL, 12.4 mmol) were added thereto, and the mixture was stirred for 15 min. Water was added to the reaction mixture, the mixture was extracted twice with ethyl acetate, and the combined organic layer was dried over anhydrous magnesium sulfate. The solvent was evaporated under reduced pressure and the obtained residue was purified by silica gel column chromatography (hexane:ethyl acetate=3:1 to 3:7) to give the title compound (855 mg, yield 62%) as a white solid.

¹H NMR (CDCl₃) δ0.30-0.35 (m, 2H), 0.57-0.63 (m, 2H), 1.19-1.32 (m, 1H), 4.04 (d, J=6.8 Hz, 2H), 5.59 (br, 1H), 6.69 (d, J=9.5 Hz, 1H), 7.19 (dd, J=8.9, 3.2 Hz, 1H), 7.74 (d, J=2.7 Hz, 1H).

Reference Example 266

2-(cyclopropylmethoxy)-5-(methoxymethoxy)pyridine

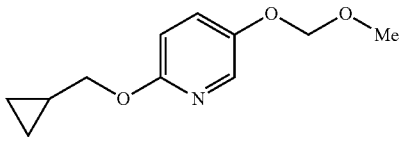 [SMILES: COCOc1ccc(OCC2CC2)nc1]

To a suspension of 6-(cyclopropylmethoxy)pyridin-3-ol (855 mg, 5.18 mmol) obtained in Reference Example 265 and potassium carbonate (1.44 g, 10.4 mmol) in DMF (15 mL) was added chloromethyl methyl ether (0.635 mL, 7.77 mmol) and the mixture was stirred at room temperature for 1 hr. The reaction was quenched with water, and the mixture was extracted with ethyl acetate. The organic layer was washed twice with saturated brine, and dried over anhydrous magnesium sulfate. The solvent was evaporated under reduced pressure and the obtained residue was purified by silica gel column chromatography (hexane:ethyl acetate=9:1 to 3:2) to give the title compound (789 mg, yield 72%) as an oil.

¹H NMR (CDCl₃) δ0.31-0.36 (m, 2H), 0.57-0.63 (m, 2H), 1.22-1.32 (m, 1H), 3.49 (s, 3H), 4.07 (d, J=7.2 Hz, 2H), 5.09 (s, 2H), 6.71 (d, J=9.1 Hz, 1H), 7.33 (dd, J=9.1, 3.0 Hz, 1H), 7.92 (d, J=3.0 Hz, 1H).

Reference Example 267

6-(cyclopropylmethoxy)-4-fluoropyridin-3-ol

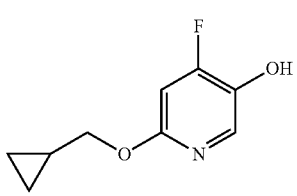 [SMILES: Oc1cnc(OCC2CC2)cc1F]

To a solution of 2-(cyclopropylmethoxy)-5-(methoxymethoxy)pyridine (789 mg, 3.77 mmol) obtained in Reference Example 266 in THF (10 mL) was added 1.6 M n-butyllithium-hexane solution (3.10 mL, 4.90 mmol) at −78° C., and the mixture was stirred at the same temperature for 30 min. To this solution was added N-fluoro-N-(phenylsulfonyl)benzenesulfonamide (1.78 g, 5.66 mmol), and the mixture was stirred at room temperature for 10 min. The reaction was quenched with water, and the mixture was extracted with ethyl acetate. The extract was dried over anhydrous magnesium sulfate. The solvent was evaporated under reduced pressure and the obtained residue was purified by silica gel column chromatography (hexane:ethyl acetate=9:1 to 7:3) to give 2-(cyclopropylmethoxy)-4-fluoro-5-(methoxymethoxy)pyridine as an oil. The 2-(cyclopropylmethoxy)-4-fluoro-5-(methoxymethoxy)pyridine was dissolved in THF (10 mL), 6N hydrochloric acid (2.90 mL, 17.4 mmol) was added thereto and the mixture was stirred at 50° C. for 1 hr. The reaction mixture was neutralized with saturated aqueous sodium hydrogen carbonate, and the mixture was extracted twice with ethyl acetate. The combined organic layer was dried over anhydrous magnesium sulfate. The solvent was evaporated under reduced pressure and the obtained residue was purified by silica gel column chromatography (hexane:ethyl acetate=17:3 to 1:1) to give the title compound (279 mg, yield 40%) as a white solid.

¹H NMR (CDCl₃) δ0.30-0.35 (m, 2H), 0.57-0.63 (m, 2H), 1.19-1.31 (m, 1H), 4.05 (d, J=6.8 Hz, 2H), 5.28 (br, 1H), 6.53 (d, J=11.0 Hz, 1H), 7.86 (d, J=11.0 Hz, 1H).

Reference Example 268

6-(cyclopropylmethoxy)-4-fluoropyridin-3-yl trifluoromethanesulfonate

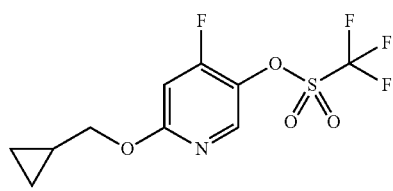 [SMILES: O=S(=O)(Oc1cnc(OCC2CC2)cc1F)C(F)(F)F]

To a solution of 6-(cyclopropylmethoxy)-4-fluoropyridin-3-ol (279 mg, 1.52 mmol) obtained in Reference Example 267 and triethylamine (0.425 mL, 3.04 mmol) in THF (10 mL) was added 1,1,1-trifluoro-N-phenyl-N-[(trifluoromethyl)sulfonyl]methanesulfonamide (814 mg, 2.28 mmol), and the mixture was stirred at room temperature for 1 hr. The solvent was evaporated under reduced pressure and the obtained residue was purified by silica gel column chromatography (hexane:ethyl acetate=19:1 to 3:1) to give the title compound (480 mg, quantitative) as a white solid.

$^1$H NMR (CDCl$_3$) δ0.32-0.37 (m, 2H), 0.60-0.66 (m, 2H), 1.20-1.33 (m, 1H), 4.15 (d, J=7.2 Hz, 2H), 6.62 (d, J=11.0 Hz, 1H), 8.11 (d, J=11.0 Hz, 1H).

Reference Example 269 methyl 6-(cyclopropylmethoxy)-4-fluoropyridine-3-carboxylate

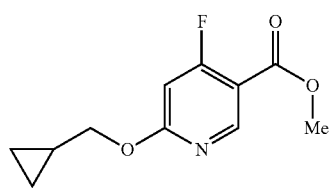 [SMILES: COC(=O)c1cnc(OCC2CC2)cc1F]

To a solution of 6-(cyclopropylmethoxy)-4-fluoropyridin-3-yl trifluoromethanesulfonate (480 mg, 1.52 mmol) obtained in Reference Example 268 and triethylamine (0.483 mL, 3.46 mmol) in a mixed solvent of DMF (5 mL)-methanol (2 mL) was added [1,1'-bis(diphenylphosphino)ferrocene]dichloropalladium(II) (141 mg, 0.173 mmol), and the mixture was stirred under a carbon monoxide atmosphere at 80° C. for 1 hr. The reaction was quenched with water, and the mixture was extracted with ethyl acetate. The organic layer was washed twice with saturated brine, and dried over anhydrous magnesium sulfate. The solvent was evaporated under reduced pressure and the obtained residue was purified by silica gel column chromatography (hexane:ethyl acetate=19:1 to 7:3) to give the title compound (275 mg, yield 71%) as an oil.

$^1$H NMR (CDCl$_3$) δ0.33-0.38 (m, 2H), 0.59-0.66 (m, 2H), 1.21-1.33 (m, 1H), 3.92 (s, 3H), 4.21 (d, J=7.2 Hz, 2H), 6.47 (d, J=11.0 Hz, 1H), 8.73 (d, J=11.0 Hz, 1H).

Reference Example 270

[6-(cyclopropylmethoxy)-4-fluoropyridin-3-yl]methanol

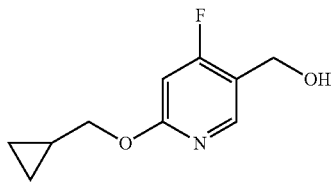

To a solution of methyl 6-(cyclopropylmethoxy)-4-fluoropyridine-3-carboxylate (275 mg, 1.22 mmol) obtained in Reference Example 269 in THF (5 mL) was added diisobutylaluminum hydride (1.5 M toluene solution, 2.04 mL, 3.06 mmol) and the mixture was stirred at room temperature for 10 min. To the reaction mixture was added sodium sulfate 10 hydrate and the mixture was stirred for 30 min. After filtration, the solvent was evaporated under reduced pressure and the obtained residue was purified by silica gel column chromatography (hexane:ethyl acetate=4:1 to 0:1) to give the title compound (194 mg, yield 81%) as an oil.

$^1$H NMR (CDCl$_3$) δ0.32-0.37 (m, 2H), 0.58-0.64 (m, 2H), 1.20-1.32 (m, 1H), 1.78 (t, J=5.9 Hz, 1H), 4.14 (d, J=7.2 Hz, 2H), 4.68 (d, J=5.7 Hz, 2H), 6.47 (d, J=11.0 Hz, 1H), 8.11 (d, J=11.0 Hz, 1H).

Reference Example 271

5-(bromomethyl)-2-(cyclopropylmethoxy)-4-fluoropyridine

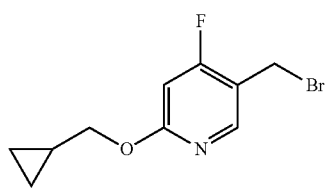 [SMILES: Fc1cc(OCC2CC2)ncc1CBr]

To a solution of [6-(cyclopropylmethoxy)-4-fluoropyridin-3-yl]methanol (200 mg, 1.01 mmol) obtained in Reference Example 270 and triphenylphosphine (345 mg, 1.31 mmol) in THF (5 mL) was added carbon tetrabromide (504 mg, 1.52 mmol), and the mixture was stirred at room temperature for 10 min. The solvent was evaporated under reduced pressure and the obtained residue was purified by silica gel column chromatography (hexane:ethyl acetate=9:1 to 1:1) to give the title compound (262 mg, quantitative) as an oil.

Reference Example 272 methyl 2-fluoro-4-hydroxybenzoate

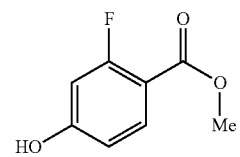 [SMILES: COC(=O)c1ccc(O)cc1F]

A solution of 2-fluoro-4-hydroxybenzoic acid (50.0 g, 294 mmol) and conc. sulfuric acid (10 mL) in methanol (700 mL) was stirred under heating at 90° C. for 16 hr. The reaction solution was concentrated, and the resulting colorless crystals were washed with water and dried to give the title compound (51 g, yield 94%) as colorless crystals.

¹H NMR (DMSO-d₆) δ 3.79 (s, 3H), 6.61-6.72 (m, 2H), 7.73-7.79 (m, 1H), 10.80 (br, 1H).

Reference Example 273

2-fluoro-4-[(2S)-tetrahydrofuran-2-ylmethoxy]benzoic acid

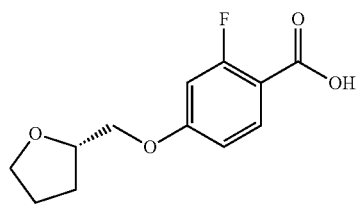 [SMILES: O=C(O)c1ccc(OC[C@@H]2CCCO2)cc1F]

To a solution of (2S)-tetrahydrofurfurylalcohol (30.0 g, 294 mmol), methyl 2-fluoro-4-hydroxybenzoate (50.0 g, 294 mmol) obtained in Reference Example 272 and triphenylphosphine (88.9 g, 339 mmol) in THF (350 mL) was slowly added dropwise 40% diethyl azodicarboxylate-toluene solution (166 mL, 339 mmol) at 0° C., and the mixture was stirred at room temperature for 2 hr. The reaction solution was concentrated, and triphenylphosphine oxide was precipitated from ethyl acetate-hexane and removed by filtration through a glass filter. The mother liquor was concentrated and the residue was purified by basic silica gel column chromatography (hexane:ethyl acetate=19:1 to 9:1) to give colorless crystals. The obtained colorless crystals were dissolved in tetrahydrofuran (500 mL), 8N aqueous sodium hydroxide solution (100 mL) was added thereto, and the mixture was stirred under heating at 60° C. for 3 hr. The reaction solution was concentrated, cooled to 0° C., and neutralized with 6N hydrochloric acid, and the mixture was extracted with ethyl acetate. The organic layer was washed with saturated brine, dried over anhydrous magnesium sulfate. The solvent was evaporated under reduced pressure to give the title compound (60.0 g, yield 85%) as colorless crystals.

¹H NMR (DMSO-d₆) δ 1.60-1.71 (m, 1H), 1.75-1.92 (m, 2H), 1.94-2.06 (m, 1H), 3.69 (q, J=6.9 Hz, 1H), 3.77 (q, J=6.9 Hz, 1H), 3.96-4.09 (m, 2H), 4.12-4.20 (m, 1H), 6.84-6.92 (m, 2H), 7.78-7.84 (m, 1H), 12.85 (br, 1H).

Reference Example 274

{2-fluoro-4-[(2S)-tetrahydrofuran-2-ylmethoxy]phenyl}methanol

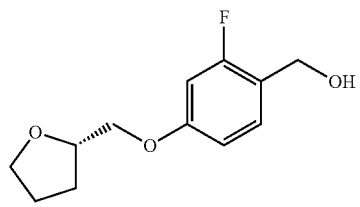 [SMILES: OCc1ccc(OC[C@@H]2CCCO2)cc1F]

To a solution of 2-fluoro-4-[(2S)-tetrahydrofuran-2-ylmethoxy]benzoic acid (1.00 g, 4.16 mmol) obtained in Reference Example 273 in THF (10 mL) was added dropwise 1M borane-THF solution (8.3 mL, 8.3 mmol), and the mixture was stirred at room temperature for 30 min. To the reaction mixture was slowly added dropwise water, and to this solution was further added water. The mixture was extracted with ethyl acetate, and the extract was washed with saturated brine, and dried over anhydrous magnesium sulfate. The solution was purified by basic silica gel column chromatography (ethyl acetate), and the solvent was evaporated to give the title compound (984 mg, quantitative) as a colorless oil.

¹H NMR (CDCl₃) δ 1.52-1.64 (m, 1H), 1.64-1.83 (m, 2H), 1.88-2.15 (m, 2H), 3.77-3.88 (m, 1H), 3.88-4.00 (m, 3H), 4.22-4.32 (m, 1H), 4.67 (d, J=6.0 Hz, 2H), 6.52-6.81 (m, 2H), 7.16-7.38 (m, 1H).

Reference Example 275

5-(cyclopropylmethoxy)-2-methylbenzonitrile

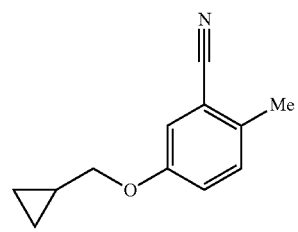 [SMILES: Cc1ccc(OCC2CC2)cc1C#N]

To a solution of 3-bromo-4-methylphenol (5.08 g, 27.1 mmol) in DMF (30 mL) were added (bromomethyl)cyclopropane (4.39 g, 32.5 mmol) and potassium carbonate (7.49 g, 54.3 mmol), and the mixture was stirred at 60° C. overnight. Then, water was added thereto, and the mixture was extracted with ethyl acetate-hexane. The extract was washed with saturated brine, and the solvent was evaporated. The obtained residue was purified by silica gel column chromatography (hexane to hexane:ethyl acetate=17:1) and the obtained oil was used for the next reaction.

To the obtained oil were added N-methylpyrrolidone (50 mL) and copper(I) cyanide (4.83 g, 54.2 mmol), and the mixture was stirred under nitrogen at 120° C. overnight. Then, water and ethyl acetate were added thereto, the resulting solid was filtered through celite, and the filtrate was extracted with ethyl acetate. The extract was washed with saturated brine, and dried over anhydrous magnesium sulfate. The solvent was evaporated under reduced pressure. The obtained residue was purified by silica gel column chromatography (hexane to hexane:ethyl acetate=17:1) to give the title compound (3.60 g, yield 71%).

¹H NMR (CDCl₃) δ0.25-0.40 (m, 2H), 0.56-0.71 (m, 2H), 1.13-1.37 (m, 1H), 2.46 (s, 3H), 3.78 (d, J=6.8 Hz, 2H), 6.99-7.10 (m, 2H), 7.19 (d, J=8.3 Hz, 1H).

Reference Example 276

2-(bromomethyl)-5-(cyclopropylmethoxy)benzonitrile

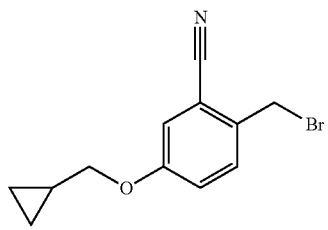 [SMILES: N#Cc1cc(OCC2CC2)ccc1CBr]

To a solution of 5-(cyclopropylmethoxy)-2-methylbenzonitrile (2.06 g, 11.0 mmol) obtained in Reference Example 275 in carbon tetrachloride (40 mL) were added N-bromosuccinimide (2.14 g, 12.1 mmol) and 2,2'-azodi(isobutyronitrile) (180 mg, 1.10 mmol) and the mixture was heated under reflux overnight. The resulting white solid was removed by filtration, and the solvent was evaporated. The resulting solid was washed with diisopropyl ether to give the title compound (1.54 g, yield 53%) as a white solid.

¹H NMR (CDCl₃) δ0.30-0.42 (m, 2H), 0.63-0.73 (m, 2H), 1.13-1.37 (m, 1H), 3.82 (d, J=6.8 Hz, 2H), 4.61 (s, 2H), 7.05-7.15 (m, 2H), 7.44 (d, J=8.7 Hz, 1H).

Reference Example 277 methyl 2-(methoxymethoxy)-4-[(4-benzyloxyphenyl)ethynyl]benzoate

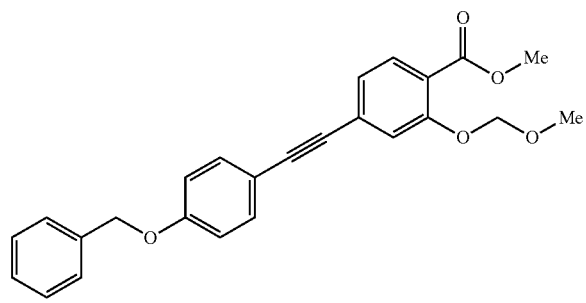 [SMILES: COCOc1cc(C#Cc2ccc(OCc3ccccc3)cc2)ccc1C(=O)OC]

Using methyl 2-hydroxy-4-iodobenzoate (5.79 g, 20.8 mmol) and 1-benzyloxy-4-ethynylbenzene (5.20 g, 25.0 mmol), an operation in the same manner as in Reference Example 47 was performed to give the title compound ((7.37 g, yield 87%) as a brown solid.

¹H NMR (CDCl₃) δ 3.54 (s, 3H), 3.90 (s, 3H), 5.09 (s, 2H), 5.28 (s, 2H), 6.96 (d, J=8.9 Hz, 2H), 7.17 (dd, J=8.1, 1.5 Hz, 1H), 7.33-7.49 (m, 8H), 7.76 (d, J=8.1 Hz, 1H).

Reference Example 278

[4-{2-[4-(cyclopropylmethoxy)phenyl]ethyl}-2-(methoxymethoxy)phenyl]methanol

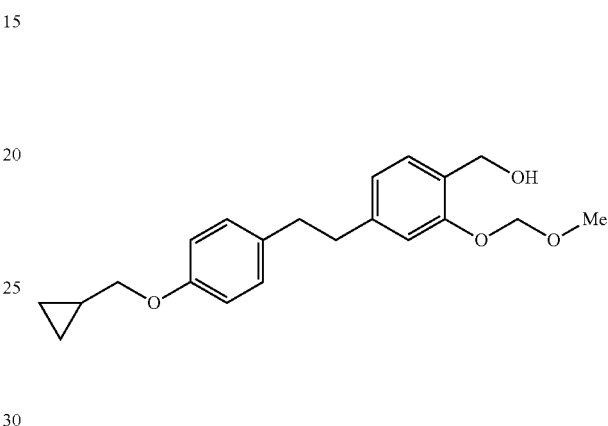

A solution of methyl 2-(methoxymethoxy)-4-[(4-benzyloxyphenyl)ethynyl]benzoate (7.37 g, 18.3 mmol) obtained in Reference Example 277 and 10% palladium carbon (50% water-containing product, 11.0 g) in ethanol (50 mL)-THF (10 mL) was stirred under a hydrogen atmosphere (normal pressure) for 2 hr. After filtration of the reaction mixture, the filtrate was concentrated under reduced pressure. To a solution of the obtained residue in DMF (50 mL) were added potassium carbonate (7.63 g, 55.2 mmol) and bromomethylcyclopropane (3.60 mL, 36.7 mmol) and the mixture was stirred at 60° C. for 1 hr. The reaction mixture was diluted with ethyl acetate, and the mixture was washed three times with saturated brine, and dried over anhydrous magnesium sulfate. The solvent was evaporated under reduced pressure and the obtained residue was purified by basic silica gel column chromatography (hexane:ethyl acetate=9:1 to 1:1) to give methyl 4-{2-[4-(cyclopropylmethoxy)phenyl]ethyl}-2-(methoxymethoxy)benzoate (4.69 g, yield 69%). A solution of methyl 4-{2-[4-(cyclopropylmethoxy)phenyl]ethyl}-2-(methoxymethoxy)benzoate (4.69 g, 12.7 mmol) in THF (10 mL) was added to a suspension of lithium aluminum hydride (481 mg, 12.7 mmol) in THF (30 mL), and the mixture was stirred at room temperature for 15 min. To the reaction mixture were successively added water (0.48 mL), 15% aqueous sodium hydroxide solution (0.48 mL) and water (1.5 mL), and the mixture was stirred at room temperature for 30 min. After filtration, the filtrate was concentrated under reduced pressure, and the obtained residue was purified by silica gel column chromatography (hexane:ethyl acetate=7:3 to 0:1) to give the title compound (4.23 g, yield 97%) as an oil.

¹H NMR (CDCl₃) δ 0.31-0.36 (m, 2H), 0.60-0.67 (m, 2H), 1.21-1.31 (m, 1H), 2.81-2.88 (m, 4H), 3.49 (s, 3H), 3.77 (d,

J=7.2 Hz, 2H), 4.67 (d, J=6.4 Hz, 2H), 5.20 (s, 2H), 6.80-6.84 (m, 3H), 6.89 (s, 1H), 7.07 (d, J=8.3 Hz, 2H), 7.20 (d, J=7.5 Hz, 1H).

Reference Example 279

4-{2-[(4-(cyclopropylmethoxy)phenyl]ethyl}-2-(methoxymethoxy)benzaldehyde

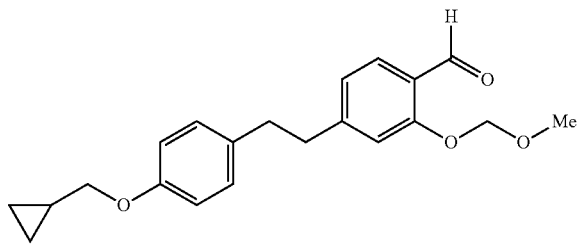 [SMILES: COCOc1cc(CCc2ccc(OCC3CC3)cc2)ccc1C=O]

Using [4-{2-[4-(cyclopropylmethoxy)phenyl]ethyl}-2-(methoxymethoxy)phenyl]methanol (4.23 g, 12.4 mmol) obtained in Reference Example 278, an operation in the same manner as in Reference Example 49 was performed to give the title compound (3.45 g, yield 81%) as an oil.

$^1$H NMR (CDCl$_3$) δ 0.31-0.36 (m, 2H), 0.61-0.67 (m, 2H), 1.21-1.31 (m, 1H), 2.82-2.95 (m, 4H), 3.51 (s, 3H), 3.77 (d, J=6.8 Hz, 2H), 5.24 (s, 2H), 6.81 (d, J=8.7 Hz, 2H), 6.89 (d, J=8.0 Hz, 1H), 6.94 (s, 1H), 7.04 (d, J=8.7 Hz, 2H), 7.75 (d, J=8.0 Hz, 1H), 10.43 (s, 1H).

Reference Example 280

4-{2-[4-(cyclopropylmethoxy)phenyl]ethyl}-2-hydroxybenzaldehyde

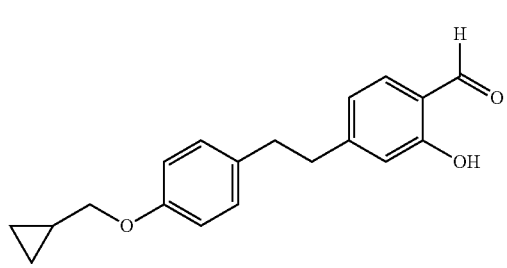 [SMILES: O=Cc1ccc(CCc2ccc(OCC3CC3)cc2)cc1O]

Using 4-{2-[4-(cyclopropylmethoxy)phenyl]ethyl}-2-(methoxymethoxy)benzaldehyde (3.52 g, 10.3 mmol) obtained in Reference Example 279, an operation in the same manner as in Reference Example 50 was performed to give the title compound (2.46 g, yield 81%) as a yellow solid.

$^1$H NMR (CDCl$_3$) δ 0.31-0.36 (m, 2H), 0.60-0.67 (m, 2H), 1.20-1.33 (m, 1H), 2.86-2.94 (m, 4H), 3.77 (d, J=6.8 Hz, 2H), 6.78-6.84 (m, 4H), 7.05 (d, J=8.7 Hz, 2H), 7.43 (d, J=8.0 Hz, 1H), 9.83 (s, 1H), 11.02 (s, 1H).

Reference Example 281

1-(6-{2-[4-(cyclopropylmethoxy)phenyl]ethyl}-1-benzofuran-2-yl)ethanone

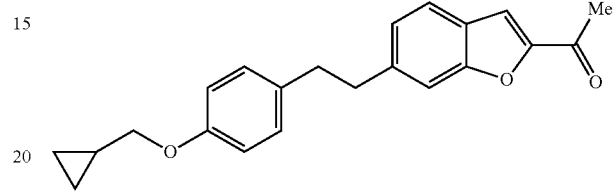

Using 4-{2-[4-(cyclopropylmethoxy)phenyl]ethyl}-2-hydroxybenzaldehyde (2.46 g, 8.30 mmol) obtained in Reference Example 280, an operation in the same manner as in Reference Example 51 was performed to give the title compound (2.77 g, quantitative) as a yellow solid.

Reference Example 282

1-(6-{2-[4-(cyclopropylmethoxy)phenyl]ethyl}-1-benzofuran-2-yl)ethanol

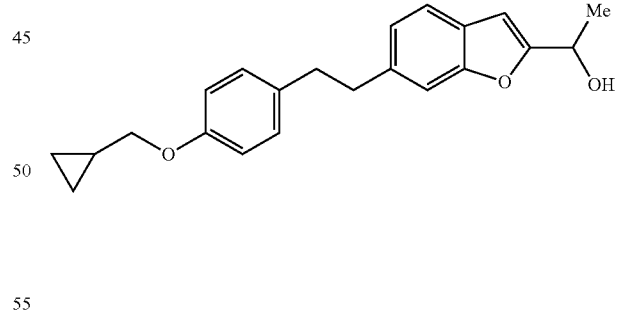

Using 1-(6-{2-[4-(cyclopropylmethoxy)phenyl]ethyl}-1-benzofuran-2-yl)ethanone (2.77 g, 8.30 mmol) obtained in Reference Example 281, an operation in the same manner as in Reference Example 52 was performed to give the title compound (2.05 g, yield 73%) as an oil.

$^1$H NMR (CDCl$_3$) δ 0.31-0.36 (m, 2H), 0.60-0.68 (m, 2H), 1.20-1.32 (m, 1H), 1.63 (d, J=6.8 Hz, 3H), 2.86-2.91 (m, 2H), 2.96-3.02 (m, 2H), 3.78 (d, J=6.8 Hz, 2H), 4.96-5.04 (m, 1H), 6.56 (s, 1H), 6.82 (d, J=8.7 Hz, 2H), 7.03 (dd, J=8.0, 1.5 Hz, 1H), 7.08 (d, J=8.7 Hz, 2H), 7.24-7.26 (m, 1H), 7.44 (d, J=8.0 Hz, 1H).

Reference Example 283

2-(1-azidoethyl)-6-{2-[4-(cyclopropylmethoxy)phenyl]ethyl}-1-benzofuran

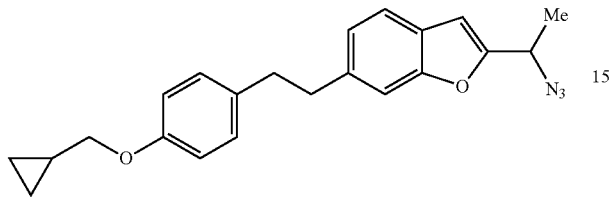

Using 1-(6-{2-[4-(cyclopropylmethoxy)phenyl]ethyl}-1-benzofuran-2-yl)ethanol (2.05 g, 6.09 mmol) obtained in Reference Example 282, an operation in the same manner as in Reference Example 28 was performed to give the title compound (2.05 g, yield 93%) as an oil.

$^1$H NMR (CDCl$_3$) δ 0.31-0.36 (m, 2H), 0.60-0.66 (m, 2H), 1.20-1.31 (m, 1H), 1.65 (d, J=6.8 Hz, 3H), 2.86-2.92 (m, 2H), 2.96-3.02 (m, 2H), 3.78 (d, J=6.8 Hz, 2H), 4.67 (q, J=6.8 Hz, 1H), 6.62 (s, 1H), 6.82 (d, J=8.7 Hz, 2H), 7.04-7.09 (m, 3H), 7.28 (s, 1H), 7.44 (d, J=8.0 Hz, 1H).

Reference Example 284 methyl 4-[(1,3-benzodioxol-5-yl)ethynyl]-2-(methoxymethoxy)benzoate

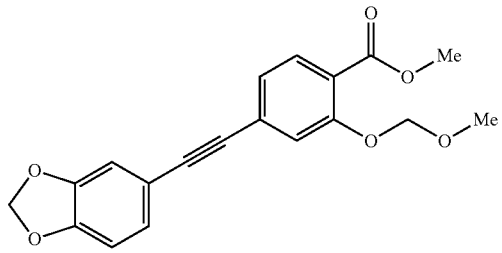 [SMILES: COCOc1cc(C#Cc2ccc3c(c2)OCO3)ccc1C(=O)OC]

Using methyl 2-hydroxy-4-iodobenzoate (1.43 g, 5.13 mmol) and 5-ethynyl-1,3-benzodioxole (900 mg, 6.16 mmol), an operation in the same manner as in Reference Example 47 was performed to give the title compound (1.32 g, yield 75%) as a brown solid.

$^1$H NMR (CDCl$_3$) δ 3.54 (s, 3H), 3.90 (s, 3H), 5.28 (s, 2H), 6.00 (s, 2H), 6.80 (d, J=8.3 Hz, 1H), 6.98 (d, J=1.5 Hz, 1H), 7.08 (dd, J=8.1, 1.7 Hz, 1H), 7.17 (dd, J=8.0, 1.5 Hz, 1H), 7.33 (d, J=1.1 Hz, 1H), 7.76 (d, J=8.0 Hz, 1H).

Reference Example 285

{4-[2-(1,3-benzodioxol-5-yl)ethyl]-2-(methoxymethoxy)phenyl}methanol

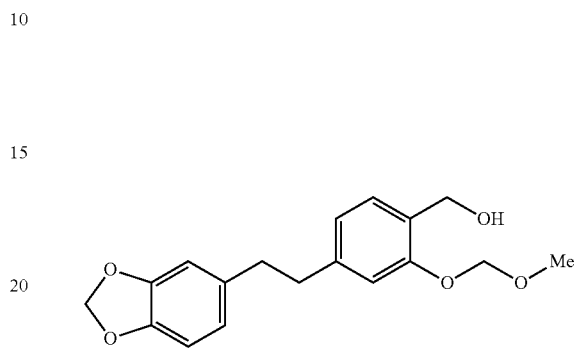

Using methyl 4-[(1,3-benzodioxol-5-yl)ethynyl]-2-(methoxymethoxy)benzoate (1.32 g, 3.88 mmol) obtained in Reference Example 284, an operation in the same manner as in Reference Example 48 was performed to give the title compound (1.02 g, yield 83%) as an oil.

$^1$H NMR (CDCl$_3$) δ 2.19 (t, J=6.4 Hz, 1H), 2.78-2.89 (m, 4H), 3.49 (s, 3H), 4.67 (d, J=6.4 Hz, 2H), 5.20 (s, 2H), 5.92 (s, 2H), 6.59-6.62 (m, 1H), 6.67 (d, J=1.9 Hz, 1H), 6.71 (d, J=8.0 Hz, 1H), 6.82 (dd, J=7.6, 1.5 Hz, 1H), 6.89 (d, J=1.5 Hz, 1H), 7.20 (d, J=7.6 Hz, 1H).

Reference Example 286

4-[2-(1,3-benzodioxol-5-yl)ethyl]-2-(methoxymethoxy)benzaldehyde

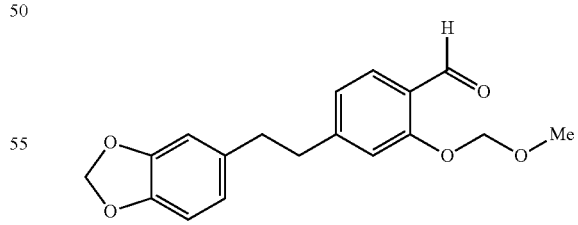

Using {4-[2-(1,3-benzodioxol-5-yl)ethyl]-2-(methoxymethoxy)phenyl}methanol (1.02 g, 3.22 mmol) obtained in Reference Example 285, an operation in the same manner as in Reference Example 49 was performed to give the title compound (741 mg, yield 73%) as an oil.

$^1$H NMR (CDCl$_3$) δ 2.81-2.94 (m, 4H), 3.51 (s, 3H), 5.25 (s, 2H), 5.92 (s, 2H), 6.56-6.60 (m, 1H), 6.65 (d, J=1.7 Hz,

1H), 6.71 (d, J=7.9 Hz, 1H), 6.89 (d, J=8.1 Hz, 1H), 6.95 (s, 1H), 7.75 (d, J=7.9 Hz, 1H), 10.44 (d, J=0.6 Hz, 1H).

Reference Example 287

4-[2-(1,3-benzodioxol-5-yl)ethyl]-2-hydroxybenzaldehyde

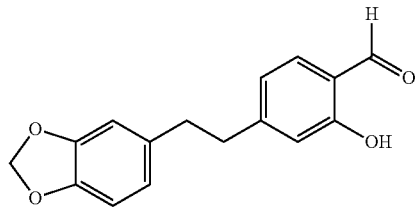 [SMILES: O=Cc1ccc(CCc2ccc3c(c2)OCO3)cc1O]

Using 4-[2-(1,3-benzodioxol-5-yl)ethyl]-2-(methoxymethoxy)benzaldehyde (741 mg, 2.36 mmol) obtained in Reference Example 286, an operation in the same manner as in Reference Example 50 was performed to give the title compound (637 mg, quantitative) as a yellow solid.

$^1$H NMR (CDCl$_3$) δ 2.81-2.93 (m, 4H), 5.92 (s, 2H), 6.57-6.60 (m, 1H), 6.65 (d, J=1.9 Hz, 1H), 6.71 (d, J=8.0 Hz, 1H), 6.79-6.82 (m, 2H), 7.44 (d, J=8.3 Hz, 1H), 9.84 (s, 1H), 11.03 (s, 1H).

Reference Example 288

1-{6-[2-(1,3-benzodioxol-5-yl)ethyl]-1-benzofuran-2-yl}ethanone

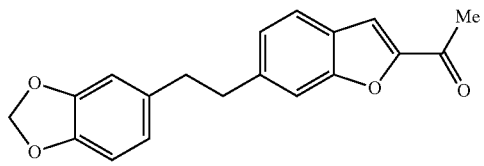 [SMILES: CC(=O)c1cc2ccc(CCc3ccc4c(c3)OCO4)cc2o1]

Using 4-[2-(1,3-benzodioxol-5-yl)ethyl]-2-hydroxybenzaldehyde (687 mg, 2.55 mmol) obtained in Reference Example 287, an operation in the same manner as in Reference Example 51 was performed to give the title compound (786 mg, quantitative) as a yellow solid.

$^1$H NMR (CDCl$_3$) δ 2.59 (s, 3H), 2.86-2.92 (m, 2H), 3.00-3.05 (m, 2H), 5.92 (s, 2H), 6.57-6.60 (m, 1H), 6.66 (d, J=1.5 Hz, 1H), 6.70 (d, J=8.0 Hz, 1H), 7.13 (dd, J=8.1, 1.3 Hz, 1H), 7.33 (s, 1H), 7.46 (d, J=1.1 Hz, 1H), 7.59 (d, J=8.0 Hz, 1H).

Reference Example 289

1-{6-[2-(1,3-benzodioxol-5-yl)ethyl]-1-benzofuran-2-yl}ethanol

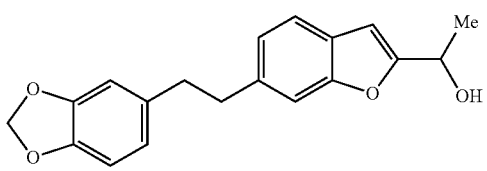 [SMILES: CC(O)c1cc2ccc(CCc3ccc4c(c3)OCO4)cc2o1]

Using 1-{6-[2-(1,3-benzodioxol-5-yl)ethyl]-1-benzofuran-2-yl}ethanone (786 mg, 2.55 mmol) obtained in Reference Example 288, an operation in the same manner as in Reference Example 52 was performed to give the title compound (617 mg, yield 78%) as a white solid.

$^1$H NMR (CDCl$_3$) δ 1.63 (d, J=6.8 Hz, 3H), 2.84-2.90 (m, 2H), 2.95-3.01 (m, 2H), 4.96-5.04 (m, 1H), 5.92 (s, 2H), 6.56 (s, 1H), 6.60-6.63 (m, 1H), 6.68 (d, J=1.5 Hz, 1H), 6.71 (d, J=7.6 Hz, 1H), 7.03 (dd, J=8.0, 1.5 Hz, 1H), 7.25 (s, 1H), 7.42 (d, J=8.0 Hz, 1H).

Reference Example 290

5-{2-[2-(1-azidoethyl)-1-benzofuran-6-yl]ethyl}-1,3-benzodioxole

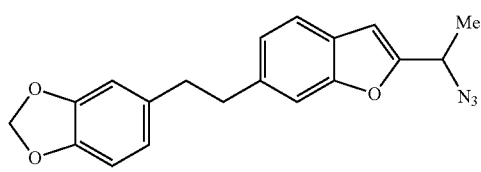 [SMILES: CC(N=[N+]=[N-])c1cc2ccc(CCc3ccc4c(c3)OCO4)cc2o1]

Using 1-{6-[2-(1,3-benzodioxol-5-yl)ethyl]-1-benzofuran-2-yl}ethanol (617 mg, 1.99 mmol) obtained in Reference Example 289, an operation in the same manner as in Reference Example 28 was performed to give the title compound (523 mg, yield 78%) as an oil.

$^1$H NMR (CDCl$_3$) δ 1.65 (d, J=6.8 Hz, 3H), 2.85-2.90 (m, 2H), 2.96-3.01 (m, 2H), 4.67 (q, J=6.8 Hz, 1H), 5.92 (s, 2H), 6.60-6.63 (m, 2H), 6.69 (d, J=1.5 Hz, 1H), 6.72 (d, J=7.6 Hz, 1H), 7.05 (dd, J=8.0, 1.5 Hz, 1H), 7.28 (s, 1H), 7.44 (d, J=8.0 Hz, 1H).

Reference Example 291

5-(2,2-dibromoethenyl)-3,3-dimethyl-2,3-dihydro-1-benzofuran

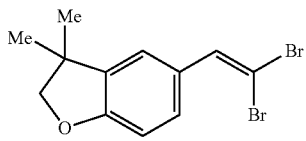 [SMILES: CC1(C)COc2ccc(C=C(Br)Br)cc21]

To a solution of 3,3-dimethyl-2,3-dihydro-1-benzofuran-5-carbaldehyde (4.18 g, 23.7 mmol) and triphenylphosphine (15.5 g, 59.3 mmol) in THF (40 mL) was added carbon tetrabromide, and the mixture was stirred at room temperature for 15 min. The solvent was evaporated under reduced pressure and the obtained residue was purified by silica gel column chromatography (hexane:ethyl acetate=49:1 to 7:3) to give the title compound (5.75 g, yield 73%) as an oil.

$^1$H NMR (CDCl$_3$) δ 1.35 (s, 6H), 4.27 (s, 2H), 6.77 (d, J=8.0 Hz, 1H), 7.31-7.35 (m, 2H), 7.41 (s, 1H).

Reference Example 292

5-ethynyl-3,3-dimethyl-2,3-dihydro-1-benzofuran

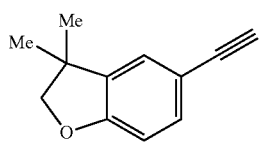

To a solution of 5-(2,2-dibromoethenyl)-3,3-dimethyl-2,3-dihydro-1-benzofuran (5.75 g, 17.3 mmol) obtained in Reference Example 291 in THF (40 mL) was added 1.6 M n-butyllithium hexane solution (23.8 mL, 38.1 mmol) at −78° C., and the mixture was stirred at the same temperature for 10 min. Water was added to the reaction mixture and the mixture was extracted with diethyl ether, and dried over anhydrous magnesium sulfate. The solvent was evaporated under reduced pressure and the obtained residue was purified by silica gel column chromatography (hexane:ethyl acetate=4:1 to 2:3) to give the title compound (2.98 g, quantitative) as an oil.

$^1$H NMR (CDCl$_3$) δ 1.33 (s, 6H), 2.97 (s, 1H), 4.25 (s, 2H), 6.72 (d, J=8.1 Hz, 1H), 7.23 (d, J=1.7 Hz, 1H), 7.29 (dd, J=8.1, 1.7 Hz, 1H)

Reference Example 293 methyl 4-[(3,3-dimethyl-2,3-dihydro-1-benzofuran-5-yl)ethynyl]-2-(methoxymethoxy)benzoate

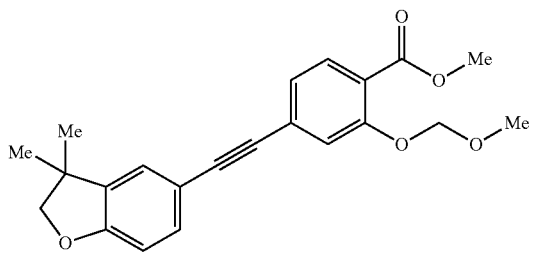 [SMILES: COCOc1cc(C#Cc2ccc3c(c2)C(C)(C)CO3)ccc1C(=O)OC]

Using methyl 2-hydroxy-4-iodobenzoate (3.40 g, 12.4 mmol) and 5-ethynyl-3,3-dimethyl-2,3-dihydro-1-benzofuran (2.98 g, 17.3 mmol) obtained in Reference Example 292, an operation in the same manner as in Reference Example 47 was performed to give the title compound (3.18 g, yield 69%) as a brown solid.

$^1$H NMR (CDCl$_3$) δ 1.36 (s, 6H), 3.54 (s, 3H), 3.90 (s, 3H), 4.28 (s, 2H), 5.28 (s, 2H), 6.77 (d, J=8.3 Hz, 1H), 7.17 (dd, J=8.0, 1.5 Hz, 1H), 7.29-7.35 (m, 3H), 7.76 (d, J=8.0 Hz, 1H).

Reference Example 294

{4-[2-(3,3-dimethyl-2,3-dihydro-1-benzofuran-5-yl)ethyl]-2-(methoxymethoxy)phenyl}methanol

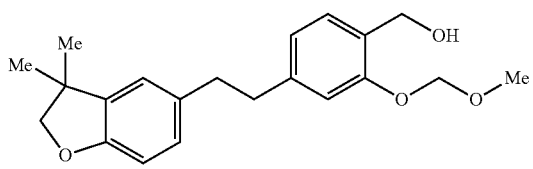 [SMILES: COCOc1cc(CCc2ccc3c(c2)C(C)(C)CO3)ccc1CO]

Using methyl 4-[(3,3-dimethyl-2,3-dihydro-1-benzofuran-5-yl)ethynyl]-2-(methoxymethoxy)benzoate (3.18 g, 8.68 mmol) obtained in Reference Example 293, an operation in the same manner as in Reference Example 48 was performed to give the title compound (2.50 g, yield 84%) as an oil.

¹H NMR (CDCl₃) δ 1.31 (s, 6H), 2.20 (t, J=6.6 Hz, 1H), 2.79-2.90 (m, 4H), 3.49 (s, 3H), 4.21 (s, 2H), 4.67 (d, J=6.6 Hz, 2H), 5.20 (s, 2H), 6.69 (d, J=8.0 Hz, 1H), 6.82-6.94 (m, 4H), 7.21 (d, J=7.5 Hz, 1H).

Reference Example 295

4-[2-(3,3-dimethyl-2,3-dihydro-1-benzofuran-5-yl)ethyl]-2-(methoxymethoxy)benzaldehyde

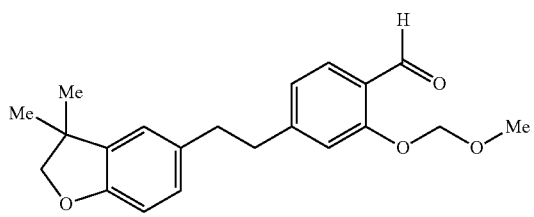 [SMILES: COCOc1cc(CCc2ccc3c(c2)C(C)(C)CO3)ccc1C=O]

Using {4-[2-(3,3-dimethyl-2,3-dihydro-1-benzofuran-5-yl)ethyl]-2-(methoxymethoxy)phenyl}methanol (2.50 g, 7.30 mmol) obtained in Reference Example 294, an operation in the same manner as in Reference Example 49 was performed to give the title compound (1.85 g, yield 74%) as an oil.

¹H NMR (CDCl₃) δ 1.30 (s, 6H), 2.83-2.95 (m, 4H), 3.51 (s, 3H), 4.21 (s, 2H), 5.24 (s, 2H), 6.69 (d, J=8.0 Hz, 1H), 6.83 (d, J=1.9 Hz, 1H), 6.88-6.93 (m, 3H), 7.76 (d, J=8.0 Hz, 1H), 10.44 (s, 1H).

Reference Example 296

4-[2-(3,3-dimethyl-2,3-dihydro-1-benzofuran-5-yl)ethyl]-2-hydroxybenzaldehyde

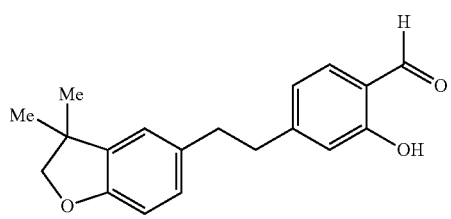 [SMILES: CC1(C)COc2ccc(CCc3ccc(C=O)c(O)c3)cc21]

Using 4-[2-(3,3-dimethyl-2,3-dihydro-1-benzofuran-5-yl)ethyl]-2-(methoxymethoxy)benzaldehyde (1.85 g, 5.43 mmol) obtained in Reference Example 295, an operation in the same manner as in Reference Example 50 was performed to give the title compound (1.41 g, yield 87%) as an oil.

¹H NMR (CDCl₃) δ 1.30 (s, 6H), 2.84-2.92 (m, 4H), 4.21 (s, 2H), 6.70 (d, J=8.0 Hz, 1H), 6.79-6.83 (m, 3H), 6.91 (dd, J=8.0, 1.9 Hz, 1H), 6.44 (d, J=8.3 Hz, 1H), 9.84 (s, 1H), 11.03 (s, 1H).

Reference Example 297

1-{6-[2-(3,3-dimethyl-2,3-dihydro-1-benzofuran-5-yl)ethyl]-1-benzofuran-2-yl}ethanone

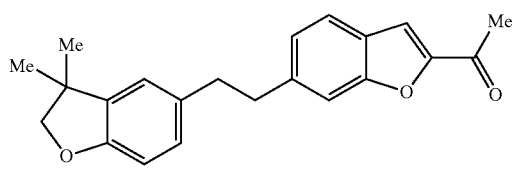 [SMILES: CC(=O)c1cc2ccc(CCc3ccc4c(c3)C(C)(C)CO4)cc2o1]

Using 4-[2-(3,3-dimethyl-2,3-dihydro-1-benzofuran-5-yl)ethyl]-2-hydroxybenzaldehyde (1.41 g, 4.76 mmol) obtained in Reference Example 296, an operation in the same manner as in Reference Example 51 was performed to give the title compound (1.59 g, quantitative) as a yellow solid.

Reference Example 298

1-{6-[2-(3,3-dimethyl-2,3-dihydro-1-benzofuran-5-yl)ethyl]-1-benzofuran-2-yl}ethanol

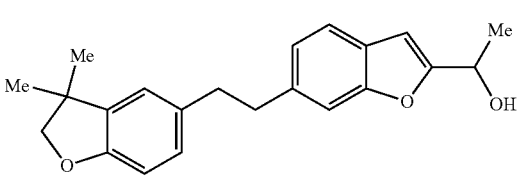 [SMILES: CC(O)c1cc2ccc(CCc3ccc4c(c3)C(C)(C)CO4)cc2o1]

Using 1-{6-[2-(3,3-dimethyl-2,3-dihydro-1-benzofuran-5-yl)ethyl]-1-benzofuran-2-yl}ethanone (1.59 g, 4.76 mmol) obtained in Reference Example 297, an operation in the same manner as in Reference Example 52 was performed to give the title compound (1.31 g, yield 81%) as a white solid.

¹H NMR (CDCl₃) δ 1.29 (s, 6H), 1.63 (d, J=6.4 Hz, 3H), 2.85-2.91 (m, 2H), 2.95-3.01 (m, 2H), 4.21 (s, 2H), 4.96-5.04 (m, 1H), 6.57 (s, 1H), 6.69-6.71 (d, J=8.3 Hz, 1H), 6.82 (d, J=1.9 Hz, 1H), 6.94 (dd, J=7.6, 1.9 Hz, 1H), 7.04 (dd, J=7.9, 1.1 Hz, 1H), 7.23 (s, 1H), 7.43 (d, J=7.9 Hz, 1H).

Reference Example 299

2-(1-azidoethyl)-6-[2-(3,3-dimethyl-2,3-dihydro-1-benzofuran-5-yl)ethyl]-1-benzofuran

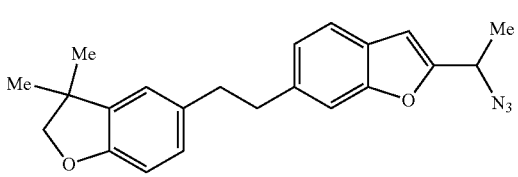 [SMILES: CC(N=[N+]=[N-])c1cc2ccc(CCc3ccc4c(c3)C(C)(C)CO4)cc2o1]

Using 1-{6-[2-(3,3-dimethyl-2,3-dihydro-1-benzofuran-5-yl)ethyl]-1-benzofuran-2-yl}ethanol (1.31 g, 3.89 mmol)

obtained in Reference Example 298, an operation in the same manner as in Reference Example 28 was performed to give the title compound (1.17 g, yield 83%) as an oil.

$^1$H NMR (CDCl$_3$) δ 1.29 (s, 6H), 1.65 (d, J=6.8 Hz, 3H), 2.86-2.92 (m, 2H), 2.96-3.02 (m, 2H), 4.21 (s, 2H), 4.67 (q, J=6.8 Hz, 1H), 6.62 (s, 1H), 6.70 (d, J=8.0 Hz, 1H), 6.81 (d, J=1.9 Hz, 1H), 6.94 (dd, J=8.0, 1.9 Hz, 1H), 7.05 (dd, J=8.0, 1.5 Hz, 1H), 7.25 (s, 1H), 7.45 (d, J=8.0 Hz, 1H).

Reference Example 300 methyl 2-fluoro-4-[(2R)-tetrahydrofuran-2-yl-methoxy]benzoate

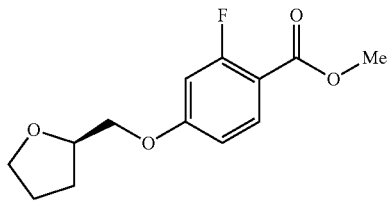 [SMILES: COC(=O)c1ccc(OC[C@H]2CCCO2)cc1F]

Using (2R)-tetrahydrofuran-2-ylmethanol (1.71 g, 10.0 mmol) and methyl 2-fluoro-4-hydroxybenzoate (1.24 g, 12.0 mmol) obtained in Reference Example 272 and in the same manner as in Reference Example 273, the title compound (2.49 g, yield 98%) was obtained as colorless crystals.

$^1$H NMR (CDCl$_3$) δ 1.70-1.81 (m, 1H), 1.93-2.15 (m, 3H), 3.80-4.01 (m, 7H), 4.24-4.32 (m, 1H), 6.64-6.76 (m, 2H), 7.80-7.90 (m, 1H).

Reference Example 301

{2-fluoro-4-[(2R)-tetrahydrofuran-2-ylmethoxy]phenyl}methanol

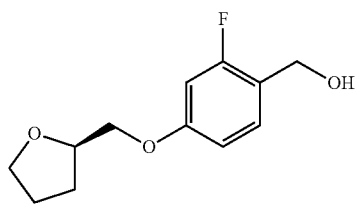 [SMILES: OCc1ccc(OC[C@H]2CCCO2)cc1F]

A solution of methyl 2-fluoro-4-[(2R)-tetrahydrofuran-2-ylmethoxy]benzoate (2.49 g, 9.79 mmol) obtained in Reference Example 300 in THF (20 mL) was added to a suspension of lithium aluminum hydride (350 mg, 9.22 mmol) in THF (10 mL), and the mixture was stirred at room temperature for 15 min. To the reaction mixture were sequentially added water (0.35 mL), 15% aqueous sodium hydroxide solution (0.35 mL) and water (1.1 mL), and the mixture was stirred at room temperature for 30 min. After filtration, the filtrate was concentrated under reduced pressure, and the obtained residue was purified by silica gel column chromatography (hexane:ethyl acetate=4:1 to 3:7) to give the title compound (2.13 g, yield 96%) as an oil.

$^1$H NMR (CDCl$_3$) δ 1.67-1.81 (m, 2H), 1.90-2.12 (m, 2H), 3.80-3.97 (m, 4H), 4.24-4.30 (m, 1H), 4.67 (d, J=6.0 Hz, 2H), 6.63-6.73 (m, 2H), 7.25-7.31 (m, 1H).

Reference Example 302 methyl 2-(methoxymethoxy)-5-[(4-methoxyphenyl)ethynyl]benzoate

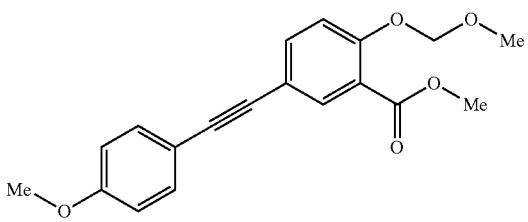 [SMILES: COCOc1ccc(C#Cc2ccc(OC)cc2)cc1C(=O)OC]

Using methyl 2-hydroxy-5-iodobenzoate (8.35 g, 30.0 mmol) and 1-methoxy-4-ethynylbenzene (4.76 g, 36.0 mmol), an operation in the same manner as in Reference Example 47 was performed to give the title compound (7.42 g, yield 70%) as an oil.

$^1$H NMR (CDCl$_3$) δ 3.52 (s, 3H), 3.83 (s, 3H), 3.90 (s, 3H), 5.27 (s, 2H), 6.84-6.90 (m, 2H), 7.17 (d, J=8.7 Hz, 1H), 7.41-7.48 (m, 2H), 7.56 (dd, J=8.7, 2.3 Hz, 1H), 7.94 (d, J=2.3 Hz, 1H).

Reference Example 303

{2-(methoxymethoxy)-5-[2-(4-methoxyphenyl)ethyl]phenyl}methanol

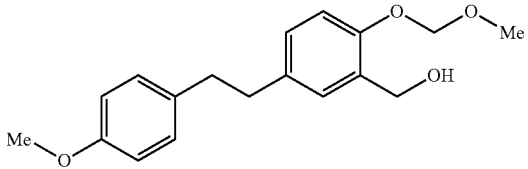 [SMILES: COCOc1ccc(CCc2ccc(OC)cc2)cc1CO]

Using methyl 2-(mathoxymethoxy)-5-[(4-methoxyphenyl)ethynyl]benzoate (7.42 g, 22.8 mmol) obtained in Reference Example 302, an operation in the same manner as in Reference Example 48 was performed to give the title compound (5.43 g, yield 79%) as a colorless oil.

¹H NMR (CDCl₃) δ 2.40 (br, 1H), 2.82 (s like, 4H), 3.46 (s, 3H), 3.77 (s, 3H), 4.67 (d, J=3.4 Hz, 2H), 5.19 (s, 2H), 6.79-6.84 (m, 2H), 6.97-7.15 (m, 5H).

Reference Example 304

2-(methoxymethoxy)-5-[2-(4-methoxyphenyl)ethyl]benzaldehyde

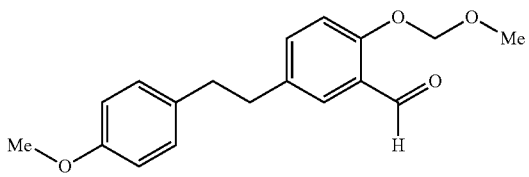 [SMILES: COCOc1ccc(CCc2ccc(OC)cc2)cc1C=O]

Using {2-(methoxymethoxy)-5-[2-(4-methoxyphenyl)ethyl]phenyl}methanol (17.0 g, 56.0 mmol) obtained in Reference Example 303, an operation in the same manner as in Reference Example 49 was performed to give the title compound (14.4 g, yield 85%) as a colorless oil.
¹H NMR (CDCl₃) δ 2.78-2.90 (m, 4H), 3.51 (s, 3H), 3.77 (s, 3H), 5.27 (s, 2H), 6.77-6.85 (m, 2H), 7.03-7.13 (m, 3H), 7.29 (dd, J=8.5, 2.4 Hz, 1H), 7.67 (d, J=2.6 Hz, 1H), 10.48 (s, 1H).

Reference Example 305

2-hydroxy-5-[2-(4-methoxyphenyl)ethyl]benzaldehyde

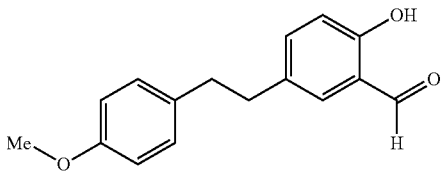 [SMILES: COc1ccc(CCc2ccc(O)c(C=O)c2)cc1]

Using 2-(methoxymethoxy)-5-[2-(4-methoxyphenyl)ethyl]benzaldehyde (2.48 g, 8.26 mmol) obtained in Reference Example 304, an operation in the same manner as in Reference Example 50 was performed to give the title compound (2.02 g, yield 96%) as a white solid.
¹H NMR (CDCl₃) δ 2.80-2.91 (m, 4H), 3.78 (s, 3H), 6.78-6.84 (m, 2H), 6.89 (d, J=8.3 Hz, 1H), 7.00-7.08 (m, 2H), 7.23-7.32 (m, 2H), 9.81 (s, 1H), 10.86 (s, 1H).

Reference Example 306

1-{5-[2-(4-methoxyphenyl)ethyl]-1-benzofuran-2-yl}ethanone

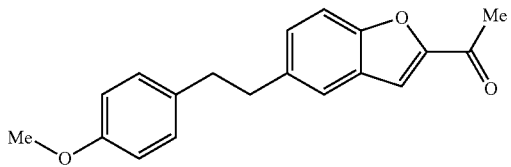 [SMILES: COc1ccc(CCc2ccc3oc(C(C)=O)cc3c2)cc1]

Using 2-hydroxy-5-[2-(4-methoxyphenyl)ethyl]benzaldehyde (2.00 g, 7.79 mmol) obtained in Reference Example 305, an operation in the same manner as in Reference Example 51 was performed to give the title compound (1.20 g, yield 52%) as a yellow solid.
¹H NMR (CDCl₃) δ 2.60 (s, 3H), 2.86-2.94 (m, 2H), 2.96-3.04 (m, 2H), 3.78 (s, 3H), 6.81 (d, J=8.7 Hz, 2H), 7.06 (d, J=8.7 Hz, 2H), 7.23-7.30 (m, 1H), 7.40-7.51 (m, 3H).

Reference Example 307

1-{5-[2-(4-methoxyphenyl)ethyl]-1-benzofuran-2-yl}ethanol

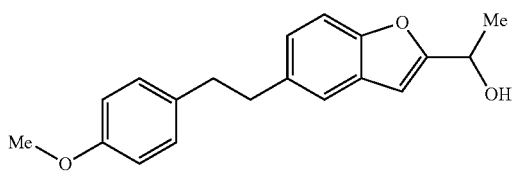 [SMILES: COc1ccc(CCc2ccc3oc(C(C)O)cc3c2)cc1]

Using 1-{5-[2-(4-methoxyphenyl)ethyl]-1-benzofuran-2-yl}ethanone (2.43 g, 8.25 mmol) obtained in Reference Example 306, an operation in the same manner as in Reference Example 52 was performed to give the title compound (1.95 g, yield 80%) as a white solid.
¹H NMR (CDCl₃) δ 1.62 (d, J=6.4 Hz, 3H), 2.11 (d, J=5.3 Hz, 1H), 2.78-3.01 (m, 4H), 3.78 (s, 3H), 4.94-5.05 (m, 1H), 6.54 (s, 1H), 6.78-6.85 (m, 2H), 7.03-7.12 (m, 3H), 7.29-7.37 (m, 2H).

Reference Example 308

2-(1-azidoethyl)-5-[2-(4-methoxyphenyl)ethyl]-1-benzofuran

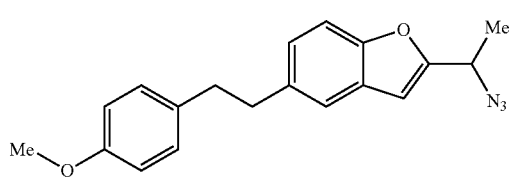 [SMILES: COc1ccc(CCc2ccc3oc(C(C)N=[N+]=[N-])cc3c2)cc1]

Using 1-[5-[2-(4-methoxyphenyl)ethyl]-1-benzofuran-2-yl]ethanol (1.90 g, 6.40 mmol) obtained in Reference Example 307, an operation in the same manner as in Reference Example 28 was performed to give the title compound (1.41 g, yield 69%) as a colorless oil.

¹H NMR (CDCl₃) δ 1.65 (d, J=7.2 Hz, 3H), 2.83-3.01 (m, 4H), 3.77 (s, 3H), 4.67 (q, J=7.0 Hz, 1H), 6.59 (s, 1H), 6.78-6.85 (m, 2H), 7.05-7.12 (M, 3H), 7.31-7.39 (m, 2H).

Reference Example 309

N-[1-(6-hydroxy-1-benzofuran-3-yl)ethyl]acetamide (two kinds)

N-[1-(6-hydroxy-1-benzofuran-3-yl)ethyl]acetamide (1.81 g) obtained in Reference Example 4 was optically resolved by high performance liquid chromatography (HPLC) under the following conditions to give two kinds of optically active forms of "retention time longer (824 mg)" and "retention time shorter (764 mg)".
<Preparative HPLC Conditions>
   column: CHIRALPAK AD (50 mmID×500 mmL)
   mobile phase: hexane:ethanol=9:1
   flow rate: 80 mL/min
   column temperature: 30° C.
   detection: UV 220 nm
<HPLC Analysis Conditions>
   column: CHIRALPAK AD (4.6 mmID×250 mmL)
   mobile phase: hexane:ethanol=9:1
   flow rate: 1.0 mL/min
   column temperature: 30° C.
   detection: UV 220 nm
   retention time of "retention time longer": 20.4 min
   retention time of "retention time shorter": 14.6 min Reference Example 310

[4-(2-cyclopropylethoxy)phenyl]methanol

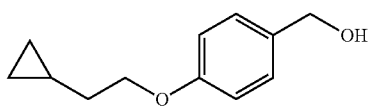 [SMILES: OCc1ccc(OCCC2CC2)cc1]

Using 4-(2-cyclopropylethoxy)benzoic acid (6.20 g, 30.1 mmol) and in the same manner as in Reference Example 274, the title compound (5.76 g, quantitative) was obtained as a white solid.

¹H NMR (CDCl₃) δ0.08-0.15 (m, 2H), 0.44-0.52 (m, 2H), 0.75-0.95 (m, 1H), 1.60-1.75 (m, 2H), 4.04 (t, J=6.6 Hz, 2H), 4.62 (s, 2H), 6.85-6.94 (m, 2H), 7.29 (d, J=8.4 Hz, 2H).

Reference Example 311

4-[(2S)-tetrahydrofuran-2-ylmethoxy]benzoic acid

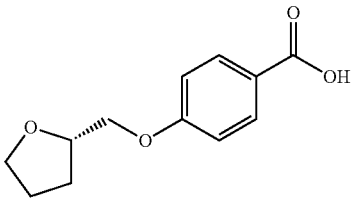 [SMILES: O=C(O)c1ccc(OC[C@@H]2CCCO2)cc1]

To a solution of (2S)-tetrahydrofuran-2-ylmethanol (49.6 g, 486 mmol), 4-methyl hydroxybenzoate (73.9 g, 486 mmol) and triphenylphosphine (147 g, 560 mmol) in THF (600 ml) was slowly added dropwise a solution (273 mL, 600 mmol) of 40% diethyl azodicarboxylate (DEAD) in toluene at 0° C., and the mixture was stirred at room temperature for 2 hr. The reaction solution was concentrated, triphenylphosphine oxide was precipitated from ethyl acetate-hexane, and removed by filtration through a glass filter, and the mother liquor was concentrated. The residue was purified by basic silica gel column chromatography (ethyl acetate:hexane=1:9) to give a colorless oil. The obtained colorless oil was dissolved in tetrahydrofuran (400 ml), methanol (300 ml) and water (100 ml), 8N aqueous sodium hydroxide solution (100 ml) was added thereto, and the mixture was stirred under heating at 90° C. for 2 hr. The reaction solution was concentrated, cooled to 0° C., and neutralized with 6N hydrochloric acid to allow precipitation of crystals. The crystals were dissolved in THF, and the solution was extracted with ethyl acetate. The organic layer was washed with saturated brine, dried over anhydrous magnesium sulfate, and the solvent was evaporated under reduced pressure to give the title compound (68 g, yield 51%) as colorless crystals.

¹H NMR (DMSO-d₆) δ 1.64-1.72 (m, 1H), 1.82-1.92 (m, 2H), 1.95-2.04 (m, 1H), 3.68 (q, J=7.2 Hz, 1H), 3.78 (q, J=7.2 Hz, 1H), 3.95-4.06 (m, 2H), 4.14-4.19 (m, 1H), 7.02 (d, J=8.7 Hz, 2H), 7.88 (d, J=8.7 Hz, 2H), 12.62 (s, 1H).

Reference Example 312

{4-[(2S)-tetrahydrofuran-2-ylmethoxy]phenyl}methanol

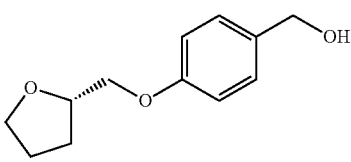 [SMILES: OCc1ccc(OC[C@@H]2CCCO2)cc1]

Using 4-[(2S)-tetrahydrofuran-2-ylmethoxy]benzoic acid (7.50 g, 33.7 mmol) obtained in Reference Example 311 and in the same manner as in Reference Example 274, the title compound (6.98 g, quantitative) was obtained as an oil.

¹H NMR (CDCl₃) δ 1.68-1.86 (m, 1H), 1.90-2.15 (m, 3H), 3.76-3.88 (m, 1H), 3.90-4.03 (m, 3H), 4.18-4.38 (m, 1H), 4.62 (s, 2H), 6.92 (d, J=8.7 Hz, 2H), 7.27 (d, J=8.7 Hz, 2H).

Reference Example 313

[4-(cyclobutylmethoxy)phenyl]methanol

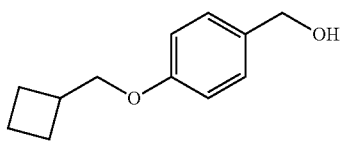 [SMILES: OCc1ccc(OCC2CCC2)cc1]

A mixture of 4-(hydroxymethyl)phenol (3.20 g, 25.8 mmol), potassium carbonate (7.12 g, 51.6 mmol) and (bromomethyl)cyclobutane (3.75 mL, 33.6 mmol) in ethanol (50 mL) was stirred at 70° C. overnight. Water was added thereto, ethanol was evaporated under reduced pressure, and the mixture was extracted twice with ethyl acetate. The combined organic layer was washed with saturated brine, and dried over anhydrous magnesium sulfate. The solvent was evaporated under reduced pressure, and the obtained residue was purified by silica gel chromatography (hexane:ethyl acetate=19:1 to 13:7), and then purified by basic silica gel chromatography (hexane:ethyl acetate=19:1 to 13:7), and the solvent was evaporated to give the title compound (1.17 g, yield 23%) as an oil.

¹H NMR (CDCl₃) δ 1.78-2.02 (m, 4H), 2.09-2.26 (m, 2H), 2.64-2.86 (111, 1H), 3.93 (d, J=6.8 Hz, 2H), 4.61 (s, 2H), 6.90 (d, J=9.0 Hz, 2H), 7.29 (d, J=9.0 Hz, 2H).

Reference Example 314

4-(cyclopropylmethoxy)-2-methylbenzoic acid

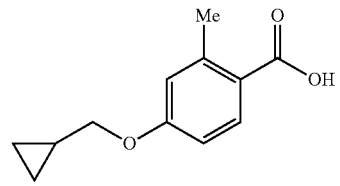 [SMILES: Cc1cc(OCC2CC2)ccc1C(=O)O]

A suspension of (bromomethyl)cyclopropane (20.0 g, 148 mmol), 4-hydroxy-2-methylbenzoic acid (10.1 g, 66.4 mmol) and potassium carbonate (22.0 g, 159 mmol) in DMF (150 mL) was stirred at 60° C. overnight. Ethyl acetate was added thereto, the mixture was left standing, and the resulting precipitate was removed by filtration. The filtrate was concentrated under reduced pressure, water was added thereto, and the mixture was extracted with ethyl acetate. The organic layer was washed with saturated brine, and dried over anhydrous sodium sulfate. The solvent was evaporated under reduced pressure. To the obtained residue were added methanol (50 mL), water (50 mL), THF (100 mL) and lithium hydroxide monohydrate (3.00 g, 71.4 mmol), and the mixture was stirred at 50° C. for 3 hr. After being allowed to cool to room temperature, the mixture was acidified with 1N hydrochloric acid, and the resulting precipitate was collected by filtration, washed with water, and dried to give the title compound (13.5 g, yield 92%) as a white solid.

¹H NMR (CDCl₃) δ0.27-0.46 (m, 2H), 0.56-0.80 (m, 2H), 1.13-1.45 (m, 1H), 2.63 (s, 3H), 3.86 (d, J=7.0 Hz, 2H), 6.67-6.94 (m, 2H), 8.05 (d, J=9.4 Hz, 1H)

Reference Example 315

[4-(cyclopropylmethoxy)-2-methylphenyl]methanol

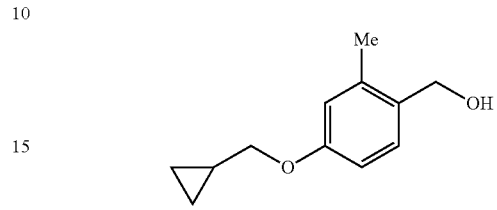

Using 4-(cyclopropylmethoxy)-2-methylbenzoic acid (1.00 g, 4.84 mmol) obtained in Reference Example 314 and in the same manner as in Reference Example 274, the title compound (868 mg, yield 94%) was obtained as a white solid.

¹H NMR (CDCl₃) δ0.25-0.45 (m, 2H), 0.55-0.73 (m, 2H), 1.17-1.32 (m, 1H), 1.46 (br, 1H), 2.35 (s, 3H), 3.79 (d, J=6.8 Hz, 2H), 4.62 (s, 2H), 6.71 (dd, J=8.3, 2.3 Hz, 1H), 6.76 (d, J=2.3 Hz, 1H), 7.21 (d, J=8.3 Hz, 1H).

Reference Example 316

5-(cyclopropylmethoxy)-3-fluoropyridine-2-carbonitrile

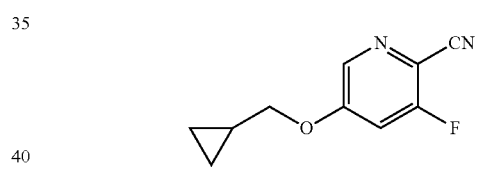

A solution (30 mL) of 3,5-difluoropyridine-2-carbonitrile (1.51 g, 10.8 mmol) in tert-butanol was added dropwise to a solution (40 mL) of sodium tert-butoxide (1.04 g, 10.8 mmol) in tert-butanol (40 mL), and the mixture was stirred at room temperature for 2 hr. The reaction mixture was diluted with ethyl acetate, and the mixture was washed with water, 10% aqueous potassium carbonate solution and saturated brine, and dried over anhydrous sodium sulfate. The solvent was evaporated under reduced pressure and the obtained residue was purified by silica gel column chromatography (hexane: ethyl acetate=3:1) to give a mixture (1.63 g) of 5-tert-butoxy-3-fluoropyridine-2-carbonitrile and 3-tert-butoxy-5-fluoropyridine-2-carbonitrile. To the obtained mixture (1.62 g, 8.34 mmol) was added 4N hydrogen chloride-dioxane (40 mL), and the mixture was stirred at 60° C. for 2 hr, and concentrated. To a solution of the obtained residue (1.46 g, 8.34 mmol) and potassium carbonate (2.31 g, 16.7 mmol) in DMF (20 mL) was added cyclopropylmethyl bromide (1.21 mL, 12.5 mmol), and the mixture was stirred at 60° C. for 16 hr. The reaction mixture was diluted with ethyl acetate, and the mixture was washed with water, 10% aqueous potassium carbonate solution and saturated brine, and dried over anhydrous sodium sulfate. The solution was purified by basic silica gel column chromatography (ethyl acetate). The solvent was evaporated under reduced pressure and the obtained residue was purified by silica gel column chromatography (hexane:ethyl acetate=1:0 to 7:3) to give the title compound (365 mg, yield 23%).

¹H NMR (CDCl₃) δ0.38-0.43 (m, 2H), 0.70-0.76 (m, 2H), 1.24-1.33 (m, 1H), 3.92 (d, J=7.2 Hz, 2H), 7.00 (dd, J=10.2, 2.4 Hz, 1H), 8.22 (dd, J=2.4, 1.2 Hz, 1H).

Reference Example 317

5-(cyclopropylmethoxy)-3-fluoropyridine-2-carbaldehyde

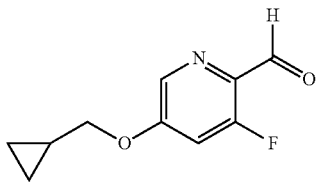 [SMILES: O=Cc1ncc(OCC2CC2)cc1F]

To a solution of 5-(cyclopropylmethoxy)-3-fluoropyridine-2-carbonitrile (363 mg, 1.89 mmol) obtained in Reference Example 316 in THF (10 mL) was added a solution (1.51 mL, 2.27 mmol) of 1.5M diisobutylaluminum hydride in toluene under ice-cooling, and the mixture was stirred for 2 hr. A solution (0.755 mL, 1.13 mmol) of 1.5M diisobutylaluminum hydride in toluene was added at room temperature, and the mixture was stirred for 16 hr. After completion of the reaction, sodium sulfate 10 hydrate was added thereto, and the mixture was diluted with ethyl acetate, and filtered through celite. To the filtrate was added 1N hydrochloric acid (10 mL), and the mixture was stirred at room temperature for 16 hr. The mixture was basified with potassium carbonate, and the mixture was extracted with ethyl acetate. The extract was washed three times with saturated brine, and dried over anhydrous sodium sulfate. The solvent was evaporated under reduced pressure to give the title compound (252 mg, yield 68%) as an oil.

¹H NMR (CDCl₃) δ 0.36-0.44 (m, 2H), 0.64-0.76 (m, 2H), 1.24-1.36 (m, 1H), 3.94 (d, J=7.2 Hz, 2H), 6.96 (dd, J=11.4, 2.4 Hz, 1H), 8.30 (d, J=1.5 Hz, 1H), 10.10 (s, 1H).

Reference Example 318

[5-(cyclopropylmethoxy)-3-fluoropyridin-2-yl]methanol

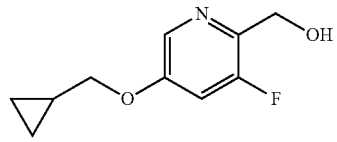 [SMILES: OCc1ncc(OCC2CC2)cc1F]

To a solution of 5-(cyclopropylmethoxy)-3-fluoropyridine-2-carbaldehyde (252 mg, 1.29 mmol) obtained in Reference Example 317 in a mixed solvent of methanol (3 mL) and THF (3 mL) was added sodium borohydride (48.8 mg, 1.29 mmol), and the mixture was stirred for 30 min. The reaction mixture was diluted with ethyl acetate, and the mixture was washed with saturated brine, and dried over anhydrous sodium sulfate. The solvent was evaporated under reduced pressure and the obtained residue was purified by silica gel column chromatography (hexane:ethyl acetate=3:1 to 1:1) to give the title compound (108 mg, yield 43%).

¹H NMR (CDCl₃) δ 0.35-0.40 (m, 2H), 0.66-0.72 (m, 2H), 1.21-1.33 (m, 1H), 3.58 (t, J=5.4 Hz, 1H), 3.85 (d, J=6.9 Hz, 2H), 4.75 (d, J=5.4 Hz, 2H), 6.96 (dd, J=10.8, 2.4 Hz, 1H), 8.09 (d, J=1.8 Hz, 1H).

Reference Example 319 cyclopropylmethyl 6-fluoro-4-methylpyridine-3-carboxylate

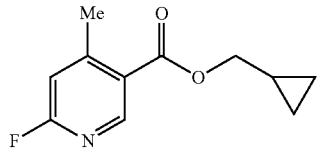 [SMILES: Cc1cc(F)ncc1C(=O)OCC1CC1]

To a solution of 6-fluoro-4-methylpyridine-3-carboxylic acid (4.94 g, 31.8 mmol), cyclopropylmethanol (3.78 mL, 47.8 mmol) and N,N-dimethylpyridin-4-amine (778 mg, 6.37 mmol) in DMF (30 mL) was added N-[3-(dimethylamino)propyl]-N'-ethylcarbodiimide hydrochloride (6.71 g, 35.0 mmol), and the mixture was stirred for 3 days. The reaction mixture was diluted with ethyl acetate, and the mixture was washed with 10% aqueous potassium carbonate solution and saturated brine, and dried over anhydrous sodium sulfate. The solution was purified by basic silica gel column chromatography (ethyl acetate). The solvent was evaporated under reduced pressure and the obtained residue was purified by silica gel column chromatography (hexane:ethyl acetate=9:1 to 3:1) to give the title compound (3.86 g, yield 58%).

¹H NMR (CDCl₃) δ 0.35-0.40 (m, 2H), 0.61-0.66 (m, 2H), 1.21-1.31 (m, 1H), 2.66 (s, 3H), 4.16 (d, J=6.9 Hz, 2H), 6.80 (m, 1H), 8.79 (s, 1H).

Reference Example 320

[6-(cyclopropylmethoxy)-4-methylpyridin-3-yl]methanol

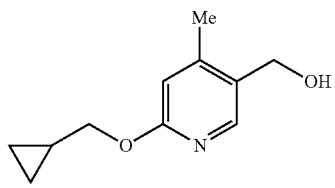 [SMILES: Cc1cc(OCC2CC2)ncc1CO]

To a solution of cyclopropylmethyl 6-fluoro-4-methylpyridine-3-carboxylate (3.85 g, 18.4 mmol) obtained in Reference Example 319 and cyclopropylmethanol (1.75 mL, 22.1 mmol) in DMF (30 mL) was added 60% sodium hydride (883 mg, 22.1 mmol) under ice-cooling. After stirring for 30 min, the mixture was stirred at room temperature for 10 min. The reaction was quenched with ice, and the mixture was extracted with ethyl acetate, washed with 10% aqueous potassium carbonate solution and saturated brine, and dried over anhydrous sodium sulfate. The solvent was evaporated under reduced pressure to give cyclopropylmethyl 6-(cyclopropylmethoxy)-4-methylpyridine-3-carboxylate (4.54 g, 94%) as an oil. To a solution of the obtained cyclopropylmethyl 6-(cyclopropylmethoxy)-4-methylpyridine-3-carboxylate (4.54 g, 17.4 mmol) in THF (100 mL) was added lithium aluminum hydride (989 mg, 26.1 mmol) under ice-cooling, and the mixture was stirred for 30 min. To the reaction mixture was slowly added sodium sulfate decahydrate, and the mixture was filtered through celite. The filtrate was concentrated, the residue was dissolved in ethyl acetate, and the solution was applied to basic silica gel column chromatography (ethyl acetate). The solvent was evaporated under reduced pressure and the obtained residue was purified by silica gel column chromatography (hexane:ethyl acetate=9:1 to 1:1) to give the title compound (2.87 g, yield 85%).

$^1$H NMR (CDCl$_3$) δ 0.31-0.36 (m, 2H), 0.57-0.62 (m, 2H), 1.22-1.29 (m, 1H), 1.58 (t, J=5.1 Hz, 1H), 2.36 (s, 3H), 4.10 (d, J=7.2 Hz, 2H), 4.62 (d, J=4.8 Hz, 2H), 6.61 (s, 1H), 7.95 (s, 1H).

Reference Example 321

(2R)-2-{[4-(bromomethyl)-3-fluorophenoxy]methyl}tetrahydrofuran

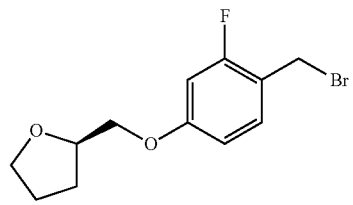 [SMILES: Fc1cc(OC[C@H]2CCCO2)ccc1CBr]

To a solution of {2-fluoro-4-[(2R)-tetrahydrofuran-2-yl-methoxy]phenyl}methanol (630 mg, 2.78 mmol) obtained in Reference Example 301 and triphenylphosphine (875 mg, 3.34 mmol) in THF (10 mL) was added carbon tetrabromide (1.29 g, 3.89 mmol), and the mixture was stirred at room temperature for 30 min, and concentrated under reduced pressure. The obtained residue was purified by silica gel chromatography to give (2R)-2-{[4-(bromomethyl)-3-fluorophenoxy]methyl}tetrahydrofuran (800 mg).

Reference Example 322

(3-bromo-4-ethoxyphenyl)methanol

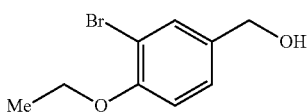 [SMILES: CCOc1ccc(CO)cc1Br]

A mixture of 2-bromo-4-(hydroxymethyl)phenol (3.00 g, 14.7 mmol), iodoethane (4.60 mL, 44.3 mmol) and potassium carbonate (6.12 g, 44.3 mmol) in ethanol (30 mL) was stirred at room temperature for 2 days. The obtained reaction mixture was filtered through celite, and the solvent was evaporated under reduced pressure. The residue was applied to silica gel chromatography (ethyl acetate). The solvent was evaporated under reduced pressure to give (3-bromo-4-ethoxyphenyl)methanol (2.98 g) as a white solid.

Reference Example 323

2-bromo-4-(bromomethyl)-1-ethoxybenzene

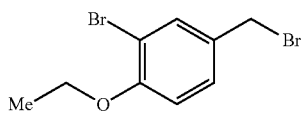 [SMILES: CCOc1ccc(CBr)cc1Br]

To (3-bromo-4-ethoxyphenyl)methanol (2.98 g) obtained in Reference Example 322 were successively added toluene (15 mL), triphenylphosphine (4.23 g, 16.2 mmol) and carbon tetrabromide (5.32 g, 16.2 mmol), and the mixture was stirred at room temperature for 30 min. The obtained reaction mixture was purified by silica gel chromatography (hexane:ethyl acetate=1:0 to 7:3) to give 2-bromo-4-(bromomethyl)-1-ethoxybenzene (2.47 g).

Example 1

N-(1-{6-[(4-ethoxybenzyl)oxy]-1-benzofuran-3-yl}ethyl)acetamide

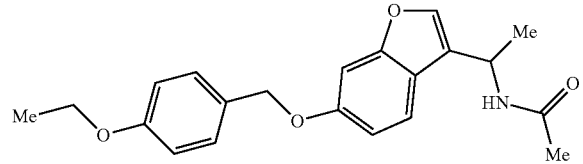 [SMILES: CCOc1ccc(COc2ccc3c(C(C)NC(C)=O)coc3c2)cc1]

To a solution of N-[1-(6-hydroxy-1-benzofuran-3-yl)ethyl]acetamide (17.8 mg, 0.0760 mmol) obtained in Reference Example 4 in DMF (5 mL) were added 4-ethoxybenzyl chloride (39.0 mg, 0.228 mmol) and potassium carbonate (52.4 mg, 0.380 mmol), and the mixture was stirred at 60° C. for 30 min. Water was added to the reaction mixture, and the mixture was extracted with ethyl acetate. The extract was washed twice with saturated brine, and dried over anhydrous magnesium sulfate. The solvent was evaporated under reduced pressure and the obtained residue was purified by preparative silica gel TLC (ethyl acetate) to give the title compound (11.2 mg, yield 42%) as a white solid.

$^1$H NMR (CDCl$_3$) δ 1.41 (t, J=7.0 Hz, 3H), 1.59 (d, J=6.8 Hz, 3H), 1.99 (s, 3H), 4.04 (q, J=7.0 Hz, 2H), 5.01 (s, 2H), 5.34-5.43 (1H, m), 5.61 (d, J=8.5 Hz, 1H), 6.89-6.96 (m, 3H), 7.06 (d, J=2.1 Hz, 1H), 7.35 (d, J=8.7 Hz, 2H), 7.43-7.47 (m, 2H).

Example 2

N-(1-{6-[(4-propylbenzyl)oxy]-1-benzofuran-3-yl}ethyl)acetamide

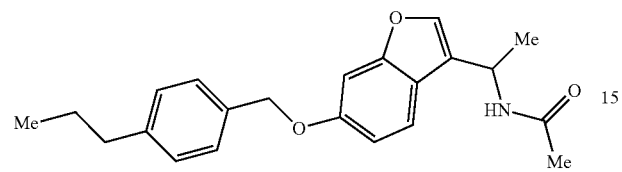

To a solution of N-[1-(6-hydroxy-1-benzofuran-3-yl)ethyl]acetamide (42.2 mg, 0.193 mmol) obtained in Reference Example 4 in DMF (5 mL) were added 4-propylbenzyl methanesulfonate (176 mg, 0.770 mmol) obtained in Reference Example 5 and potassium carbonate (107 mg, 0.770 mmol), and the mixture was stirred at 70° C. for 30 min. Water was added to the reaction mixture, and the mixture was extracted with ethyl acetate. The extract was washed twice with saturated brine, and dried over anhydrous magnesium sulfate. The solvent was evaporated under reduced pressure and the obtained residue was purified by preparative silica gel TLC (hexane:ethyl acetate=1:9) to give the title compound (47.3 mg, yield 70%) as a white solid.

$^1$H NMR (CDCl$_3$) δ 0.94 (t, J=7.4 Hz, 3H), 1.58 (d, J=6.8 Hz, 3H), 1.60-1.70 (m, 2H), 1.98 (s, 3H), 2.57-2.62 (m, 2H), 5.05 (s, 2H), 5.33-5.43 (1H, m), 5.64 (d, J=7.6 Hz, 1H), 6.95 (dd, J=8.7, 2.3 Hz, 1H), 7.06 (d, J=2.3 Hz, 1H), 7.19 (d, J=8.3 Hz, 2H), 7.35 (d, J=8.3 Hz, 2H), 7.42 (d, J=1.1 Hz, 1H), 7.46 (d, J=8.7 Hz, 1H).

Example 3

N-[1-(6-{[4-(1-methylethoxy)benzyl]oxy}-1-benzofuran-3-yl)ethyl]acetamide

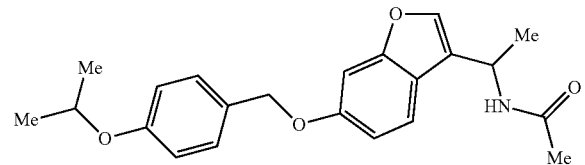 [SMILES: CC(=O)NC(C)c1coc2cc(OCc3ccc(OC(C)C)cc3)ccc12]

To a solution of N-[1-(6-hydroxy-1-benzofuran-3-yl)ethyl]acetamide (35.3 mg, 0.161 mmol) obtained in Reference Example 4 in DMF (5 mL) were added 1-(chloromethyl)-4-(1-methylethoxy)benzene (119 mg, 0.644 mmol) and potassium carbonate (89.0 mg, 0.644 mmol), and the mixture was stirred at 70° C. for 30 min. Water was added to the reaction mixture, and the mixture was extracted with ethyl acetate. The extract was washed twice with saturated brine, and dried over anhydrous magnesium sulfate. The solvent was evaporated under reduced pressure and the obtained residue was purified by preparative silica gel TLC (hexane:ethyl acetate=1:9) to give the title compound (38.0 mg, yield 64%) as a white solid.

$^1$H NMR (CDCl$_3$) δ 1.33 (d, J=6.0 Hz, 6H), 1.57 (d, J=6.8 Hz, 3H), 1.98 (s, 3H), 4.49-4.61 (m, 1H), 5.00 (s, 2H), 5.33-5.42 (1H, m), 5.68 (br, 1H), 6.89 (d, J=8.7 Hz, 2H), 6.94 (dd, J=8.6, 2.2 Hz, 1H), 7.06 (d, J=2.2 Hz, 1H), 7.34 (d, J=8.6 Hz, 2H), 7.42 (s, 1H), 7.45 (d, J=8.6 Hz, 1H).

Example 4

N-[1-(6-{[4-(1H-pyrazol-1-yl)benzyl]oxy}-1-benzofuran-3-yl)ethyl]acetamide

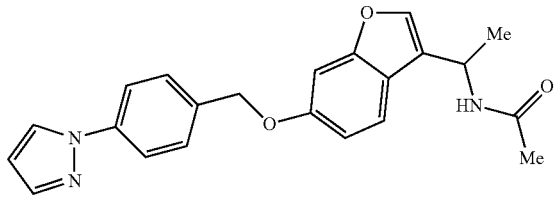 [SMILES: CC(=O)NC(C)c1coc2cc(OCc3ccc(-n4cccn4)cc3)ccc12]

To a solution of N-[1-(6-hydroxy-1-benzofuran-3-yl)ethyl]acetamide (35.0 mg, 0.160 mmol) obtained in Reference Example 4 in THF (5 mL) were added [4-(1H-pyrazol-1-yl)phenyl]methanol (41.8 mg, 0.240 mmol), triphenylphosphine (63.0 mg, 0.240 mmol) and 2.2 M diethyl azodicarboxylate toluene solution (0.110 mL, 0.240 mmol), and the mixture was stirred at room temperature for 30 min. The solvent was evaporated under reduced pressure and the obtained residue was purified by preparative HPLC to give the title compound (29.4 mg, yield 33%) as a white solid.

<Preparative HPLC Conditions> preparation system: Waters large scale preparation system (UV
Purification System)
column: Develosil ODS-UG-10
column temperature: room temperature (25° C.)
detection: UV 220 nm
mobile phase: A (0.1% aqueous trifluoro acetic acid solution), B: 0.1% trifluoroacetic acid acetonitrile solution
gradient: 0.00 min (A/B=95/5), 1.00 min (A/B=95/5), 2.00 min (A/B=80/20), 5.00 min (A/B=5/95), 5.10 min (A/B=0/100), 7.00 min (A/B=100/0)
flow rate: 150 mL/min $^1$H NMR (CDCl$_3$) δ 1.59 (d, J=7.0 Hz, 3H), 2.00 (s, 3H), 5.13 (s, 2H), 5.35-5.44 (1H, m), 5.59 (d, J=8.7 Hz, 1H), 6.47 (dd, J=2.5, 1.9 Hz, 1H), 6.97 (dd, J=8.6, 2.2 Hz, 1H), 7.07 (d, J=2.1 Hz, 1H), 7.44 (d, J=1.1 Hz, 1H), 7.48 (d, J=8.6 Hz, 1H), 7.53 (d, J=8.7 Hz, 2H), 7.71 (d, J=8.6 Hz, 2H), 7.73 (s, 1H), 7.93 (d, J=2.2 Hz, 1H).

Example 5

N-[1-(6-{[4-(ethylsulfanyl)benzyl]oxy}-1-benzofuran-3-yl)ethyl]acetamide

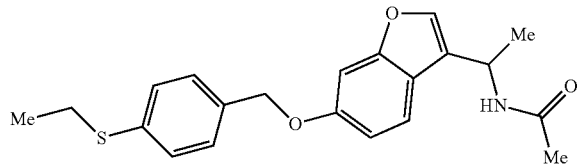 [SMILES: CCSc1ccc(COc2ccc3c(C(C)NC(C)=O)coc3c2)cc1]

To a solution of N-[1-(6-hydroxy-1-benzofuran-3-yl)ethyl]acetamide (35.0 mg, 0.161 mmol) obtained in Reference Example 4 in DMF (5 mL) were added 1-(chloromethyl)-4-(ethylsulfanyl)benzene (120 mg, 0.664 mmol) and potassium carbonate (89.0 mg, 0.644 mmol), and the mixture was stirred at 70° C. for 20 min. Water was added to the reaction mixture, and the mixture was extracted with ethyl acetate. The extract was washed twice with saturated brine, and dried over anhydrous magnesium sulfate. The solvent was evaporated under reduced pressure and the obtained residue was purified by preparative silica gel TLC (hexane:ethyl acetate=2:8) to give the title compound (50.1 mg, yield 94%) as a white solid.

$^1$H NMR (CDCl$_3$) δ 1.32 (t, J=7.4 Hz, 3H), 1.58 (d, J=6.4 Hz, 3H), 1.98 (s, 3H), 2.95 (q, J=7.4 Hz, 2H), 5.05 (s, 2H), 5.33-5.43 (1H, m), 5.64 (d, J=8.7 Hz, 1H), 6.94 (dd, J=8.7, 2.3 Hz, 1H), 7.04 (d, J=2.3 Hz, 1H), 7.29-7.38 (m, 4H), 7.43 (d, J=1.1 Hz, 1H), 7.46 (d, J=8.3 Hz, 1H).

Example 6

N-(1-{6-[(4-ethoxybenzyl)oxy]-1,2-benzisoxazol-3-yl}ethyl)acetamide

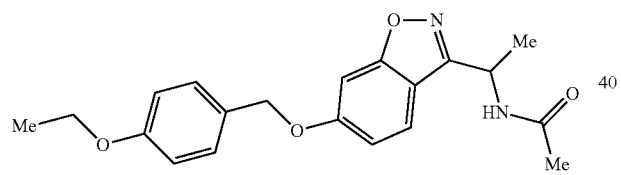

To a solution of N-[1-(6-hydroxy-1,2-benzisoxazol-3-yl)ethyl]acetamide (470 mg, 2.13 mmol) obtained in Reference Example 10 and potassium carbonate (447 mg, 3.20 mmol) in DMF (5 mL) was added 4-ethoxybenzyl chloride (364 mg, 2.13 mmol), and the mixture was stirred under heating at 70° C. for 30 min. To the reaction mixture was added ethyl acetate, and the mixture was washed with saturated brine, and dried over anhydrous sodium sulfate. The solvent was evaporated under reduced pressure, and the obtained residue was triturated with ethyl acetate to give the title compound (103 mg, yield 14%).

$^1$H NMR (CDCl$_3$) δ 1.42 (t, J=6.9 Hz, 3H), 1.65 (d, J=6.9 Hz, 3H), 2.05 (s, 3H), 4.04 (q, J=6.9 Hz, 2H), 5.05 (s, 2H), 5.61 (m, 1H), 5.57 (1H, s), 6.19 (d, J=7.8 Hz, 1H), 6.91 (d, J=8.7 Hz, 2H), 6.97 (dd, J=1.8, 9.0 Hz, 1H), 7.04 (d, J=1.8 Hz, 1H), 7.35 (d, J=8.7 Hz, 2H), 7.56 (d, J=9.0 Hz, 1H).

Example 7

N-(1-{7-[(4-ethoxyphenoxy)methyl][1,2,4]triazolo[4,3-a]pyridin-3-yl}ethyl)acetamide

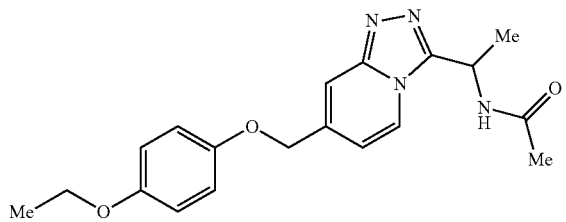 [SMILES: CCOc1ccc(OCc2ccn3c(C(C)NC(C)=O)nnc3c2)cc1]

To a solution of N-[2-(2-{4-[(4-ethoxyphenoxy)methyl]pyridin-2-yl}hydrazino)-1-methyl-2-oxoethyl]acetamide (166 mg, 0.446 mmol) obtained in Reference Example 13, triphenylphosphine (140 mg, 0.535 mmol) and azido(trimethyl)silane (0.0710 mL, 0.535 mmol) in THF (3 mL) was added 40% diethyl azodicarboxylate toluene solution (0.243 mL, 0.535 mmol) under ice-cooling, and the mixture was stirred at room temperature for 2 hr. The reaction mixture was diluted with ethyl acetate, the resulting powder was collected and washed successively with ethyl acetate and diisopropyl ether to give the title compound (96.7 mg, yield 61%).

$^1$H NMR (DMSO-d$_6$) δ 1.28 (t, J=6.9 Hz, 3H), 1.64 (d, J=7.2 Hz, 3H), 1.82 (s, 3H), 3.93 (q, J=6.9 Hz, 2H), 5.12 (s, 2H), 5.56 (m, 1H), 6.84 (d, J=9.0 Hz, 2H), 6.96 (d, J=9.0 Hz, 2H), 7.01 (d, J=7.2 Hz, 1H), 7.74 (s, 1H), 8.32 (d, J=7.2 Hz, 1H), 8.54 (d, J=8.1 Hz, 1H)

Example 8

N-(1-{6-[(4-ethoxyphenoxy)methyl]-1-benzofuran-3-yl}ethyl)acetamide

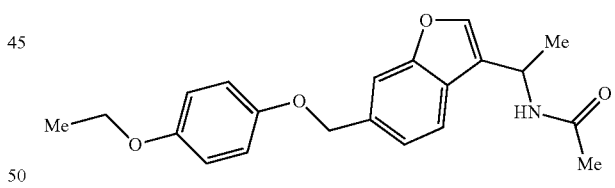

To a solution of 3-(1-azidoethyl)-6-[(4-ethoxyphenoxy)methyl]-1-benzofuran (114 mg, 0.338 mmol) obtained in Reference Example 22 and water (0.3 mL) in THF (3 mL) was added triphenylphosphine (132 mg, 0.507 mmol). Then, the mixture was stirred at 50° C. overnight. The reaction mixture was dried over anhydrous magnesium sulfate, and the desiccant was filtered off. Acetic anhydride (0.064 mL, 0.68 mmol) was added to the filtrate, and the mixture was stirred at room temperature for 5 min. After stirring, the solvent was evaporated under reduced pressure, and the obtained residue was purified by basic silica gel column chromatography (hexane to hexane:ethyl acetate=1:4), and preparative silica gel TLC (hexane:ethyl acetate=2:3) to give the title compound (6.4 mg, yield 5%) as a white solid.

$^1$H NMR (CDCl$_3$) δ 1.38 (t, J=7.0 Hz, 3H), 1.61 (d, J=6.8 Hz, 3H), 2.00 (s, 3H), 3.98 (q, J=7.0 Hz, 2H), 5.12 (s, 2H), 5.39-5.48 (m, 1H), 5.57 (1H, s, 1H), 6.82 (d, J=9.1 Hz, 2H), 6.91 (d, J=9.1 Hz, 2H), 7.30 (d, J=8.3 Hz, 1H), 7.49-7.66 (m, 3H).

Example 9

N-(1-{6-[(4-ethoxybenzyl)oxy]-1-benzofuran-2-yl}ethyl)acetamide

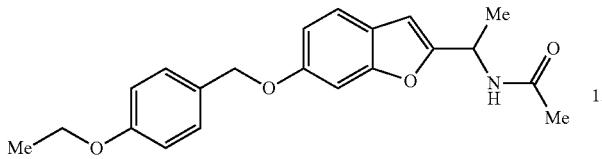

To a solution of p-ethoxybenzylalcohol (416 mg, 2.74 mmol) in toluene (1 mL) was added thionyl chloride (1.0 mL). The solution was stirred at room temperature for 10 min, and the solvent was evaporated. To the obtained residue were added DMF (1 mL), N-[1-(6-hydroxy-1-benzofuran-2-yl)ethyl]acetamide (200 mg, 0.913 mmol) obtained in Reference Example 27 and 60% sodium hydride (55 mg, 1.37 mmol). The reaction mixture was stirred at room temperature for 30 min, saturated brine was added thereto, and the mixture was extracted with ethyl acetate. The obtained organic layer was washed with saturated brine, and dried over anhydrous magnesium sulfate. After evaporation of the solvent, the obtained residue was purified by basic silica gel column chromatography (hexane:ethyl acetate=9:1 to ethyl acetate), and triturated with diethyl ether to give the title compound (155 mg, yield 48%).

$^1$H NMR (CDCl$_3$) δ 1.42 (t, J=6.9 Hz, 3H), 1.55 (d, J=7.3 Hz, 3H), 2.01 (s, 3H), 4.04 (q, J=6.9 Hz, 2H), 5.01 (s, 2H), 5.25-5.37 (m, 1H), 5.79 (br, 1H), 6.48 (s, 1H), 6.89-6.92 (m, 3H), 7.03 (s, 1H), 7.35-7.38 (m, 3H).

Example 10

N-(1-{6-[(3-ethoxybenzyl)oxy]-1-benzofuran-2-yl}ethyl)acetamide

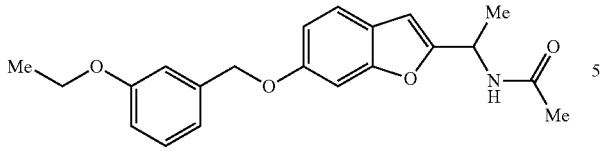

To a solution of m-ethoxybenzylalcohol (276 mg, 1.82 mmol) in toluene (2 mL) was added thionyl chloride (0.66 mL). The solution was stirred at room temperature for 5 min, and the solvent was evaporated. To the obtained residue were added DMF (2 mL), N-[1-(6-hydroxy-1-benzofuran-2-yl)ethyl]acetamide (200 mg, 0.913 mmol) obtained in Reference Example 27, and potassium carbonate (252 mg, 1.82 mmol). The reaction mixture was stirred at 50° C. overnight, saturated brine was added thereto, and the mixture was extracted with ethyl acetate. The obtained organic layer was washed with saturated brine, and dried over anhydrous magnesium sulfate. After evaporation of the solvent, the obtained residue was purified by basic silica gel column chromatography (hexane to hexane:ethyl acetate=2:3), and triturated with diisopropyl ether and hexane to give the title compound (60.9 mg, yield 19%).

$^1$H NMR (CDCl$_3$) δ 1.41 (t, J=7.2 Hz, 3H), 1.54 (d, J=6.8 Hz, 3H), 2.01 (s, 3H), 4.05 (q, J=7.2 Hz, 2H), 5.07 (s, 2H), 5.26-5.37 (m, 1H), 5.78 (br, 1H), 6.48 (s, 1H), 6.85 (dd, J=7.8, 2.1 Hz, 1H), 6.90-6.95 (m, 1H), 6.98-7.05 (m, 3H), 7.26 (d, J=8.3 Hz, 1H), 7.37 (d, J=8.4 Hz, 1H).

Example 11 tert-butyl (1-{6-[(4-ethoxyphenoxy)methyl]-1-benzofuran-2-yl}ethyl)carbamate

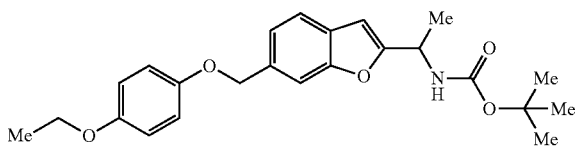 [SMILES: CCOc1ccc(OCc2ccc3cc(C(C)NC(=O)OC(C)(C)C)oc3c2)cc1]

To a solution of tert-butyl {1-[6-(hydroxymethyl)-1-benzofuran-2-yl]ethyl}carbamate (88.0 mg, 0.302 mmol) obtained in Reference Example 30, 4-ethoxyphenol (62.6 mg, 0.453 mmol) and triphenylphosphine (119 mg, 0.453 mmol) in THF (5 mL) was added 2.2 M diethyl azodicarboxylate toluene solution (0.210 mL, 0.460 mmol), and the mixture was stirred at room temperature for 15 min. The solvent was evaporated under reduced pressure and the obtained residue was purified by preparative silica gel TLC (hexane:ethyl acetate=1:9) to give the title compound (55.2 mg, yield 44%) as an oil.

$^1$H NMR (CDCl$_3$) δ 1.38 (t, J=7.0 Hz, 3H), 1.45 (s, 9H), 1.54 (d, J=6.8 Hz, 3H), 3.97 (2H, q, J=6.8 Hz), 4.86-4.90 (m, 1H), 5.00 (br, 1H), 5.10 (s, 2H), 6.53 (s, 1H), 6.80-6.84 (m, 2H), 6.88-6.93 (m, 2H), 7.24-7.26 (m, 1H), 7.48-7.51 (m, 2H).

Example 12

N-(1-[(6-[(4-ethoxyphenoxy)methyl]-1-benzofuran-2-yl]ethyl)acetamide

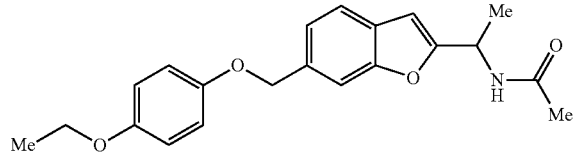

A solution (5 mL) of tert-butyl (1-{6-[(4-ethoxyphenoxy)methyl]-1-benzofuran-2-yl}ethyl)carbamate (49.5 mg, 0.121 mmol) obtained in Example 11 in 4N hydrogen chloride-ethyl acetate was stirred at room temperature for 30 min. The solvent was evaporated under reduced pressure and the obtained residue was dissolved in pyridine (3 mL)-acetic anhydride (3 mL), and the solution was stirred at room temperature for 15 min. The solvent was evaporated under reduced pressure and the obtained residue was purified by preparative silica gel TLC (hexane:ethyl acetate=1:3) to give the title compound (16.7 mg, yield 39%) as a white solid.

$^1$H NMR (CDCl$_3$) δ 1.38 (t, J=7.0 Hz, 3H), 1.56 (d, J=6.8 Hz, 3H), 2.02 (s, 3H), 3.98 (2H, q, J=6.8 Hz), 5.11 (s, 2H), 5.31-5.40 (m, 1H), 5.81 (d, J=7.7 Hz, 1H), 6.56 (s, 1H), 6.80-6.85 (m, 2H), 6.88-6.93 (2H, m), 7.24-7.27 (m, 1H), 7.48-7.54 (m, 2H).

Example 13

N-[1-(6-{[4-(1-methylethoxy)benzyl]oxy}-1-benzofuran-2-yl)ethyl]acetamide

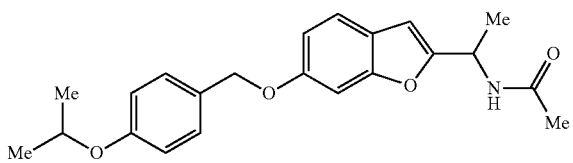

Using 4-(1-methylethoxy)benzyl alcohol (291 mg, 1.81 mmol), N-[1-(6-hydroxy-1-benzofuran-2-yl)ethyl]acetamide (200 mg, 0.913 mmol) obtained in Reference Example 27 and potassium carbonate (251 mg, 1.81 mmol), an operation in the same manner as in Example 10 was performed to give the title compound (185 mg, yield 55%) as a white solid.

$^1$H NMR (CDCl$_3$) δ 1.34 (d, J=6.1 Hz, 6H), 1.53-1.57 (m, 3H), 2.01 (s, 3H), 4.49-4.62 (m, 1H), 5.01 (s, 2H), 5.25-5.38 (m, 1H), 5.75 (br, 1H), 6.48 (s, 1H), 6.87-6.95 (m, 3H), 7.04 (d, J=1.9 Hz, 1H), 7.27-7.41 (m, 3H).

Example 14

N-[1-(6-{[4-(cyclohexylmethoxy)benzyl]oxy}-1-benzofuran-2-yl)ethyl]acetamide

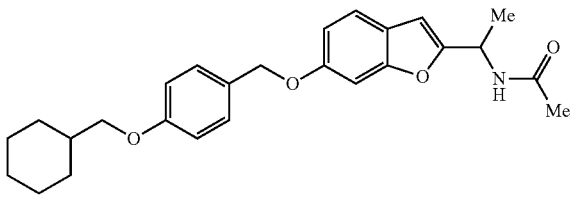 [SMILES: CC(=O)NC(C)c1cc2ccc(OCc3ccc(OCC4CCCCC4)cc3)cc2o1]

Using 4-(cyclohexylmethoxy)benzyl alcohol (398 mg, 1.81 mmol), N-[1-(6-hydroxy-1-benzofuran-2-yl)ethyl]acetamide (200 mg, 0.913 mmol) obtained in Reference Example 27 and potassium carbonate (251 mg, 1.81 mmol), an operation in the same manner as in Example 10 was performed to give the title compound (286 mg, yield 74%) as a white solid.

$^1$H NMR (CDCl$_3$) δ 0.90-1.43 (m, 5H), 1.49-1.59 (m, 3H), 1.65-1.92 (m, 6H), 2.01 (s, 3H), 3.76 (d, J=6.4 Hz, 2H), 5.01 (s, 2H), 5.22-5.41 (m, 1H), 5.75 (br, 1H), 6.48 (s, 1H), 6.85-6.95 (m, 3H), 7.04 (d, J=2.1 Hz, 1H), 7.31-7.42 (m, 3H).

Example 15

N-(1-{6-[(4-ethoxybenzyl)oxy]-1,3-benzoxazol-2-yl}ethyl)acetamide

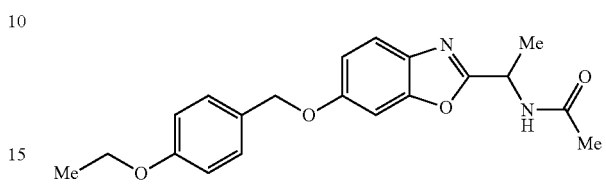

Using N-[1-(6-hydroxy-1,3-benzoxazol-2-yl)ethyl]acetamide (103 mg, 0.468 mmol) obtained in Reference Example 33, potassium carbonate (97.0 mg, 0.702 mmol) and 4-ethoxybenzyl chloride (79.8 mg, 0.468 mmol), an operation in the same manner as in Example 6 was performed, and the obtained residue was triturated with diisopropyl ether to give the title compound (120 mg, yield 72%).

$^1$H NMR (CDCl$_3$) δ 1.42 (t, J=6.9 Hz, 3H), 1.61-1.66 (m, 5H), 2.08 (s, 3H), 4.04 (q, J=6.9 Hz, 2H), 5.02 (s, 2H), 5.38 (m, 1H), 6.28 (d, J=6.9 Hz, 1H), 6.90 (d, J=8.7 Hz, 2H), 6.98 (dd, J=2.4, 8.7 Hz, 1H), 7.08 (d, J=2.4 Hz, 1H), 7.33 (d, J=8.7 Hz, 2H), 7.54 (d, J=8.7 Hz, 1H).

Example 16

N-[1-(6-{[4-(1-methylethoxy)phenoxy]methyl}-1-benzofuran-2-yl)ethyl]acetamide

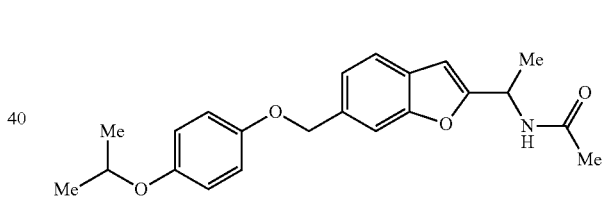

To a solution of tert-butyl {1-[6-(hydroxymethyl)-1-benzofuran-2-yl]ethyl}carbamate (280 mg, 0.962 mmol) obtained in Reference Example 30, 4-(1-methylethoxy)phenol (220 mg, 1.44 mmol) and triphenylphosphine (378 mg, 1.44 mmol) in THF (10 mL) was added 2.2 M diethyl azodicarboxylate toluene solution (0.660 mL, 1.45 mmol), and the mixture was stirred at room temperature for 15 min. The solvent was evaporated under reduced pressure and the obtained residue was purified by silica gel column chromatography (hexane:ethyl acetate=19:1 to 3:2) to give tert-butyl [1-(6-{[4-(1-methylethoxy)phenoxy]methyl}-1-benzofuran-2-yl)ethyl]carbamate as an oil. A solution (8 mL) of this oil in 4N hydrogen chloride-ethyl acetate was stirred at room temperature for 30 min. The solvent was evaporated under reduced pressure, the obtained residue was dissolved in pyridine (5 mL)-acetic anhydride (5 mL), and the solution was stirred at room temperature for 15 min. The solvent was evaporated under reduced pressure and the obtained residue was purified by silica gel column chromatography (hexane:ethyl acetate=1:1 to ethyl acetate) to give the title compound (125 mg, yield 42%) as a white solid.

$^1$H NMR (CDCl$_3$) δ 1.30 (d, J=6.1 Hz, 6H), 1.56 (d, J=6.8 Hz, 3H), 2.02 (s, 3H), 4.35-4.45 (m, 1H), 5.10 (s, 2H), 5.30-

5.40 (m, 1H), 5.80 (d, J=8.3 Hz, 1H), 6.56 (s, 1H), 6.80-6.85 (m, 2H), 6.87-6.91 (m, 2H), 7.26 (dd, J=8.0, 1.5 Hz, 1H), 7.48-7.52 (m, 2H).

Example 17

N-(1-{6-[(4-propoxyphenoxy)methyl]-1-benzofuran-2-yl}ethyl)acetamide

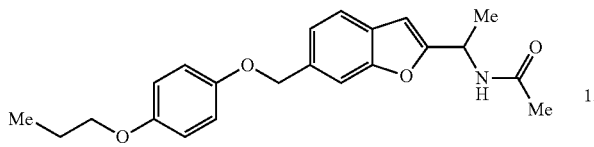

To a solution of tert-butyl {1-[6-(hydroxymethyl)-1-benzofuran-2-yl]ethyl}carbamate (280 mg, 0.962 mmol) obtained in Reference Example 30, 4-propoxyphenol (220 mg, 1.44 mmol) and triphenylphosphine (378 mg, 1.44 mmol) in THF (10 mL) was added 2.2 M diethyl azodicarboxylate toluene solution (0.660 mL, 1.45 mmol), and the mixture was stirred at room temperature for 15 min. The solvent was evaporated under reduced pressure and the obtained residue was purified by silica gel column chromatography (hexane:ethyl acetate=19:1 to 3:2) to give tert-butyl (1-[6-[(4-propoxyphenoxy)methyl]-1-benzofuran-2-yl]ethyl)carbamate as an oil. A solution (8 mL) of this oil in 4N hydrogen chloride-ethyl acetate was stirred at room temperature for 30 min. The solvent was evaporated under reduced pressure, the obtained residue was dissolved in pyridine (5 mL)-acetic anhydride (5 and the solution was stirred at room temperature for 15 min. The solvent was evaporated under reduced pressure and the obtained residue was purified by silica gel column chromatography (hexane:ethyl acetate=1:1 to ethyl acetate) to give the title compound (76.9 mg, yield 22%) as a white solid.
$^1$H NMR (CDCl$_3$) δ 1.02 (t, J=7.4 Hz, 3H), 1.56 (d, J=6.8 Hz, 3H), 1.72-1.84 (2H, m), 2.02 (s, 3H), 3.86 (t, J=6.6 Hz, 2H), 5.11 (s, 2H), 5.31-5.40 (m, 1H), 5.79 (d, J=8.7 Hz, 1H), 6.56 (s, 1H), 6.81-6.85 (m, 2H), 6.88-6.92 (m 2H), 7.26 (dd, J=7.8, 1.4 Hz, 1H), 7.49-7.52 (m, 2H).

Example 18

N-(1-{5-[(4-ethoxybenzyl)oxy]-1-benzofuran-2-yl}ethyl)acetamide

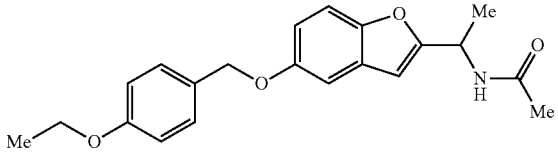

To a solution of N-[1-(5-hydroxy-1-benzofuran-2-yl)ethyl]acetamide (50.0 mg, 0.228 mmol) obtained in Reference Example 38 in anhydrous DMF (1 mL) were added 4-ethoxybenzyl chloride (77.6 mg, 0.456 mmol) and potassium carbonate (62.9 mg, 0.456 mmol). The reaction mixture was stirred at 50° C. overnight, saturated brine was added thereto, and the mixture was extracted with ethyl acetate. The extract was washed with saturated brine, and dried over anhydrous magnesium sulfate. The solution was passed through silica gel, the solvent was evaporated under reduced pressure, and the obtained white solid was washed with diethyl ether to give the title compound (62.4 mg, yield 77%).
$^1$H NMR (CDCl$_3$) δ 1.42 (t, J=7.0 Hz, 3H), 1.55 (d, J=7.0 Hz, 3H), 2.02 (s, 3H), 4.04 (q, J=7.0 Hz, 2H), 4.99 (s, 2H), 5.26-5.40 (m, 1H), 5.79 (br, 1H), 6.49 (s, 1H), 6.84-6.96 (m, 3H), 7.04 (d, J=2.4 Hz, 1H), 7.28-7.39 (m, 3H).

Example 19

N-(1-{6-[(4-ethoxybenzyl)oxy]-1-benzothiophen-2-yl}ethyl)acetamide

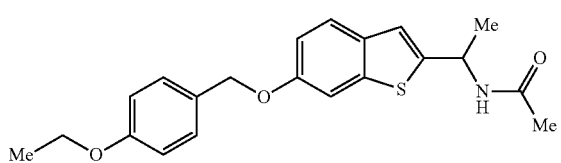

Using N-[1-(6-hydroxy-1-benzothiophen-2-yl)ethyl]acetamide (53.6 mg, 0.228 mmol) obtained in Reference Example 46, anhydrous DMF (1 mL), 4-ethoxybenzyl chloride (77.6 mg, 0.456 mmol) and potassium carbonate (62.9 mg, 0.456 mmol), an operation in the same manner as in Example 18 was performed to give the title compound (59.5 mg, yield 71%) as a white solid.
$^1$H NMR (CDCl$_3$) δ 1.42 (t, J=7.0 Hz, 3H), 1.61 (d, J=6.8 Hz, 3H), 2.01 (s, 3H), 4.04 (q, J=7.0 Hz, 2H), 5.03 (s, 2H), 5.36-5.50 (m, 1H), 5.70 (br, 1H), 6.91 (d, J=8.5 Hz, 2H), 7.02 (dd, J=8.7, 2.3 Hz, 1H), 7.09 (s, 1H), 7.32 (d, J=2.3 Hz, 1H), 7.36 (d, J=8.5 Hz, 2H), 7.57 (d, J=9.4 Hz, 1H).

Example 20

N-(1-[6-[2-(4-ethoxyphenyl)ethyl]-1-benzofuran-2-yl]ethyl)acetamide

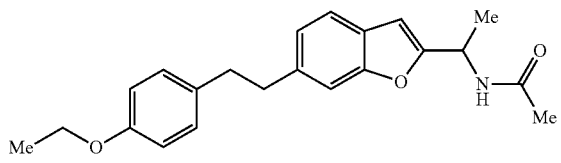

To a solution of 2-(1-azidoethyl)-6-[2-(4-ethoxyphenyl)ethyl]-1-benzofuran (237 mg, 0.707 mmol) obtained in Reference Example 53 in THF (5 mL) was added triphenylphosphine (278 mg, 1.06 mmol), and the mixture was stirred at 60° C. for 30 min. To the reaction mixture was added water (0.5 mL), and the mixture was stirred at 60° C. for 15 hr. The reaction mixture was allowed to cool to room temperature, saturated aqueous sodium hydrogen carbonate solution (1 mL) and di-tert-butyl bicarbonate (0.20 mL, 0.870 mmol) were added thereto, and the mixture was stirred at room temperature for 15 min. To the reaction mixture was added saturated brine, and the mixture was extracted twice with ethyl acetate. The extract was dried over anhydrous magnesium sulfate, and the solvent was evaporated under reduced pressure. The obtained residue was purified by silica gel column chromatography (hexane:ethyl acetate=9:1 to 1:1) to give tert-butyl (1-{6-[2-(4-ethoxyphenyl)ethyl]-1-benzofuran-2-yl}ethyl)carbamate (240 mg). This was dissolved in 4N hydrogen chloride-ethyl acetate (5 mL), and the mixture was stirred at room temperature for 30 min. The solvent was evaporated under reduced pressure, the obtained residue was dissolved in pyridine (3 mL)-acetic anhydride (3 mL), and the solution was stirred at room temperature for 15 min. The solvent was evaporated under reduced pressure and the obtained residue was purified by silica gel column chromatography (hexane:ethyl acetate=1:1 to ethyl acetate) to give the title compound (179 mg, yield 72%) as a white solid.

$^1$H NMR (CDCl$_3$) δ 1.39 (t, J=7.0 Hz, 3H), 1.54 (d, J=6.8 Hz, 3H), 2.00 (s, 3H), 2.85-2.90 (m, 2H), 2.95-3.01 (m, 2H), 4.00 (q, J=7.0 Hz, 2H), 5.27-5.37 (m, 1H), 5.93 (d, J=8.0 Hz, 1H), 6.50 (s, 1H), 6.80 (d, J=8.7 Hz, 2H), 7.02 (d, J=8.7 Hz, 2H), 7.22 (s, 1H), 7.39 (d, J=8.0 Hz, 1H).

Example 21

N-(1-{6-[(4-ethoxybenzyl)oxy]-7-methyl-1-benzofuran-2-yl}ethyl)acetamide

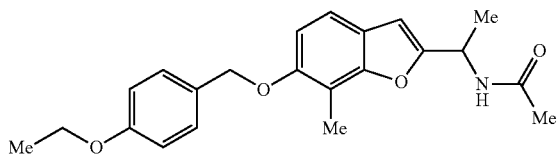 [SMILES: CCOc1ccc(COc2ccc3cc(C(C)NC(C)=O)oc3c2C)cc1]

To a solution of 2-(1-azidoethyl)-6-[(4-ethoxybenzyl)oxy]-7-methyl-1-benzofuran (227 mg, 0.646 mmol) obtained in Reference Example 57 in THF (10 mL) was added triphenylphosphine (255 mg, 0.969 mmol), and the mixture was stirred at 60° C. for 30 min. To the reaction mixture was added water (0.1 mL), and the mixture was stirred at 60° C. for 15 hr. The solvent was evaporated under reduced pressure and the obtained residue was purified by basic silica gel column chromatography (hexane:ethyl acetate=3:1 to 3:7) to give 1-[6-[(4-ethoxybenzyl)oxy]-7-methyl-1-benzofuran-2-yl]ethanamine. This was dissolved in pyridine (3 mL)-acetic anhydride (3 mL), and the solution was stirred at room temperature for 15 min. The solvent was evaporated under reduced pressure, and the residue was washed with ethyl acetate to give the title compound (67.5 mg, yield 28%) as a white solid.

$^1$H NMR (CDCl$_3$) δ 1.42 (t, J=7.0 Hz, 3H), 1.55-1.57 (m, 3H), 2.02 (s, 3H), 2.38 (s, 3H), 4.04 (q, J=7.0 Hz, 2H), 5.03 (s, 2H), 5.27-5.37 (m, 1H), 5.79 (d, J=8.0 Hz, 1H), 6.48 (s, 1H), 6.89-6.91 (m, 3H), 7.22-7.29 (m, 1H), 7.35 (d, J=8.3 Hz, 2H).

Example 22

N-(1-{5-[(4-ethoxyphenoxy)methyl]-1-benzothiophen-2-yl}ethyl)acetamide

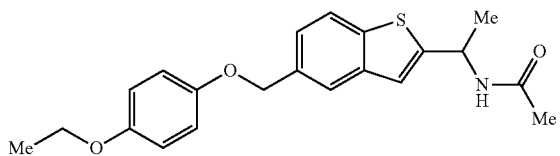

To a solution of tert-butyl {1-[5-(hydroxymethyl)-1-benzothiophen-2-yl]ethyl}carbamate (384 mg, 1.25 mmol) obtained in Reference Example 62, 4-ethoxyphenol (259 mg, 1.88 mmol) and triphenylphosphine (494 mg, 1.88 mmol) in THF (10 mL) was added 2.2 M diethyl azodicarboxylate toluene solution (0.855 mL, 1.88 mmol), and the mixture was stirred at room temperature for 15 min. The solvent was evaporated under reduced pressure and the obtained residue was purified by silica gel column chromatography (hexane:ethyl acetate=9:1 to 1:1) to give tert-butyl (1-{5-[(4-ethoxyphenoxy)methyl]-1-benzothiophen-2-yl}ethyl)carbamate as an oil. A solution (5 mL) of this oil in 4N hydrogen chloride-ethyl acetate was stirred at room temperature for 30 min. The solvent was evaporated under reduced pressure, the obtained residue was dissolved in pyridine (3 mL)-acetic anhydride (3 mL), and the solution was stirred at room temperature for 15 min. The solvent was evaporated under reduced pressure, and the residue was washed with diisopropyl ether to give the title compound (135 mg, yield 44%) as a white solid.

$^1$H NMR (CDCl$_3$) δ 1.38 (t, J=7.0 Hz, 3H), 1.63 (d, J=6.8 Hz, 3H), 2.02 (s, 3H), 3.98 (q, J=7.0 Hz, 2H), 5.11 (s, 2H), 5.43-5.52 (m, 1H), 5.73 (d, J=8.1 Hz, 1H), 6.80-6.84 (m, 2H), 6.88-6.92 (m, 2H), 7.18 (s, 1H), 7.36 (dd, J=8.3, 1.7 Hz, 1H), 7.75 (d, J=1.7 Hz, 1H), 7.77 (d, J=8.3 Hz, 1H).

Example 23

N-(1-[5-[(4-ethoxyphenoxy)methyl]-4-methyl-1-benzofuran-2-yl]ethyl)acetamide

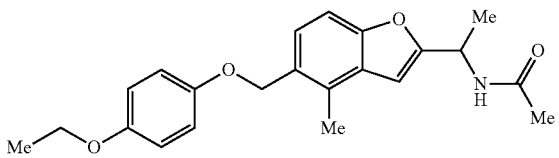 [SMILES: CCOc1ccc(OCc2ccc3oc(C(C)NC(C)=O)cc3c2C)cc1]

To a solution of tert-butyl {1-[5-(hydroxymethyl)-4-methyl-1-benzofuran-2-yl]ethyl}carbamate (85.6 mg, 0.281 mmol) obtained in Reference Example 68, 4-ethoxyphenol (58.1 mg, 0.421 mmol) and triphenylphosphine (110 mg, 0.421 mmol) in THF (5 mL) was added 2.2 M diethyl azodicarboxylate toluene solution (0.191 mL, 0.421 mmol), and the mixture was stirred at room temperature for 15 min. The solvent was evaporated under reduced pressure and the obtained residue was purified by silica gel column chromatography (hexane:ethyl acetate=9:1 to 1:1) to give tert-butyl (1-{5-[(4-ethoxyphenoxy)methyl]-4-methyl-1-benzofuran-2-yl}ethyl)carbamate as an oil. A solution (3 mL) of this oil in 4N hydrogen chloride-ethyl acetate was stirred at room temperature for 30 min. The solvent was evaporated under reduced pressure, the obtained residue was dissolved in pyridine (3 mL)-acetic anhydride (3 mL), and the solution was stirred at room temperature for 15 min. The solvent was evaporated under reduced pressure and the obtained residue was purified by preparative HPLC to give the title compound (3.00 mg, yield 6.6%) as a white solid.

<Preparative HPLC Conditions>
preparation system: Waters large scale preparation system (UV Purification System)
column: Develosil ODS-UG-10
column temperature: room temperature (25° C.)
detection: UV 220 nm
mobile phase: A (0.1% aqueous trifluoro acetic acid solution), B: 0.1% trifluoroacetic acid acetonitrile solution gradient: 0.00 min (A/B=95/5), 1.00 min (A/B=95/5), 2.00 min (A/B=80/20), 5.00 min (A/B=5/95), 5.10 min (A/B=0/100), 7.00 min (A/B=100/0)

flow rate: 150 ml/min $^1$H NMR (CDCl$_3$) δ 1.39 (t, J=7.0 Hz, 3H), 1.57 (d, J=7.2 Hz, 3H), 2.03 (s, 3H), 2.49 (s, 3H), 3.99 (q, J=7.0 Hz, 2H), 5.05 (s, 2H), 5.34-5.41 (m, 1H), 5.81 (d, J=8.0 Hz, 1H), 6.62 (s, 1H), 6.82-6.86 (m, 2H), 6.89-6.94 (m, 2H), 7.23-7.32 (m, 2H).

Example 24

N-(1-{5-[2-(4-ethoxyphenyl)ethyl]-1-benzofuran-2-yl}ethyl)acetamide

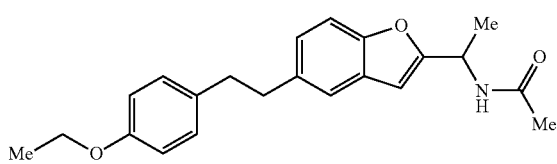 [SMILES: CCOc1ccc(CCc2ccc3oc(C(C)NC(C)=O)cc3c2)cc1]

To a solution of 2-(1-azidoethyl)-5-[2-(4-ethoxyphenyl)ethyl]-1-benzofuran (400 mg, 1.19 mmol) obtained in Reference Example 75 in THF (5 mL) was added triphenylphosphine (469 mg, 1.79 mmol), and the mixture was stirred at 60° C. for 30 min. To the reaction mixture was added water (0.1 mL), and the mixture was stirred at 60° C. for 15 hr. The solvent was evaporated under reduced pressure and the obtained residue was purified by basic silica gel column chromatography (hexane:ethyl acetate=3:1 to 1:4) to give 1-{5-[2-(4-ethoxyphenyl)ethyl]-1-benzofuran-2-yl}ethanamine. This was dissolved in pyridine (3 mL)-acetic anhydride (3 mL), and the solution was stirred at room temperature for 15 min. The solvent was evaporated under reduced pressure, and the residue was washed with diethyl ether to give the title compound (251 mg, yield 60%) as a white solid.

$^1$H NMR (CDCl$_3$) δ 1.40 (t, J=7.0 Hz, 3H), 1.56 (d, J=6.8 Hz, 3H), 2.02 (s, 3H), 2.83-2.89 (m, 2H), 2.93-2.98 (m, 2H), 4.01 (q, J=7.0 Hz, 2H), 5.29-5.39 (m, 1H), 5.78 (d, J=8.0 Hz, 1H), 6.49 (s, 1H), 6.80 (d, J=8.3 Hz, 2H), 7.04-7.08 (m, 3H), 7.28 (d, J=1.5 Hz, 1H), 7.32 (d, J=8.3 Hz, 1H).

Example 25

N-(1-{5-[(4-ethoxybenzyl)oxy]-1,3-benzothiazol-2-yl}ethyl)acetamide

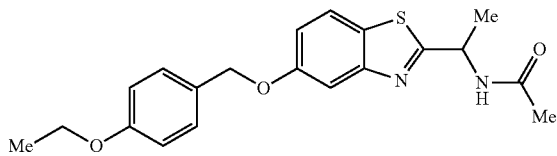

Using N-[1-(5-hydroxy-1,3-benzothiazol-2-yl)ethyl]acetamide (10.5 mg, 0.0444 mmol) obtained in Reference Example 80, potassium carbonate (18.4 mg, 0.133 mmol) and 4-ethoxybenzyl chloride (7.6 mg, 0.044 mmol), an operation in the same manner as in Example 6 was performed, and the obtained residue was triturated with ethyl acetate to give the title compound (7.4 mg, yield 45%).

$^1$H NMR (CDCl$_3$) δ 1.42 (t, J=6.9 Hz, 3H), 1.66 (d, J=6.9 Hz, 3H). 2.08 (s, 3H), 4.04 (q, J=6.9 Hz, 2H), 5.06 (s, 2H), 5.46 (m, 1H), 6.37 (d, J=6.9 Hz, 1H), 6.90 (d, J=9.0 Hz, 2H), 7.08 (dd, J=2.7, 8.7 Hz, 1H), 7.35 (d, J=9.0 Hz, 2H), 7.53 (d, J=2.7 Hz, 1H), 7.69 (d, J=8.7 Hz, 1H).

Example 26

N-(1-{6-[(4-ethoxyphenoxy)methyl]-1,3-benzothiazol-2-yl}ethyl)acetamide

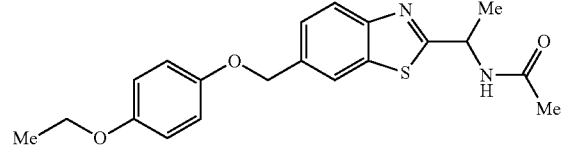 [SMILES: CCOc1ccc(OCc2ccc3nc(C(C)NC(C)=O)sc3c2)cc1]

To a solution of N-{1-[6-(hydroxymethyl)-1,3-benzothiazol-2-yl]ethyl}acetamide (150 mg, 0.599 mmol) obtained in Reference Example 85, 4-ethoxyphenol (99.3 mg, 0.719 mmol) and triphenylphosphine (189 mg, 0.719 mmol) in THF (6 mL) was added 2.2 M diethyl azodicarboxylate toluene solution (0.327 mL, 0.719 mmol), and the mixture was stirred at room temperature for 1 hr. The solvent was evaporated under reduced pressure, and the obtained residue was purified by silica gel column chromatography (hexane:ethyl acetate=1:1 to ethyl acetate), and triturated with a small amount of ethyl acetate to give the title compound (25.7 mg, yield 12%).

$^1$H NMR (CDCl$_3$) δ 1.39 (t, J=6.9 Hz, 3H), 1.68 (d, J=6.9 Hz, 3H), 2.09 (s, 3H), 3.97 (q, J=6.9 Hz, 2H), 5.13 (s, 2H), 5.48 (m, 1H), 6.40 (d, J=6.9 Hz, 1H), 6.82 (d, J=9.3 Hz, 2H), 6.90 (d, J=9.3 Hz, 2H), 7.51 (dd, J=1.5, 8.4 Hz, 1H), 7.93 (d, J=1.5 Hz, 1H), 7.96 (d, J=8.4 Hz, 1H).

Example 27 optically active forms (two kinds) of N-(1-{5-[(4-ethoxybenzyl)oxy]-1-benzofuran-2-yl}ethyl)acetamide

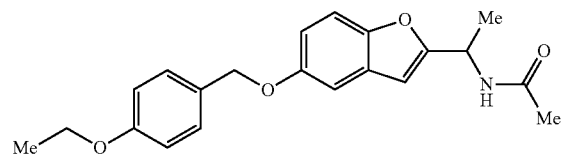 [SMILES: CCOc1ccc(COc2ccc3oc(C(C)NC(C)=O)cc3c2)cc1]

N-(1-{5-[(4-Ethoxybenzyl)oxy]-1-benzofuran-2-yl}ethyl)acetamide (478 mg) obtained in Example 18 was optically resolved by high performance liquid chromatography (HPLC) under the following conditions to give two kinds of optically active forms of "retention time longer (233 mg)" and "retention time shorter (231 mg)".

<Preparative HPLC Conditions>
column: CHIRALPAK AS (50 mmID×500
mobile phase: hexane:ethanol=1:9
flow rate: 45 mL/min
column temperature: 25° C.
detection: UV 220 nm
compound injection volume: 478 mg/96 mL
<HPLC Analysis Conditions> column: CHIRALPAK AS (4.6 mmID×250 mmL)

mobile phase: hexane:ethanol=1:9 flow rate: 1.0 mL/min column temperature: 30° C.

detection: UV 220 nm retention time of "retention time longer": 27.24 min retention time of "retention time shorter": 12.28 min Example 28

N-(1-{5-[(2-chloro-4-ethoxybenzyl)oxy]-1-benzofuran-2-yl}ethyl)acetamide

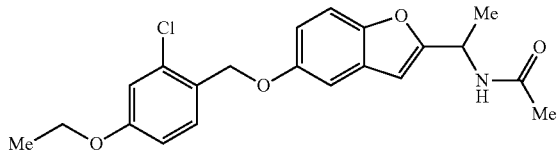 [SMILES: CCOc1ccc(COc2ccc3oc(C(C)NC(C)=O)cc3c2)c(Cl)c1]

Using N-[1-(5-hydroxy-1-benzofuran-2-yl)ethyl]acetamide (100 mg, 0.456 mmol) obtained in Reference Example 38, anhydrous DMF (1 mL), 1-(bromomethyl)-2-chloro-4-ethoxybenzene (291 mg, 1.17 mmol) and potassium carbonate (126 mg, 0.913 mmol), an operation in the same manner as in Example 18 was performed to give the title compound (88.6 mg, yield 50%) as a white solid.

$^1$H NMR (CDCl$_3$) δ 1.41 (t, J=7.0 Hz, 3H), 1.55 (d, J=7.0 Hz, 3H), 2.02 (s, 3H), 4.02 (q, J=7.0 Hz, 2H), 5.10 (s, 2H), 5.24-5.41 (m, 1H), 5.78 (br, 1H), 6.50 (s, 1H), 6.80 (dd, J=8.6, 2.4 Hz, 1H), 6.94 (m, 2H), 7.05 (d, J=2.4 Hz, 1H), 7.33 (d, J=8.9 Hz, 1H), 7.42 (d, J=8.5 Hz, 1H)

Example 29

N-(1-{5-[(4-propoxyphenoxy)methyl]-1-benzofuran-2-yl}ethyl)acetamide

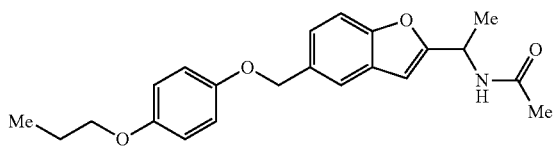 [SMILES: CCCOc1ccc(OCc2ccc3oc(C(C)NC(C)=O)cc3c2)cc1]

Using N-{1-[5-(hydroxymethyl)-1-benzofuran-2-yl]ethyl}acetamide (500 mg, 2.14 mmol) obtained in Reference Example 90, 4-propoxyphenol (487 mg, 3.21 mmol), triphenylphosphine (841 mg, 3.21 mmol), THF (4.3 mL) and 2.2 M diethyl azodicarboxylate toluene solution (1.5 mL, 3.2 mmol), a method in the same manner as in Example 11 was performed, and the obtained residue was triturated with diisopropyl ether to give the title compound (276 mg, yield 35%).

$^1$H NMR (CDCl$_3$) δ 1.02 (t, J=7.4 Hz, 3H), 1.57 (d, J=7.0 Hz, 3H), 1.72-1.84 (m, 2H), 2.02 (s, 3H), 3.86 (t, J=6.7 Hz, 2H), 5.07 (s, 2H), 5.31-5.41 (m, 1H), 5.79 (br, 1H), 6.55 (s, 1H), 6.82 (d, J=9.3 Hz, 2H), 6.89 (d, J=9.3 Hz, 2H), 7.31 (dd, J=8.5, 1.8 Hz, 1H), 7.43 (d, J=8.5 Hz, 1H), 7.57 (d, J=1.8 Hz, 1H).

Example 30

N-[1-(5-{[4-(1-methylethoxy)phenoxy]methyl}-1-benzofuran-2-yl)ethyl]acetamide

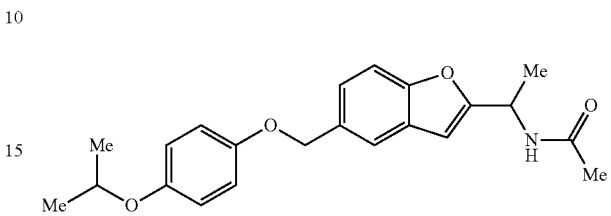

Using N-{1-[5-(hydroxymethyl)-1-benzofuran-2-yl]ethyl}acetamide (500 mg, 2.14 mmol) obtained in Reference Example 90, 4-(1-methylethoxy)phenol (487 mg, 3.21 mmol), triphenylphosphine (841 mg, 3.21 mmol), THF (4.3 mL) and 2.2 M diethyl azodicarboxylate toluene solution (1.5 mL, 3.2 mmol), a method in the same manner as in Example 11 was performed, and the obtained residue was triturated with diisopropyl ether to give the title compound (299 mg, yield 38%).

$^1$H NMR (CDCl$_3$) δ 1.30 (d, J=5.5 Hz, 6H), 1.57 (d, J=7.2 Hz, 3H), 2.03 (s, 3H), 4.35-4.48 (m, 2H), 5.07 (s, 2H), 5.31-5.41 (m, 1H), 5.79 (br, 1H), 6.56 (s, 1H), 6.82 (d, J=9.3 Hz, 2H), 6.89 (d, J=9.3 Hz, 2H), 7.31 (dd, J=8.5, 1.8 Hz, 1H), 7.43 (d, J=8.5 Hz, 1H), 7.57 (d, J=1.8 Hz, 1H).

Example 31

N-(1-{5-[(4-ethoxyphenoxy)methyl]furo[3,2-b]pyridin-2-yl}ethyl)acetamide

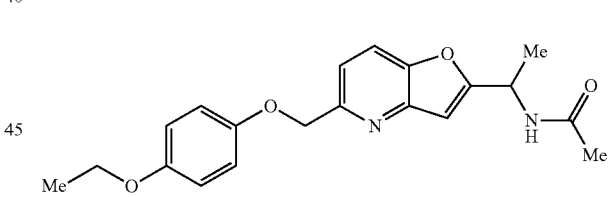

To a solution of 2-(1-azidoethyl)-5-[(4-ethoxyphenoxy)methyl]furo[3,2-b]pyridine (118 mg, 0.351 mmol) obtained in Reference Example 96 in THF (5 mL) was added triphenylphosphine (155 mg, 0.590 mmol), and the mixture was stirred at 60° C. for 30 min. To the reaction mixture was added water (0.1 mL), and the mixture was stirred at 60° C. for 15 hr. The solvent was evaporated under reduced pressure and the obtained residue was purified by basic silica gel column chromatography (ethyl acetate) to give 1-{5-[(4-ethoxyphenoxy)methyl]furo[3,2-b]pyridin-2-yl}ethanamine. This was dissolved in pyridine (2 mL)-acetic anhydride (2 mL), and the solution was stirred at room temperature for 15 min. The solvent was evaporated under reduced pressure, and the residue was washed with ethyl acetate to give the title compound (72.7 mg, yield from 2-(1-azidoethyl)-5-[(4-ethoxyphenoxy)methyl]furo[3,2-b]pyridine 58%) as a white solid.

$^1$H NMR (CDCl$_3$) δ 1.38 (t, J=7.0 Hz, 3H), 1.59 (d, J=6.8 Hz, 3H), 2.05 (s, 3H), 3.97 (q, J=7.0 Hz, 2H), 5.22 (s, 2H), 5.37-5.47 (m, 1H), 5.80 (d, J=7.6 Hz, 1H), 6.75 (s, 1H), 6.79-6.85 (m, 2H), 6.88-6.93 (m, 2H), 7.43 (d, J=8.3 Hz, 1H), 7.70 (d, J=8.7 Hz, 1H).

Example 32

N-(1-{6-[2-(4-propoxyphenyl)ethyl]-1-benzofuran-2-yl}ethyl)acetamide

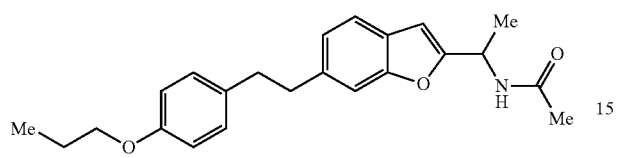

A solution of 1-{6-[2-(4-propoxyphenyl)ethyl]-1-benzofuran-2-yl}ethanamine (320 mg, 0.989 mmol) obtained in Reference Example 104 in pyridine (3 mL)-acetic anhydride (3 mL) was stirred at room temperature for 15 min. The solvent was evaporated under reduced pressure and the obtained residue was purified by basic silica gel column chromatography (hexane:ethyl acetate=4:1 to 1:4) to give the title compound (197 mg, yield 54%) as a white solid.

$^1$H NMR (CDCl$_3$) δ 1.03 (t, J=7.4 Hz, 3H), 1.55 (d, J=4.9 Hz, 3H), 1.74-1.86 (m, 2H), 2.02 (s, 3H), 2.85-2.91 (m, 2H), 2.96-3.01 (m, 2H), 3.90 (t, J=6.6 Hz, 2H), 5.29-5.39 (m, 1H), 5.79 (d, J=6.8 Hz, 1H), 6.52 (s, 1H), 6.81 (d, J=8.7 Hz, 2H), 7.03 (dd, J=8.0, 1.1 Hz, 1H), 7.08 (d, J=8.7 Hz, 1H), 7.24 (s, 1H), 7.40 (d, J=8.0 Hz, 1H).

Example 33

N-(1-{5-[2-(4-propoxyphenyl)ethyl]-1-benzofuran-2-yl}ethyl)methane sulfonamide

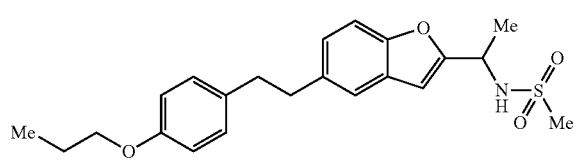 [SMILES: CCCOc1ccc(CCc2ccc3oc(C(C)NS(C)(=O)=O)cc3c2)cc1]

To a solution of 1-{6-[2-(4-propoxyphenyl)ethyl]-1-benzofuran-2-yl}ethanamine (325 mg, 1.01 mmol) obtained in Reference Example 104 in THF (5 mL) were added triethylamine (0.282 mL, 2.02 mmol) and methanesulfonyl chloride (0.0940 mL, 1.20 mmol), and the mixture was stirred at room temperature for 10 min. To the reaction mixture was added saturated aqueous sodium hydrogen carbonate solution, and the mixture was extracted with ethyl acetate, and the extract was dried over anhydrous magnesium sulfate. The solvent was evaporated under reduced pressure and the obtained residue was purified by silica gel column chromatography (hexane:ethyl acetate=3:1 to 2:3) to give the title compound (225 mg, yield 55%) as a white solid.

$^1$H NMR (CDCl$_3$) δ 1.03 (t, J=7.4 Hz, 3H), 1.66 (d, J=7.0 Hz, 3H), 1.74-1.86 (m, 2H), 2.85 (s, 3H), 2.87-2.92 (m, 2H), 2.97-3.02 (m, 2H), 3.90 (t, J=6.6 Hz, 2H), 4.67 (d, J=8.3 Hz, 1H), 4.78-4.88 (m, 1H), 6.60 (s, 1H), 6.81 (d, J=8.7 Hz, 2H), 7.05-7.09 (m, 3H), 7.25 (s, 1H), 7.43 (d, J=7.9 Hz, 1H).

Example 34 ethyl 3-oxo-3-[(1-{6-[2-(4-propoxyphenyl)ethyl]-1-benzofuran-2-yl}ethyl)amino]propanoate

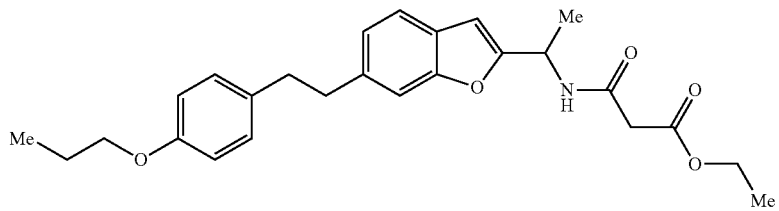 [SMILES: CCCOc1ccc(CCc2ccc3cc(C(C)NC(=O)CC(=O)OCC)oc3c2)cc1]

To a solution of 1-{6-[2-(4-propoxyphenyl)ethyl]-1-benzofuran-2-yl}ethanamine (370 mg, 1.15 mmol) obtained in Reference Example 104 in DMF (5 mL) were added 3-ethoxy-3-oxopropanoic acid (227 mg, 1.72 mmol), 1-hydroxybenzotriazole (233 mg, 1.72 mmol) and 1-ethyl-3-(3-dimethylaminopropyl)carbodiimide hydrochloride (330 mg, 1.72 mmol), and the mixture was stirred at room temperature for 15 hr. Water was added to the reaction mixture, and the mixture was extracted with ethyl acetate. The organic layer was washed twice with saturated brine and dried over anhydrous magnesium sulfate, and the solvent was evaporated. The obtained residue was purified by silica gel column chromatography (hexane:ethyl acetate=3:1 to 2:3) to give the title compound (236 mg, yield 47%) as a white solid.

$^1$H NMR (CDCl$_3$) δ 1.03 (t, J=7.4 Hz, 3H), 1.29 (t, J=7.3 Hz, 3H), 1.59 (d, J=4.7 Hz, 3H), 1.74-1.86 (m, 2H), 2.85-2.91 (m, 2H), 2.95-3.01 (m, 2H), 3.35 (s, 2H), 3.90 (t, J=6.6 Hz, 2H), 4.21 (t, J=7.3 Hz, 2H), 5.32-5.42 (m, 1H), 6.53 (s, 1H), 6.82 (d, J=8.7 Hz, 2H), 7.03 (dd, J=7.9, 1.3 Hz, 1H), 7.08 (d, J=8.7 Hz, 2H), 7.40 (d, J=7.9 Hz, 1H), 7.53 (d, J=8.1 Hz, 1H).

Example 35

3-oxo-3-[(1-[6-[2-(4-propoxyphenyl)ethyl]-1-benzofuran-2-yl]ethyl)amino]propanoic acid

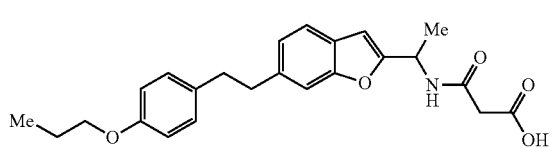 [SMILES: CCCOc1ccc(CCc2ccc3cc(C(C)NC(=O)CC(=O)O)oc3c2)cc1]

To a solution of ethyl 3-oxo-3-[(1-{6-[2-(4-propoxyphenyl)ethyl]-1-benzofuran-2-yl}ethyl)amino]propanoate (214 mg, 0.489 mmol) obtained in Example 34 in THF-methanol (5 mL-3 mL) was added 1N aqueous sodium hydroxide solution (0.750 mL, 0.750 mmol), and the mixture was stirred at room temperature for 15 min. The reaction mixture was acidified with 1N hydrochloric acid and extracted twice with ethyl acetate, and the combined organic layer was dried over anhydrous magnesium sulfate. The solvent was evaporated, and the residue was washed with diethyl ether to give the title compound (158 mg, yield 79%) as a white solid.

$^1$H NMR (CDCl$_3$) δ 1.03 (t, J=7.4 Hz, 3H), 1.61 (d, J=7.0 Hz, 3H), 1.74-1.85 (m, 2H), 2.85-2.91 (m, 2H), 2.96-3.02 (m, 2H), 3.34 (s, 2H), 3.90 (t, J=6.6 Hz, 2H), 5.33-5.42 (m, 1H), 6.56 (s, 1H), 6.81 (d, J=8.7 Hz, 2H), 7.03-7.08 (m, 3H), 7.22 (s, 1H), 7.41 (d, J=7.9 Hz, 1H).

Example 36

N-(1-[5-[(4-ethoxyphenoxy)methyl]-1,3-benzoxazol-2-yl]ethyl)acetamide

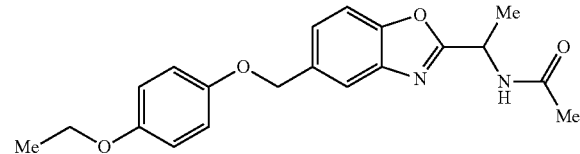 [SMILES: CCOc1ccc(OCc2ccc3sc(C(C)NC(C)=O)nc3c2)cc1]

To a solution of N-{1-[5-(hydroxymethyl)-1,3-benzoxazol-2-yl]ethyl}acetamide (25.0 mg, 0.107 mmol) obtained in Reference Example 109, 4-ethoxyphenol (17.7 mg, 0.128 mmol) and triphenylphosphine (polystyrene-supported, 1.84 mol/g, 145 mg, 0.267 mmol) in THF (2 mL) was added 2.2 M diethyl azodicarboxylate toluene solution (0.0582 mL, 0.128 mmol), and the mixture was stirred at room temperature for 2 hr. The resin was filtered off, and the filtrate was concentrated under reduced pressure. The obtained residue was purified by preparative silica gel TLC (ethyl acetate), and triturated with diisopropyl ether to give the title compound (2.2 mg, yield 5.8%).

$^1$H NMR (CDCl$_3$) δ 1.38 (t, J=6.9 Hz, 3H), 1.64 (d, J=7.2 Hz, 3H), 2.09 (s, 3H), 3.97 (q, J=6.9 Hz, 2H), 5.10 (s, 2H), 5.42 (ms, 1H), 6.36 (br, 1H), 6.81 (d, J=9.0 Hz, 2H), 6.89 (d, J=9.0 Hz, 2H), 7.40 (d, J=8.1 Hz, 1H), 7.50 (d, J=8.1 Hz, 1H), 7.73 (s, 1H).

Example 37

N-(1-{5-[(4-ethoxyphenoxy)methyl]-1,3-benzothiazol-2-30 yl}ethyl)acetamide

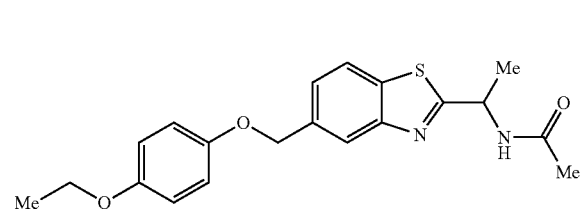

Using N-{1-[5-(hydroxymethyl)-1,3-benzothiazol-2-yl]ethyl}acetamide (150 mg, 0.599 mmol) obtained in Reference Example 114 and 4-ethoxyphenol (99.3 mg, 0.719 mmol), a method in the same manner as in Example 36 was performed, and the obtained residue was triturated with diisopropyl ether to give the title compound (82.8 mg, yield 37%).

$^1$H NMR (CDCl$_3$) δ 1.38 (t, J=6.9 Hz, 3H), 1.67 (d, J=6.9 Hz, 3H), 2.09 (s, 3H), 3.97 (q, J=6.9 Hz, 2H), 5.15 (s, 2H), 5.48 (m, 1H). 6.39 (d, J=7.2 Hz, 1H), 6.82 (d, J=9.0 Hz, 2H), 6.90 (d, J=9.0 Hz, 2H), 7.44 (dd, J=1.5, 8.4 Hz, 1H), 7.84 (d, J=8.4 Hz, 1H), 8.03 (d, J=1.5 Hz, 1H).

Example 38

N-(1-{6-[2-(4-ethoxyphenyl)ethyl]-4-methyl-1-benzofuran-2-yl}ethyl)acetamide

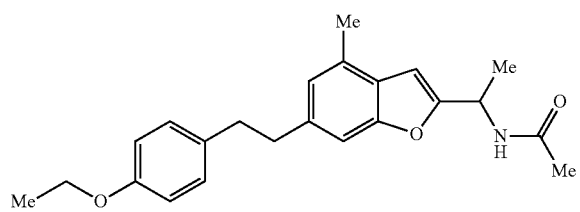 [SMILES: CCOc1ccc(CCc2cc(C)c3cc(C(C)NC(C)=O)oc3c2)cc1]

To a solution of 2-(1-azidoethyl)-6-[2-(4-ethoxyphenyl)ethyl]-4-methyl-1-benzofuran (816 mg, 2.34 mmol) obtained in Reference Example 124 in THF (10 mL) was added triphenylphosphine (919 mg, 3.50 mmol), and the mixture was stirred at 60° C. for 30 min. To the reaction mixture was added water (0.2 mL), and the mixture was stirred at 60° C. for 15 hr. The solvent was evaporated under reduced pressure and the obtained residue was purified by basic silica gel column chromatography (hexane:ethyl acetate=7:13 to 1:3) to give 1-{6-[2-(4-ethoxyphenyl)ethyl]-4-methyl-1-benzofuran-2-yl}ethanamine. This was dissolved in pyridine (3 mL)-acetic anhydride (3 mL), and the solution was stirred at room temperature for 15 min. The solvent was evaporated under reduced pressure and the residue was washed with diethyl ether and hexane to give the title compound (458 mg, yield 53%) as a white solid.

$^1$H NMR (CDCl$_3$) δ 1.40 (t, J=7.2 Hz, 3H), 1.56 (d, J=7.2 Hz, 3H), 2.01 (s, 3H), 2.44 (s, 3H), 2.83-2.89 (m, 2H), 2.91-2.97 (m, 2H), 4.01 (q, J=7.2 Hz, 2H), 5.28-5.38 (m, 1H), 5.82 (d, J=7.2 Hz, 1H), 6.53 (s, 1H), 6.81 (d, J=8.3 Hz, 2H), 6.85 (s, 1H), 7.08-7.10 (m, 3H).

Example 39

N-(1-{5-[(4-ethoxybenzyl)oxy]-1-benzothiophen-2-yl}ethyl)acetamide

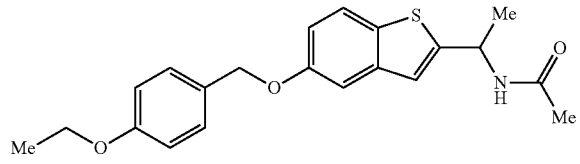

Using N-[1-(5-hydroxy-1-benzothiophen-2-yl)ethyl]acetamide (100 mg, 0.425 mmol) obtained in Reference Example 132, anhydrous DMF (1.4 mL), 4-ethoxybenzyl chloride (144 mg, 0.855 mmol) and potassium carbonate (117 mg, 0.850 mmol), an operation in the same manner as in Example 18 was performed to give the title compound (135 mg, yield 86%).

¹H NMR (CDCl₃) δ 1.42 (t, J=7.2 Hz, 3H), 1.62 (d, J=6.8 Hz, 3H), 2.01 (s, 3H), 4.04 (q, J=7.2 Hz, 2H), 5.02 (s, 2H), 5.35-5.53 (m, 1H), 5.71 (s, 1H), 6.90 (d, J=8.6 Hz, 2H), 7.01 (dd, J=8.7, 2.7 Hz, 1H), 7.10 (s, 1H), 7.23 (d, J=2.7 Hz, 1H), 7.35 (d, J=8.6 Hz, 1H), 7.63 (d, J=8.7 Hz, 1H).

Example 40

N-(1-{5-[(4-ethoxyphenoxy)methyl]-1-benzofuran-2-yl}ethyl)acetamide

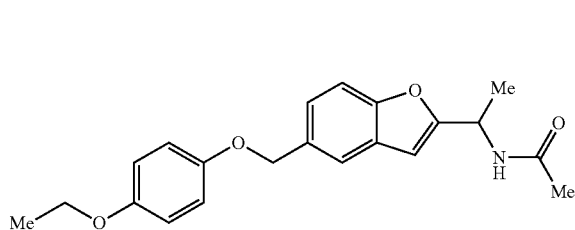 [SMILES: CCOc1ccc(OCc2ccc3oc(C(C)NC(C)=O)cc3c2)cc1]

Using N-{1-[5-(hydroxymethyl)-1-benzofuran-2-yl]ethyl}acetamide (137 mg, 0.587 mmol) obtained in Reference Example 90, 4-ethoxyphenol (121 mg, 0.881 mmol), triphenylphosphine (polystyrene-supported, 1.84 mol/g, 798 mg, 1.48 mmol), THF (4.3 mL) and 2.2 M diethyl azodicarboxylate toluene solution (0.32 mL, 0.70 mmol), a method in the same manner as in Example 36 was performed, and the obtained residue was triturated with diisopropyl ether to give the title compound (66.4 mg, yield 32%).

¹H NMR (CDCl₃) δ 1.38 (t, J=7.1 Hz, 3H), 1.57 (d, J=7.2 Hz, 3H), 2.03 (s, 3H), 3.97 (q, J=7.1 Hz, 2H), 5.07 (s, 2H), 5.31-5.41 (m, 1H), 5.79 (br, 1H), 6.56 (s, 1H), 6.82 (d, J=9.3 Hz, 2H), 6.89 (d, J=9.3 Hz, 2H), 7.31 (dd, J=8.5, 1.8 Hz, 1H), 7.43 (d, J=8.5 Hz, 1H), 7.57 (d, J=1.8 Hz, 1H).

Example 41

N-(1-{6-[(4-ethoxybenzyl)oxy]-1,3-benzothiazol-2-yl}ethyl)acetamide

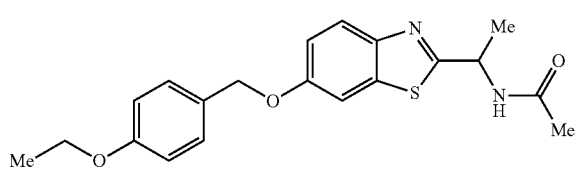 [SMILES: CCOc1ccc(COc2ccc3nc(C(C)NC(C)=O)sc3c2)cc1]

Using N-[1-(6-hydroxy-1,3-benzothiazol-2-yl)ethyl]acetamide (72.7 mg, 0.308 mmol) obtained in Reference Example 137, potassium carbonate (128 mg, 0.923 mmol) and 4-ethoxybenzyl chloride (57.8 mg, 0.338 mmol), an operation in the same manner as in Example 6 was performed, and the obtained residue was triturated with diisopropyl ether to give the title compound (88.2 mg, yield 77%).

¹H NMR (CDCl₃) δ 1.42 (t, J=6.9 Hz, 3H), 1.66 (d, J=6.9 Hz, 3H), 2.08 (s, 3H), 4.04 (q, J=6.9 Hz, 2H), 5.04 (s, 2H), 5.44 (m, 1H), 6.38 (d, J=7.8 Hz, 1H), 6.91 (d, J=9.0 Hz, 2H), 7.11 (dd, J=2.4, 8.7 Hz, 1H), 7.32-7.36 (m, 3H), 7.84 (d, J=8.7 Hz, 1H).

Example 42

N-(1-{5-[(4-ethoxybenzyl)oxy]-1,3-benzoxazol-2-yl}ethyl)acetamide

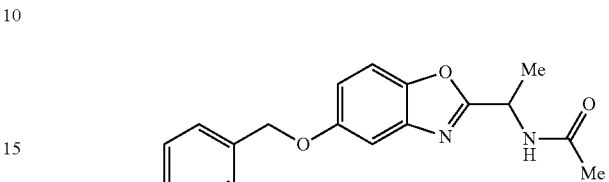

Using N-[1-(5-hydroxy-1,3-benzoxazol-2-yl)ethyl]acetamide (112 mg, 0.509 mmol) obtained in Reference Example 142, potassium carbonate (211 mg, 1.53 mmol) and 4-ethoxybenzyl chloride (95.5 mg, 0.559 mmol), an operation in the same manner as in Example 6 was performed, and the obtained residue was triturated with diisopropyl ether to give the title compound (140 mg, yield 78%).

¹H NMR (CDCl₃) δ 1.42 (t, J=6.9 Hz, 3H), 1.62 (d, J=6.9 Hz, 3H), 2.08 (s, 3H), 4.03 (q, J=6.9 Hz, 2H), 5.01 (s, 2H), 5.39 (m, 1H), 6.25 (d, J=7.8 Hz, 1H), 6.90 (d, J=8.7 Hz, 2H), 6.98 (dd, J=2.4, 9.0 Hz, 1H), 7.22 (d, J=2.4 Hz, 1H), 7.32-7.39 (m, 3H).

Example 43

N-[1-(6-{2-[4-(trifluoromethoxy)phenyl]ethyl}-1-benzofuran-2-yl)ethyl]acetamide

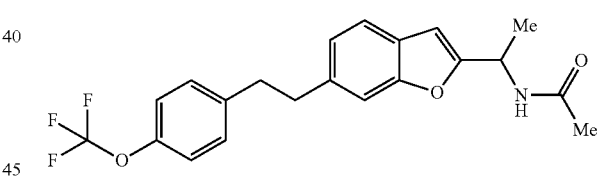

To a solution of 2-(1-azidoethyl)-6-{2-[4-(trifluoromethoxy)phenyl]ethyl}-1-benzofuran (825 mg, 2.20 mmol) obtained in Reference Example 149 in THF (10 mL) was added triphenylphosphine (865 mg, 3.30 mmol), and the mixture was stirred at 60° C. for 30 min. To the reaction mixture was added water (0.2 mL), and the mixture was stirred at 60° C. for 15 hr. The solvent was evaporated under reduced pressure and the obtained residue was purified by basic silica gel column chromatography (hexane:ethyl acetate=7:3 to 1:3) to give 1-(6-{2-[4-(trifluoromethoxy)phenyl]ethyl}-1-benzofuran-2-yl)ethanamine. This was dissolved in pyridine (3 mL)-acetic anhydride (3 mL), and the solution was stirred at room temperature for 15 min. The solvent was evaporated under reduced pressure and the obtained residue was purified by silica gel column chromatography (hexane:ethyl acetate=3:7 to 0:1) to give the title compound (686 mg, yield from 2-(1-azidoethyl)-6-{2-[4-(trifluoromethoxy)phenyl]ethyl}-1-benzofuran 60%) as a white solid.

¹H NMR (CDCl₃) δ 1.56 (d, J=8.0 Hz, 3H), 2.02 (s, 3H), 2.92-3.04 (m, 4H), 5.29-5.39 (m, 1H), 5.79 (d, J=8.0 Hz, 1H), 6.52 (s, 1H), 7.01 (dd, J=8.0, 1.1 Hz, 1H), 7.09-7.19 (m, 4H), 7.22 (s, 1H), 7.41 (d, J=8.0 Hz, 1H).

Example 44

N-(1-{6-[2-(4-butoxyphenyl)ethyl]-1-benzofuran-2-yl}ethyl)acetamide

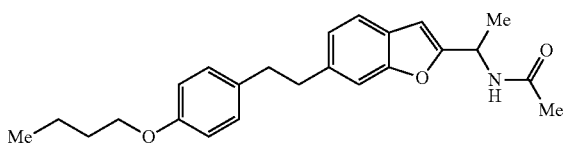 [SMILES: CCCCOc1ccc(CCc2ccc3cc(C(C)NC(C)=O)oc3c2)cc1]

To a solution of 2-(1-azidoethyl)-6-[2-(4-butoxyphenyl)ethyl]-1-benzofuran (553 mg, 1.53 mmol) obtained in Reference Example 156 in THF (10 mL) was added triphenylphosphine (599 mg, 2.28 mmol), and the mixture was stirred at 60° C. for 30 min. To the reaction mixture was added water (0.2 mL), and the mixture was stirred at 60° C. for 15 hr. The solvent was evaporated under reduced pressure and the obtained residue was purified by basic silica gel column chromatography (hexane:ethyl acetate=7:3 to 1:4) to give 1-{6-[2-(4-butoxyphenyl)ethyl]-1-benzofuran-2-yl}ethanamine. This was dissolved in pyridine (3 mL)-acetic anhydride (3 mL), and the solution was stirred at room temperature for 15 min. The solvent was evaporated under reduced pressure and the obtained residue was purified by silica gel column chromatography (hexane:ethyl acetate=1:1 to ethyl acetate) to give the title compound (448 mg, yield from 2-(1-azidoethyl)-6-[2-(4-butoxyphenyl)ethyl]-1-benzofuran 77%) as a white solid.

$^1$H NMR (CDCl$_3$) δ 0.96 (t, J=7.4 Hz, 3H), 1.42-1.49 (m, 2H), 1.53 (d, J=6.8 Hz, 3H), 1.70-1.79 (m, 2H), 1.98 (s, 3H), 2.84-2.90 (m, 2H), 2.94-3.00 (m, 2H), 3.92 (t, J=6.5 Hz, 2H), 5.26-5.36 (m, 1H), 6.07 (d, J=8.3 Hz, 1H), 6.49 (s, 1H), 6.80 (d, J=8.7 Hz, 2H), 7.02 (dd, J=7.9, 1.3 Hz, 1H), 7.06 (d, J=8.7 Hz, 2H), 7.22 (s, 1H), 7.38 (d, J=7.9 Hz, 1H).

Example 45

N-(1-{6-[(4-ethoxyphenoxy)methyl]-1-benzothiophen-2-yl}ethyl)acetamide

To a solution of tert-butyl {1-[6-(hydroxymethyl)-1-benzothiophen-2-yl]ethyl}carbamate (286 mg, 0.931 mmol) obtained in Reference Example 161, 4-ethoxyphenol (193 mg, 1.40 mmol) and triphenylphosphine (368 mg, 1.40 mmol) in THF (10 mL) was added 2.2 M diethyl azodicarboxylate toluene solution (0.640 mL, 1.41 mmol), and the mixture was stirred at room temperature for 15 min. The solvent was evaporated under reduced pressure and the obtained residue was purified by silica gel column chromatography (hexane:ethyl acetate=9:1 to 1:1) to give tert-butyl (1-{6-[(4-ethoxyphenoxy)methyl]-1-benzothiophen-2-yl}ethyl)carbamate as an oil. A solution (5 mL) of this oil in 4N hydrogen chloride-ethyl acetate was stirred at room temperature for 30 min. The solvent was evaporated under reduced pressure, the obtained residue was dissolved in pyridine (3 mL)-acetic anhydride (3 mL), and the solution was stirred at room temperature for 15 min. The solvent was evaporated under reduced pressure, and the residue was washed with diethyl ether to give the title compound (89.6 mg, yield from tert-butyl{1-[6-(hydroxymethyl)-1-benzothiophen-2-yl]ethyl}carbamate 26%) as a white solid.

$^1$H NMR (CDCl$_3$) δ 1.38 (t, J=7.0 Hz, 3H), 1.63 (d, J=6.8 Hz, 3H), 2.02 (s, 3H), 3.98 (q, J=7.0 Hz, 2H), 5.11 (s, 2H), 5.43-5.52 (m, 1H), 5.74 (d, J=8.1 Hz, 1H), 6.80-6.85 (m, 2H), 6.88-6.93 (m, 2H), 7.18 (s, 1H), 7.37 (dd, J=8.1, 1.4 Hz, 1H), 7.70 (d, J=8.1 Hz, 1H), 7.84 (s, 1H).

Example 46

N-(1-{6-[2-(4-propoxyphenyl)ethyl]-1-benzofuran-2-30 yl}ethyl)glycinamide hydrochloride

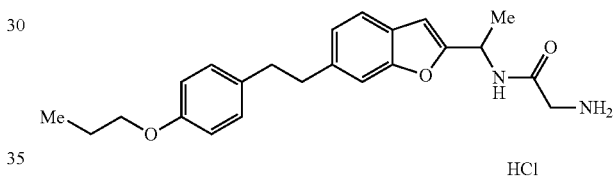

To a solution of 1-{6-[2-(4-propoxyphenyl)ethyl]-1-benzofuran-2-yl}ethanamine (325 mg, 1.01 mmol) obtained in Reference Example 104 in DMF (5 mL) were added Boc-glycine (266 mg, 1.52 mmol), 1-hydroxybenzotriazole (206 mg, 1.52 mmol) and 1-ethyl-3-(3-dimethylaminopropyl)carbodiimide hydrochloride (292 mg, 1.52 mmol), and the mixture was stirred at room temperature for 15 hr. Water was added to the reaction mixture, and the mixture was extracted with ethyl acetate. The organic layer was washed twice with saturated brine and dried over anhydrous magnesium sulfate, and the solvent was evaporated. The obtained residue was purified by silica gel column chromatography (hexane:ethyl acetate=4:1 to 2:3) to give tert-butyl {2-oxo-2-[(1-{6-[2-(4-propoxyphenyl)ethyl]-1-benzofuran-2-yl}ethyl)amino]ethyl}carbamate as a white solid. A solution (3 mL) of the solid in 4N hydrogen chloride-ethyl acetate was stirred at room temperature for 30 min. The precipitated solid was collected by filtration and washed with diethyl ether to give the title compound (218 mg, yield from 1-{6-[2-(4-propoxyphenyl)ethyl]-1-benzofuran-2-yl}ethanamine 52%) as a white solid.

$^1$H NMR (CDCl$_3$) δ 0.96 (t, J=7.4 Hz, 3H), 1.49 (d, J=6.8 Hz, 3H), 1.64-1.76 (m, 2H), 2.82-2.87 (m, 2H), 2.92-2.97 (m, 2H), 3.59 (d, J=5.3 Hz, 2H), 3.68 (d, J=4.5 Hz, 1H), 3.87 (t,

J=6.6 Hz, 2H), 5.11-5.21 (m, 1H), 6.73 (s, 1H), 6.81 (d, J=8.3 Hz, 2H), 7.07-7.12 (m, 3H), 7.35 (s, 1H), 7.46 (d, J=8.0 Hz, 1H), 8.13 (br, 2H).

Example 47 optically active forms (two kinds) of N-(1-{6-[2-(4-propoxyphenyl)ethyl]-1-benzofuran-2-yl}ethyl)acetamide

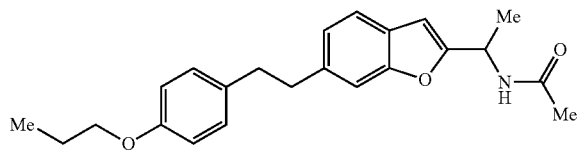

N-(1-{6-[2-(4-propoxyphenyl)ethyl]-1-benzofuran-2-yl}ethyl)acetamide (110 mg) obtained in Example 32 was optically resolved by high performance liquid chromatography (HPLC) under the following conditions to give two kinds of optically active forms of "retention time longer (47.2 mg)" and "retention time shorter (50.1 mg)".
<Preparative HPLC Conditions>
  column: CHIRALPAK AS (50 mmID×500 mmL)
  mobile phase: hexane:ethanol=9:1
  flow rate: 80 mL/min
  column temperature: 30° C.
  detection: UV 220 nm
  compound injection volume: 110 mg/44 ml (hexane:ethanol=9:1)
<HPLC Analysis Conditions>
  column: CHIRALPAK AS (4.6 mmID×250 mmL)
  mobile phase: hexane:ethanol=9:1
  flow rate: 1.0 mL/min
  column temperature: 30° C.
  detection: UV 220 nm
  retention time of "retention time longer": 13.09 min
  retention time of "retention time shorter": 9.98 min

Example 48

N-(1-{5-[(2-fluoro-4-ethoxybenzyl)oxy]-1-benzofuran-2-yl}ethyl)acetamide

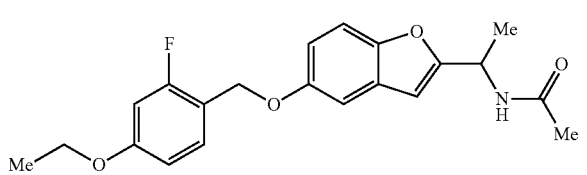

Using N-[1-(5-hydroxy-1-benzofuran-2-yl)ethyl]acetamide (100 mg, 0.456 mmol) obtained in Reference Example 38, anhydrous DMF (1 mL), 1-(bromomethyl)-2-fluoro-4-ethoxybenzene (233 mg, 0.948 mmol) and potassium carbonate (126 mg, 0.913 mmol), an operation in the same manner as in Example 18 was performed to give the title compound (93.6 mg, yield 55%).

$^1$H NMR (CDCl$_3$) δ 1.41 (t, J=7.0 Hz, 3H), 1.55 (d, J=7.0 Hz, 3H), 2.02 (s, 3H), 4.02 (q, J=7.0 Hz, 2H), 5.05 (s, 2H), 5.26-5.41 (m, 1H), 5.80 (br, 1H), 6.50 (s, 1H), 6.59-6.71 (m, 2H), 6.92 (dd, J=8.9, 2.5 Hz, 1H), 7.06 (d, J=2.4 Hz, 1H), 7.29-7.41 (m, 2H).

Example 49

N-(1-{5-[(4-ethoxybenzyl)sulfanyl]-1-benzofuran-2-yl}ethyl)acetamide

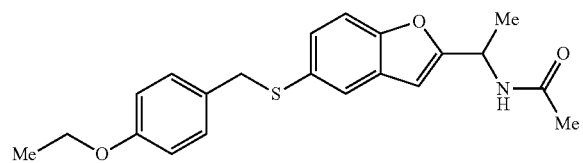

To a solution of N-[1-(5-bromo-1-benzofuran-2-yl)ethyl]acetamide (1.00 g, 3.55 mmol) obtained in Reference Example 163 in 1,2-dimethoxyethane (20 mL) were added tris(dibenzylideneacetone)dipalladium(0) (81.1 mg, 0.0885 mmol), (9,9-dimethyl-9H-xanthen-4,5-diyl)bis(diphenylphosphane) (Xantphos, 102 mg, 0.177 mmol), N,N-diisopropylethylamine (915 mg, 7.10 mmol) and 2-ethylhexyl 2-mercaptopropionate (928 mg, 4.26 mmol), and the mixture was refluxed overnight under a nitrogen atmosphere. Brine was added thereto, and the mixture was extracted twice with ethyl acetate. The extract was washed with saturated brine, and dried over magnesium sulfate. The residue was passed through silica gel, and the solvent was evaporated under reduced pressure to give an oil.

To the obtained oil were added THF (9 mL), ethanol (1 mL) and sodium ethoxide (482 mg, 7.10 mmol), and the mixture was stirred at 40° C. for 1 hr. To the reaction mixture was added 1N hydrochloric acid, and the mixture was extracted twice with ethyl acetate. The extract was washed with saturated brine, and dried over anhydrous sodium sulfate. The solvent was evaporated under reduced pressure, and the obtained residue was purified by silica gel column chromatography (hexane to hexane:ethyl acetate=1:4) to give a mixture (750 mg) of N-[1-(5-sulfanyl-1-benzofuran-2-yl)ethyl]acetamide and N-[1-(5-bromo-1-benzofuran-2-yl)ethyl]acetamide.

To a solution of the obtained mixture (750 mg) of N-[1-(5-sulfanyl-1-benzofuran-2-yl)ethyl]acetamide and N-[1-(5-bromo-1-benzofuran-2-yl)ethyl]acetamide in anhydrous DMF (6.4 mL) were added 4-ethoxybenzyl chloride (1.09 g, 6.38 mmol) and potassium carbonate (880 mg, 0.456 mmol), and the reaction mixture was stirred at room temperature overnight. Saturated brine was added thereto, and the mixture was extracted twice with ethyl acetate. The extract was washed with saturated brine, and dried over anhydrous magnesium sulfate. The solvent was evaporated under reduced pressure, and the obtained residue was purified by silica gel column chromatography (hexane:ethyl acetate=4:1 to 1:4), and the obtained solid was washed with diethyl ether to give N-(1-{5-[(4-ethoxybenzyl)sulfanyl]-1-benzofuran-2-yl}ethyl)acetamide (205 mg, yield from (N-[1-(5-{[tert-butyl(dimethyl)silyl]oxy}-1-benzothiophen-2-yl)ethyl]acetamide 16%).

$^1$H NMR (CDCl$_3$) δ 1.39 (t, J=7.0 Hz, 3H), 1.56 (d, J=7.2 Hz, 3H), 2.02 (s, 3H), 3.94-4.05 (m, 4H), 5.29-5.36 (m, 1H), 5.77 (br, 1H), 6.48 (s, 1H), 6.77 (d, J=8.7 Hz, 2H), 7.11 (d, J=8.7 Hz, 2H), 7.20-7.25 (m, 1H), 7.28-7.33 (m, 1H), 7.48 (d, J=1.5 Hz, 1H).

Example 50

N-(1-{5-[(4-ethoxybenzyl)sulfonyl]-1-benzofuran-2-yl}ethyl)acetamide

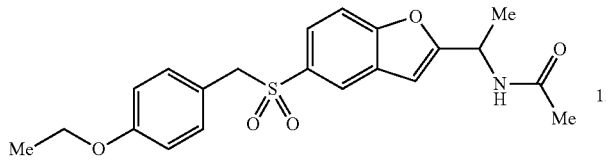

To a solution of N-(1-{5-[(4-ethoxybenzyl)sulfanyl]-1-benzofuran-2-yl}ethyl)acetamide (100 mg, 0.271 mmol) obtained in Example 49 in ethyl acetate (2 mL) was added 75% m-chloroperbenzoic acid (79.8 mg, 0.324 mmol), and the mixture was stirred at room temperature for 1.5 hr. To the reaction mixture was added aqueous sodium hydrogen carbonate solution, and the mixture was extracted twice with ethyl acetate. The extract was washed with saturated brine, and dried over anhydrous magnesium sulfate. The solvent was evaporated under reduced pressure, and the obtained residue was purified by silica gel column chromatography (hexane:ethyl acetate=4:1 to ethyl acetate), and washed with diethyl ether to give the title compound (19.1 mg, yield 18%).

$^1$H NMR (CDCl$_3$) δ 1.40 (t, J=7.0 Hz, 3H), 1.59 (d, J=7.2 Hz, 3H), 2.05 (s, 3H), 4.00 (q, J=7.0 Hz, 2H), 4.26 (s, 2H), 5.27-5.52 (m, 1H), 5.81 (br, 1H), 6.60 (s, 1H), 6.75 (d, J=8.8 Hz, 2H), 6.96 (d, J=8.8 Hz, 2H), 7.45 (d, J=8.8 Hz, 1H), 7.49 (dd, J=8.8, 1.1 Hz, 1H), 7.84 (d, J=1.1 Hz, 1H).

Example 51

N-(1-{5-[(4-ethoxybenzyl)sulfinyl]-1-benzofuran-2-yl}ethyl)acetamide

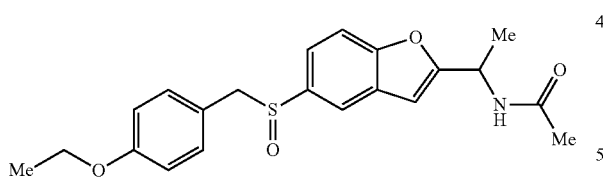

To a solution of N-(1-[5-[(4-ethoxybenzyl)sulfanyl]-1-benzofuran-2-yl]ethyl)acetamide (100 mg, 0.271 mmol) obtained in Example 49 in ethyl acetate (2 mL) was added 75% m-chloroperbenzoic acid (79.8 mg, 0.324 mmol), and the mixture was stirred at room temperature for 1.5 hr. Aqueous sodium hydrogen carbonate solution was added thereto, and the mixture was extracted twice with ethyl acetate. The extract was washed with saturated brine, and dried over anhydrous magnesium sulfate. The solvent was evaporated under reduced pressure, and the obtained residue was purified by silica gel column chromatography (hexane:ethyl acetate=4:1 to ethyl acetate), and the obtained solid was washed with diethyl ether to give the title compound (25.5 mg, yield 25%).

$^1$H NMR (CDCl$_3$) δ 1.40 (t, J=7.0 Hz, 3H), 1.59 (d, J=6.8 Hz, 3H), 2.05 (s, 3H), 3.88-4.11 (m, 4H), 5.31-5.45 (m, 1H), 5.88 (br, 1H), 6.56 (s, 1H), 6.74 (d, J=8.7 Hz, 2H), 6.85 (d, J=8.7 Hz, 2H), 7.21 (dd, J=8.6, 1.7 Hz, 1H), 7.45 (d, J=8.6 Hz, 1H), 7.58 (d, J=1.7 Hz, 1H).

Example 52

N-(1-{5-chloro-6-[(4-ethoxybenzyl)oxy]-1-benzofuran-2-yl}ethyl)acetamide

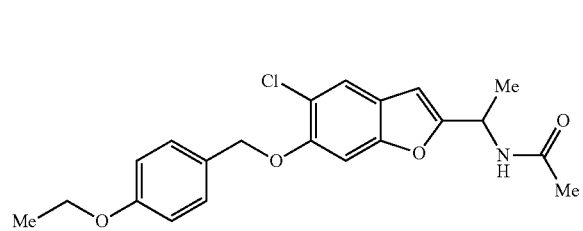 [SMILES: CCOc1ccc(COc2cc3oc(C(C)NC(C)=O)cc3cc2Cl)cc1]

Using N-[1-(5-chloro-6-hydroxy-1-benzofuran-2-yl)ethyl]acetamide (100 mg, 0.394 mmol) obtained in Reference Example 168, anhydrous DMF (1 mL), 4-ethoxybenzyl chloride (133 mg, 0.787 mmol) and potassium carbonate (108 mg, 0.787 mmol), an operation in the same manner as in Example 18 was performed to give the title compound (112 mg, yield 73%) as a white solid.

$^1$H NMR (CDCl$_3$) δ 1.42 (t, J=7.0 Hz, 3H), 1.54 (d, J=7.0 Hz, 3H), 2.02 (s, 3H), 4.04 (q, J=7.0 Hz, 2H), 5.10 (s, 2H), 5.24-5.38 (m, 1H), 5.74 (br, 1H), 6.44 (s, 1H), 6.91 (d, J=8.7 Hz, 2H), 7.06 (s, 1H), 7.39 (d, J=8.7 Hz, 2H), 7.49 (s, 1H).

Example 53

4-[({2-[1-(acetylamino)ethyl]-1-benzofuran-5-yl}oxy)methyl]phenyl acetate

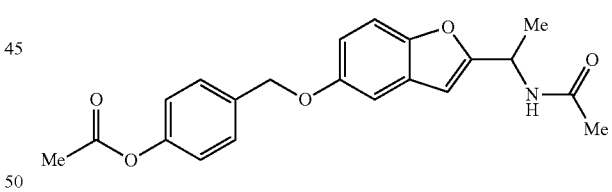

Using N-[1-(5-hydroxy-1-benzofuran-2-yl)ethyl]acetamide (1.00 g, 4.56 mmol) obtained in Reference Example 38, 4-acetoxybenzylalcohol (984 mg, 5.93 mmol), triphenylphosphine (polystyrene-supported, 1.84 mol/g, 3.22 g, 5.93 mmol), THF (50 mL) and 2.2 M diethyl azodicarboxylate toluene solution (2.7 mL, 5.9 mmol), the method in the same manner as in Example 3 was performed, and the obtained residue was triturated with diethyl ether to give the title compound (177 mg, yield 11%).

$^1$H NMR (CDCl$_3$) δ 1.55 (d, J=6.9 Hz, 3H), 2.02 (s, 3H), 2.30 (s, 3H), 5.07 (s, 2H), 5.26-5.40 (m, 1H), 5.79 (d, J=7.7

Hz, 1H), 6.50 (s, 1H), 6.93 (dd, J=8.9, 2.6 Hz, 1H), 7.03 (d, J=2.6 Hz, 1H), 7.08-7.15 (m, 2H), 7.33 (d, J=8.9 Hz, 1H), 7.45 (d, J=8.7 Hz, 2H).

Example 54

N-(1-{(6-[2-(4-ethoxyphenyl)ethyl]-1-benzothiophen-2-yl}ethyl)acetamide

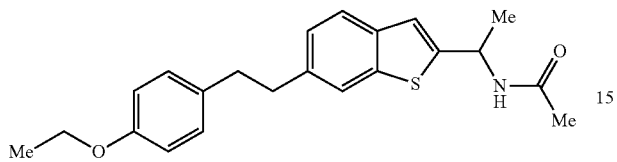

To a solution of 2-(1-azidoethyl)-6-[2-(4-ethoxyphenyl) ethyl]-1-benzothiophene (168 mg, 0.478 mmol) obtained in Reference Example 175 in THF (5 mL) was added triphenylphosphine (188 mg, 0.717 mmol), and the mixture was stirred at 60° C. for 30 min. To the reaction mixture was added water (0.1 mL), and the mixture was stirred at 60° C. for 15 hr. The solvent was evaporated under reduced pressure and the obtained residue was purified by basic silica gel column chromatography (hexane:ethyl acetate=7:3 to 1:4) to give 1-{6-[2-(4-ethoxyphenyl)ethyl]-1-benzothiophen-2-yl}ethanamine. This was dissolved in pyridine (3 mL)-acetic anhydride (3 mL), and the solution was stirred at room temperature for 15 min. The solvent was evaporated under reduced pressure, and the residue was washed with diethyl ether to give the title compound (97.1 mg, yield from (2-(1-azidoethyl)-6-[2-(4-ethoxyphenyl)ethyl]-1-benzothiophene 55%) as a white solid.

$^1$H NMR (CDCl$_3$) δ 1.40 (t, J=7.0 Hz, 3H), 1.62 (d, J=6.8 Hz, 3H), 2.02 (s, 3H), 2.86-2.91 (m, 2H), 2.95-3.01 (m, 2H), 4.01 (q, J=7.0 Hz, 2H), 5.41-5.50 (m, 1H), 5.72 (d, J=8.7 Hz, 1H), 6.80 (d, J=8.7 Hz, 2H), 7.07 (d, J=8.7 Hz, 2H), 7.12-7.16 (m, 2H), 7.55 (s, 1H), 7.60 (d, J=8.3 Hz, 1H).

Example 55

N-[(1-{6-[2-(4-propoxyphenyl)ethyl]-1-benzofuran-2-yl}ethyl)carbamoyl]methanesulfonamide

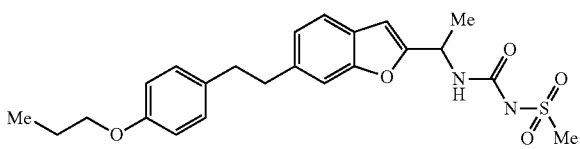 [SMILES: CCCOc1ccc(CCc2ccc3cc(C(C)NC(=O)NS(C)(=O)=O)oc3c2)cc1]

To a solution of 1-{6-[2-(4-propoxyphenyl)ethyl]-1-benzofuran-2-yl}ethanamine (325 mg, 1.01 mmol) obtained in Reference Example 104 in DMF (5 mL) were added pyridine (0.120 mL, 1.50 mmol) and phenyl chloroformate (0.152 mL, 1.20 mmol), and the mixture was stirred at room temperature for 30 min. To the reaction mixture were added methanesulfonamide (115 mg, 1.20 mmol), 1,8-diazabicyclo[5.4.0] undec-7-ene (0.380 mL, 1.40 mmol) and 4-dimethylaminopyridine (171 mg, 1.40 mmol), and the mixture was stirred at 50° C. for 30 min. The reaction mixture was acidified with 1N hydrochloric acid, and extracted with ethyl acetate, and the extract was dried over anhydrous magnesium sulfate. The solvent was evaporated under reduced pressure and the obtained residue was purified by silica gel column chromatography (hexane:ethyl acetate=4:1 to 2:3) to give the title compound (63.5 mg, yield 14%) as a white solid.

$^1$H NMR (CDCl$_3$) δ 0.96 (t, J=7.4 Hz, 3H), 1.47 (d, J=7.0 Hz, 3H), 1.64-1.76 (m, 2H), 2.81-2.86 (m, 2H), 2.91-2.97 (m, 2H), 3.23 (s, 3H), 3.86 (t, J=6.6 Hz, 2H), 4.94-5.03 (m, 1H), 6.67 (s, 1H), 6.81 (d, J=8.7 Hz, 2H), 7.02 (d, J=8.3 Hz, 1H), 7.06-7.12 (m, 3H), 7.38 (s, 1H), 7.46 (d, J=7.9 Hz, 1H), 10.01 (br, 1H).

Example 56

N-(1-{6-[2-(6-ethoxypyridin-3-yl)ethyl]-1-benzofuran-2-yl}ethyl)acetamide

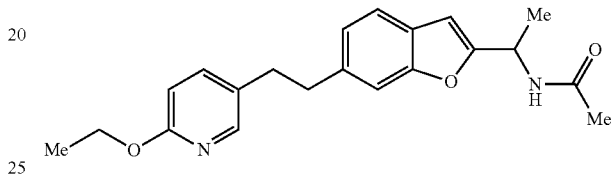

To a solution of 5-{2-[2-(1-azidoethyl)-1-benzofuran-6-yl]ethyl}-2-ethoxypyridine (259 mg, 0.770 mmol) obtained in Reference Example 183 in THF (5 mL) was added triphenylphosphine (242 mg, 0.924 mmol), and the mixture was stirred at 60° C. for 30 min. To the reaction mixture was added water (0.1 mL), and the mixture was stirred at 60° C. for 15 hr. The solvent was evaporated under reduced pressure and the obtained residue was purified by basic silica gel column chromatography (hexane:ethyl acetate=7:3 to 1:4) to give 1-{6-[2-(6-ethoxypyridin-3-yl)ethyl]-1-benzofuran-2-yl}ethanamine. This was dissolved in pyridine (2.5 mL)-acetic anhydride (2.5 mL), and the solution was stirred at room temperature for 15 min. The solvent was evaporated under reduced pressure, and the residue was washed with diethyl ether to give the title compound (120 mg, yield from 5-{2-[2-(1-azidoethyl)-1-benzofuran-6-yl]ethyl}-2-ethoxypyridine 44%) as a white solid.

$^1$H NMR (CDCl$_3$) δ 1.38 (t, J=7.2 Hz, 3H), 1.56 (d, J=6.8 Hz, 3H), 2.02 (s, 3H), 2.84-2.89 (m, 2H), 2.95-3.00 (m, 2H), 4.31 (q, J=7.2 Hz, 2H), 5.29-5.39 (m, 1H), 5.84 (d, J=7.4 Hz, 1H), 6.52 (s, 1H), 6.63 (d, J=8.5 Hz, 1H), 7.00 (dd, J=7.9, 1.3 Hz, 1H), 7.20 (s, 1H), 7.34 (dd, J=8.5, 2.5 Hz, 1H), 7.40 (d, J=7.9 Hz, 1H), 7.89 (d, J=2.5 Hz, 1H).

Example 57

N-(1-{6-[2-(5-ethoxypyridin-2-1)ethyl]-1-benzofuran-2-yl}ethyl)acetamide

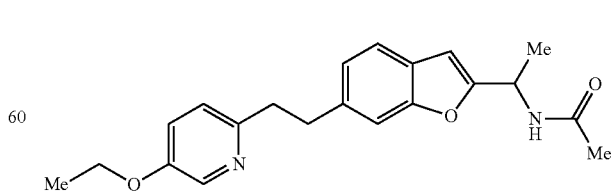

To a solution of 2-{2-[2-(1-azidoethyl)-1-benzofuran-6-yl]ethyl}-5-ethoxypyridine (512 mg, 1.53 mmol) obtained in Reference Example 191 in THF (10 mL) was added triphenylphosphine (599 mg, 2.29 mmol), and the mixture was stirred at 60° C. for 30 min. To the reaction mixture was added water (0.1 mL), and the mixture was stirred at 60° C. for 15 hr. The solvent was evaporated under reduced pressure and the obtained residue was purified by basic silica gel column chromatography (hexane:ethyl acetate=7:3 to 1:4) to give 1-{6-[2-(5-ethoxypyridin-2-yl)ethyl]-1-benzofuran-2-yl}ethanamine. This was dissolved in pyridine (3 mL)-acetic anhydride (3 mL), and the solution was stirred at room temperature for 15 min. The solvent was evaporated under reduced pressure and the obtained residue was purified by silica gel column chromatography (hexane:ethyl acetate=1:1 to ethyl acetate) to give the title compound (435 mg, yield from 1-{6-[2-(5-ethoxypyridin-2-yl)ethyl]-1-benzofuran-2-yl}ethanol 80%) as a white solid.

$^1$H NMR (CDCl$_3$) δ 1.43 (t, J=7.0 Hz, 3H), 1.55 (d, J=7.0 Hz, 3H), 2.02 (s, 3H), 3.02-3.15 (m, 4H), 4.06 (q, J=7.0 Hz, 2H), 5.28-5.38 (m, 1H), 5.84 (br, 1H), 6.51 (s, 1H), 6.97 (d, J=8.5 Hz, 1H), 7.03-7.10 (m, 2H), 7.25 (s, 1H), 7.39 (d, J=7.9 Hz, 1H), 8.25 (d, J=2.8 Hz, 1H).

Example 58

N-(1-{6-[(4-ethoxyphenoxy)methyl]-1,3-benzoxazol-2-yl}ethyl)acetamide

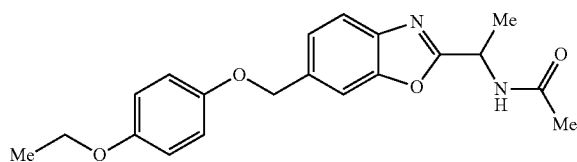 [SMILES: CCOc1ccc(OCc2ccc3nc(C(C)NC(C)=O)oc3c2)cc1]

Using N-{1-[6-(hydroxymethyl)-1,3-benzoxazol-2-yl]ethyl}acetamide (22.2 mg, 0.0948 mmol) obtained in Reference Example 196 and 4-ethoxyphenol (26.2 mg, 0.190 mmol), an operation in the same manner as in Example 36 was performed, and the obtained residue was triturated with hexane to give the title compound (7.3 mg, yield 22%).

$^1$H NMR (CDCl$_3$) δ 1.39 (t, J=6.9 Hz, 3H), 1.64 (d, J=6.9 Hz, 3H), 2.09 (s, 3H), 3.97 (q, J=6.9 Hz, 2H), 5.12 (s, 2H), 5.42 (m, 1H), 6.25 (br, 1H), 6.82 (d, J=9.0 Hz, 2H), 6.89 (d, J=9.0 Hz, 2H), 7.37 (d, J=7.8 Hz, 1H), 7.60 (s, 1H), 7.66 (d, J=7.8 Hz, 1H).

Example 59 tert-butyl (1-{5-[(4-ethoxyphenoxy)methyl]-1H-benzimidazol-2-yl}ethyl)carbamate

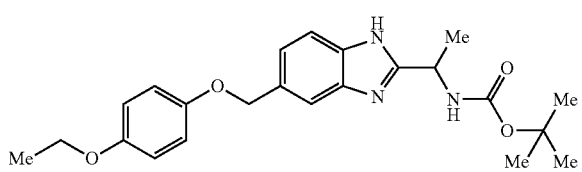 [SMILES: CCOc1ccc(OCc2ccc3[nH]c(C(C)NC(=O)OC(C)(C)C)nc3c2)cc1]

Using tert-butyl {1-[5-(hydroxymethyl)-1H-benzimidazol-2-yl]ethyl}carbamate (398 mg, 1.37 mmol) obtained in Reference Example 30199 and 4-ethoxyphenol (377 mg, 2.73 mmol), a method in the same manner as in Example 36 was performed, and the obtained residue was triturated with diisopropyl ether to give the title compound (86.9 mg, yield 16%).

$^1$H NMR (CDCl$_3$) δ 1.38 (t, J=6.9 Hz, 3H), 1.46 (s, 9H), 1.73 (d, J=6.9 Hz, 3H), 3.97 (q, J=6.9 Hz, 2H), 4.97 (m, 1H), 5.11 (s, 2H), 5.13 (m, 1H), 6.81 (d, J=9.0 Hz, 2H), 6.91 (d, J=9.0 Hz, 2H), 7.29 (m, 1H), 7.39-7.49 (m, 1H), 7.71-7.77 (m, 1H), 10.18 (br, 1H).

Example 60

N-(1-{5-[(4-ethoxyphenoxy)methyl]-1H-benzimidazol-2-yl}ethyl)acetamide

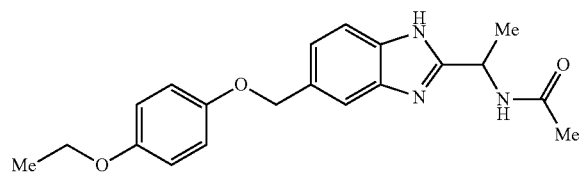 [SMILES: CCOc1ccc(OCc2ccc3[nH]c(C(C)NC(C)=O)nc3c2)cc1]

To a solution of 1-{5-[(4-ethoxyphenoxy)methyl]-1H-benzimidazol-2-yl}ethanamine dihydrochloride (55.2 mg, 0.144 mmol) obtained in Reference Example 200 in DMF (1 mL) were added triethylamine (0.0599 mL, 0.431 mmol) and acetic anhydride (0.0163 mL, 0.172 mmol), and the mixture was stirred at room temperature for 2 hr. The reaction mixture was diluted with ethyl acetate, and the mixture was washed with 10% aqueous potassium carbonate solution and saturated brine, and dried over anhydrous sodium sulfate. This solution was applied to basic silica gel column chromatography (ethyl acetate). The solvent was evaporated under reduced pressure, and the obtained residue was triturated with diisopropyl ether to give the title compound (31.2 mg, yield 56.5%).

$^1$H NMR (CDCl$_3$) δ 1.37 (t, J=6.9 Hz, 3H), 1.68 (d, J=7.2 Hz, 3H), 2.00 (s, 3H), 3.96 (q, J=6.9 Hz, 2H), 5.09 (s, 2H), 5.28 (m, 1H), 6.77-6.82 (m, 2H), 6.85-6.90 (m, 2H), 7.21 (d, J=7.5 Hz, 1H), 7.29 (dd, J=1.5, 8.1 Hz, 1H), 7.54 (d, J=8.1 Hz, 1H), 7.60 (s, 1H).

Example 61

N-(1-{5-[(4-ethoxybenzyl)oxy]-1H-benzimidazol-2-yl}ethyl)acetamide

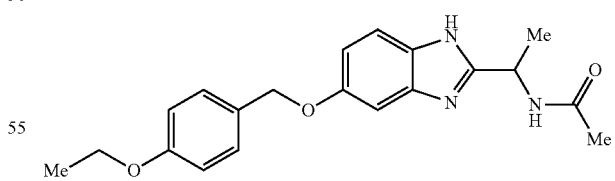

A suspension of N-[1-(5-hydroxy-1H-benzimidazol-2-yl)ethyl]acetamide (62.0 mg, 0.283 mmol) obtained in Reference Example 204, potassium carbonate (78.2 mg, 0.566 mmol) and 4-ethoxybenzyl chloride (48.3 mg, 0.283 mmol) in DMF (1 mL) was stirred under heating at 60° C. for 1 hr. The reaction mixture was diluted with ethyl acetate, and the mixture was washed with 10% aqueous potassium carbonate solution and saturated brine, and dried over anhydrous sodium sulfate. This solution was applied to basic silica gel column chromatography (ethyl acetate). The solvent was evaporated under reduced pressure, and the obtained residue was purified by silica gel column chromatography (hexane: ethyl acetate=1:1 to methanol:ethyl acetate=1:9). The obtained crude product was purified by preparative basic silica gel TLC (ethyl acetate) and triturated with diisopropyl ether to give the title compound (3.8 mg, yield 3.8%).

$^1$H NMR (CDCl$_3$) δ 1.41 (t, J=6.9 Hz, 3H), 1.67 (d, J=6.9 Hz, 3H), 2.00 (s, 3H), 4.02 (q, J=6.9 Hz, 2H), 4.98 (s, 2H), 5.23 (m, 1H), 6.72 (d, J=6.9 Hz, 1H), 6.88 (d, J=8.4 Hz, 2H), 6.91 (dd, J=2.4, 8.7 Hz, 1H), 6.97 (s, 1H), 7.06 (br, 1H), 7.33 (d, J=8.4 Hz, 2H), 7.43 (br, 1H).

Examples 62 to 74

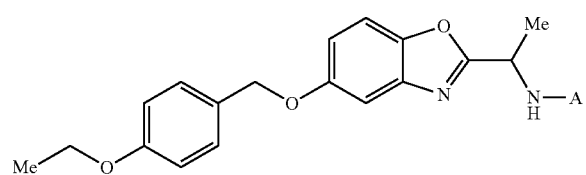

A solution (0.50 mL, 0.0600 mmol) of 1-{5-[(4-ethoxybenzyl)oxy]-1-benzofuran-2-yl}ethanamine obtained in Reference Example 207 in 0.12 M DMF, a 0.18 M solution (0.50 mL, 0.0900 mmol) of the corresponding carboxylic acid in DMF, and a 0.18 M solution (0.50 mL, each 0.0900 mmol) of 1-hydroxybenzotriazole and 1-ethyl-3-(3'-dimethylaminopropyl)carbodiimide hydrochloride in DMF were mixed at room temperature, and the mixture was stirred as it was for 4 hr. To the reaction mixture were added ethyl acetate (3.0 mL) and 2% aqueous sodium hydrogen carbonate solution (1.5 mL) and the mixture was shaken. The organic layer was recovered by upper layer Phase Septube (manufactured by Wako Pure Chemical Industries, Ltd.). The solvent was evaporated under reduced pressure, and the residue was dissolved in DMSO-methanol (1:1, 1.0 mL), and the solution was purified by preparative HPLC to give the object compound (purity not less than 80%, LC/MS analysis).

Examples 75 to 84

To a mixed solution of a 0.12 M solution (0.50 mL, 0.0600 mmol) of 1-{5-[(4-ethoxybenzyl)oxy]-1-benzofuran-2-yl}ethanamine obtained in Reference Example 207 in DMF and a 0.24 M solution (0.50 mL, 0.120 mmol) of triethylamine in DMF was added the corresponding acid chloride or sulfonyl chloride (0.0900 mmol) at room temperature, and the mixture was stirred as it was for 24 hr. To the reaction mixture were added ethyl acetate (3.0 mL) and 2% aqueous sodium hydrogen carbonate solution (1.5 mL) and the mixture was shaken. The organic layer was recovered by upper layer Phase Septube (manufactured by Wako Pure Chemical Industries, Ltd.). The solvent was evaporated under reduced pressure, and the residue was dissolved in DMSO-methanol (1:1, 1.0 mL), and the solution was purified by preparative HPLC to give the object compound (purity not less than 80%, LC/MS analysis).

Examples 85 to 93

To a 0.12 M solution (0.50 mL, 0.0600 mmol) of 1-{5-[(4-ethoxybenzyl)oxy]-1-benzofuran-2-yl}ethanamine obtained in Reference Example 207 in DMF was added a 0.18 M solution (0.50 mL, 0.0900 mmol) of the corresponding isocyanate in DMF at room temperature, and the mixture was stirred for 24 hr. To the reaction mixture were added ethyl acetate (3.0 mL) and 2% aqueous sodium hydrogen carbonate solution (1.5 mL) and the mixture was shaken. The organic layer was recovered by upper layer Phase Septube (manufactured by Wako Pure Chemical Industries, Ltd.). The solvent was evaporated under reduced pressure, and the residue was dissolved in DMSO-methanol (1:1, 1.0 mL) and the solution was purified by preparative HPLC.

The purification by preparative HPLC in the above-mentioned Examples was performed under the following conditions.

apparatus: Gilson Inc. High-throughput purification system column: YMC CombiPrep ODS-A S-5 μm, 50×20 mm solvent: SOLUTION A; 10 mM aqueous hydrogencarbonate ammonium solution, SOLUTION B; acetonitrile gradient cycle: 0 min (SOLUTION A/SOLUTION B=95/5), 1.00 min (SOLUTION A/SOLUTION B=95/5), 5.20 min (SOLUTION A/SOLUTION B=5/95), 6.40 min (SOLUTION A/SOLUTION B=5/95), 6.50 min (SOLUTION A/SOLUTION B=95/5), 6.60 min (SOLUTION A/SOLUTION B=95/5)

flow rate: 20 mL/min, detection method: UV 220 nm

The structural formulas and mass spectrum data of the compounds obtained in Examples 62 to 93 are shown in Table 1 and Table 2.

TABLE 1

| Ex. No. | A | MS (m/Z) |
|---|---|---|
| 62 | −C(=O)−Me | 368 |
| 63 | −C(=O)−cyclopropyl | 380 |
| 64 | −C(=O)−CH(Me)$_2$ | 382 |
| 65 | −C(=O)−CH$_2$−CH(Me)$_2$ | 396 |

TABLE 1-continued

Structure: 4-ethoxybenzyl ether of 5-hydroxybenzofuran with 2-(1-aminoethyl) substituent, NH–A

| Ex. No. | A | MS (m/Z) |
|---|---|---|
| 66 | acetyl-2-furyl | 406 |
| 67 | acetyl-cyclopentyl | 408 |
| 68 | acetyl-phenyl (benzoyl-methyl) | 416 |
| 69 | acetyl-(pyridin-2-yl) | 417 |
| 70 | acetyl-(pyridin-3-yl) | 417 |
| 71 | acetyl-(pyridin-4-yl) | 417 |
| 72 | acetyl-(5-methylisoxazol-3-yl) | 421 |
| 73 | acetyl-(thiazol-5-yl) | 423 |

TABLE 1-continued

| Ex. No. | A | MS (m/Z) |
|---|---|---|
| 74 | acetyl-(2,5-dimethylfuran-3-yl) | 434 |
| 75 | 2-oxopentyl (CH₂CH₂Me ketone) | 382 |
| 76 | methoxyacetyl (CH₂OMe ketone) | 384 |
| 77 | acetyl-(isoxazol-5-yl) | 407 |
| 78 | acetyl-(tetrahydropyran-4-yl) | 424 |

TABLE 2

Structure: 4-ethoxybenzyl ether of 5-hydroxybenzofuran with 2-(1-aminoethyl) substituent, NH–A

| Ex. No. | A | MS (m/Z) |
|---|---|---|
| 79 | phenylacetyl (CH₂Ph ketone) | 430 |

TABLE 2-continued
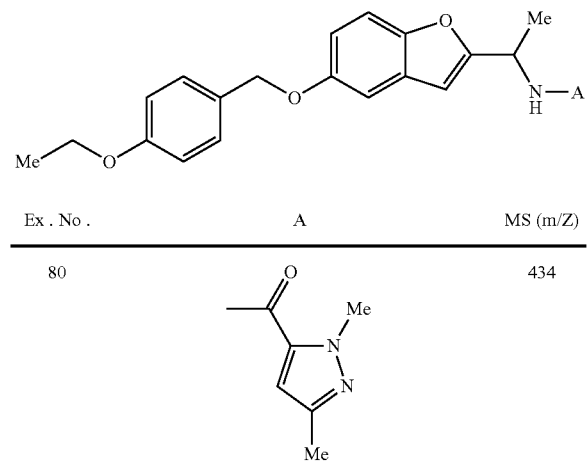
| Ex. No. | A | MS (m/Z) |
|---|---|---|
| 80 | 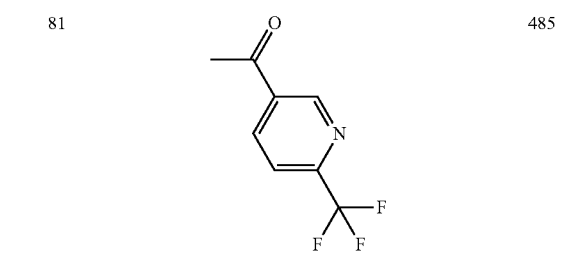 | 434 |
| 81 | 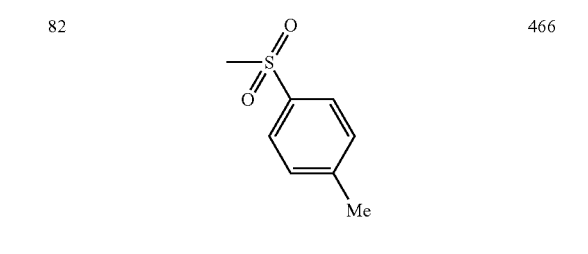 | 485 |
| 82 | 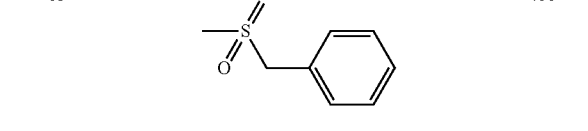 | 466 |
| 83 | 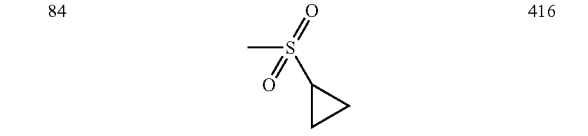 | 466 |
| 84 | 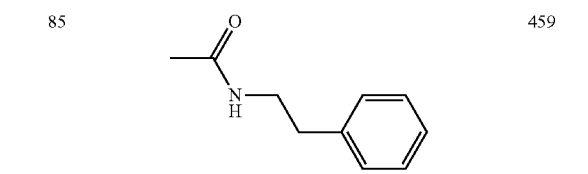 | 416 |
| 85 | 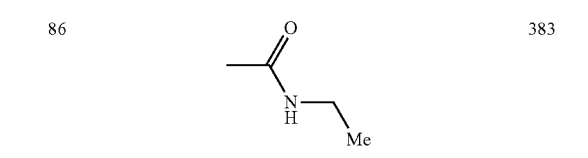 | 459 |
| 86 | 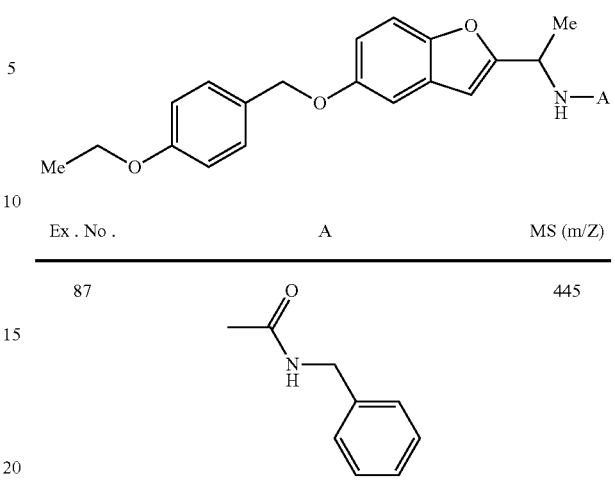 | 383 |
TABLE 2-continued
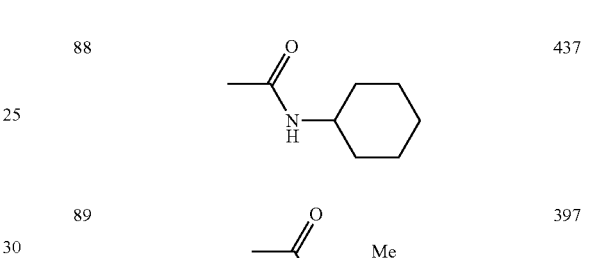
| Ex. No. | A | MS (m/Z) |
|---|---|---|
| 87 | 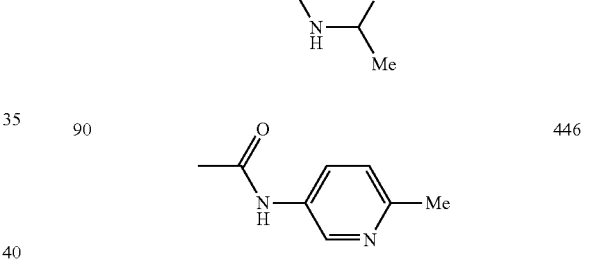 | 445 |
| 88 | 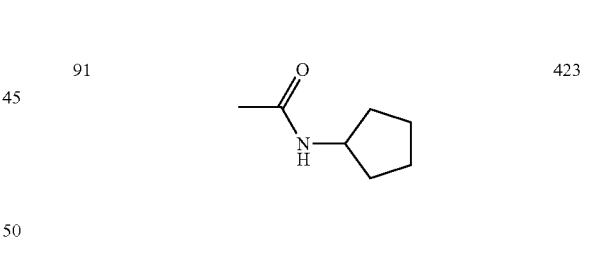 | 437 |
| 89 | 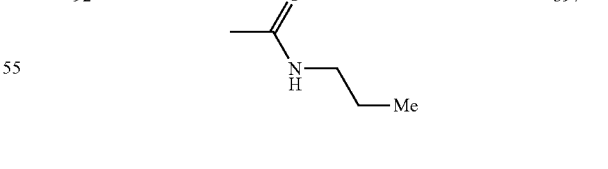 | 397 |
| 90 | 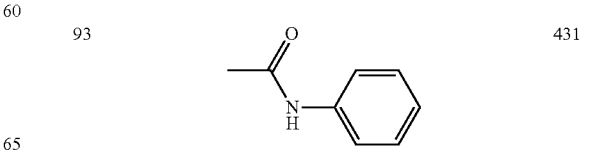 | 446 |
| 91 | | 423 |
| 92 | | 397 |
| 93 | | 431 |

Example 94

N-(1-{6-[2-(2,3-dihydro-1-benzofuran-5-yl)ethyl]-1-benzofuran-2-yl}ethyl)acetamide

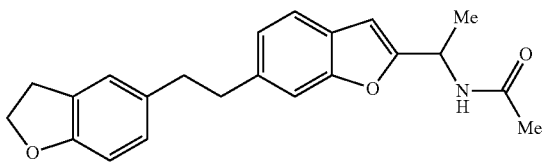 [SMILES: CC(=O)NC(C)c1cc2ccc(CCc3ccc4c(c3)CCO4)cc2o1]

To a solution of 2-(1-azidoethyl)-6-[2-(2,3-dihydro-1-benzofuran-5-yl)ethyl]-1-benzofuran (394 mg, 1.18 mmol) obtained in Reference Example 214 in THF (10 mL) was added triphenylphosphine (465 mg, 1.77 mmol), and the mixture was stirred at 60° C. for 30 min. To the reaction mixture was added water (0.1 mL), and the mixture was stirred at 60° C. for 15 hr. The solvent was evaporated under reduced pressure and the obtained residue was purified by basic silica gel column chromatography (hexane:ethyl acetate=7:3 to 1:4) to give 1-{6-[2-(2,3-dihydro-1-benzofuran-5-yl)ethyl]-1-benzofuran-2-yl}ethanamine. This was dissolved in pyridine (3 mL)-acetic anhydride (3 mL), and the solution was stirred at room temperature for 15 min. The solvent was evaporated under reduced pressure and the obtained residue was purified by silica gel column chromatography (hexane:ethyl acetate-1:1 to ethyl acetate) to give the title compound (313 mg, yield from 2-(1-azidoethyl)-6-[2-(2,3-dihydro-1-benzofuran-5-yl)ethyl]-1-benzofuran 76%) as a white solid.

$^1$H NMR (CDCl$_3$) δ 1.56 (d, J=7.2 Hz, 3H), 2.02 (s, 3H), 2.84-2.90 (m, 2H), 2.95-3.01 (m, 2H), 3.18 (t, J=8.7 Hz, 2H), 4.55 (t, J=8.7 Hz, 2H), 5.29-5.39 (m, 1H), 5.80 (d, J=8.0 Hz, 1H), 6.52 (s, 1H), 6.89 (d, J=8.3 Hz, 1H), 6.90 (d, J=8.3 Hz, 1H), 7.03-7.05 (m, 2H), 7.25 (s, 1H), 7.41 (d, J=8.0 Hz, 1H).

Example 95

N-[1-(6-{2-[4-(methoxymethoxy)phenyl]ethyl}-1-benzofuran-2-yl)ethyl]acetamide

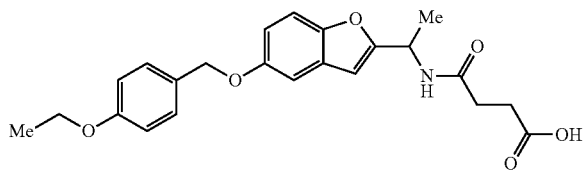 [SMILES: CCOc1ccc(COc2ccc3oc(C(C)NC(=O)CCC(=O)O)cc3c2)cc1]

To a solution of 2-(1-azidoethyl)-6-{2-[4-(methoxymethoxy)phenyl]ethyl}-1-benzofuran (263 mg, 0.748 mmol) obtained in Reference Example 219 in THF (10 mL) was added triphenylphosphine (236 mg, 0.898 mmol), and the mixture was stirred at 60° C. for 30 min. To the reaction mixture was added water (0.1 mL), and the mixture was stirred at 60° C. for 15 hr. The solvent was evaporated under reduced pressure and the obtained residue was purified by basic silica gel column chromatography (hexane:ethyl acetate=7:3 to 1:4) to give 1-(6-{2-[4-(methoxymethoxy)phenyl]ethyl}-1-benzofuran-2-yl)ethanamine. This was dissolved in pyridine (3 mL)-acetic anhydride (3 mL), and the solution was stirred at room temperature for 15 min. The solvent was evaporated under reduced pressure and the obtained residue was purified by silica gel column chromatography (hexane:ethyl acetate-1:1 to ethyl acetate) to give the title compound (219 mg, yield from 2-(1-azidoethyl)-6-{2-[4-(methoxymethoxy)phenyl]ethyl}-1-benzofuran 79%) as a white solid.

$^1$H NMR (CDCl$_3$) δ 1.56 (d, J=7.0 Hz, 3H), 2.02 (s, 3H), 2.86-2.92 (m, 2H), 2.96-3.02 (m, 2H), 3.48 (s, 3H), 5.15 (s, 2H), 5.29-5.39 (m, 1H), 5.84 (br, 1H), 6.52 (s, 1H), 6.95 (d, J=8.7 Hz, 2H), 7.04 (dd, J=7.9, 1.3 Hz, 1H), 7.10 (d, J=8.7 Hz, 2H), 7.25 (s, 1H), 7.41 (d, J=7.9 Hz, 1H).

Example 96

4-[(1-{5-[(4-ethoxybenzyl)oxy]-1-benzofuran-2-yl}ethyl)amino]-4-oxobutanoic acid

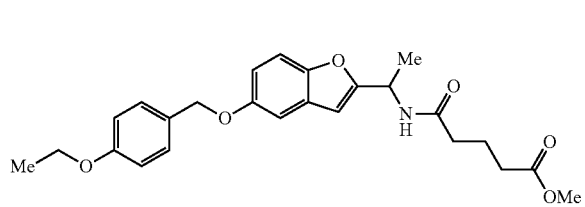 [SMILES: CCOc1ccc(COc2ccc3oc(C(C)NC(=O)CCCC(=O)OC)cc3c2)cc1]

To a solution of 1-{5-[(4-ethoxybenzyl)oxy]-1-benzofuran-2-yl}ethanamine (50.0 mg, 0.160 mmol) obtained in Reference Example 207 in THF (1.0 mL) was added dihydrofuran-2,5-dione (16.1 mg, 0.160 mmol), and the mixture was stirred at room temperature for 1 hr. The resulting solid was collected by filtration, and washed with diisopropyl ether to give the title compound (56.0 mg, yield 85%).

$^1$H NMR (CDCl$_3$) δ 1.32 (t, J=7.0 Hz, 3H), 1.42 (d, J=7.0 Hz, 3H), 2.34-2.46 (m, 4H), 4.02 (q, J=7.0 Hz, 2H), 5.01 (s, 2H), 5.02-5.14 (m, 1H), 6.61 (s, 1H), 6.85-6.95 (m, 3H), 7.15 (d, J=2.4 Hz, 1H), 7.36 (d, J=8.7 Hz, 2H), 7.41 (d, J=8.9 Hz, 1H), 8.41 (d, J=8.1 Hz, 1H).

Example 97 methyl 5-[(1-{5-[(4-ethoxybenzyl)oxy]-1-benzofuran-2-yl}ethyl)amino]-5-oxopentanoate Using 1-{5-[(4-ethoxybenzyl)oxy]-1-benzofuran-2-yl}ethanamine (100 mg, 0.320 mmol) obtained in Reference Example 207, DMF (5 mL), 5-methoxy-5-oxopentanoic acid (51.6 mg, 0.353 mmol), 1-hydroxybenzotriazole (48.7 mg, 0.353 mmol) and 1-ethyl-3-(3-dimethylaminopropyl)carbodiimide hydrochloride (67.4 mg, 0.353 mmol), an operation in the same manner as in Example 46 was performed to give the title, compound (37.7 mg, yield 27%) as a white solid.

$^1$H NMR (CDCl$_3$) δ 1.41 (t, J=7.0 Hz, 3H), 1.54 (d, J=7.0 Hz, 3H), 1.91-2.05 (m, 2H), 2.23-2.31 (m, 2H), 2.39 (t, J=7.1 Hz, 2H), 3.66 (s, 3H), 4.04 (q, J=7.0 Hz, 2H), 4.99 (s, 2H), 5.25-5.41 (m, 1H), 5.92 (d, J=8.3 Hz, 1H), 6.48 (s, 1H), 6.83-6.97 (m, 3H), 7.04 (d, J=2.4 Hz, 1H), 7.31 (d, J=9.0 Hz, 1H), 7.35 (d, J=8.9 Hz, 2H).

Example 98

5-[(1-{5-[(4-ethoxybenzyl)oxy]-1-benzofuran-2-yl}ethyl)amino]-5-oxopentanoic acid

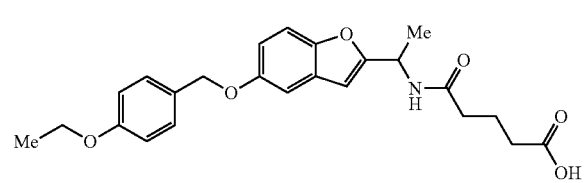 [SMILES: CCOc1ccc(COc2ccc3oc(C(C)NC(=O)CCCC(=O)O)cc3c2)cc1]

Using methyl 5-[(1-{5-[(4-ethoxybenzyl)oxy]-1-benzofuran-2-yl}ethyl)amino]-5-oxopentanoate (214 mg, 0.489 mmol) obtained in Example 97, methanol (2.0 mL) and 8N aqueous sodium hydroxide solution (0.10 mL, 0.82 mmol), an operation in the same manner as in Example 35 was performed to give the title compound (10.2 mg, yield 30%) as a white solid.

$^1$H NMR (CDCl$_3$) δ 1.32 (t, J=6.8 Hz, 3H), 1.42 (d, J=6.8 Hz, 3H), 1.60-1.74 (m, 2H), 1.88-1.95 (m, 2H), 2.11 (t, J=7.4 Hz, 2H), 4.02 (q, J=6.8 Hz, 2H), 5.01 (s, 2H), 5.03-5.16 (m, 1H), 6.59 (s, 1H), 6.83-6.90 (m, 1H), 6.92 (d, J=8.7 Hz, 2H), 7.16 (d, J=2.3 Hz, 1H), 7.36 (d, J=8.3 Hz, 2H), 7.40 (d, J=9.1 Hz, 1H).

Example 99

1-(1-{5-[(4-ethoxybenzyl)oxy]-1-benzofuran-2-yl}ethyl)-3-methylurea

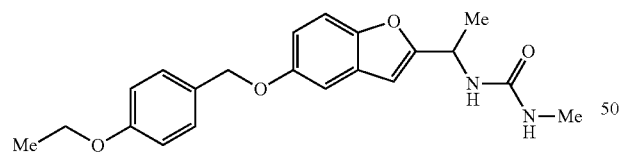

To a solution of 1-{5-[(4-ethoxybenzyl)oxy]-1-benzofuran-2-yl}ethanamine (50.0 mg, 0.160 mmol) obtained in Reference Example 20207 in pyridine (0.50 mL) was added methyl isocyanate (0.019 mL, 0.32 mmol), and the mixture was stirred at room temperature for 10 min. The reaction mixture was concentrated under reduced pressure, and the obtained solid was washed with ethyl acetate to give the title compound (22.4 mg, yield 38%).

$^1$H NMR (CDCl$_3$) δ 1.41 (t, J=7.0 Hz, 3H), 1.54 (d, J=6.8 Hz, 3H), 2.78 (d, J=4.9 Hz, 3H), 4.04 (q, J=7.0 Hz, 2H), 4.28-4.38 (m, 1H), 4.64 (d, J=8.1 Hz, 1H), 4.99 (s, 2H), 5.04-5.18 (m, 1H), 6.48 (s, 1H), 6.86-6.93 (m, 3H), 7.03 (d, J=2.6 Hz, 1H), 7.30 (d, J=9.0 Hz, 1H), 7.35 (d, J=8.8 Hz, 2H).

Example 100

1-(1-{(5-[(4-ethoxybenzyl)oxy]-1-benzofuran-2-yl}ethyl)urea

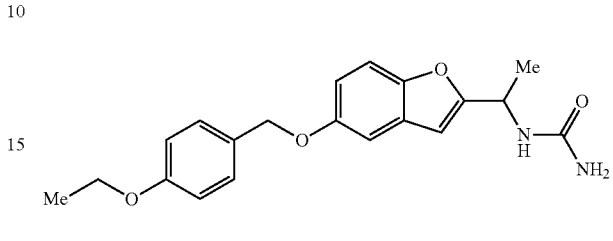

To a solution of 1-{5-[(4-ethoxybenzyl)oxy]-1-benzofuran-2-yl}ethanamine (50.0 mg, 0.160 mmol) obtained in Reference Example 207 in THF (1.0 mL) was added trichloroacetyl isocyanate (0.029 mL, 0.24 mmol) under ice-cooling, and the mixture was stirred for 5 min. 8M Ammonia methanol solution (0.80 L) was added thereto, and the mixture was stirred at room temperature overnight. The reaction mixture was concentrated under reduced pressure, and the residue was purified by silica gel column chromatography (hexane:ethyl acetate=3:2 to ethyl acetate), and triturated with diisopropyl ether to give the title compound (6.0 mg, yield 11%).

$^1$H NMR (CDCl$_3$) δ 1.33 (t, J=7.0 Hz, 3H), 1.41 (d, J=7.0 Hz, 3H), 4.02 (q, J=7.0 Hz, 2H), 4.82-4.97 (m, 1H), 5.00 (s, 2H), 5.52 (s, 2H), 6.48 (d, J=8.5 Hz, 1H), 6.55 (s, 1H), 6.82-6.96 (m, 3H), 7.15 (d, J=2.4 Hz, 1H), 7.30-7.45 (m, 3H).

Example 101

N-{1-[6-(benzyloxy)-1-benzofuran-2-yl]ethyl}acetamide

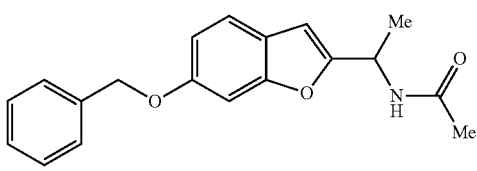 [SMILES: CC(=O)NC(C)c1cc2ccc(OCc3ccccc3)cc2o1]

To a solution of 1-[(6-(benzyloxy)-1-benzofuran-2-yl]ethanamine (14.4 g, 53.9 mmol) obtained in Reference Example 25 in methylene chloride (200 mL) were added pyridine (8.7 mL, 110 mmol) and acetic anhydride (6.1 mL, 65 mmol), and the mixture was stirred at room temperature for 1 hr. Water was added thereto, and the mixture was washed with 0.5N hydrochloric acid. The aqueous layer was extracted with methylene chloride. The combined organic layer was dried over anhydrous sodium sulfate. The solvent was evaporated to give the title compound (15.0 g, yield 90%) as a white solid.

¹H NMR (CDCl₃) δ 1.53 (d, J=6.6 Hz, 3H), 2.00 (s, 3H), 5.09 (s, 2H), 5.28-5.33 (m, 1H), 5.94 (d, J=7.8 Hz, 1H), 6.47 (s, 1H), 6.92 (dd, J=8.4, 2.1 Hz, 1H), 7.03 (d, J=2.1 Hz, 1H), 7.30-7.48 (m, 6H).

Example 102

N-{1-[5-(benzyloxy)-1,3-benzothiazol-2-yl]ethyl}acetamide

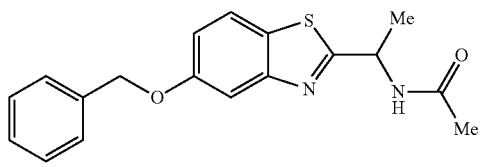 [SMILES: CC(=O)NC(C)c1nc2cc(OCc3ccccc3)ccc2s1]

To a solution of 2-ethylhexyl 3-([2-[(N-acetylalanyl)amino]-4-(benzyloxy)phenyl]sulfanyl)propanoate (812 mg, 1.54 mmol) obtained in Reference Example 78 in THF (7 mL) was added 28% sodium methoxide methanol solution (2 mL) under a nitrogen atmosphere, and the mixture was stirred at room temperature for 1 hr. The reaction mixture was ice-cooled, trifluoroacetic acid (4 mL) was slowly added, and the mixture was stirred under heating at 80° C. for 16 hr. The reaction mixture was diluted with ethyl acetate, and the mixture was washed with 10% aqueous potassium carbonate solution and saturated brine, and dried over anhydrous sodium sulfate. This solution was applied to basic silica gel column chromatography (ethyl acetate). The solvent was evaporated under reduced pressure, and the obtained residue was purified by silica gel column chromatography (hexane:ethyl acetate=1:1 to ethyl acetate), and triturated with diisopropyl ether to give the title compound (275 mg, yield 55%).

¹H NMR (CDCl₃) δ 1.65 (d, J=6.9 Hz, 3H), 2.06 (s, 3H), 5.13 (s, 2H), 5.45 (m, 1H), 6.51 (d, J=6.6 Hz, 1H), 7.09 (dd, J=2.4, 8.7 Hz, 1H), 7.30-7.46 (m, 5H), 7.52 (d, J=2.4 Hz, 1H), 7.68 (d, J=8.7 Hz, 1H).

Example 103

N-{1-[6-(benzyloxy)-1,3-benzothiazol-2-yl]ethyl}acetamide

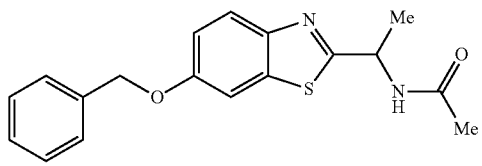 [SMILES: CC(=O)NC(C)c1nc2ccc(OCc3ccccc3)cc2s1]

Using 2-ethylhexyl 3-({2-[(N-acetylalanyl)amino]-5-(benzyloxy)phenyl}sulfanyl)propanoate (2.24 g, 4.24 mmol) obtained in Reference Example 135, a method in the same manner as in Example 102 was performed, and the obtained residue was triturated with diisopropyl ether to give the title compound (932 mg, yield 68%).

¹H NMR (CDCl₃) δ 1.65 (d, J=6.9 Hz, 3H), 2.08 (s, 3H), 5.12 (s, 2H), 5.44 (m, 1H), 6.38 (d, J=9.0 Hz, 1H), 7.14 (dd, J=2.7, 9.0 Hz, 1H), 7.31-7.46 (m, 6H), 7.85 (d, J=9.0 Hz, 1H).

Example 104 tert-butyl {1-[5-(benzyloxy)-1H-benzimidazol-2-yl]ethyl}carbamate

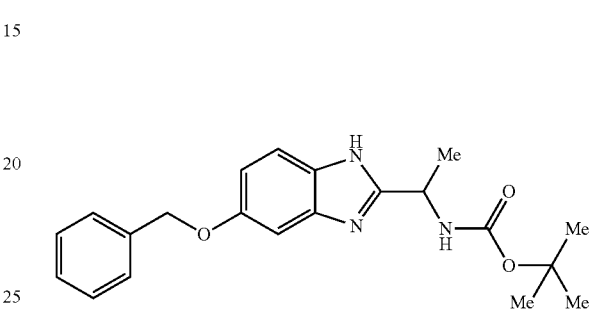

To a solution of N-(tert-butoxycarbonyl)-D,L-alanine (3.49 g, 18.4 mmol) and triethylamine (2.56 mL, 18.4 mmol) in THF (100 mL) was added 2-methylpropyl chlorocarbonate (2.39 mL, 18.4 mmol) under ice-cooling, and the mixture was stirred for 30 min. To this solution was added 4-(benzyloxy)-2-nitroaniline (3.00 g, 12.3 mmol), and the mixture was heated under reflux at 90° C. for 16 hr under a nitrogen atmosphere. After being allowed to cool to room temperature, the reaction mixture was diluted with ethyl acetate, and the mixture was washed with 0.5N hydrochloric acid, 10% aqueous potassium carbonate solution and saturated brine, and dried over anhydrous sodium sulfate. This solution was applied to basic silica gel column chromatography (ethyl acetate). The solvent was evaporated under reduced pressure to give tert-butyl (2-{[4-(benzyloxy)-2-nitrophenyl]amino}-1-methyl-2-oxoethyl)carbamate (5.10 g) as a crude product. To a solution (66 mL) of the obtained oil (5.10 g, 12.3 mmol) in 90% aqueous acetic acid was slowly added zinc powder (8.03 g, 123 mmol) under ice-cooling, and the mixture was stirred for 30 min. The reaction mixture was filtered through celite, and the filtrate was stirred under heating at 70° C. for 2 hr. The reaction mixture was allowed to cool to room temperature, and the solvent was evaporated under reduced pressure. The obtained residue was diluted with ethyl acetate, and the mixture was washed with 10% aqueous potassium carbonate solution and saturated brine, and dried over anhydrous sodium sulfate. The solution was applied to basic silica gel column chromatography (ethyl acetate), and the solvent was evaporated under reduced pressure. The obtained residue was purified by silica gel column chromatography (hexane:ethyl acetate=1:1 to ethyl acetate), and triturated with diisopropyl ether to give the title compound (663 mg, yield in 3 steps 15%).

¹H NMR (DMSO-d₆) δ 1.40 (s, 9H), 1.44 (d, J=6.9 Hz, 3H), 4.80 (m, 1H), 5.11 (s, 2H), 6.83 (dd, J=2.1, 8.7 Hz, 1H), 7.03 (br, 1H), 7.30-7.47 (nt, 7H), 11.95 (br, 1H).

Example 105

N-{1-[5-(benzyloxy)-1H-benzimidazol-2-yl]ethyl}acetamide

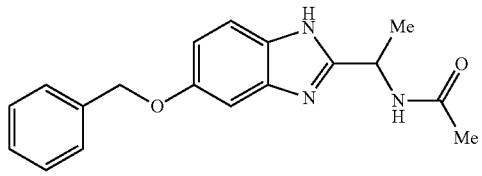 [SMILES: CC(=O)NC(C)c1nc2cc(OCc3ccccc3)ccc2[nH]1]

Using 1-[5-(benzyloxy)-1H-benzimidazol-2-yl]ethanamine dihydrochloride (400 mg, 1.09 mmol) obtained in Reference Example 202, the method in the same manner as in Reference Example 10 was performed, and the obtained residue was triturated with ethyl acetate and hexane to give the title compound (320 mg, yield 95%).

¹H NMR (CDCl₃) δ 1.68 (d, J=6.9 Hz, 3H), 2.00 (s, 3H), 5.08 (s, 2H), 5.23 (m, 1H), 6.69 (d, J=7.2 Hz, 1H), 6.95 (dd, J=2.4, 8.7 Hz, 1H), 7.06 (br, 1H), 7.27-7.44 (m, 6H), 10.40 (br, 1H).

Example 106

N-[(1S)-1-{5-[2-(4-ethoxyphenyl)ethyl]furo[2,3-b]pyridin-2-yl}ethyl]acetamide

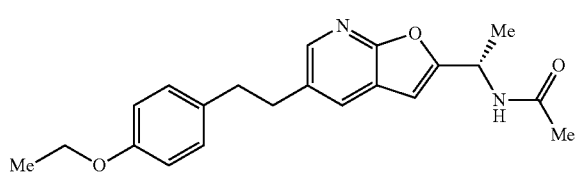 [SMILES: CCOc1ccc(CCc2cnc3oc([C@H](C)NC(C)=O)cc3c2)cc1]

To a solution of N-[(1S)-1-(5-bromofuro[2,3-b]pyridin-2-yl)ethyl]acetamide (200 mg, 0.706 mmol) obtained in Reference Example 222 in THF (3 mL) were added bisdiphenylphosphinoferrocenepalladium(II) chloride (28.8 mg, 0.0353 mmol) and 2-(4-ethoxyphenyl)ethylmagnesium bromide (THF solution 0.7 M, 3.03 mL, 2.12 mmol), and the mixture was heated under reflux for 30 min under a nitrogen atmosphere. The mixture was allowed to cool to room temperature, water was added thereto, and the mixture was extracted with ethyl acetate. The extract was washed with saturated brine, and dried over anhydrous sodium sulfate. The solution was applied to basic silica gel column chromatography (ethyl acetate), and the obtained residue was triturated with ethyl acetate to give the title compound (44.8 mg, yield 18%) as a white solid.

¹H NMR (CDCl₃) δ 1.40 (t, J=7.0 Hz, 3H), 1.56-1.58 (m, 3H), 2.01 (s, 3H), 2.87-2.99 (m, 4H), 3.99 (q, J=7.0 Hz, 2H), 5.30-5.35 (m, 1H), 5.89 (d, J=8.1 Hz, 1H), 6.49 (s, 1H), 6.79 (d, J=8.4 Hz, 2H), 7.02 (d, J=8.4 Hz, 2H), 7.56 (d, J=2.1 Hz, 1H), 8.03 (d, J=2.1 Hz, 1H)

Example 107

N-[(1S)-1-{6-[2-(4-ethoxyphenyl)ethyl]furo[3,2-b]pyridin-2-yl}ethyl]acetamide

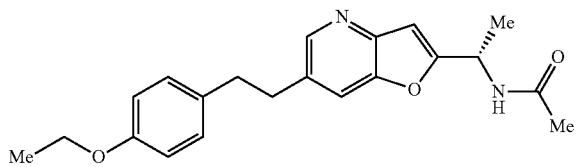 [SMILES: CCOc1ccc(CCc2cnc3cc([C@H](C)NC(C)=O)oc3c2)cc1]

Using N-[(1S)-1-(6-bromofuro[3,2-b]pyridin-2-yl)ethyl]acetamide (237 mg, 0.837 mmol) obtained in Reference Example 225, bisdiphenylphosphinoferrocenepalladium(II) chloride (34.2 mg, 0.0419 mmol) and 2-(4-ethoxyphenyl)ethylmagnesium bromide (THF solution 0.7 M, 3.59 mL, 2.51 mmol), a method in the same manner as in Example 106 was performed, and the obtained residue was triturated with diisopropyl ether to give the title compound (77.0 mg, yield 26%) as a white solid.

¹H NMR (CDCl₃) δ 1.40 (t, J=7.0 Hz, 3H), 1.58 (d, J=7.2 Hz, 3H), 2.04 (s, 3H), 2.87-3.03 (m, 4H), 3.99 (q, J=7.0 Hz, 2H), 5.36-5.41 (m, 1H), 5.80 (d, J=8.1 Hz, 1H), 6.71 (m, 1H), 6.81 (d, J=8.4 Hz, 2H), 7.04 (d, J=8.4 Hz, 2H), 7.42 (s, 1H), 8.29 (d, J=1.5 Hz, 1H)

Example 108

N-[1-(5-{[4-(cyclopropylmethoxy)benzyl]oxy}-1-benzofuran-2-yl)ethyl]acetamide

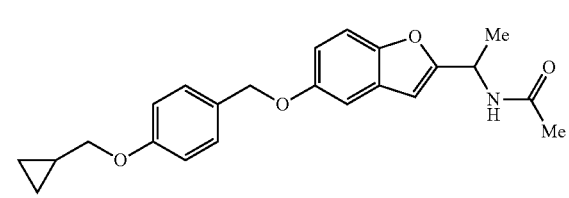 [SMILES: CC(=O)NC(C)c1cc2cc(OCc3ccc(OCC4CC4)cc3)ccc2o1]

To a solution of [4-(cyclopropylmethoxy)phenyl]methanol (200 mg, 1.12 mmol) and DMF (1 drop) in THF (2 mL) was added thionyl chloride (0.098 mL, 1.35 mmol), and the mixture was stirred at room temperature for 30 min and concentrated under reduced pressure. To the obtained residue were added DMF (4 mL), N-[1-(5-hydroxy-1-benzofuran-2-yl)ethyl]acetamide (224 mg, 1.02 mmol) obtained in Reference Example 38 and potassium carbonate (211 mg, 1.53 mmol), and the mixture was stirred overnight at 70° C. Water was added thereto and the mixture was extracted with ethyl acetate. The extract was washed with 10% aqueous potassium carbonate solution and saturated brine, and dried over anhydrous sodium sulfate. The solution was applied to basic silica gel column chromatography (ethyl acetate). The solvent was evaporated, and the residue was triturated with a small amount of ethyl acetate to give the title compound (178 mg, yield 46%).

¹H NMR (CDCl₃) δ0.32-0.37 (m, 2H), 0.62-0.68 (m, 2H), 1.23-1.28 (m, 1H), 1.55 (d, J=8.4 Hz, 3H), 2.02 (s, 3H), 3.80 (d, J=6.9 Hz, 2H), 4.99 (s, 2H), 5.30-5.35 (m, 1H), 5.77 (d, J=8.7 Hz, 1H), 6.48 (s, 1H), 6.89-6.93 (m, 3H), 7.02 (d, J=2.4 Hz, 1H), 7.29-7.35 (m, 3H).
  elemental analysis value as C₂₃H₂₅NO₄
  Calculated: C, 72.80; H, 6.64; N, 3.69.
  experiment value: C, 72.41; H, 6.75; N, 3.70.

Example 109

N-[1-(5-{[2-chloro-4-(cyclopropylmethoxy)benzyl]oxy}-1-benzofuran-2-yl)ethyl]acetamide

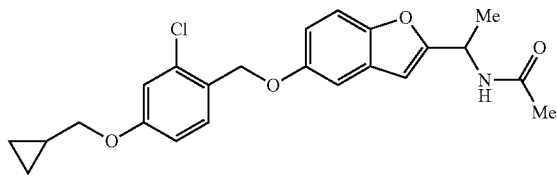 [SMILES: CC(=O)NC(C)c1cc2cc(OCc3ccc(OCC4CC4)cc3Cl)ccc2o1]

To a solution of [2-chloro-4-(cyclopropylmethoxy)phenyl]methanol (216 mg, 1.02 mmol) obtained in Reference Example 227 and DMF (1 drop) in THF (2 mL) was added thionyl chloride (0.089 mL, 1.22 mmol), and the mixture was stirred at room temperature for 30 min and concentrated under reduced pressure. To the obtained residue were added DMF (2 mL), N-[1-(5-hydroxy-1-benzofuran-2-yl)ethyl]acetamide (202 mg, 0.923 mmol) obtained in Reference Example 38 and potassium carbonate (191 mg, 1.38 mmol), and the mixture was stirred at 70° C. overnight. Water was added thereto and the mixture was extracted with ethyl acetate. The extract was washed with 10% aqueous potassium carbonate solution and saturated brine, and dried over anhydrous sodium sulfate. The solution was applied to basic silica gel column chromatography (ethyl acetate), and the obtained residue was triturated with a small amount of ethyl acetate to give the title compound (120 mg, yield 31%).
  ¹H NMR (CDCl₃) δ0.32-0.37 (m, 2H), 0.62-0.67 (m, 2H), 1.24-1.28 (m, 1H), 1.55 (d, J=6.9 Hz, 3H), 2.02 (s, 3H), 3.78 (d, J=6.9 Hz, 2H), 5.10 (s, 2H), 5.30-5.35 (m, 1H), 5.76 (d, J=8.7 Hz, 1H), 6.49 (s, 1H), 6.81 (dd, J=8.4, 2.4 Hz, 1H), 6.92-6.96 (m, 2H), 7.04 (d, J=2.4 Hz, 1H), 7.32 (d, J=8.7 Hz, 1H), 7.41 (d, J=8.4 Hz, 1H).
  elemental analysis value as C₂₃H₂₄NO₄Cl
  Calculated: C, 66.74; H, 5.84; N, 3.38.
  experiment value: C, 66.36; H, 5.84; N, 3.36.

Example 110

N-[1-(5-{[4-(cyclopropylmethoxy)-2-fluorobenzyl]oxy}-1-benzofuran-2-yl)ethyl]acetamide

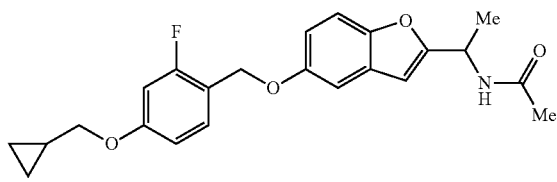 [SMILES: CC(=O)NC(C)c1cc2cc(OCc3ccc(OCC4CC4)cc3F)ccc2o1]

To a solution of [4-(cyclopropylmethoxy)-2-fluorophenyl]methanol (269 mg, 1.37 mmol) obtained in Reference Example 230 and DMF (1 drop) in THF (2 mL) was added thionyl chloride (0.120 mL, 1.64 mmol), and the mixture was stirred at room temperature for 30 min and concentrated under reduced pressure. To the obtained residue were added DMF (2 mL), N-[1-(5-hydroxy-1-benzofuran-2-yl)ethyl]acetamide (200 mg, 0.912 mmol) obtained in Reference Example 38 and potassium carbonate (252 mg, 1.82 mmol), and the mixture was stirred at 70° C. overnight. Water was added thereto and the mixture was extracted with ethyl acetate. The extract was washed with 10% aqueous potassium carbonate solution and saturated brine, and dried over anhydrous sodium sulfate. The residue was applied to basic silica gel column chromatography (ethyl acetate), and triturated with diisopropyl ether to give the title compound (330 mg, yield 92%).
  ¹H NMR (CDCl₃) δ0.32-0.37 (m, 2H), 0.62-0.68 (m, 2H), 1.24-1.29 (m, 1H), 1.55 (d, J=7.2 Hz, 3H), 2.02 (s, 3H), 3.78 (d, J=6.9 Hz, 2H), 5.05 (s, 2H), 5.30-5.34 (m, 1H), 5.78 (d, J=8.4 Hz, 1H), 6.48 (d, J=0.6 Hz, 1H), 6.61-6.71 (m, 2H), 6.91 (dd, J=9.0, 2.7 Hz, 1H), 7.05 (d, J=2.7 Hz, 1H), 7.29-7.38 (m, 2H).
  elemental analysis value for C₂₃H₂₄NO₄F
  Calculated: C, 69.51; H, 6.09; N, 3.52.
  Found: C, 69.44; H, 6.16; N, 3.53.

Example 111

1:1 mixture of N-{(1R)-1-[(2R)-6-{[4-(cyclopropylmethoxy)phenyl]ethynyl}-2,3-dihydro-1-benzofuran-2-yl]ethyl}acetamide and N-{(1S)-1-[(2S)-6-[([4-(cyclopropylmethoxy)phenyl]ethynyl]-2,3-dihydro-1-benzofuran-2-yl]ethyl}acetamide

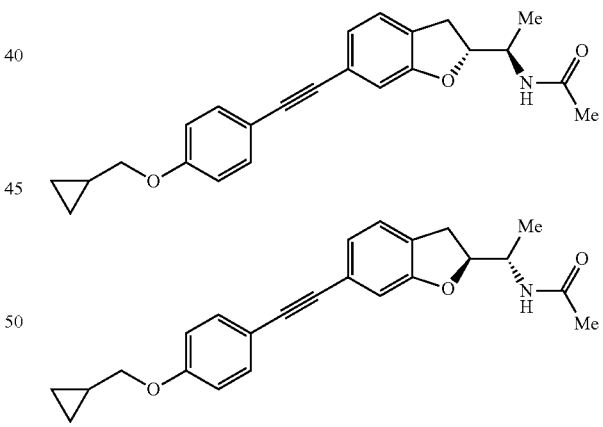

A solution of 1-(cyclopropylmethoxy)-4-ethynylbenzene (292 mg, 1.70 mmol) obtained in Reference Example 233, a 1:1 mixture (less polar mixture) (500 mg, 1.42 mmol) (obtained in Reference Example 229) of (2R)-2-[(1R)-1-(acetylamino)ethyl]-2,3-dihydro-1-benzofuran-6-yl trifluoromethanesulfonate and (2S)-2-[(1S)-1-(acetylamino)ethyl]-2,3-dihydro-1-benzofuran-6-yl trifluoromethanesulfonate, and copper(I) iodide (27.0 mg, 0.142 mmol) in a mixed solvent of DMF-triethylamine (6 ml-1.5 ml) was deaerated, bis(triphenylphosphine)palladium(II) chloride (50.0 mg, 0.071 mmol) was added thereto, and the mixture was stirred under heating at 80° C. for 16 hr under a nitrogen atmosphere. The reaction mixture was diluted with ethyl acetate, and the mixture was washed with water and saturated brine, and dried over anhydrous sodium sulfate. The solution was purified by basic silica gel column chromatography (ethyl acetate), and the solvent was evaporated under reduced pressure. The obtained residue was triturated with ethyl acetate and diisopropyl ether (1:2) to give the title compound (247 mg, yield 47%).

$^1$H NMR (CDCl$_3$) δ 0.33-0.38 (m, 2H), 0.63-0.69 (m, 2H), 1.24-1.30 (m, 1H), 1.29 (d, J=8.1 Hz, 3H), 1.90 (s, 3H), 2.98-3.06 (m, 1H), 3.17-3.25 (m, 1H), 3.81 (d, J=6.9 Hz, 2H), 4.30-4.37 (m, 1H), 4.75-4.82 (m, 1H), 5.44 (d, J=8.7 Hz, 1H), 6.84-6.89 (m, 3H), 7.00-7.10 (m, 2H), 7.40-7.44 (m, 2H).

elemental analysis value as C$_{24}$H$_{25}$NO$_3$·0.1H$_2$O
Calculated: C, 76.41; H, 6.73; N, 3.71.
experiment value: C, 76.13; H, 6.70; N, 3.69.

Example 112

1:1 mixture of N-{(1S)-1-[(2R)-6-{[4-(cyclopropylmethoxy)phenyl]ethynyl}-2,3-dihydro-1-benzofuran-2-yl]ethyl}acetamide and N-{(1R)-1-[(2S)-6-{[4-(cyclopropylmethoxy)phenyl]ethynyl}-2,3-dihydro-1-benzofuran-2-yl]ethyl}acetamide

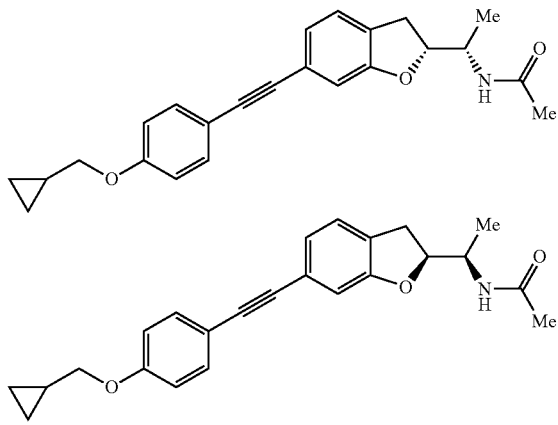

A solution of 1-(cyclopropylmethoxy)-4-ethynylbenzene (292 mg, 1.70 mmol) obtained in Reference Example 233, a 1:1 mixture (more polar mixture) (500 mg, 1.42 mmol) (obtained in Reference Example 229) of (2R)-2-[(1S)-1-(acetylamino)ethyl]-2,3-dihydro-1-benzofuran-6-yl trifluoromethanesulfonate and (2S)-2-[(1R)-1-(acetylamino)ethyl]-2,3-dihydro-1-benzofuran-6-yl trifluoromethanesulfonate, and copper(I) iodide (27.0 mg, 0.142 mmol) in a mixed solvent of DMF-triethylamine (6 ml-1.5 mL) was deaerated, bis(triphenylphosphine)palladium(II) chloride (50.0 mg, 0.071 mmol) was added thereto, and the mixture was stirred under heating at 80° C. for 16 hr under a nitrogen atmosphere. The reaction mixture was diluted with ethyl acetate, and the mixture was washed with water and saturated brine, and dried over anhydrous sodium sulfate. The solution was purified by basic silica gel column chromatography (ethyl acetate), and the solvent was evaporated under reduced pressure. The obtained residue was triturated with ethyl acetate and diisopropyl ether (1:2) to give the title compound (197 mg, yield 37%).

$^1$H NMR (CDCl$_3$) δ 0.33-0.38 (m, 2H), 0.63-0.69 (m, 2H), 1.09 (d, J=6.6 Hz, 3H), 1.28 (m, 1H), 2.02 (s, 3H), 2.91-2.99 (m, 1H), 3.28-3.37 (m, 1H), 3.81 (d, J=6.9 Hz, 2H), 4.19-4.24 (m, 1H), 4.84-4.90 (m, 1H), 5.74 (d, J=8.7 Hz, 1H), 6.84-6.87 (m, 3H), 6.99-7.11 (m, 2H), 7.43 (d, J=8.7 Hz, 2H).

elemental analysis value as C$_{24}$H$_{25}$NO$_3$
Calculated: C, 76.77; H, 6.71; N, 3.73.
experiment value: C, 76.82; H, 6.71; N, 3.65.

Example 113

N-[1-(5-{[3-chloro-4-(cyclopropylmethoxy)benzyl]oxy}-1-benzofuran-2-yl)ethyl]acetamide

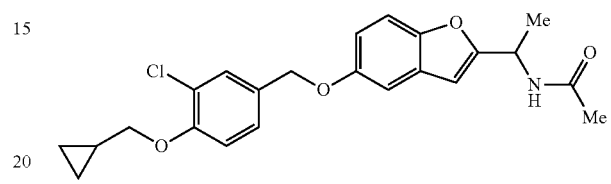

To a solution of [3-chloro-4-(cyclopropylmethoxy)phenyl]methanol (291 mg, 1.37 mmol) obtained in Reference Example 234 and DMF (1 drop) in THF (2 mL) was added thionyl chloride (0.120 mL, 1.64 mmol), and the mixture was stirred at room temperature for 30 min and concentrated under reduced pressure. To the obtained residue were added DMF (2 mL), N-[1-(5-hydroxy-1-benzofuran-2-yl)ethyl]acetamide (200 mg, 0.912 mmol) obtained in Reference Example 38 and potassium carbonate (252 mg, 1.82 mmol), and the mixture was stirred at 70° C. overnight. Water was added thereto and the mixture was extracted with ethyl acetate. The extract was washed with 10% aqueous potassium carbonate solution and saturated brine, and dried over anhydrous sodium sulfate. The solution was applied to basic silica gel column chromatography (ethyl acetate), and the residue was triturated with ethyl acetate and diisopropyl ether (1:1) to give the title compound (284 mg, yield 75%).

$^1$H NMR (CDCl$_3$) δ 0.36-0.41 (m, 2H), 0.62-0.67 (m, 2H), 1.26-1.34 (m, 1H), 1.55 (d, J=6.9 Hz, 3H), 2.02 (s, 3H), 3.88 (d, J=6.6 Hz, 2H), 4.97 (s, 2H), 5.30-5.35 (m, 1H), 5.78 (d, J=8.1 Hz, 1H), 6.49 (s, 1H), 6.89-6.92 (m, 2H), 7.01 (d, J=2.1 Hz, 1H), 7.23-7.26 (m, 1H), 7.31 (d, J=9.0 Hz, 1H), 7.45 (d, J=2.1 Hz, 1H).

elemental analysis value as C$_{23}$H$_{24}$NO$_4$Cl
Calculated: C, 66.74; H, 5.84; N, 3.38.
experiment value: C, 69.64; H, 5.83; N, 3.28.

Example 114

N-[(1R)-1-{(2R)-6-[(4-propoxyphenyl)ethynyl]-2,3-dihydro-1-benzofuran-2-yl}ethyl]acetamide

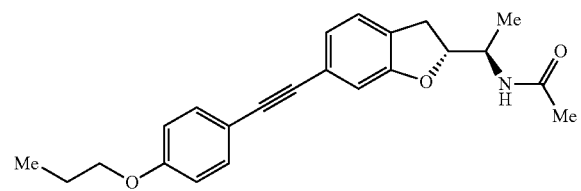 [SMILES: CCCOc1ccc(C#Cc2ccc3c(c2)O[C@@H]([C@@H](C)NC(C)=O)C3)cc1]

Using 1-ethynyl-4-propoxybenzene (43.5 mg, 0.272 mmol), (2R)-2-[(1R)-1-(acetylamino)ethyl]-2,3-dihydro-1-benzofuran-6-yl trifluoromethanesulfonate (retention time shorter) (80.0 mg, 0.226 mmol) obtained in Reference Example 231, copper(I) iodide (4.3 mg, 0.023 mmol), (triphenylphosphine)palladium(II) chloride (7.9 mg, 0.011 mmol) and DMF-triethylamine (2 mL-0.5 mL), an operation in the same manner as in Example 111 was performed, and the obtained residue was triturated with hexane and diisopropyl ether (1:1) to give the title compound (40.2 mg, yield 49%).

$^1$H NMR (CDCl$_3$) δ 1.04 (t, J=7.5 Hz, 3H), 1.34 (d, J=6.9 Hz, 3H), 1.76-1.88 (m, 2H), 1.90 (s, 3H), 2.98-3.06 (m, 1H), 3.17-3.26 (m, 1H), 3.93 (t, J=6.6 Hz, 2H), 4.31-4.37 (m, 1H), 4.75-4.82 (m, 1H), 5.45 (d, J=8.7 Hz, 1H), 6.83-6.90 (m, 3H), 7.00-7.10 (m, 2H), 7.41-7.46 (m, 2H).

Example 115

N-[(1S)-1-{(2S)-6-[(4-propoxyphenyl)ethynyl]-2,3-dihydro-1-benzofuran-2-yl}ethyl]acetamide

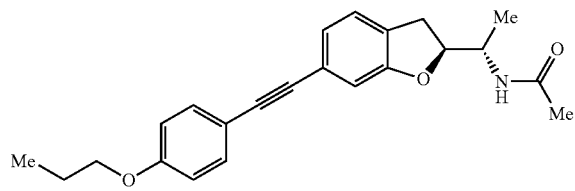 [SMILES: CCCOc1ccc(C#Cc2ccc3c(c2)O[C@H]([C@H](C)NC(C)=O)C3)cc1]

Using 1-ethynyl-4-propoxybenzene (43.5 mg, 0.272 mmol), (2S)-2-[(1S)-1-(acetylamino)ethyl]-2,3-dihydro-1-benzofuran-6-yl trifluoromethanesulfonate (retention time longer) (80.0 mg, 0.226 mmol) obtained in Reference Example 231, copper(I) iodide (4.3 mg, 0.023 mmol), (triphenylphosphine)palladium(II) chloride (7.9 mg, 0.011 mmol) and DMF-triethylamine (2 mL-0.5 mL), an operation in the same manner as in Example 111 was performed, and the obtained residue was triturated with hexane and diisopropyl ether (1:1) to give the title compound (52.8 mg, yield 64%).

$^1$H NMR (CDCl$_3$) δ 1.04 (t, J=7.5 Hz, 3H), 1.34 (d, J=6.9 Hz, 3H), 1.76-1.88 (m, 2H), 1.90 (s, 3H), 2.97-3.06 (m, 1H), 3.17-3.26 (m, 1H), 3.93 (t, J=6.6 Hz, 2H), 4.31-4.37 (m, 1H), 4.75-4.82 (m, 1H), 5.45 (d, J=9.3 Hz, 1H), 6.83-6.90 (m, 3H), 7.00-7.10 (m, 2H), 7.41-7.46 (m, 2H).

Example 116

N-[1-(5-{[4-(cyclopropylmethoxy)-2-fluorobenzyl]oxy}-1-benzofuran-2-yl)ethyl]acetamide (two kinds)

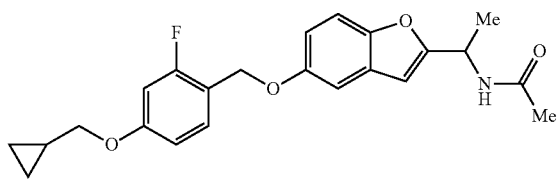 [SMILES: CC(=O)NC(C)c1cc2cc(OCc3ccc(OCC4CC4)cc3F)ccc2o1]

N-[1-(5-{[4-(cyclopropylmethoxy)-2-fluorobenzyl]oxy}-1-benzofuran-2-yl)ethyl]acetamide (268 mg) obtained in Example 110 was optically resolved by high performance liquid chromatography (HPLC) under the following conditions to give two kinds of optically active forms of "retention time longer (120 mg)" and "retention time shorter (129 mg)".

<Preparative HPLC Conditions>
    column: CHIRALPAK AD (50 mmID×500 mmL)
    mobile phase: hexane:ethanol=1:1
    flow rate: 60 mL/min
    column temperature: 30° C.
    detection: UV 220 nm
    compound injection volume: 30 mg/60 mL <HPLC Analysis Conditions>
    column: CHIRALPAK AD (4.6 mmID×250 mL)
    mobile phase: hexane:ethanol=17:3
    flow rate: 1.0 ml/min
    column temperature: 30° C.
    detection: UV 220 nm
    retention time of "retention time longer": 13.9 min
    retention time of "retention time shorter": 9.9 min Example 117

1:1 mixture of N-{(1R)-1-[(2R)-6-{[4-(benzyloxy)phenyl]ethynyl}-2,3-dihydro-1-benzofuran-2-yl]ethyl}acetamide and N-{(1S)-1-[(2S)-6-{[4-(benzyloxy)phenyl]ethynyl}-2,3-dihydro-1-benzofuran-2-yl]ethyl}acetamide

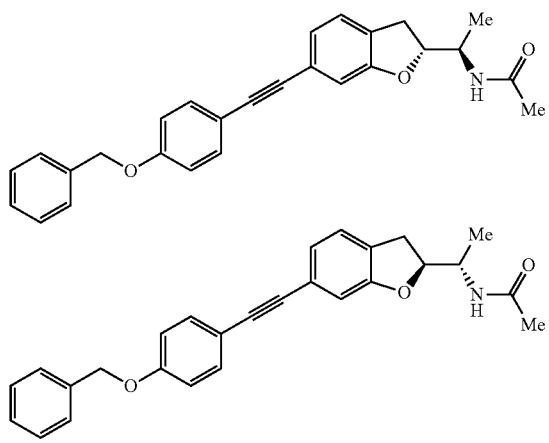

To a solution of 1-(benzyloxy)-4-ethynylbenzene (283 mg, 1.36 mmol), a 1:1 mixture (less polar mixture) (400 mg, 1.13 mmol) (obtained in Reference Example 229) of (2R)-2-[(1R)-1-(acetylamino)ethyl]-2,3-dihydro-1-benzofuran-6-yl trifluoromethanesulfonate and (2S)-2-[(1S)-1-(acetylamino)ethyl]-2,3-dihydro-1-benzofuran-6-yl trifluoromethanesulfonate, and copper(I) iodide (21.6 mg, 0.113 mmol) in DMF-triethylamine (4 mL-1 mL) was added (triphenylphosphine)palladium(II) chloride (39.7 mg, 0.057 mmol), and the mixture was deaerated and stirred under heating at 80° C. for 16 hr under a nitrogen atmosphere. The reaction mixture was diluted with ethyl acetate, and the mixture was washed with water and saturated brine, and dried over anhydrous sodium sulfate. The solution was purified by basic silica gel column chromatography (ethyl acetate), and the solvent was evaporated under reduced pressure. The residue was triturated with ethyl acetate to give the title compound (218 mg, yield 47%).

$^1$H NMR (CDCl$_3$) δ 1.34 (d, J=6.6 Hz, 3H), 1.90 (s, 3H), 2.98-3.06 (m, 1H), 3.17-3.26 (m, 1H), 4.31-4.36 (m, 1H), 4.75-4.82 (m, 1H), 5.08 (s, 2H), 5.45 (d, J=8.4 Hz, 1H), 6.90-6.95 (m, 3H), 7.00-7.10 (m, 2H), 7.33-7.46 (m, 7H).

Example 118

1:1 mixture of N-{(1S)-1-[(2R)-6-{[4-(benzyloxy)phenyl]ethynyl}-2,3-dihydro-1-benzofuran-2-yl]ethyl}acetamide and N-{(1R)-1-[(2S)-6-{[4-(benzyloxy)phenyl]ethynyl}-2,3-dihydro-1-benzofuran-2-yl]ethyl}acetamide

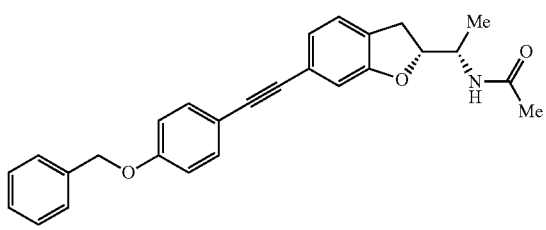

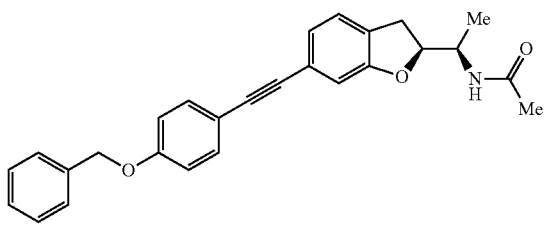

To a solution of 1-(benzyloxy)-4-ethynylbenzene (377 mg, 1.81 mmol), a 1:1 mixture (more polar mixture) (533 mg, 1.51 mmol) (obtained in Reference Example 229) of (2R)-2-[(1S)-1-(acetylamino)ethyl]-2,3-dihydro-1-benzofuran-6-yl trifluoromethanesulfonate and (2S)-2-[(1R)-1-(acetylamino)ethyl]-2,3-dihydro-1-benzofuran-6-yl trifluoromethanesulfonate, and copper(I) iodide (28.7 mg, 0.151 mmol) in DMF-triethylamine (6 mL-1.5 mL) was added (triphenylphosphine)palladium(II) chloride (52.9 mg, 0.075 mmol), and the mixture was deaerated and stirred under heating at 80° C. for 16 hr under a nitrogen atmosphere. The reaction mixture was diluted with ethyl acetate, and the mixture was washed with water and saturated brine, and dried over anhydrous sodium sulfate. The solution was purified by basic silica gel column chromatography (ethyl acetate), and the solvent was evaporated under reduced pressure, and the residue was triturated with ethyl acetate to give the title compound (331 mg, yield 53%).

$^1$H NMR (CDCl$_3$) δ 1.09 (d, J=6.9 Hz, 3H), 2.02 (s, 3H), 2.92-3.00 (m, 1H), 3.28-3.67 (m, 1H), 4.18-4.24 (m, 1H), 4.84-4.90 (m, 1H), 5.08 (s, 2H), 5.73 (br, 1H), 6.88 (s, 1H), 6.94 (d, J=8.7 Hz, 2H), 7.00-7.11 (m, 2H), 7.32-7.46 (m, 7H).

Example 119

1:1 mixture of N-[(1R)-1-{(2R)-6-[2-(4-hydroxyphenyl)ethyl]-2,3-dihydro-1-benzofuran-2-yl}ethyl]acetamide and N-[(1S)-1-{(2S)-6-[2-(4-hydroxyphenyl)ethyl]-2,3-dihydro-1-benzofuran-2-yl}ethyl]acetamide

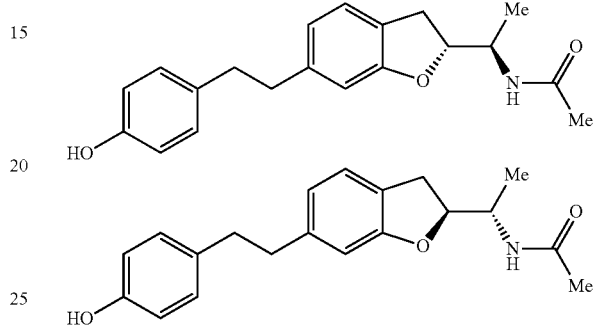

A solution of a 1:1 mixture (125 mg, 0.304 mmol) (obtained in Example 117) of N-{(1R)-1-[(2R)-6-{[4-(benzyloxy)phenyl]ethynyl}-2,3-dihydro-1-benzofuran-2-yl]ethyl}acetamide and N-{(1S)-1-[(2S)-6-{[4-(benzyloxy)phenyl]ethynyl}-2,3-dihydro-1-benzofuran-2-yl]ethyl}acetamide, and 10% palladium carbon (50% water-containing product, 300 mg) in THF (3 mL) was stirred for 3 hr under a hydrogen atmosphere (normal pressure). After filtration, the filtrate was concentrated under reduced pressure, and the residue was triturated with diisopropyl ether to give the title compound (90.0 mg, yield 91%). This was used for the next reaction without purification.

Example 120

1:1 mixture of N-[(1S)-1-{(2R)-6-[2-(4-hydroxyphenyl)ethyl]-2,3-dihydro-1-benzofuran-2-yl}ethyl]acetamide and N-[(1R)-1-{(2S)-6-[2-(4-hydroxyphenyl)ethyl]-2,3-dihydro-1-benzofuran-2-yl}ethyl]acetamide

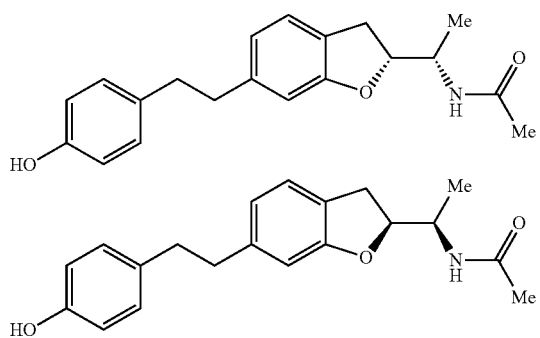

A solution of a 1:1 mixture (323 mg, 0.785 mmol) (obtained in Example 118) of N-{(1S)-1-[(2R)-6-{[4-(benzyloxy)phenyl]ethynyl}-2,3-dihydro-1-benzofuran-2-yl]

ethyl}acetamide and N-{(1R)-1-[(2S)-6-{[4-(benzyloxy)phenyl]ethynyl}-2,3-dihydro-1-benzofuran-2-yl]ethyl}acetamide, and 10% palladium carbon (50% water-containing product, 1.00 g) in THF (8 mL) was stirred for 2 hr under a hydrogen atmosphere (normal pressure). After filtration, the filtrate was concentrated under reduced pressure, and the residue was triturated with diisopropyl ether to give the title compound (212 mg, yield 83%). This was used for the next reaction without purification.

Example 121

1:1 mixture of N-{(1R)-1-[(2R)-6-{2-[4-(cyclopropylmethoxy)phenyl]ethyl}-2,3-dihydro-1-benzofuran-2-yl]ethyl}acetamide and N-{(1S)-1-[(2S)-6-{2-[4-(cyclopropylmethoxy)phenyl]ethyl}-2,3-dihydro-1-benzofuran-2-yl]ethyl}acetamide

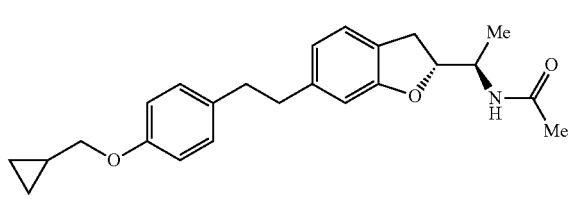

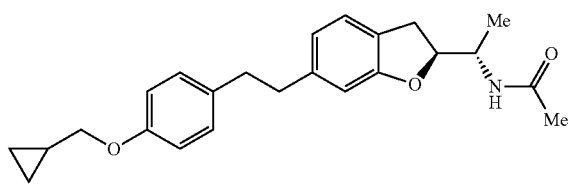

A solution of a 1:1 mixture (85.2 mg, 0.262 mmol) (obtained in Example 119) of N-[(1R)-1-{(2R)-6-[2-(4-hydroxyphenyl)ethyl]-2,3-dihydro-1-benzofuran-2-yl}ethyl]acetamide and N-[(1S)-1-{(2S)-6-[2-(4-hydroxyphenyl)ethyl]-2,3-dihydro-1-benzofuran-2-yl}ethyl]acetamide, bromomethylcyclopropane (0.051 mL, 0.524 mmol) and potassium carbonate (109 mg, 0.785 mmol) in ethanol (1.5 mL) was stirred under heating at 60° C. for 16 hr. The reaction mixture was diluted with ethyl acetate, and the mixture was washed with 10% aqueous potassium carbonate solution and saturated brine, and dried over anhydrous sodium sulfate. The solution was applied to basic silica gel column chromatography (ethyl acetate). The solvent was evaporated under reduced pressure, and the residue was triturated with a small amount of diisopropyl ether and hexane to give the title compound (86.3 mg, yield 87%).

$^1$H NMR (CDCl$_3$) δ0.31-0.36 (m, 2H), 0.61-0.67 (m, 2H), 1.27-1.28 (m, 1H), 1.33 (d, J=6.9 Hz, 3H), 1.90 (s, 3H), 2.82 (s-like, 4H), 2.92-3.00 (m, 1H), 3.11-3.19 (m, 1H), 3.77 (d, J=6.9 Hz, 2H), 4.29-4.35 (m, 1H), 4.71-4.77 (m, 1H), 5.49 (d, J=9.3 Hz, 1H), 6.62 (s, 1H), 6.66 (d, J=7.8 Hz, 1H), 6.81 (d, J=8.4 Hz, 2H), 7.02 (d, J=7.5 Hz, 1H), 7.07 (d, J=8.4 Hz, 2H).

elemental analysis value as C$_{24}$H$_{29}$NO$_3$
Calculated: C, 75.96; H, 7.70; N, 3.69.
experiment value: C, 75.92; H, 7.64; N, 3.71.

Example 122

1:1 mixture of N-{(1S)-1-[(2R)-6-{2-[4-(cyclopropylmethoxy)phenyl]ethyl}-2,3-dihydro-1-benzofuran-2-yl]ethyl}acetamide and N-{(1R)-1-[(2S)-6-{2-[4-(cyclopropylmethoxy)phenyl]ethyl}-2,3-dihydro-1-benzofuran-2-yl]ethyl}acetamide

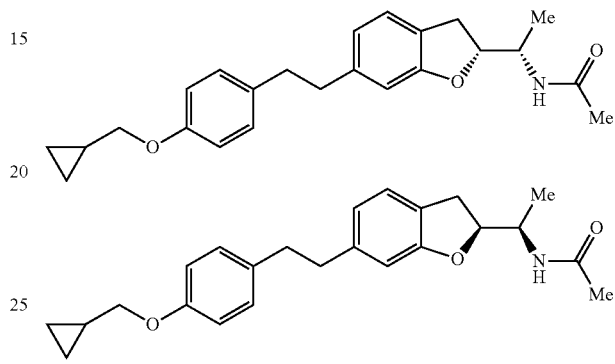

A solution of a 1:1 mixture (200 mg, 0.615 mmol) (obtained in Example 120) of N-[(1S)-1-{(2R)-6-[2-(4-hydroxyphenyl)ethyl]-2,3-dihydro-1-benzofuran-2-yl}ethyl]acetamide and N-[(1R)-1-{(2S)-6-[2-(4-hydroxyphenyl)ethyl]-2,3-dihydro-1-benzofuran-2-yl}ethyl]acetamide, bromomethylcyclopropane (0.119 mL, 1.23 mmol) and potassium carbonate (255 mg, 1.84 mmol) in ethanol (3 mL) was stirred under heating at 60° C. for 16 hr. The reaction mixture was diluted with ethyl acetate, and the mixture was washed with 10% aqueous potassium carbonate solution and saturated brine, and dried over anhydrous sodium sulfate. The solution was applied to basic silica gel column chromatography (ethyl acetate). The solvent was evaporated under reduced pressure, and the residue was triturated with diisopropyl ether to give the title compound (201 mg, yield 86%).

$^1$H NMR (CDCl$_3$) δ0.33-0.36 (m, 2H), 0.60-0.67 (m, 2H), 1.10 (d, J=6.6 Hz, 3H), 1.24-1.29 (m, 1H), 2.01 (s, 3H), 2.82 (s-like, 4H), 2.88-2.95 (m, 1H), 3.23-3.31 (m, 1H), 3.77 (d, J=6.6 Hz, 2H), 4.17-4.24 (m, 1H), 4.79-4.86 (m, 1H), 5.75 (d, J=9.0 Hz, 1H), 6.57 (s, 1H), 6.65 (dd, J=7.5, 1.5 Hz, 1H), 6.81 (d, J=8.7 Hz, 2H), 7.01-7.07 (m, 3H).

elemental analysis value for C$_{24}$H$_{29}$NO$_3$
Calculated: C, 75.96; H, 7.70; N, 3.69.
experiment value: C, 76.02; H, 7.72; N, 3.68.

Example 123

N-(1-{6-[2-(4-ethoxyphenyl)ethyl]furo[2,3-b]pyridin-2-yl}ethyl)acetamide

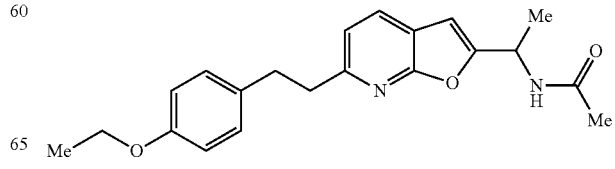

To a solution of N-[1-(6-chlorofuro[2,3-b]pyridin-2-yl)ethyl]acetamide (18.6 mg, 0.0782 mmol) obtained in Reference Example 237 in dimethoxyethane (3 mL) were added bisdiphenylphosphinoferrocenepalladium(II) chloride (12.2 mg, 0.0149 mmol) and 2-(4-ethoxyphenyl)ethylmagnesium bromide (THF solution 0.7 M, 2.0 mL, 1.4 mmol), and the mixture was refluxed for 30 min under a nitrogen atmosphere. Saturated aqueous ammonium chloride solution was added thereto, and the mixture was extracted twice with ethyl acetate. The extract was washed with saturated brine, and dried over anhydrous magnesium sulfate. The solvent was evaporated under reduced pressure, and the obtained residue was purified by silica gel column chromatography (hexane:ethyl acetate=4:1 to 3:7) to give the title compound (9.4 mg, yield 34%) as a white solid.

$^1$H NMR (CDCl$_3$) δ 1.40 (t, J=7.0 Hz, 3H), 1.54-1.62 (m, 3H), 2.01 (s, 3H), 2.96-3.19 (m, 4H), 4.00 (q, J=7.0 Hz, 2H), 5.27-5.41 (m, 1H), 5.89 (d, J=8.7 Hz, 1H), 6.53 (s, 1H), 6.81 (d, J=8.7 Hz, 2H), 7.00 (d, J=7.8 Hz, 1H), 7.11 (d, J=8.7 Hz, 2H), 7.72 (d, J=7.8 Hz, 1H)

Example 124

N-(1-{6-[2-(4-ethoxyphenyl)ethyl]-1-benzofuran-2-yl}ethyl)isoxazol-3-amine

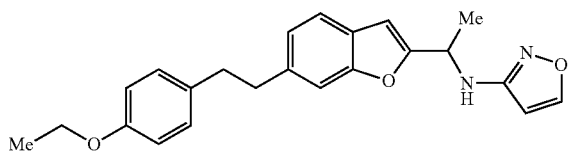 [SMILES: CCOc1ccc(CCc2ccc3cc(C(C)Nc4ccon4)oc3c2)cc1]

To a solution of N-(1-{6-[2-(4-ethoxyphenyl)ethyl]-1-benzofuran-2-yl}ethyl)-N-isoxazol-3-yl-4-nitrobenzefle-sulfoflamide (127 mg, 0.226 mmol) obtained in Reference Example 238 in DMF (1 mL) were added sulfanylacetic acid (0.166 mL, 1.81 mmol) and lithium hydroxide dihydrate (75.6 mg, 1.81 mmol), and the mixture was stirred at 70° C. overnight. Aqueous sodium hydrogen carbonate solution was added thereto, and the mixture was extracted with ethyl acetate. The extract was washed with saturated brine, and dried over anhydrous magnesium sulfate. The solvent was evaporated under reduced pressure, and the residue was passed through basic silica gel, and the solvent was evaporated under reduced pressure. The obtained solid was washed with diisopropyl ether to give the title compound (22.6 mg, yield 27%) as a white solid.

$^1$H NMR (CDCl$_3$) δ 1.40 (t, J=7.0 Hz, 3H), 1.66 (d, J=6.8 Hz, 3H), 2.80-3.04 (m, 4H), 4.01 (q, J=7.0 Hz, 2H), 4.30 (d, J=7.9 Hz, 1H), 4.77-4.97 (m, 1H), 5.86 (d, J=1.5 Hz, 1H), 6.55 (s, 1H), 6.76-6.86 (m, 2H), 7.02 (d, J=7.9 Hz, 1H), 7.05-7.13 (m, 2H), 7.24 (s, 1H), 7.39 (d, J=7.9 Hz, 1H), 8.05 (d, J=1.5 Hz, 1H).

Example 125

N-(1-{6-[(E)-2-(4-ethoxyphenyl)ethenyl]-1-benzofuran-2-yl}ethyl)acetamide

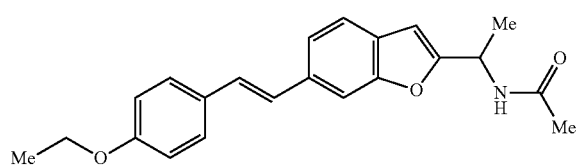 [SMILES: CCOc1ccc(/C=C/c2ccc3cc(C(C)NC(C)=O)oc3c2)cc1]

To a solution of 2-[1-(acetylamino)ethyl]-1-benzofuran-6-yl trifluoromethanesulfonate (300 mg, 0.854 mmol) obtained in Reference Example 239, 1-ethenyl-4-ethoxybenzene (0.638 mL, 4.27 mmol) and triethylamine (1.27 mL, 8.54 mmol) in anhydrous DMF (2 mL) was added bisdiphenylphosphinoferrocenepalladium(II) chloride (34.8 mg, 0.0427 mmol), and the mixture was stirred at 100° C. for 2 days under a nitrogen atmosphere. 1N Aqueous sodium hydroxide solution was added thereto, and the mixture was extracted twice with ethyl acetate. The extract was washed with saturated brine, and dried over anhydrous magnesium sulfate. The solvent was evaporated under reduced pressure, and the obtained residue was purified by silica gel column chromatography (hexane:ethyl acetate=9:1 to 2:3) to give the title compound (25.6 mg, yield 9%) as a white solid.

$^1$H NMR (CDCl$_3$) δ 1.43 (q, J=7.0 Hz, 3H), 1.50-1.64 (m, 3H), 2.03 (s, 3H), 4.06 (q, J=7.0 Hz, 2H), 5.26-5.47 (m, 1H), 5.80 (d, J=8.7 Hz, 1H), 6.54 (s, 1H), 6.85-6.93 (m, 2H), 7.02 (d, J=18.0 Hz, 1H), 7.09 (d, J=18.0 Hz, 1H), 7.33-7.40 (m, 1H), 7.42-7.50 (m, 3H), 7.54 (s, 1H).

Example 126

N-[1-(6-{2-[4-(cyclopropylmethoxy)phenyl]ethyl}-1-benzofuran-2-yl)ethyl]-3,4-dimethylisoxazol-5-amine

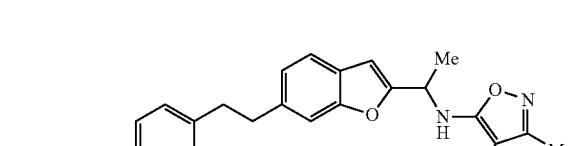

Using N-[1-(6-{2-[4-(cyclopropylmethoxy)phenyl]ethyl}-1-benzofuran-2-yl)ethyl]-N-(3,4-dimethylisoxazol-5-yl)-4-nitrobenzenesulfonamide (125 mg, 0.247 mmol) obtained in Reference Example 240, DMF (1 mL), sulfanylacetic acid (0.166 mL, 1.81 mmol) and lithium hydroxide dihydrate (75.6 mg, 1.81 mmol), an operation in the same manner as in Example 124 was performed to give the title compound (44.5 mg, yield 42%) as a white solid.

$^1$H NMR (CDCl$_3$) δ 0.29-0.39 (m, 2H), 0.60-0.71 (m, 2H), 1.17-1.34 (m, 1H), 1.66 (d, J=6.8 Hz, 3H), 1.74 (s, 3H), 2.10 (s, 3H), 2.83-3.04 (m, 4H), 3.78 (d, J=6.8 Hz, 2H), 4.25 (d,

J=9.1 Hz, 1H), 4.93-5.12 (m, 1H), 6.53 (s, 1H), 6.74-6.86 (m, 2H), 7.02 (dd, J=8.0, 1.5 Hz, 1H), 7.05-7.11 (m, 2H), 7.24 (s, 1H), 7.39 (d, J=8.1 Hz, 1H).

Example 127

N-[1-(5-{[4-(cyclopropylmethoxy)-3-fluorobenzyl]oxy}-1-benzofuran-2-yl)ethyl]acetamide

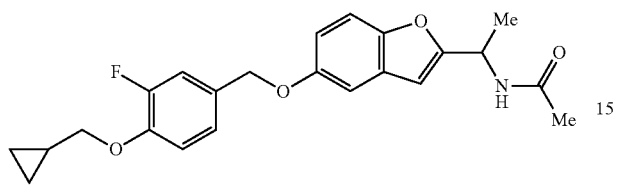

To a solution of [4-(cyclopropylmethoxy)-3-fluorophenyl]methanol (268 mg, 1.36 mmol) obtained in Reference Example 241 in toluene (2 mL) was added thionyl chloride (0.196 mL, 2.72 mmol), and the mixture was stirred at room temperature for 30 min and concentrated under reduced pressure. To the obtained residue were added DMF (2 mL), N-[1-(5-hydroxy-1-benzofuran-2-yl)ethyl]acetamide (200 mg, 0.913 mmol) obtained in Reference Example 38 and potassium carbonate (252 mg, 1.83 mmol), and the mixture was stirred at 60° C. overnight. Water was added thereto and the mixture was extracted with ethyl acetate. The extract was washed with 10% aqueous potassium carbonate solution and saturated brine, and dried over anhydrous sodium sulfate. The solution was purified by basic silica gel column chromatography (hexane:ethyl acetate=19:1 to 2:3), the solvent was evaporated, and the obtained solid was washed with diisopropyl ether to give the title compound (309 mg, yield 57%).

$^1$H NMR (CDCl$_3$) δ0.31-0.40 (m, 2H), 0.61-0.69 (m, 2H), 1.23-1.38 (m, 1H), 1.55 (d, J=7.2 Hz, 3H), 2.02 (s, 3H), 3.87 (d, J=7.2 Hz, 2H), 4.98 (s, 2H), 5.26-5.39 (m, 1H), 5.80 (d, J=7.9 Hz, 1H), 6.49 (s, 1H), 6.88-6.98 (m, 2H), 7.02 (d, J=2.6 Hz, 1H), 7.10 (d, J=8.3 Hz, 1H), 7.18 (dd, J=12.1, 1.9 Hz, 1H), 7.32 (d, J=9.0 Hz, 1H).

Example 128

N-[1-(6-{[4-(cyclopropylmethoxy)benzyl]oxy}-1-benzofuran-2-yl)ethyl]acetamide

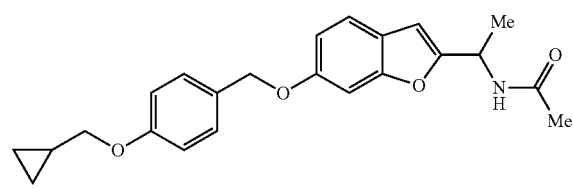 [SMILES: CC(=O)NC(C)c1cc2ccc(OCc3ccc(OCC4CC4)cc3)cc2o1]

To a solution of [4-(cyclopropylmethoxy)phenyl]methanol (243 mg, 1.36 mmol) in toluene (2 mL) was added thionyl chloride (0.196 mL, 2.72 mmol), and the mixture was stirred at room temperature for 30 min, and concentrated under reduced pressure. To the obtained residue were added DMF (2 mL), N-[1-(5-hydroxy-1-benzofuran-2-yl)ethyl]acetamide (200 mg, 0.913 mmol) obtained in Reference Example 38 and potassium carbonate (252 mg, 1.83 mmol), and the mixture was stirred at 50° C. overnight. Water was added thereto and the mixture was extracted with ethyl acetate. The extract was washed with 10% aqueous potassium carbonate solution and saturated brine, and dried over anhydrous sodium sulfate. The solution was purified by basic silica gel column chromatography (hexane:ethyl acetate=4:1 to 2:3), the solvent was evaporated, and the obtained solid was washed with diisopropyl ether to give the title compound (139 mg, yield 40%).

$^1$H NMR (CDCl$_3$) δ0.31-0.39 (m, 2H), 0.60-0.70 (m, 2H), 1.21-1.35 (m, 1H), 1.54 (d, J=7.2 Hz, 3H), 2.01 (s, 3H), 3.81 (d, J=6.8 Hz, 2H), 5.01 (s, 2H), 5.25-5.37 (m, 1H), 5.77 (d, J=7.9 Hz, 1H), 6.48 (s, 1H), 6.87-6.96 (m, 3H), 7.03 (d, J=1.9 Hz, 1H), 7.35-7.38 (m, 3H).

Example 129

N-{(1R)-1-[(2R)-6-{[4-(cyclopropylmethoxy)phenyl]ethynyl}-2,3-dihydro-1-benzofuran-2-yl]ethyl}acetamide and N-{(1S)-1-[(2S)-6-{[4-(cyclopropylmethoxy)phenyl]ethynyl}-2,3-dihydro-1-benzofuran-2-yl]ethyl}acetamide (two kinds)

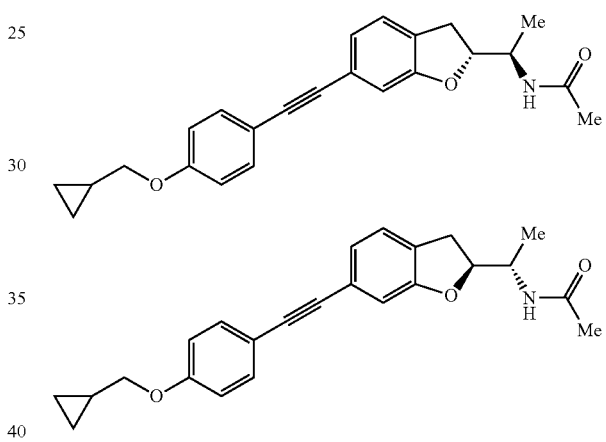

One is "retention time longer", and the other is "retention time shorter".

A 1:1 mixture (194 mg) (obtained in Example 111) of N-{(1R)-1-[(2R)-6-{[4-(cyclopropylmethoxy)phenyl]ethynyl}-2,3-dihydro-1-benzofuran-2-yl]ethyl}acetamide and N-{(18)-1-[(28)-6-{[4-(cyclopropylmethoxy)phenyl]ethynyl}-2,3-dihydro-1-benzofuran-2-yl]ethyl}acetamide was optically resolved by high performance liquid chromatography (HPLC) under the following conditions to give two kinds of optically active forms of "retention time longer (94 mg)" and "retention time shorter (91 mg)".

<Preparative HPLC Conditions>
column: CHIRALPAK AD (50 mmID×500 mL)
mobile phase: hexane:ethanol=17:3
flow rate: 80 mL/min
column temperature: 30° C.
detection: UV 220 nm <HPLC Analysis Conditions>
column: CHIRALPAK AD-H (4.6 mmID×250 mL)
mobile phase: hexane:ethanol=17:3
flow rate: 1.0 mL/min
column temperature: 30° C.
detection: UV 220 nm
retention time of "retention time longer": 17.5 min
retention time of "retention time shorter": 13.1 min

Example 130

N-{(1R)-1-[(2R)-6-{2-[4-(cyclopropylmethoxy)phenyl]ethyl}-2,3-dihydro-1-benzofuran-2-yl]ethyl}acetamide and N-{(1S)-1-[(2S)-6-{2-[4-(cyclopropylmethoxy)phenyl]ethyl}-2,3-dihydro-1-benzofuran-2-yl]ethyl}acetamide (two kinds)

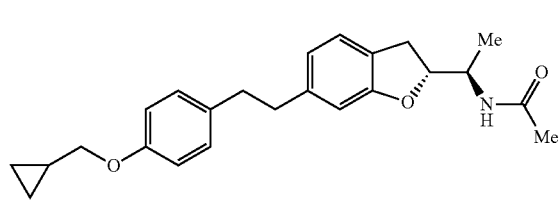

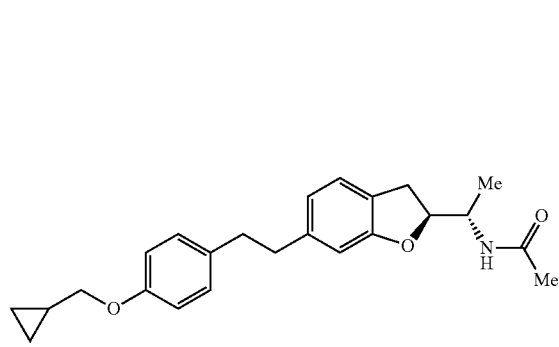

One is "retention time longer", and the other is "retention time shorter".

A 1:1 mixture (390 mg) (obtained in Example 121) of N-{(1R)-1-[(2R)-6-{2-[4-(cyclopropylmethoxy)phenyl]ethyl}-2,3-dihydro-1-benzofuran-2-yl]ethyl}acetamide and N-[(1S)-1-[(2S)-6-{2-[4-(cyclopropylmethoxy)phenyl]ethyl}-2,3-dihydro-1-benzofuran-2-yl]ethyl}acetamide was optically resolved by high performance liquid chromatography (HPLC) under the following conditions to give two kinds of optically active forms of "retention time longer (167 mg)" and "retention time shorter (170 mg)".

<Preparative HPLC Conditions>
    column: CHIRALPAK OJ-H (50 mmID×500 mmL)
    mobile phase: $CO_2$:methanol=13:7
    flow rate: 50 mL/min
    column temperature: 35° C.
    detection: UV 220 nm
    compound injection volume: 1.0 mL at 20 mg/mL (in methanol)
<HPLC Analysis Conditions>
    column: CHIRALPAK OJ-H (4.6 mmID×250 mmL)
    mobile phase: $CO_2$:methanol=3:2
    pressure: 100 bar
    flow rate: 4.0 ml/min
    column temperature: 35° C.
    detection: UV 220 nm
    retention time of "retention time longer": 1.26 min
    retention time of "retention time shorter": 1.00 min

Example 131

N-{(1S)-1-[(2R)-6-{2-[4-(cyclopropylmethoxy)phenyl]ethyl}-2,3-dihydro-1-benzofuran-2-yl]ethyl}acetamide and N-{(1R)-1-[(2S)-6-{2-[4-(cyclopropylmethoxy)phenyl]ethyl}-2,3-dihydro-1-benzofuran-2-yl]ethyl}acetamide (two kinds)

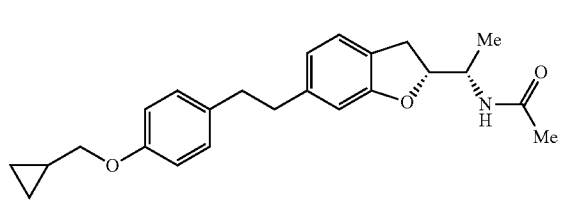

One is "retention time longer", and the other is "retention time shorter".

A 1:1 mixture (150 mg) (obtained in Example 122) of N-{(1S)-1-[(2R)-6-[(2-[4-(cyclopropylmethoxy)phenyl]ethyl}-2,3-dihydro-1-benzofuran-2-yl]ethyl]acetamide and N-{(1R)-1-[(2S)-6-{2-[4-(cyclopropylmethoxy)phenyl]ethyl}-2,3-dihydro-1-benzofuran-2-yl]ethyl}acetamide was optically resolved by high performance liquid chromatography (HPLC) under the following conditions to give two kinds of optically active forms of "retention time longer (62.0 mg)" and "retention time shorter (57.6 mg)".

<Preparative HPLC Conditions>
    column: CHIRALPAK OJ-H (50 mmID×500 mL)
    mobile phase: $CO_2$:methanol=6:4
    flow rate: 50 mL/min
    column temperature: 35° C.
    detection: UV 220 nm
    compound injection volume: 4.0 mL at 3.0 mg/ml (in methanol)
<HPLC Analysis Conditions>
    column: CHIRALPAK OJ-H (4.6 mmID×250 mmL)
    mobile phase: $CO_2$:methanol=3:2
    pressure: 100 bar
    flow rate: 4.0 ml/min
    column temperature: 35° C.
    detection: UV 220 nm
    compound injection volume: 0.005 ml at 1.5 mg/mL (in methanol)
    retention time of "retention time longer": 1.31 min
    retention time of "retention time shorter": 1.06 min

Example 132

N-[1-(5-{[4-(cyclopropylmethoxy)benzyl]oxy}-1-benzofuran-2-yl)ethyl]acetamide (two kinds)

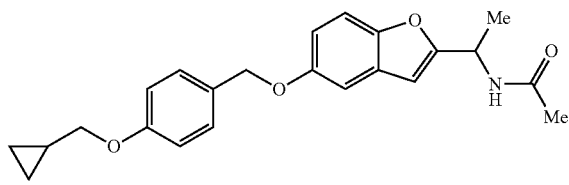

N-[1-(5-{[4-(cyclopropylmethoxy)benzyl]oxy}-1-benzofuran-2-yl)ethyl]acetamide (115 mg) obtained in Example 108 was optically resolved by high performance liquid chromatography (HPLC) under the following conditions to give two kinds of optically active forms of "retention time longer (53 mg)" and "retention time shorter (53 mg)".

<Preparative HPLC Conditions>
 column: CHIRALPAK AD (50 mmID×500 mmL)
 mobile phase: hexane:ethanol=17:3
 flow rate: 80 ml/min
 column temperature: 30° C.
 detection: UV 220 nm
 compound injection volume: 60 mg/300 mL
<HPLC Analysis Conditions>
 column: CHIRALPAK AD (4.6 mmID×250 mmL)
 mobile phase: hexane:ethanol=17:3
 flow rate: 1.0 mL/min
 column temperature: 30° C.
 detection: UV 220 nm
 retention time of "retention time longer": 16.5 min
 retention time of "retention time shorter": 11.5 min

Example 133

N-{(1S)-1-[(2R)-6-{[4-(cyclopropylmethoxy)phenyl]ethynyl}-2,3-dihydro-1-benzofuran-2-yl]ethyl}acetamide and N-{(1R)-1-[(2S)-6-{[4-(cyclopropylmethoxy)phenyl]ethynyl}-2,3-dihydro-1-benzofuran-2-yl]ethyl}acetamide (two kinds)

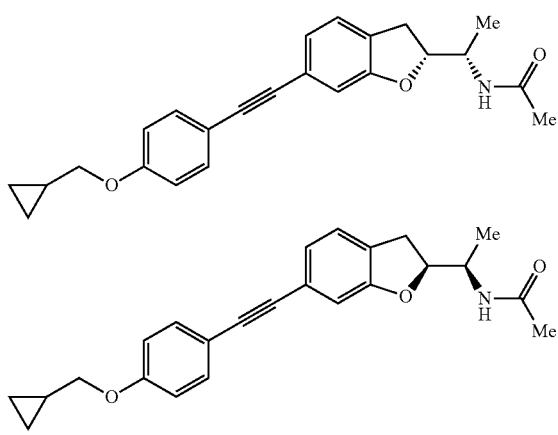

One is "retention time longer", and the other is "retention time shorter".

A 1:1 mixture (148 mg) (obtained in Example 112) of N-{(1S)-1-[(2R)-6-{[4-(cyclopropylmethoxy)phenyl]ethynyl}-2,3-dihydro-1-benzofuran-2-yl]ethyl}acetamide and N-{(1R)-1-[(2S)-6-{[4-(cyclopropylmethoxy)phenyl]ethynyl}-2,3-dihydro-1-benzofuran-2-yl]ethyl}acetamide was optically resolved by high performance liquid chromatography (HPLC) under the following conditions to give two kinds of optically active forms of "retention time longer (53 mg)" and "retention time shorter (69 mg)".

<Preparative HPLC Conditions>
 column: CHIRALPAK AD (50 mmID×500 mL)
 mobile phase: hexane:ethanol=17:3
 flow rate: 80 mL/min
 column temperature: 30° C.
 detection: UV 220 nm
 compound injection volume: 70 mg/200 mL
<HPLC Analysis Conditions>
 column: CHIRALPAK AD (4.6 mmID×250 mmL)
 mobile phase: hexane:ethanol=17:3
 flow rate: 1.0 mL/min
 column temperature: 30° C.
 detection: UV 220 nm
 retention time of "retention time longer": 17.2 min
 retention time of "retention time shorter": 13.6 min

Example 134

N-[1-(5-{[2-chloro-4-(cyclopropylmethoxy)benzyl]oxy}-1-benzofuran-2-yl)ethyl]acetamide (two kinds)

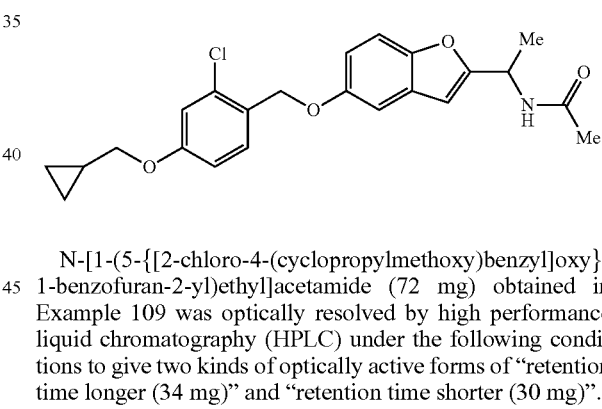

N-[1-(5-{[2-chloro-4-(cyclopropylmethoxy)benzyl]oxy}-1-benzofuran-2-yl)ethyl]acetamide (72 mg) obtained in Example 109 was optically resolved by high performance liquid chromatography (HPLC) under the following conditions to give two kinds of optically active forms of "retention time longer (34 mg)" and "retention time shorter (30 mg)".

<Preparative HPLC Conditions>
 column: CHIRALPAK AD (50 mmID×500 mL)
 mobile phase: hexane:ethanol=17:3
 flow rate: 80 mL/min
 column temperature: 30° C.
 detection: UV 220 nm
 compound injection volume: 72 mg/200 mL
<HPLC Analysis Conditions>
 column: CHIRALPAK AD (4.6 mmID×250 mmL)
 mobile phase: hexane:ethanol=17:3
 flow rate: 1.0 mL/min
 column temperature: 30° C.
 detection: UV 220 nm
 retention time of "retention time longer": 12.5 min
 retention time of "retention time shorter": 9.1 min

Example 135

N-(1-{6-[2-(4-ethoxyphenyl)ethyl]furo[3,2-c]pyridin-2-yl}ethyl)acetamide

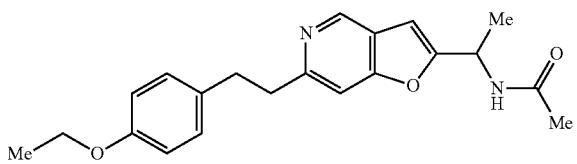 [SMILES: CCOc1ccc(CCc2cc3oc(C(C)NC(C)=O)cc3cn2)cc1]

To a solution of 2-(1-azidoethyl)-6-[2-(4-ethoxyphenyl)ethyl]furo[3,2-c]pyridine (622 mg, 1.85 mmol) obtained in Reference Example 246 in THF (5 mL) was added triphenylphosphine (582 mg, 2.20 mmol), and the mixture was stirred at 60° C. for 30 min. To the reaction mixture was added water (1.0 mL), and the mixture was stirred at 60° C. for 15 hr. The solvent was evaporated under reduced pressure and the obtained residue was purified by basic silica gel column chromatography (hexane:ethyl acetate1:1 to 0:1) to give 1-{6-[2-(4-ethoxyphenyl)ethyl]furo[3,2-c]pyridin-2-yl}ethanamine. This was dissolved in pyridine (3 mL)-acetic anhydride (3 mL), and the solution was stirred at room temperature for 15 min. The solvent was evaporated under reduced pressure and the obtained residue was purified by basic silica gel column chromatography (hexane:ethyl acetate=1:1 to 0:1, ethyl acetate:methanol=1:0 to 9:1) to give the title compound (444 mg, yield from 2-(1-azidoethyl)-6-[2-(4-ethoxyphenyl)ethyl]furo[3,2-c]pyridine 68%) as a white solid.

$^1$H NMR (CDCl$_3$) δ 1.39 (t, J=7.0 Hz, 3H), 1.56 (d, J=6.8 Hz, 3H), 2.03 (s, 3H), 2.99-3.04 (m, 2H), 3.13-3.17 (m, 2H), 4.00 (q, J=7.0 Hz, 2H), 5.31-5.40 (m, 1H), 5.84 (d, J=8.3 Hz, 1H), 6.58 (s, 1H), 6.80 (d, J=8.7 Hz, 2H), 7.10 (d, J=8.7 Hz, 2H), 7.14 (s, 1H), 8.77 (s, 1H).

Example 136

N-(1-{5-[2-(4-ethoxyphenyl)ethyl]furo[2,3-c]pyridin-2-yl}ethyl)acetamide

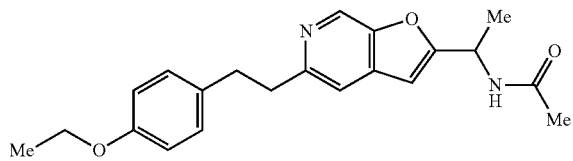 [SMILES: CCOc1ccc(CCc2cc3cc(C(C)NC(C)=O)oc3cn2)cc1]

To a solution of 2-(1-azidoethyl)-5-[2-(4-ethoxyphenyl)ethyl]furo[2,3-c]pyridine (1.20 g, 3.57 mmol) obtained in Reference Example 252 in THF (10 mL) was added triphenylphosphine (1.13 g, 4.28 mmol), and the mixture was stirred at 60° C. for 30 min. To the reaction mixture was added water (1.0 mL), and the mixture was stirred at 60° C. for 15 hr. The solvent was evaporated under reduced pressure and the obtained residue was dissolved in pyridine (5 mL)-acetic anhydride (5 mL), and the solution was stirred at room temperature for 15 min. The solvent was evaporated under reduced pressure and the obtained residue was purified by silica gel column chromatography (hexane:ethyl acetate=2:3 to 0:1, ethyl acetate:methanol=1:0 to 9:1) to give the title compound (781 mg, yield 62%) as a white solid.

$^1$H NMR (CDCl$_3$) δ 1.39 (t, J=7.0 Hz, 3H), 1.58 (d, J=7.2 Hz, 3H), 2.04 (s, 3H), 2.97-3.03 (m, 2H), 3.08-3.15 (m, 2H), 4.00 (q, J=7.0 Hz, 2H), 5.33-5.42 (m, 1H), 5.84 (d, J=7.9 Hz, 1H), 6.51 (s, 1H), 6.79 (d, J=8.7 Hz, 2H), 7.09 (d, J=8.7 Hz, 2H), 7.20 (d, J=0.8 Hz, 1H), 8.74 (s, 1H).

Example 137

N-[1-(6-{[5-(cyclopropylmethoxy)pyridin-2-yl]ethynyl}-1-benzofuran-2-yl)ethyl]acetamide

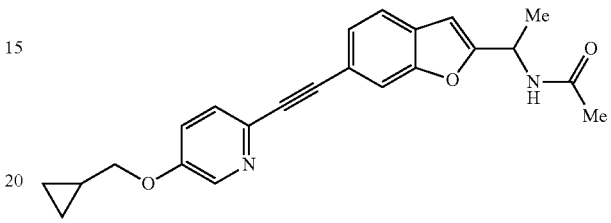

To a solution of 2-[1-(acetylamino)ethyl]-1-benzofuran-6-yl trifluoromethanesulfonate (150 mg, 0.427 mmol) obtained in Reference Example 239 in DMF (3 mL)-triethylamine (1 mL) were added 5-(cyclopropylmethoxy)-2-ethynylpyridine (148 mg, 0.854 mmol) obtained in Reference Example 254, copper(I) iodide (8.20 mg, 0.0427 mmol) and bis(triphenylphosphine)palladium(II) chloride (30.0 mg, 0.0427 mmol), and the mixture was stirred at 100° C. for 18 hr under an argon stream. The reaction mixture was diluted with ethyl acetate, and the mixture was washed three times with saturated brine, and dried over anhydrous magnesium sulfate. The solvent was evaporated under reduced pressure and the obtained residue was purified by basic silica gel column chromatography (hexane:ethyl acetate=2:3 to 0:1) to give the title compound (69.6 mg, yield 43%) as a yellow solid.

$^1$H NMR (CDCl$_3$) δ 0.36-0.41 (m, 2H), 0.66-0.72 (m, 2H), 1.23-1.34 (m, 1H), 1.58 (d, J=6.8 Hz, 3H), 2.04 (s, 3H), 3.89 (d, J=6.8 Hz, 2H), 5.32-5.42 (m, 1H), 5.84 (d, J=8.3 Hz, 1H), 6.57 (s, 1H), 7.17 (dd, J=8.5, 3.0 Hz, 1H), 7.41-7.49 (m, 3H), 7.64 (s, 1H), 8.32 (d, J=3.0 Hz, 1H).

Example 138

N-[1-(6-{[6-(cyclopropylmethoxy)pyridin-3-yl]ethynyl}-1-benzofuran-2-yl)ethyl]acetamide

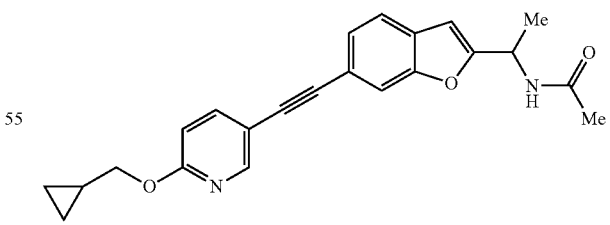

To a solution of 2-[1-(acetylamino)ethyl]-1-benzofuran-6-yl trifluoromethanesulfonate (150 mg, 0.427 mmol) obtained in Reference Example 239 in DMF (3 mL)-triethylamine (1 mL) were added 2-(cyclopropylmethoxy)-5-ethynylpyridine (148 mg, 0.854 mmol) obtained in Reference Example 256, copper(I) iodide (8.20 mg, 0.0427 mmol) and bis(triphenylphosphine)palladium(II) chloride (30.0 mg, 0.0427 mmol), and the mixture was stirred at 100° C. for 15 hr under an argon stream. The reaction mixture was diluted with ethyl acetate, and the mixture was washed three times with saturated brine, and dried over anhydrous magnesium sulfate. The solvent was evaporated under reduced pressure and the obtained residue was purified by silica gel column chromatography (hexane:ethyl acetate=3:7 to 0:1) to give the title compound (103 mg, yield 64%) as a yellow solid.

$^1$H NMR (CDCl$_3$) δ 0.34-0.39 (m, 2H), 0.60-0.66 (m, 2H), 1.23-1.34 (m, 1H), 1.57-1.59 (m, 3H), 2.04 (s, 3H), 4.16 (d, J=7.2 Hz, 2H), 5.32-5.42 (m, 1H), 5.81 (d, J=8.3 Hz, 1H), 6.57 (s, 1H), 6.76 (d, J=8.6 Hz, 1H), 7.36-7.39 (m, 1H), 7.47 (d, J=7.9 Hz, 1H), 7.58 (s, 1H), 7.70 (dd, J=8.5, 2.5 Hz, 1H), 8.33 (d, J=1.9 Hz, 1H).

Example 139

N-{(1S)-1-[(2S)-6-{[6-(cyclopropylmethoxy)pyridin-3-yl]ethynyl}-2,3-dihydro-1-benzofuran-2-yl]ethyl}acetamide

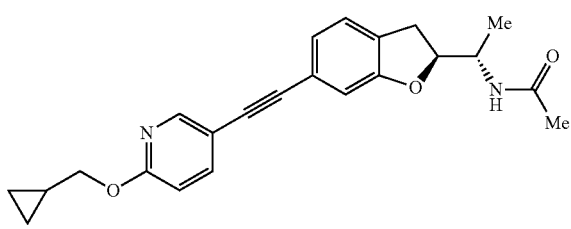 [SMILES: CC(=O)N[C@@H](C)[C@@H]1Cc2ccc(C#Cc3ccc(OCC4CC4)nc3)cc2O1]

Using 2-(cyclopropylmethoxy)-5-ethynylpyridine (353 mg, 2.04 mmol) obtained in Reference Example 256, (2S)-2-[(1S)-1-(acetylamino)ethyl]-2,3-dihydro-1-benzofuran-6-yl trifluoromethanesulfonate (retention time longer, 600 mg, 1.70 mmol) obtained in Reference Example 231, copper(I) iodide (32.3 mg, 0.170 mmol), (triphenylphosphine)palladium(II) chloride (59.6 mg, 84.9 mmol) and DMF-triethylamine (6 mL-1.5 mL), an operation in the same manner as in Example 111 was performed, and the obtained residue was triturated with diisopropyl ether to give the title compound (133 mg, yield 21%).

$^1$H NMR (CDCl$_3$) δ 0.33-0.39 (m, 2H), 0.59-0.66 (m, 2H), 1.24-1.30 (m, 1H), 1.34 (d, J=6.9 Hz, 1H), 1.90 (s, 3H), 2.99-3.26 (m, 2H), 4.14 (d, J=6.9 Hz, 2H), 4.31-4.37 (m, 1H), 4.76-4.82 (m, 1H), 5.45 (d, J=5.7 Hz, 1H), 6.73-6.76 (m, 1H), 6.90 (s, 1H), 7.01-7.11 (m, 2H), 7.66 (dd, J=2.4, 8.7 Hz, 1H), 8.28 (m, 1H).

Example 140

N-[1-(5-{[4-(cyclopropylmethoxy)-2-fluorobenzyl]oxy}-2,3-dihydro-1-benzofuran-2-yl)ethyl]acetamide

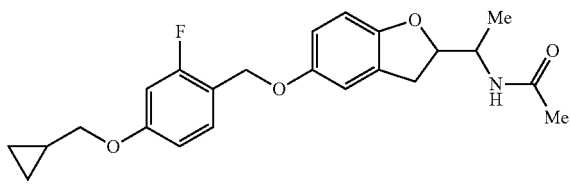

To a solution of [4-(cyclopropylmethoxy)-2-fluorophenyl]methanol (793 mg, 4.04 mmol) obtained in Reference Example 230 and DMF (1 drop) in THF (10 mL) was added thionyl chloride (0.443 mL, 6.06 mmol), and the mixture was stirred at room temperature for 30 min and concentrated under reduced pressure. To the obtained residue were added DMF (10 mL), N-[1-(5-hydroxy-2,3-dihydro-1-benzofuran-2-yl)ethyl]acetamide (447 mg, 2.02 mmol) obtained in Reference Example 258 and potassium carbonate (1.40 g, 10.1 mmol), and the mixture was stirred at 60° C. for 2 hr. Water was added thereto and the mixture was extracted with ethyl acetate. The extract was washed twice with saturated brine, and dried over anhydrous magnesium sulfate. The solvent was evaporated under reduced pressure and the obtained residue was purified by silica gel column chromatography (hexane:ethyl acetate=3:7 to 0:1) to give the title compound (520 mg, yield 64%) as an oil.

$^1$H NMR (CDCl$_3$) δ 0.32-0.37 (m, 2H), 0.62-0.68 (m, 2H), 1.10 (d, J=6.8 Hz, 1.5H), 1.21-1.30 (m, 1H), 1.33 (d, J=6.8 Hz, 1.5H), 1.91 (s, 1.5H), 2.01 (s, 1.5H), 2.90-3.03 (m, 1H), 3.12-3.33 (m, 1H), 3.78 (d, J=6.8 Hz, 2H), 4.17-4.36 (m, 1H), 4.70-4.85 (m, 1H), 4.95 (s, 2H), 5.53 (d, J=9.1 Hz, 0.5H), 5.78 (d, J=8.7 Hz, 0.5H), 6.61-6.74 (m, 4H), 6.80 (s, 1H), 7.30-7.36 (m, 1H).

Example 141

N-[1-(5-{[4-(cyclopropylmethoxy)-2-fluorobenzyl]oxy}-2,3-dihydro-1-benzofuran-2-yl)ethyl]acetamide (two kinds)

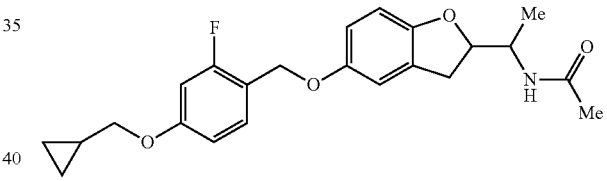

N-[1-(5-{[4-(cyclopropylmethoxy)-2-fluorobenzyl]oxy}-2,3-dihydro-1-benzofuran-2-yl)ethyl]acetamide (432 mg) obtained in Example 140 was optically resolved by high performance liquid chromatography (HPLC) under the following conditions to give two kinds of optically active fonts of "retention time longer (201 mg)" and "retention time shorter (209 mg)".

<Preparative HPLC Conditions>
    column: CHIRALPAK AS (50 mmID×500 mmL)
    mobile phase: hexane:ethanol=2:8
    flow rate: 60 mL/min
    column temperature: 30° C.
    detection: UV 220 nm
    compound injection volume: 216 mg/30 mL
<HPLC Analysis Conditions>
    column: CHIRALPAK AS (4.6 mmID×250 mmL)
    mobile phase: hexane:ethanol=2:8
    flow rate: 0.5 mL/min
    column temperature: 40° C.
    detection: UV 220 nm
    retention time of "retention time longer": 15.9 min
    retention time of "retention time shorter": 8.3 min

Example 142

N-{(1S)-1-[(2S)-6-{[6-(cyclopropylmethoxy)-4-fluoropyridin-3-yl]methoxy}-2,3-dihydro-1-benzofuran-2-yl]ethyl}acetamide

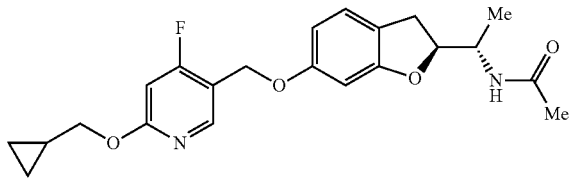 [SMILES: CC(=O)N[C@@H](C)[C@@H]1Cc2ccc(OCc3cnc(OCC4CC4)cc3F)cc2O1]

N-{(1S)-1-[(2S)-6-hydroxy-2,3-dihydro-1-benzofuran-2-yl]ethyl}acetamide (100 mg, 0.453 mmol) obtained in Reference Example 259, 5-(bromomethyl)-2-(cyclopropylmethoxy)-4-fluoropyridine (262 mg, 1.01 mmol) obtained in Reference Example 271 and potassium carbonate (125 mg, 0.906 mmol) were mixed, and the mixture was stirred at 60° C. for 1 hr. Water was added thereto and the mixture was extracted with ethyl acetate. The extract was washed twice with saturated brine, and dried over anhydrous magnesium sulfate. The solvent was evaporated under reduced pressure and the obtained residue was purified by basic silica gel column chromatography (hexane:ethyl acetate=3:2 to 0:1) to give the title compound (180 mg, yield 99%) as an oil.

$^1$H NMR (CDCl$_3$) δ 0.32-0.37 (m, 2H), 0.58-0.65 (m, 2H), 1.22-1.30 (m, 1H), 1.33 (d, J=6.8 Hz, 3H), 1.91 (s, 3H), 2.88-2.98 (m, 1H), 3.09-3.18 (m, 1H), 4.14 (d, J=6.8 Hz, 2H), 4.29-4.35 (m, 1H), 4.75-4.81 (m, 1H), 4.97 (s, 2H), 5.49 (d, J=8.7 Hz, 1H), 6.43-6.51 (m, 3H), 7.02 (d, J=8.0 Hz, 1H), 8.17 (d, J=11.0 Hz, 1H).

Example 143

N-{(1S)-1-[(2S)-6-{[6-(cyclopropylmethoxy)-2-fluoropyridin-3-yl]methoxy}-2,3-dihydro-1-benzofuran-2-yl]ethyl}acetamide

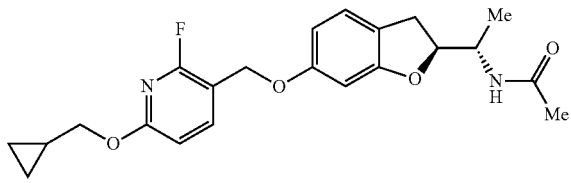

N-{(1S)-1-[(2S)-6-hydroxy-2,3-dihydro-1-benzofuran-2-yl]ethyl}acetamide (100 mg, 0.453 mmol) obtained in Reference Example 259, 3-(bromomethyl)-6-(cyclopropylmethoxy)-2-fluoropyridine (262 mg, 1.01 mmol) obtained in Reference Example 263 and potassium carbonate (125 mg, 0.906 mmol) were mixed, and the mixture was stirred at 60° C. for 1 hr. Water was added thereto and the mixture to was extracted with ethyl acetate. The extract was washed twice with saturated brine, and dried over anhydrous magnesium sulfate. The solvent was evaporated under reduced pressure and the obtained residue was purified by basic silica gel column chromatography (hexane:ethyl acetate=3:2 to 0:1) to give the title compound (161 mg, yield 88%) as an oil.

$^1$H NMR (CDCl$_3$) δ 0.32-0.37 (m, 2H), 0.59-0.65 (m, 2H), 1.22-1.30 (m, 1H), 1.33 (d, J=6.8 Hz, 3H), 1.91 (s, 3H), 2.90-3.00 (m, 1H), 3.09-3.17 (m, 1H), 4.11 (d, J=7.2 Hz, 2H), 4.29-4.37 (m, 1H), 4.74-4.81 (m, 1H), 4.97 (s, 2H), 5.48 (d, J=9.1 Hz, 1H), 6.42-6.48 (m, 2H), 6.66 (dd, J=8.1, 1.0 Hz, 1H), 7.01 (d, J=8.0 Hz, 1H), 7.77 (dd, J=9.8, 8.0 Hz, 1H).

Example 144

N-{(1S)-1-[(2S)-6-{[4-(cyclopropylmethoxy)benzyl]oxy}-2,3-dihydro-1-benzofuran-2-yl]ethyl}acetamide

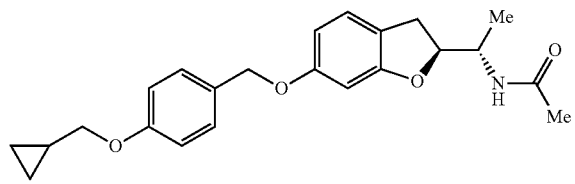 [SMILES: CC(=O)N[C@@H](C)[C@@H]1Cc2ccc(OCc3ccc(OCC4CC4)cc3)cc2O1]

To a solution of [4-(cyclopropylmethoxy)phenyl]methanol (2.75 g, 15.4 mmol) in toluene (15 mL) was added thionyl chloride (1.5 mL, 21 mmol), and the mixture was stirred at room temperature for 30 min, and concentrated under reduced pressure. To the obtained residue were added DMF (10 mL), N-{(1S)-1-[(2S)-6-hydroxy-2,3-dihydro-1-benzofuran-2-yl]ethyl}acetamide (2.28 g, 10.3 mmol) obtained in Reference Example 259 and potassium carbonate (5.69 g, 41.2 mmol), and the mixture was stirred at 70° C. overnight. Water was added thereto and the mixture was extracted with ethyl acetate. The extract was washed with saturated brine, and dried over anhydrous magnesium sulfate. The solvent was evaporated under reduced pressure and the obtained residue was purified by silica gel column chromatography (hexane:ethyl acetate=19:1 to 1:1), and crystallized from acetone-heptane to give the title compound (2.24 g, yield 58%).

$^1$H NMR (CDCl$_3$) δ 0.30-0.42 (m, 2H), 0.61-0.70 (m, 2H), 1.19-1.36 (m, 1H), 1.33 (d, J=6.8 Hz, 3H), 1.91 (s, 3H), 2.85-3.01 (m, 1H), 3.06-3.18 (m, 1H), 3.80 (d, J=6.8 Hz, 2H), 4.21-4.38 (m, 1H), 4.60-4.85 (m, 1H), 4.93 (s, 2H), 5.49 (d, J=9.4 Hz, 1H), 6.38-6.51 (m, 2H), 6.86-6.94 (m, 2H), 7.00 (d, J=8.3 Hz, 1H), 7.29-7.36 (m, 2H).

Example 145

N-{(1S)-1-[(2S)-6-{[4-(cyclopropylmethoxy)-2-fluorobenzyl]oxy}-2,3-dihydro-1-benzofuran-2-yl]ethyl}acetamide

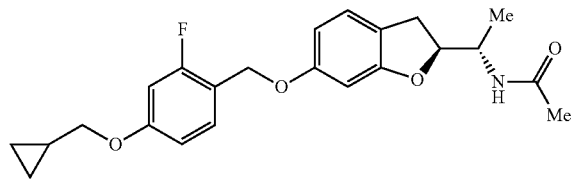

To a solution of [4-(cyclopropylmethoxy)-2-fluorophenyl]methanol (265 mg, 1.36 mmol) obtained in Reference Example 230 in toluene (2 mL) was added thionyl chloride (0.20 mL, 2.7 mmol), and the mixture was stirred at room temperature for 30 min, and concentrated under reduced pressure. To the obtained residue were added DMF (1.5 mL), N-{(1S)-1-[(2S)-6-hydroxy-2,3-dihydro-1-benzofuran-2-yl]

ethyl}acetamide (200 mg, 0.904 mmol) obtained in Reference Example 259 and potassium carbonate (498 mg, 3.62 mmol), and the mixture was stirred at 60° C. overnight. Water was added thereto and the mixture was extracted with ethyl acetate. The extract was washed with saturated brine, and dried over anhydrous magnesium sulfate. The solution was applied to basic silica gel column chromatography (ethyl acetate), and the obtained residue was triturated with diisopropyl ether-diethyl ether to give the title compound (303 mg, yield 84%) as a white solid.

$^{1}$H NMR (CDCl$_3$) δ 0.31-0.42 (m, 2H), 0.61-0.71 (m, 2H), 1.19-1.30 (m, 1H), 1.33 (d, J=6.8 Hz, 3H), 1.91 (s, 3H), 2.87-2.99 (m, 1H), 3.07-3.19 (m, 1H), 3.79 (d, J=6.8 Hz, 2H), 4.23-4.38 (m, 1H), 4.60-4.85 (m, 1H), 4.99 (s, 2H), 5.50 (d, J=8.7 Hz, 1H), 6.42-6.50 (m, 2H), 6.64 (dd, J=11.9, 2.4 Hz, 1H), 6.70 (dd, J=8.3, 2.6 Hz, 1H), 7.01 (d, J=7.9 Hz, 1H), 7.34 (t, J=8.7 Hz, 1H).

Example 146

N-{(1S)-1-[(2S)-6-({2-fluoro-4-[(2S)-tetrahydrofuran-2-ylmethoxy]benzyl}oxy)-2,3-dihydro-1-benzofuran-2-yl]ethyl}acetamide

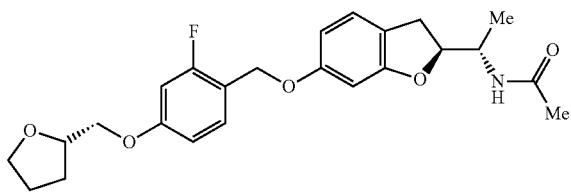

To a solution of {2-fluoro-4-[(2S)-tetrahydrofuran-2-ylmethoxy]phenyl}methanol (153 mg, 0.677 mmol) obtained in Reference Example 274 in toluene (1 mL) was added thionyl chloride (0.063 mL, 0.90 mmol), and the mixture was stirred at room temperature for 30 min, and concentrated under reduced pressure. To the obtained residue were added DMF (2 mL), N-{(1S)-1-[(2S)-6-hydroxy-2,3-dihydro-1-benzofuran-2-yl]ethyl}acetamide (100 mg, 0.451 mmol) obtained in Reference Example 259 and potassium carbonate (249 mg, 1.81 mmol), and the mixture was stirred at 70° C. overnight. Water was added thereto and the mixture was extracted with ethyl acetate. The extract was washed with saturated brine, and dried over anhydrous magnesium sulfate. The solution was applied to basic silica gel column chromatography (ethyl acetate), and the obtained residue was triturated with diisopropyl ether to give the title compound (135 mg, yield 70%) as a white solid.

$^{1}$H NMR (CDCl$_3$) δ 1.32 (d, J=6.8 Hz, 3H), 1.70-1.82 (m, 1H), 1.87-2.15 (m, 6H), 2.84-3.01 (m, 1H), 3.06-3.21 (m, 1H), 3.77-4.00 (m, 4H), 4.19-4.40 (m, 2H), 4.60-4.85 (m, 1H), 4.99 (s, 2H), 5.53 (d, J=8.7 Hz, 1H), 6.40-6.52 (m, 2H), 6.62-6.79 (m, 2H), 7.00 (d, J=7.9 Hz, 1H), 7.34 (t, J=8.1 Hz, 1H).

Example 147

N-{(1S)-1-[(2S)-6-{[2-cyano-4-(cyclopropylmethoxy)benzyl]oxy}-2,3-dihydro-1-benzofuran-2-yl]ethyl}acetamide

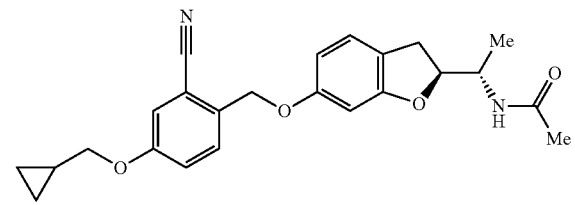 [SMILES: CC(=O)N[C@@H](C)[C@@H]1Cc2ccc(OCc3ccc(OCC4CC4)cc3C#N)cc2O1]

A solution of 2-(bromomethyl)-5-(cyclopropylmethoxy)benzonitrile (180 mg, 0.677 mmol) obtained in Reference Example 276, N-{(1S)-1-[(2S)-6-hydroxy-2,3-dihydro-1-benzofuran-2-yl]ethyl}acetamide (100 mg, 0.451 mmol) obtained in Reference Example 259 and potassium carbonate (186 mg, 1.35 mmol) in DMF (2 mL) was stirred at 70° C. overnight. Thereafter, water was added thereto, and the mixture was extracted with ethyl acetate. This extract was washed with saturated brine, and dried over anhydrous magnesium sulfate. The solution was applied to basic silica gel column chromatography (ethyl acetate), and the obtained residue was triturated with diisopropyl ether to give the title compound (140 mg, yield 74%) as a white solid.

$^{1}$H NMR (CDCl$_3$) δ 0.31-0.43 (m, 2H), 0.63-0.74 (m, 2H), 1.19-1.37 (m, 4H), 1.92 (s, 3H), 2.89-3.00 (m, 1H), 3.07-3.20 (m, 1H), 3.78-3.87 (m, 2H), 4.20-4.40 (m, 1H), 4.60-4.85 (m, 1H), 5.11 (s, 2H), 5.51 (d, J=9.0 Hz, 1H), 6.43-6.52 (m, 2H), 7.02 (d, J=8.3 Hz, 1H), 7.11-7.18 (m, 2H), 7.52 (d, J=8.7 Hz, 1H).

Example 148

N-[1-(5-{[5-(cyclopropylmethoxy)-3-fluoropyridin-2-yl]methoxy}-1-benzofuran-2-yl)ethyl]acetamide

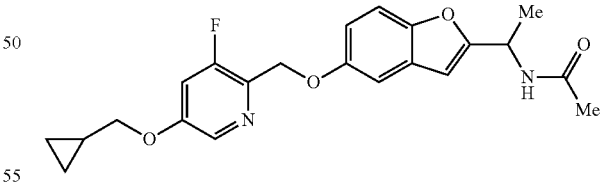

To a solution of [5-(cyclopropylmethoxy)-3-fluoropyridin-2-yl]methanol (108 mg, 0.548 mmol) obtained in Reference Example 318, N-[1-(5-hydroxy-1-benzofuran-2-yl) ethyl]acetamide (retention time longer, 120 mg, 0.548 mmol) obtained in Reference Example 257 and polystyrene-supported triphenylphosphine (496 mg, 1.10 mmol) in THF (5 mL) was added dimethoxyethyl azodicarboxylate (154 mg, 0.657 mmol), and the mixture was stirred at room temperature for 3 days. After filtration, the solvent was evaporated under reduced pressure and the obtained residue was purified by basic silica gel column chromatography (hexane:ethyl acetate=1:1 to 0:1), and triturated with diisopropyl ether to give the title compound (97.2 mg, yield 45%).

$^1$H NMR (CDCl$_3$) δ 0.37-0.39 (m, 2H), 0.68-0.70 (m, 2H), 1.26-1.29 (m, 1H), 1.55 (d, J=6.9 Hz, 3H), 2.02 (s, 3H), 3.86 (d, J=6.9 Hz, 2H), 5.18 (d, J=2.1 Hz, 2H), 5.18-5.34 (m, 1H), 5.75 (d, J=6.9 Hz, 1H), 6.50 (s, 1H), 6.94-6.98 (m, 2H), 7.12 (d, J=3.0 Hz, 1H), 7.30 (d, J=9.3 Hz, 1H), 8.17 (d, J=1.5 Hz, 1H).

Example 149

N-[1-(5-{[6-(cyclopropylmethoxy)-4-methylpyridin-3-yl]methoxy}-1-benzofuran-2-yl)ethyl]acetamide

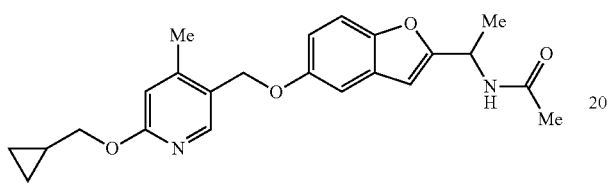

To a solution of [6-(cyclopropylmethoxy)-4-methylpyridin-3-yl]methanol (132 mg, 0.684 mmol) obtained in Reference Example 320, N-[1-(5-hydroxy-1-benzofuran-2-yl)ethyl]acetamide (retention time longer, 150 mg, 0.684 mmol) obtained in Reference Example 257 and polystyrene-supported triphenylphosphine (619 mg, 1.37 mmol) in THF (7 mL) was added dimethoxyethyl azodicarboxylate (192 mg, 0.821 mmol), and the mixture was stirred at room temperature for 16 hr. After filtration, the solvent was evaporated under reduced pressure and the obtained residue was purified by basic silica gel column chromatography (hexane:ethyl acetate=1:1 to 0:1), and triturated with diisopropyl ether to give the title compound (105 mg, yield 39%).

$^1$H NMR (CDCl$_3$) δ 0.32-0.37 (m, 2H), 0.57-0.64 (m, 2H), 1.24-1.30 (m, 1H), 1.56 (d, J=6.9 Hz, 3H), 2.02 (s, 3H), 2.36 (s, 3H), 4.11 (d, J=6.9 Hz, 2H), 4.96 (s, 2H), 5.31-5.36 (m, 1H), 5.76 (d, J=6.9 Hz, 1H), 6.51 (s, 1H), 6.65 (s, 1H), 6.90 (dd, J=9.0, 2.7 Hz, 1H), 7.07 (d, J=2.7 Hz, 1H), 7.32 (d, J=8.7 Hz, 1H), 8.05 (s, 1H).

Example 150

N-[1-(6-{2-[4-(cyclopropylmethoxy)phenyl]ethyl}-1-benzofuran-2-yl)ethyl]acetamide

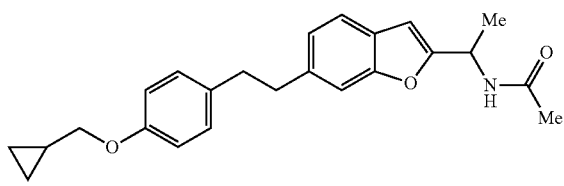 [SMILES: CC(=O)NC(C)c1cc2ccc(CCc3ccc(OCC4CC4)cc3)cc2o1]

To a solution of 2-(1-azidoethyl)-6-[2-[4-(cyclopropylmethoxy)phenyl]ethyl]-1-benzofuran (2.05 g, 5.67 mmol) obtained in Reference Example 283 in THF (30 mL)-water (5 mL) was added triphenylphosphine (1.79 g, 6.81 mmol), and the mixture was stirred at 60° C. for 15 hr. The solvent was evaporated under reduced pressure and the obtained residue was purified by basic silica gel column chromatography (hexane:ethyl acetate=3:1 to 1:4) to give 1-(6-{2-[4-(cyclopropy-lmethoxy)phenyl]ethyl}-1-benzofuran-2-yl)ethanamine. This was dissolved in pyridine (10 mL)-acetic anhydride (10 mL), and the solution was stirred at room temperature for 15 min. The solvent was evaporated under reduced pressure and the obtained residue was purified by purified by basic silica gel column chromatography (ethyl acetate) to give the title compound (1.40 g, yield from (2-(1-azidoethyl)-6-{2-[4-(cyclopropylmethoxy)phenyl]ethyl}-1-benzofuran 65%) as a white solid.

$^1$H NMR (CDCl$_3$) δ 0.31-0.36 (m, 2H), 0.60-0.66 (m, 2H), 1.22-1.33 (m, 1H), 1.55 (d, J=6.8 Hz, 3H), 2.01 (s, 3H), 2.85-2.91 (m, 2H), 2.95-3.01 (m, 2H), 3.77 (d, J=6.8 Hz, 2H), 5.28-5.38 (m, 1H), 5.82 (d, J=8.3 Hz, 1H), 6.51 (s, 1H), 6.82 (d, J=8.7 Hz, 2H), 7.03 (dd, J=8.0, 1.1 Hz, 1H), 7.07 (d, J=8.7 Hz, 2H), 7.23 (s, 1H), 7.40 (d, J=8.0 Hz, 1H).

Example 151

N-(1-{6-[2-(1,3-benzodioxol-5-yl)ethyl]-1-benzofuran-2-yl}ethyl)acetamide

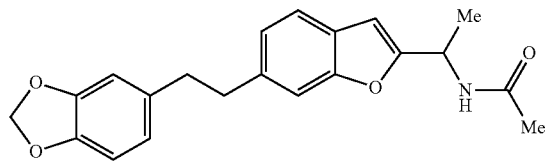 [SMILES: CC(=O)NC(C)c1cc2ccc(CCc3ccc4c(c3)OCO4)cc2o1]

To a solution of 5-{2-[2-(1-azidoethyl)-1-benzofuran-6-yl]ethyl}-1,3-benzodioxole (523 mg, 1.56 mmol) obtained in Reference Example 290 in THF (10 mL) was added triphenylphosphine (491 mg, 1.87 mmol), and the mixture was stirred at 60° C. for 30 min. To the reaction mixture was added water (1 mL), and the mixture was stirred at 60° C. for 15 hr. The solvent was evaporated under reduced pressure and the obtained residue was purified by basic silica gel column chromatography (hexane:ethyl acetate=13:7 to 0:1) to give 1-{6-[(2-(1,3-benzodioxol-5-yl)ethyl]-1-benzofuran-2-yl}ethanamine. This was dissolved in pyridine (5 mL)-acetic anhydride (5 mL), and the solution was stirred at room temperature for 15 min. The solvent was evaporated under reduced pressure and the obtained residue was purified by silica gel column chromatography (hexane:ethyl acetate=1:1 to ethyl acetate) to give the title compound (367 mg, yield from 5-{2-[2-(1-azidoethyl)-1-benzofuran-6-yl]ethyl}-1,3-benzodioxole 67%) as a white solid.

$^1$H NMR (CDCl$_3$) δ 1.56 (d, J=6.8 Hz, 3H), 2.02 (s, 3H), 2.84-2.89 (m, 2H), 2.95-3.00 (m, 2H), 5.29-5.39 (m, 1H), 5.81 (d, J=7.7 Hz, 1H), 5.92 (s, 2H), 6.52 (s, 1H), 6.60-6.63

(m, 1H), 6.68 (d, J=1.5 Hz, 1H), 6.72 (d, J=7.7 Hz, 1H), 7.02 (dd, J=7.9, 1.1 Hz, 1H), 7.23 (s, 1H), 7.40 (d, J=7.9 Hz, 1H).

Example 152

N-(1-{6-[2-(3,3-dimethyl-2,3-dihydro-1-benzofuran-5-yl)ethyl]-1-benzofuran-2-yl}ethyl)acetamide

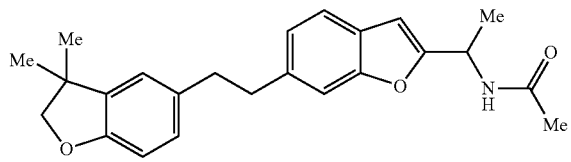 [SMILES: CC(=O)NC(C)c1cc2ccc(CCc3ccc4c(c3)C(C)(C)CO4)cc2o1]

To a solution of 2-(1-azidoethyl)-6-[2-(3,3-dimethyl-2,3-dihydro-1-benzofuran-5-yl)ethyl]-1-benzofuran (1.17 g, 3.70 mmol) obtained in Reference Example 299 in THF (20 mL) was added triphenylphosphine (1.17 g, 4.44 mmol), and the mixture was stirred at 60° C. for 30 min. To the reaction mixture was added water (2 mL), and the mixture was stirred at 60° C. for 2.5 hr. The solvent was evaporated under reduced pressure and the obtained residue was purified by basic silica gel column chromatography (hexane:ethyl acetate=7:3 to 1:4) to give 1-{6-[2-(3,3-dimethyl-2,3-dihydro-1-benzofuran-5-yl)ethyl]-1-benzofuran-2-yl}ethanamine. This was dissolved in pyridine (5 mL)-acetic anhydride (5 mL), and the solution was stirred at room temperature for 15 min. The solvent was evaporated under reduced pressure and the obtained residue was purified by silica gel column chromatography (hexane:ethyl acetate=1:1 to ethyl acetate) to give the title compound (978 mg, yield from 2-(1-azidoethyl)-6-[2-(3,3-dimethyl-2,3-dihydro-1-benzofuran-5-yl)ethyl]-1-benzofuran 70%) as a white solid.

$^1$H NMR (CDCl$_3$) δ 1.29 (s, 6H), 1.55 (d, J=6.8 Hz, 3H), 2.02 (s, 3H), 2.85-2.91 (m, 2H), 2.95-3.01 (m, 2H), 4.21 (s, 2H), 5.29-5.38 (m, 1H), 5.80 (d, J=7.6 Hz, 1H), 6.52 (s, 1H), 6.70 (d, J=8.3 Hz, 1H), 6.81 (d, J=1.9 Hz, 1H), 6.94 (dd, J=8.0, 2.0 Hz, 1H), 7.03 (dd, J=7.8, 1.3 Hz, 1H), 7.20 (s, 1H), 7.40 (d, J=8.0 Hz, 1H).

Example 153

N-[1-(5-{[6-(cyclopropylmethoxy)-2-fluoropyridin-3-yl]methoxy}-1-benzofuran-2-yl)ethyl]acetamide

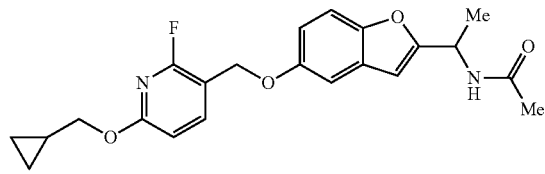

To a solution of [6-(cyclopropylmethoxy)-2-fluoropyridin-3-yl]methanol (99.0 mg, 0.502 mmol) obtained in Reference Example 262 in THF (5 mL) were added triethylamine (0.140 mL, 1.00 mmol) and methanesulfonyl chloride (0.595 mL, 0.753 mmol), and the mixture was stirred at room temperature for 30 min. The reaction mixture was diluted with ethyl acetate, and the mixture was washed with saturated aqueous sodium hydrogen carbonate solution, and dried over anhydrous magnesium sulfate. The solvent was evaporated under reduced pressure, and to a solution of the obtained residue and N-[1-(5-hydroxy-1-benzofuran-2-yl)ethyl]acetamide (retention time longer, 73.4 mg, 0.335 mmol) obtained in Reference Example 257 in DMF (5 mL) was added potassium carbonate (92.7 mg, 0.670 mmol). The mixture was stirred at 60° C. for 1 hr, water was added thereto and the mixture was extracted with ethyl acetate. The extract was washed twice with saturated brine, and dried over anhydrous magnesium sulfate. The solvent was evaporated under reduced pressure and the obtained residue was purified by preparative TLC (hexane:ethyl acetate=1:9) to give the title compound (37.7 mg, yield 28%) as a white solid.

$^1$H NMR (CDCl$_3$) δ 0.32-0.37 (m, 2H), 0.59-0.65 (m, 2H), 1.21-1.34 (m, 1H), 1.55 (d, J=6.8 Hz, 3H), 2.02 (s, 3H), 4.11 (d, J=7.2 Hz, 2H), 5.03 (s, 2H), 5.28-5.38 (m, 1H), 5.77 (d, J=8.3 Hz, 1H), 6.50 (s, 1H), 6.64 (d, J=8.3 Hz, 1H), 6.91 (dd, J=8.9, 2.5 Hz, 1H), 7.05 (d, J=2.3 Hz, 1H), 7.33 (d, J=9.1 Hz, 1H), 7.76-7.82 (m, 1H).

Example 154

N-[1-(5-{[6-(cyclopropylmethoxy)-4-fluoropyridin-3-yl]methoxy}-1-benzofuran-2-yl)ethyl]acetamide

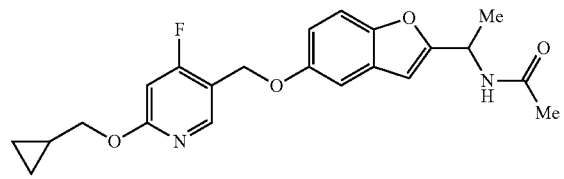 [SMILES: CC(=O)NC(C)c1cc2cc(OCc3cnc(OCC4CC4)cc3F)ccc2o1]

To a solution of N-[1-(5-hydroxy-1-benzofuran-2-yl)ethyl]acetamide (retention time longer, 1.31 g, 5.96 mmol) obtained in Reference Example 257 and 5-(bromomethyl)-2-(cyclopropylmethoxy)-4-fluoropyridine (2.32 g, 8.93 mmol) obtained in Reference Example 271 in DMF (15 mL) was added potassium carbonate (1.65 mg, 11.9 mmol), and the mixture was stirred at 60° C. for 45 min. Water was added thereto and the mixture was extracted with ethyl acetate. The extract was washed twice with saturated brine, and dried over anhydrous magnesium sulfate. The solvent was evaporated under reduced pressure and the obtained residue was purified by basic silica gel column chromatography (hexane:ethyl acetate=3:2 to 0:1) to give the title compound (1.90 g, yield 80%) as a white solid.

$^1$H NMR (CDCl$_3$) δ 0.32-0.37 (m, 2H), 0.58-0.64 (m, 2H), 1.20-1.33 (m, 1H), 1.56 (d, J=6.8 Hz, 3H), 2.02 (s, 3H), 4.14 (d, J=7.2 Hz, 2H), 5.04 (s, 2H), 5.29-5.38 (m, 1H), 5.79 (d,

J=8.0 Hz, 1H), 6.48-6.51 (m, 2H), 6.91 (dd, J=8.7, 2.7 Hz, 1H), 7.07 (d, J=2.7 Hz, 1H), 7.33 (d, J=9.1 Hz, 1H), 8.19 (d, J=10.2 Hz, 1H).

Example 155

N-{1-[5-({2-fluoro-4-[(2R)-tetrahydrofuran-2-yl-methoxy]benzyl}oxy)-1-benzofuran-2-yl]ethyl}acetamide

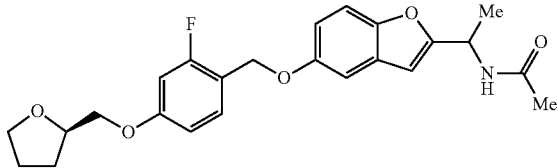 [SMILES: CC(=O)NC(C)c1cc2cc(OCc3ccc(OC[C@H]4CCCO4)cc3F)ccc2o1]

To a solution of (2R)-2-{[4-(bromomethyl)-3-fluorophenoxy]methyl}tetrahydrofuran (800 mg, 2.78 mmol) obtained in Reference Example 321 in DMF (5 mL) were added N-[1-(5-hydroxy-1-benzofuran-2-yl)ethyl]acetamide (retention time longer) (219 mg, 1.00 mmol) obtained in Reference Example 257 and potassium carbonate (415 mg, 3.00 mmol), and the mixture was stirred at 70° C. for 45 min. Water was added thereto and the mixture was extracted with ethyl acetate. The extract was washed twice with saturated brine, and dried over anhydrous magnesium sulfate. The solvent was evaporated under reduced pressure and the obtained residue was purified by basic silica gel column chromatography (hexane:ethyl acetate=1:1 to 0:1) to give the title compound (292 mg, yield 68%) as a white solid.

$^1$H NMR (CDCl$_3$) δ 1.55 (d, J=5.7 Hz, 3H), 1.69-1.81 (m, 1H), 1.90-2.13 (m, 6H), 3.80-3.97 (m, 4H), 4.22-4.30 (m, 1H), 5.05 (s, 2H), 5.28-5.38 (m, 1H), 5.78 (d, J=8.3 Hz, 1H), 6.50 (s, 1H), 6.65-6.74 (m, 2H), 6.92 (dd, J=8.7, 2.7 Hz, 1H), 7.05 (d, J=2.7 Hz, 1H), 7.30-7.39 (m, 2H).

Example 156

N-(1-{5-[2-(4-methoxyphenyl)ethyl]-1-benzofuran-2-yl}ethyl)acetamide

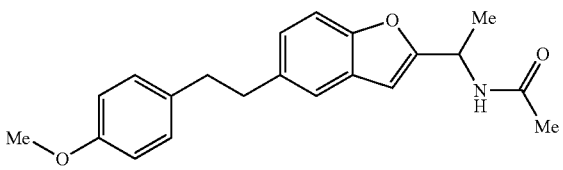 [SMILES: COc1ccc(CCc2ccc3oc(C(C)NC(C)=O)cc3c2)cc1]

To a solution of 2-(1-azidoethyl)-5-[2-(4-methoxyphenyl)ethyl]-1-benzofuran (1.39 g, 4.33 mmol) obtained in Reference Example 308 in THF (20 mL) was added triphenylphosphine (1.36 g, 5.20 mmol), and the mixture was stirred at 60° C. for 1 hr. To the reaction mixture was added water (2 mL), and the mixture was stirred at 60° C. for 15 hr. The solvent was evaporated under reduced pressure and the obtained residue was purified by basic silica gel column chromatography (hexane:ethyl acetate=1:1 to 0:1) to give 1-{5-[2-(4-methoxyphenyl)ethyl]-1-benzofuran-2-yl}ethanamine. This was dissolved in pyridine (30 mL)-acetic anhydride (15 mL), and the solution was stirred at room temperature for 2 hr. The solvent was evaporated under reduced pressure and the obtained residue was recrystallized from hexane-ethyl acetate to give the title compound (978 mg, yield 81%) as colorless crystals.

$^1$H NMR (CDCl$_3$) δ 1.56 (d, J=6.8 Hz, 3H), 2.02 (s, 3H), 2.82-3.00 (m, 4H), 3.79 (s, 3H), 5.28-5.40 (m, 1H), 5.82 (d, J=7.9 Hz, 1H), 6.49 (s, 1H), 6.78-6.85 (m, 2H), 7.03-7.11 (m, 3H), 7.27-7.35 (m, 2H).

Example 157

N-(1-{5-[2-(4-hydroxyphenyl)ethyl]-1-benzofuran-2-yl}ethyl)acetamide

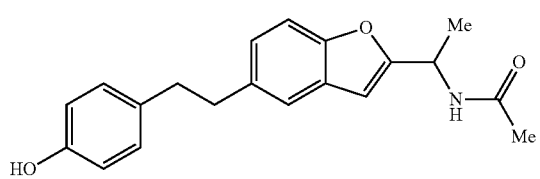 [SMILES: CC(=O)NC(C)c1cc2cc(CCc3ccc(O)cc3)ccc2o1]

To a solution of N-(1-{5-[2-(4-methoxyphenyl)ethyl]-1-benzofuran-2-yl}ethyl)acetamide (922 mg, 2.73 mmol) obtained in Example 156 in methylene chloride (50 mL) was added 1M boron tribromide-methylene chloride solution (5.46 mL, 5.46 mmol) at −78° C., and the mixture was stirred at the same temperature for 4 hr. The reaction mixture was warmed to 0° C., and methanol was added thereto. The solvent was evaporated under reduced pressure, and the residue was extracted with ethyl acetate and water. The organic layer was washed with saturated brine, and dried over anhydrous magnesium sulfate. The solvent was evaporated under reduced pressure and the obtained residue was recrystallized from hexane-ethyl acetate to give the title compound (774 mg, yield 88%) as colorless crystals.

$^1$H-NMR (DMSO-d$_6$) δ 1.43 (d, J=6.8 Hz, 3H), 1.85 (s, 3H), 2.71-2.96 (m, 4H), 5.03-5.16 (m, 1H), 6.59-6.69 (m, 3H), 6.98 (d, J=8.3 Hz, 2H), 7.08 (d, J=8.3 Hz, 1H), 7.32-7.43 (m, 2H), 8.37 (d, J=8.3 Hz, 1H), 9.10 (br s, 1H).

Example 158

N-(1-{5-[2-(4-propoxyphenyl)ethyl]-1-benzofuran-2-yl}ethyl)acetamide

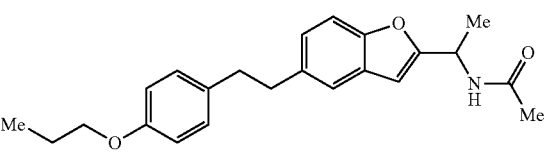 [SMILES: CCCOc1ccc(CCc2ccc3oc(C(C)NC(C)=O)cc3c2)cc1]

A suspension of N-(1-{5-[2-(4-hydroxyphenyl)ethyl]-1-benzofuran-2-yl}ethyl)acetamide (333 mg, 1.03 mmol) obtained in Example 157, bromopropane (1.08 g, 6.37 mmol) and potassium carbonate (924 mg, 6.68 mmol) in DMF (10 mL) was stirred at 80° C. for 2 days. Water was added thereto, and the mixture was extracted with ethyl acetate. The extract was washed with saturated brine, and dried over anhydrous magnesium sulfate. The solution was applied to silica gel column chromatography (hexane:ethyl acetate=9:11 to 0:1), and recrystallized from hexane-ethyl acetate to give the title compound (294 mg, yield 78%) as colorless crystals.

¹H NMR (CDCl₃) δ 1.03 (t, J=7.3 Hz, 3H), 1.56 (d, J=6.8 Hz, 3H), 1.72-1.87 (m, 2H), 2.01 (s, 3H), 2.82-3.00 (m, 4H), 3.89 (t, J=6.6 Hz, 2H), 5.28-5.39 (m, 1H), 5.83 (d, J=8.3 Hz, 1H), 6.49 (s, 1H), 6.77-6.84 (m, 2H), 7.03-7.09 (m, 3H), 7.27-7.35 (m, 2H).

Example 159

N-[1-(5-{2-[4-(cyclopropylmethoxy)phenyl]ethyl}-1-benzofuran-2-yl)ethyl]acetamide

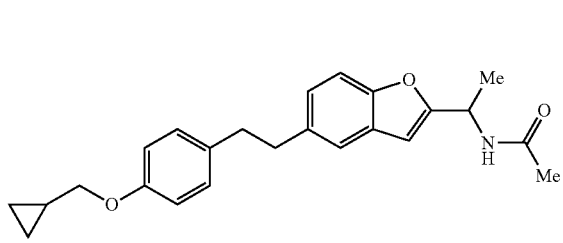

Using N-(1-{5-[2-(4-hydroxyphenyl)ethyl]-1-benzofuran-2-yl}ethyl)acetamide (328 mg, 1.01 mmol) obtained in Example 157 and (bromomethyl)cyclopropane (3.97 g, 29.3 mmol) and in the same manner as in Example 158, the title compound was obtained (122 mg, yield 32%) as colorless crystals.

¹H NMR (CDCl₃) δ 0.30-0.37 (m, 2H), 0.59-0.68 (m, 2H), 1.19-1.34 (m, 1H), 1.56 (d, J=7.2 Hz, 3H), 2.02 (s, 3H), 2.81-3.00 (m, 4H), 3.77 (d, J=6.8 Hz, 2H), 5.28-5.40 (m, 1H), 5.80 (d, J=8.0 Hz, 1H), 6.49 (s, 1H), 6.78-6.84 (m, 2H), 7.03-7.09 (m, 3H), 7.27-7.35 (m, 2H).

Example 160

N-(1-{5-[2-(4-butoxyphenyl)ethyl]-1-benzofuran-2-yl}ethyl)acetamide

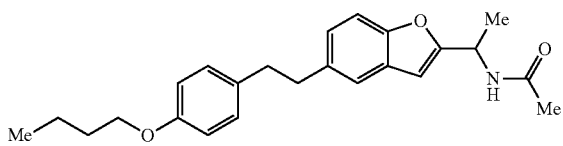 [SMILES: CCCCOc1ccc(CCc2ccc3oc(C(C)NC(C)=O)cc3c2)cc1]

Using N-(1-{5-[2-(4-hydroxyphenyl)ethyl]-1-benzofuran-2-yl}ethyl)acetamide (124 mg, 0.348 mmol) obtained in Example 157 and bromobutane (263 mg, 1.92 mmol) and in the same manner as in Example 158, the title compound was obtained (96.3 mg, yield 66%) as colorless crystals.

¹H NMR (CDCl₃) δ 0.97 (t, J=7.3 Hz, 3H), 1.42-1.60 (m, 5H), 1.69-1.82 (m, 2H), 2.02 (s, 3H), 2.82-2.99 (m, 4H), 3.93 (t, J=6.6 Hz, 2H), 5.27-5.40 (m, 1H), 5.81 (d, J=8.3 Hz, 1H), 6.49 (s, 1H), 6.78-6.84 (m, 2H), 7.03-7.09 (m, 3H), 7.28-7.35 (m, 2H).

Example 161

N-[1-(6-{[4-(cyclopropylmethoxy)-2-fluorobenzyl]oxy}-1-benzofuran-3-yl)ethyl]acetamide

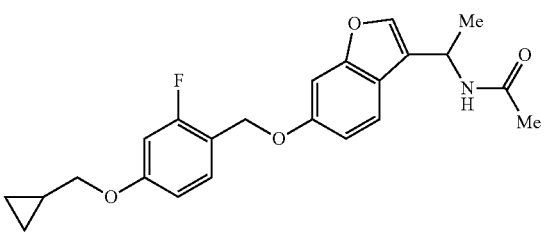 [SMILES: CC(=O)NC(C)c1coc2cc(OCc3ccc(OCC4CC4)cc3F)ccc12]

To a solution of [4-(cyclopropylmethoxy)-2-fluorophenyl]methanol (414 mg, 2.10 mmol) obtained in Reference Example 230 in toluene (10 mL) was added thionyl chloride (752 mg, 6.32 mmol), and the mixture was stirred at room temperature for 1 hr and concentrated under reduced pressure. To the obtained 1-(chloromethyl)-4-(cyclopropylmethoxy)-2-fluorobenzene (199 mg, 0.93 mmol) were added DMF (10 mL), N-[1-(6-hydroxy-1-benzofuran-3-yl)ethyl]acetamide (136 mg, 0.619 mmol) obtained in Reference Example 4 and potassium carbonate (171 mg, 1.24 mmol), and the mixture was stirred at 50° C. for 3 hr. Water was added thereto and the mixture was extracted with ethyl acetate. The extract was washed with saturated brine, and dried over anhydrous sodium sulfate. The 15 solvent was evaporated under reduced pressure and the obtained residue was purified by basic silica gel column chromatography (hexane:ethyl acetate=50:50 to 0:100), and recrystallized from hexane-ethyl acetate to give the title compound (132 mg, yield 53%) as colorless crystals.

¹H NMR (CDCl₃) δ 0.31-0.38 (m, 2H), 0.61-0.70 (m, 2H), 1.20-1.33 (m, 1H), 1.59 (d, J=6.8 Hz, 3H), 1.99 (s, 3H), 3.79 (d, J=6.8 Hz, 2H), 5.07 (s, 2H), 5.33-5.45 (m, 1H), 5.57 (d, J=8.7 Hz, 1H), 6.61-6.73 (m, 2H), 6.94 (dd, J=8.7, 2.3 Hz, 1H), 7.08 (d, J=2.3 Hz, 1H), 7.33-7.40 (m, 1H), 7.43-7.49 (m, 2H).

Example 162

N-[1-(6-{[4-(cyclopropylmethoxy)benzyl]oxy}-1-benzofuran-3-yl)ethyl]acetamide

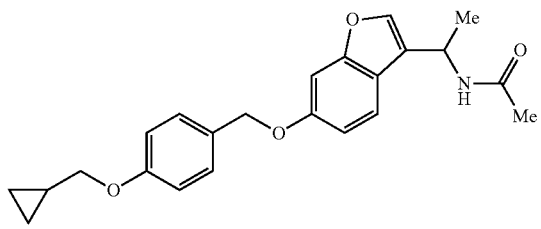 [SMILES: CC(=O)NC(C)c1coc2cc(OCc3ccc(OCC4CC4)cc3)ccc12]

To a solution of [4-(cyclopropylmethoxy)phenyl]methanol (428 mg, 2.40 mmol) in toluene (10 mL) was added thionyl chloride (856 mg, 7.20 mmol), and the mixture was stirred at room temperature for 1 hr and concentrated under reduced pressure. To the obtained 1-(chloromethyl)-4-(cyclopropylmethoxy)benzene (179 mg, 0.910 mmol) were added DMF (10 mL), N-[1-(6-hydroxy-1-benzofuran-3-yl)ethyl]acetamide (133 mg, 0.607 mmol) obtained in Reference Example 4 and potassium carbonate (168 mg, 1.21 mmol) and the mixture was stirred at 50° C. for 17 hr. Water was added thereto and the mixture was extracted with ethyl acetate. The extract was washed with saturated brine, and dried over anhydrous sodium sulfate. The solvent was evaporated under reduced pressure and the obtained residue was purified by basic silica gel column chromatography (hexane:ethyl acetate=50:50 to 0:100) and recrystallized from hexane-ethyl acetate to give the title compound (110 mg, yield 48%) as colorless crystals.

$^1$H NMR (CDCl$_3$) δ 0.31-0.39 (m, 2H), 0.60-0.69 (m, 2H), 1.20-1.34 (m, 1H), 1.59 (d, J=6.8 Hz, 3H), 1.99 (s, 3H), 3.81 (d, J=6.8 Hz, 2H), 5.02 (s, 2H), 5.33-5.45 (m, 1H), 5.56 (d, J=8.3 Hz, 1H), 6.89-6.97 (m, 3H), 7.06 (d, J=2.3 Hz, 1H), 7.33-7.38 (m, 2H), 7.41-7.49 (m, 2H).

Example 163

N-[1-(6-{[6-(cyclopropylmethoxy)-4-fluoropyridin-3-yl]methoxy}-1-benzofuran-3-yl)ethyl]acetamide

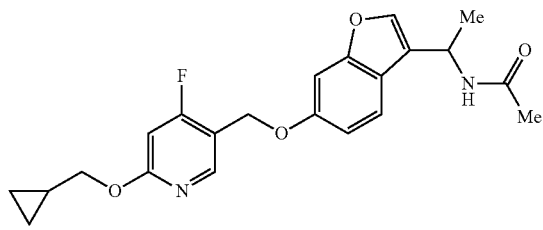

To a solution of N-[1-(6-hydroxy-1-benzofuran-3-yl)ethyl]acetamide (retention time longer) (127 mg, 0.577 mmol) obtained in Reference Example 309 and 5-(bromomethyl)-2-(cyclopropylmethoxy)-4-fluoropyridine (125 mg, 0.481 mmol) obtained in Reference Example 271 in DMF (10 mL) was added potassium carbonate (99.7 mg, 0.721 mmol), and the mixture was stirred at 60° C. for 18 hr. Water was added thereto and the mixture was extracted with ethyl acetate. The extract was washed with saturated brine, and dried over anhydrous magnesium sulfate. The solvent was evaporated under reduced pressure and the obtained residue was purified by basic silica gel column chromatography (hexane:ethyl acetate=1:1 to 0:1) and recrystallized from hexane-ethyl acetate to give the title compound (87.5 mg, yield 46%) as colorless crystals.

$^1$H NMR (CDCl$_3$) δ 0.30-0.38 (m, 2H), 0.58-0.66 (m, 2H), 1.20-1.36 (m, 1H), 1.59 (d, J=6.8 Hz, 3H), 2.00 (s, 3H), 4.14 (d, J=7.2 Hz, 2H), 5.06 (s, 2H), 5.34-5.46 (m, 1H), 5.57 (d, J=8.3 Hz, 1H), 6.50 (d, J=10.9 Hz, 1H), 6.93 (dd, J=8.7, 2.3 Hz, 1H), 7.09 (d, J=1.9 Hz, 1H), 7.44-7.52 (m, 2H), 8.20 (d, J=10.2 Hz, 1H).

Example 164

N-[1-(6-{[6-(cyclopropylmethoxy)-2-fluoropyridin-3-yl]methoxy}-1-benzofuran-3-yl)ethyl]acetamide

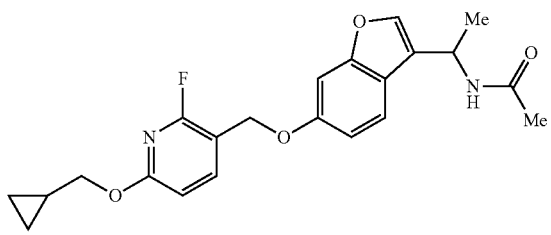

To a solution of N-[1-(6-hydroxy-1-benzofuran-3-yl)ethyl]acetamide (retention time longer) (142 mg, 0.647 mmol) obtained in Reference Example 309 and 3-(bromomethyl)-6-(cyclopropylmethoxy)-2-fluoropyridine (140 mg, 0.539 mmol) obtained in Reference Example 263 in DMF (10 mL) was added potassium carbonate (112 mg, 0.808 mmol), and the mixture was stirred at 60° C. for 18 hr. Water was added thereto and the mixture was extracted with ethyl acetate. The extract was washed with saturated brine, and dried over anhydrous magnesium sulfate. The solvent was evaporated under reduced pressure and the obtained residue was purified by basic silica gel column chromatography (hexane:ethyl acetate=1:1 to 0:1), and recrystallized from hexane-ethyl acetate to give the title compound (89.5 mg, yield 42%) as colorless crystals.

$^1$H NMR (CDCl$_3$) δ 0.31-0.39 (m, 2H), 0.58-0.66 (m, 2H), 1.21-1.35 (m, 1H), 1.59 (d, J=6.8 Hz, 3H), 2.00 (s, 3H), 4.11 (d, J=7.2 Hz, 2H), 5.05 (s, 2H), 5.37-5.44 (m, 1H), 5.57 (d, J=8.7 Hz, 1H), 6.66 (d, J=7.2 Hz, 1H), 6.93 (dd, J=8.7, 2.3 Hz, 1H), 7.07 (d, J=1.9 Hz, 1H), 7.44-7.51 (m, 2H), 7.79 (dd, J=9.8, 8.3 Hz, 1H).

Example 165

N-(1-{6-[2-(4-hydroxyphenyl)ethyl]-1-benzofuran-2-yl}ethyl)acetamide

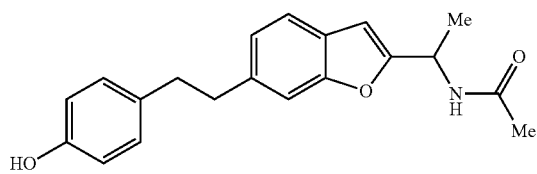 [SMILES: CC(=O)NC(C)c1cc2ccc(CCc3ccc(O)cc3)cc2o1]

To a solution of N-[1-(6-{2-[4-(methoxymethoxy)phenyl]ethyl}-1-benzofuran-2-yl)ethyl]acetamide (200 mg, 0.545°mmol) obtained in Example 95 in THF (5 mL) was added 6N hydrochloric acid (0.910 mL), and the mixture was stirred at 60° C. for 40 min. The reaction mixture was neutralized with saturated aqueous sodium hydrogen carbonate solution and extracted twice with ethyl acetate, and the combined organic layer was dried over anhydrous magnesium sulfate. The solvent was evaporated and the obtained solid

Example 166

N-[1-(6-{2-[4-(2-methoxyethoxy)phenyl]ethyl}-1-benzofuran-2-yl)ethyl]acetamide

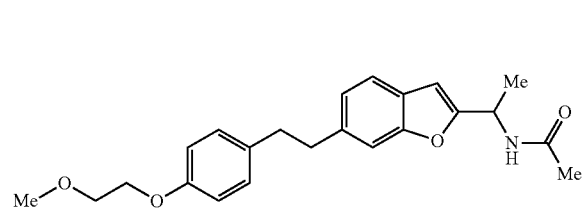

Using N-(1-{6-[2-(4-hydroxyphenyl)ethyl]-1-benzofuran-2-yl}ethyl)acetamide (32.3 mg, 0.100 mmol) obtained in Example 165 and 2-chloroethyl methyl ether (0.0189 mL, 0.200 mmol) and in the same manner as in Example 158, the title compound was obtained (9.4 mg, yield 25%) as a white solid.

$^1$H NMR (CDCl$_3$) δ 1.54-1.60 (m, 3H), 2.02 (s, 3H), 2.84-3.03 (m, 4H), 3.45 (s, 3H), 3.72-3.78 (m, 2H), 4.08-4.14 (m, 2H), 5.28-5.40 (m, 1H), 5.79 (d, J=8.7 Hz, 1H), 6.52 (s, 1H), 6.84 (d, J=8.6 Hz, 2H), 7.02 (d, J=8.0 Hz, 1H), 7.07 (d, J=8.6 Hz, 2H), 7.22 (m, 1H), 7.40 (d, J=8.0 Hz, 1H).

Example 167

N-[1-(6-{2-[4-(3-methoxypropoxy)phenyl]ethyl}-1-benzofuran-2-yl)ethyl]acetamide

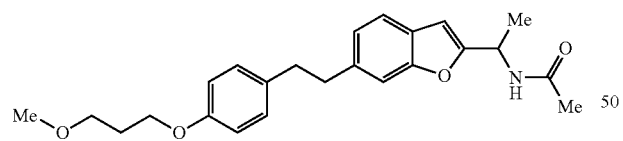

Using N-(1-{6-[2-(4-hydroxyphenyl)ethyl]-1-benzofuran-2-yl}ethyl)acetamide (32.3 mg, 0.100 mmol) obtained in Example 165 and 1-bromomethoxypropane (0.0306 mL, 0.200 mmol) and in the same manner as in Example 158, the title compound was obtained (10.5 mg, yield 27%) as a white solid.

$^1$H NMR (CDCl$_3$) δ 1.52-1.63 (m, 3H), 2.00-2.10 (m, 2H), 2.02 (s, 3H), 2.83-3.06 (m, 4H), 3.35 (s, 3H), 3.55 (t, J=6.1 Hz, 2H), 4.03 (t, J=6.1 Hz, 2H), 5.28-5.40 (m, 1H), 5.80 (d, J=8.0 Hz, 1H), 6.52 (s, 1H), 6.82 (d, J=8.6 Hz, 2H), 7.03 (d, J=8.0 Hz, 1H), 7.08 (d, J=8.6 Hz, 2H), 7.21-7.29 (m, 1H), 7.40 (d, J=8.0 Hz, 1H).

Example 168

N-[1-(6-{2-[4-(2-methylpropoxy)phenyl]ethyl}-1-benzofuran-2-yl)ethyl]acetamide

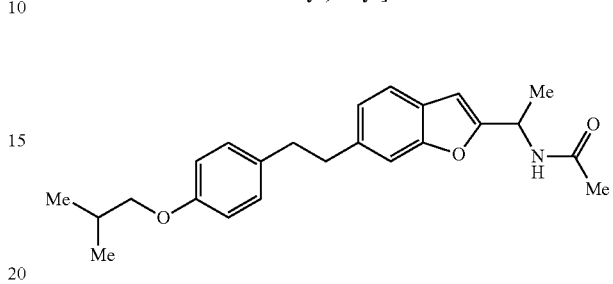

Using N-(1-{6-[2-(4-hydroxyphenyl)ethyl]-1-benzofuran-2-yl}ethyl)acetamide (32.3 mg, 0.100 mmol) obtained in Example 165 and 1-bromo-2-methylpropane (0.0225 mL, 0.200 mmol) and in the same manner as in Example 158, the title compound was obtained (10.3 mg, yield 27%) as a white solid.

$^1$H NMR (CDCl$_3$) δ 1.02 (d, J=6.8 Hz, 6H), 1.53-1.58 (m, 3H), 2.00-2.09 (m, 4H), 2.83-3.06 (m, 4H), 3.70 (d, J=6.4 Hz, 2H), 5.27-5.40 (m, 1H), 5.78 (d, J=8.7 Hz, 1H), 6.52 (s, 1H), 6.81 (d, J=8.6 Hz, 2H), 7.03 (dd, J=8.0, 1.5 Hz, 1H), 7.08 (d, J=8.6 Hz, 2H), 7.24 (s, 1H), 7.40 (d, J=8.0 Hz, 1H).

Example 169

N-{1-[6-(2-{4-[2-(methylsulfanyl)ethoxy]phenyl}ethyl)-1-benzofuran-2-yl]ethyl}acetamide

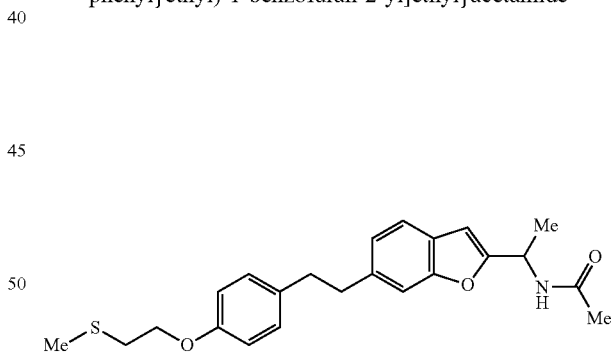

Using N-(1-{6-[2-(4-hydroxyphenyl)ethyl]-1-benzofuran-2-yl}ethyl)acetamide (150 mg, 0.464 mmol) obtained in Example 165 and 2-chloroethylmethylsulfide (0.182 mL, 1.86 mmol) and in the same manner as in Example 158, the title compound was obtained (91.9 mg, yield 50%) as a white solid.

$^1$H NMR (CDCl$_3$) δ 1.51-1.62 (m, 3H), 2.02 (s, 3H), 2.21 (s, 3H), 2.81-3.09 (m, 6H), 4.14 (t, J=6.8 Hz, 2H), 5.27-5.41 (m, 1H), 5.79 (d, J=9.0 Hz, 1H), 6.52 (s, 1H), 6.82 (d, J=8.5

Hz, 2H), 7.03 (d, J=7.9 Hz, 1H), 7.08 (d, J=8.5 Hz, 2H), 7.23 (s, 1H), 7.40 (d, J=7.9 Hz, 1H).

Example 170

N-[1-(6-{2-[4-(cyclopentyloxy)phenyl]ethyl}-1-benzofuran-2-yl)ethyl]acetamide

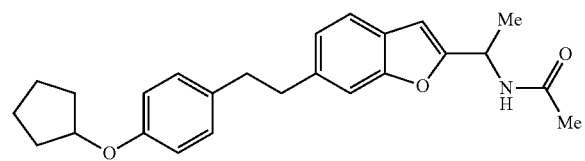 [SMILES: CC(=O)NC(C)c1cc2ccc(CCc3ccc(OC4CCCC4)cc3)cc2o1]

Using N-(1-{6-[2-(4-hydroxyphenyl)ethyl]-1-benzofuran-2-yl}ethyl)acetamide (40.0 mg, 0.123 mmol) obtained in Example 165 and bromocyclopentane (0.147 mL, 1.85 mmol) and in the same manner as in Example 158, the title compound was obtained (11.9 mg, yield 25%) as a white solid.

$^1$H NMR (CDCl$_3$) δ 1.42-1.93 (m, 11H), 2.02 (s, 3H), 2.80-3.04 (m, 4H), 4.73 (br, 1H), 5.25-5.44 (m, 1H), 5.77 (d, J=8.3 Hz, 1H), 6.52 (s, 1H), 6.79 (d, J=8.3 Hz, 2H), 6.98-7.11 (m, 3H), 7.26 (s, 1H), 7.40 (d, J=7.5 Hz, 1H).

Example 171

N-(1-{5-[(2-methyl-1,3-benzoxazol-6-yl)methoxy]-1-benzofuran-2-yl}ethyl)acetamide

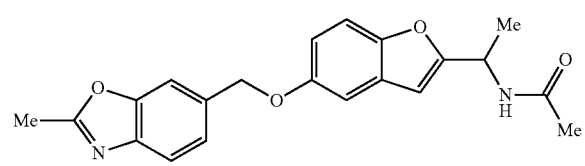 [SMILES: CC(=O)NC(C)c1cc2cc(OCc3ccc4nc(C)oc4c3)ccc2o1]

To a suspension of (2-methyl-1,3-benzoxazol-6-yl)methanol (66.5 mg, 0.408 mmol) in toluene (1 mL) were added carbon tetrabromide (135 mg, 0.408 mmol) and triphenylphosphine (106 mg, 0.408 mmol) and the mixture was stirred at room temperature for 30 min. The reaction mixture was directly applied to silica gel, and concentrated to dryness to give 6-(bromomethyl)-2-methyl-1,3-benzoxazole as an oil. To the obtained oil (92.0 mg, 0.408 mmol) were added DMF (4 mL), N-[1-(5-hydroxy-1-benzofuran-2-yl)ethyl]acetamide (30.0 mg, 0.136 mmol) obtained in Reference Example 38 and potassium carbonate (37.8 mg, 0.274 mmol), and the mixture was stirred at 50° C. for 2 hr. The reaction mixture was directly purified by basic silica gel column chromatography (hexane:ethyl acetate-4:1 to 3:7), and the solvent was evaporated. The residue was triturated with a small amount of ethyl acetate and diethyl ether to give the title compound (17.8 mg, yield 36%) as a white solid.

$^1$H NMR (CDCl$_3$) δ 1.50-1.56 (m, 3H), 2.02 (s, 3H), 2.64 (s, 3H), 5.19 (s, 2H), 5.26-5.41 (m, 1H), 5.76 (d, J=9.5 Hz, 1H), 6.49 (s, 1H), 6.94 (dd, J=8.7, 2.7 Hz, 1H), 7.05 (d, J=2.3 Hz, 1H), 7.30-7.40 (m, 2H), 7.58 (s, 1H), 7.64 (d, J=8.4 Hz, 1H).

Example 172

N-[1-(6-{2-[4-(pyridin-2-yloxy)phenyl]ethyl}-1-benzofuran-2-yl)ethyl]acetamide

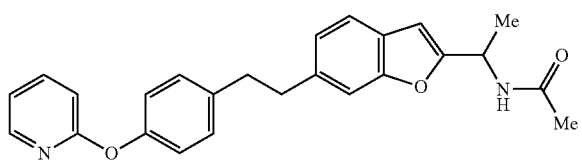 [SMILES: CC(=O)NC(C)c1cc2ccc(CCc3ccc(Oc4ccccn4)cc3)cc2o1]

N-(1-{6-[2-(4-hydroxyphenyl)ethyl]-1-benzofuran-2-yl}ethyl)acetamide (40.0 mg, 0.123 mmol) obtained in Example 165, 2-fluoropyridine (0.0369 mL, 0.371 mmol) and potassium carbonate (51.3 mg, 0.371 mmol) were stirred in DMSO (0.5 mL) at 100° C. for 2 days. The reaction mixture was purified by basic silica gel column chromatography (hexane:ethyl acetate=1:0 to 2:3), and the solvent was evaporated. The residue was triturated with a small amount of diisopropyl ether to give the title compound (17.1 mg, yield 35%) as a white solid.

$^1$H NMR (CDCl$_3$) δ 1.48-1.71 (m, 3H), 2.02 (s, 3H), 2.90-3.12 (m, 4H), 5.28-5.43 (m, 1H), 5.78 (d, J=8.3 Hz, 1H), 6.53 (s, 1H), 6.89 (d, J=8.3 Hz, 1H), 6.94-7.01 (m, 1H), 7.02-7.10 (m, 3H), 7.16-7.35 (m, 3H), 7.42 (d, J=8.0 Hz, 1H), 7.62-7.74 (m, 1H), 8.14-8.26 (m, 1H).

Example 173

N-[1-(6-{2-[4-(cyclobutylmethoxy)phenyl]ethyl}-1-benzofuran-2-yl)ethyl]acetamide

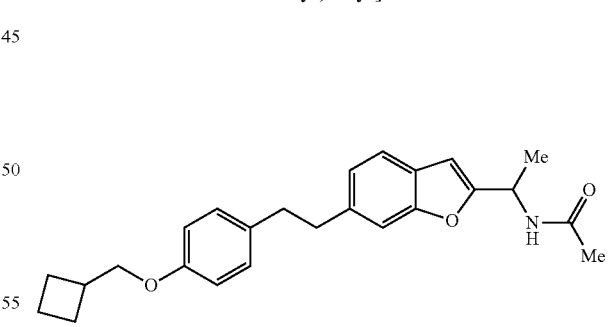

Using N-(1-{6-[2-(4-hydroxyphenyl)ethyl]-1-benzofuran-2-yl}ethyl)acetamide (150 mg, 0.464 mmol) obtained in Example 165 and (bromomethyl)cyclobutane (0.155 mL, 1.39 mmol) and in the same manner as in Example 158, the title compound was obtained (127 mg, yield 70%) as a white solid.

$^1$H NMR (CDCl$_3$) δ 1.54-1.58 (m, 3H), 1.79-2.00 (m, 4H), 2.02 (s, 3H), 2.07-2.20 (m, 2H), 2.69-2.83 (m, 1H), 2.84-3.03 (m, 4H), 3.90 (d, J=6.8 Hz, 2H), 5.28-5.40 (m, 1H), 5.77 (d,

J=7.6 Hz, 1H), 6.52 (s, 1H), 6.78-6.85 (m, 2H), 7.03 (dd, J=8.0, 1.1 Hz, 1H), 7.08 (d, J=8.3 Hz, 2H), 7.24 (s, 1H), 7.40 (d, J=8.0 Hz, 1H).

Example 174

N-[1-(6-{2-[4-(2-cyclopropylethoxy)phenyl]ethyl}-1-benzofuran-2-yl)ethyl]acetamide

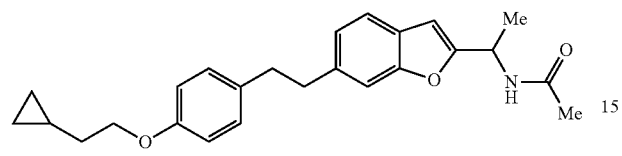

To a solution of N-(1-{6-[2-(4-hydroxyphenyl)ethyl]-1-benzofuran-2-yl}ethyl)acetamide (50.0 mg, 0.154 mmol) obtained in Example 165, 2-cyclopropylethanol (0.0529 mL, 0.616 mmol) and triphenylphosphine (161 mg, 0.616 mmol) in THF (1 mL) were added di(methoxyethyl) azodicarboxylate (144 mg, 0.616 mmol), and the mixture was stirred at room temperature for 30 min. The reaction mixture was directly purified by basic silica gel column chromatography (hexane:ethyl acetate=1:0 to 2:3), and the solvent was evaporated. The residue was triturated with a small amount of diisopropyl ether and hexane to give the title compound (25.9 mg, yield 43%) as a white solid.

$^1$H NMR (CDCl$_3$) δ 0.09-0.15 (m, 2H), 0.43-0.53 (m, 2H), 0.78-0.94 (m, 1H), 1.47-1.61 (m, 3H), 1.63-1.70 (m, 2H), 2.02 (s, 3H), 2.82-3.04 (m, 4H), 4.01 (t, J=6.6 Hz, 2H), 5.26-5.43 (m, 1H), 5.79 (br, 1H), 6.52 (s, 1H), 6.78-6.87 (m, 2H), 7.00-7.11 (m, 3H), 7.24 (s, 1H), 7.40 (d, J=8.1 Hz, 1H).

Example 175

N-(1-{6-[(3-bromo-4-ethoxybenzyl)oxy]-1-benzofuran-2-yl}ethyl)acetamide

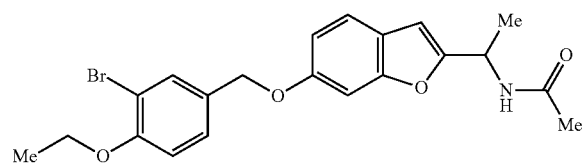 [SMILES: CCOc1ccc(COc2ccc3cc(C(C)NC(C)=O)oc3c2)cc1Br]

To 2-bromo-4-(bromomethyl)-1-ethoxybenzene (2.47 g) obtained in Reference Example 323 were added DMF (10 mL), N-[1-(6-hydroxy-1-benzofuran-2-yl)ethyl]acetamide (1.40 g, 6.39 mmol) obtained in Reference Example 27 and potassium carbonate (1.76 g, 12.8 mmol), and the mixture was stirred at 100° C. overnight. Water was added thereto and the mixture was extracted three times with ethyl acetate. The combined organic layer was washed with saturated brine, and dried over magnesium sulfate. The solvent was evaporated under reduced pressure, and the residue was purified by basic silica gel column chromatography (hexane:ethyl acetate=9:1 to 2:3), and the solvent was evaporated. The residue was triturated with a small amount of hexane and diisopropyl ether to give the title compound (1.28 g, yield 46%) as a white solid.

$^1$H NMR (CDCl$_3$) δ 1.48 (t, J=7.0 Hz, 3H), 1.47-1.54 (m, 3H), 2.02 (s, 3H), 4.11 (q, J=7.0 Hz, 2H), 4.99 (s, 2H), 5.23-5.42 (m, 1H), 5.76 (d, J=8.3 Hz, 1H), 6.49 (s, 1H), 6.85-6.96 (m, 2H), 7.02 (d, J=1.9 Hz, 1H), 7.32 (dd, J=8.5, 2.1 Hz, 1H), 7.38 (d, J=8.3 Hz, 1H), 7.64 (d, J=2.2 Hz, 1H).

Example 176

N-[1-(6-{2-[4-(cyclopropylmethoxy)phenyl]ethyl}-1-benzofuran-2-yl)ethyl]isoxazol-3-amine

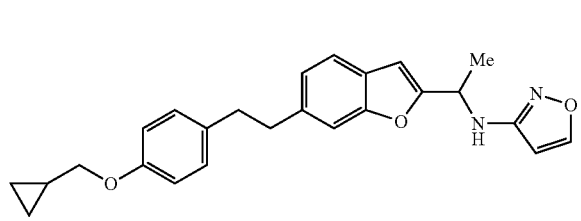 [SMILES: CC(Nc1ccon1)c1cc2ccc(CCc3ccc(OCC4CC4)cc3)cc2o1]

To a solution of 1-(6-{2-[4-(cyclopropylmethoxy)phenyl]ethyl}-1-benzofuran-2-yl)ethanol (100 mg, 0.298 mmol) obtained in Reference Example 282 in THF (2 mL) was added thionyl chloride (0.0390 ml 0.535 mmol), and the mixture was stirred at room temperature for 1 hr. To the reaction mixture was added aqueous sodium hydrogen carbonate solution, and the mixture was extracted twice with ethyl acetate. The combined organic layer was washed with saturated brine, and dried over magnesium sulfate. The solvent was evaporated under reduced pressure and to the obtained residue were added DMF (1 mL), sodium iodide (80.0 mg, 0.573 mmol) and 3-aminoisoxazole (0.0266 mL, 0.358 mmol), and the mixture was stirred at 60° C. for 1 hr. Water was added to the reaction mixture, and the mixture was extracted twice with ethyl acetate. The combined organic layer was washed with saturated brine, and dried over magnesium sulfate. The solvent was evaporated under reduced pressure and the obtained residue was purified by silica gel column chromatography (hexane:ethyl acetate=1:0 to 3:2), and the solvent was evaporated. The residue was triturated with a small amount of hexane, diisopropyl ether and toluene to give the title compound (18.6 mg, yield 16%) as a white solid.

$^1$H NMR (CDCl$_3$) δ 0.29-0.39 (m, 2H), 0.59-0.71 (m, 2H), 1.18-1.35 (m, 1H), 1.66 (d, J=6.8 Hz, 3H), 2.81-3.04 (m, 4H), 3.78 (d, J=6.8 Hz, 2H), 4.30 (d, J=8.0 Hz, 1H), 4.80-4.98 (m, 1H), 5.86 (d, J=1.9 Hz, 1H), 6.55 (s, 1H), 6.82 (d, J=8.3 Hz, 2H), 7.02 (d, J=8.0 Hz, 1H), 7.08 (d, J=8.3 Hz, 2H), 7.23 (s, 1H), 7.39 (d, J=8.0 Hz, 1H), 8.04 (d, J=2.1 Hz, 1H).

Example 177

N-[1-(6-{2-[4-(cyclopropylmethoxy)phenyl]ethyl}-1-benzofuran-2-yl)ethyl]aniline 4-toluenesulfonate

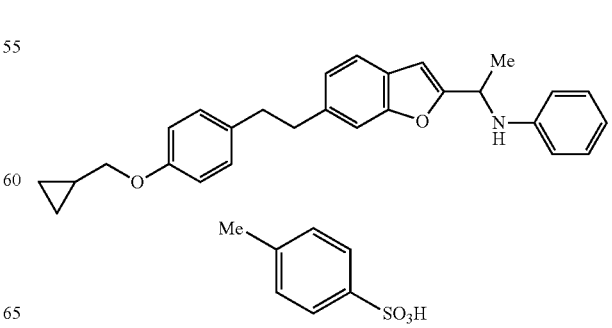

To a solution of 1-(6-{2-[4-(cyclopropylmethoxy)phenyl]ethyl}-1-benzofuran-2-yl)ethanone (50.0 mg, 0.149 mmol) obtained in Reference Example 281 and aniline (13.9 mg, 0.149 mmol) in THF (0.5 mL)-methanol (0.5 mL) was added decaborane (18.2 mg 0.149 mmol), and the mixture was stirred at room temperature for 1 hr. Water was added to the reaction mixture, and the mixture was extracted twice with ethyl acetate. The combined organic layer was washed with saturated brine, and dried over magnesium sulfate. The solvent was evaporated under reduced pressure and the obtained residue was purified by silica gel column chromatography (hexane:ethyl acetate=1:0 to 3:2) and basic silica gel column chromatography (hexane:ethyl acetate=1:0 to 3:2). After evaporation of the solvent, to a solution of the obtained oil in ethyl acetate was added 4-toluenesulfonic acid monohydrate (13.6 mg, 0.0715 mmol), and the mixture was stirred at room temperature. The resulting solid was collected by filtration to give the title compound (19.9 mg, yield 23%) as a white solid.

$^1$H NMR (CDCl$_3$) δ0.26-0.42 (m, 2H), 0.57-0.68 (m, 2H), 1.18-1.34 (m, 1H), 1.76 (d, J=7.2 Hz, 3H), 2.35 (s, 3H), 2.73-3.02 (m, 4H), 3.77 (d, J=6.8 Hz, 2H), 4.80 (q, J=6.8 Hz, 1H), 6.61 (s, 1H), 6.81 (d, J=8.7 Hz, 2H), 6.98 (d, J=8.0 Hz, 1H), 7.02-7.09 (m, 3H), 7.09-7.17 (m, 4H), 7.20 (d, J=7.2 Hz, 1H), 7.20-7.30 (m, 3H), 7.78 (d, J=8.4 Hz, 2H).

Example 178

N-(1-{6-[(3-cyclopropyl-4-ethoxybenzyl)oxy]-1-benzofuran-2-yl}ethyl)acetamide

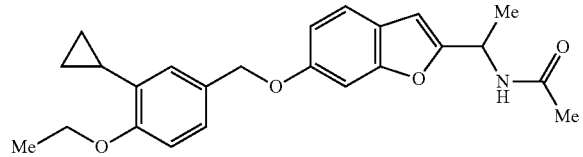 [SMILES: CCOc1ccc(COc2ccc3cc(C(C)NC(C)=O)oc3c2)cc1C1CC1]

A solution of N-(1-{6-[(3-bromo-4-ethoxybenzyl)oxy]-1-benzofuran-2-yl}ethyl)acetamide (100 mg, 0.231 mmol) obtained in Example 175, cyclopropylboronic acid (58.9 mg, 0.693 mmol), tert-butoxy potassium (77.6 mg, 0.693 mmol), tricyclohexylphosphine (6.50 mg, 0.0231 mmol) and palladium(II) acetate (2.60 mg, 0.0115 mmol) in toluene (4 mL) was stirred under argon at 100° C. overnight. To the reaction mixture was added aqueous sodium hydrogen carbonate solution, and the mixture was extracted twice with ethyl acetate. The combined organic layer was washed with saturated brine, and dried over magnesium sulfate. The solvent was evaporated under reduced pressure and the obtained residue was purified by basic silica gel column chromatography (hexane:ethyl acetate=9:1 to 1:1) and triturated with a small amount of hexane and diisopropyl ether to give the title compound (54.6 mg, yield 60%) as a white solid.

$^1$H NMR (CDCl$_3$) δ0.63-0.72 (m, 2H), 0.89-0.97 (m, 2H), 1.45 (t, J=7.2 Hz, 3H), 1.49-1.55 (m, 3H), 2.01 (s, 3H), 2.15-2.30 (m, 1H), 4.07 (q, J=7.2 Hz, 2H), 4.96 (s, 2H), 5.25-5.39 (m, 1H), 5.75 (d, J=6.0 Hz, 1H), 6.48 (s, 1H), 6.83 (d, J=8.3 Hz, 1H), 6.87-6.94 (m, 2H), 7.03 (d, J=2.3 Hz, 1H), 7.18 (dd, J=8.3, 2.3 Hz, 1H), 7.36 (d, J=8.7 Hz, 1H).

Example 179

N-[1-(6-{2-[4-(cyclopropylmethoxy)phenyl]ethyl}-1-benzofuran-2-yl)ethyl]-3-methylisoxazol-5-amine

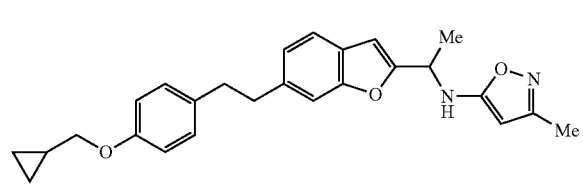 [SMILES: Cc1cc(NC(C)c2cc3ccc(CCc4ccc(OCC5CC5)cc4)cc3o2)on1]

To a solution of 1-(6-{2-[4-(cyclopropylmethoxy)phenyl]ethyl}-1-benzofuran-2-yl)ethanol (300 mg, 0.893 mmol) obtained in Reference Example 282 in toluene (2 mL) was added thionyl chloride (0.116 ml 1.61 mmol), and the mixture was stirred at room temperature for 30 min. The solvent was evaporated under reduced pressure. To the obtained residue were added DMF (2 mL) and 5-amino-3-methylisoxazole (262 mg, 2.68 mmol), and the mixture was stirred at 70° C. overnight. The reaction mixture was purified by basic silica gel column chromatography (hexane:ethyl acetate=19:1 to 3:2), and the solvent was evaporated. The residue was triturated with a small amount of hexane and diisopropyl ether to give the title compound (79.0 mg, yield 21%) as a white solid.

$^1$H NMR (CDCl$_3$) δ0.30-0.40 (m, 2H), 0.59-0.68 (m, 2H), 1.18-1.35 (m, 1H), 1.66 (d, J=6.8 Hz, 3H), 2.14 (s, 3H), 2.84-3.03 (m, 4H), 3.78 (d, J=6.8 Hz, 2H), 4.59-4.71 (m, 1H), 4.75 (d, J=7.5 Hz, 1H), 4.88 (s, 1H), 6.53 (s, 1H), 6.76-6.86 (m, 2H), 7.03 (dd, J=7.9, 1.5 Hz, 1H), 7.06-7.12 (m, 2H), 7.22-7.25 (m, 1H), 7.40 (d, J=7.8 Hz, 1H).

Example 180

N-[1-(6-{2-[4-(cyclopropylmethoxy)phenyl]ethyl}-1-benzofuran-2-yl)ethyl]-5-methylisoxazol-3-amine

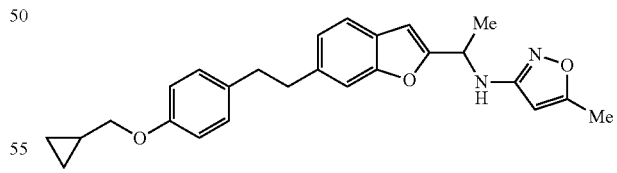

Using 1-(6-{2-[4-(cyclopropylmethoxy)phenyl]ethyl}-1-benzofuran-2-yl)ethanol (300 mg, 0.893 mmol) obtained in Reference Example 282 and 3-amino-5-methylisoxazole (262 mg, 2.68 mmol) and in the same manner as in Example 179, the title compound was obtained (79.0 mg, yield 21%) as a white solid.

$^1$H NMR (CDCl$_3$) δ0.29-0.38 (m, 2H), 0.57-0.69 (m, 2H), 1.19-1.35 (m, 1H), 1.64 (d, J=6.8 Hz, 3H), 2.27 (s, 3H), 2.83-3.04 (m, 4H), 3.78 (d, J=6.8 Hz, 2H), 4.18 (d, J=8.7 Hz,

1H), 4.74-4.92 (m, 1H), 5.51 (s, 1H), 6.54 (s, 1H), 6.74-6.86 (m, 2H), 7.02 (d, J=7.9 Hz, 1H), 7.05-7.11 (m, 2H), 7.23 (s, 1H), 7.39 (d, J=7.8 Hz, 1H).

Example 181

N-[1-(6-{2-[4-(cyclopropylmethoxy)phenyl]ethyl}-1-benzofuran-2-yl)ethyl]-1,2,4-thiadiazol-5-amine

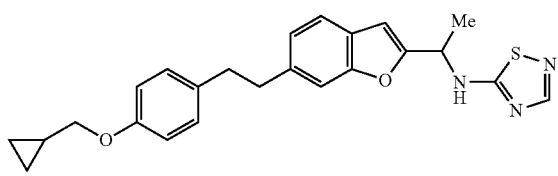 [SMILES: CC(Nc1ncns1)c1cc2ccc(CCc3ccc(OCC4CC4)cc3)cc2o1]

Using 1-(6-{2-[4-(cyclopropylmethoxy)phenyl]ethyl}-1-benzofuran-2-yl)ethanol (300 mg, 0.893 mmol) obtained in Reference Example 282 and 5-amino-1,2,4-thiadiazole (270 mg, 2.68 mmol) and in the same manner as in Example 179, the title compound was obtained (25.3 mg, yield 7%) as a white solid.

$^1$H NMR (CDCl$_3$) δ0.31-0.39 (m, 2H), 0.58-0.69 (m, 2H), 1.18-1.35 (m, 1H), 1.75 (d, J=6.8 Hz, 3H), 2.82-3.09 (m, 4H), 3.77 (d, J=6.8 Hz, 2H), 4.78-4.93 (m, 1H), 6.13 (d, J=7.5 Hz, 1H), 6.63 (s, 1H), 6.78-6.87 (m, 2H), 7.01-7.11 (m, 3H), 7.24 (s, 1H), 7.42 (d, J=7.8 Hz, 1H), 7.93 (s, 1H).

Example 182

N-[1-(6-{2-[4-(cyclopropylmethoxy)phenyl]ethyl}-1-benzofuran-2-yl)ethyl]-4-methylisoxazol-3-amine

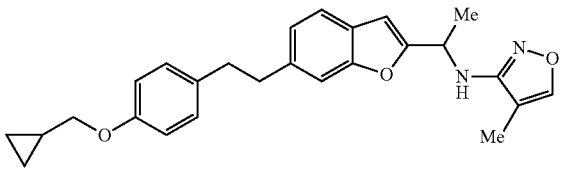 [SMILES: Cc1conc1NC(C)c1cc2ccc(CCc3ccc(OCC4CC4)cc3)cc2o1]

Using 1-(6-{2-[4-(cyclopropylmethoxy)phenyl]ethyl}-1-benzofuran-2-yl)ethanol (300 mg, 0.893 mmol) obtained in Reference Example 282 and 4-methylisoxazol-3-amine (284 mg, 2.90 mmol) and in the same manner as in Example 179, the title compound was obtained (59.2 mg, yield 16%) as a white solid.

$^1$H NMR (CDCl$_3$) δ0.29-0.40 (m, 2H), 0.59-0.68 (m, 2H), 1.20-1.35 (m, 1H), 1.68 (d, J=6.8 Hz, 3H), 1.89 (s, 3H), 2.79-3.06 (m, 4H), 3.78 (d, J=6.8 Hz, 2H), 3.91 (d, J=7.6 Hz, 1H), 4.92-5.14 (m, 1H), 6.58 (s, 1H), 6.82 (d, J=8.7 Hz, 2H), 7.02 (d, J=8.0 Hz, 1H), 7.08 (d, J=8.7 Hz, 2H), 7.22-7.25 (m, 1H), 7.40 (d, J=8.0 Hz, 1H), 7.83 (s, 1H).

Example 183

N-[1-(5-{[4-(2-cyclopropylethoxy)benzyl]oxy}-1-benzofuran-2-yl)ethyl]acetamide

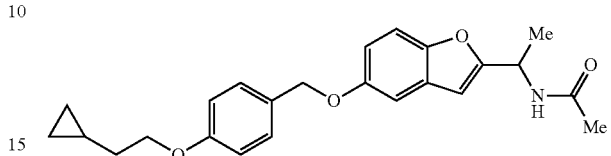

To a solution of [4-(2-cyclopropylethoxy)phenyl]methanol (391 mg, 2.04 mmol) obtained in Reference Example 310 in toluene (2 mL) was added thionyl chloride (0.295 mL, 4.09 mmol), and the mixture was stirred at room temperature for 30 min, and concentrated under reduced pressure. To the obtained residue were added DMF (2 mL), N-[1-(5-hydroxy-1-benzofuran-2-yl)ethyl]acetamide (300 mg, 1.36 mmol) obtained in Reference Example 38 and potassium carbonate (756 mg, 5.48 mmol) and the mixture was stirred at 70° C. overnight. Water was added thereto and the mixture was extracted with ethyl acetate. The extract was washed with saturated brine, and dried over anhydrous sodium sulfate. The solvent was evaporated under reduced pressure and the obtained residue was applied to basic silica gel column chromatography (ethyl acetate) and triturated with diisopropyl ether to give the title compound (486 mg, yield 91%) as a white solid.

$^1$H NMR (CDCl$_3$) δ0.09-0.17 (m, 2H), 0.44-0.53 (m, 2H), 0.75-0.95 (m, 1H), 1.51-1.59 (m, 3H), 1.60-1.70 (m, 2H), 2.02 (s, 3H), 4.04 (t, J=6.8 Hz, 2H), 5.00 (s, 2H), 5.27-5.40 (m, 1H), 5.78 (d, J=7.9 Hz, 1H), 6.49 (s, 1H), 6.87-6.96 (m, 3H), 7.04 (d, J=2.6 Hz, 1H), 7.29-7.39 (m, 3H).

Example 184

N-{1-[5-({4-[(2S)-tetrahydrofuran-2-ylmethoxy]benzyl}oxy)-1-benzofuran-2-yl]ethyl}acetamide

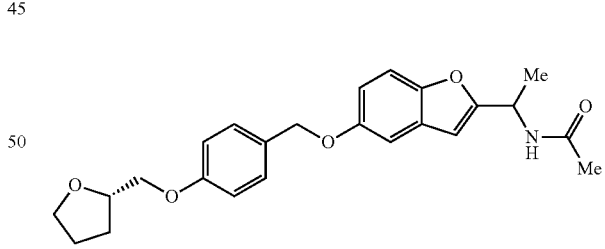

To a solution of {4-[(2S)-tetrahydrofuran-2-ylmethoxy]phenyl}methanol (424 mg, 2.04 mmol) obtained in Reference Example 312 in toluene (2 mL) was added thionyl chloride (0.295 mL, 4.09 mmol), and the mixture was stirred at room temperature for 30 min, and concentrated under reduced pressure. To the obtained residue were added DMF (2 mL), N-[1-(5-hydroxy-1-benzofuran-2-yl)ethyl]acetamide (300 mg, 1.36 mmol) obtained in Reference Example 38 and potassium carbonate (756 mg, 5.48 mmol), and the mixture was stirred at 70° C. overnight. Water was added thereto and the mixture was extracted with ethyl acetate. The extract was washed with saturated brine, and dried over anhydrous sodium sulfate. The solvent was evaporated under reduced pressure and the obtained residue was applied to basic silica gel column chromatography (ethyl acetate) and triturated with diisopropyl ether to give the title compound (466 mg, yield 84%) as a white solid.

¹H NMR (CDCl₃) δ 1.55 (d, J=6.9 Hz, 3H), 1.69-1.84 (m, 1H), 1.84-2.16 (m, 3H), 2.02 (s, 3H), 3.79-4.03 (m, 4H), 4.22-4.35 (m, 1H), 5.00 (s, 2H), 5.24-5.38 (m, 1H), 5.80 (d, J=8.3 Hz, 1H), 6.49 (s, 1H), 6.87-6.97 (m, 3H), 7.03 (d, J=2.3 Hz, 1H), 7.28-7.40 (m, 3H).

Example 185

N-[1-(5-{[4-(cyclobutylmethoxy)benzyl]oxy}-1-benzofuran-2-yl)ethyl]acetamide

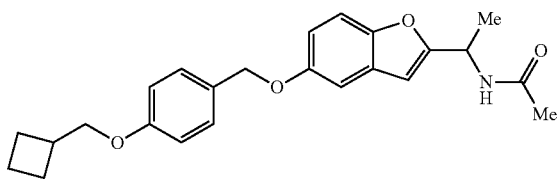 [SMILES: CC(=O)NC(C)c1cc2cc(OCc3ccc(OCC4CCC4)cc3)ccc2o1]

To a solution of [4-(cyclobutylmethoxy)phenyl]methanol (392 mg, 2.04 mmol) obtained in Reference Example 313 in toluene (2 mL) was added thionyl chloride (0.295 mL, 4.09 mmol), and the mixture was stirred at room temperature for 30 min, and concentrated under reduced pressure. To the obtained residue were added DMF (2 mL), N-[1-(5-hydroxy-1-benzofuran-2-yl)ethyl]acetamide (300 mg, 1.36 mmol) obtained in Reference Example 38 and potassium carbonate (756 mg, 5.48 mmol) and the mixture was stirred at 70° C. overnight. Water was added thereto and the mixture was extracted with ethyl acetate. The extract was washed with saturated brine, and dried over anhydrous sodium sulfate. The solvent was evaporated under reduced pressure and the obtained residue was applied to basic silica gel column chromatography (ethyl acetate) and triturated with diisopropyl ether to give the title compound (482 mg, yield 90%) as a white solid.

¹H NMR (CDCl₃) δ 1.78-1.99 (m, 4H), 2.01 (s, 3H), 2.08-2.25 (m, 2H), 2.65-2.87 (m, 1H), 3.93 (d, J=6.8 Hz, 2H), 5.00 (s, 2H), 5.19-5.40 (m, 1H), 5.78 (d, J=8.3 Hz, 1H), 6.49 (s, 1H), 6.83-6.97 (m, 3H), 7.04 (d, J=2.6 Hz, 1H), 7.29-7.40 (m, 3H).

Example 186

N-[1-(5-{[4-(cyclopropylmethoxy)-2-methylbenzyl]oxy}-1-benzofuran-2-yl)ethyl]acetamide

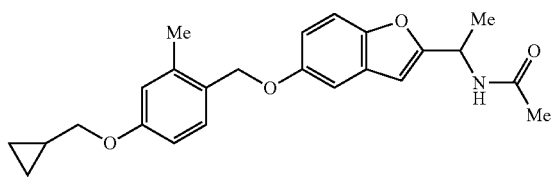 [SMILES: CC(=O)NC(C)c1cc2cc(OCc3ccc(OCC4CC4)cc3C)ccc2o1]

To a solution of [4-(cyclopropylmethoxy)-2-methylphenyl]methanol (262 mg, 1.37 mmol) obtained in Reference Example 315 in toluene (2 mL) was added thionyl chloride (0.196 mL, 2.71 mmol), and the mixture was stirred at room temperature for 30 min, and concentrated under reduced pressure. To the obtained residue were added DMF (2 mL), N-[1-(5-hydroxy-1-benzofuran-2-yl)ethyl]acetamide (200 mg, 0.913 mmol) obtained in Reference Example 38 and potassium carbonate (503 mg, 3.65 mmol), and the mixture was stirred at 60° C. overnight. Water was added thereto and the mixture was extracted with ethyl acetate. The extract was washed with saturated brine, and dried over anhydrous sodium sulfate. The solvent was evaporated under reduced pressure and the obtained residue was applied to basic silica gel column chromatography (ethyl acetate) and triturated with hexane-diisopropyl ether to give the title compound (222 mg, yield 62%) as a white solid.

¹H NMR (CDCl₃) δ 0.27-0.41 (m, 2H), 0.56-0.71 (m, 2H), 1.23-1.31 (m, 1H), 1.55 (d, J=6.8 Hz, 3H), 2.02 (s, 3H), 2.36 (s, 3H), 3.80 (d, J=7.2 Hz, 2H), 4.97 (s, 2H), 5.30-5.36 (m, 1H), 5.81 (d, J=8.0 Hz, 1H), 6.50 (s, 1H), 6.72 (dd, J=8.1, 2.5 Hz, 1H), 6.79 (d, J=2.3 Hz, 1H), 6.92 (dd, J=8.7, 2.7 Hz, 1H), 7.03 (d, J=2.7 Hz, 1H), 7.26-7.35 (m, 2H).

Example 187

N-[1-(5-{[2-fluoro-4-((2S)-tetrahydrofuran-2-ylmethoxy)benzyl]oxy}-1-benzofuran-2-yl)ethyl]acetamide

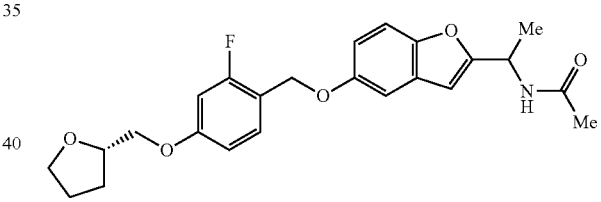

To a solution of {2-fluoro-4-[(2S)-tetrahydrofuran-2-ylmethoxy]phenyl}methanol (103 mg, 0.457 mmol) obtained in Reference Example 274 in toluene (1 mL) was added thionyl chloride (0.0630 mL, 0.912 mmol), and the mixture was stirred at room temperature for 30 min, and concentrated under reduced pressure. To the obtained residue were added DMF (1 mL), N-[1-(5-hydroxy-1-benzofuran-2-yl)ethyl]acetamide (retention time longer) (50.0 mg, 0.228 mmol) obtained in Reference Example 257 and potassium carbonate (157 mg, 1.14 mmol) and the mixture was stirred at 70° C. overnight. Water was added thereto and the mixture was extracted with ethyl acetate. The extract was washed with saturated brine, and dried over anhydrous magnesium sulfate. The solvent was evaporated under reduced pressure and the obtained residue was applied to basic silica gel column chromatography (ethyl acetate) and triturated with diisopropyl ether to give the title compound (85.5 mg, yield 88%) as a white solid.

¹H NMR (CDCl₃) δ 1.55 (d, J=6.8 Hz, 3H), 1.67-1.84 (m, 1H), 1.85-2.16 (m, 6H), 3.78-3.99 (m, 4H), 4.17-4.32 (m,

1H), 5.05 (s, 2H), 5.25-5.39 (m, 1H), 5.81 (d, J=8.3 Hz, 1H), 6.49 (s, 1H), 6.60-6.78 (m, 3H), 7.05 (d, J=2.7 Hz, 1H), 7.28-7.41 (m, 2H).

Example 188

N-[1-(6-{[4-(cyclopropylmethoxy)-2-fluorobenzyl]oxy}-1-benzofuran-3-yl)ethyl]acetamide (two kinds)

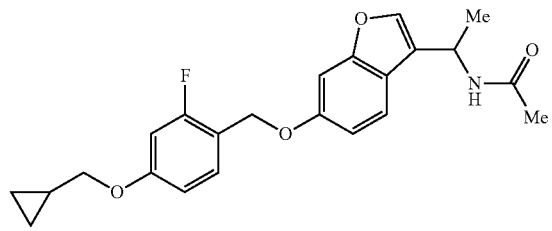 [SMILES: CC(=O)NC(C)c1coc2cc(OCc3ccc(OCC4CC4)cc3F)ccc12]

N-[1-(6-{[4-(cyclopropylmethoxy)-2-fluorobenzyl]oxy}-1-benzofuran-3-yl)ethyl]acetamide (610 mg) obtained in Example 161 was optically resolved by high performance liquid chromatography (HPLC) under the following conditions to give two kinds of optically active forms of "retention time longer (285 mg)" and "retention time shorter (286 mg)".
<Preparative HPLC Conditions>
    column: CHIRALCEL OJ (50 mmID×500 mmL)
    mobile phase: hexane:ethanol=7:3
    flow rate: 60 mL/min
    column temperature: 40° C.
    detection: UV 220 nm
<HPLC Analysis Conditions>
    column: CHIRALCEL OJ (4.6 mmID×250 mmL)
    mobile phase: hexane:ethanol=7:3
    flow rate: 0.5 mL/min
    column temperature: 40° C.
    detection: UV 220 nm
    retention time of "retention time longer": 19.5 min
    retention time of "retention time shorter": 15.0 min Example 189

N-(1-{6-[(2-(4-butoxyphenyl)ethyl]-1-benzofuran-2-yl}ethyl)acetamide (two kinds)

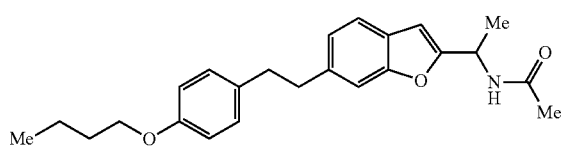 [SMILES: CCCCOc1ccc(CCc2ccc3cc(C(C)NC(C)=O)oc3c2)cc1]

N-(1-{6-[2-(4-butoxyphenyl)ethyl]-1-benzofuran-2-yl}ethyl)acetamide (340 mg) obtained in Example 44 was optically resolved by high performance liquid chromatography (HPLC) under the following conditions to give two kinds of optically active forms of "retention time longer (132 mg)" and "retention time shorter (158 mg)".
<Preparative HPLC Conditions>
    column: CHIRALPAK AS (50 mmID×500 mmL)
    mobile phase: hexane:ethanol=9:1
    flow rate: 80 mL/min
    column temperature: 25° C.
    detection: UV 220 nm
<HPLC Analysis Conditions>
    column: CHIRALPAK AS (4.6 mmID×250 mmL)
    mobile phase: hexane:ethanol=9:1
    flow rate: 1.0 mL/min
    column temperature: 30° C.
    detection: UV 220 nm
    retention time of "retention time longer": 13.4 min
    retention time of "retention time shorter": 10.3 min Example 190

N-(1-{6-[2-(4-ethoxyphenyl)ethyl]-1-benzofuran-2-yl}ethyl)acetamide (two kinds)

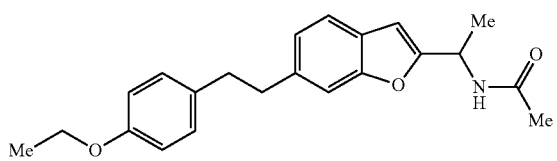 [SMILES: CCOc1ccc(CCc2ccc3cc(C(C)NC(C)=O)oc3c2)cc1]

N-(1-{6-[2-(4-ethoxyphenyl)ethyl]-1-benzofuran-2-yl}ethyl)acetamide (295 mg) obtained in Example 20 was optically resolved by high performance liquid chromatography (HPLC) under the following conditions to give two kinds of optically active forms of "retention time longer (141 mg)" and "retention time shorter (133 mg)".
<Preparative HPLC Conditions>
    column: CHIRALPAK AS (50 mmID×500 mmL)
    mobile phase: hexane:ethanol=9:1
    flow rate: 80 mL/min
    column temperature: 25° C.
    detection: UV 220 nm
<HPLC Analysis Conditions>
    column: CHIRALPAK AS (4.6 mmID×250 mmL)
    mobile phase: hexane:ethanol=9:1
    flow rate: 1.0 mL/min
    column temperature: 30° C.
    detection: UV 220 nm
    retention time of "retention time longer": 19.1 min
    retention time of "retention time shorter": 13.7 min Example 191

N-[1-(6-{2-[4-(cyclopropylmethoxy)phenyl]ethyl}-1-benzofuran-2-yl)ethyl]acetamide (two kinds)

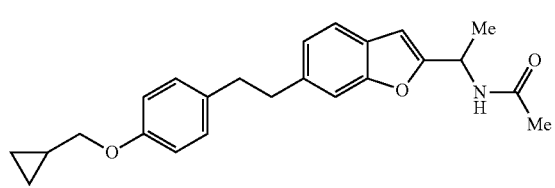 [SMILES: CC(=O)NC(C)c1cc2ccc(CCc3ccc(OCC4CC4)cc3)cc2o1]

N-[1-(6-{2-[4-(cyclopropylmethoxy)phenyl]ethyl}-1-benzofuran-2-yl)ethyl]acetamide (340 mg) obtained in Example 150 was optically resolved by high performance liquid chromatography (HPLC) under the following conditions to give two kinds of optically active forms of "retention time longer (136 mg)" and "retention time shorter (149 mg)".

<Preparative HPLC Conditions>
  column: CHIRALPAK AS (50 mmID×500 mmL)
  mobile phase: hexane:ethanol=9:1
  flow rate: 80 mL/min
  column temperature: 25° C.
  detection: UV 220 nm
<HPLC Analysis Conditions>
  column: CHIRALPAK AS (4.6 mmID×250 mL)
  mobile phase: hexane:ethanol=9:1
  flow rate: 1.0 mL/min
  column temperature: 30° C.
  detection: UV 220 nm
  retention time of "retention time longer": 16.9 min
  retention time of "retention time shorter": 13.0 min Experimental Example 1

The ACC2 inhibitory action of the compound of the present invention was evaluated by the following method.
(1) Cloning of Human ACC2 Gene and Preparation of Recombinant Baculovirus Human ACC2 gene was cloned by PCR using a human skeletal muscle cDNA library (Clontech) as a template and Primer 1 and Primer 2 shown below. Primer 1 and Primer 2 were prepared by adding SalI, XbaI restriction enzyme recognition sequences based on the information of the base sequence of human ACC2 gene (Genbank Accession U89344).

```
Primer 1:
                                            (SEQ ID NO: 1)
5'-AAAAGTCGACCCACCATGGTCTTGCTTCTTTGTCTATCTTG-3'

Primer 2:
                                            (SEQ ID NO: 2)
5'-TTTTTCTAGATCAGGTAGAGGCCGGGCTGTCCATG-3'
```

PCR was performed using Pyrobest DNA polymerase (TAKARA BIO INC.). The obtained PCR product was cloned to pT7 Blue vector (Novagen) and, after confirmation of the base sequence, digested with restriction enzymes SalI and XbaI. The obtained DNA fragment was inserted into pFAST-BacHTa (Invitrogen) digested with restriction enzymes SalI and XbaI to give expression plasmid ACC2/pFAST-BacHTa.

A plasmid for expression of ACC2 without a mitochondrial targeting sequence was prepared by PCR using the expression plasmid as a template, and Primer 3 (SalI restriction enzyme recognition sequence was added) and Primer 4 prepared by reference to the information of human ACC2 gene base sequence (Genbank Accession U89344).

```
Primer 3:
                                            (SEQ ID NO: 3)
5'-CCAGGTCGACCCGCCAACGGGACTGGGACACAAGG-3'

Primer 4:
                                            (SEQ ID NO: 4)
5'-CGCACTCTCAGTTTCCCGGATTCCC-3'
```

PCR was performed using Pyrobest-DNA polymerase (TAKARA BIO INC.). The obtained PCR product was cloned to pT7 Blue vector (Novagen) and, after confirmation of the base sequence, digested with restriction enzymes SalI and AflII. The obtained DNA fragment was inserted into ACC2/pFAST-BacHTa digested with restriction enzymes SalI and AflII to give expression plasmid ACC2mito7/pFAST-BacHTa.

Using the expression plasmid ACC2mito7/pFAST-BacHTa and BAC-TO-BAC Baculovirus Expression System (Invitrogen), virus stock BAC-ACC2 of recombinant Baculovirus (N terminal deleted (hereinafter Nd)) was prepared.
(2) Preparation of ACC2 (Nd) Protein SF-9 cells (Invitrogen) were inoculated to a medium (2 L) for insect cells (Sf-900IISFM medium (Invitrogen) containing 10% fetal bovine serum (Trace), 50 mg/L Gentamicin (Invitrogen), 0.1% Pluronic F-68 (Invitrogen)) at $0.5 \times 10^6$ cells/mL, and cultured with shaking in Wave Bioreactor (Wave) at 27° C., 20 rpm, rocking angle 6°, oxygen concentration 30%.

On day 4 of the culture, 3 L of the medium for insect cells was added, the rocking angle was set to 8°, and the cells were cultured. On day 5 of the culture, 100 ml of recombinant Baculovirus BAC-ACC2 (Nd) was added, 5 L of the medium for insect cells was further added, the rocking angle was set to 11°, and the cells were cultured for 3 days. The culture medium was centrifuged at 1000×g for 10 min to give virus-infected cells. The cells were washed with phosphate buffered saline (Invitrogen) and centrifuged under the same conditions. The obtained cells were cryopreserved at −80° C.

The cryopreserved cells were thawed in ice and suspended in 900 ml of 25 mM HEPES buffer (pH 7.5) containing 10% Glycerol, 0.13 M NaCl, 1 mM EDTA, 25 mM Sodium β-Glycerophosphate and 1 mM Sodium Orthovanadate, and supplemented with Complete Protease Inhibitor (Nippon Boehringer Ingelheim Co., Ltd.). The obtained suspension was homogenized three times in a polytron homogenizer (Kinematica) at 20,000 rpm for 30 sec. The obtained cell disruption solution was clarified by centrifugation at 31000×g for 60 min, and filtered through a 0.45 µm filter. The filtrate was passed through a column packed with 60 mL of Ni-NTA Super Flow Gel (QUIAGEN) at a flow rate of about 5 mL/min. The column was washed with buffer A (50 mM HEPES (pH 7.5) containing 0.3 M NaCl), further washed with buffer A containing 20 mM Imidazole, and eluted with buffer A containing 100 mM Imidazole. The eluate was concentrated with Vivaspin 20 (Vivascience) with a molecular weight cut off of 30K. The obtained concentrate was dialyzed against 50 mM HEPES (pH 7.5) containing 10 mM $MgCl_2$, 2 mM Dithiothreitol, 10 mM Tripotassium Citrate and 0.3 M NaCl. The inner dialysate was filtered through a 0.22 µm filter to give ACC2 (Nd). The obtained ACC2 (Nd) was cryopreserved at −80° C.
(3) Measurement of ACC2 Inhibitory Activity ACC2 (Nd) (1.1 mg/ml) obtained in the above-mentioned (2) was diluted with an enzyme reaction buffer (50 mM HEPES (pH 7.5), 10 mM $MgCl_2$, 10 mM Tripotassium Citrate, 2 mM Dithiothreitol, 0.75 mg/ml Fatty acid free BSA) to a concentration of 6.4 µg/ml, and the mixture was added to each well of a 384 well assay plate (Nunc 265196) by 10 µl. A test compound was dissolved in dimethyl sulfoxide (DMSO) and the mixture was diluted with an enzyme reaction buffer and the resulting solution (5 µl) was added to each well. The mixture was incubated at 30° C. for 60 min. Then, a substrate solution (50 mM $KHCO_3$, 200 µM ATP, 200 µM Acetyl-CoA, 5 µl) was added to each well, and the mixture was reacted at 30° C. for 20 min (test compound addition group).

In addition, a reaction was performed in the same manner as above and without adding the test compound (test compound non-addition group).

Furthermore, a reaction was performed in the same manner as above and without adding the test compound and Acetyl-CoA (control group).

The reaction was quenched by adding a malachite green solution to each of the obtained reaction mixtures by 5 μl and stirring the mixtures. The obtained reaction mixture was left standing at room temperature for 20 min, and absorbance (620 nm) was measured using wallac1420 (PerkinElmer Japan Co., Ltd.). The above-mentioned malachite green solution was prepared by mixing Solution A (0.12% malachite green solution, prepared with $5NH_2SO_4$, preserved at 4° C. in shading), Solution B (7.5% aqueous ammonium molybdate solution, prepared when in use) and Solution C (11% aqueous Tween 20 solution, preserved at room temperature) at a ratio of Solution A:Solution B:Solution C=100:25:2 (volume ratio).

ACC2 inhibitory rate (%) was determined according to the following calculation formula. The calculation results are shown in Table 3 together with those of Experimental Example 2.

(1−(absorbance of test compound addition group−
absorbance of control group)+(absorbance of test
compound non-addition group−absorbance of
control group))×100

Experimental Example 2

The ACC1 inhibitory action of the compound of the present invention was evaluated by the following method.
(1) Cloning of Human ACC1 Gene and Preparation of Recombinant Baculovirus Human ACC1 gene was cloned by PCR using a human liver cDNA library (Clontech) as a template and Primer 1 and Primer 2 shown below. Primer 1 and Primer 2 were prepared by adding SalI, NotI restriction enzyme recognition sequences based on the information of the base sequence of human ACC1 gene (Genbank Accession U19822).

```
Primer 1:
                                      (SEQ ID NO: 5)
5'-AAAAGTCGACCCACCATGGATGAACCTTCTCCCTTGGCCC-3'

Primer 2:
                                      (SEQ ID NO: 6)
5'-AAAAGCGGCCGCCTACGTAGAAGGGGAGTCCATAGTG-3'
```

PCR was performed using Pyrobest DNA polymerase (TAKARA BIO INC.). The obtained PCR product was cloned to pT7 Blue vector (Novagen) and, after confirmation of the base sequence, digested with restriction enzymes SalI and NotI. The obtained DNA fragment was inserted into pFAST-BacHTc (Invitrogen) digested with restriction enzymes SalI and NotI to give expression plasmid ACC1/pFAST-BacHTc.

Using the expression plasmid ACC1/pFAST-BacHTc and BAC-TO-BAC Baculovirus Expression System (Invitrogen), virus stock BAC-ACC1 of recombinant Baculovirus was prepared.
(2) Preparation of ACC1 Protein SF-9 cells (Invitrogen) were inoculated to a medium (1 L) for insect cells (Sf-900IISFM medium (Invitrogen) containing 10% fetal bovine serum (Trace), 50 mg/L Gentamicin (Invitrogen), 0.1% Pluronic F-68 (Invitrogen)) at $1 \times 10^6$ cells/mL, and cultured with shaking in 2 L meyer at 27° C., 100 rpm.

After 24 hr of the culture, 10 mL of recombinant Baculovirus BAC-ACC1 was added, and the cells were cultured for 3 days. The culture medium was centrifuged at 1000×g for 5 min to give virus-infected cells. The cells were washed with phosphate buffered saline (Invitrogen) and centrifuged under the same conditions. The obtained cells were cryopreserved at −80° C.

The cryopreserved cells were thawed in ice and suspended in 100 mL of 25 mM HEPES buffer (pH 7.5) containing 10% Glycerol, 0.13 M NaCl, 1 mM EDTA, 25 mM Sodium O-Glycerophosphate and 1 mM Sodium Orthovanadate, and supplemented with Complete Protease Inhibitor (Nippon Boehringer Ingelheim Co., Ltd.). The obtained suspension was homogenized three times in a polytron homogenizer (Kinematica) at 20,000 rpm for 30 sec. The obtained cell disruption solution was clarified by centrifugation at 185700×g for 50 min, and filtered through a 0.45 μm filter. The filtrate was passed through a column packed with 12 ml of Ni-NTA Super Flow Gel (QUIAGEN) at a flow rate of about 5 mL/min. The column was washed with buffer A (50 mM HEPES (pH 7.5) containing 0.3 M NaCl), further washed with buffer A containing 20 mM Imidazole, and eluted with buffer A containing 100 mM Imidazole. The eluate was concentrated with Vivaspin 20 (Vivascience) with a molecular weight cut off of 30K. The obtained concentrate was dialyzed against Sephadex G-25 (Amersham Biosciences, 358 mL) equilibrated with 50 mM HEPES (pH 7.5) containing 10 mM $MgCl_2$, 2 mM Dithiothreitol, 10 mM Tripotassium Citrate and 0.3 M NaCl. The inner dialysate was concentrated with Vivaspin 20 (Vivascience) with molecular weight cut off of 30K, and concentrate was filtered through a 0.22 μm filter to give ACC1. The obtained ACC1 was cryopreserved at −80° C.
(3) Measurement of ACC1 Inhibitory Activity ACC1 (0.93 mg/ml) obtained in the above-mentioned (2) was diluted with an enzyme reaction buffer (50 mM HEPES (pH 7.5), 10 mM $MgCl_2$, 10 mM Tripotassium Citrate, 2 mM Dithiothreitol, 0.75 mg/ml Fatty acid free BSA) to a concentration of 8 μg/ml, and the mixture was added to each well of a 384 well assay plate (Nunc 265196) by 10 μl. A test compound was dissolved in dimethyl sulfoxide (DMSO) and the mixture was diluted with an enzyme reaction buffer and the resulting solution (5 μl) was added to each well. The mixture was incubated at 30° C. for 60 min. Then, a substrate solution (50 mM $KHCO_3$, 200 μM ATP, 200 μM Acetyl-CoA, 5 μl) was added to each well, and the mixture was reacted at 30° C. for 20 min (test compound addition group).

In addition, a reaction was performed in the same manner as above and without adding the test compound (test compound non-addition group).

Furthermore, a reaction was performed in the same manner as above and without adding the test compound and Acetyl-CoA (control group).

The reaction was quenched by adding a malachite green solution to each of the obtained reaction mixtures by 5 μl and stirring the mixtures. The obtained reaction mixture was left standing at room temperature for 20 min, and absorbance (620 nm) was measured using wallac1420 (PerkinElmer Japan Co., Ltd.). The above-mentioned malachite green solution was prepared by mixing Solution A (0.12% malachite green solution, prepared with $5NH_2SO_4$, preserved at 4° C. in shading), Solution B (7.5% aqueous ammonium molybdate solution, prepared when in use) and Solution C (11% aqueous Tween 20 solution, preserved at room temperature) at a ratio of Solution A:Solution B:Solution 2 100:25:2 (volume ratio).

ACC1 inhibitory rate (%) was determined in the same manner as in the aforementioned Experimental Example 1-(3). The inhibitory rates against ACC1 and ACC2 at 10 μm are shown in Table 3.

TABLE 3

| Example No. | ACC1 10 μM inhibitory rate (%) | ACC2 10 μM inhibitory rate (%) |
|---|---|---|
| 18 | 15 | 85 |
| 19 | 24 | 78 |
| 20 | 23 | 83 |
| 27 | 18 | 76 |
| 28 | 19 | 81 |
| 32 | 36 | 84 |
| 37 | −4 | 77 |
| 39 | 17 | 80 |
| 42 | 1 | 76 |
| 44 | 35 | 78 |
| 47 | 37 | 91 |
| 48 | 10 | 78 |
| 94 | 19 | 80 |
| 95 | 43 | 80 |
| 107 | 12 | 70 |
| 110 | 40 | 78 |
| 111 | 30 | 78 |
| 115 | 25 | 76 |
| 116 (retention time longer) | 24 | 63 |
| 121 | 35 | 73 |
| 123 | 8 | 78 |
| 124 | 16 | 81 |
| 125 | 33 | 83 |
| 129 (retention time longer) | 51 | 86 |
| 130 (retention time longer) | 25 | 62 |
| 132 (retention time longer) | 46 | 91 |
| 134 (retention time longer) | 33 | 55 |
| 135 | 14 | 81 |
| 138 | 22 | 70 |
| 139 | 37 | 100 |
| 140 | 20 | 66 |
| 141 (retention time shorter) | 41 | 95 |
| 142 | 42 | 74 |
| 143 | 8 | 73 |
| 144 | 48 | 88 |
| 145 | 42 | 88 |
| 146 | 40 | 84 |
| 150 | 27 | 81 |
| 152 | 39 | 78 |
| 153 | 24 | 70 |
| 154 | 39 | 78 |
| 164 | 50 | 93 |
| 169 | 23 | 75 |
| 170 | 30 | 84 |
| 174 | 34 | 80 |
| 175 | 15 | 74 |
| 176 | 31 | 88 |
| 189 (retention time shorter) | 37 | 77 |
| 190 (retention time longer) | 29 | 79 |
| 191 (retention time shorter) | 20 | 75 |

As shown in Table 3, the compound of the present invention has a superior ACC2 inhibitory action. It shows only a low activity against ACC1, and has superior ACC2 selectivity.

Formulation Example 1

Production of Capsules

| | |
|---|---|
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2

Production of Tablets

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture was punched by a tableting machine, whereby 1000 tablets containing 30 mg of the compound of Example 1 per tablet are obtained.

INDUSTRIAL APPLICABILITY

The compound of the present invention has ACC (acetyl-CoA carboxylase) inhibitory action, and is useful for the prophylaxis or treatment of obesity, diabetes, hypertension, hyperlipidemia, cardiac failure, diabetic complications, metabolic syndrome, sarcopenia, cancer and the like.

This application is based on patent application Nos. 276171/2008, 037468/2009 and 142769/2009 filed in Japan, the contents of which are hereby incorporated by reference.

The invention claimed is:

1. A compound represented by the formula (I),

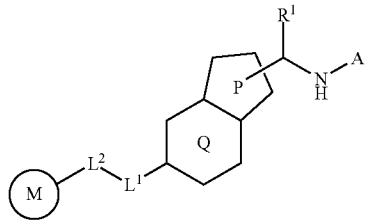

(I)

wherein
A is
a $C_{1-6}$ alkyl-carbonyl group;
ring M is
a benzene ring optionally substituted by 1 to 3 substituents selected from the group consisting of
(1) a halogen atom,
(2) a $C_{1-6}$ alkyl group,
(3) a $C_{1-6}$ alkoxy group optionally substituted by 1 to 3 substituents selected from the group consisting of (i) a halogen atom, (ii) a $C_{1-6}$ alkoxy group, (iii) a $C_{3-10}$ cycloalkyl group, (iv) a heterocyclic group, and (v) a $C_{6-14}$ aryl group,
(4) a $C_{3-10}$ cycloalkoxy group optionally substituted by 1 to 3 substituents selected from the group consisting of (i) a halogen atom and (ii) a $C_{1-6}$ alkoxy group, and
(5) a hydroxy group;
ring P and ring Q are condensed to form

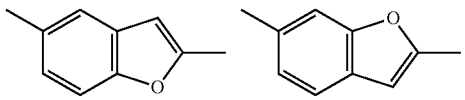

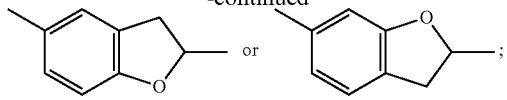

$R^1$ is a $C_{1-6}$ alkyl group or a $C_{3-6}$ cycloalkyl group;
(1) $L^1$ and $L^2$ are independently methylene or O, or
(2) $L^1$ and $L^2$ in combination form vinylene or ethynylene,
or a salt thereof.

2. The compound or salt of claim 1, wherein $R^1$ is a $C_{1-6}$ alkyl group.

3. The compound or salt of claim 1, wherein ring P and ring Q are condensed to form

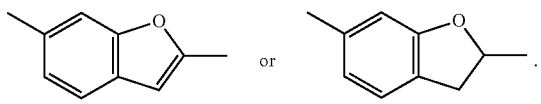

4. N-{(1S)-1-[(2S)-6-{[4-(Cyclopropylmethoxy)benzyl]oxy}-2,3-dihydro-1-benzofuran-2-yl]ethyl}acetamide or a salt thereof.

5. N-{(1S)-1-[(2S)-6-{[4-(Cyclopropylmethoxy)-2-fluorobenzyl]oxy}-2,3-dihydro-1-benzofuran-2-yl]ethyl}acetamide or a salt thereof.

6. N-(1-{6-[2-(4-Ethoxyphenyl)ethyl]-1-benzofuran-2-yl}ethyl)acetamide or a salt thereof.

7. N-[1-(5-{[4-(Cyclopropylmethoxy)benzyl]oxy}-1-benzofuran-2-yl)ethyl]acetamide or a salt thereof.

8. A pharmaceutical composition comprising the compound or salt of claim 1, and a pharmacologically acceptable carrier.

9. A method for the treatment of obesity, diabetes, hyperlipidemia, diabetic complications or metabolic syndrome in a mammal, which comprises administering an effective amount of the compound or salt of claim 1 to the mammal.

* * * * *

SEQUENCE LISTING

<160> NUMBER OF SEQ ID NOS: 6

<210> SEQ ID NO 1
<211> LENGTH: 41
<212> TYPE: DNA
<213> ORGANISM: Artificial sequence
<220> FEATURE:
<223> OTHER INFORMATION: Synthetic construct; PCR primer for hACC2 gene cloning

<400> SEQUENCE: 1
aaaagtcgac ccaccatggt cttgcttctt tgtctatctt g    41

<210> SEQ ID NO 2
<211> LENGTH: 35
<212> TYPE: DNA
<213> ORGANISM: Artificial sequence
<220> FEATURE:
<223> OTHER INFORMATION: Synthetic construct; PCR primer for hACC2 gene
      cloning

<400> SEQUENCE: 2
tttttctaga tcaggtagag gccgggctgt ccatg    35

<210> SEQ ID NO 3
<211> LENGTH: 35
<212> TYPE: DNA
<213> ORGANISM: Artificial sequence
<220> FEATURE:
<223> OTHER INFORMATION: Synthetic construct; PCR primer for
      constuction of ACC2-expressing plasmid

<400> SEQUENCE: 3
ccaggtcgac ccgccaacgg gactgggaca caagg    35

<210> SEQ ID NO 4
<211> LENGTH: 25
<212> TYPE: DNA
<213> ORGANISM: Artificial sequence
<220> FEATURE:
<223> OTHER INFORMATION: Synthetic construct; PCR primer for
      constuction of ACC2-expressing plasmid

<400> SEQUENCE: 4
cgcactctca gtttcccgga ttccc    25

<210> SEQ ID NO 5
<211> LENGTH: 40
<212> TYPE: DNA
<213> ORGANISM: Artificial sequence
<220> FEATURE:
<223> OTHER INFORMATION: Synthetic construct; PCR primer for hACC1 gene
      cloning

<400> SEQUENCE: 5
aaaagtcgac ccaccatgga tgaaccttct cccttggccc    40

<210> SEQ ID NO 6
<211> LENGTH: 37
<212> TYPE: DNA
<213> ORGANISM: Artificial sequence
<220> FEATURE:
<223> OTHER INFORMATION: Synthetic construct; PCR primer for hACC1 gene
      cloning

<400> SEQUENCE: 6
aaaagcggcc gcctacgtag aaggggagtc catagtg    37